United States Patent
Grether et al.

(10) Patent No.: US 9,409,866 B2
(45) Date of Patent: Aug. 9, 2016

(54) PYRIDINE-2-AMIDES USEFUL AS CB2 AGONISTS

(71) Applicant: Hoffmann-La Roche Inc., Little Falls, NJ (US)

(72) Inventors: Uwe Grether, Efringen-Kirchen (DE); Atsushi Kimbara, Tokyo (JP); Matthias Nettekoven, Grenzach-Wyhlen (DE); Fabienne Ricklin, Hombourg (FR); Stephan Roever, Inzlingen (DE); Mark Rogers-Evans, Bottmingen (CH); Didier Rombach, Mulhouse (FR); Tanja Schulz-Gasch, Ziefen (CH); Matthias Westphal, Zurich (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 14/648,412

(22) PCT Filed: Dec. 4, 2013

(86) PCT No.: PCT/EP2013/075442
§ 371 (c)(1),
(2) Date: May 29, 2015

(87) PCT Pub. No.: WO2014/086805
PCT Pub. Date: Jun. 12, 2014

(65) Prior Publication Data
US 2015/0344429 A1    Dec. 3, 2015

(30) Foreign Application Priority Data
Dec. 7, 2012 (EP) .................. 12196029

(51) Int. Cl.
| | | |
|---|---|---|
| C07D 213/81 | (2006.01) |
| C07D 401/04 | (2006.01) |
| A61K 31/444 | (2006.01) |
| C07D 405/12 | (2006.01) |
| C07D 491/107 | (2006.01) |
| C07D 413/14 | (2006.01) |
| C07D 401/06 | (2006.01) |
| C07D 401/12 | (2006.01) |
| C07D 405/04 | (2006.01) |
| C07D 409/12 | (2006.01) |
| C07D 413/12 | (2006.01) |
| C07D 417/12 | (2006.01) |
| C07D 417/14 | (2006.01) |
| C07D 491/10 | (2006.01) |

(52) U.S. Cl.
CPC ........... *C07D 213/81* (2013.01); *C07D 401/04* (2013.01); *C07D 401/06* (2013.01); *C07D 401/12* (2013.01); *C07D 405/04* (2013.01); *C07D 405/12* (2013.01); *C07D 409/12* (2013.01); *C07D 413/12* (2013.01); *C07D 413/14* (2013.01); *C07D 417/12* (2013.01); *C07D 417/14* (2013.01); *C07D 491/10* (2013.01); *C07D 491/107* (2013.01)

(58) Field of Classification Search
None
See application file for complete search history.

(56) References Cited

U.S. PATENT DOCUMENTS

| 2008/0085905 A1 | 4/2008 | Dietz et al. |
| 2012/0065212 A1 | 3/2012 | Hebeisen et al. |

FOREIGN PATENT DOCUMENTS

| WO | 2008/040649 A2 | 4/2008 |
| WO | 2012/032018 A1 | 3/2012 |
| WO | 2012/168350 A1 | 12/2012 |

OTHER PUBLICATIONS

Dubois et al., "A new pathway to substituted 6-chloro-2-pyridinecarboxylic acid derivatives from the reaction of 4,6-dichloro-2-oxa-5-aza-bicylo[2.2.2]oct-5-en-3-ones with nucleophiles" Tetrahedron 52(20);6997-7002 (1996).
International Search Report issued in International Application No. PCT/EP2013/075225, dated Jan. 17, 2014 (in 2 pages).
International Search Report issued in International Application No. PCT/EP2013/075442, dated Feb. 17, 2014 (in 2 pages).
International Search Report issued in International Application No. PCT/EP2013/075443, dated Feb. 18, 2014 (in 3 pages).
International Search Report issued in International Application No. PCT/EP2013/075444, dated Jan. 22, 2014 (in 4 pages).
Sammakia et al., "Total Synthesis of Caerulomycin C via the Halogen Dance Reaction" Organic Letters 4(14):2385-2388 (2002).

*Primary Examiner* — Zinna Northington Davis
(74) *Attorney, Agent, or Firm* — Genentech, Inc.; Alex Andrus

(57) ABSTRACT

The invention relates to a compound of formula (I) wherein $R^1$ to $R^4$ are defined as in the description and in the claims. The compound of formula (I) is a CB2 agonist and can be used as an active ingredient in a medicament.

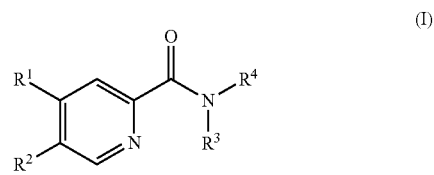

19 Claims, No Drawings

PYRIDINE-2-AMIDES USEFUL AS CB2 AGONISTS

CROSS-REFERENCE TO RELATED APPLICATIONS

This application is a 371 application of International Application No. PCT/EP2013/075442, filed on Dec. 4, 2013, which claims priority to European Patent Application No. 12196029.8, filed on Dec. 7, 2012, the entire contents of which are incorporated herein by reference.

The present invention relates to organic compounds useful for therapy and/or prophylaxis in a mammal, and in particular to compounds that are preferential agonists of the Cannabinoid Receptor 2.

The invention relates in particular to a compound of formula (I)

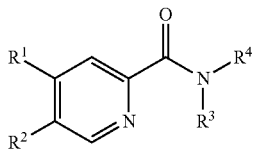

wherein $R^1$ is halogen, halophenyl, cycloalkylalkoxy, halophenylalkyl, oxetanyloxy, haloalkoxy, halophenylalkoxy or alkyloxetanylalkoxy;

$R^2$ is halogen, cycloalkyl, haloazetidinyl, halopyrrolidinyl, hydroxyoxetanyl, cycloalkenyl, halocycloakyl or halooxetanyl;

one of $R^3$ and $R^4$ is hydrogen or alkyl and the other one is —$(CR^5R^6)$—$(CR^7R^8)_n$—$R^9$;

or $R^3$ and $R^4$ together with the nitrogen atom to which they are attached form 2-oxo-5-aza-spiro[3.4]octyl, haloazetidinyl or halopyrrolidinyl;

$R^5$ and $R^6$ are independently selected from hydrogen, alkyl, cycloalkylalkyl, haloalkyl, cycloalkyl, alkylsulfonylalkyl, phenylalkoxyalkyl, hydroxyalkyl, haloazetidinylalkyl, haloazetidinylcarbonyl, 2-oxa-6-azaspiro[3,3]heptanylcarbonyl, alkylaminocarbonyl, dialkylaminocarbonyl, aminocarbonyl, azetidinylcarbonyl, oxetanylalkyl and alkyloxetanyl;

or $R^5$ and $R^6$ together with the carbon atom to which they are attached form cycloalkyl, oxetanyl, oxanyl or dioxothietanyl;

$R^7$ and $R^8$ are independently selected from hydrogen, alkyl and cycloalkyl;

or $R^7$ and $R^8$ together with the carbon atom to which they are attached form cycloalkyl;

$R^9$ is alkyl, alkoxycarbonyl, hydroxyl, hydroxyalkyl, aminocarbonyl, cyano, pyridinyl, alkylaminocarbonyl, thiazol-2-yl, oxazol-2-yl, 5-alkyl-[1,2,4]oxadiazol-3-yl, alkyltetrazolyl, alkylthiazol-2-yl, 1H-tetrazolyl, 5-amino-[1,2,4]-oxadiazol-3-yl, 5-alkyl-[1,3,4]-oxadiazol-2-yl, azetidinylcarbonyl, haloazetidinylcarbonyl, 6-oxa-1-azaspiro[3.3]heptanyl, 5-phenyl-[1,3,4]-oxadiazol-2-yl or haloalkylaminocarbonyl; and n is 0 or 1;

provided that when $R^3$ and $R^4$ are both alkyl at the same time, then $R^1$ and $R^2$ are not both halogen at the same time;

or a pharmaceutically acceptable salt or ester thereof.

The compound of formula (I) is particularly useful in the treatment or prophylaxis of e.g. pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis.

The compound of formula (I) is in particular useful in the treatment or prophylaxis of diabetic retinopathy, retinal vein occlusion or uveitis.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in preclinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemicpreconditioning.

Recent data indicates that endocannabinnoids and their receptors, in particular CB2 might be involved in pre-conditioning and contribute to prevent reperfusion injury by down-regulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl, propyl, isopropyl, isobutyl, tert.-butyl and neopentyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl, cyclobutyl, cyclopentyl and cyclohexyl.

The term "cycloalkenyl", alone or in combination, signifies a cycloalkenyl ring with 3 to 8 carbon atoms and particularly a cycloalkenyl ring with 3 to 6 carbon atoms. A particular example of cycloalkenyl is cyclobutenyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy. Particular "alkoxy" are methoxy and ethoxy, and in particular methoxy.

The term "oxy", alone or in combination, signifies the —O— group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Particular "haloalkyl" are trifluoromethyl and trifluoroethyl, in particular trifluoromethyl.

The term "haloalkoxy", alone or in combination, denotes an alkoxy group substituted with at least one halogen, particularly substituted with one to five halogens, particularly one to three halogens. Particular "haloalkoxy" are trifluoroethyloxy, trifluoropropyloxy, fluoroethyloxy, difluoroethyloxy and fluoropropyloxy. Further particular "haloalkoxy" are trifluoroethoxy and trifluoropropyloxy.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—$NH_2$), the secondary amino group (—NH—), or the tertiary amino group (—N—).

The term "aminocarbonyl, alone or in combination, signifies the —C(O)—$NH_2$ group.

The term "sulfonyl", alone or in combination, means the —$SO_2$ group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3$^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to a compound of formula (I) wherein $R^1$ is halogen, halophenyl, cycloalkylalkoxy, halophenylalkyl, oxetanyloxy, haloalkoxy or halophenylalkoxy;

$R^2$ is halogen, cycloalkyl, haloazetidinyl or halopyrrolidinyl;

one of $R^3$ and $R^4$ is hydrogen or alkyl and the other one is —(CR$^5$R$^6$)—(CR$^7$R$^8$)$_n$—R$^9$;

or $R^3$ and $R^4$ together with the nitrogen atom to which they are attached form 2-oxo-5-aza-spiro[3.4]octyl or haloazetidinyl;

$R^5$ and $R^6$ are independently selected from hydrogen, alkyl, cycloalkylalkyl, haloalkyl, cycloalkyl and alkylsulfonylalkyl;

or $R^5$ and $R^6$ together with the carbon atom to which they are attached form cycloalkyl or oxetanyl;

$R^7$ and $R^8$ are independently selected from hydrogen, alkyl and cycloalkyl;

or $R^7$ and $R^8$ together with the carbon atom to which they are attached form cycloalkyl;

$R^9$ is alkyl, alkoxycarbonyl, hydroxyl, hydroxyalkyl, aminocarbonyl, cyano, pyridinyl, alkylaminocarbonyl, thiazol-2-yl, oxazol-2-yl or 5-alkyl-[1,2,4]oxadiazol-3-yl; and n is 0 or 1;

or a pharmaceutically acceptable salt or ester thereof.

In the definition of $R^3$ and $R^4$, a particular haloazetidinyl is difluoroazetidinyl.

In the definition of $R^5$ and $R^6$ forming a ring together with the carbon atom to which they are attached, particular cycloalkyl are cyclopentyl and cyclohexyl.

In the definition of $R^7$ and $R^8$ forming a ring together with the carbon atom to which they are attached, particular cycloalkyl are cyclopentyl and cyclohexyl.

The invention relates in particular to:

A compound of formula (I) wherein $R^1$ is haloalkoxy;

A compound of formula (I) wherein $R^1$ is trifluoroethoxy, trifluoropropyloxy, difluoroethyloxy, fluoroethyloxy or fluoropropyloxy;

A compound of formula (I) wherein $R^1$ is trifluoroethoxy or trifluoropropyloxy;

A compound of formula (I) wherein $R^1$ is iodo, chlorophenyl, cyclopropylmethyloxy, cyclobutylmethyloxy, fluorophenylmethyl, oxetanyloxy, trifluoroethoxy, fluorophenylmethoxy or trifluoropropyloxy;

A compound of formula (I) wherein $R^2$ is cycloalkyl or haloazetidinyl;

A compound of formula (I) wherein $R^2$ is cyclopropyl, cyclobutyl or difluoroazetidinyl;

A compound of formula (I) wherein $R^2$ is chloro, bromo, cyclopropyl, cyclobutyl, difluoroazetidinyl or difluoropyrrolidinyl;

A compound of formula (I) wherein one of $R^3$ and $R^4$ is hydrogen and the other one is —(CR$^5$R$^6$)—(CR$^7$R$^8$)$_n$—R$^9$;

A compound of formula (I) wherein $R^5$ and $R^6$ are independently selected from alkyl, cycloalkylalkyl, alkylsulfonylalkyl and cycloalkyl, or $R^5$ and $R^6$ together with the carbon atom to which they are attached form dioxothietanyl;

A compound of formula (I) wherein $R^5$ and $R^6$ are independently selected from methyl, cyclopropylmethyl, methylsulfonylmethyl and cyclopropyl, or $R^5$ and $R^6$ together with the carbon atom to which they are attached form dioxothietanyl;

A compound of formula (I) wherein $R^5$ and $R^6$ are independently selected from alkyl, cycloalkylalkyl and alkylsulfonylalkyl;

A compound of formula (I) wherein one of $R^5$ and $R^6$ is alkyl and the other one is cycloalkylalkyl or alkylsulfonylalkyl;

A compound of formula (I) wherein $R^5$ and $R^6$ are independently selected from methyl, cyclopropylmethyl and methylsulfonylmethyl;

A compound of formula (I) wherein one of $R^5$ and $R^6$ is methyl and the other one is cyclopropylmethyl or methylsulfonylmethyl;

A compound of formula (I) wherein $R^5$ and $R^6$ independently selected from hydrogen, methyl, ethyl, propyl, butyl, pentyl, in particular neopentyl, cyclopropyl, cyclopropylmethyl, trifluoromethyl or methylsulfonylmethyl;

A compound of formula (I) wherein $R^7$ and $R^8$ are independently selected from hydrogen, methyl and ethyl, or $R^7$ and $R^8$ together with the carbon atom to which they are attached form cyclopentyl or cyclohexyl;

A compound of formula (I) wherein $R^7$ and $R^8$ are both hydrogen at the same time;

A compound of formula (I) wherein $R^9$ is 5-alkyl-[1,2,4]oxadiazol-3-yl or aminocarbonyl;

A compound of formula (I) wherein R⁹ is 5-methyl-[1,2,4]oxadiazol-3-yl or aminocarbonyl;

A compound of formula (I) wherein R⁹ is 5-alkyl-[1,2,4]oxadiazol-3-yl;

A compound of formula (I) wherein R⁹ is 5-methyl-[1,2,4]oxadiazol-3-yl; and

A compound of formula (I) wherein n is 0.

The invention also relates in particular to a compound of formula (I) selected from 2-[(5-Chloro-4-iodo-pyridine-2-carbonyl)-amino]-2-methyl-propionic acid methyl ester;

5-Chloro-4-(3-chloro-phenyl)-pyridine-2-carboxylic acid (2-hydroxy-1,1-dimethyl-ethyl)-amide;

5-Chloro-4-(3-chloro-phenyl)-pyridine-2-carboxylic acid ((S)-1-carbamoyl-3-methyl-butyl)-amide;

5-Chloro-4-cyclopropylmethoxy-pyridine-2-carboxylic acid ((S)-1-carbamoyl-2-cyclopropyl-ethyl)-amide;

5-Chloro-4-cyclopropylmethoxy-pyridine-2-carboxylic acid (1-hydroxy-cyclohexylmethyl)-amide;

5-Chloro-4-cyclopropylmethoxy-pyridine-2-carboxylic acid (1-hydroxymethyl-cyclopentyl)-amide;

5-Chloro-4-cyclopropylmethoxy-pyridine-2-carboxylic acid ((S)-1-hydroxymethyl-3-methyl-butyl)-amide;

5-Chloro-4-cyclopropylmethoxy-pyridine-2-carboxylic acid (cyano-dimethyl-methyl)-amide;

5-Bromo-4-cyclopropylmethoxy-pyridine-2-carboxylic acid ((R)-1-carbamoyl-3-methyl-butyl)-amide;

5-Chloro-4-cyclopropylmethoxy-pyridine-2-carboxylic acid ((S)-1-hydroxymethyl-1,2-dimethyl-propyl)-amide;

5-Chloro-4-cyclopropylmethoxy-pyridine-2-carboxylic acid ((R)-1-hydroxymethyl-2-methyl-propyl)-amide;

5-Chloro-4-cyclobutylmethoxy-pyridine-2-carboxylic acid ((R)-1-hydroxymethyl-1,2-dimethyl-propyl)-amide;

5-Chloro-4-cyclopropylmethoxy-pyridine-2-carboxylic acid ((R)-1-hydroxymethyl-butyl)-amide;

5-Chloro-4-cyclopropylmethoxy-pyridine-2-carboxylic acid ((R)-1-hydroxymethyl-1,2-dimethyl-propyl)-amide;

5-Chloro-4-(4-fluoro-benzyl)-pyridine-2-carboxylic acid ((R)-1-hydroxymethyl-1,2-dimethyl-propyl)-amide;

5-Chloro-4-cyclopropylmethoxy-pyridine-2-carboxylic acid ((R)-2,2,2-trifluoro-1-pyridin-2-yl-ethyl)-amide;

5-Chloro-4-cyclopropylmethoxy-pyridine-2-carboxylic acid (3-hydroxy-2,2-dimethyl-propyl)-amide;

5-Chloro-4-cyclopropylmethoxy-pyridine-2-carboxylic acid [1-(2-hydroxy-ethyl)-2-methyl-propyl]-amide;

5-Chloro-4-cyclopropylmethoxy-pyridine-2-carboxylic acid (1-cyclopropyl-3-hydroxy-propyl)-amide;

5-Chloro-4-cyclopropylmethoxy-pyridine-2-carboxylic acid (1-hydroxymethyl-cyclopentylmethyl)-amide;

5-Chloro-4-cyclopropylmethoxy-pyridine-2-carboxylic acid (1-ethyl-1-hydroxymethyl-propyl)-amide;

5-Chloro-4-cyclopropylmethoxy-pyridine-2-carboxylic acid ((S)-2,2,2-trifluoro-1-pyridin-3-yl-ethyl)-amide;

5-Chloro-4-(oxetan-3-yloxy)-pyridine-2-carboxylic acid ((S)-2,2-dimethyl-1-methylcarbamoyl-propyl)-amide;

5-Chloro-4-(2,2,2-trifluoro-ethoxy)-pyridine-2-carboxylic acid ((S)-2,2-dimethyl-1-methylcarbamoyl-propyl)-amide;

5-Chloro-4-cyclopropylmethoxy-pyridine-2-carboxylic acid (1-hydroxymethyl-1,3-dimethyl-butyl)-amide;

5-Chloro-4-cyclopropylmethoxy-pyridine-2-carboxylic acid (1-hydroxymethyl-1-methyl-propyl)-amide;

5-Chloro-4-cyclopropylmethoxy-pyridine-2-carboxylic acid ((S)-1-hydroxymethyl-1,3-dimethyl-butyl)-amide;

5-Chloro-4-cyclopropylmethoxy-pyridine-2-carboxylic acid ((R)-1-hydroxymethyl-1,3-dimethyl-butyl)-amide;

5-Chloro-4-cyclopropylmethoxy-pyridine-2-carboxylic acid ((R)-1-hydroxymethyl-2,2-dimethyl-propyl)-amide;

5-Chloro-4-cyclopropylmethoxy-pyridine-2-carboxylic acid ((R)-1-hydroxymethyl-1-methyl-propyl)-amide;

Methyl 3-({[5-chloro-4-(cyclopropylmethoxy)pyridin-2-yl]carbonyl}amino)-2,3-dimethylbutanoate 5-Chloro-4-cyclopropylmethoxy-pyridine-2-carboxylic acid (3-thiazol-2-yl-oxetan-3-yl)-amide;

5-Chloro-4-cyclopropylmethoxy-pyridine-2-carboxylic acid (1-hydroxymethyl-1-methyl-butyl)-amide;

5-Chloro-4-cyclopropylmethoxy-pyridine-2-carboxylic acid ((S)-1,1-dimethyl-2-methylcarbamoyl-propyl)-amide;

5-Chloro-4-cyclopropylmethoxy-pyridine-2-carboxylic acid ((R)-1,1-dimethyl-2-methylcarbamoyl-propyl)-amide;

5-Chloro-4-cyclopropylmethoxy-pyridine-2-carboxylic acid (3-oxazol-2-yl-oxetan-3-yl)-amide;

5-Chloro-4-cyclopropylmethoxy-pyridine-2-carboxylic acid ((S)-1-hydroxymethyl-1-methyl-butyl)-amide;

5-Chloro-4-(2,2,2-trifluoro-ethoxy)-pyridine-2-carboxylic acid (2,2-dimethyl-1-thiazol-2-yl-propyl)-amide;

5-Chloro-4-(oxetan-3-yloxy)-pyridine-2-carboxylic acid (2,2-dimethyl-1-thiazol-2-yl-propyl)-amide;

5-Chloro-4-(4-fluoro-benzyloxy)-pyridine-2-carboxylic acid ((S)-2,2,2-trifluoro-1-pyridin-3-yl-ethyl)-amide;

5-Chloro-4-(4-fluoro-benzyl)-pyridine-2-carboxylic acid ((S)-2,2,2-trifluoro-1-pyridin-3-yl-ethyl)-amide;

5-Cyclopropyl-4-cyclopropylmethoxy-pyridine-2-carboxylic acid (3-thiazol-2-yl-oxetan-3-yl)-amide;

5-Cyclopropyl-4-cyclopropylmethoxy-pyridine-2-carboxylic acid (2,2-dimethyl-1-thiazol-2-yl-propyl)-amide;

5-Cyclopropyl-4-cyclopropylmethoxy-pyridine-2-carboxylic acid [1-cyclopropyl-1-(5-methyl-[1,2,4]oxadiazol-3-yl)-ethyl]-amide;

5-Cyclopropyl-4-cyclopropylmethoxy-pyridine-2-carboxylic acid (1-ethyl-1-methylcarbamoyl-propyl)-amide;

5-Cyclopropyl-4-cyclopropylmethoxy-pyridine-2-carboxylic acid (2,2,2-trifluoro-1-pyridin-2-yl-ethyl)-amide;

5-Cyclopropyl-4-cyclopropylmethoxy-pyridine-2-carboxylic acid ((S)-1-carbamoyl-3-methyl-butyl)-amide;

5-Cyclopropyl-4-(2,2,2-trifluoro-ethoxy)-pyridine-2-carboxylic acid ((S)-2,2-dimethyl-1-methylcarbamoyl-propyl)-amide;

5-Cyclopropyl-4-(2,2,2-trifluoro-ethoxy)-pyridine-2-carboxylic acid [1-cyclopropyl-1-(5-methyl-[1,2,4]oxadiazol-3-yl)-ethyl]-amide;

5-Cyclopropyl-4-(2,2,2-trifluoro-ethoxy)-pyridine-2-carboxylic acid (2,2-dimethyl-1-thiazol-2-yl-propyl)-amide;

5-Cyclopropyl-4-(2,2,2-trifluoro-ethoxy)-pyridine-2-carboxylic acid (2,2,2-trifluoro-1-pyridin-2-yl-ethyl)-amide;

5-Cyclopropyl-4-(2,2,2-trifluoro-ethoxy)-pyridine-2-carboxylic acid ((S)-1-carbamoyl-3-methyl-butyl)-amide;

4-Cyclopropylmethoxy-5-(3,3-difluoro-azetidin-1-yl)-pyridine-2-carboxylic acid (1-hydroxymethyl-cyclopropyl)-amide;

5-Cyclopropyl-4-(2,2,2-trifluoro-ethoxy)-pyridine-2-carboxylic acid (1-ethyl-1-hydroxymethyl-propyl)-amide;

5-Cyclopropyl-4-(2,2,2-trifluoro-ethoxy)-pyridine-2-carboxylic acid (1-hydroxymethyl-cyclohexyl)-amide;

5-Cyclopropyl-4-cyclopropylmethoxy-pyridine-2-carboxylic acid (1-hydroxy-cyclopentylmethyl)-amide;

5-Cyclopropyl-4-cyclopropylmethoxy-pyridine-2-carboxylic acid (1-hydroxy-cyclohexylmethyl)-amide;

5-Cyclopropyl-4-cyclopropylmethoxy-pyridine-2-carboxylic acid (2-hydroxy-butyl)-amide;

5-Cyclopropyl-4-cyclopropylmethoxy-pyridine-2-carboxylic acid (2-hydroxy-2-methyl-propyl)-amide;

5-Cyclopropyl-4-(2,2,2-trifluoro-ethoxy)-pyridine-2-carboxylic acid (2-hydroxy-2-methyl-propyl)-amide;
5-Cyclopropyl-4-(2,2,2-trifluoro-ethoxy)-pyridine-2-carboxylic acid [(S)-1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [1-cyclopropyl-1-(5-methyl-[1,2,4]oxadiazol-3-yl)-ethyl]-amide;
5-Cyclopropyl-4-((R)-2,2,2-trifluoro-1-methyl-ethoxy)-pyridine-2-carboxylic acid (3-carbamoylmethyl-oxetan-3-yl)-amide;
5-Cyclopropyl-4-((S)-2,2,2-trifluoro-1-methyl-ethoxy)-pyridine-2-carboxylic acid (3-carbamoylmethyl-oxetan-3-yl)-amide;
5-Cyclopropyl-4-(2,2,2-trifluoro-ethoxy)-pyridine-2-carboxylic acid ((R)-1-carbamoylmethyl-3-methyl-butyl)-amide;
5-Cyclopropyl-4-(2,2,2-trifluoro-ethoxy)-pyridine-2-carboxylic acid [(R)-2-cyclopropyl-1-methyl-1-(5-methyl-[1,2,4]oxadiazol-3-yl)-ethyl]-amide;
5-Cyclopropyl-4-(2,2,2-trifluoro-ethoxy)-pyridine-2-carboxylic acid [(S)-2-cyclopropyl-1-methyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Cyclopropyl-4-(2,2,2-trifluoro-ethoxy)-pyridine-2-carboxylic acid tert-butylamide;
[5-Cyclopropyl-4-(2,2,2-trifluoro-ethoxy)-pyridin-2-yl]-(2-oxa-5-aza-spiro[3.4]oct-5-yl)-methanone;
5-Cyclopropyl-4-((R)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Cyclopropyl-4-((R)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [(R)-1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [(S)-1-cyclopropyl-1-(5-methyl-[1,2,4]oxadiazol-3-yl)-ethyl]-amide;
[5-Cyclopropyl-4-(2,2,2-trifluoro-ethoxy)-pyridin-2-yl]-(3,3-difluoro-azetidin-1-yl)-methanone;
5-Cyclopropyl-4-(2,2,2-trifluoro-ethoxy)-pyridine-2-carboxylic acid (1-carbamoyl-1-methyl-propyl)-amide;
5-(3,3-Difluoro-azetidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide;
5-(3,3-Difluoro-pyrrolidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;
5-Cyclopropyl-4-(2,2,2-trifluoro-ethoxy)-pyridine-2-carboxylic acid (1-carbamoyl-1,3-dimethyl-butyl)-amide;
5-Chloro-4-(2,2,2-trifluoro-ethoxy)-pyridine-2-carboxylic acid [1,3,3-trimethyl-1-(5-methyl-[1,2,4]oxadiazol-3-yl)-butyl]-amide;
5-Cyclopropyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;
5-Chloro-4-(2,2,2-trifluoro-ethoxy)-pyridine-2-carboxylic acid (3-dimethylcarbamoylmethyl-oxetan-3-yl)-amide;
5-(3,3-Difluoro-azetidin-1-yl)-4-(2,2,2-trifluoro-ethoxy)-pyridine-2-carboxylic acid [(R)-1-cyclopropyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [(S)-1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [(R)-2-cyclopropyl-1-methyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [(S)-2-cyclopropyl-1-methyl-1-(5-methyl-[1,2,4]oxadiazol-3-yl)-ethyl]-amide;
5-Chloro-4-(2,2,2-trifluoro-ethoxy)-pyridine-2-carboxylic acid [(R)-2-cyclopropyl-1-methyl-1-(5-methyl-[1,2,4]oxadiazol-3-yl)-ethyl]-amide;
5-Chloro-4-(2,2,2-trifluoro-ethoxy)-pyridine-2-carboxylic acid [(S)-2-cyclopropyl-1-methyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;
5-(3,3-Difluoro-azetidin-1-yl)-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Cyclopropyl-4-(2,2,2-trifluoro-ethoxy)-pyridine-2-carboxylic acid [1,3,3-trimethyl-1-(5-methyl-[1,2,4]oxadiazol-3-yl)-butyl]-amide;
5-Cyclopropyl-4-(2,2,2-trifluoro-ethoxy)-pyridine-2-carboxylic acid [(S)-2-methanesulfonyl-1-methyl-1-(5-methyl-[1,2,4]oxadiazol-3-yl)-ethyl]-amide;
5-Cyclopropyl-4-(2,2,2-trifluoro-ethoxy)-pyridine-2-carboxylic acid [(R)-2-methanesulfonyl-1-methyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide;
5-(3,3-Difluoro-azetidin-1-yl)-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;
5-Cyclopropyl-4-(2,2,2-trifluoro-ethoxy)-pyridine-2-carboxylic acid [(R)-1,3,3-trimethyl-1-(5-methyl-[1,2,4]oxadiazol-3-yl)-butyl]-amide;
5-Cyclopropyl-4-(2,2,2-trifluoro-ethoxy)-pyridine-2-carboxylic acid [(S)-1,3,3-trimethyl-1-(5-methyl-[1,2,4]oxadiazol-3-yl)-butyl]-amide;
5-Cyclopropyl-4-cyclopropylmethoxy-pyridine-2-carboxylic acid tert-butyl-ethyl-amide;
5-Cyclopropyl-4-(2,2,2-trifluoro-ethoxy)-pyridine-2-carboxylic acid tert-butyl-ethyl-amide;

5-Cyclobutyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide;

5-Cyclobutyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;

5-Cyclobutyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide; and 5-Cyclobutyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide.

The invention further relates in particular to a compound of formula (I) selected from:

5-cyclopropyl-N-[2-(5-methyl-1,2,4-oxadiazol-3-yl)-1-phenylmethoxypropan-2-yl]-4-(2,2,2-trifluoroethoxy)pyridine-2-carboxamide;

5-cyclopropyl-N-[1-hydroxy-2-(5-methyl-1,2,4-oxadiazol-3-yl)propan-2-yl]-4-(2,2,2-trifluoroethoxy)pyridine-2-carboxamide;

(2S)-1-[5-cyclopropyl-4-(cyclopropylmethoxy)pyridine-2-carbonyl]-4,4-difluoropyrrolidine-2-carboxamide;

(2S)-1-[5-cyclopropyl-4-(2,2,2-trifluoroethoxy)pyridine-2-carbonyl]-4,4-difluoropyrrolidine-2-carboxamide;

5-cyclobutyl-N-[(2R)-1-cyclopropyl-2-(5-methyl-1,2,4-oxadiazol-3-yl)propan-2-yl]-4-(2,2,2-trifluoroethoxy)pyridine-2-carboxamide;

5-cyclobutyl-N-[(2S)-1-cyclopropyl-2-(5-methyl-1,2,4-oxadiazol-3-yl)propan-2-yl]-4-(2,2,2-trifluoroethoxy)pyridine-2-carboxamide;

5-cyclobutyl-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

5-cyclobutyl-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

5-cyclobutyl-N-[1-cyclopropyl-2-(5-methyl-1,2,4-oxadiazol-3-yl)propan-2-yl]-4-[(2S)-1,1,1-trifluoropropan-2-yl]oxypyridine-2-carboxamide;

5-cyclobutyl-N-[1-cyclopropyl-2-(5-methyl-1,2,4-oxadiazol-3-yl)propan-2-yl]-4-[(2S)-1,1,1-trifluoropropan-2-yl]oxypyridine-2-carboxamide;

(2R)-1-[5-cyclopropyl-4-(2,2,2-trifluoroethoxy)pyridine-2-carbonyl]-4,4-difluoropyrrolidine-2-carboxamide;

N-[1-cyclopropyl-2-(5-methyl-1,2,4-oxadiazol-3-yl)propan-2-yl]-5-(3-hydroxyoxetan-3-yl)-4-(2,2,2-trifluoroethoxy)pyridine-2-carboxamide;

5-cyclobutyl-N-[(2S)-2-(5-methyl-1,2,4-oxadiazol-3-yl)-1-methylsulfonylpropan-2-yl]-4-(2,2,2-trifluoroethoxy)pyridine-2-carboxamide;

5-cyclobutyl-N-[(2R)-2-(5-methyl-1,2,4-oxadiazol-3-yl)-1-methylsulfonylpropan-2-yl]-4-(2,2,2-trifluoroethoxy)pyridine-2-carboxamide;

5-(1-hydroxycyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

5-(cyclobuten-1-yl)-N-[2-(5-methyl-1,2,4-oxadiazol-3-yl)-1-methylsulfonylpropan-2-yl]-4-(2,2,2-trifluoroethoxy)pyridine-2-carboxamide;

5-cyclopropyl-N-[1-(3,3-difluoroazetidin-1-yl)-2-(5-methyl-1,2,4-oxadiazol-3-yl)propan-2-yl]-4-(2,2,2-trifluoroethoxy)pyridine-2-carboxamide;

5-(1-hydroxycyclobutyl)-N-[2-(5-methyl-1,2,4-oxadiazol-3-yl)-1-methylsulfonylpropan-2-yl]-4-(2,2,2-trifluoroethoxy)pyridine-2-carboxamide;

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

N-[1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide;

5-(3-fluorooxetan-3-yl)-N-[(2S)-2-(5-methyl-1,2,4-oxadiazol-3-yl)-1-methylsulfonylpropan-2-yl]-4-(2,2,2-trifluoroethoxy)pyridine-2-carboxamide;

5-(3-fluorooxetan-3-yl)-N-[(2R)-2-(5-methyl-1,2,4-oxadiazol-3-yl)-1-methylsulfonylpropan-2-yl]-4-(2,2,2-trifluoroethoxy)pyridine-2-carboxamide;

N-(1-amino-2-methyl-3-methylsulfonyl-1-oxopropan-2-yl)-5-cyclopropyl-4-(2,2,2-trifluoroethoxy)pyridine-2-carboxamide;

N-[(2R)-1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide;

N-[(2S)-1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide;

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

N-[1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide;

5-cyclopropyl-N-[(2S)-1-hydroxy-2-(5-methyl-1,2,4-oxadiazol-3-yl)propan-2-yl]-4-(2,2,2-trifluoroethoxy)pyridine-2-carboxamide;

5-cyclopropyl-N-[(2R)-1-hydroxy-2-(5-methyl-1,2,4-oxadiazol-3-yl)propan-2-yl]-4-(2,2,2-trifluoroethoxy)pyridine-2-carboxamide;

N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide;

N-(2-cyano-1-cyclopropylpropan-2-yl)-5-(3-fluorooxetan-3-yl)-4-[(2S)-1,1,1-trifluoropropan-2-yl]oxypyridine-2-carboxamide;

N-[1-cyclopropyl-1-(5-methyl-1,2,4-oxadiazol-3-yl)ethyl]-5-(3-fluorooxetan-3-yl)-4-[(2S)-1,1,1-trifluoropropan-2-yl]oxypyridine-2-carboxamide;

5-cyclopropyl-N-[1-cyclopropyl-2-(5-methyl-1,2,4-oxadiazol-3-yl)propan-2-yl]-4-(2,2-difluoroethoxy)pyridine-2-carboxamide;

5-cyclopropyl-N-[1-cyclopropyl-2-(5-methyl-1,2,4-oxadiazol-3-yl)propan-2-yl]-4-(2-fluoroethoxy)pyridine-2-carboxamide;

5-cyclopropyl-N-[1-(3,3-difluoroazetidin-1-yl)-2-(5-methyl-1,2,4-oxadiazol-3-yl)-1-oxopropan-2-yl]-4-(2,2,2-trifluoroethoxy)pyridine-2-carboxamide;

5-cyclopropyl-N-[2-(5-methyl-1,2,4-oxadiazol-3-yl)-1-(2-oxa-6-azaspiro[3.3]heptan-6-yl)-1-oxopropan-2-yl]-4-(2,2,2-trifluoroethoxy)pyridine-2-carboxamide;

5-cyclopropyl-N-[1-(methylamino)-2-(5-methyl-1,2,4-oxadiazol-3-yl)-1-oxopropan-2-yl]-4-(2,2,2-trifluoroethoxy)pyridine-2-carboxamide;

5-cyclopropyl-N-[1-cyclopropyl-2-(2-methyltetrazol-5-yl)propan-2-yl]-4-(2,2,2-trifluoroethoxy)pyridine-2-carboxamide;

5-cyclopropyl-N-[1-cyclopropyl-2-(1-methyltetrazol-5-yl)propan-2-yl]-4-(2,2,2-trifluoroethoxy)pyridine-2-carboxamide;

5-cyclopropyl-N-[4-(4-methyl-1,3-thiazol-2-yl)oxan-4-yl]-4-(2,2,2-trifluoroethoxy)pyridine-2-carboxamide;
5-cyclopropyl-N-[4-(5-methyl-1,3-thiazol-2-yl)oxan-4-yl]-4-(2,2,2-trifluoroethoxy)pyridine-2-carboxamide;
5-cyclopropyl-N-[(2R)-1-cyclopropyl-2-(5-methyl-1,2,4-oxadiazol-3-yl)propan-2-yl]-4-(2,2-difluoroethoxy)pyridine-2-carboxamide;
5-cyclopropyl-N-[(2S)-1-cyclopropyl-2-(5-methyl-1,2,4-oxadiazol-3-yl)propan-2-yl]-4-(2,2-difluoroethoxy)pyridine-2-carboxamide;
5-cyclopropyl-N-[(2R)-1-cyclopropyl-2-(5-methyl-1,2,4-oxadiazol-3-yl)propan-2-yl]-4-(2-fluoroethoxy)pyridine-2-carboxamide;
5-cyclopropyl-N-[(2S)-1-cyclopropyl-2-(5-methyl-1,2,4-oxadiazol-3-yl)propan-2-yl]-4-(2-fluoroethoxy)pyridine-2-carboxamide;
5-cyclopropyl-N-[1-cyclopropyl-2-(4-methyl-1,3-thiazol-2-yl)propan-2-yl]-4-(2,2,2-trifluoroethoxy)pyridine-2-carboxamide;
5-cyclopropyl-N-[1-cyclopropyl-2-(1H-tetrazol-5-yl)propan-2-yl]-4-(2,2,2-trifluoroethoxy)pyridine-2-carboxamide;
N-[3-(2-amino-2-oxoethyl)-1,1-dioxothietan-3-yl]-5-cyclopropyl-4-(2,2,2-trifluoroethoxy)pyridine-2-carboxamide;
5-cyclopropyl-N-[2,2-dimethyl-1-(5-methyl-1,2,4-oxadiazol-3-yl)propyl]-4-(2,2,2-trifluoroethoxy)pyridine-2-carboxamide;
5-cyclopropyl-N-[2,2-dimethyl-1-(1H-tetrazol-5-yl)propyl]-4-(2,2,2-trifluoroethoxy)pyridine-2-carboxamide;
5-cyclopropyl-N-[2,2-dimethyl-1-(2-methyltetrazol-5-yl)propyl]-4-(2,2,2-trifluoroethoxy)pyridine-2-carboxamide;
5-cyclopropyl-N-[2,2-dimethyl-1-(1-methyltetrazol-5-yl)propyl]-4-(2,2,2-trifluoroethoxy)pyridine-2-carboxamide;
N-[2-(5-amino-1,2,4-oxadiazol-3-yl)-1-cyclopropylpropan-2-yl]-5-cyclopropyl-4-(2,2,2-trifluoroethoxy)pyridine-2-carboxamide;
N-[(1R)-1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide;
N-[(1S)-1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide;
N-[1-cyclopropyl-1-(5-methyl-1,2,4-oxadiazol-3-yl)ethyl]-5-(3-fluorooxetan-3-yl)-4-[(2S)-1,1,1-trifluoropropan-2-yl]oxypyridine-2-carboxamide;
N-[1-cyclopropyl-1-(5-methyl-1,2,4-oxadiazol-3-yl)ethyl]-5-(3-fluorooxetan-3-yl)-4-[(2S)-1,1,1-trifluoropropan-2-yl]oxypyridine-2-carboxamide;
N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide;
N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide;
N-[(2S)-3,3-dimethyl-1-(methylamino)-1-oxobutan-2-yl]-5-(3-fluorooxetan-3-yl)-4-[(2S)-1,1,1-trifluoropropan-2-yl]oxypyridine-2-carboxamide;
5-cyclopropyl-N-[1-cyclopropyl-2-(5-methyl-1,3,4-oxadiazol-2-yl)propan-2-yl]-4-(2,2,2-trifluoroethoxy)pyridine-2-carboxamide;
5-cyclopropyl-N-[2,2-dimethyl-1-(5-methyl-1,3,4-oxadiazol-2-yl)propyl]-4-(2,2,2-trifluoroethoxy)pyridine-2-carboxamide;
N-[2,2-dimethyl-1-(5-methyl-1,3,4-oxadiazol-2-yl)propyl]-5-(3-fluorooxetan-3-yl)-4-[(2S)-1,1,1-trifluoropropan-2-yl]oxypyridine-2-carboxamide;
N-[1-cyclopropyl-2-(5-methyl-1,3,4-oxadiazol-2-yl)propan-2-yl]-5-(3-fluorooxetan-3-yl)-4-[(2S)-1,1,1-trifluoropropan-2-yl]oxypyridine-2-carboxamide;
5-cyclopropyl-N-[1-cyclopropyl-2-(5-methyl-1,3-thiazol-2-yl)propan-2-yl]-4-(2,2,2-trifluoroethoxy)pyridine-2-carboxamide;
5-cyclopropyl-N-[(1R)-2,2-dimethyl-1-(5-methyl-1,3,4-oxadiazol-2-yl)propyl]-4-(2,2,2-trifluoroethoxy)pyridine-2-carboxamide;
5-cyclopropyl-N-[(1S)-2,2-dimethyl-1-(5-methyl-1,3,4-oxadiazol-2-yl)propyl]-4-(2,2,2-trifluoroethoxy)pyridine-2-carboxamide;
N-[1-amino-2-(5-methyl-1,2,4-oxadiazol-3-yl)-1-oxopropan-2-yl]-5-cyclopropyl-4-(2,2,2-trifluoroethoxy)pyridine-2-carboxamide;
5-cyclopropyl-N-[1-(dimethylamino)-2-(5-methyl-1,2,4-oxadiazol-3-yl)-1-oxopropan-2-yl]-4-(2,2,2-trifluoroethoxy)pyridine-2-carboxamide;
N-[1-(azetidin-1-yl)-2-(5-methyl-1,2,4-oxadiazol-3-yl)-1-oxopropan-2-yl]-5-cyclopropyl-4-(2,2,2-trifluoroethoxy)pyridine-2-carboxamide;
5-(3-fluorooxetan-3-yl)-N-[1-(methylamino)-2-(5-methyl-1,2,4-oxadiazol-3-yl)-1-oxopropan-2-yl]-4-[(2S)-1,1,1-trifluoropropan-2-yl]oxypyridine-2-carboxamide;
5-cyclopropyl-N-[(2R)-1-cyclopropyl-2-(5-methyl-1,3,4-oxadiazol-2-yl)propan-2-yl]-4-(2,2,2-trifluoroethoxy)pyridine-2-carboxamide;
5-cyclopropyl-N-[(2S)-1-cyclopropyl-2-(5-methyl-1,3,4-oxadiazol-2-yl)propan-2-yl]-4-(2,2,2-trifluoroethoxy)pyridine-2-carboxamide;
N-(1-amino-3-cyclopropyl-2-methyl-1-oxopropan-2-yl)-5-cyclopropyl-4-(2,2,2-trifluoroethoxy)pyridine-2-carboxamide;
5-cyclopropyl-N-[(2S)-1-(methylamino)-2-(5-methyl-1,2,4-oxadiazol-3-yl)-1-oxopropan-2-yl]-4-(2,2,2-trifluoroethoxy)pyridine-2-carboxamide;
5-cyclopropyl-N-[(2R)-1-(methylamino)-2-(5-methyl-1,2,4-oxadiazol-3-yl)-1-oxopropan-2-yl]-4-(2,2,2-trifluoroethoxy)pyridine-2-carboxamide;
5-cyclopropyl-N-[3-cyclopropyl-2-methyl-1-(methylamino)-1-oxopropan-2-yl]-4-(2,2,2-trifluoroethoxy)pyridine-2-carboxamide;
5-cyclopropyl-N-[2-(5-methyl-1,3,4-oxadiazol-2-yl)-1-(oxetan-3-yl)propan-2-yl]-4-[(2S)-1,1,1-trifluoropropan-2-yl]oxypyridine-2-carboxamide;
5-cyclopropyl-N-[2-(5-methyl-1,3,4-oxadiazol-2-yl)-1-(oxetan-3-yl)propan-2-yl]-4-(2,2,2-trifluoroethoxy)pyridine-2-carboxamide;
N-[1-(5-amino-1,2,4-oxadiazol-3-yl)-2,2-dimethylpropyl]-5-cyclopropyl-4-(2,2,2-trifluoroethoxy)pyridine-2-carboxamide;
N-(3-amino-1-cyclopropyl-3-oxopropyl)-5-cyclopropyl-4-(2,2,2-trifluoroethoxy)pyridine-2-carboxamide;
N-(1-amino-3,3-dimethyl-1-oxobutan-2-yl)-5-cyclopropyl-4-(2,2,2-trifluoroethoxy)pyridine-2-carboxamide;
5-cyclopropyl-N-[1-(dimethylamino)-3,3-dimethyl-1-oxobutan-2-yl]-4-(2,2,2-trifluoroethoxy)pyridine-2-carboxamide;
N-[1-(azetidin-1-yl)-3,3-dimethyl-1-oxobutan-2-yl]-5-cyclopropyl-4-(2,2,2-trifluoroethoxy)pyridine-2-carboxamide;
5-cyclopropyl-N-[1-(3,3-difluoroazetidin-1-yl)-3,3-dimethyl-1-oxobutan-2-yl]-4-(2,2,2-trifluoroethoxy)pyridine-2-carboxamide;

5-cyclopropyl-N-[3,3-dimethyl-1-(6-oxa-1-azaspiro[3.3]
heptan-1-yl)-1-oxobutan-2-yl]-4-(2,2,2-trifluoroethoxy)
pyridine-2-carboxamide;
N-(1-amino-3,3-dimethyl-1-oxobutan-2-yl)-5-cyclopropyl-
4-[(2S)-1,1,1-trifluoropropan-2-yl]oxypyridine-2-car-
boxamide;
5-cyclopropyl-N-[3,3-dimethyl-1-(methylamino)-1-oxobu-
tan-2-yl]-4-[(2S)-1,1,1-trifluoropropan-2-yl]oxypyridine-
2-carboxamide;
5-cyclopropyl-N-[1-(dimethylamino)-3,3-dimethyl-1-ox-
obutan-2-yl]-4-[(2S)-1,1,1-trifluoropropan-2-yl]oxypyri-
dine-2-carboxamide;
N-[1-(azetidin-1-yl)-3,3-dimethyl-1-oxobutan-2-yl]-5-cy-
clopropyl-4-[(2S)-1,1,1-trifluoropropan-2-yl]oxypyri-
dine-2-carboxamide;
5-cyclopropyl-N-[1-(3,3-difluoroazetidin-1-yl)-3,3-dim-
ethyl-1-oxobutan-2-yl]-4-[(2S)-1,1,1-trifluoropropan-2-
yl]oxypyridine-2-carboxamide;
5-cyclopropyl-N-[3,3-dimethyl-1-(6-oxa-1-azaspiro[3.3]
heptan-1-yl)-1-oxobutan-2-yl]-4-[(2S)-1,1,1-trifluoropro-
pan-2-yl]oxypyridine-2-carboxamide;
5-cyclopropyl-N-[(1R)-2,2-dimethyl-1-(1-methyltetrazol-5-
yl)propyl]-4-(2,2,2-trifluoroethoxy)pyridine-2-carboxa-
mide;
5-cyclopropyl-N-[(1S)-2,2-dimethyl-1-(1-methyltetrazol-5-
yl)propyl]-4-(2,2,2-trifluoroethoxy)pyridine-2-carboxa-
mide;
N-[(2R)-2-(5-amino-1,2,4-oxadiazol-3-yl)-1-cyclopropyl-
propan-2-yl]-5-cyclopropyl-4-(2,2,2-trifluoroethoxy)py-
ridine-2-carboxamide;
N-[(2S)-2-(5-amino-1,2,4-oxadiazol-3-yl)-1-cyclopropyl-
propan-2-yl]-5-cyclopropyl-4-(2,2,2-trifluoroethoxy)py-
ridine-2-carboxamide;
5-cyclopropyl-N-[(1R)-2,2-dimethyl-1-(2-methyltetrazol-5-
yl)propyl]-4-(2,2,2-trifluoroethoxy)pyridine-2-carboxa-
mide;
5-cyclopropyl-N-[(1S)-2,2-dimethyl-1-(2-methyltetrazol-5-
yl)propyl]-4-(2,2,2-trifluoroethoxy)pyridine-2-carboxa-
mide;
5-cyclopropyl-N-[(1R)-2,2-dimethyl-1-(5-methyl-1,2,4-
oxadiazol-3-yl)propyl]-4-(2,2,2-trifluoroethoxy)pyridine-
2-carboxamide;
5-cyclopropyl-N-[(1S)-2,2-dimethyl-1-(5-methyl-1,2,4-
oxadiazol-3-yl)propyl]-4-(2,2,2-trifluoroethoxy)pyridine-
2-carboxamide;
N-[1-(5-amino-1,2,4-oxadiazol-3-yl)-2,2-dimethylpropyl]-
5-cyclopropyl-4-[(2S)-1,1,1-trifluoropropan-2-yl]oxypy-
ridine-2-carboxamide;
5-cyclopropyl-N-[2,2-dimethyl-1-(5-methyl-1,2,4-oxadia-
zol-3-yl)propyl]-4-[(2S)-1,1,1-trifluoropropan-2-yl]oxy-
pyridine-2-carboxamide;
5-cyclopropyl-4-[(3-methyloxetan-3-yl)methoxy]-N-[2-(5-
phenyl-1,3,4-oxadiazol-2-yl)propan-2-yl]pyridine-2-car-
boxamide;
5-cyclopropyl-N-[2,2-dimethyl-1-(2-methyltetrazol-5-yl)
propyl]-4-[(2S)-1,1,1-trifluoropropan-2-yl]oxypyridine-
2-carboxamide;
5-cyclopropyl-N-[2,2-dimethyl-1-(1-methyltetrazol-5-yl)
propyl]-4-[(2S)-1,1,1-trifluoropropan-2-yl]oxypyridine-
2-carboxamide;
N-[1-(5-amino-1,2,4-oxadiazol-3-yl)-2,2-dimethylpropyl]-
5-cyclopropyl-4-[(2S)-1,1,1-trifluoropropan-2-yl]oxypy-
ridine-2-carboxamide;
N-[1-(5-amino-1,2,4-oxadiazol-3-yl)-2,2-dimethylpropyl]-
5-cyclopropyl-4-[(2S)-1,1,1-trifluoropropan-2-yl]oxypy-
ridine-2-carboxamide;
5-cyclopropyl-N-[2,2-dimethyl-1-(5-methyl-1,2,4-oxadia-
zol-3-yl)propyl]-4-[(2S)-1,1,1-trifluoropropan-2-yl]oxy-
pyridine-2-carboxamide;
5-cyclopropyl-N-[2,2-dimethyl-1-(5-methyl-1,2,4-oxadia-
zol-3-yl)propyl]-4-[(2S)-1,1,1-trifluoropropan-2-yl]oxy-
pyridine-2-carboxamide;
N-[3-(2-amino-2-oxoethyl)oxetan-3-yl]-4-(cyclopropyl-
methoxy)-5-(3,3-difluoroazetidin-1-yl)pyridine-2-car-
boxamide;
N-[3-(2-amino-2-oxoethyl)oxetan-3-yl]-5-(3,3-difluoroaze-
tidin-1-yl)-4-(2,2,2-trifluoroethoxy)pyridine-2-carboxa-
mide;
5-cyclopropyl-N-[(2S)-3,3-dimethyl-1-(methylamino)-1-
oxobutan-2-yl]-4-(2,2,2-trifluoroethoxy)pyridine-2-car-
boxamide;
5-cyclopropyl-N-[(2R)-3,3-dimethyl-1-(methylamino)-1-
oxobutan-2-yl]-4-(2,2,2-trifluoroethoxy)pyridine-2-car-
boxamide;
N-[(1R)-1-(5-amino-1,2,4-oxadiazol-3-yl)-2,2-dimethyl-
propyl]-5-cyclopropyl-4-(2,2,2-trifluoroethoxy)pyridine-
2-carboxamide;
N-[(1S)-1-(5-amino-1,2,4-oxadiazol-3-yl)-2,2-dimethylpro-
pyl]-5-cyclopropyl-4-(2,2,2-trifluoroethoxy)pyridine-2-
carboxamide;
5-cyclopropyl-N-[(2R)-1-cyclopropyl-2-(1-methyltetrazol-
5-yl)propan-2-yl]-4-(2,2,2-trifluoroethoxy)pyridine-2-
carboxamide;
5-cyclopropyl-N-[2-cyclopropyl-4-(methylamino)-4-oxobu-
tan-2-yl]-4-(2,2,2-trifluoroethoxy)pyridine-2-carboxam-
ide;
N-(4-amino-2-cyclopropyl-4-oxobutan-2-yl)-5-cyclopro-
pyl-4-(2,2,2-trifluoroethoxy)pyridine-2-carboxamide;
5-cyclopropyl-N-[3-[2-(methylamino)-2-oxoethyl]oxetan-
3-yl]-4-(2,2,2-trifluoroethoxy)pyridine-2-carboxamide;
5-cyclopropyl-N-[3-[2-(methylamino)-2-oxoethyl]oxetan-
3-yl]-4-[(2S)-1,1,1-trifluoropropan-2-yl]oxypyridine-2-
carboxamide;
5-(3,3-difluoroazetidin-1-yl)-N-[3-[2-(methylamino)-2-
oxoethyl]oxetan-3-yl]-4-(2,2,2-trifluoroethoxy)pyridine-
2-carboxamide;
5-cyclopropyl-N-[3-(3-fluoropropylcarbamoyl)pentan-3-
yl]-4-[(3-methyloxetan-3-yl)methoxy]pyridine-2-car-
boxamide;
N-[3-[[3-chloro-2-fluoropropyl]carbamoyl]pentan-3-yl]-5-
cyclopropyl-4-[(3-methyloxetan-3-yl)methoxy]pyridine-
2-carboxamide;
5-cyclopropyl-N-[3-hydroxy-3-methyl-1-(methylamino)-1-
oxobutan-2-yl]-4-(2,2,2-trifluoroethoxy)pyridine-2-car-
boxamide;
5-cyclopropyl-N-[3-fluoro-3-methyl-1-(methylamino)-1-
oxobutan-2-yl]-4-(2,2,2-trifluoroethoxy)pyridine-2-car-
boxamide;
5-cyclopropyl-N-[3-hydroxy-3-methyl-1-(methylamino)-1-
oxobutan-2-yl]-4-[(2S)-1,1,1-trifluoropropan-2-yl]oxy-
pyridine-2-carboxamide;
N-(1-amino-3,3-dimethyl-1-oxobutan-2-yl)-5-cyclopropyl-
4-[(2S)-1,1,1-trifluoropropan-2-yl]oxypyridine-2-car-
boxamide;
N-(1-amino-3,3-dimethyl-1-oxobutan-2-yl)-5-cyclopropyl-
4-[(2S)-1,1,1-trifluoropropan-2-yl]oxypyridine-2-car-
boxamide;
5-cyclopropyl-N-[(2S)-2-cyclopropyl-4-(methylamino)-4-
oxobutan-2-yl]-4-(2,2,2-trifluoroethoxy)pyridine-2-car-
boxamide;
5-cyclopropyl-N-[(2R)-2-cyclopropyl-4-(methylamino)-4-
oxobutan-2-yl]-4-(2,2,2-trifluoroethoxy)pyridine-2-car-
boxamide;

N-[(2S)-4-amino-2-cyclopropyl-4-oxobutan-2-yl]-5-cyclopropyl-4-(2,2,2-trifluoroethoxy)pyridine-2-carboxamide;
N-[(2R)-4-amino-2-cyclopropyl-4-oxobutan-2-yl]-5-cyclopropyl-4-(2,2,2-trifluoroethoxy)pyridine-2-carboxamide;
5-cyclopropyl-N-[(5-methyl-1,3,4-oxadiazol-2-yl)-(3-methyloxetan-3-yl)methyl]-4-(2,2,2-trifluoroethoxy)pyridine-2-carboxamide;
5-cyclopropyl-N-[(5-methyl-1,3,4-oxadiazol-2-yl)-(3-methyloxetan-3-yl)methyl]-4-[(2S)-1,1,1-trifluoropropan-2-yl]oxypyridine-2-carboxamide;
5-cyclopropyl-N-[2-cyclopropyl-4-(methylamino)-4-oxobutan-2-yl]-4-[(2S)-1,1,1-trifluoropropan-2-yl]oxypyridine-2-carboxamide;
N-(4-amino-2-cyclopropyl-4-oxobutan-2-yl)-5-cyclopropyl-4-[(2S)-1,1,1-trifluoropropan-2-yl]oxypyridine-2-carboxamide;
5-cyclopropyl-N-[2-cyclopropyl-4-(methylamino)-4-oxobutan-2-yl]-4-[(2S)-1,1,1-trifluoropropan-2-yl]oxypyridine-2-carboxamide;
5-cyclopropyl-N-[2-cyclopropyl-4-(methylamino)-4-oxobutan-2-yl]-4-[(2S)-1,1,1-trifluoropropan-2-yl]oxypyridine-2-carboxamide;
N-[2-amino-1-(3-methyloxetan-3-yl)-2-oxoethyl]-5-cyclopropyl-4-[(2S)-1,1,1-trifluoropropan-2-yl]oxypyridine-2-carboxamide;
5-cyclopropyl-N-[3-hydroxy-3-methyl-1-(methylamino)-1-oxobutan-2-yl]-4-[(2S)-1,1,1-trifluoropropan-2-yl]oxypyridine-2-carboxamide;
5-cyclopropyl-N-[3-hydroxy-3-methyl-1-(methylamino)-1-oxobutan-2-yl]-4-[(2S)-1,1,1-trifluoropropan-2-yl]oxypyridine-2-carboxamide;
5-cyclopropyl-N-[(5-methyl-1,2,4-oxadiazol-3-yl)-(3-methyloxetan-3-yl)methyl]-4-[(2S)-1,1,1-trifluoropropan-2-yl]oxypyridine-2-carboxamide;
5-cyclopropyl-N-[(5-methyl-1,2,4-oxadiazol-3-yl)-(3-methyloxetan-3-yl)methyl]-4-[(2S)-1,1,1-trifluoropropan-2-yl]oxypyridine-2-carboxamide;
N-(1-amino-3,3-dimethyl-1-oxobutan-2-yl)-5-(3,3-difluoroazetidin-1-yl)-4-(2,2,2-trifluoroethoxy)pyridine-2-carboxamide;
N-(1-amino-3,3-dimethyl-1-oxobutan-2-yl)-4-(cyclopropylmethoxy)-5-(3,3-difluoroazetidin-1-yl)pyridine-2-carboxamide;
N-(4-amino-2-cyclopropyl-4-oxobutan-2-yl)-5-cyclopropyl-4-[(2S)-1,1,1-trifluoropropan-2-yl]oxypyridine-2-carboxamide;
N-(4-amino-2-cyclopropyl-4-oxobutan-2-yl)-5-cyclopropyl-4-[(2S)-1,1,1-trifluoropropan-2-yl]oxypyridine-2-carboxamide;
N-[(2R)-1-amino-3,3-dimethyl-1-oxobutan-2-yl]-4-(cyclopropylmethoxy)-5-(3,3-difluoroazetidin-1-yl)pyridine-2-carboxamide;
N-[(2S)-1-amino-3,3-dimethyl-1-oxobutan-2-yl]-4-(cyclopropylmethoxy)-5-(3,3-difluoroazetidin-1-yl)pyridine-2-carboxamide;
N-[(2R)-1-amino-3,3-dimethyl-1-oxobutan-2-yl]-5-(3,3-difluoroazetidin-1-yl)-4-(2,2,2-trifluoroethoxy)pyridine-2-carboxamide;
N-[(2S)-1-amino-3,3-dimethyl-1-oxobutan-2-yl]-5-(3,3-difluoroazetidin-1-yl)-4-(2,2,2-trifluoroethoxy)pyridine-2-carboxamide;
N-[3-(2-amino-2-oxoethyl)-1,1-dioxothietan-3-yl]-5-(3,3-difluoroazetidin-1-yl)-4-(2,2,2-trifluoroethoxy)pyridine-2-carboxamide;
N-[3-(2-amino-2-oxoethyl)-1,1-dioxothietan-3-yl]-5-(3-fluorooxetan-3-yl)-4-[(2S)-1,1,1-trifluoropropan-2-yl]oxypyridine-2-carboxamide;
N-[3-(2-amino-2-oxoethyl)-1,1-dioxothietan-3-yl]-5-cyclopropyl-4-[(2S)-1,1,1-trifluoropropan-2-yl]oxypyridine-2-carboxamide;
N-[3-(2-amino-2-oxoethyl)-1,1-dioxothietan-3-yl]-4-(cyclopropylmethoxy)-5-(3,3-difluoroazetidin-1-yl)pyridine-2-carboxamide;
N-[(1R)-2-amino-1-(3-methyloxetan-3-yl)-2-oxoethyl]-5-cyclopropyl-4-(2,2,2-trifluoroethoxy)pyridine-2-carboxamide;
N-[(1S)-2-amino-1-(3-methyloxetan-3-yl)-2-oxoethyl]-5-cyclopropyl-4-(2,2,2-trifluoroethoxy)pyridine-2-carboxamide;
N-[(2S)-4-amino-2-cyclopropyl-4-oxobutan-2-yl]-5-cyclopropyl-4-(2-fluoroethoxy)pyridine-2-carboxamide;
N-[(2R)-4-amino-2-cyclopropyl-4-oxobutan-2-yl]-5-cyclopropyl-4-(2-fluoroethoxy)pyridine-2-carboxamide;
N-[(2S)-4-amino-2-cyclopropyl-4-oxobutan-2-yl]-5-cyclopropyl-4-(2,2-difluoroethoxy)pyridine-2-carboxamide;
N-[(2R)-4-amino-2-cyclopropyl-4-oxobutan-2-yl]-5-cyclopropyl-4-(2,2-difluoroethoxy)pyridine-2-carboxamide;
N-[3-(2-amino-2-oxoethyl)-1,1-dioxothietan-3-yl]-5-cyclopropyl-4-(2,2-difluoroethoxy)pyridine-2-carboxamide;
N-[(2S)-4-amino-2-cyclopropyl-4-oxobutan-2-yl]-5-(3,3-difluoroazetidin-1-yl)-4-(2,2,2-trifluoroethoxy)pyridine-2-carboxamide;
N-[(2R)-4-amino-2-cyclopropyl-4-oxobutan-2-yl]-5-(3,3-difluoroazetidin-1-yl)-4-(2,2,2-trifluoroethoxy)pyridine-2-carboxamide;
N-(4-amino-2-cyclopropyl-4-oxobutan-2-yl)-5-(3-fluorooxetan-3-yl)-4-[(2S)-1,1,1-trifluoropropan-2-yl]oxypyridine-2-carboxamide;
N-(4-amino-2-cyclopropyl-4-oxobutan-2-yl)-5-(3-fluorooxetan-3-yl)-4-[(2S)-1,1,1-trifluoropropan-2-yl]oxypyridine-2-carboxamide;
5-cyclopropyl-4-(2-fluoroethoxy)-N-[(2R)-2-(5-methyl-1,2,4-oxadiazol-3-yl)-1-methylsulfonylpropan-2-yl]pyridine-2-carboxamide;
5-cyclopropyl-4-(2-fluoroethoxy)-N-[(2S)-2-(5-methyl-1,2,4-oxadiazol-3-yl)-1-methylsulfonylpropan-2-yl]pyridine-2-carboxamide;
N-[3-(2-amino-2-oxoethyl)-1,1-dioxothietan-3-yl]-5-cyclopropyl-4-(2-fluoroethoxy)pyridine-2-carboxamide;
5-cyclopropyl-N-[3-[2-(methylamino)-2-oxoethyl]-1,1-dioxothietan-3-yl]-4-(2,2,2-trifluoroethoxy)pyridine-2-carboxamide;
(S)-5-cyclopropyl-4-(2,2-difluoroethoxy)-N-(2-(5-methyl-1,2,4-oxadiazol-3-yl)-1-(methylsulfonyl)propan-2-yl)picolinamide;
(R)-5-cyclopropyl-4-(2,2-difluoroethoxy)-N-(2-(5-methyl-1,2,4-oxadiazol-3-yl)-1-(methylsulfonyl)propan-2-yl)picolinamide;
5-(1-fluorocyclobutyl)-N-[3-[2-(methylamino)-2-oxoethyl]-1,1-dioxothietan-3-yl]-4-(2,2,2-trifluoroethoxy)pyridine-2-carboxamide;
N-[3-(2-amino-2-oxoethyl)-1,1-dioxothietan-3-yl]-5-(1-fluorocyclobutyl)-4-(2,2,2-trifluoroethoxy)pyridine-2-carboxamide;
5-cyclopropyl-N—((R)-1-cyclopropyl-2-(5-methyl-1,2,4-oxadiazol-3-yl)propan-2-yl)-4-((S)-1-fluoropropan-2-yloxy)picolinamide;
5-cyclopropyl-N—((S)-1-cyclopropyl-2-(5-methyl-1,2,4-oxadiazol-3-yl)propan-2-yl)-4-((S)-1-fluoropropan-2-yloxy)picolinamide;
5-cyclopropyl-N—((R)-1-cyclopropyl-2-(5-methyl-1,2,4-oxadiazol-3-yl)propan-2-yl)-4-((R)-1-fluoropropan-2-yloxy)picolinamide;

5-cyclopropyl-N—((S)-1-cyclopropyl-2-(5-methyl-1,2,4-oxadiazol-3-yl)propan-2-yl)-4-((R)-1-fluoropropan-2-yloxy)picolinamide;

N-[3-(2-amino-2-oxoethyl)-1,1-dioxothietan-3-yl]-5-cyclopropyl-4-[(2S)-1-fluoropropan-2-yl]oxypyridine-2-carboxamide;

N-[3-(2-amino-2-oxoethyl)-1,1-dioxothietan-3-yl]-5-cyclopropyl-4-[(2R)-1-fluoropropan-2-yl]oxypyridine-2-carboxamide;

N-(4-amino-2-cyclopropyl-4-oxobutan-2-yl)-5-cyclopropyl-4-((S)-1-fluoropropan-2-yloxy)picolinamide;

N-(4-amino-2-cyclopropyl-4-oxobutan-2-yl)-5-cyclopropyl-4-((R)-1-fluoropropan-2-yloxy)picolinamide;

5-cyclopropyl-4-((S)-1-fluoropropan-2-yloxy)-N—((S)-2-(5-methyl-1,2,4-oxadiazol-3-yl)-1-(methylsulfonyl)propan-2-yl)picolinamide;

5-cyclopropyl-4-((S)-1-fluoropropan-2-yloxy)-N—((R)-2-(5-methyl-1,2,4-oxadiazol-3-yl)-1-(methylsulfonyl)propan-2-yl)picolinamide;

5-cyclopropyl-4-((R)-1-fluoropropan-2-yloxy)-N—((S)-2-(5-methyl-1,2,4-oxadiazol-3-yl)-1-(methylsulfonyl)propan-2-yl)picolinamide;

5-cyclopropyl-4-((R)-1-fluoropropan-2-yloxy)-N—((R)-2-(5-methyl-1,2,4-oxadiazol-3-yl)-1-(methylsulfonyl)propan-2-yl)picolinamide;

N-[3-(2-amino-2-oxoethyl)-1,1-dioxothietan-3-yl]-5-cyclobutyl-4-(2,2,2-trifluoroethoxy)pyridine-2-carboxamide;

N-(4-amino-2-cyclopropyl-4-oxobutan-2-yl)-5-(1-fluorocyclobutyl)-4-(2,2,2-trifluoroethoxy)picolinamide;

N-[3-(2-amino-2-oxoethyl)-1,1-dioxothietan-3-yl]-5-(1-fluorocyclobutyl)-4-[(2S)-1,1,1-trifluoropropan-2-yl]oxypyridine-2-carboxamide;

N-[3-(2-amino-2-oxoethyl)-1,1-dioxothietan-3-yl]-4-(2,2-difluoroethoxy)-5-(1-fluorocyclobutyl)pyridine-2-carboxamide;

(S)—N-(1-cyclopropyl-1-(5-methyl-1,2,4-oxadiazol-3-yl)ethyl)-5-(1-fluorocyclobutyl)-4-(2,2,2-trifluoroethoxy)picolinamide;

(R)—N-(1-cyclopropyl-1-(5-methyl-1,2,4-oxadiazol-3-yl)ethyl)-5-(1-fluorocyclobutyl)-4-(2,2,2-trifluoroethoxy)picolinamide;

N—((S)-4-amino-2-cyclopropyl-4-oxobutan-2-yl)-5-cyclopropyl-4-((S)-1-fluoropropan-2-yloxy)picolinamide;

N—((R)-4-amino-2-cyclopropyl-4-oxobutan-2-yl)-5-cyclopropyl-4-((S)-1-fluoropropan-2-yloxy)picolinamide;

N—((S)-4-amino-2-cyclopropyl-4-oxobutan-2-yl)-5-cyclopropyl-4-((R)-1-fluoropropan-2-yloxy)picolinamide;

N—((R)-4-amino-2-cyclopropyl-4-oxobutan-2-yl)-5-cyclopropyl-4-((R)-1-fluoropropan-2-yloxy)picolinamide;

N-[(2S)-4-amino-2-cyclopropyl-4-oxobutan-2-yl]-5-(1-fluorocyclobutyl)-4-(2,2,2-trifluoroethoxy)pyridine-2-carboxamide;

N-[(2R)-4-amino-2-cyclopropyl-4-oxobutan-2-yl]-5-(1-fluorocyclobutyl)-4-(2,2,2-trifluoroethoxy)pyridine-2-carboxamide; and 5-chloro-N-(1-cyclopropyl-1-(5-methyl-1,2,4-oxadiazol-3-yl)ethyl)-4-(2-fluoroethoxy)picolinamide.

The invention also relates in particular to a compound of formula (I) selected from 5-Cyclopropyl-4-(2,2,2-trifluoro-ethoxy)-pyridine-2-carboxylic acid [(R)-2-cyclopropyl-1-methyl-1-(5-methyl-[1,2,4]oxadiazol-3-yl)-ethyl]-amide;

5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;

5-(3,3-Difluoro-azetidin-1-yl)-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;

5-Cyclobutyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide;

5-Cyclobutyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;

5-Cyclobutyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide; and 5-Cyclobutyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide.

The invention particularly relates to a compound of formula (I) selected from:

5-cyclopropyl-N-[1-cyclopropyl-2-(5-methyl-1,2,4-oxadiazol-3-yl)propan-2-yl]-4-(2,2-difluoroethoxy)pyridine-2-carboxamide;

5-cyclopropyl-N-[1-cyclopropyl-2-(5-methyl-1,2,4-oxadiazol-3-yl)propan-2-yl]-4-(2-fluoroethoxy)pyridine-2-carboxamide;

5-cyclopropyl-N-[(2S)-1-cyclopropyl-2-(5-methyl-1,2,4-oxadiazol-3-yl)propan-2-yl]-4-(2,2-difluoroethoxy)pyridine-2-carboxamide;

5-cyclopropyl-N-[(2S)-1-cyclopropyl-2-(5-methyl-1,2,4-oxadiazol-3-yl)propan-2-yl]-4-(2-fluoroethoxy)pyridine-2-carboxamide;

N-[3-(2-amino-2-oxoethyl)-1,1-dioxothietan-3-yl]-5-cyclopropyl-4-(2,2,2-trifluoroethoxy)pyridine-2-carboxamide;

5-cyclopropyl-N-[1-cyclopropyl-2-(5-methyl-1,3,4-oxadiazol-2-yl)propan-2-yl]-4-(2,2,2-trifluoroethoxy)pyridine-2-carboxamide;

5-cyclopropyl-N-[(2S)-1-cyclopropyl-2-(5-methyl-1,3,4-oxadiazol-2-yl)propan-2-yl]-4-(2,2,2-trifluoroethoxy)pyridine-2-carboxamide;

N-(4-amino-2-cyclopropyl-4-oxobutan-2-yl)-5-cyclopropyl-4-(2,2,2-trifluoroethoxy)pyridine-2-carboxamide;

N-(4-amino-2-cyclopropyl-4-oxobutan-2-yl)-5-cyclopropyl-4-[(2S)-1,1,1-trifluoropropan-2-yl]oxypyridine-2-carboxamide;

N-(4-amino-2-cyclopropyl-4-oxobutan-2-yl)-5-cyclopropyl-4-[(2S)-1,1,1-trifluoropropan-2-yl]oxypyridine-2-carboxamide;

N-[3-(2-amino-2-oxoethyl)-1,1-dioxothietan-3-yl]-5-cyclopropyl-4-[(2S)-1,1,1-trifluoropropan-2-yl]oxypyridine-2-carboxamide;

N-[(2R)-4-amino-2-cyclopropyl-4-oxobutan-2-yl]-5-cyclopropyl-4-(2-fluoroethoxy)pyridine-2-carboxamide; and N-[(2R)-4-amino-2-cyclopropyl-4-oxobutan-2-yl]-5-cyclopropyl-4-(2,2-difluoroethoxy)pyridine-2-carboxamide.

The compound (−)-5-Cyclopropyl-4-(2,2,2-trifluoroethoxy)-pyridine-2-carboxylic acid [2-cyclopropyl-1-methyl-1-(5-methyl-[1,2,4]oxadiazol-3-yl)-ethyl]-amide is a particular object of the invention.

The compound (+)-5-(3,3-Difluoro-azetidin-1-yl)-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide is another particular object of the invention.

The compound N-(4-amino-2-cyclopropyl-4-oxobutan-2-yl)-5-cyclopropyl-4-[(2S)-1,1,1-trifluoropropan-2-yl]oxypyridine-2-carboxamide is also a particular object of the invention.

The compound N-(4-amino-2-cyclopropyl-4-oxobutan-2-yl)-5-cyclopropyl-4-[(2S)-1,1,1-trifluoropropan-2-yl]oxy-pyridine-2-carboxamide is a further particular object of the invention.

The compound N-[3-(2-amino-2-oxoethyl)-1,1-dioxothi-etan-3-yl]-5-cyclopropyl-4-[(2S)-1,1,1-trifluoropropan-2-yl]oxypyridine-2-carboxamide is another particular object of the invention.

The compound (–)-N-[4-amino-2-cyclopropyl-4-oxobu-tan-2-yl]-5-cyclopropyl-4-(2-fluoroethoxy)pyridine-2-carboxamide is also a particular object of the invention.

The compound N-[(2R)-4-amino-2-cyclopropyl-4-oxobu-tan-2-yl]-5-cyclopropyl-4-(2,2-difluoroethoxy)pyridine-2-carboxamide is a further particular object of the invention.

The compound 5-cyclopropyl-4-((S)-1-fluoropropan-2-yloxy)-N—((S)-2-(5-methyl-1,2,4-oxadiazol-3-yl)-1-(methylsulfonyl)propan-2-yl)picolinamide is another particular object of the invention.

The compounds of formula (I) can be prepared by a process which comprises coupling a compound of formula II

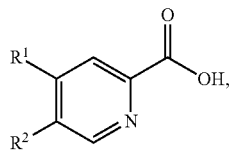

wherein $R^1$ an $R^2$ are as defined herein before, with an amine of the formula III

wherein $R^3$ and $R^4$ are as defined herein before, by amide coupling methods known in the art, as for example with the help of an amide coupling agent under basic conditions, and, if desired, converting the resulting compound of formula (I) into a pharmaceutically acceptable salt thereof.

Compounds of formula III or II may contain functional groups that would interfere with the coupling procedures described for the amide coupling step (II to I). In this case it is understood that III or II need to be suitably protected by methods known in the art before conducting the amide coupling procedure and compounds need to be deprotected after the coupling step by methods known in the art to deliver compounds of formula (I).

Coupling agents for the reaction of compounds of formula II with amines of formula III are for example N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), or O-benzotriazole-N,N,N',N'-tetramethyl-uronium-hexafluoro-phosphate (HBTU). Particular coupling agents are TBTU and HATU. Suitable bases include triethylamine, N-methylmorpholine and particularly diisopropylethylamine. Alternative methods known in the art may commence by preparing the acid chloride from II and coupling with an amine of formula III in the presence of a suitable base.

In the following schemes and description, $R^1$ to $R^4$ have, unless otherwise indicated, the meaning of $R^1$ to $R^4$ as defined above.

The synthesis of the compounds with the general structure (I) can, for example, be accomplished according to the following schemes.

Following the procedure according to scheme 1, compound AA (5-chloro-4-iodo-2-pyridinecarboxylic acid, CAN 120643-06-3) can be used as starting material for a subset of compounds where $R^2$=Cl. AA can be synthesized by a person skilled in the art as described in the literature.

Scheme 1

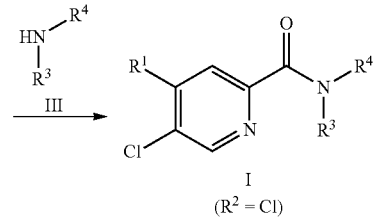

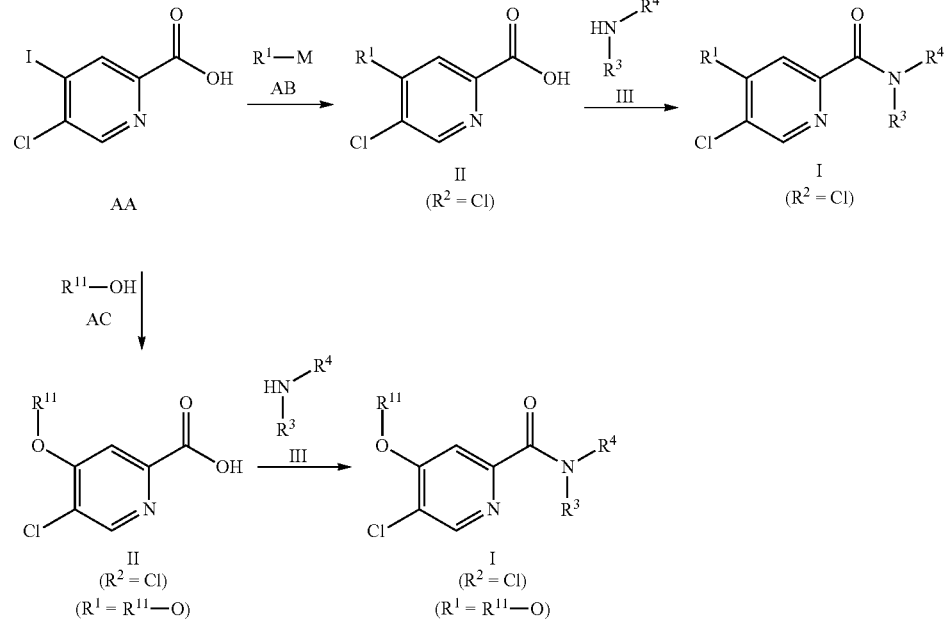

Compound II ($R^2$=Cl) can be prepared from AA by coupling a suitably substituted aryl, heteroaryl or alkenyl metal species of formula AB, particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane. Optionally, alkenyl containing $R^1$ residues can be transformed to the corresponding alkyl congeners II using conditions described in the literature such as e.g. via a hydrogenation reaction using hydrogen gas in the presence of a catalyst such as palladium on carbon in a solvent such as ethanol or ethyl acetate particularly at ambient temperature.

Compounds II ($R^2$=Cl; $R^1$=$R^{11}$—O—; $R^{11}$=cycloalkylalkyl, alkoxyalkyl, cycloalkyl, oxetanyl, halophenylalkyl or haloalkyl) can be prepared from AA by reaction with a suitably substituted primary or secondary alcohol AC in the presence of a base, for example potassium tert-butoxide, in an inert solvent, for example dimethylformamide or tetrahydrofurane, at temperatures ranging from room temperature to the reflux temperature of the solvent, particularly at elevated temperature as for example 80° C.

Compounds of formula I can be prepared from II and the corresponding amine of formula III by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and O-benzotriazole-N,N,N',N'-tetramethyl-uronium-hexafluoro-phosphate (HBTU) can be employed to affect such transformation. A convenient method is to use for example HBTU and a base, for example DIEA in an inert solvent such as for example dimethylformamide at room temperature.

Amines III are either commercially available, described in the literature, can be synthesized by a person skilled in the art or as described in the experimental part.

If one of the starting materials, compounds of formulae AA, AC or III, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If one or more compounds of formulae AA to AC, II or III contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Compounds II ($R^2$=Cl; $R^1$=$R^{11}$—O—; $R^{11}$=cycloalkylalkyl, oxetanylalkyl, haloalkyl) can alternatively be prepared following the procedure according to scheme 2, where compound BA (2,5-dichloro-4-pyridinol, CAN 847664-65-7) can be used as starting material. BA is commercially available or can be synthesized by a person skilled in the art as described in the literature.

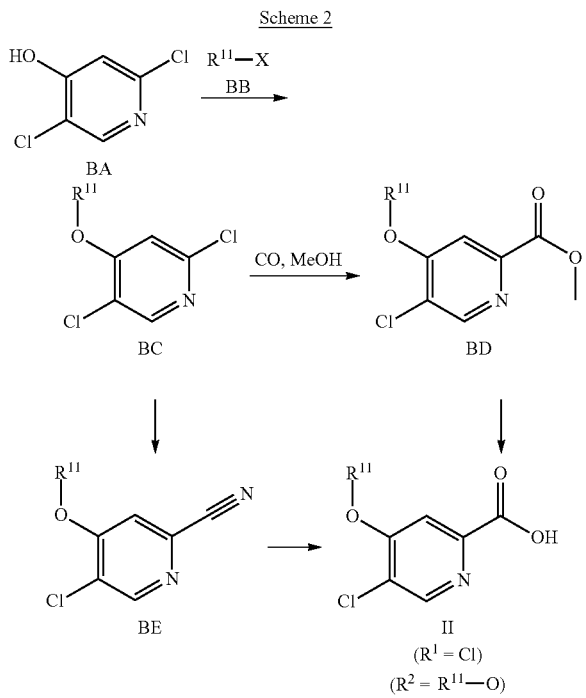

Scheme 2

Compound BC can be prepared from BA by reaction with a suitably substituted alkylhalogenide or suitably substituted alkyltriflate BB (X=triflate or halogen) in the presence of a base, for example potassium tert-butoxide, in an inert solvent, for example tetrahydrofurane, at temperatures ranging from room temperature to the reflux temperature of the solvent, particularly at reflux temperature.

Compounds of the general formula BD can be obtained from compounds of the general formula BC by palladium (II), particularly [1,1-bis(diphenylphosphino)ferrocene]dichloropalladium catalyzed carbonylation in the presence of a suitable base such as a tertiary amine base, particularly triethylamine in a suitable solvent such as an alcohol, particularly methanol.

The saponification of the ester of general formula BD by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to the acid of general formula II which can further elaborated to compounds of the general formula I as already described in Scheme 1.

Compounds of the general formula BE can be obtained from compounds of the general formula BC by palladium (II), particularly [1,1-bis(diphenylphosphino)ferrocene]dichloropalladium catalyzed cyanation in the presence of a suitable cyanide reagent such as a zinc(II) cyanide in a suitable solvent such as dimethylformamide.

The saponification of the nitrile of general formula BE by methods well known to those skilled in the art—using e.g. aqueous LiOH, NaOH or KOH in an alcoholic solvent such as ethanol at a reflux temperature of the solvent employed, or using aqueous HCl at reflux temperature—leads to the acid of general formula II which can further elaborated to compounds of the general formula I as already described in Scheme 1.

If the compounds of formulae BB contain one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If the compounds of formulae BB contain chiral centers, compounds of formula II can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Compounds II where $R^2$=Cl and $R^1$ is an arylmethyl-residue can be prepared following the procedure according to scheme 3, where compound BA (2,5-dichloro-4-pyridinol, CAN 847664-65-7) can be used as starting material. BA is commercially available or can be synthesized by a person skilled in the art as described in the literature.

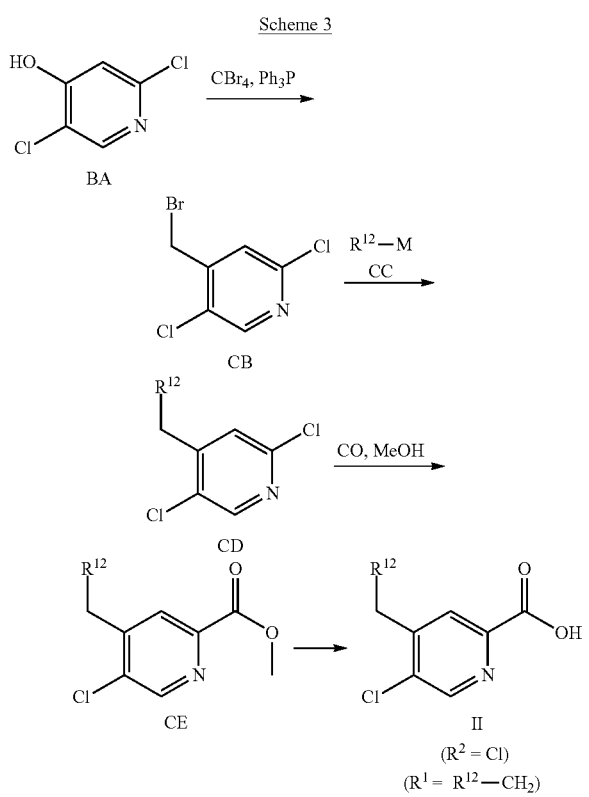

Scheme 3

Compound CB can be prepared from BA with tetrabromomethane and triphenylphosphine in an inert solvent, for example dichloromethane, at temperatures ranging from 0° C. to the reflux temperature of the solvent, particularly at 0° C.

Compounds of general formula CD can be prepared from CB by coupling a suitably substituted aryl or heteroaryl metal species of formula CC($R^{12}$=halophenyl; M=e.g. B(OH)$_2$ or a boronic acid pinacol ester), particularly an arylboronic acid or arylboronic acid ester in the presence of a suitable catalyst, in particular a palladium catalyst and more particularly palladium(II)acetate/triphenylphosphine mixtures or palladium (II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile and dimethoxyethane.

Compounds of the general formula CE can be obtained from compounds of the general formula CD by palladium (II), particularly [1,1-bis(diphenylphosphino)ferrocene] dichloropalladium catalyzed carbonylation in the presence of a suitable base such as a tertiary amine base, particularly triethylamine in a suitable solvent such as an alcohol, particularly methanol.

The saponification of the ester of general formula CE by methods well known to the ones skilled in the art—using e.g. aqueous LiOH, NaOH or KOH in tetrahydrofuran/ethanol or another suitable solvent at temperatures between 0° C. and the reflux temperature of the solvent employed—leads to the acid of general formula II which can further elaborated to compounds of the general formula I as already described in Scheme 1.

If the compounds of formulae CC contain one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, $3^{rd}$ edition) can be introduced before the critical step applying methods well known in the art. Such protecting groups can be removed at a later stage of the synthesis using standard methods known in the art.

If the compounds of formulae CC contain chiral centers, compounds of formula II can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention thus further relates to a process for the preparation of a compound of formula (I) comprising the reaction of a compound of formula (B)

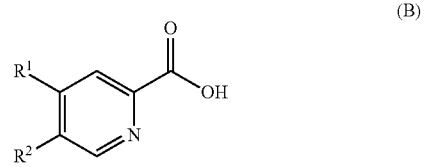

(B)

in the presence of $NHR^3R^4$, an amide coupling agent and a base, wherein $R^1$ to $R^4$ are as defined above.

If desired, the resulting compound of formula (I) can be converted into a pharmaceutically acceptable salt thereof.

Compounds of formula (B) or $NHR^3R^4$ may contain functional groups that would interfere with the coupling procedures described for the amide coupling step. In this case it is understood that they need to be suitably protected by methods known in the art before conducting the amide coupling procedure, and resulting compounds need to be deprotected after the coupling step by methods known in the art to deliver compounds of formula (I).

Coupling agents for the reaction of compounds of formula (B) with amines of formula $NHR^3R^4$ are, for example, as defined above.

The invention also relates in particular to:

The use of a compound of formula (I) for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis;

A compound of formula (I) for the treatment or prophylaxis pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis; and A method for the treatment or prophylaxis of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis, which method comprises administering an effective amount of a compound of formula (I) to a patient in need thereof.

The invention particularly relates to a compound of formula (I) for the treatment or prophylaxis of ischemia, reperfusion injury, liver fibrosis or kidney fibrosis, in particular ischemia or reperfusion injury.

The invention further particularly relates to a compound of formula (I) for the treatment or prophylaxis of diabetic retinopathy, retinal vein occlusion or uveitis.

The invention is further directed to a compound of formula (I), when manufactured according to a process according to the invention.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

MS=mass spectrometry; EI=electron ionization; ESI=electrospray; NMR data are reported in parts per million (δ) relative to internal tetramethylsilane and are referenced to the deuterium lock signal from the sample solvent (DMSO-$d_6$ unless otherwise stated); coupling constants (J) are in Hertz, mp=melting point; bp=boiling point; DCM=dichloromethane; DIEA=N-ethyl-N-isopropylpropan-2-amine; DBU=1,8-Diazabicyclo[5.4.0]undec-7-ene; DMF=dimethylformamide; DMSO=dimethyl-sulfoxide; dppf=1,1'-bis(diphenylphosphino)ferrocene; HATU=2-(3H-[1,2,3]triazolo[4,5-b]pyridin-3-yl)-1,1,3,3-tetramethylisouronium hexafluorophosphate(V); HBTU=O-benzotriazole-N,N,N',N'-tetramethyl-uronium-hexafluoro-phosphate; HPLC=LC=high performance liquid chromatography; m-CPBA=meta-chloroperoxybenzoic acid; Rt=retention time; TBTU=O-(benzotriazol-1-yl)-N,N,N',N'-tetramethyl-uronium-tetrafluoroborate; TEMPO=2,2,6,6-tetra-methylpiperidine 1-oxyl radical; TBME32 methyl tert-butylether, THF=tetrahydrofuran; TFA=trifluoroacetic acid; tlc=thin layer chromatography; CAN=CAS Registry Number.

Example 1

2-[(5-Chloro-4-iodo-pyridine-2-carbonyl)-amino]-2-methyl-propionic acid methyl ester

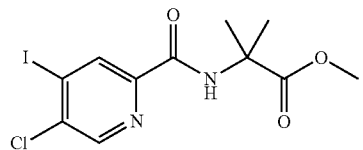 [SMILES: COC(=O)C(C)(C)NC(=O)c1cc(I)c(Cl)cn1]

To a solution of 5-chloro-4-iodo-2-pyridinecarboxylic acid (CAN 120643-06-3, 100 mg, 353 μmol) in DMF (2 mL) was added TBTU (170 mg, 529 μmol) and 2-methyl-alanine methyl ester hydrochloride (59.6 mg, 388 μmol) to give a light yellow suspension. DIEA (308 μL, 1.77 mmol) was added and the reaction mixture was stirred for 3 h. The crude reaction mixture was concentrated in vacuo and the residue was purified by flash chromatography (silica, heptane/ethyl acetate gradient) to deliver the desired compound (40.5 mg, 30%) as yellow oil. MS (ESI, m/z): 382.9 (MH$^+$).

Example 2

5-Chloro-4-(3-chlorophenyl)-pyridine-2-carboxylic acid (2-hydroxy-1,1-dimethyl-ethyl)-amide

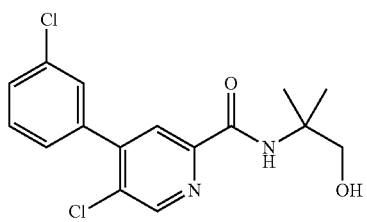 [SMILES: CC(C)(CO)NC(=O)c1cc(-c2cccc(Cl)c2)c(Cl)cn1]

a) 5-Chloro-4-(3-chlorophenyl)-pyridine-2-carboxylic acid

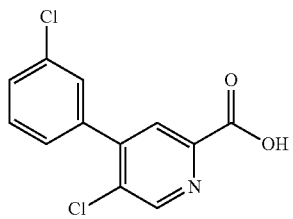 [SMILES: O=C(O)c1cc(-c2cccc(Cl)c2)c(Cl)cn1]

To a solution of 5-chloro-4-iodo-pyridine-2-carboxylic acid (CAN 120643-06-3, 500 mg, 1.76 mmol) in toluene (10 mL) was added with stirring the [1,1-bis(diphenylphosphino)ferrocene]dichloropalladium DCM complex (144 mg, 0.176 mmol), B-(3-chlorophenyl)-boronic acid (552 mg, 3.53 mmol) and sodium carbonate (467 mg, 4.41 mmol) in water (3 mL). The resulting mixture was stirred at 80° C. for 23 h, cooled, poured onto ice/water, acidified with hydrochloric acid (15 mL, 1 N) and partitioned between water and ethyl acetate. The organic portion was washed with brine, combined, dried over Na$_2$SO$_4$, filtered and concentrated. The crude product precipitated as brown solid from the concentrated solution and was used without further purification in the next step. MS (ESI, m/z): 268.1 (M).

b) 5-Chloro-4-(3-chlorophenyl)-pyridine-2-carboxylic acid (2-hydroxy-1,1-dimethyl-ethyl)-amide The title compound was synthesized in analogy to Example 1, using 5-chloro-4-(3-chlorophenyl)-pyridine-2-carboxylic acid and 2-amino-2-methyl-1-propanol (CAN 124-68-5) as starting materials and isolated (13 mg, 38%) as colorless oil; MS (ESI, m/z): 339.0, 341.0 (MH⁺).

Example 3

5-Chloro-4-(3-chloro-phenyl)-pyridine-2-carboxylic acid ((S)-1-carbamoyl-3-methyl-butyl)-amide

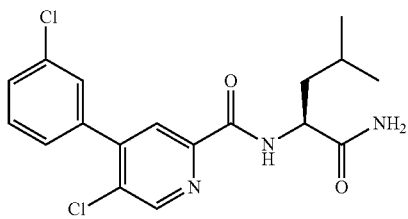 [SMILES: CC(C)C[C@H](NC(=O)c1cc(-c2cccc(Cl)c2)c(Cl)cn1)C(N)=O]

The title compound was synthesized in analogy to Example 1, using 5-chloro-4-(3-chlorophenyl)-pyridine-2-carboxylic acid and (2S)-2-amino-4-methyl-pentanamide (CAN 687-51-4) as starting materials and isolated (8 mg, 21%) as colorless oil; MS (ESI, m/z): 380.1, 382.1 (MH⁺).

Example 4

5-Chloro-4-cyclopropylmethoxy-pyridine-2-carboxylic acid ((S)-1-carbamoyl-2-cyclopropyl-ethyl)-amide

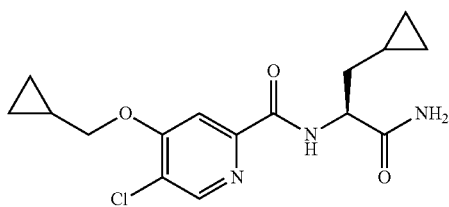 [SMILES: NC(=O)[C@H](CC1CC1)NC(=O)c1cc(OCC2CC2)c(Cl)cn1]

a) 5-Chloro-4-cyclopropylmethoxy-pyridine-2-carboxylic acid

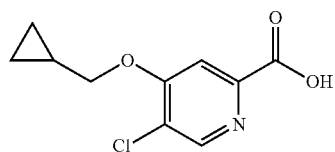 [SMILES: O=C(O)c1cc(OCC2CC2)c(Cl)cn1]

To a solution of 5-chloro-4-iodo-pyridine-2-carboxylic acid (CAN 120643-06-3, 600 mg, 2.12 mmol) in THF (20 mL) and DMF (2 mL) was added with stirring potassium tert-butoxide (1.0 g, 8.91 mmol) and cyclopropanemethanol (1.5 mL, 18.8 mmol). The resulting mixture was stirred at 80° C. for 25 h, cooled, acidified with hydrochloric acid (25 mL, 1 N) and partitioned into ethyl acetate. The organic portions were combined, dried over Na₂SO₄, filtered and concentrated. The residue was purified by prep. HPLC (Gemini NX, acetonitrile/water gradient) to give the title compound (276 mg, 57%) as light yellow solid. MS (ESI, m/z): 228.4 (MH⁺).

b) 5-Chloro-4-cyclopropylmethoxy-pyridine-2-carboxylic acid ((S)-1-carbamoyl-2-cyclopropyl-ethyl)-amide The title compound was synthesized in analogy to Example 1, using 5-chloro-4-cyclopropylmethoxy-pyridine-2-carboxylic acid and (S)-α-amino-cyclopropanepropanamide (CAN 156077-93-9) as starting materials and isolated (18 mg, 53%) as white solid; MS (ESI, m/z): 338.3 (MH⁺).

Example 5

5-Chloro-4-cyclopropylmethoxy-pyridine-2-carboxylic acid (1-hydroxy-cyclohexylmethyl)-amide

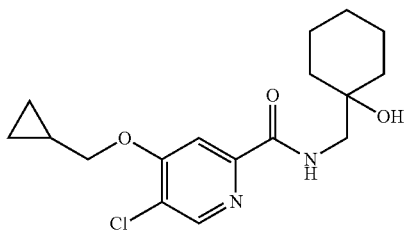 [SMILES: O=C(NCC1(O)CCCCC1)c1cc(OCC2CC2)c(Cl)cn1]

The title compound was synthesized in analogy to Example 1, using 5-chloro-4-cyclopropylmethoxy-pyridine-2-carboxylic acid and 1-(aminomethyl)-cyclohexanol (CAN 4000-72-0) as starting materials and isolated (19.2 mg, 57%) as white solid; MS (ESI, m/z): 339.1 (MH⁺).

Example 6

5-Chloro-4-cyclopropylmethoxy-pyridine-2-carboxylic acid (1-hydroxymethyl-cyclopentyl)-amide

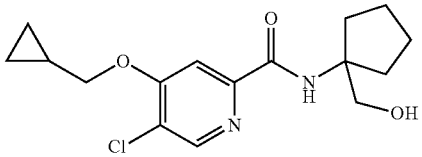 [SMILES: O=C(NC1(CO)CCCC1)c1cc(OCC2CC2)c(Cl)cn1]

The title compound was synthesized in analogy to Example 1, using 5-chloro-4-cyclopropylmethoxy-pyridine-2-carboxylic acid and 1-amino-cyclopentanemethanol (CAN 10316-79-7) as starting materials and isolated (40 mg, quant.) as white solid; MS (ESI, m/z): 325.1 (MH⁺).

Example 7

5-Chloro-4-cyclopropylmethoxy-pyridine-2-carboxylic acid ((S)-1-hydroxymethyl-3-methyl-butyl)-amide

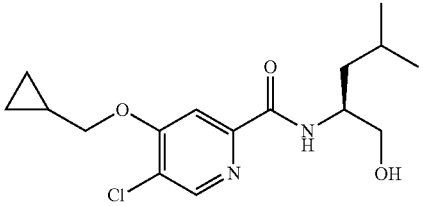

The title compound was synthesized in analogy to Example 1, using 5-chloro-4-cyclopropylmethoxy-pyridine-2-carboxylic acid and (2S)-2-amino-4-methyl-1-pentanol (CAN 7533-40-6) as starting materials and isolated (19.4 mg, 59%) as white solid; MS (ESI, m/z): 327.1 (MH⁺).

Example 8

5-Chloro-4-cyclopropylmethoxy-pyridine-2-carboxylic acid (cyano-dimethyl-methyl)-amide

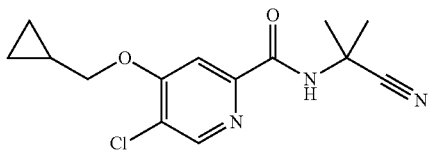 [SMILES: CC(C)(C#N)NC(=O)c1cc(OCC2CC2)c(Cl)cn1]

The title compound was synthesized in analogy to Example 1, using 5-chloro-4-cyclopropylmethoxy-pyridine-2-carboxylic acid and 2-amino-2-methyl-propanenitrile (CAN 19355-69-2 as starting materials and isolated (50 mg, 78%) as colorless oil; LC-MS (UV peak area, m/z) 93.8%, 294.1001 (MH⁺).

Example 9

5-Bromo-4-cyclopropylmethoxy-pyridine-2-carboxylic acid ((S)-1-carbamoyl-3-methyl-butyl)-amide

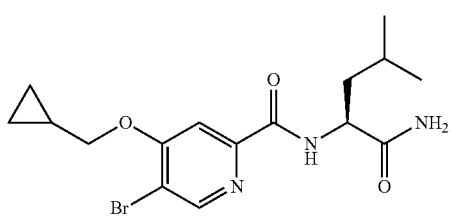 [SMILES: CC(C)C[C@H](NC(=O)c1cc(OCC2CC2)c(Br)cn1)C(N)=O]

a)
5-Bromo-4-(cyclopropylmethoxy)-2-methylpyridine 1-oxide

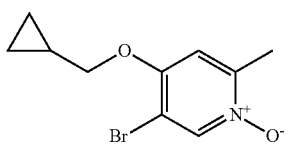

Powdered NaOH (3 g, 75 mmol) was added to a suspension of 5-bromo-2-methyl-4-nitropyridine 1-oxide (11.7 g, 50 mmol; CAN 62516-08-9) in cyclopropylmethanol (89 g, 100 mL, 1.23 mol). The mixture was stirred for 4 h at 80° C. After evaporation to dryness ethyl acetate (400 mL) and water (400 mL) were added. The layers were separated and the aqueous phase was extracted four more times with ethyl acetate (250 mL). The combined extracts were washed with brine, dried over Na₂SO₄ and filtered. The filtrate was concentrated to a volume of 100 mL and heptane (100 mL) was added dropwise under stirring. The precipitate was collected washed with ethyl acetate/heptane 1/2 (3×20 mL) and dried in vacuo to give the title compound (10.4 g, 80%) as light brown solid; LC-MS (UV peak area, m/z) 100%, 258.0125 (MH⁺).

b) (5-Bromo-4-(cyclopropylmethoxy)pyridin-2-yl)methanol

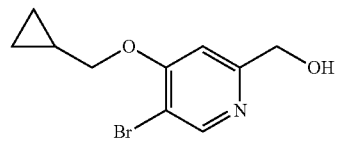 [SMILES: OCc1cc(OCC2CC2)c(Br)cn1]

Trifluoroacetic anhydride (24.4 g, 16.2 mL, 116 mmol) was added dropwise over a period of 10 min. to an ice cold solution of 5-bromo-4-(cyclopropylmethoxy)-2-methylpyridine 1-oxide (10.0 g, 38.7 mmol) in dichloromethane (100 mL). The ice bath was removed and the mixture was stirred at ambient temperature for 65 h. Under cooling 5.4N aqueous NaOH solution (50 mL) was added and the mixture was extracted with dichloromethane/methanol 9/1 (3×200 mL). The combined extracts were dried over Na₂SO₄, filtered and the filtrated was brought to dryness under reduced pressure. The residue was crystallized from ethyl acetate/heptane to yield the title compound (9 g, 90%) as brown solid; LC-MS (UV peak area, m/z) 99.5%, 258.0130 (MH⁺).

c) 5-Bromo-4-(cyclopropylmethoxy)picolinic acid

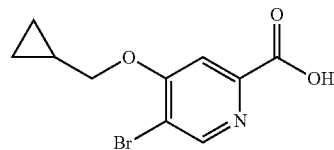 [SMILES: O=C(O)c1cc(OCC2CC2)c(Br)cn1]

Aqueous phosphate buffer (6.7 mL, pH=6.7) and 2,2,6,6-tetramethylpiperidine 1-oxyl (17 mg, 81 μmol) were added to a solution of (5-bromo-4-(cyclopropylmethoxy)pyridin-2-yl)methanol (300 mg, 1.16 mmol) in acetonitrile (6 mL). The mixture was warmed to 35° C. Water (4.6 mL) and a solution of sodium hypochlorite (17 mg, 14 μL, 23 μmol) in water (2.3 mL) were added within 2 h. After 20 h the mixture was cooled to ambient temperature, water (40 mL) and 2N aqueous NaOH solution (8 mL) were added. The mixture was poured onto an ice cold aqueous Na₂SO₃ solution (1.6 g Na₂SO₃ in 30 mL of water), acidified with 2N aqueous HCl solution and extracted with ethyl acetate (3×100 mL). The combined extracts were washed with brine, dried over Na₂SO₄ and filtered. The filtrate was evaporated to dryness under reduced pressure to give the title compound (86 mg, 27%) as off-white solid which was used in the next step without further purification; MS (ESI, m/z): 271.9 (MH⁻).

d) 5-Bromo-4-cyclopropylmethoxy-pyridine-2-carboxylic acid ((S)-1-carbamoyl-3-methyl-butyl)-amide The title compound was synthesized in analogy to Example 1, using 5-bromo-4-(cyclopropylmethoxy)picolinic acid and (2S)-2-amino-4-methyl-pentanamide (CAN 687-51-4) as starting materials and isolated (16 mg, 47%) as yellow oil; MS (ESI, m/z): 385.9 (MH⁺).

Example 10

5-Chloro-4-cyclopropylmethoxy-pyridine-2-carboxylic acid ((S)-1-hydroxymethyl-1,2-dimethyl-propyl)-amide

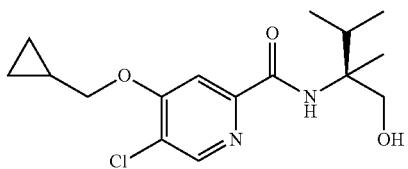 [SMILES: CC(C)[C@@](C)(CO)NC(=O)c1cc(OCC2CC2)c(Cl)cn1]

The title compound was synthesized in analogy to Example 1, using 5-chloro-4-cyclopropylmethoxy-pyridine-2-carboxylic acid and (2S)-2-amino-2,3-dimethyl-1-butanol (CAN 7533-40-6) as starting materials and isolated (21 mg, 73%) as colorless oil; MS (ESI, m/z): 327.2 (MH⁺).

Example 11

5-Chloro-4-cyclopropylmethoxy-pyridine-2-carboxylic acid ((R)-1-hydroxymethyl-2-methyl-propyl)-amide

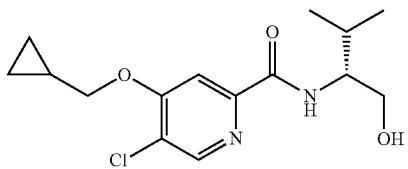 [SMILES: CC(C)[C@H](CO)NC(=O)c1cc(OCC2CC2)c(Cl)cn1]

The title compound was synthesized in analogy to Example 1, using 5-chloro-4-cyclopropylmethoxy-pyridine-2-carboxylic acid and (2R)-2-amino-3-methyl-1-butanol (CAN 4276-09-9) as starting materials and isolated (51 mg, 54%) as colorless oil; MS (ESI, m/z): 313.1 (MH⁺).

Example 12

5-Chloro-4-cyclobutylmethoxy-pyridine-2-carboxylic acid ((R)-1-hydroxymethyl-1,2-dimethyl-propyl)-amide

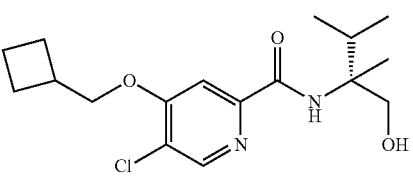 [SMILES: CC(C)[C@](C)(CO)NC(=O)c1cc(OCC2CCC2)c(Cl)cn1]

a) 2,5-Dichloro-4-cyclobutylmethoxy-pyridine

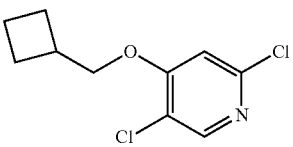 [SMILES: Clc1cc(OCC2CCC2)c(Cl)cn1]

To a solution of 2,5-dichloro-4-pyridinol (CAN 847664-65-7, 660 mg, 4.02 mmol) in THF (20 mL) and DMF (20 mL) was added with stirring sodium tert-butoxide (1.16 g, 12.1 mmol) and (bromomethyl)-cyclobutane (CAN 17247-58-4, 2.26 mL, 20.1 mmol). The resulting mixture was stirred at 80° C. for 20 h, cooled and concentrated. The residue was partitioned between water and ethyl acetate; the organic portions were combined, dried over Na₂SO₄, filtered and concentrated. The crude material was purified by flash chromatography (silica, heptane/ethyl acetate gradient) to give the title compound (466 mg, 50%) as white solid. LC-MS (UV peak area, m/z) 97.8%, 232.0293 (MH⁺).

b) 5-Chloro-4-cyclobutylmethoxy-pyridine-2-carboxylic acid methyl ester

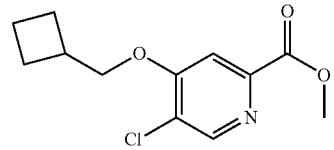 [SMILES: COC(=O)c1cc(OCC2CCC2)c(Cl)cn1]

To a solution of 2,5-dichloro-4-cyclobutylmethoxy-pyridine (480 mg, 2.07 mmol) in methanol (6 mL) and DMF (20 mL) was added with stirring the [1,1-bis(diphenylphosphino)ferrocene]dichloropalladium DCM complex (101 mg, 0.124 mmol) and triethylamine (0.435 mL, 3.1 mmol). The resulting solution was stirred in a CO atmosphere (70 bar) at 100° C. for 20 hours. The mixture was concentrated and purified by flash chromatography, eluting with a heptane/ethyl acetate gradient on silica to produce the title compound (446 mg, 84%) as off-white solid. MS (ESI, m/z): 256.1 (MH⁺).

c) 5-Chloro-4-cyclobutylmethoxy-pyridine-2-carboxylic acid

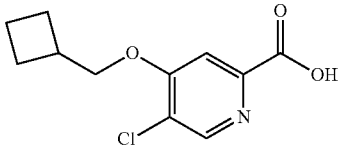 [SMILES: O=C(O)c1cc(OCC2CCC2)c(Cl)cn1]

To a solution of 5-chloro-4-cyclobutylmethoxy-pyridine-2-carboxylic acid methyl ester (339 mg, 1.33 mmol) in THF (10 mL) was added sodium hydroxide solution (2.65 mL, 1 N). The resulting solution was stirred at room temperature for 2 hours, and afterwards acidified with hydrochloric acid (10 mL, 1N) and poured into ethyl acetate (50 mL). The phases were separated and the water phase was extracted with additional ethyl acetate; the organic portions were combined, dried over Na$_2$SO$_4$, filtered and concentrated. The crude material (286 mg, 89%) a white solid, was sufficiently pure to be used in the next step without further purification. MS (ESI, m/z): 240.1 (M−H$^-$).

d) 5-Chloro-4-cyclobutylmethoxy-pyridine-2-carboxylic acid ((R)-1-hydroxymethyl-1,2-dimethyl-propyl)-amide To a solution of 5-chloro-4-cyclobutylmethoxy-pyridine-2-carboxylic acid (60 mg, 249 µmol) in acetonitrile (2 mL) was added HATU (123 mg, 324 µmol), (2R)-2-amino-2,3-dimethyl-1-butanol (CAN 155158-75-1, 32.1 mg, 274 µmol) and DIEA (217 µL, 1.25 mmol). The brownish reaction mixture was stirred for 18 h at room temperature. The crude reaction mixture was concentrated in vacuo and the residue was purified by flash chromatography (silica, heptane/ethyl acetate gradient) and finally chiral chromatography (ChiralPak AD, heptane/ethanol 9:1) to deliver the desired compound (27.3 mg, 43%) as colorless oil. MS (ESI, m/z): 341.1 (MH$^+$).

Example 13

5-Chloro-4-cyclopropylmethoxy-pyridine-2-carboxylic acid ((R)-1-hydroxymethyl-butyl)-amide

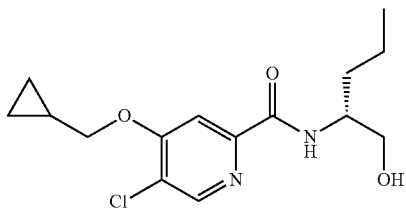 [SMILES: CCC[C@H](CO)NC(=O)c1cc(OCC2CC2)c(Cl)cn1]

The title compound was synthesized in analogy to Example 12d, using 5-chloro-4-cyclopropylmethoxy-pyridine-2-carboxylic acid and (2R)-2-amino-1-pentanol (CAN 80696-30-6) as starting materials and isolated (72 mg, 77%) as colorless oil; LC-MS (UV peak area, m/z) 100%, 313.1311 (MH$^+$).

Example 14

5-Chloro-4-cyclopropylmethoxy-pyridine-2-carboxylic acid ((R)-1-hydroxymethyl-1,2-dimethyl-propyl)-amide

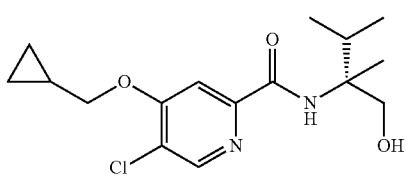 [SMILES: CC(C)[C@](C)(CO)NC(=O)c1cc(OCC2CC2)c(Cl)cn1]

The title compound was synthesized in analogy to Example 1, using 5-chloro-4-cyclopropylmethoxy-pyridine-2-carboxylic acid and (2R)-2-amino-2,3-dimethyl-1-butanol (CAN 155158-75-1) as starting materials and isolated (19 mg, 19%) as colorless oil; LC-MS (UV peak area, m/z) 98.6%, 327.1464 (MH$^+$).

Example 15

5-Chloro-4-(4-fluoro-benzyl)-pyridine-2-carboxylic acid ((R)-1-hydroxymethyl-1,2-dimethyl-propyl)-amide

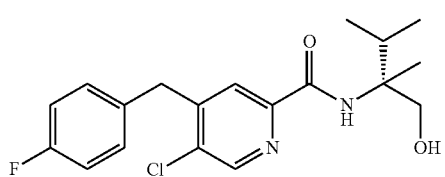 [SMILES: CC(C)[C@](C)(CO)NC(=O)c1cc(Cc2ccc(F)cc2)c(Cl)cn1]

a) 4-Bromomethyl-2,5-dichloro-pyridine

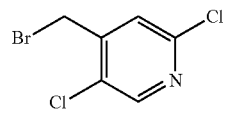

To a suspension of 2,5-dichloro-4-pyridinemethanol (CAN 866039-42-1, 1.10 g, 6.18 mmol) in DCM (25 mL) was added at 0° C. with stirring tetrabromomethane (2.05 g, 6.18 mmol) and a solution of triphenylphosphine (1.62 g, 6.18 mmol) in DCM (5 mL). The resulting mixture was stirred at 0° C. for 1 h and concentrated. The residue was purified by flash chromatography (silica, heptane/ethyl acetate gradient) to give the title compound (619 mg, 42%) as yellow oil. LC-MS (UV peak area, m/z) 98%, 241.0 (MH$^+$).

b) 2,5-Dichloro-4-(4-fluorobenzyl)-pyridine

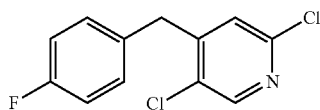 [SMILES: Fc1ccc(Cc2cc(Cl)ncc2Cl)cc1]

To a solution of 4-bromomethyl-2,5-dichloro-pyridine (500 mg, 2.08 mmol) in toluene (10 mL) was added with stirring the [1,1-bis(diphenylphos-phino)ferrocene]dichloropalladium DCM complex (74 mg, 0.101 mmol), B-(3-fluorophenyl)-boronic acid (290 mg, 2.08 mmol) and sodium carbonate (440 mg, 4.15 mmol) in water (2 mL). The resulting mixture was stirred at 80° C. for 3 h, cooled, poured onto water (20 mL), and partitioned between water and ethyl acetate. The organic portions were combined, dried over Na$_2$SO$_4$, filtered and concentrated. The residue was purified by flash chromatography (silica, heptane/ethyl acetate gradient) to give the title compound (241 mg, 32%) as white solid. LC-MS (UV peak area, m/z) 70%, 255.0, 257.0 (M+).

c)
5-Chloro-4-(4-fluorobenzyl)-pyridine-2-carboxylic acid methyl ester

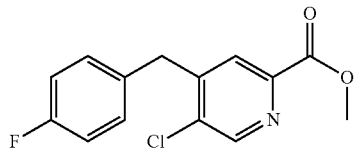 [SMILES: COC(=O)c1cc(Cc2ccc(F)cc2)c(Cl)cn1]

To a solution of 2,5-dichloro-4-(4-fluorobenzyl)-pyridine (241 mg, 0.94 mmol) in methanol (3 mL) was added with stirring the [1,1-bis(diphenylphos-phino)ferrocene]dichloropalladium DCM complex (46.1 mg, 0.057 mmol) and triethylamine (0.198 mL, 1.41 mmol). The resulting solution was stirred in a CO atmosphere (70 bar) at 100° C. for 20 hours. The mixture was concentrated and purified by flash chromatography, eluting with a heptane/ethyl acetate gradient on silica to produce the title compound (198 mg, 75%) as white solid. LC-MS (UV peak area, m/z) 78.4%, 280.0539 (MH+).

d)
5-Chloro-4-(4-fluorobenzyl)-pyridine-2-carboxylic acid

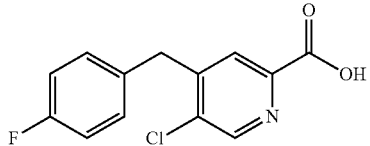 [SMILES: O=C(O)c1cc(Cc2ccc(F)cc2)c(Cl)cn1]

To a solution of 5-chloro-4-(4-fluorobenzyl)-pyridine-2-carboxylic acid methyl ester (190 mg, 0.68 mmol) in THF (10 mL) was added sodium hydroxide solution (1.36 mL, 1 N). The resulting solution was stirred at room temperature for 2 hours, and afterwards acidified with hydrochloric acid (15 mL, 1N) and poured into ethyl acetate (50 mL). The phases were separated and the water phase was extracted with additional ethyl acetate; the organic portions were combined, dried over Na$_2$SO$_4$, filtered and concentrated. The crude material (186 mg, quant.) a white solid, was sufficiently pure to be used in the next step without further purification. MS (ESI, m/z): 264.0 (M−H−).

e) 5-Chloro-4-(4-fluoro-benzyl)-pyridine-2-carboxylic acid ((R)-1-hydroxymethyl-1,2-dimethyl-propyl)-amide The title compound was synthesized in analogy to Example 1, using 5-chloro-4-(4-fluorobenzyl)-pyridine-2-carboxylic acid and (2R)-2-amino-2,3-dimethyl-1-butanol (CAN 155158-75-1) as starting materials and isolated (29 mg, 25%) as colorless oil; LC-MS (UV peak area, m/z) 100%, 365.1428 (MH+).

Example 16

(+)-5-Chloro-4-cyclopropylmethoxy-pyridine-2-carboxylic acid (2,2,2-trifluoro-1-pyridin-2-yl-ethyl)-amide

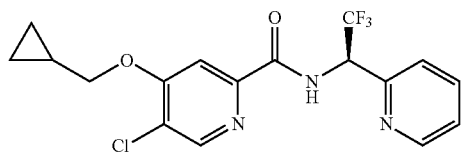 [SMILES: O=C(N[C@H](c1ccccn1)C(F)(F)F)c1cc(OCC2CC2)c(Cl)cn1]

The title compound was synthesized in analogy to Example 1, using 5-chloro-4-cyclopropylmethoxy-pyridine-2-carboxylic acid and α-(trifluoromethyl)-2-pyridinemethanamine (CAN 503173-14-6) as starting materials. The racemate (96 mg, 83%) was separated into its enantiomers by preparative chiral HPLC (ChiralPak AD, isopropanol/heptane) and the title compound was isolated as colorless oil; LC-MS (UV peak area, m/z) 100%, 386.0882 (MH+). $[\alpha]_D^{20}$=+22.4 (MeOH).

Example 17

5-Chloro-4-cyclopropylmethoxy-pyridine-2-carboxylic acid (3-hydroxy-2,2-dimethyl-propyl)-amide

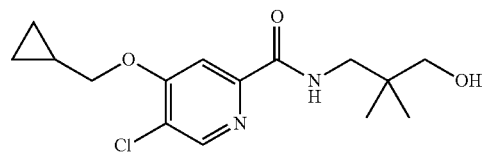 [SMILES: CC(C)(CO)CNC(=O)c1cc(OCC2CC2)c(Cl)cn1]

The title compound was synthesized in analogy to Example 12d, using 5-chloro-4-cyclopropylmethoxy-pyridine-2-carboxylic acid and 3-amino-2,2-dimethyl-1-propanol (CAN 26734-09-8) as starting materials and isolated (23 mg, 74%) as colorless oil; LC-MS (UV peak area, m/z) 100%, 313.1315 (MH+).

Example 18

5-Chloro-4-cyclopropylmethoxy-pyridine-2-carboxylic acid [1-(2-hydroxy-ethyl)-2-methyl-propyl]-amide

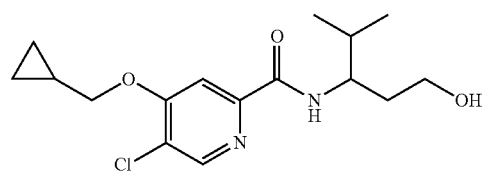 [SMILES: CC(C)C(CCO)NC(=O)c1cc(OCC2CC2)c(Cl)cn1]

The title compound was synthesized in analogy to Example 12d, using 5-chloro-4-cyclopropylmethoxy-pyridine-2-carboxylic acid and 3-amino-4-methyl-1-pentanol (CAN 26734-09-8) as starting materials and isolated (21 mg, 64%) as colorless oil; LC-MS (UV peak area, m/z) 100%, 327.1473 (MH⁺).

Example 19

5-Chloro-4-cyclopropylmethoxy-pyridine-2-carboxylic acid (1-cyclopropyl-3-hydroxy-propyl)-amide

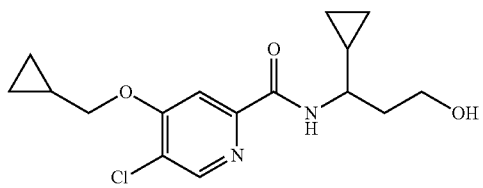 [SMILES: O=C(NC(CCO)C1CC1)c1cc(OCC2CC2)c(Cl)cn1]

The title compound was synthesized in analogy to Example 12d, using 5-chloro-4-cyclopropylmethoxy-pyridine-2-carboxylic acid and γ-amino-cyclopropanepropanol (CAN 683220-79-3) as starting materials and isolated (27 mg, 83%) as colorless oil; LC-MS (UV peak area, m/z) 97.6%, 325.1313 (MH⁺).

Example 20

5-Chloro-4-cyclopropylmethoxy-pyridine-2-carboxylic acid (1-hydroxymethyl-cyclopentylmethyl)-amide

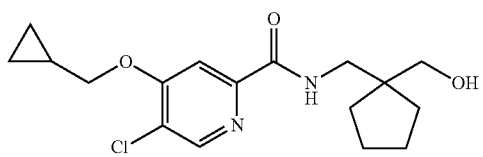 [SMILES: O=C(NCC1(CO)CCCC1)c1cc(OCC2CC2)c(Cl)cn1]

The title compound was synthesized in analogy to Example 12d, using 5-chloro-4-cyclopropylmethoxy-pyridine-2-carboxylic acid and 1-(aminomethyl)-cyclopentanemethanol (CAN 2239-31-8) as starting materials and isolated (35 mg, quant.) as colorless oil; LC-MS (UV peak area, m/z) 100%, 339.1470 (MH⁺).

Example 21

5-Chloro-4-cyclopropylmethoxy-pyridine-2-carboxylic acid (1-ethyl-1-hydroxymethyl-propyl)-amide

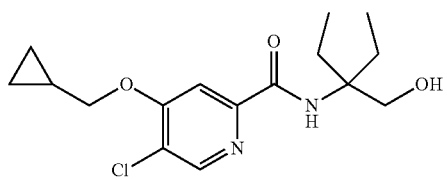 [SMILES: CCC(CC)(CO)NC(=O)c1cc(OCC2CC2)c(Cl)cn1]

The title compound was synthesized in analogy to Example 12d, using 5-chloro-4-cyclopropylmethoxy-pyridine-2-carboxylic acid and 2-amino-2-ethyl-1-butanol (CAN 19792-52-0) as starting materials and isolated (22 mg, 67% as colorless oil; LC-MS (UV peak area, m/z) 98%, 327.1470 (MH⁺).

Example 22

5-Chloro-4-cyclopropylmethoxy-pyridine-2-carboxylic acid ((S)-2,2,2-trifluoro-1-pyridin-3-yl-ethyl)-amide

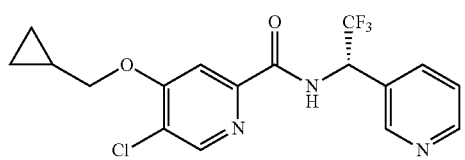 [SMILES: O=C(N[C@@H](c1cccnc1)C(F)(F)F)c1cc(OCC2CC2)c(Cl)cn1]

The title compound was synthesized in analogy to Example 12d, using 5-chloro-4-cyclopropylmethoxy-pyridine-2-carboxylic acid and (αS)-α-(trifluoromethyl)-3-pyridinemethanamine (CAN 749839-26-7) as starting materials and isolated (21 mg, 54%) as colorless oil; LC-MS (m/z), 386.0870 (MH⁺).

Example 23

5-Chloro-4-(oxetan-3-yloxy)-pyridine-2-carboxylic acid ((S)-2,2-dimethyl-1-methylcarbamoyl-propyl)-amide

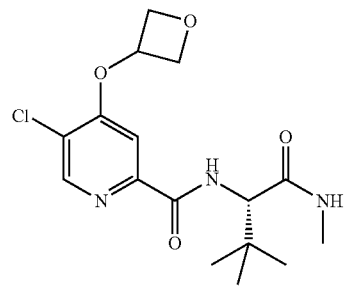 [SMILES: CNC(=O)[C@@H](NC(=O)c1cc(OC2COC2)c(Cl)cn1)C(C)(C)C]

a) 5-Chloro-4-(oxetan-3-yloxy)-pyridine-2-carboxylic acid

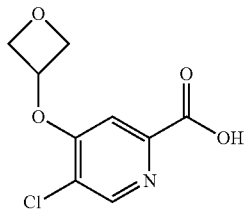 [SMILES: O=C(O)c1cc(OC2COC2)c(Cl)cn1]

To a solution of 5-chloro-4-iodo-pyridine-2-carboxylic acid (CAN 120643-06-3, 360 mg, 1.27 mmol) in DMF (10 mL) was added with stirring Oxetan-3-ol (CAN 7748-36-9, 104 mg, 1.4 mmol) and sodium hydride 60% (107 mg, 2.67 mmol). The resulting mixture was stirred at room temperature for 30 min and at 120° C. for 25 h, cooled and the reaction mixture was concentrated in vacuo. The residue was suspended with ethylacetate, transferred into a separatory funnel and extracted with 4.0 mL of 0.5M aqueous solution hydrochloric acid. The organic phase was collected and the aqueous phase was back-extracted with ethylacetate. The organic phases were combined, dried over sodium sulfate and evaporated down to dryness to give the title compound (323 mg, 111%) as a solid which was used crude without any further purification. MS (ESI, m/z): 228.4 (M−H⁺)

b) 5-Chloro-4-(oxetan-3-yloxy)-pyridine-2-carboxylic acid ((S)-2,2-dimethyl-1-methylcarbamoyl-propyl)-amide To a solution of 5-Chloro-4-(oxetan-3-yloxy)-pyridine-2-carboxylic acid (Example 23a, 35 mg, 152 µmol) in DMF (1 mL) was added HATU (58 mg, 152 µmol) and DIEA (66.6 µL, 381 µmol). The reaction mixture was then stirred at room temperature for 30 min, followed by addition of (S)-2-amino-N,3,3-trimethylbutanamide (CAN 89226-12-0, 22 mg, 152 µmol). The reaction mixture was stirred for 3 h. The crude reaction mixture was directly purified by preparative HPLC to deliver the desired compound (17.5 mg, 32%) as a yellow oil. MS (ESI, m/z): 356.5 (M+H⁺).

Example 24

5-Chloro-4-(2,2,2-trifluoro-ethoxy)-pyridine-2-carboxylic acid ((S)-2,2-dimethyl-1-methylcarbamoyl-propyl)-amide

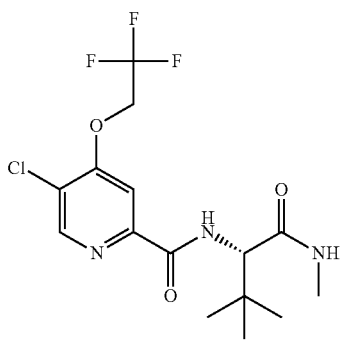 [SMILES: CNC(=O)[C@@H](NC(=O)c1cc(OCC(F)(F)F)c(Cl)cn1)C(C)(C)C]

a) 2,5-Dichloro-4-(2,2,2-trifluoro-ethoxy)-pyridine

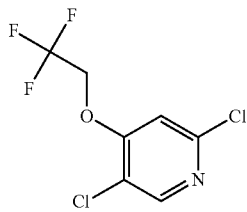 [SMILES: FC(F)(F)COc1cc(Cl)ncc1Cl]

To a solution of 2,5-dichloropyridin-4-ol (CAN 847664-65-7, 1.5 g, 9.15 mmol) in DMF (15 ml) in a microwave vial were added cesium carbonate (4.47 g, 13.7 mmol) and 2,2,2-trifluoroethyl trifluoromethanesulfonate (3.18 g, 13.7 mmol). The vial was sealed and heated at 90° C. overnight. The reaction mixture was diluted with ethylacetate and extracted with water. The organic phase was collected and the aqueous phase was back-extracted with ethylacetate. Organic phases were combined, dried over magnesium sulfate and concentrated in vacuo. The residue was purified by flash chromatography eluting with a heptane/ethylacetate gradient on silica to yield the titled compound as a colorless oil (1.33 g, 59%). MS (ESI, m/z): 246.2 (M+H⁺).

b) 5-Chloro-4-(2,2,2-trifluoro-ethoxy)-pyridine-2-carbonitrile

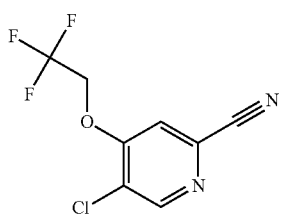 [SMILES: N#Cc1cc(OCC(F)(F)F)c(Cl)cn1]

To a solution of 2,5-dichloro-4-(2,2,2-trifluoroethoxy)-pyridine (Example 24a, 1.48 g, 6.02 mmol) in dry DMF (30 mL) under an argon atmosphere was added dicyanozinc (707 mg, 6.02 mmol), 1,1'-bis(diphenylphosphino)ferrocene (267 mg, 481 µmol) and tris(dibenzylideneacetone) dipalladium(0) (275 mg, 301 µmol). The reaction was stirred at 100° C. for 18 h, cooled and filtered through a pad of celite. The filtrate was diluted with ethylacetate and extracted with a 1.0M aqueous solution of sodium bicarbonate. The organic phase was collected and the aqueous solution was back-extracted with ethylacetate. The organic phases were combined, dried over sodium sulfate and evaporated down to dryness. The residue was purified by flash chromatography on silica eluting with a heptane/ethylacetate gradient to yield the title compound (1.04 g, 73%) as a yellow oil. MS (ESI, m/z): 237.3 (M+H⁺).

c) 5-Chloro-4-(2,2,2-trifluoro-ethoxy)-pyridine-2-carboxylic acid

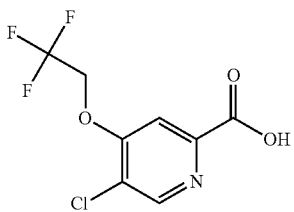 [SMILES: O=C(O)c1cc(OCC(F)(F)F)c(Cl)cn1]

To a solution of 5-Chloro-4-(2,2,2-trifluoro-ethoxy)-pyridine-2-carbonitrile (Example 24b, 800 mg, 3.38 mmol) in ethanol (10 ml) was added 4.0M aqueous solution of potassium hydroxide (4.65 ml, 18.6 mmol). The reaction was stirred for 30 min at 90° C. under microwave radiation. The reaction mixture was diluted with ethylacetate, poured into a separatory funnel and extracted with 1N aqueous solution hydrochloric acid. The organic phase was collected, dried over sodium sulfate and evaporated down to dryness to yield a crude product (540 mg, 62.5%) which was used without any further purification. MS (ESI, m/z): 256.4 (M+H⁺).

d) 5-Chloro-4-(2,2,2-trifluoro-ethoxy)-pyridine-2-carboxylic acid ((S)-2,2-dimethyl-1-methylcarbamoyl-propyl)-amide To a solution of 5-Chloro-4-(2,2,2-trifluoro-ethoxy)-pyridine-2-carboxylic acid (Example 24c, 72 mg, 282 µmol) in DMF (1 mL) was added 4-(4,6-dimethoxyl-1,3,5-triazin-2-yl)-4-methylmorpholininium chloride (CAN 3945-69-5, 82 mg, 296 µmol) and DIEA (34.5 µL, 296 µmol). The reaction mixture was then stirred at room temperature for 30 min, followed by addition of (S)-2-amino-N,3,3-trimethylbutanamide (CAN 89226-12-0, 43 mg, 296 µmol). The reaction mixture was stirred for 3 h. The crude reaction mixture was directly purified by preparative HPLC to deliver the desired compound (65 mg, 60%) as white solid. MS (ESI, m/z): 382.4 (M+H$^+$).

Example 25

5-Chloro-4-cyclopropylmethoxy-pyridine-2-carboxylic acid (1-hydroxymethyl-1,3-dimethyl-butyl)-amide

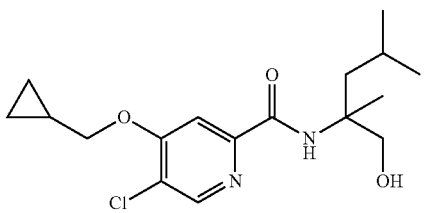 [SMILES: CC(C)CC(C)(CO)NC(=O)c1cc(OCC2CC2)c(Cl)cn1]

The title compound was synthesized in analogy to Example 1, using 5-chloro-4-cyclopropylmethoxy-pyridine-2-carboxylic acid and 2-amino-2,4-dimethyl-1-pentanol (CAN 13893-55-5) as starting materials and isolated (193 mg, quant.) as colorless oil; LC-MS (UV peak area, m/z) 100%, 341.1623 (MH$^+$).

Example 26

5-Chloro-4-cyclopropylmethoxy-pyridine-2-carboxylic acid (1-hydroxymethyl-1-methyl-propyl)-amide

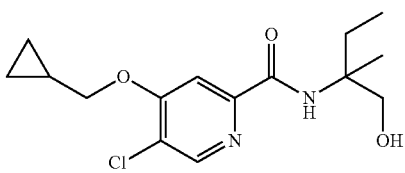 [SMILES: CCC(C)(CO)NC(=O)c1cc(OCC2CC2)c(Cl)cn1]

The title compound was synthesized in analogy to Example 1, using 5-chloro-4-cyclopropylmethoxy-pyridine-2-carboxylic acid and 2-amino-2-methyl-1-butanol (CAN 10196-30-2) as starting materials and isolated (75 mg, 55%) as colorless oil; LC-MS (UV peak area, m/z) 100%, 313.1322 (MH$^+$).

Example 27

(−)-5-Chloro-4-cyclopropylmethoxy-pyridine-2-carboxylic acid (1-hydroxymethyl-1,3-dimethyl-butyl)-amide

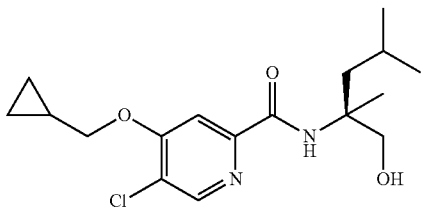 [SMILES: CC(C)C[C@@](C)(CO)NC(=O)c1cc(OCC2CC2)c(Cl)cn1]

The racemate (Example 25) was separated into its enantiomers by preparative chiral HPLC (Reprosil Chiral NR, isopropanol/heptane) and the title compound was isolated as colorless oil; LC-MS (UV peak area, m/z) 100%, 341.1632 (MH$^+$). $[\alpha]_D^{20}$=−3.0 (MeOH).

Example 28

(+)-5-Chloro-4-cyclopropylmethoxy-pyridine-2-carboxylic acid (1-hydroxymethyl-1,3-dimethyl-butyl)-amide

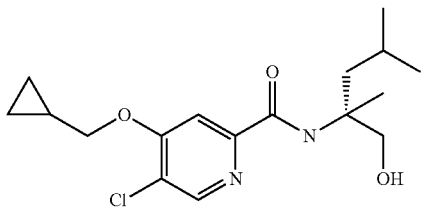 [SMILES: CC(C)C[C@](C)(CO)NC(=O)c1cc(OCC2CC2)c(Cl)cn1]

The racemate (Example 25) was separated into its enantiomers by preparative chiral HPLC (Reprosil Chiral NR, isopropanol/heptane) and the title compound was isolated as colorless oil; LC-MS (UV peak area, m/z) 100%, 341.1630 (MH$^+$). $[\alpha]_D^{20}$=+5.2 (MeOH).

Example 29

5-Chloro-4-cyclopropylmethoxy-pyridine-2-carboxylic acid ((R)-1-hydroxymethyl-2,2-dimethyl-propyl)-amide

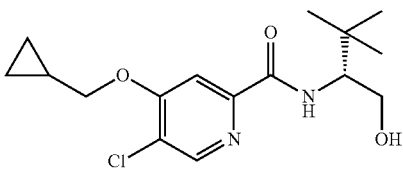 [SMILES: CC(C)(C)[C@H](CO)NC(=O)c1cc(OCC2CC2)c(Cl)cn1]

The title compound was synthesized in analogy to Example 1, using 5-chloro-4-cyclopropylmethoxy-pyridine-2-carboxylic acid and (2R)-2-amino-3,3-dimethyl-1-butanol (CAN 112245-09-7) as starting materials and isolated (80 mg, 80%) as colorless oil; LC-MS (UV peak area, m/z) 100%, 327.1476 (MH⁺).

Example 30

(−)-5-Chloro-4-cyclopropylmethoxy-pyridine-2-carboxylic acid (1-hydroxymethyl-1-methyl-propyl)-amide

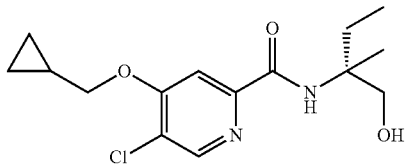 [SMILES: CC[C@](C)(CO)NC(=O)c1cc(OCC2CC2)c(Cl)cn1]

The racemate (Example 26) was separated into its enantiomers by preparative chiral HPLC (ChiralPak AD, isopropanol/heptane) and the title compound was isolated as colorless oil; MS (ESI, m/z): 313.1 (MH⁺).

Example 31

Methyl 3-({[5-chloro-4-(cyclopropylmethoxy)pyridin-2-yl]carbonyl}amino)-2,3-dimethylbutanoate

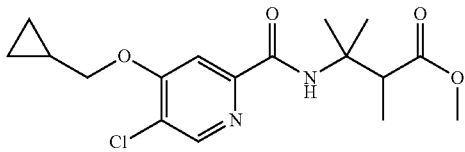 [SMILES: COC(=O)C(C)C(C)(C)NC(=O)c1cc(OCC2CC2)c(Cl)cn1]

The title compound was synthesized in analogy to Example 1, using 5-chloro-4-cyclopropylmethoxy-pyridine-2-carboxylic acid and 3-amino-2,3-dimethyl-butanoic acid methyl ester (CAN 89855-37-8) as starting materials and isolated (126 mg, 81%) as colorless oil; LC-MS (UV peak area, m/z) 100%, 355.1427 (MH+).

Example 32

5-Chloro-4-cyclopropylmethoxy-pyridine-2-carboxylic acid (3-thiazol-2-yl-oxetan-3-yl)-amide

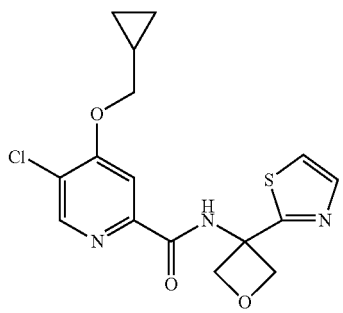 [SMILES: O=C(NC1(c2nccs2)COC1)c1cc(OCC2CC2)c(Cl)cn1]

a) 2-Methyl-propane-2-sulfinic acid (3-thiazol-2-yl-oxetan-3-yl)-amide

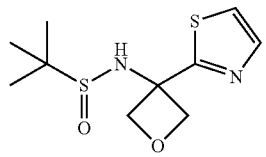 [SMILES: CC(C)(C)S(=O)NC1(c2nccs2)COC1]

A solution of n-butyllithium in hexanes (1.6 M, 2.5 mL, 3.99 mmol) was added dropwise to a solution of thiazole (364 mg, 4.23 mmol) in tetrahydrofuran (30 mL) at −78° C. The resulting mixture was stirred for 30 min at −78° C. before a solution of 2-methyl-n-(oxetan-3-ylidene)propane-2-sulfinamide (CAN 1158098-73-7, 500 mg, 2.85 mmol) in tetrahydrofuran (3.5 mL) was added dropwise at −78° C. The reaction solution was stirred for an additional 30 min at −78° C. before being warmed to 22° C., and then was quenched with saturated aqueous ammonium chloride solution. The crude reaction mixture was then partitioned between water and ethyl acetate. The aqueous layer was further extracted with ethyl acetate and the organic layers were combined. The combined layers were washed with saturated aqueous sodium chloride solution, and the washed solution was dried with sodium sulfate and evaporated down to dryness. The crude product was purified by flash-column chromatography (40% ethyl acetate-hexanes, grading to 100% ethyl acetate, then flushing with 10% methanol-dichloromethane) to give the title compound (495 mg, 67%). MS (ESI, m/z): 261.0 (M+H⁺).

b) 3-(thiazol-2-yl)oxetan-3-amine hydrochloride

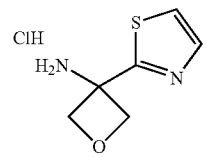

A 4.0 M solution of hydrochloric acid (117 μL, 467 μmol) in dioxane was added to a solution of 2-Methyl-propane-2-sulfinic acid (3-thiazol-2-yl-oxetan-3-yl)-amide (Example 32a, 81 mg, 311 μmol) in methanol (0.5 mL) at 0° C. The mixture was stirred at 0° C. for 5 min before the solvents were removed under reduced pressure. The resulting white solid was triturated with diethyl ether and filtered off. The solid was further washed with diethyl ether and dried under high vacuum to yield the title compound (42 mg, 70%) as a white solid. MS (ESI, m/z): 157.1 (M+H⁺).

c) 5-Chloro-4-cyclopropylmethoxy-pyridine-2-carboxylic acid (3-thiazol-2-yl-oxetan-3-yl)-amide The title compound was synthesized in analogy to Example 24d, using 5-Chloro-4-(2,2-trifluoro-ethoxy)-pyridine-2-carboxylic acid (Example 4a) and 3-(thiazol-2-yl)

Example 33

5-Chloro-4-cyclopropylmethoxy-pyridine-2-carboxylic acid (1-hydroxymethyl-1-methyl-butyl)-amide

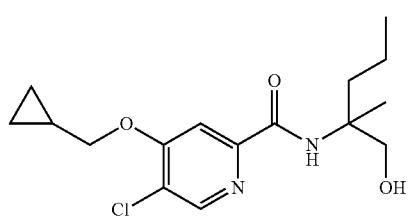 [SMILES: CCCC(C)(CO)NC(=O)c1cc(OCC2CC2)c(Cl)cn1]

The title compound was synthesized in analogy to Example 1, using 5-chloro-4-cyclopropylmethoxy-pyridine-2-carboxylic acid and 2-amino-2-methyl-1-pentanol (CAN 13893-61-3) as starting materials and isolated (21 mg, 71%) as colorless oil; MS (ESI, m/z): 327.2 (MH$^+$).

Example 34

(−)-5-Chloro-4-cyclopropylmethoxy-pyridine-2-carboxylic acid (1,1-dimethyl-2-methylcarbamoyl-propyl)-amide

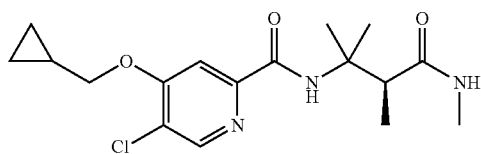 [SMILES: CNC(=O)[C@@H](C)C(C)(C)NC(=O)c1cc(OCC2CC2)c(Cl)cn1]

The racemate (Example 31) was separated into its enantiomers by preparative chiral HPLC (Reprosil Chiral NR, isopropanol/heptane) and the title compound was isolated as colorless oil; LC-MS (UV peak area, m/z) 100%, 354.1583 (MH$^+$). $[\alpha]_D^{20}$=−7.1 (MeOH).

Example 35

(+)-5-Chloro-4-cyclopropylmethoxy-pyridine-2-carboxylic acid (1,1-dimethyl-2-methylcarbamoyl-propyl)-amide

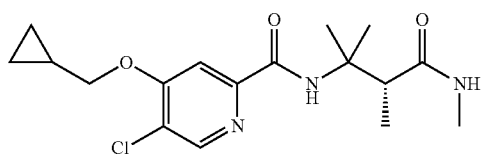 [SMILES: CNC(=O)[C@H](C)C(C)(C)NC(=O)c1cc(OCC2CC2)c(Cl)cn1]

The racemate (Example 31) was separated into its enantiomers by preparative chiral HPLC (Reprosil Chiral NR, isopropanol/heptane) and the title compound was isolated as colorless oil; LC-MS (UV peak area, m/z) 100%, 354.1578 (MH$^+$). $[\alpha]_D^{20}$=+10.4 (MeOH).

Example 36

5-Chloro-4-cyclopropylmethoxy-pyridine-2-carboxylic acid (3-oxazol-2-yl-oxetan-3-yl)-amide

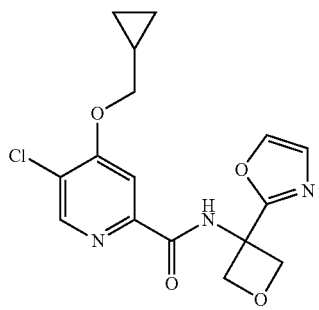 [SMILES: O=C(NC1(c2ncco2)COC1)c1cc(OCC2CC2)c(Cl)cn1]

To a solution of oxazole (217 mg, 3.14 mmol) in 8 mL dry THF under argon at room temperature was added BH$_3$.THF (3.14 ml, 3.14 mmol), the reaction mixture was stirred at room temperature for 15 minutes, cooled down to −75° C. followed by slow addition of BuLi (1.96 ml, 3.14 mmol). The resulting reaction mixture was stirred at −75° C. for 30 minutes and a solution of 2-methyl-N-(oxetan-3-ylidene)propane-2-sulfinamide (CAN 1158098-73-7, 0.5 g, 2.85 mmol) in 4 mL dry THF was added. The reaction mixture was stirred at −75° C. for 30 minutes, then the reaction was let to warm up to room temperature and was stirred for 1 hour. The reaction was quenched by addition of 1 mL of an aqueous solution 7N ammonium chloride and reaction mixture was stirred for 15 minutes. The mixture was diluted with ethylacetate, poured into a separatory funnel and extracted with water. The organic phase was collected, dried over sodium sulfate and evaporated down to dryness to give a yellow oil. The crude material was used without any further purification. To a solution of the former crude oil (697 mg, 2.85 mmol) in methanol (9 ml) cooled down to 0° C. was added a 4.0M solution of hydrochloric acid in dioxane (2.14 ml, 8.56 mmol). The reaction mixture was stirred at 0° C. for 1 hour. The reaction mixture was concentrated in vacuo, the residue was dissolved in diethyl ether and a precipitate formed. The suspension was stored in the fridge for 2 hours and then precipitate was collected by filtration. The collected solid was dried under high vacuum for 2 hours to give a crude yellow solid which was used without any purification. The crude solid was used to synthesize the title compound in analogy to Example 24d, using 5-Chloro-4-cyclopropylmethoxy-pyridine-2-carboxylic acid (Example 4a) as starting material and could be isolated (15 mg, 39%) as white solid; MS (ESI, m/z): 350.5 (M+H$^+$).

Example 37

(−)-5-Chloro-4-cyclopropylmethoxy-pyridine-2-carboxylic acid (1-hydroxymethyl-1-methyl-butyl)-amide

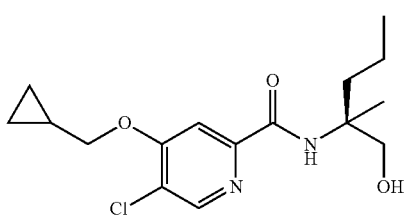 [SMILES: CCC[C@@](C)(CO)NC(=O)c1cc(OCC2CC2)c(Cl)cn1]

The racemate (Example 33) was separated into its enantiomers by preparative chiral HPLC (Reprosil Chiral NR, ethanol/heptane) and the title compound was isolated as colorless oil; MS (ESI, m/z): 327.2 (MH$^+$).

Example 38

5-Chloro-4-(2,2,2-trifluoro-ethoxy)-pyridine-2-carboxylic acid (2,2-dimethyl-1-thiazol-2-yl-propyl)-amide

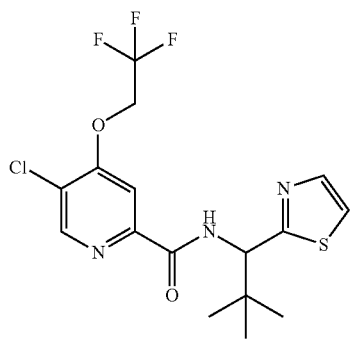 [SMILES: CC(C)(C)C(NC(=O)c1cc(OCC(F)(F)F)c(Cl)cn1)c1nccs1]

The title compound was synthesized in analogy to Example 24d, using 5-Chloro-4-(2,2,2-trifluoro-ethoxy)-pyridine-2-carboxylic acid (Example 24c) and 2,2-Dimethyl-1-thiazol-2-yl-propylamine (CAN 1247122-26-4) as starting materials and isolated (72 mg, 51%) as white solid; MS (ESI, m/z): 408.3 (M+H$^+$).

Example 39

5-Chloro-4-(oxetan-3-yloxy)-pyridine-2-carboxylic acid (2,2-dimethyl-1-thiazol-2-yl-propyl)-amide

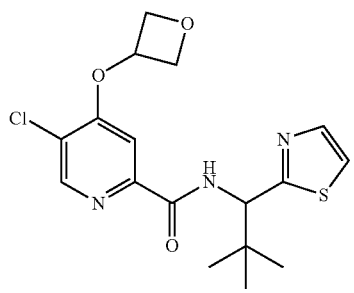 [SMILES: CC(C)(C)C(NC(=O)c1cc(OC2COC2)c(Cl)cn1)c1nccs1]

The title compound was synthesized in analogy to Example 24d, using 5-Chloro-4-(oxetan-3-yloxy)-pyridine-2-carboxylic acid (Example 23a) and 2,2-Dimethyl-1-thiazol-2-yl-propylamine (CAN 1247122-26-4) as starting materials and isolated (21.6 mg, 37%) as white solid; MS (ESI, m/z): 382.3 (M+H$^+$).

Example 40

5-Chloro-4-(4-fluoro-benzyloxy)-pyridine-2-carboxylic acid ((S)-2,2,2-trifluoro-1-pyridin-3-yl-ethyl)-amide

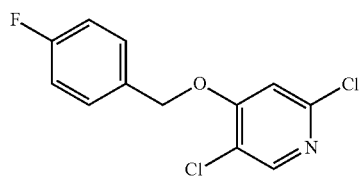 [SMILES: Fc1ccc(COc2cc(Cl)ncc2Cl)cc1]

a) 2,5-Dichloro-4-(4-fluoro-benzyloxy)-pyridine

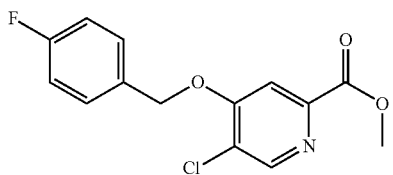 [SMILES: COC(=O)c1cc(OCc2ccc(F)cc2)c(Cl)cn1]

The title compound was synthesized in analogy to Example 12a, using 2,5-dichloro-4-pyridinol (CAN 847664-65-7) and 1-(bromomethyl)-4-fluoro-benzene (CAN 459-46-1) as starting materials and isolated (1.03 g, 62%) as white solid; LC-MS (UV peak area, m/z) 98.6%, 272.0040 (MH$^+$).

b) 5-Chloro-4-(4-fluoro-benzyloxy)-pyridine-2-carboxylic acid methyl ester

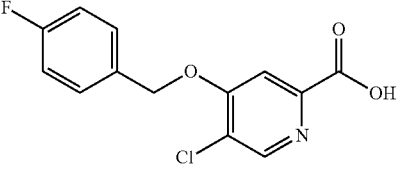 [SMILES: O=C(O)c1cc(OCc2ccc(F)cc2)c(Cl)cn1]

The title compound was synthesized in analogy to Example 12b, using 2,5-dichloro-4-(4-fluoro-benzyloxy)-pyridine as starting material and isolated (0.72 g, 64%) as white solid; LC-MS (UV peak area, m/z) 100%, 296.0491 (MH$^+$).

c) 5-Chloro-4-(4-fluoro-benzyloxy)-pyridine-2-carboxylic acid

The title compound was synthesized in analogy to Example 12c, using 5-chloro-4-(4-fluoro-benzyloxy)-pyridine-2-carboxylic acid methyl ester as starting material and isolated (0.127 g, 67%) as white solid; MS (ESI, m/z): 280.1 (M−H⁻).

d) 5-Chloro-4-(4-fluoro-benzyloxy)-pyridine-2-carboxylic acid ((S)-2,2,2-trifluoro-1-pyridin-3-yl-ethyl)-amide The title compound was synthesized in analogy to Example 12d, using 5-chloro-4-(4-fluoro-benzyloxy)-pyridine-2-carboxylic acid and (αS)-α-(trifluoromethyl)-3-pyridinemethanamine hydrochloride (1:1) (CAN 749839-26-7) as starting materials and isolated (26 mg, 83%) as colorless oil; MS (ESI, m/z): 440.3 (MH⁺).

Example 41

5-Chloro-4-(4-fluoro-benzyl)-pyridine-2-carboxylic acid ((S)-2,2,2-trifluoro-1-pyridin-3-yl-ethyl)-amide

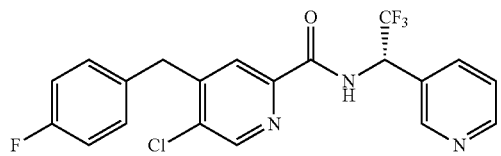 [SMILES: O=C(N[C@@H](c1cccnc1)C(F)(F)F)c1cc(Cc2ccc(F)cc2)c(Cl)cn1]

The title compound was synthesized in analogy to Example 12d, using 5-chloro-4-(4-fluorobenzyl)-pyridine-2-carboxylic acid and (αS)-α-(trifluoromethyl)-3-pyridinemethanamine hydrochloride (1:1) (CAN 749839-26-7) as starting materials and isolated (23 mg, 71%) as colorless oil; MS (ESI, m/z): 424.2 (MH⁺).

Example 42

5-Cyclopropyl-4-cyclopropylmethoxy-pyridine-2-carboxylic acid (3-thiazol-2-yl-oxetan-3-yl)-amide

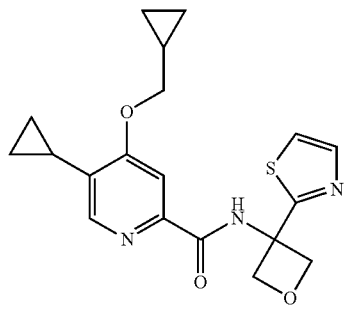 [SMILES: O=C(NC1(c2nccs2)COC1)c1cc(OCC2CC2)c(C2CC2)cn1]

a) 3-Bromo-4-cyclopropylmethoxy-pyridine

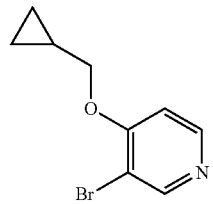 [SMILES: Brc1cnccc1OCC1CC1]

To a solution of 3-bromo-4-chloropyridine (CAN 36953-42-1, 5 g, 26.0 mmol) in dry DMF (60 ml) under an argon atmosphere at room temperature was added cyclopropylmethanol (CAN 2516-33-8, 1.97 g, 27.3 mmol) and sodium hydride 60% (1.09 g, 27.3 mmol) by portions. The resulting reaction was stirred at room temperature until gas evolution stopped. The reaction mixture was then stirred at 100° C. for 3 h. The reaction was cooled down to room temperature, quenched by addition of water and the reaction mixture was concentrated in vacuo. The residue was dissolved in ethylacetate, extracted with 1.0M aqueous solution sodium bicarbonate, organic phase dried over sodium sulfate and evaporated down to dryness. The crude was purified by flash chromatography on silica eluting with a heptane/ethylacetate gradient to yield the titled compound (5.8 gr, 98%) as a light yellow oil. MS (ESI, m/z): 228.1 (M+H⁺).

b) 3-Cyclopropyl-4-cyclopropylmethoxy-pyridine

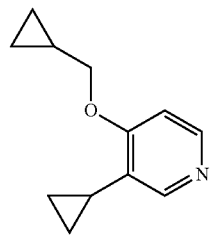 [SMILES: c1cc(OCC2CC2)c(C2CC2)cn1]

To a solution of 3-Bromo-4-cyclopropylmethoxy-pyridine (Example 42a, 4.1 g, 18.0 mmol) in a mixture of toluene (55 ml) and water (6.5 ml) was added potassium cyclopropyltrifluoroborate (CAN 1065010-87-8, 2.79 g, 18.9 mmol), palladium(II) acetate (80.7 mg, 360 µmol), butyldi-1-adamantylphosphine (CAN 321921-71-5, 193 mg, 539 µmol) and cesium carbonate (14.6 g, 44.9 mmol). The reaction mixture was stirred at 115° C. for 16 h, cooled down to room temperature and filtered through a pad of celite. The filtrate was poured into a separatory funnel, diluted with ethylacetate and extracted with water. The organic phase was collected, dried over sodium sulfate and evaporated down to dryness. The crude was purified by flash chromatography on silica eluting with a heptane/(solution 3% triethylamine in ethylacetate) gradient to yield the title compound (2.67 gr, 78.5%) as a yellow oil. MS (ESI, m/z): 190.3 (M+H⁺).

c) 5-Cyclopropyl-4-cyclopropylmethoxy-pyridine-2-carboxylic acid

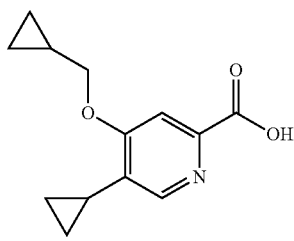 [SMILES: O=C(O)c1cc(OCC2CC2)c(C2CC2)cn1]

To a solution of N,N-Dimethylethanolamine (CAN 108-01-0, 2.372 g, 3.08 mL, 30.6 mmol) in hexane cooled at −15° C. under an argon atmosphere was slowly added BuLi 1.6M in Hexane (38.2 mL, 61.1 mmol). The reaction was stirred at −15° C. during 20 minutes and was then cooled down to −78° C. before addition of 3-cyclopropyl-4-cyclopropylmethoxy-pyridine (Example 42b, 2.314 g, 12.2 mmol). The reaction was stirred 1 hour at −78° C. followed by addition of carbon dioxide (2.09 g, 47.6 mmol) (pellets from a dry ice dispenser) into the mixture. A white precipitate formed and the reaction was slowly warmed up to −20° C. The reaction was quenched with water, stirred 5 minutes and the volatiles were removed in vacuo. The residue was suspended into ethylacetate and extracted with 19 mL of a 2.0M aqueous solution hydrochloric acid. The organic phase was collected, dried over sodium sulfate and evaporated down to dryness to give an yellow oil. The former oil was dissolved in diethylether which gave a white precipitate. The suspension was stored at 0° C. for 1 hour and the solution was separated from the white solid. The white solid was dried under high vacuum to give the titled compound (815 mg, 66%). MS (ESI, m/z): 234.2 (M+H+).

d) 5-Cyclopropyl-4-cyclopropylmethoxy-pyridine-2-carboxylic acid (3-thiazol-2-yl-oxetan-3-yl)-amide The title compound was synthesized in analogy to Example 24d, using 5-Cyclopropyl-4-cyclopropylmethoxy-pyridine-2-carboxylic acid (Example 42c) and 3-(thiazol-2-yl)oxetan-3-amine hydrochloride (Example 32b) as starting materials and isolated (16 mg, 29%) as colorless oil; MS (ESI, m/z): 372.2 (M+H+).

Example 43

5-Cyclopropyl-4-cyclopropylmethoxy-pyridine-2-carboxylic acid (2,2-dimethyl-1-thiazol-2-yl-propyl)-amide

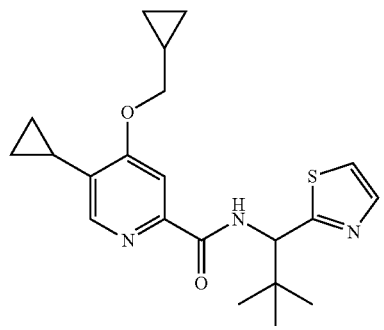 [SMILES: CC(C)(C)C(NC(=O)c1cc(OCC2CC2)c(C2CC2)cn1)c1nccs1]

The title compound was synthesized in analogy to Example 24d, using 5-Cyclopropyl-4-cyclopropylmethoxy-pyridine-2-carboxylic acid (Example 42c) and 2,2-Dimethyl-1-thiazol-2-yl-propylamine (CAN 1247122-26-4) as starting materials and isolated (15 mg, 26%) as white solid; MS (ESI, m/z): 386.4 (M+H+).

Example 44

5-Cyclopropyl-4-cyclopropylmethoxy-pyridine-2-carboxylic acid [1-cyclopropyl-1-(5-methyl-[1,2,4]oxadiazol-3-yl)-ethyl]-amide

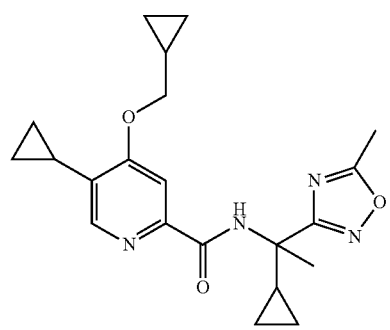 [SMILES: Cc1nc(C(C)(NC(=O)c2cc(OCC3CC3)c(C3CC3)cn2)C2CC2)no1]

The title compound was synthesized in analogy to Example 24d, using 5-Cyclopropyl-4-cyclopropylmethoxy-pyridine-2-carboxylic acid (Example 42c) and 1-Cyclopropyl-1-(5-methyl-[1,2,4]oxadiazol-3-yl)-ethylamine (CAN 1155536-64-3) as starting materials and isolated (13 mg, 23%) as colorless oil; MS (ESI, m/z): 383.6 (M+H+)

Example 45

5-Cyclopropyl-4-cyclopropylmethoxy-pyridine-2-carboxylic acid (1-ethyl-1-methylcarbamoyl-propyl)-amide

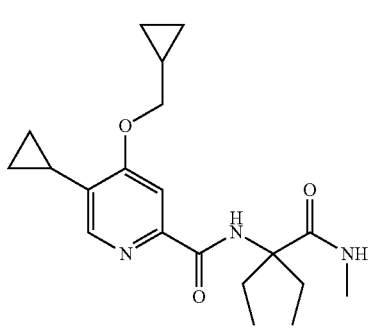 [SMILES: CCC(CC)(NC(=O)c1cc(OCC2CC2)c(C2CC2)cn1)C(=O)NC]

a) 2-(tert-Butoxycarbonylamino)-2-ethylbutanoic acid

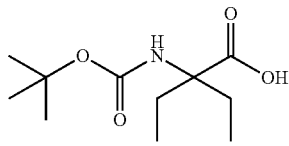 [SMILES: CCC(CC)(NC(=O)OC(C)(C)C)C(=O)O]

3-aminopentane-3-carboxylic acid (CAN 2566-29-2, 2.0 g, 15.3 mmol) was combined with dioxane (100 mL) to give a colorless suspension. Sodium hydroxide (22.7 ml, 22.7 mmol, 1N) was added dropwise at 0° C. within 10 min to give a colorless solution. Di-tert-butyl dicarbonate (CAN 24424-99-5, 6.7 g, 30.9 mmol) was added in three portions. The reaction was stirred for 30 min to give a colorless suspension. Then dioxane (30 mL) was added (using less solvent resulted in a thick suspension) and the mixture was stirred for 17 h at ambient temperature. The reaction mixture was concentrated in vacuo to a volume of 50 mL and poured into 200 mL water. Then the mixture was washed with ethyl acetate (3×80 ml). The aqueous layers were combined, 2N hydrochloric acid was added to adjust the pH to 2, and the mixture was extracted with ethyl acetate (3×60 mL). The organic layers were combined, dried over anhydrous sodium sulfate and concentrated in vacuo to give product (1.0 g, 28%).

b) tert-Butyl 3-(methylcarbamoyl)pentan-3-ylcarbamate

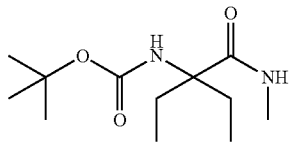 [SMILES: CCC(CC)(NC(=O)OC(C)(C)C)C(=O)NC]

A mixture of 2-(tert-butoxycarbonylamino)-2-ethylbutanoic acid (Example 45a, 400 mg, 2 mmol), HBTU (CAN 94790-37-1, 1.3 g, 3 mmol), triethylamine (0.7 g, 7 mmol) in DMF (10 mL) was stirred for 30 min, then methanamine hydrochloride (CAN 593-51-1, 260 mg, 6 mmol) was added into the mixture and the solution was stirred overnight. After that, the solution was diluted with water (20 mL) and extracted with ethyl acetate (3×30 mL), the combined organic layer was washed with water (3×50 mL) and brine (60 mL), then evaporated to dryness. The crude product (0.18 g, 45%) obtained as a light yellow solid was used for the next step directly without any purification.

c) 2-Amino-2-ethyl-N-methyl-butyramide hydrochloride

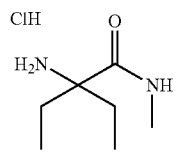

A mixture of tert-butyl 3-(methylcarbamoyl)pentan-3-yl-carbamate (0.18 g, 0.74 mmol) in 10 ml saturated hydrochloride in ethyl acetate was stirred for 60 min at room temperature. Then the solution was evaporated to dryness to obtain the product (80 mg, 75%) as a light yellow solid. MS (ESI, m/z): 145.2 (M+H+)

d) 5-Cyclopropyl-4-cyclopropylmethoxy-pyridine-2-carboxylic acid (1-ethyl-1-methylcarbamoyl-propyl)-amide The title compound was synthesized in analogy to Example 24d, using 5-Cyclopropyl-4-cyclopropylmethoxy-pyridine-2-carboxylic acid (Example 42c) and 2-Amino-2-ethyl-N-methyl-butyramide hydrochloride (Example 45c) as starting materials and isolated (23 mg, 71%) as colorless oil; MS (ESI, m/z): 360.6 (M+H+).

Example 46

5-Cyclopropyl-4-cyclopropylmethoxy-pyridine-2-carboxylic acid (2,2,2-trifluoro-1-pyridin-2-yl-ethyl)-amide

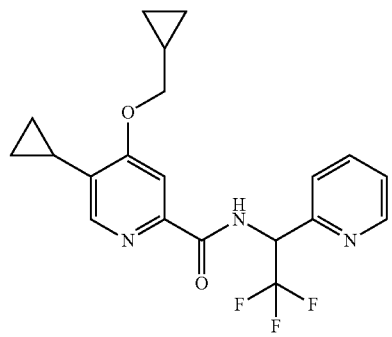 [SMILES: O=C(NC(c1ccccn1)C(F)(F)F)c1cc(OCC2CC2)c(C2CC2)cn1]

The title compound was synthesized in analogy to Example 24d, using 5-Cyclopropyl-4-cyclopropylmethoxy-pyridine-2-carboxylic acid (Example 42c) and 2,2,2-Trifluoro-1-pyridin-2-yl-ethylamine (CAN 503173-14-6) as starting materials and isolated (17.2 mg, 29%) as colorless oil; MS (ESI, m/z): 392.5 (M+H+).

Example 47

5-Cyclopropyl-4-cyclopropylmethoxy-pyridine-2-carboxylic acid ((S)-1-carbamoyl-3-methyl-butyl)-amide

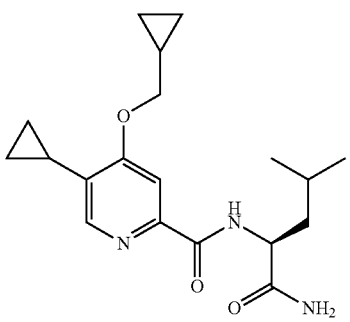 [SMILES: CC(C)C[C@H](NC(=O)c1cc(OCC2CC2)c(C2CC2)cn1)C(N)=O]

The title compound was synthesized in analogy to Example 24d, using 5-Cyclopropyl-4-cyclopropylmethoxy-pyridine-2-carboxylic acid (Example 42c) and (S)-2-Amino-4-methyl-pentanoic acid amide (CAN 687-51-4) as starting materials and isolated (10.5 mg, 20%) as colorless oil; MS (ESI, m/z): 346.6 (M+H+).

Example 48

5-Cyclopropyl-4-(2,2,2-trifluoro-ethoxy)-pyridine-2-carboxylic acid ((S)-2,2-dimethyl-1-methylcarbamoyl-propyl)-amide

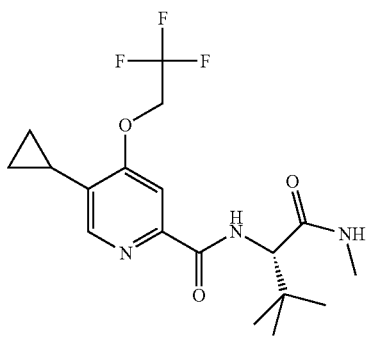 [SMILES: CNC(=O)[C@@H](NC(=O)c1cc(OCC(F)(F)F)c(C2CC2)cn1)C(C)(C)C]

a) 4-Chloro-3-cyclopropyl-pyridine

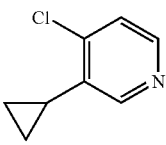

To a solution of 3-bromo-4-chloropyridine (CAN 36953-42-1, 4 g, 20.8 mmol) in a mixture of toluene (72 ml) and water (8.5 ml) under an argon atmosphere were added potassium cyclopropyltrifluoroborate (3.23 g, 21.8 mmol), palladium (II) acetate (93.3 mg, 416 µmol), butyldi-1-adamantylphosphine (224 mg, 624 µmol) and cesium carbonate (16.9 g, 52.0 mmol). The reaction mixture was stirred overnight at 115° C., cooled down to room temperature and filtered through a pad of celite. The filtrate was poured into a separatory funnel, diluted with ethyl acetate and extracted with an aqueous solution 1.0M sodium bicarbonate. The organic phase was collected, dried over sodium sulfate and evaporated down to dryness. The crude material was purified by flash chromatography on silica eluting with a heptane/(solution 3% triethylamine in ethyl acetate) gradient to yield the title product (2.39 g, 75%) as a yellow liquid. MS (ESI, m/z): 154.0 (M+H+).

b) 4-Chloro-5-cyclopropyl-pyridine-2-carboxylic acid

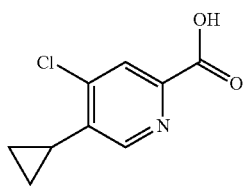 [SMILES: O=C(O)c1cc(Cl)c(C2CC2)cn1]

To a solution of N,N-Dimethylethanolamine (CAN 108-01-0, 1.89 g, 2.13 ml, 21.2 mmol) in dry Hexane (40 ml) under an argon atmosphere at −15° C. was slowly added BuLi 1.6M in Hexane (26.4 ml, 42.3 mmol). The reaction mixture was stirred at −15° C. for 15 minutes, then reaction mixture was cooled down to −78° C. followed by addition of a solution of 4-chloro-3-cyclopropylpyridine (Example 48a, 1.3 g, 8.46 mmol) in dry toluene (9 ml). The resulting reaction mixture was stirred at −78° C. for 1 hour. Addition of carbon dioxide (3.72 g, 84.6 mmol) (pellets from a dry ice dispenser) into the mixture. The reaction mixture was let to warm up to −15° C. and kept at −15° C. for 1 hour. The reaction was quenched by addition of water and stirred at r.t for 15 min. The reaction mixture was diluted with ethyl acetate, poured into a separatory funnel and extracted with 4.0M aqueous solution hydrochloric acid (21.2 ml, 84.6 mmol). The organic phase was collected and the aqueous was back-extracted twice with ethylacetate. All organic phases were combined, dried over sodium sulfate and evaporated down to dryness to give a yellow oil. The former oil was dissolved in diethylether which gave a white suspension. The suspension was kept at 0° C. for few hours. The precipitate was collected by filtration, dried under high vacuum to yield the title compound (886 mg, 53%) as a white solid. MS (ESI, m/z): 196.0 (M−H$^+$).

c) 5-Cyclopropyl-4-(2,2,2-trifluoro-ethoxy)-pyridine-2-carboxylic acid

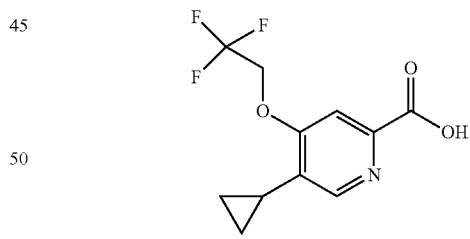

To a solution of 4-Chloro-5-cyclopropyl-pyridine-2-carboxylic acid (Example 48b, 680 mg, 3.44 mmol) were added 2,2,2-trifluoroethanol (CAN 75-89-8, 1.03 g, 746 µl, 10.3 mmol) and sodium hydride 60% (551 mg, 13.8 mmol) by portions. The reaction mixture was stirred at room temperature for 30 min and then stirred at 120° C. for 18 h. The reaction mixture was cooled down, diluted with ethylacetate and poured in a separatory funnel. The mixture was extracted with an aqueous 4.0M solution hydrochloric acid (6.88 ml, 27.5 mmol). The organic phase was collected. The organic phase was dried over sodium sulfate and evaporated down to dryness. The crude material was purified by flash chromatography on silica eluting with a dichloromethane/methanol gradient to yield the title compound (420 mg, 47%) as light brown solid. MS (ESI, m/z): 260.2 (M–H⁺)

d) 5-Cyclopropyl-4-(2,2,2-trifluoro-ethoxy)-pyridine-2-carboxylic acid ((S)-2,2-dimethyl-1-methyl-carbamoyl-propyl)-amide The title compound was synthesized in analogy to Example 24d, using 5-Cyclopropyl-4-(2,2,2-trifluoro-ethoxy)-pyridine-2-carboxylic acid (Example 48c) and (S)-2-amino-N,3,3-trimethylbutanamide (CAN 89226-12-0) as starting materials and isolated (115 mg, 52%) as a white solid; MS (ESI, m/z): 388.5 (M+H⁺).

Example 49

5-Cyclopropyl-4-(2,2,2-trifluoro-ethoxy)-pyridine-2-carboxylic acid [1-cyclopropyl-1-(5-methyl-[1,2,4]oxadiazol-3-yl)-ethyl]-amide

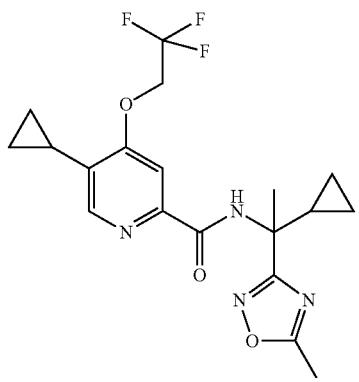 [SMILES: Cc1nc(C(C)(NC(=O)c2cc(OCC(F)(F)F)c(C3CC3)cn2)C2CC2)no1]

The title compound was synthesized in analogy to Example 24d, using 5-Cyclopropyl-4-(2,2,2-trifluoro-ethoxy)-pyridine-2-carboxylic acid (Example 48c) and 1-Cyclopropyl-1-(5-methyl-[1,2,4]oxadiazol-3-yl)-ethylamine (CAN 1155536-64-3) as starting materials and isolated (190 mg, 27%) as alight yellow oil; MS (ESI, m/z): 411.0 (M+H⁺).

Example 50

5-Cyclopropyl-4-(2,2,2-trifluoro-ethoxy)-pyridine-2-carboxylic acid (2,2-dimethyl-1-thiazol-2-yl-propyl)-amide

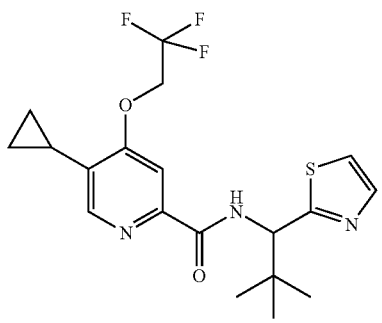 [SMILES: CC(C)(C)C(NC(=O)c1cc(OCC(F)(F)F)c(C2CC2)cn1)c1nccs1]

The title compound was synthesized in analogy to Example 24d, using 5-Cyclopropyl-4-(2,2,2-trifluoro-ethoxy)-pyridine-2-carboxylic acid (Example 48c) and 2,2-Dimethyl-1-thiazol-2-yl-propylamine (CAN 1247122-26-4) as starting materials and isolated (15 mg, 32%) as a white solid; MS (ESI, m/z): 414.5 (M+H⁺).

Example 51

5-Cyclopropyl-4-(2,2,2-trifluoro-ethoxy)-pyridine-2-carboxylic acid (2,2,2-trifluoro-1-pyridin-2-yl-ethyl)-amide

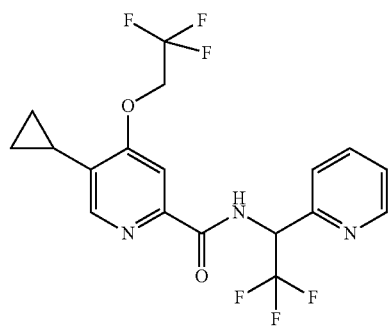 [SMILES: O=C(NC(c1ccccn1)C(F)(F)F)c1cc(OCC(F)(F)F)c(C2CC2)cn1]

The title compound was synthesized in analogy to Example 24d, using 5-Cyclopropyl-4-(2,2,2-trifluoro-ethoxy)-pyridine-2-carboxylic acid (Example 48c) and 2,2,2-Trifluoro-1-pyridin-2-yl-ethylamine (CAN 503173-14-6) as starting materials and isolated (17 mg, 26%) as a white solid; MS (ESI, m/z): 420.5 (M+H⁺).

Example 52

5-Cyclopropyl-4-(2,2,2-trifluoro-ethoxy)-pyridine-2-carboxylic acid ((S)-1-carbamoyl-3-methyl-butyl)-amide

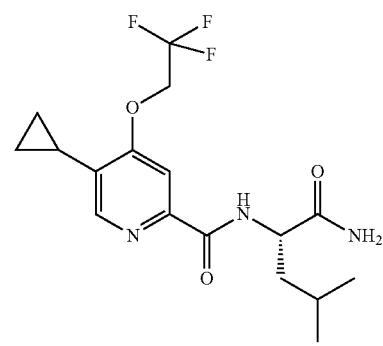 [SMILES: CC(C)C[C@H](NC(=O)c1cc(OCC(F)(F)F)c(C2CC2)cn1)C(N)=O]

The title compound was synthesized in analogy to Example 24d, using 5-Cyclopropyl-4-(2,2,2-trifluoro-ethoxy)-pyridine-2-carboxylic acid (Example 48c) and (S)-2-Amino-4-methyl-pentanoic acid amide (CAN 687-51-4) as starting materials and isolated (13.5 mg, 24%) as a white solid; MS (ESI, m/z): 374.0 (M+H⁺).

Example 53

4-Cyclopropylmethoxy-5-(3,3-difluoro-azetidin-1-yl)-pyridine-2-carboxylic acid (1-hydroxymethyl-cyclopropyl)-amide

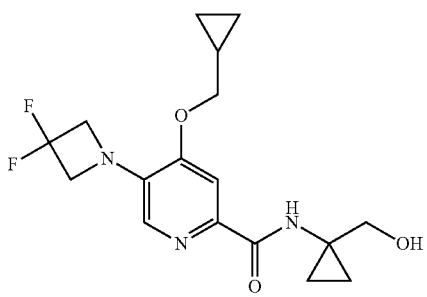 [SMILES: O=C(NC1(CO)CC1)c1cc(OCC2CC2)c(N2CC(F)(F)C2)cn1]

a) 3-Bromo-4-cyclopropylmethoxy-pyridine

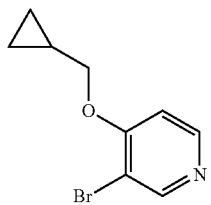 [SMILES: Brc1cnccc1OCC1CC1]

To a solution of 3-bromo-4-chloropyridine (CAN 36953-42-1, 8 g, 41.6 mmol) in dry DMF (100 ml) under argon atmosphere at room temperature were added cyclopropylmethanol (CAN 2516-33-8, 3.15 g, 3.45 ml, 43.6 mmol) and by portions sodium hydride 60% (1.75 g, 43.6 mmol). The resulting reaction was stirred at room temperature until gas evolution stopped. The reaction mixture was then stirred at 100° C. for 3 hours, cooled down to room temperature and quenched by addition of water. The reaction mixture was concentrated in vacuo. The residue was dissolved in ethylacetate and extracted with an aqueous solution 1.0M sodium bicarbonate. The organic phase was collected, dried over sodium sulfate and evaporated down to dryness. The crude material was purified by flash chromatography on silica eluting with a heptane/ethylacetate gradient to yield the title compound (8.25 g, 87%) as a light yellow oil. MS (ESI, m/z): 228.2 (M+H$^+$).

b) 3-Bromo-4-cyclopropylmethoxy-pyridine 1-oxide

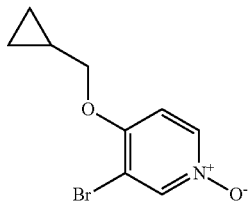 [SMILES: [O-][n+]1ccc(OCC2CC2)c(Br)c1]

To a solution of 3-Bromo-4-cyclopropylmethoxy-pyridine (Example 53a, 1 g, 4.38 mmol) in dichloromethane was added 3-Chloro-benzenecarboperoxoic acid (1.47 g, 6.58 mmol) and the reaction mixture was stirred at room temperature for 3 hours. The reaction mixture was poured into 250 mL dichloromethane and extracted with 75 mL of an aqueous solution 1M sodium bicarbonate. The organic layers was collected, dried over sodium sulfate and concentrated in vacuo. The crude material was purified by flash chromatography on silica eluting with a dichloromethane/methanol gradient to yield the title compound (954 mg, 89%) as a white solid. MS (ESI, m/z): 244.2 (M+H$^+$).

c) 5-Bromo-4-cyclopropylmethoxy-pyridine-2-carbonitrile

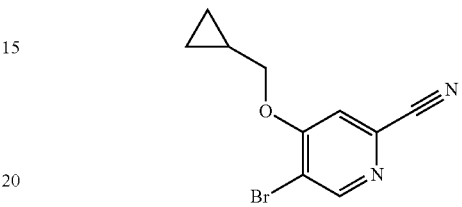

In a 100 mL pear-shaped flask, 3-Bromo-4-cyclopropylmethoxy-pyridine 1-oxide (Example 53b, 954 mg, 3.91 mmol) was combined with dichloromethane (15 ml) to give a white suspension and trimethylsilanecarbonitrile (485 mg, 611 µl, 4.89 mmol) was added dropwise followed by addition of dimethylcarbamic chloride (525 mg, 448 µl, 4.89 mmol). After 15 minutes the white suspension had become a yellow solution and the reaction mixture was stirred at room temperature for 20 hours. Saturated aqueous solution sodium carbonate (3 ml) was added while stirring. The mixture was poured into dichloromethane and extracted with water. The organic layer was dried over sodium sulfate and concentrated in vacuo. The crude material was purified by flash chromatography on silica eluting with a heptane/ethylacetate gradient to yield the title compound (301 mg, 30%) as a white solid. MS (ESI, m/z): 253.0 (M+H$^+$).

d) 4-Cyclopropylmethoxy-5-(3,3-difluoro-azetidin-1-yl)-pyridine-2-carbonitrile

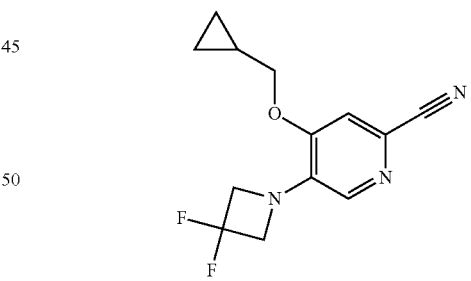

To a solution of 5-Bromo-4-cyclopropylmethoxy-pyridine-2-carbonitrile (Example 53c, 150 mg, 593 µmol) in dry toluene (3.95 ml) under an argon atmosphere in a microwave vial were added 3,3-difluoroazetidine hydrochloride (CAN 288315-03-7, 84.4 mg, 652 µmol), palladium(II) acetate (13.3 mg, 59.3 µmol), BINAP (36.9 mg, 59.3 µmol) and cesium carbonate (386 mg, 1.19 mmol). The reaction mixture was stirred at 120° C. for 45 minutes under microwave radiation. The reaction mixture was filtered over a pad of celite and the filtrate was concentrated in vacuo. The residue was dissolved in ethylacetate and extracted with an aqueous solution of 1.0M sodium bicarbonate. The organic phase was collected, dried over sodium sulfate and evaporated down to dryness. The crude material was purified by flash chromatography on silica eluting with a heptane/ethylacetate gradient to yield the title compound (157 mg, 79%) as a white solid. MS (ESI, m/z): 266.2 (M+H$^+$).

e) 4-Cyclopropylmethoxy-5-(3,3-difluoro-azetidin-1-yl)-pyridine-2-carboxylic acid

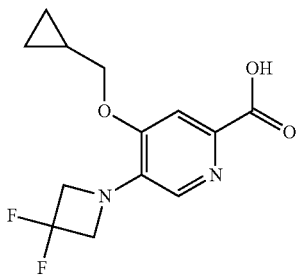 [SMILES: O=C(O)c1cc(OCC2CC2)c(N2CC(F)(F)C2)cn1]

In a microwave vial, 4-Cyclopropylmethoxy-5-(3,3-difluoro-azetidin-1-yl)-pyridine-2-carbonitrile (Example 53d, 125 mg, 471 µmol) was combined with Ethanol (1.4 ml) to give a white suspension. An 4.0M aqueous solution of potassium hydroxide (648 µl, 2.59 mmol) was added and the reaction mixture was stirred at 105° C. for 2.5 hours. The reaction mixture was poured into 15 mL ethylacetate and extracted with an 7.0M aqueous solution of hydrochloric acid (1 mL). The organic layers was collected, dried over sodium sulfate and concentrated in vacuo to yield the title compound (132 mg, 49%) as a crude white solid which was used without any further purification. MS (ESI, m/z): 285.2 (M+H$^+$).

f) 4-Cyclopropylmethoxy-5-(3,3-difluoro-azetidin-1-yl)-pyridine-2-carboxylic acid (1-hydroxymethyl-cyclopropyl)-amide The title compound was synthesized in analogy to Example 24d, using 4-Cyclopropylmethoxy-5-(3,3-difluoro-azetidin-1-yl)-pyridine-2-carboxylic acid (Example 53e) and (1-aminocyclopropyl)methanol (CAN 107017-72-1) as starting materials and isolated (85 mg, 51%) as a waxy solid; MS (ESI, m/z): 354.3 (M+H$^+$).

Example 54

5-Cyclopropyl-4-(2,2,2-trifluoro-ethoxy)-pyridine-2-carboxylic acid (1-ethyl-1-hydroxymethyl-propyl)-amide

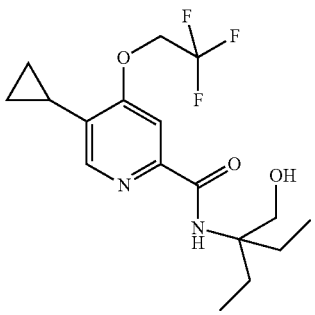 [SMILES: CCC(CC)(CO)NC(=O)c1cc(OCC(F)(F)F)c(C2CC2)cn1]

To a solution of 5-Cyclopropyl-4-(2,2,2-trifluoro-ethoxy)-pyridine-2-carboxylic acid (Example 48c, 20 mg, 77 µmol) in DMF (1.5 mL) was added HATU (32 mg, 84 µmol) and DIPEA (15 µl, 84 µmol). The reaction mixture was stirred at roomtemperature for 20 minutes followed by addition of 2-amino-2-ethylbutan-1-ol (CAN 19792-52-0, 10 mg, 84 µmol). The reaction was stirred at room temperature overnight and was poured into 15 mL of a saturated aqueous solution of sodium bicarbonate. The solution was extracted three times with 10 mL dichloromethane. The organic phases were combined, dried over sodium sulfate and evaporated down to dryness. The crude material was purified by flash chromatography on silica, eluting with a heptane/ethylacetate gradient to yield the titled compound (16 mg, 58%) as white solid. MS (ESI, m/z): 361.1 (M+H$^+$).

Example 55

5-Cyclopropyl-4-(2,2,2-trifluoro-ethoxy)-pyridine-2-carboxylic acid (1-hydroxymethyl-cyclohexyl)-amide

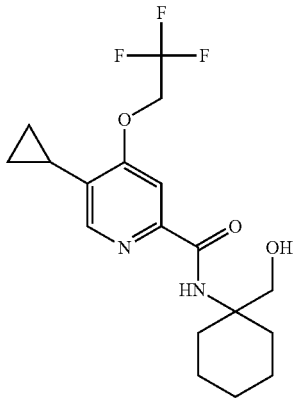 [SMILES: O=C(NC1(CO)CCCCC1)c1cc(OCC(F)(F)F)c(C2CC2)cn1]

The title compound was synthesized in analogy to Example 54, using 5-Cyclopropyl-4-(2,2,2-trifluoro-ethoxy)-pyridine-2-carboxylic acid (Example 48c) and (1-aminocyclohexyl)methanol (CAN 4313-56-8) as starting materials and isolated (55 mg, 53%) as a white solid; MS (ESI, m/z): 373.0 (M+H$^+$).

Example 56

5-Cyclopropyl-4-cyclopropylmethoxy-pyridine-2-carboxylic acid (1-hydroxy-cyclopentylmethyl)-amide

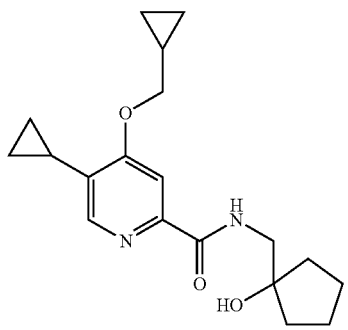 [SMILES: O=C(NCC1(O)CCCC1)c1cc(OCC2CC2)c(C2CC2)cn1]

The title compound was synthesized in analogy to Example 54, using 5-Cyclopropyl-4-cyclopropylmethoxy-pyridine-2-carboxylic acid (Example 42c) and 1-(aminomethyl)cyclopentanol hydrochloride (CAN 76066-27-8) as starting materials and isolated (71 mg, 63%) as a white solid; MS (ESI, m/z): 331.0 (M+H⁺).

Example 57

5-Cyclopropyl-4-cyclopropylmethoxy-pyridine-2-carboxylic acid (1-hydroxy-cyclohexylmethyl)-amide

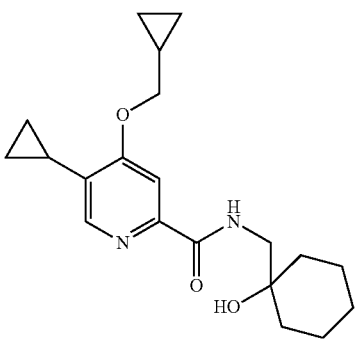 [SMILES: O=C(NCC1(O)CCCCC1)c1cc(OCC2CC2)c(C2CC2)cn1]

The title compound was synthesized in analogy to Example 54, using 5-Cyclopropyl-4-cyclopropylmethoxy-pyridine-2-carboxylic acid (Example 42c) and 1-(aminomethyl)cyclohexanol hydrochloride (CAN 19968-85-5) as starting materials and isolated (70.5 mg, 58%) as a white solid; MS (ESI, m/z): 345.1 (M+H⁺).

Example 58

5-Cyclopropyl-4-cyclopropylmethoxy-pyridine-2-carboxylic acid (2-hydroxy-butyl)-amide

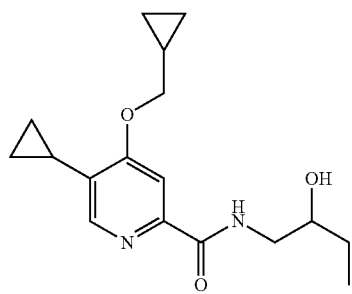 [SMILES: CCC(O)CNC(=O)c1cc(OCC2CC2)c(C2CC2)cn1]

The title compound was synthesized in analogy to Example 54, using 5-Cyclopropyl-4-cyclopropylmethoxy-pyridine-2-carboxylic acid (Example 42c) and 1-aminobutan-2-ol (CAN 13552-21-1) as starting materials and isolated (65 mg, 32%) as colorless oil; MS (ESI, m/z): 305.5 (M+H⁺).

Example 59

5-Cyclopropyl-4-cyclopropylmethoxy-pyridine-2-carboxylic acid (2-hydroxy-2-methyl-propyl)-amide

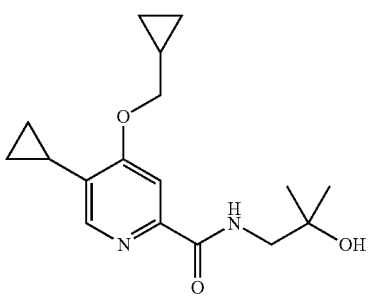 [SMILES: CC(C)(O)CNC(=O)c1cc(OCC2CC2)c(C2CC2)cn1]

The title compound was synthesized in analogy to Example 54, using 5-Cyclopropyl-4-cyclopropylmethoxy-pyridine-2-carboxylic acid (Example 42c) and 1-amino-2-methylpropan-2-ol (CAN 2854-16-2) as starting materials and isolated (59 mg, 65%) as colorless oil; MS (ESI, m/z): 305.5 (M+H⁺).

Example 60

5-Cyclopropyl-4-(2,2,2-trifluoro-ethoxy)-pyridine-2-carboxylic acid (2-hydroxy-2-methyl-propyl)-amide

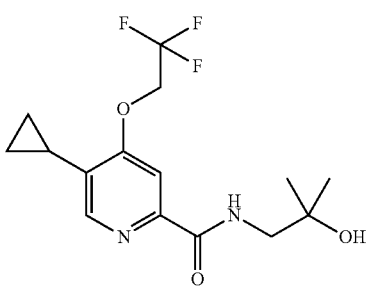 [SMILES: CC(C)(O)CNC(=O)c1cc(OCC(F)(F)F)c(C2CC2)cn1]

The title compound was synthesized in analogy to Example 24d, using 5-Cyclopropyl-4-(2,2,2-trifluoro-ethoxy)-pyridine-2-carboxylic acid (Example 48c) and 1-amino-2-methylpropan-2-ol (CAN 2854-16-2) as starting materials and isolated (28 mg, 34%) as a yellow oil; MS (ESI, m/z): 333.5 (M+H⁺).

Example 61

5-Cyclopropyl-4-(2,2,2-trifluoro-ethoxy)-pyridine-2-carboxylic acid [1-cyclopropyl-1-(5-methyl-[1,2,4]oxadiazol-3-yl)-ethyl]-amide (enantiomer A)

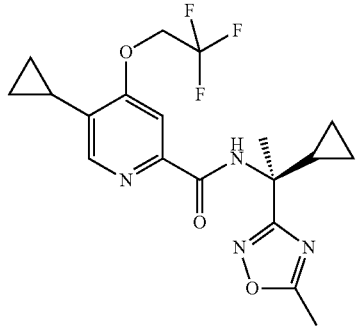 [SMILES: Cc1nc([C@@](C)(NC(=O)c2cc(OCC(F)(F)F)c(C3CC3)cn2)C2CC2)no1]

The racemate (Example 49) was separated into its enantiomers by preparative chiral HPLC (Chiralpak AD, isopropanol/heptane) and the title compound was the first enantiomer collected and isolated as colorless oil; MS (ESI, m/z): 411.1 (M+H$^+$).

Example 62

5-Chloro-4-(2,2,2-trifluoro-ethoxy)-pyridine-2-carboxylic acid [1-cyclopropyl-1-(5-methyl-[1,2,4]oxadiazol-3-yl)-ethyl]-amide

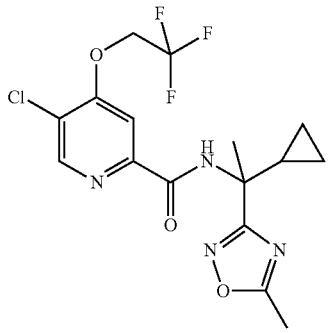 [SMILES: Cc1nc(C(C)(NC(=O)c2cc(OCC(F)(F)F)c(Cl)cn2)C2CC2)no1]

The title compound was synthesized in analogy to Example 24d, using 5-Chloro-4-(2,2,2-trifluoro-ethoxy)-pyridine-2-carboxylic acid (Example 24c) and 1-Cyclopropyl-1-(5-methyl-[1,2,4]oxadiazol-3-yl)-ethylamine (CAN 1155536-64-3) as starting materials and isolated (27.7 mg, 35%) as colorless oil; MS (ESI, m/z): 405.0 (M+H$^+$).

Example 63

5-Cyclopropyl-4-((R)-2,2,2-trifluoro-1-methyl-ethoxy)-pyridine-2-carboxylic acid (3-carbamoylmethyl-oxetan-3-yl)-amide

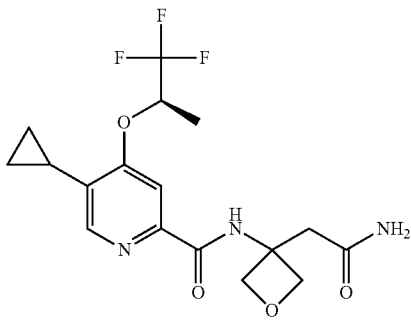 [SMILES: C[C@@H](Oc1cc(C(=O)NC2(CC(N)=O)COC2)ncc1C1CC1)C(F)(F)F]

a) 2-(3-Amino-oxetan-3-yl)-acetamide

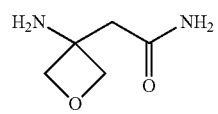

To a microwave tube was added ethyl 2-(3-aminooxetan-3-yl)acetate (CAN 1207175-54-9, 400 mg, 2.51 mmol) followed by toluene (8.0 ml) and 25% ammonium hydroxide (7.2 g, 8.0 ml, 51.4 mmol). The tube was sealed and the reaction mixture was stirred vigorously at room temperature for 6 days. The reaction mixture was concentrated in vacuo and azeotroped several times with 20 ml toluene. The crude solid was dried under high-vacuum at 40° C. to dryness to yield the title compound (290 mg, 89%) as a white solid. MS (ESI, m/z): 131.1 (M+H$^+$).

b) 4-Chloro-5-cyclopropyl-pyridine-2-carboxylic acid (3-carbamoylmethyl-oxetan-3-yl)-amide

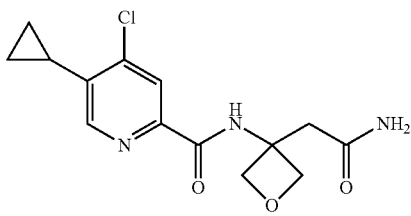 [SMILES: NC(=O)CC1(NC(=O)c2cc(Cl)c(C3CC3)cn2)COC1]

To a solution of 4-chloro-5-cyclopropyl-pyridine-2-carboxylic acid (Example 48b, 200 mg, 1.01 mmol) in DMF (4.0 ml) were added TBTU (357 mg, 1.11 mmol) and DIEA (654 mg, 866 μl, 5.06 mmol) and the reaction mixture was stirred at room temperature for 20 minutes. Addition of 2-(3-aminooxetan-3-yl)acetamide (158 mg, 1.21 mmol) and the reaction was stirred at room temperature for 18 hours. The reaction mixture was diluted with ethyl acetate and extracted with water. The organic phase was collected, dried over sodium sulfate and evaporated down to dryness. The crude material was purified by flash chromatography on silica, eluting with a ethyl acetate/heptane gradient to yield the title compound (80 mg, 26%) as a yellow solid. MS (ESI, m/z): 310.0 (M+H$^+$).

c) 5-Cyclopropyl-4-((R)-2,2,2-trifluoro-1-methyl-ethoxy)-pyridine-2-carboxylic acid (3-carbamoylmethyl-oxetan-3-yl)-amide To a solution of 4-Chloro-5-cyclopropyl-pyridine-2-carboxylic acid (3-carbamoylmethyl-oxetan-3-yl)-amide (Example 63b, 40 mg, 129 µmol) in dry DMF (1.5 mL) in a microwave-vial were added (R)-1,1,1-trifluoropropan-2-ol (CAN 17628-73-8, 42.1 mg, 258 µmol) and sodium hydride 60% (15.5 mg, 387 µmol) and the reaction mixture was stirred at room temperature for 10 minutes. The reaction mixture was heated to 100° C. for 30 minutes under microwave radiation. The reaction was directly purified by preparative HPLC without any work-up to yield the title compound (3.5 mg, 7.0%) as a grey solid. MS (ESI, m/z): 388.0 (M+H$^+$).

Example 64

5-Cyclopropyl-4-((S)-2,2,2-trifluoro-1-methyl-ethoxy)-pyridine-2-carboxylic acid (3-carbamoylmethyl-oxetan-3-yl)-amide

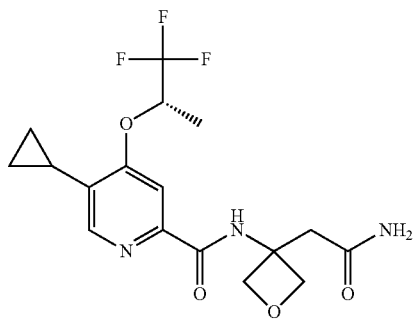 [SMILES: C[C@H](Oc1cc(C(=O)NC2(CC(N)=O)COC2)ncc1C1CC1)C(F)(F)F]

The title compound was synthesized in analogy to Example 63c, using 4-Chloro-5-cyclopropyl-pyridine-2-carboxylic acid (3-carbamoylmethyl-oxetan-3-yl)-amide (Example 63b) and (S)-1,1,1-trifluoropropan-2-ol (CAN 3539-97-7) as starting materials and isolated (9 mg, 18%) as light brown solid; MS (ESI, m/z): 388.0 (M+H$^+$).

Example 65

5-Cyclopropyl-4-(2,2,2-trifluoro-ethoxy)-pyridine-2-carboxylic acid (1-carbamoylmethyl-3-methyl-butyl)-amide (enantiomer A)

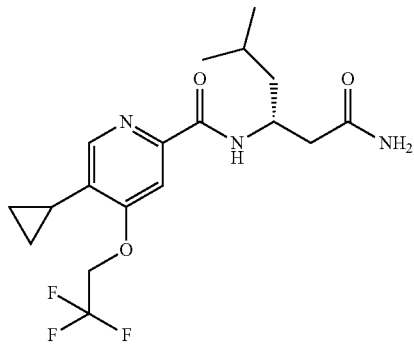 [SMILES: CC(C)C[C@H](CC(N)=O)NC(=O)c1cc(OCC(F)(F)F)c(C2CC2)cn1]

The title compound was synthesized in analogy to Example 63b, using 5-Cyclopropyl-4-(2,2,2-trifluoro-ethoxy)-pyridine-2-carboxylic acid (Example 48c) and 3-amino-5-methylhexanamide hydrochloride (CAN 93169-29-0) as starting materials to yield the racemate mixture. The racemate was separated into its enantiomers by preparative chiral HPLC (Chiralpak AD, isopropanol/heptane) and the title compound was the first enantiomer collected and isolated as colorless oil; MS (ESI, m/z): 388.0 (M+H$^+$).

Example 66

5-Cyclopropyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide (enantiomer A)

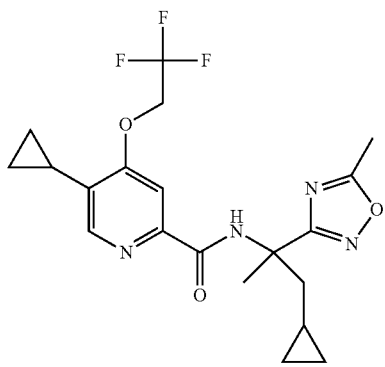 [SMILES: Cc1nc(C(C)(CC2CC2)NC(=O)c2cc(OCC(F)(F)F)c(C3CC3)cn2)no1]

a) 2-Amino-3-cyclopropyl-2-methyl-propionitrile

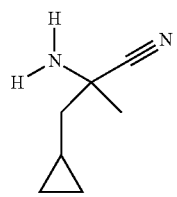

To a round bottom flask equipped with a condenser was added magnesium sulfate (4.33 g, 35.9 mmol), sodium cyanide (3.52 g, 71.9 mmol) and ammonium chloride (1.92 g, 35.9 mmol). The solids were slurried in a 7.0M solution of ammonia in methanol (30.8 ml, 216 mmol) at room temperature. To the resulting suspension was added 1-cyclopropyl-propan-2-one (CAN 4160-75-2, 8.3 g, 71.9 mmol) in one portion. The reaction mixture was stirred at room temperature for 4 hours. The solvents were removed under reduced pressure. The resulting slurry of the inorganic salts and product were diluted with tert-butylmethylether and solvent removed at reduced pressure. This process was repeated three times before the resulting suspension was filtered to remove the inorganic salts. The filtrate was then evaporated down to dryness to yield the crude product (7.9 g, 89%) as a yellow oil. MS (ESI, m/z): 125.3 (M+H$^+$).

b) (1-Cyano-2-cyclopropyl-1-methyl-ethyl)-carbamic acid benzyl ester

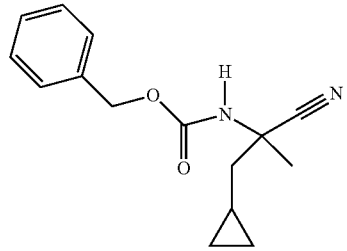 [SMILES: CC(C#N)(CC1CC1)NC(=O)OCc1ccccc1]

To a solution of 2-Amino-3-cyclopropyl-2-methyl-propionitrile (Example 66a, 5.01 g, 30.9 mmol) in dry THF (119 mL) was added DIEA (12.1 mL, 67.9 mmol) and benzyl carbonochloridate (CAN 501-53-1, 5.57 mL, 37.1 mmol). The reaction was stirred at 45° C. for 18 hours. The reaction mixture was concentrated under reduced pressure. The residue was dissolved in ethylacetate and extracted with an 1.0M aqueous solution of sodium bicarbonate. The organic layer was dried over sodium sulfate and evaporated down to dryness. The crude material was purified by flash chromatography eluting with a gradient of heptane/ethylacetate to yield the title compound (6.2, 60%) as a colorless oil. MS (ESI, m/z): 259.5 (M+H$^+$).

c) [2-Cyclopropyl-1-(N-hydroxycarbamimidoyl)-1-methyl-ethyl]-carbamic acid benzyl ester

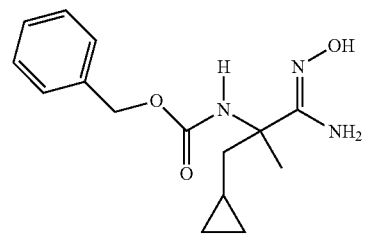 [SMILES: CC(CC1CC1)(NC(=O)OCc1ccccc1)/C(N)=N/O]

To a solution of (1-Cyano-2-cyclopropyl-1-methyl-ethyl)-carbamic acid benzyl ester (Example 66b, 795 mg, 3.08 mmol) in ethanol (10 ml) were added triethylamine (343 mg, 472 µl, 3.39 mmol) and hydroxylamine hydrochloride (214 mg, 3.08 mmol). The reaction mixture was stirred at 60° C. for 18 hours. The reaction mixture was concentrated in vacuo. The residue was dissolved in ethyl acetate and extracted with an 1.0M aqueous solution of sodium bicarbonate. The organic phase was dried over sodium sulfate and evaporated down to dryness. The crude material was purified by flash chromatography on silica eluting with a heptane/ethyl acetate gradient to yield the title compound (640 mg, 71%) as a white solid. MS (ESI, m/z): 292.5 (M+H$^+$).

d) [2-Cyclopropyl-1-methyl-1-(5-methyl-[1,2,4]oxadiazol-3-yl)-ethyl]-carbamic acid benzyl ester

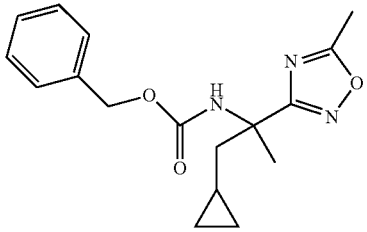 [SMILES: Cc1nc(C(C)(CC2CC2)NC(=O)OCc2ccccc2)no1]

To a solution of acetic acid (139 mg, 132 µl, 2.31 mmol) in dry DMF (8 ml) under an argon atmosphere was added carbonyldiimidazole (374 mg, 2.31 mmol) and the reaction mixture was stirred at room temperature for 45 minutes. Addition of a solution of [2-Cyclopropyl-1-(N-hydroxycarbamimidoyl)-1-methyl-ethyl]-carbamic acid benzyl ester (Example 66c, 0.64 g, 2.2 mmol) in dry DMF (4 ml) and the resulting reaction mixture was stirred at room temperature for 2 hours. The reaction was then stirred at 130° C. under microwave radiation for 30 minutes. The reaction mixture was concentrated in vacuo. The residue was dissolved in ethylacetate and extracted with an 1.0M aqueous solution of sodium bicarbonate. The organic phase was dried over sodium sulfate and evaporated down to dryness. The crude material was purified by flash chromatography on silica eluting with a heptane/ethylacetate gradient to yield the title compound (542 mg, 78%) as a yellow oil. MS (ESI, m/z): 316.5 (M+H$^+$).

e) 2-Cyclopropyl-1-methyl-1-(5-methyl-[1,2,4]oxadiazol-3-yl)-ethylamine

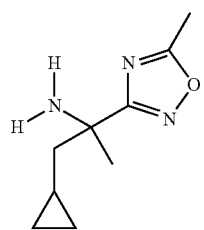

To a solution of [2-Cyclopropyl-1-methyl-1-(5-methyl-[1,2,4]oxadiazol-3-yl)-ethyl]-carbamic acid benzyl ester (Example 66d, 540 mg, 1.71 mmol) in ethanol (10 ml) under argon atmosphere was added palladium on charcoal 10% (54.7 mg, 514 µmol). The reaction was stirred at room temperature under a pressure of 2.5 bar hydrogen for 2 hours. The reaction mixture was filtered through a pad celite and the filter cake was washed two times with ethanol. The filtrate was evaporated down to dryness to yield the title compound (163 mg, 53%) as crude yellow oil which was used with any purification. MS (ESI, m/z): 182.2 (M+H$^+$).

f) 5-Cyclopropyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide

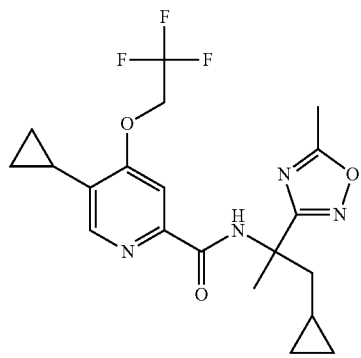 [SMILES: Cc1nc(C(C)(CC2CC2)NC(=O)c2cc(OCC(F)(F)F)c(C3CC3)cn2)no1]

The title compound was synthesized in analogy to Example 63b, using 5-Cyclopropyl-4-(2,2,2-trifluoro-ethoxy)-pyridine-2-carboxylic acid (Example 48c) and 2-Cyclopropyl-1-methyl-1-(5-methyl-[1,2,4]oxadiazol-3-yl)-ethylamine (Example 66e) as starting materials and the racemate was isolated (43 mg, 32%) as a colorless oil. The racemate was separated into its enantiomers by preparative chiral HPLC (Chiralpak AD, isopropanol/heptane) and the title compound was the first enantiomer collected and isolated as a colorless oil; MS (ESI, m/z): 425.5 (M+H$^+$). The collected enantiomer shows levorotation properties according to the observed optical activity measured during preparative chiral HPLC.

Example 67

5-Cyclopropyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide (enantiomer B)

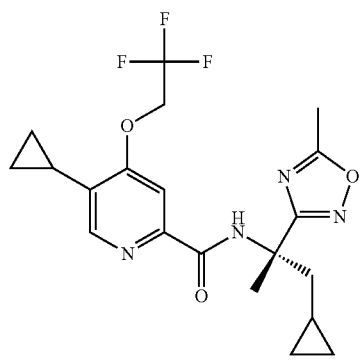 [SMILES: Cc1nc([C@](C)(CC2CC2)NC(=O)c2cc(OCC(F)(F)F)c(C3CC3)cn2)no1]

The racemate (Example 66f) was separated into its enantiomers by preparative chiral HPLC (Chiralpak AD, isopropanol/heptane) and the title compound was the second enantiomer collected and isolated as colorless oil; MS (ESI, m/z): 425.6 (M+H$^+$).

Example 68

5-Cyclopropyl-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (epimer A)

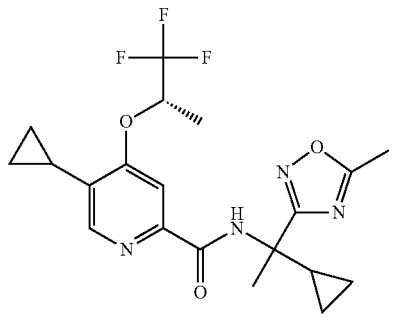 [SMILES: Cc1nc(C(C)(NC(=O)c2cc(O[C@@H](C)C(F)(F)F)c(C3CC3)cn2)C2CC2)no1]

a) 5-Cyclopropyl-4-((S)-2,2,2-trifluoro-1-methyl-ethoxy)-pyridine-2-carboxylic acid

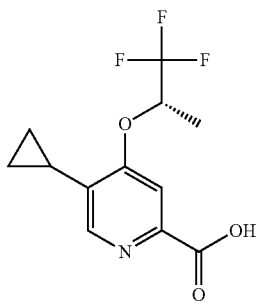 [SMILES: C[C@H](Oc1cc(C(=O)O)ncc1C1CC1)C(F)(F)F]

To a solution of 4-Chloro-5-cyclopropyl-pyridine-2-carboxylic acid (Example 48b, 0.87 g, 4.4 mmol) in dry DMF (12.0 ml) under an argon atmosphere were added (S)-1,1,1-trifluoropropan-2-ol (CAN 3539-97-7, 1.00 g, 8.8 mmol) and potassium tert-butoxide (1.48 g, 13.2 mmol). The reaction mixture was stirred at room temperature for 30 minutes and stirred at 120° C. for one hour under microwave radiation. DMF was removed in vacuo and the residue was dissolved in ethyl acetate. The solution was extracted with 20 mL of an 2.0M aqueous solution of hydrochloric acid. The organic phase was collected and the aqueous phase was back-extracted with ethyl acetate. The organic phases were combined, dried over sodium sulfate and evaporated down to dryness. The crude material was purified by flash chromatography on silica eluting with a dichloromethane/(3% solution formic acid in methanol) gradient to yield the title compound (505 mg, 33%) as a light brown solid. MS (ESI, m/z): 276.4 (M+H$^+$).

b) 5-Cyclopropyl-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (epimer A)

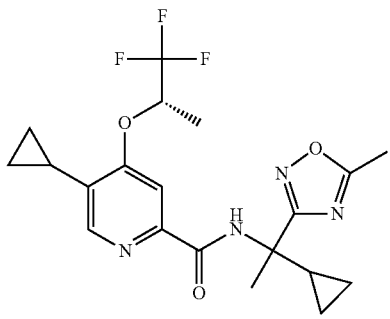 [SMILES: Cc1nc(C(C)(NC(=O)c2cc(O[C@@H](C)C(F)(F)F)c(C3CC3)cn2)C2CC2)no1]

The mixture of epimers was synthesized in analogy to Example 63b, using 5-Cyclopropyl-4-((S)-2,2,2-trifluoro-1-methyl-ethoxy)-pyridine-2-carboxylic acid (Example 68a) and 1-Cyclopropyl-1-(5-methyl-[1,2,4]oxadiazol-3-yl)-ethylamine (CAN 1155536-64-3) as starting materials and isolated (135 mg, 58%) as a light yellow oil. The mixture of epimers was separated into its epimers by preparative chiral HPLC (Chiralpak AD, ethanol/heptane) and the title compound was the first epimer collected and isolated as colorless oil; MS (ESI, m/z): 425.5 (M+H$^+$).

Example 69

5-Cyclopropyl-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (epimer B)

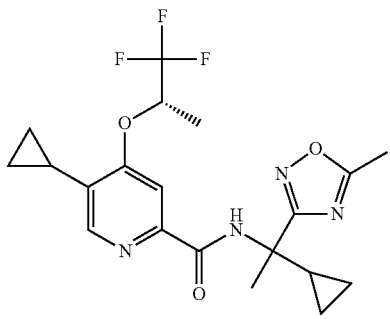 [SMILES: Cc1nc(C(C)(NC(=O)c2cc(O[C@@H](C)C(F)(F)F)c(C3CC3)cn2)C2CC2)no1]

The mixture of epimers (Example 68b) was separated into its epimers by preparative chiral HPLC (Chiralpak AD, ethanol/heptane) and the title compound was the second epimer collected and isolated as colorless oil; MS (ESI, m/z): 425.5 (M+H$^+$).

Example 70

5-Cyclopropyl-4-(2,2,2-trifluoro-ethoxy)-pyridine-2-carboxylic acid tert-butylamide

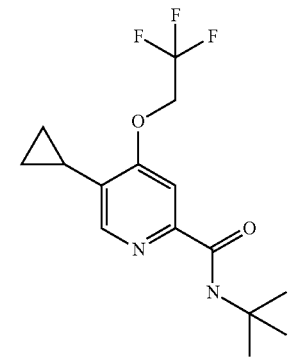 [SMILES: CC(C)(C)NC(=O)c1cc(OCC(F)(F)F)c(C2CC2)cn1]

The title compound was synthesized in analogy to Example 63b, using 5-Cyclopropyl-4-(2,2,2-trifluoro-ethoxy)-pyridine-2-carboxylic acid (Example 48c) and 2-methylpropan-2-amine (CAN 75-64-9) as starting materials and isolated (12.5 mg, 17%) as colorless oil; MS (ESI, m/z): 317.1 (M+H$^+$).

Example 71

[5-Cyclopropyl-4-(2,2,2-trifluoro-ethoxy)-pyridin-2-yl]-(2-oxa-5-aza-spiro[3.4]oct-5-yl)-methanone

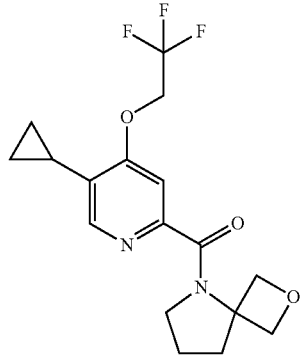 [SMILES: O=C(c1cc(OCC(F)(F)F)c(C2CC2)cn1)N1CCCC12COC2]

The title compound was synthesized in analogy to Example 63b, using 5-Cyclopropyl-4-(2,2,2-trifluoro-ethoxy)-pyridine-2-carboxylic acid (Example 48c) and 2-Oxa-5-aza-spiro[3.4]octane oxalate (CAN 1380571-82-3) as starting materials and isolated (37.6 mg, 46%) as colorless oil; MS (ESI, m/z): 357.1 (M+H$^+$).

Example 72

5-Cyclopropyl-4-((R)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (epimer A)

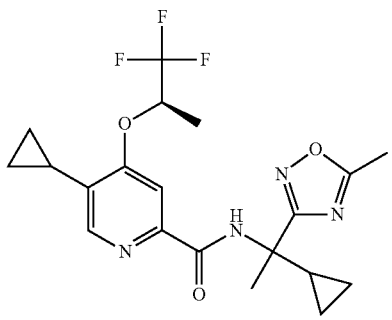 [SMILES: Cc1nc(C(C)(NC(=O)c2cc(O[C@H](C)C(F)(F)F)c(C3CC3)cn2)C2CC2)no1]

a) 5-Cyclopropyl-4-((R)-2,2,2-trifluoro-1-methyl-ethoxy)-pyridine-2-carboxylic acid

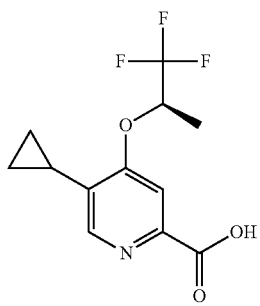 [SMILES: C[C@@H](Oc1cc(C(=O)O)ncc1C1CC1)C(F)(F)F]

The title compound was synthesized in analogy to Example 68a, using 4-Chloro-5-cyclopropyl-pyridine-2-carboxylic acid (Example 48b) and (R)-1,1,1-trifluoropropan-2-ol (CAN 17628-73-8) as starting materials and isolated (231 mg, 41%) as light brown solid; MS (ESI, m/z): 276.5 (M+H$^+$).

b) 5-Cyclopropyl-4-((R)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (epimer A)

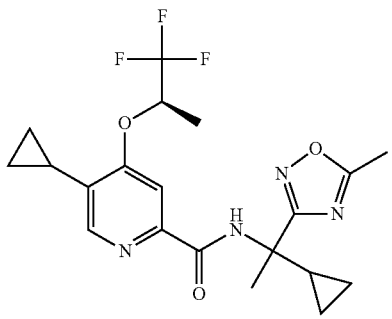 [SMILES: Cc1nc(C(C)(NC(=O)c2cc(O[C@H](C)C(F)(F)F)c(C3CC3)cn2)C2CC2)no1]

The mixture of epimers was synthesized in analogy to Example 63b, using 5-Cyclopropyl-4-((R)-2,2,2-trifluoro-1-methyl-ethoxy)-pyridine-2-carboxylic acid (Example 73a) and 1-Cyclopropyl-1-(5-methyl-[1,2,4]oxadiazol-3-yl)-ethylamine (CAN 1155536-64-3) as starting materials and isolated (135 mg, 70%) as light yellow oil. The mixture of epimers was separated by preparative chiral HPLC (Chiralpak AD, isopropanol/heptane) and the title compound was the first epimer collected and isolated as colorless oil; MS (ESI, m/z): 425.5 (M+H$^+$).

Example 73

5-Cyclopropyl-4-((R)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (epimer B)

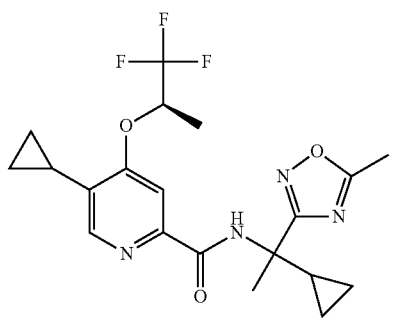 [SMILES: Cc1nc(C(C)(NC(=O)c2cc(O[C@H](C)C(F)(F)F)c(C3CC3)cn2)C2CC2)no1]

The mixture of epimers were separated by preparative chiral HPLC (Chiralpak AD, isopropanol/heptane) and the title compound was the second epimer collected and isolated as colorless oil; MS (ESI, m/z): 425.5 (M+H$^+$).

Example 74

5-Chloro-4-(2,2,2-trifluoro-ethoxy)-pyridine-2-carboxylic acid [1-cyclopropyl-1-(5-methyl-[1,2,4]oxadiazol-3-yl)-ethyl]-amide (enantiomer A)

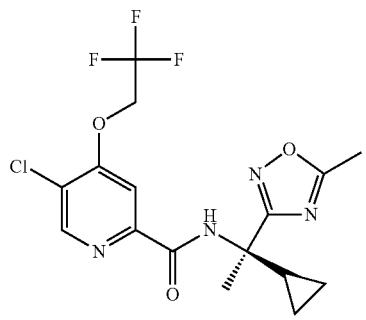 [SMILES: Cc1nc([C@](C)(NC(=O)c2cc(OCC(F)(F)F)c(Cl)cn2)C2CC2)no1]

81

The racemate (Example 62) was separated into its enantiomers by preparative chiral HPLC (Chiralpak AD, isopropanol/heptane) and the title compound was the first enantiomer collected and isolated as colorless oil; MS (ESI, m/z): 405.3 (M+H⁺).

Example 75

5-Chloro-4-(2,2,2-trifluoro-ethoxy)-pyridine-2-carboxylic acid [1-cyclopropyl-1-(5-methyl-[1,2,4]oxadiazol-3-yl)-ethyl]-amide (enantiomer B)

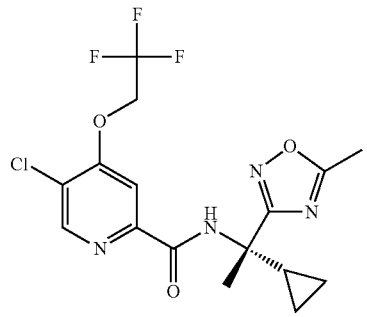 [SMILES: Cc1nc([C@@](C)(NC(=O)c2cc(OCC(F)(F)F)c(Cl)cn2)C2CC2)no1]

The racemate (Example 62) was separated into its enantiomers by preparative chiral HPLC (Chiralpak AD, isopropanol/heptane) and the title compound was the second enantiomer collected and isolated as colorless oil; MS (ESI, m/z): 405.3 (M+H⁺).

Example 76

[5-Cyclopropyl-4-(2,2,2-trifluoro-ethoxy)-pyridin-2-yl]-(3,3-difluoro-azetidin-1-yl)-methanone

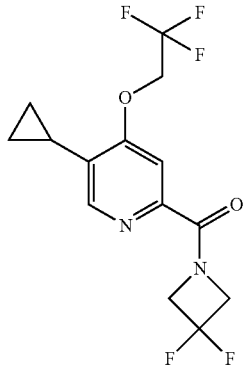 [SMILES: O=C(c1cc(OCC(F)(F)F)c(C2CC2)cn1)N1CC(F)(F)C1]

The title compound was synthesized in analogy to Example 63b, using 5-Cyclopropyl-4-(2,2,2-trifluoro-ethoxy)-pyridine-2-carboxylic acid (Example 48c) and 3,3-difluoroazetidine hydrochloride (CAN 288315-03-7) as starting materials and isolated (21 mg, 37%) as colorless oil; MS (ESI, m/z): 337.4 (M+H⁺).

82

Example 77

5-Cyclopropyl-4-(2,2,2-trifluoro-ethoxy)-pyridine-2-carboxylic acid (1-carbamoyl-1-methyl-propyl)-amide

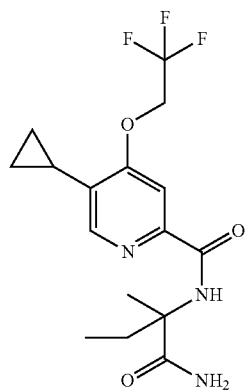 [SMILES: CCC(C)(NC(=O)c1cc(OCC(F)(F)F)c(C2CC2)cn1)C(N)=O]

The title compound was synthesized in analogy to Example 63b, using 5-Cyclopropyl-4-(2,2,2-trifluoro-ethoxy)-pyridine-2-carboxylic acid (Example 48c) and 2-Methyl-2-methylamino-butyramide hydrochloride (CAN 18305-22-1) as starting materials and isolated (19.6 mg, 16%) as a white solid; MS (ESI, m/z): 360.5 (M+H⁺).

Example 78

5-(3,3-Difluoro-azetidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide

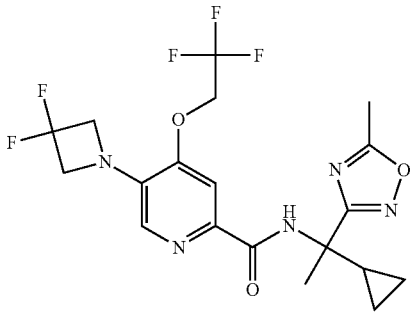 [SMILES: Cc1nc(C(C)(NC(=O)c2cc(OCC(F)(F)F)c(N3CC(F)(F)C3)cn2)C2CC2)no1]

a) 3-Bromo-4-(2,2,2-trifluoro-ethoxy)-pyridine

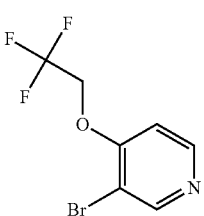 [SMILES: FC(F)(F)COc1ccncc1Br]

The title compound was synthesized in analogy to Example 53a, using 3-bromo-4-chloropyridine (CAN 36953-42-1) and 2,2,2-trifluoroethanol (CAN 75-89-8) as starting materials and isolated (7.4 g, 78%) as a yellow oil; MS (ESI, m/z): 256.1 (M+H⁺).

b) 3-Bromo-4-(2,2,2-trifluoro-ethoxy)-pyridine 1-oxide

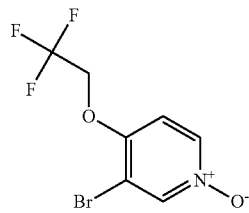 [SMILES: [O-][n+]1ccc(OCC(F)(F)F)c(Br)c1]

The title compound was synthesized in analogy to Example 53b, using 3-Bromo-4-(2,2,2-trifluoro-ethoxy)-pyridine (Example 78a) as starting material and isolated (5.7 g, 72%) as a white solid; MS (ESI, m/z): 272.2 (M+H⁺).

c) 5-Bromo-4-(2,2,2-trifluoro-ethoxy)-pyridine-2-carbonitrile

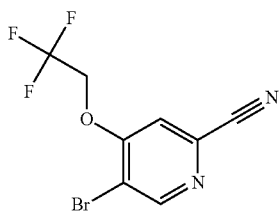

The title compound was synthesized in analogy to Example 53c, using 3-Bromo-4-(2,2,2-trifluoro-ethoxy)-pyridine 1-oxide (Example 78b) as starting material and isolated (587 mg, 28%) as a white solid; MS (ESI, m/z): 281.0 (M+H⁺).

d) 5-Bromo-4-(2,2,2-trifluoro-ethoxy)-pyridine-2-carboxylic acid

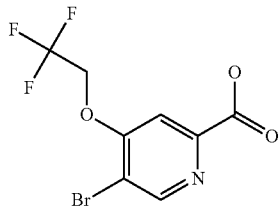 [SMILES: O=C(O)c1cc(OCC(F)(F)F)c(Br)cn1]

A solution of 5-Bromo-4-(2,2,2-trifluoro-ethoxy)-pyridine-2-carbonitrile (Example 78c, 1 g, 3.56 mmol) in sulfuric acid 97% (5 ml) was stirred at 120° C. for 2 h and a 6.0M aqueous solution of sodium nitrite (2.08 ml, 12.5 mmol, Eq: 3.5) was then slowly added to it at r.t. The resulting reaction mixture was stirred at room temperature for 30 minutes and stirred at 80° C. for 1 hour. The reaction was diluted by addition of 20 gr of ice and the pH was adjusted to 1-2 by addition of sodium hydroxide pellets by portions. A precipitate formed and was filtered off, dried under high vacuum to yield the title compound (1.02 g, 95%) as a white solid. MS (ESI, m/z): 300.2 (M+H⁺).

e) 5-Bromo-4-(2,2,2-trifluoro-ethoxy)-pyridine-2-carboxylic acid (methyl-cyano-cyclopropyl-methyl)-amide

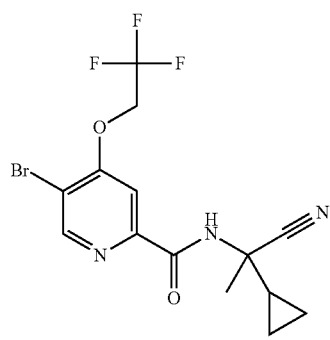 [SMILES: CC(C#N)(NC(=O)c1cc(OCC(F)(F)F)c(Br)cn1)C1CC1]

To a solution of 5-Bromo-4-(2,2,2-trifluoro-ethoxy)-pyridine-2-carboxylic acid (Example 78d, 1.0 g, 3.33 mmol) dry DMF (15 ml) were added TBTU (1.12 g, 3.5 mmol) and triethylamine (675 mg, 929 µl, 6.67 mmol). The reaction mixture was stirred at room temperature for 30 minutes followed by addition of 2-amino-2-cyclopropylpropanenitrile (CAN 37024-73-0, 404 mg, 3.67 mmol). The reaction was stirred at room temperature for 18 hours. The reaction mixture was poured into a separatory funnel, diluted with ethylacetate and extracted with an 1.0M aqueous solution of sodium bicarbonate. The organic phase was collected and the aqueous phase was back-extracted with ethylacetate. The organic phases were combined, dried over sodium sulfate and evaporated down to dryness. The crude material was purified by flash chromatography on silica eluting a heptane/ethylacetate gradient to yield the title compound (910 mg, 70%) as a light yellow oil. MS (ESI, m/z): 392.3 (M+H⁺).

f) 5-Bromo-4-(2,2,2-trifluoro-ethoxy)-pyridine-2-carboxylic acid [1-cyclopropyl-1-(N-hydroxycarbamimidoyl)-ethyl]-amide

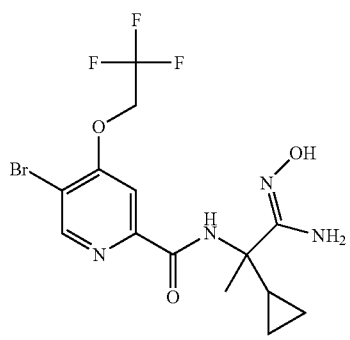 [SMILES: CC(NC(=O)c1cc(OCC(F)(F)F)c(Br)cn1)(/C(N)=N/O)C1CC1]

To a solution of 5-Bromo-4-(2,2,2-trifluoro-ethoxy)-pyridine-2-carboxylic acid (methyl-cyano-cyclopropyl-methyl)-amide (Example 78e, 900 mg, 2.29 mmol) in ethanol (15 ml)

were added triethylamine (244 mg, 336 µl, 2.41 mmol) and hydroxylamine hydrochloride (167 mg, 2.41 mmol). The reaction mixture was then stirred at 65° C. for 18 hours. Volatiles were removed in vacuo and the residue was dissolved in ethylacetate which was extracted with an 1.0M aqueous solution of sodium bicarbonate. The organic phase was dried over sodium sulfate and evaporated down to dryness. The crude material was purified by flash chromatography on silica eluting with a heptane/ethylacetate gradient to yield the title compound (576 mg, 59%) as a white solid. MS (ESI, m/z): 425.3 (M+H$^+$).

g) 5-Bromo-4-(2,2,2-trifluoro-ethoxy)-pyridine-2-carboxylic acid [1-cyclopropyl-1-(5-methyl-[1,2,4] oxadiazol-3-yl)-ethyl]-amide

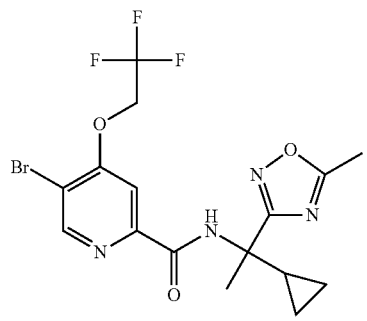 [SMILES: Cc1nc(C(C)(NC(=O)c2cc(OCC(F)(F)F)c(Br)cn2)C2CC2)no1]

To a solution of 5-Bromo-4-(2,2,2-trifluoro-ethoxy)-pyridine-2-carboxylic acid [1-cyclopropyl-1-(N-hydroxycarbamimidoyl)-ethyl]-amide (Example 78f, 800 mg, 1.88 mmol) in dry DMF (10 ml) was added triethylamine (190 mg, 262 µl, 1.88 mmol) followed by addition of acetic anhydride (192 mg, 1.88 mmol). The reaction mixture was stirred at room temperature for 1 hours and was then stirred at 125° C. for 30 min under microwave radiation. DMF was removed in vacuo and the residue was dissolved in ethylacetate which was extracted with an 1.0M aqueous solution of sodium bicarbonate. The organic phase was dried over sodium sulfate and evaporated down to dryness. The crude material was purified by flash chromatography on silica eluting with a heptane/ethylacetate gradient to yield the title compound (492 mg, 47%) as a light yellow oil. MS (ESI, m/z): 449.3 (M+H$^+$).

h) 5-(3,3-Difluoro-azetidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide To a solution of 5-Bromo-4-(2,2,2-trifluoro-ethoxy)-pyridine-2-carboxylic acid [1-cyclopropyl-1-(5-methyl-[1,2,4] oxadiazol-3-yl)-ethyl]-amide (Example 78g, 0.05 g, 111 µmol) in dry Toluene (1 ml) under argon atmosphere were added palladium(II) acetate (3.75 mg, 16.7 µmol), BINAP (10.4 mg, 16.7 µmol), cesium carbonate (90.7 mg, 278 µmol) and 3,3-difluoroazetidine hydrochloride (CAN 288315-03-7, 15.9 mg, 122 µmol). The reaction mixture was stirred at 120° C. for 45 minutes under microwave radiation. The reaction mixture was filtered through a pad of Celite and the filtrate was concentrated in vacuo. The residue was dissolved in ethylacetate and extracted with an 1.0M aqueous solution of sodium bicarbonate. The organic phase was dried over sodium sulfate and evaporated down to dryness. The crude material was purified by flash chromatography on silica eluting with a heptane/ethylacetate gradient to yield the title compound (14.2 mg, 28%) as a white solid. MS (ESI, m/z): 462.4 (M+H$^+$).

Example 79

5-(3,3-Difluoro-pyrrolidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide

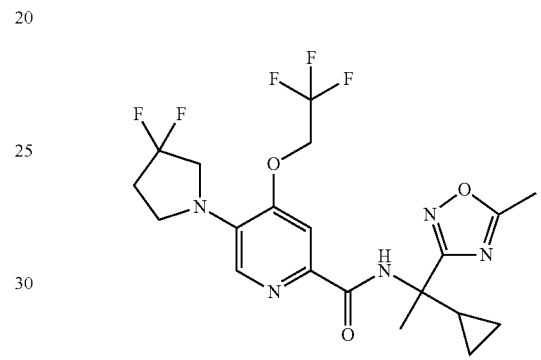

The title compound was synthesized in analogy to Example 78h, using 5-Bromo-4-(2,2,2-trifluoro-ethoxy)-pyridine-2-carboxylic acid [1-cyclopropyl-1-(5-methyl-[1,2,4] oxadiazol-3-yl)-ethyl]-amide (Example 78g) and 3,3-difluoropyrrolidine hydrochloride (CAN 163457-23-6) as starting materials and isolated (17 mg, 32%) as a white solid; MS (ESI, m/z): 476.4 (M+H$^+$).

Example 80

5-Chloro-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide

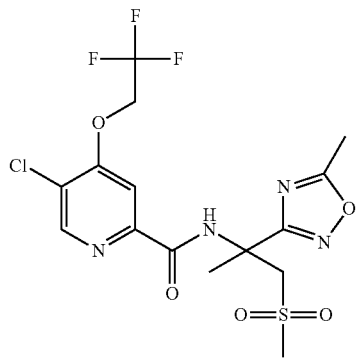

87 a)
2-Amino-3-methanesulfonyl-2-methyl-propionitrile

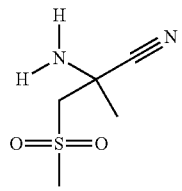

To a solution of 1-(methylsulfonyl)propan-2-one (CAN 5000-46-4, 15 g, 110 mmol) in water (60 ml) and ammonia aqueous 25% (10 ml) was added ammonium chloride (7.07 g, 132 mmol). The reaction mixture was stirred at room temperature for 1 hour followed by addition of potassium cyanide (9.32 g, 143 mmol). The reaction mixture was then stirred at room temperature for 18 hours. The reaction mixture was then poured into a mixture of ice/water and the aqueous phase was extracted three times with ethylacetate. The organic phases were combined, dried over sodium sulfate and evaporated down to dryness. The crude material was purified by flash chromatography on silica eluting with a heptane/ethylacetate gradient to yield the title compound (8.12 gr, 45%) as a light yellow solid. MS (ESI, m/z): 163.2 (M+H$^+$).

b) 5-Chloro-4-(2,2,2-trifluoro-ethoxy)-pyridine-2-carboxylic acid (1-cyano-2-methanesulfonyl-1-methyl-ethyl)-amide

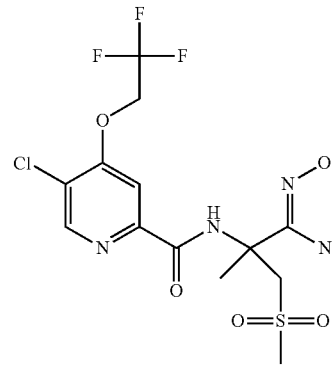 [SMILES: CC(CS(C)(=O)=O)(NC(=O)c1cc(OCC(F)(F)F)c(Cl)cn1)/C(N)=N/O]

The title compound was synthesized in analogy to Example 78e, using 5-Chloro-4-(2,2,2-trifluoro-ethoxy)-pyridine-2-carboxylic acid (Example 24c) and 2-Amino-3-methanesulfonyl-2-methyl-propionitrile (Example 80a) as starting materials and isolated (583 mg, 56%) as a white solid; MS (ESI, m/z): 400.9 (M+H$^+$).

88 c) 5-Chloro-4-(2,2,2-trifluoro-ethoxy)-pyridine-2-carboxylic acid [1-(N-hydroxycarbamimidoyl)-2-methanesulfonyl-1-methyl-ethyl]-amide The title compound was synthesized in analogy to Example 78f, using 5-Chloro-4-(2,2,2-trifluoro-ethoxy)-pyridine-2-carboxylic acid (1-cyano-2-methanesulfonyl-1-methyl-ethyl)-amide (Example 80d) as starting material and isolated (332 mg, 53%) as a white solid; MS (ESI, m/z): 433.3 (M+H$^+$).

d) 5-Chloro-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide The title compound was synthesized in analogy to Example 78g, using 5-Chloro-4-(2,2,2-trifluoro-ethoxy)-pyridine-2-carboxylic acid [1-(N-hydroxycarbamimidoyl)-2-methanesulfonyl-1-methyl-ethyl]-amide (Example 80c) as starting material and isolated (7.6 mg, 14%) as a white solid; MS (ESI, m/z): 457.3 (M+H$^+$).

Example 81

5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide

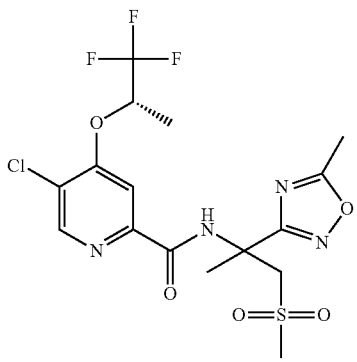 [SMILES: Cc1nc(C(C)(CS(C)(=O)=O)NC(=O)c2cc(O[C@@H](C)C(F)(F)F)c(Cl)cn2)no1]

a) 5-Cyclopropyl-4-((S)-2,2,2-trifluoro-1-methyl-ethoxy)-pyridine-2-carboxylic acid (1-cyano-2-methanesulfonyl-1-methyl-ethyl)-amide

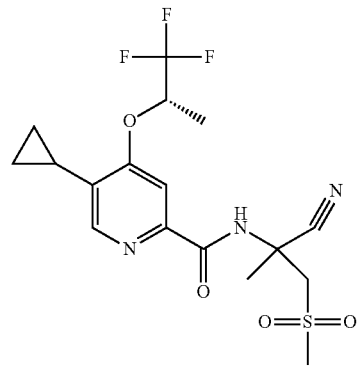 [SMILES: C[C@H](Oc1cc(C(=O)NC(C)(C#N)CS(C)(=O)=O)ncc1C1CC1)C(F)(F)F]

The title compound was synthesized in analogy to Example 78e, using 5-Cyclopropyl-4-((S)-2,2,2-trifluoro-1-methyl-ethoxy)-pyridine-2-carboxylic acid (Example 68a) and 2-Amino-3-methanesulfonyl-2-methyl-propionitrile (Example 80a) as starting materials and isolated (503 mg, 54%) as a white solid; MS (ESI, m/z): 420.4 (M+H$^+$).

b) 5-Cyclopropyl-4-((S)-2,2,2-trifluoro-1-methyl-ethoxy)-pyridine-2-carboxylic acid [1-(N-hydroxy-carbamimidoyl)-2-methanesulfonyl-1-methyl-ethyl]-amide

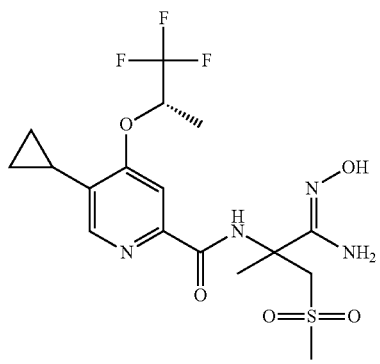 [SMILES: C[C@H](Oc1cc(C(=O)NC(C)(CS(C)(=O)=O)/C(N)=N/O)ncc1C1CC1)C(F)(F)F]

The title compound was synthesized in analogy to Example 78f, using 5-Cyclopropyl-4-((S)-2,2,2-trifluoro-1-methyl-ethoxy)-pyridine-2-carboxylic acid (1-cyano-2-methanesulfonyl-1-methyl-ethyl)-amide (Example 81a) as starting material and isolated (257 mg, 48%) as a white solid; MS (ESI, m/z): 453.5 (M+H$^+$).

c) 5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide The title compound was synthesized in analogy to Example 78g, using 5-Cyclopropyl-4-((S)-2,2,2-trifluoro-1-methyl-ethoxy)-pyridine-2-carboxylic acid [1-(N-hydroxy-carbamimidoyl)-2-methanesulfonyl-1-methyl-ethyl]-amide (Example 81b) as starting material and isolated (8.1 mg, 15%) as a white solid; MS (ESI, m/z): 477.4 (M+H$^+$).

Example 82

5-Cyclopropyl-4-(2,2,2-trifluoro-ethoxy)-pyridine-2-carboxylic acid (1-carbamoyl-1,3-dimethyl-butyl)-amide

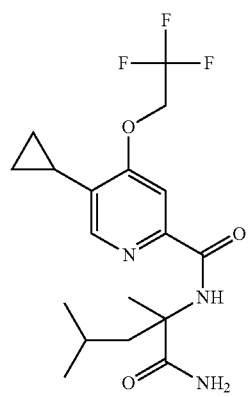 [SMILES: CC(C)CC(C)(NC(=O)c1cc(OCC(F)(F)F)c(C2CC2)cn1)C(N)=O]

The title compound was synthesized in analogy to Example 23b, using 5-Cyclopropyl-4-(2,2,2-trifluoro-ethoxy)-pyridine-2-carboxylic acid (Example 48c) and 2-amino-2,4-dimethylpentanamide (CAN 113509-60-7) as starting materials and isolated (41 mg, 32%) as a white solid; MS (ESI, m/z): 388.2 (M+H$^+$).

Example 83

5-Chloro-4-(2,2,2-trifluoro-ethoxy)-pyridine-2-carboxylic acid [1,3,3-trimethyl-1-(5-methyl-[1,2,4]oxadiazol-3-yl)-butyl]-amide

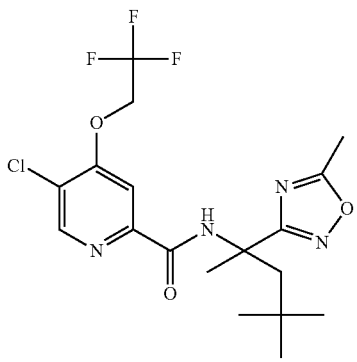 [SMILES: Cc1nc(C(C)(CC(C)(C)C)NC(=O)c2cc(OCC(F)(F)F)c(Cl)cn2)no1]

a) 5-Chloro-4-(2,2,2-trifluoro-ethoxy)-pyridine-2-carboxylic acid (1-cyano-1,3,3-trimethyl-butyl)-amide

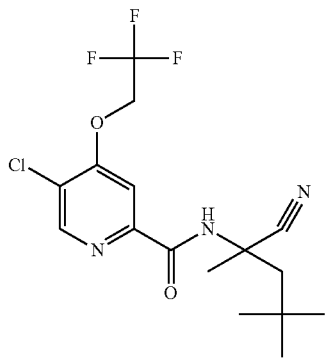 [SMILES: CC(C)(C)CC(C)(C#N)NC(=O)c1cc(OCC(F)(F)F)c(Cl)cn1]

The title compound was synthesized in analogy to Example 78e, using 5-Chloro-4-(2,2,2-trifluoro-ethoxy)-pyridine-2-carboxylic acid (Example 24c) and 2-amino-2,4,4-trimethylpentanenitrile (CAN 65260-84-6) as starting materials and isolated (643 mg, 87%) as a yellow oil; MS (ESI, m/z): 378.4 (M+H$^+$).

b) 5-Chloro-4-(2,2,2-trifluoro-ethoxy)-pyridine-2-carboxylic acid [1-(N-hydroxycarbamimidoyl)-1,3,3-trimethyl-butyl]-amide

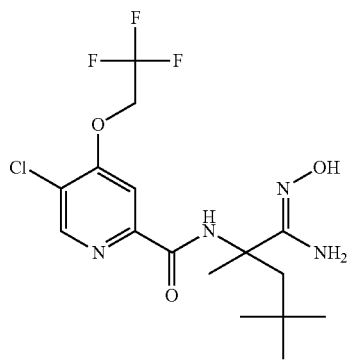 [SMILES: CC(C)(C)CC(C)(NC(=O)c1cc(OCC(F)(F)F)c(Cl)cn1)/C(N)=N/O]

The title compound was synthesized in analogy to Example 78f, using 5-Chloro-4-(2,2,2-trifluoro-ethoxy)-pyridine-2-carboxylic acid (1-cyano-1,3,3-trimethyl-butyl)-amide (Example 83a) as starting material and isolated (375 mg, 53%) as a white solid; MS (ESI, m/z): 411.4 (M+H$^+$).

c) 5-Chloro-4-(2,2,2-trifluoro-ethoxy)-pyridine-2-carboxylic acid [1,3,3-trimethyl-1-(5-methyl-[1,2,4]oxadiazol-3-yl)-butyl]-amide The title compound was synthesized in analogy to Example 78g, using 5-Chloro-4-(2,2,2-trifluoro-ethoxy)-pyridine-2-carboxylic acid [1-(N-hydroxycarbamimidoyl)-1,3,3-trimethyl-butyl]-amide (Example 83b) as starting material and isolated (15.3 mg, 29%) as colorless oil; MS (ESI, m/z): 435.5 (M+H$^+$).

Example 84

5-Cyclopropyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide

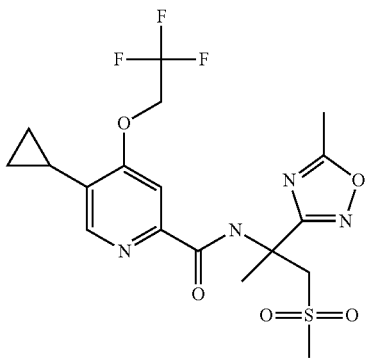 [SMILES: Cc1nc(C(C)(CS(C)(=O)=O)NC(=O)c2cc(OCC(F)(F)F)c(C3CC3)cn2)no1]

a) 5-Bromo-4-(2,2,2-trifluoro-ethoxy)-pyridine-2-carboxylic acid (1-cyano-2-methanesulfonyl-1-methyl-ethyl)-amide

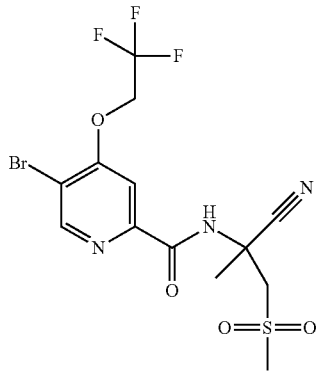 [SMILES: CC(C#N)(CS(C)(=O)=O)NC(=O)c1cc(OCC(F)(F)F)c(Br)cn1]

The title compound was synthesized in analogy to Example 78e, using 5-Bromo-4-(2,2,2-trifluoro-ethoxy)-pyridine-2-carboxylic acid (Example 78d) and 2-Amino-3-methanesulfonyl-2-methyl-propionitrile (Example 80a) as starting material and isolated (570 mg, 77%) as a yellow oil; MS (ESI, m/z): 444.3 (M+H$^+$).

b) 5-Bromo-4-(2,2,2-trifluoro-ethoxy)-pyridine-2-carboxylic acid [1-(N-hydroxycarbamimidoyl)-2-methanesulfonyl-1-methyl-ethyl]-amide

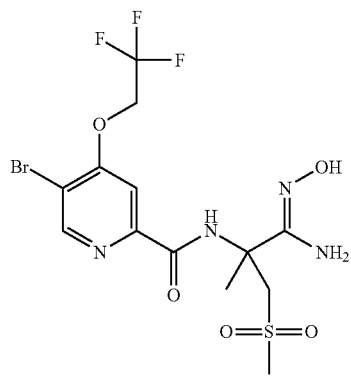 [SMILES: CC(CS(C)(=O)=O)(NC(=O)c1cc(OCC(F)(F)F)c(Br)cn1)/C(N)=N/O]

The title compound was synthesized in analogy to Example 78f, using 5-Bromo-4-(2,2,2-trifluoro-ethoxy)-pyridine-2-carboxylic acid (1-cyano-2-methanesulfonyl-1-methyl-ethyl)-amide (Example 84a) as starting material and isolated (151 mg, 25%) as a white solid; MS (ESI, m/z): 477.3 (M+H$^+$).

c) 5-Bromo-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide

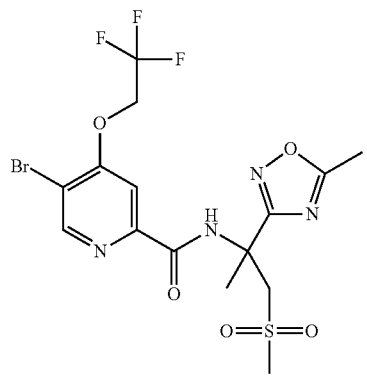 [SMILES: Cc1nc(C(C)(CS(C)(=O)=O)NC(=O)c2cc(OCC(F)(F)F)c(Br)cn2)no1]

The title compound was synthesized in analogy to Example 78g, using 5-Bromo-4-(2,2,2-trifluoro-ethoxy)-pyridine-2-carboxylic acid [1-(N-hydroxycarbamimidoyl)-2-methanesulfonyl-1-methyl-ethyl]amide (Example 84b) as starting material and isolated (132 mg, 72%) as a yellow oil; MS (ESI, m/z): 501.4 (M+H$^+$).

d) 5-Cyclopropyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide To a solution of 5-Bromo-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide (Example 84c, 60 mg, 120 µmol) in dry THF (0.5 ml) under an argon atmosphere was added tetrakis(tripehylphosphine) palladium(0) (13.8 mg, 12.0 µmol) followed by cyclopropylzinc(II) bromide solution 0.5M in THF (527 µl, 263 µmol). The reaction mixture was then stirred at 100° C. under microwave radiation for 90 min. The reaction mixture was concentrated in vacuo. The residue was dissolved in ethylacetate and solution was extracted with an 1.0M aqueous solution of sodium bicarbonate. The organic phase was dried over sodium sulfate and evaporated down to dryness. The crude material was purified by preparative HPLC to yield the title compound (5.9 mg, 11%) as white solid. MS (ESI, m/z): 463.4 (M+H$^+$).

Example 85

5-Chloro-4-(2,2,2-trifluoro-ethoxy)-pyridine-2-carboxylic acid (3-dimethylcarbamoylmethyl-oxetan-3-yl)-amide

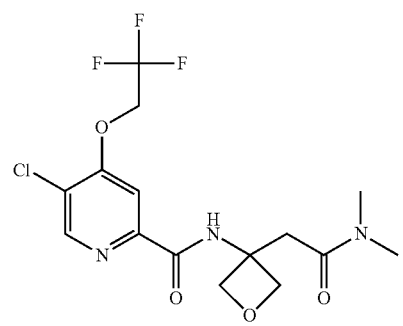 [SMILES: CN(C)C(=O)CC1(NC(=O)c2cc(OCC(F)(F)F)c(Cl)cn2)COC1]

a) 2-(3-Amino-oxetan-3-yl)-N,N-dimethyl-acetamide

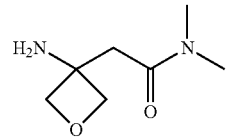

In a microwave tube was added ethyl 2-(3-aminooxetan-3-yl)acetate (CAN 1207175-54-9, 470 mg, 2.95 mmol). Toluene (7.0 ml) and 40%-dimethylamine solution in water (8.9 g, 10.0 ml, 79.0 mmol) were added. The tube was sealed and the reaction mixture was stirred vigorously at room temperature for 7 days. The reaction mixture was concentrated in vacuo and azeotroped several times with 30 mL toluene. The crude solid was dried under high vacuum at 40° C. for 3 hours to yield the title compound (405 mg, 87%). MS (ESI, m/z): 159.1 (M+H$^+$).

b) 5-Chloro-4-(2,2,2-trifluoro-ethoxy)-pyridine-2-carboxylic acid (3-dimethylcarbamoylmethyl-oxetan-3-yl)-amide The title compound was synthesized in analogy to Example 23b, using 5-Chloro-4-(2,2,2-trifluoro-ethoxy)-pyridine-2-carboxylic acid (Example 24c) and 2-(3-Amino-oxetan-3-yl)-N,N-dimethyl-acetamide as starting materials and isolated (4 mg, 5%) as colorless oil; MS (ESI, m/z): 396.4 (M+H$^+$).

Example 86

4-(3-Chloro-phenyl)-pyridine-2-carboxylic acid tert-butyl-methyl-amide

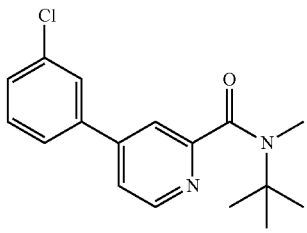 [SMILES: CN(C(=O)c1cc(-c2cccc(Cl)c2)ccn1)C(C)(C)C]

The title compound was synthesized in analogy to Example 1, using 4-(3-chlorophenyl)picolinic acid (CAN 1207725-34-5) and N,2-dimethylpropan-2-amine (CAN 14610-37-8) as starting materials and isolated (10 mg, 77%) as colorless oil; MS (ESI, m/z): 303.4 (MH$^+$).

Example 87

5-(3,3-Difluoro-azetidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide (enantiomer A)

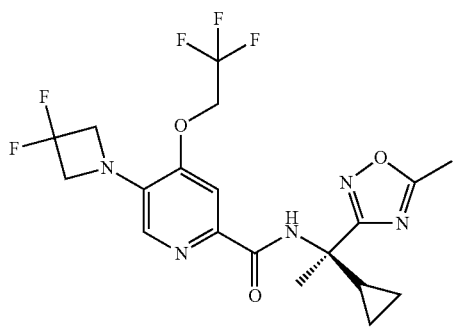 [SMILES: Cc1nc([C@](C)(NC(=O)c2cc(OCC(F)(F)F)c(N3CC(F)(F)C3)cn2)C2CC2)no1]

The racemate (Example 78h) was separated into its enantiomers by preparative chiral HPLC (Chiralpak AD, isopropanol/heptane) and the title compound was the first enantiomer collected and isolated as colorless oil; MS (ESI, m/z): 462.4 (M+H$^+$).

Example 88

5-(3,3-Difluoro-azetidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide (enantiomer B)

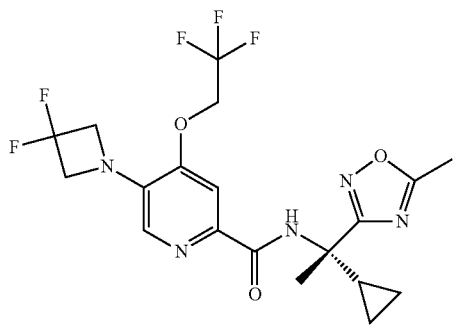 [SMILES: Cc1nc([C@@](C)(NC(=O)c2cc(OCC(F)(F)F)c(N3CC(F)(F)C3)cn2)C2CC2)no1]

The racemate (Example 78h) was separated into its enantiomers by preparative chiral HPLC (Chiralpak AD, isopropanol/heptane) and the title compound was the second enantiomer collected and isolated as colorless oil; MS (ESI, m/z): 462.4 (M+H$^+$).

Example 89

5-Chloro-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide

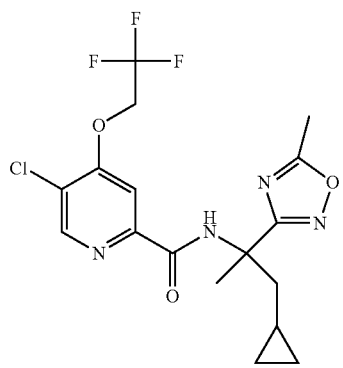 [SMILES: Cc1nc(C(C)(CC2CC2)NC(=O)c2cc(OCC(F)(F)F)c(Cl)cn2)no1]

The title compound was synthesized in analogy to Example 23b, using 5-Chloro-4-(2,2,2-trifluoro-ethoxy)-pyridine-2-carboxylic acid (Example 24c) and 2-Cyclopropyl-1-methyl-1-(5-methyl-[1,2,4]oxadiazol-3-yl)-ethylamine (Example 66e) as starting materials and isolated (29 mg, 51%) as colorless oil; MS (ESI, m/z): 419.5 (M+H$^+$).

Example 90

5-(3,3-Difluoro-azetidin-1-yl)-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide

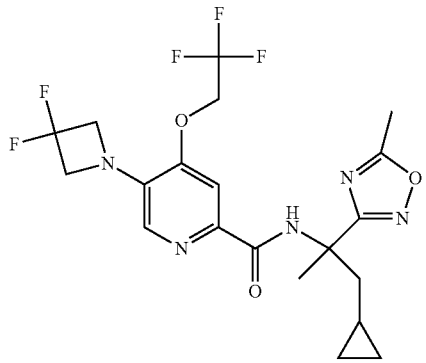 [SMILES: Cc1nc(C(C)(CC2CC2)NC(=O)c2cc(OCC(F)(F)F)c(N3CC(F)(F)C3)cn2)no1]

a) 5-Bromo-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide

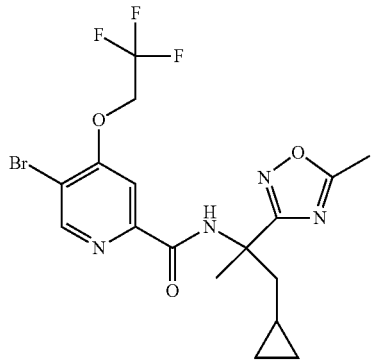 [SMILES: Cc1nc(C(C)(CC2CC2)NC(=O)c2cc(OCC(F)(F)F)c(Br)cn2)no1]

The title compound was synthesized in analogy to Example 78e, using 5-Bromo-4-(2,2,2-trifluoro-ethoxy)-pyridine-2-carboxylic acid (Example 78d) and 2-Cyclopropyl-1-methyl-1-(5-methyl-[1,2,4]oxadiazol-3-yl)-ethylamine (Example 66e) as starting materials and isolated (89 mg, 58%) as colorless oil; MS (ESI, m/z): 463.4 (M+H$^+$).

b) 5-(3,3-Difluoro-azetidin-1-yl)-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide The title compound was synthesized in analogy to Example 78h, using 5-Bromo-4-(2,2,2-trifluoro-ethoxy)-pyridine-2-carboxylic acid [2-cyclopropyl-1-methyl-1-(5-methyl-[1,2,4]oxadiazol-3-yl)-ethyl]amide (Example 90a) as starting material and isolated (30 mg, 33%) as colorless oil; MS (ESI, m/z): 476.5 (M+H$^+$).

Example 91

5-(3,3-Difluoro-azetidin-1-yl)-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide (enantiomer A)

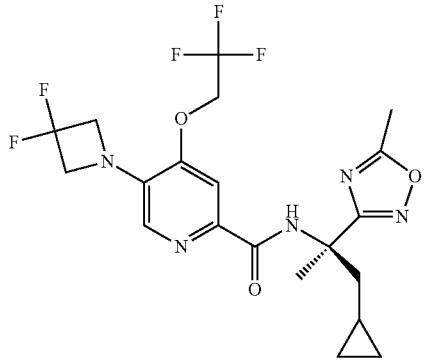 [SMILES: Cc1nc([C@@](C)(CC2CC2)NC(=O)c2cc(OCC(F)(F)F)c(N3CC(F)(F)C3)cn2)no1]

The racemate (Example 90) was separated into its enantiomers by preparative chiral HPLC (Reprosil Chiral NR, isopropanol/heptane) and the title compound was the first enantiomer collected and isolated as colorless oil; MS (ESI, m/z): 476.6 (M+H$^+$).

Example 92

5-(3,3-Difluoro-azetidin-1-yl)-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide (enantiomer B)

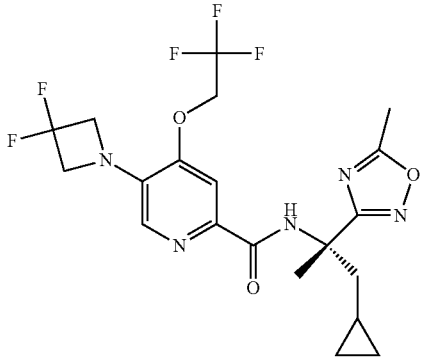 [SMILES: Cc1nc([C@](C)(CC2CC2)NC(=O)c2cc(OCC(F)(F)F)c(N3CC(F)(F)C3)cn2)no1]

The racemate (Example 90) was separated into its enantiomers by preparative chiral HPLC (Reprosil Chiral NR, isopropanol/heptane) and the title compound was the second enantiomer collected and isolated as colorless oil; MS (ESI, m/z): 476.6 (M+H$^+$).

Example 93

5-Chloro-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide (enantiomer A)

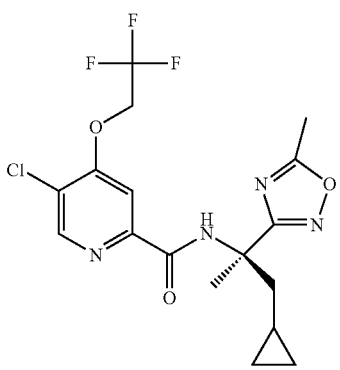 [SMILES: Cc1nc([C@@](C)(CC2CC2)NC(=O)c2cc(OCC(F)(F)F)c(Cl)cn2)no1]

The racemate (Example 89) was separated into its enantiomers by preparative chiral HPLC (Reprosil Chiral NR, isopropanol/heptane) and the title compound was the first enantiomer collected and isolated as colorless oil; MS (ESI, m/z): 419.4 (M+H$^+$).

Example 94

5-Chloro-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide (enantiomer B)

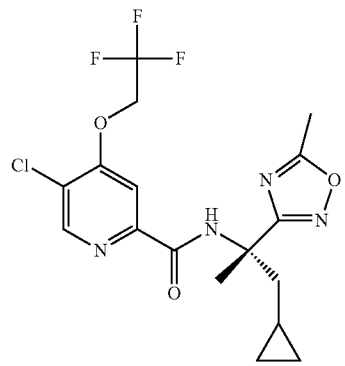 [SMILES: Cc1nc([C@](C)(CC2CC2)NC(=O)c2cc(OCC(F)(F)F)c(Cl)cn2)no1]

The racemate (Example 89) was separated into its enantiomers by preparative chiral HPLC (Reprosil Chiral NR, isopropanol/heptane) and the title compound was the second enantiomer collected and isolated as colorless oil; MS (ESI, m/z): 419.4 (M+H$^+$).

Example 95

5-(3,3-Difluoro-azetidin-1-yl)-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide

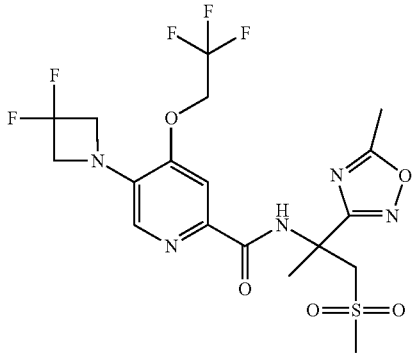 [SMILES: Cc1nc(C(C)(CS(C)(=O)=O)NC(=O)c2cc(OCC(F)(F)F)c(N3CC(F)(F)C3)cn2)no1]

The title compound was synthesized in analogy to Example 78h, using 5-Bromo-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide (Example 84c) as starting material and isolated (8 mg, 10%) as colorless oil; MS (ESI, m/z): 514.4 (M+H$^+$).

Example 96

5-(3,3-Difluoro-azetidin-1-yl)-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (epimer B)

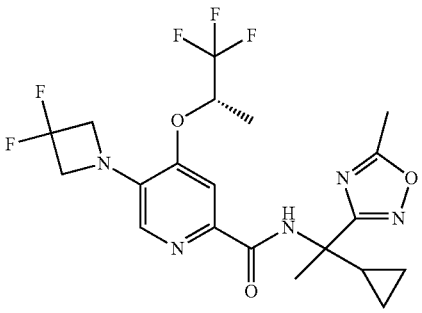 [SMILES: Cc1nc(C(C)(NC(=O)c2cc(O[C@@H](C)C(F)(F)F)c(N3CC(F)(F)C3)cn2)C2CC2)no1]

a) 3-Bromo-4-((S)-2,2,2-trifluoro-1-methyl-ethoxy)-pyridine

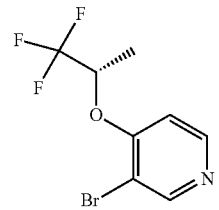

The title compound was synthesized in analogy to Example 78a, using 3-bromo-4-chloropyridine (CAN 36953-42-1) and (S)-1,1,1-trifluoropropan-2-ol (CAN 3539-97-7) as starting materials and isolated (28 g, 82%) as a yellow oil; MS (ESI, m/z): 270.4 (M+H$^+$).

b) 3-Bromo-4-((S)-2,2,2-trifluoro-1-methyl-ethoxy)-pyridine 1-oxide

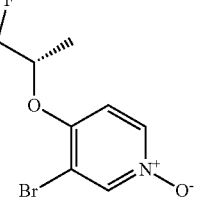

The title compound was synthesized in analogy to Example 78b, using 3-Bromo-4-((S)-2,2,2-trifluoro-1-methyl-ethoxy)-pyridine (Example 96a) as starting material and isolated (23 g, 70%) as a white solid; MS (ESI, m/z): 286.3 (M+H$^+$).

c) 5-Bromo-4-((S)-2,2,2-trifluoro-1-methyl-ethoxy)-pyridine-2-carbonitrile

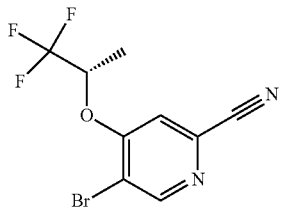 [SMILES: C[C@H](Oc1cc(C#N)ncc1Br)C(F)(F)F]

The title compound was synthesized in analogy to Example 78c, using 3-Bromo-4-((S)-2,2,2-trifluoro-1-methyl-ethoxy)-pyridine 1-oxide (Example 96b) as starting material and isolated (5.4 g, 23%) as a white solid; MS (ESI, m/z): 295.4 (M+H$^+$).

d) 5-Bromo-4-((S)-2,2,2-trifluoro-1-methyl-ethoxy)-pyridine-2-carboxylic acid

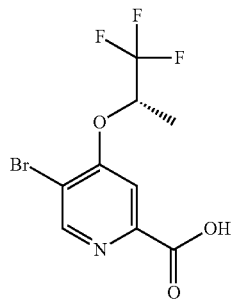 [SMILES: C[C@H](Oc1cc(C(=O)O)ncc1Br)C(F)(F)F]

The title compound was synthesized in analogy to Example 78d, using 5-Bromo-4-((S)-2,2,2-trifluoro-1-methyl-ethoxy)-pyridine-2-carbonitrile (Example 96c) as starting material and isolated (3.24 g, 76%) as a white solid; MS (ESI, m/z): 312.3 (M−H$^+$).

e) 5-Bromo-4-((S)-2,2,2-trifluoro-1-methyl-ethoxy)-pyridine-2-carboxylic acid (methyl-cyano-cyclopropyl-methyl)-amide

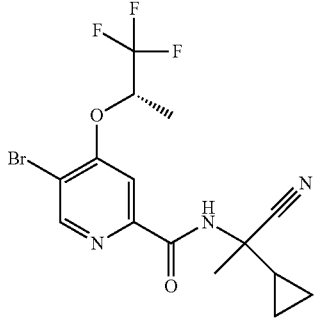 [SMILES: C[C@H](Oc1cc(C(=O)NC(C)(C#N)C2CC2)ncc1Br)C(F)(F)F]

The title compound was synthesized in analogy to Example 78e, using 5-Bromo-4-((S)-2,2,2-trifluoro-1-methyl-ethoxy)-pyridine-2-carboxylic acid (methyl-cyano-cyclopropyl-methyl)-amide (Example 96d) and 2-amino-2-cyclopropylpropanenitrile (CAN 37024-73-0) as starting materials and isolated (650 mg, 84%) as an orange oil; MS (ESI, m/z): 406.8 (M+H$^+$).

f) 5-Bromo-4-((S)-2,2,2-trifluoro-1-methyl-ethoxy)-pyridine-2-carboxylic acid [1-cyclopropyl-1-(N-hydroxycarbamimidoyl)-ethyl]-amide

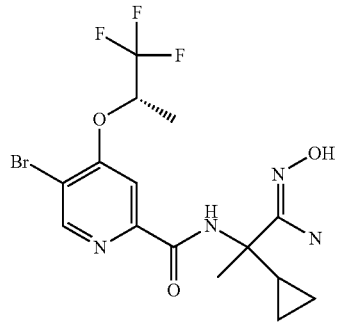 [SMILES: C[C@H](Oc1cc(C(=O)NC(C)(/C(N)=N/O)C2CC2)ncc1Br)C(F)(F)F]

The title compound was synthesized in analogy to Example 78f, using 5-Bromo-4-((S)-2,2,2-trifluoro-1-methyl-ethoxy)-pyridine-2-carboxylic acid (methyl-cyano-cyclopropyl-methyl)-amide (Example 96e) as starting material and isolated (280 mg, 40%) as a white solid; MS (ESI, m/z): 439.5 (M+H$^+$).

g) 5-Bromo-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide

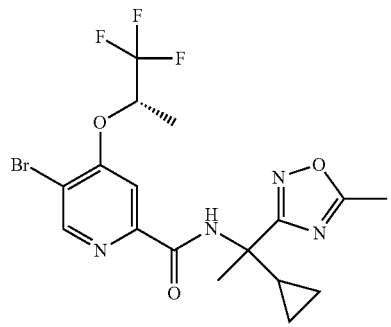 [SMILES: Cc1nc(C(C)(NC(=O)c2cc(O[C@@H](C)C(F)(F)F)c(Br)cn2)C2CC2)no1]

The title compound was synthesized in analogy to Example 78g, using 5-Bromo-4-((S)-2,2,2-trifluoro-1-methyl-ethoxy)-pyridine-2-carboxylic acid [1-cyclopropyl-1-(N-hydroxycarbamimidoyl)-ethyl]-amide (Example 96f as starting material and isolated (230 mg, 79%) as a yellow oil; MS (ESI, m/z): 463.5 (M+H⁺).

h) 5-(3,3-Difluoro-azetidin-1-yl)-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (epimer B)

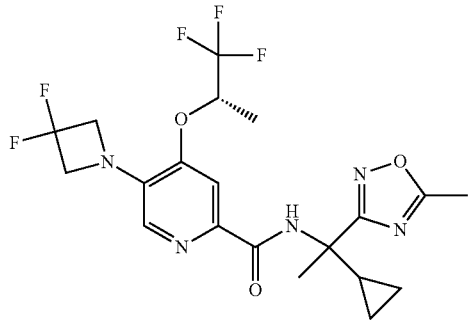 [SMILES: Cc1nc(C(C)(NC(=O)c2cc(O[C@@H](C)C(F)(F)F)c(N3CC(F)(F)C3)cn2)C2CC2)no1]

The mixture of epimers was synthesized in analogy to Example 78h, using 5-Bromo-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide (Example 96g) as starting material and isolated (230 mg, 79%) as a yellow oil. The mixture of epimers was separated by preparative chiral HPLC (Chiralpak AD, ethanol/heptane) and the title compound was the second epimer collected and isolated as colorless oil; MS (ESI, m/z): 476.2 (M+H⁺). The collected epimer shows dextrorotation properties according to the observed optical activity measured during preparative chiral HPLC.

Example 97

5-Cyclopropyl-4-(2,2,2-trifluoro-ethoxy)-pyridine-2-carboxylic acid [1,3,3-trimethyl-1-(5-methyl-[1,2,4]oxadiazol-3-yl)-butyl]-amide

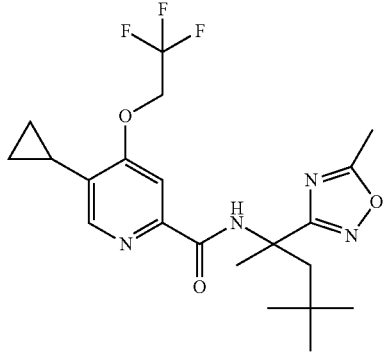 [SMILES: Cc1nc(C(C)(CC(C)(C)C)NC(=O)c2cc(OCC(F)(F)F)c(C3CC3)cn2)no1]

a) 5-Bromo-4-(2,2,2-trifluoro-ethoxy)-pyridine-2-carboxylic acid (1-cyano-1,3,3-trimethyl-butyl)-amide

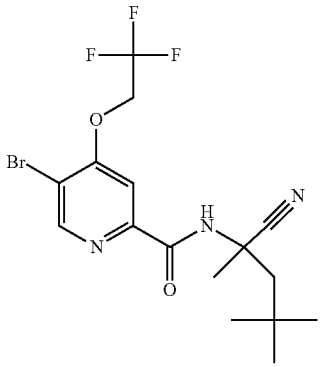 [SMILES: CC(C)(C)CC(C)(C#N)NC(=O)c1cc(OCC(F)(F)F)c(Br)cn1]

The title compound was synthesized in analogy to Example 78e, using 5-Bromo-4-(2,2,2-trifluoro-ethoxy)-pyridine-2-carboxylic acid (Example 78d) and 2-amino-2,4,4-trimethylpentanenitrile (CAN 65260-84-6) as starting materials and isolated (643 mg, 87%) as a yellow oil; MS (ESI, m/z): 422.3 (M+H⁺).

b) 5-Bromo-4-(2,2,2-trifluoro-ethoxy)-pyridine-2-carboxylic acid [1-(N-hydroxycarbamimidoyl)-1,3,3-trimethyl-butyl]-amide

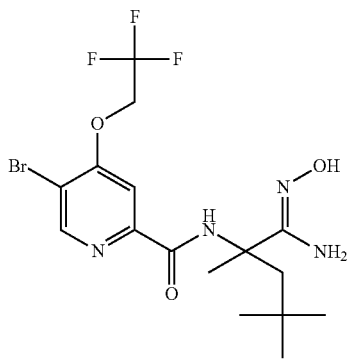

The title compound was synthesized in analogy to Example 78f, using 5-Bromo-4-(2,2,2-trifluoro-ethoxy)-pyridine-2-carboxylic acid (1-cyano-1,3,3-trimethyl-butyl)-amide (Example 97a) as starting material and isolated (375 mg, 53%) as a white solid; MS (ESI, m/z): 455.1 (M+H⁺).

c) 5-Bromo-4-(2,2,2-trifluoro-ethoxy)-pyridine-2-carboxylic acid [1-(N-hydroxycarbamimidoyl)-1,3,3-trimethyl-butyl]-amide

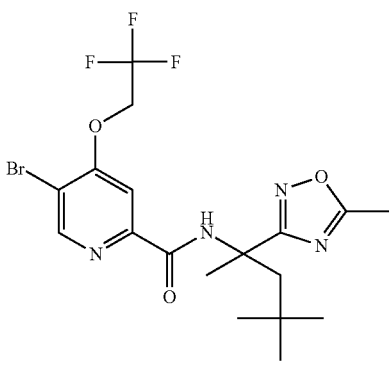 [SMILES: Cc1nc(C(C)(CC(C)(C)C)NC(=O)c2cc(OCC(F)(F)F)c(Br)cn2)no1]

The title compound was synthesized in analogy to Example 78g, using 5-Bromo-4-(2,2,2-trifluoro-ethoxy)-pyridine-2-carboxylic acid [1-(N-hydroxycarbamimidoyl)-1,3,3-trimethyl-butyl]-amide (Example 97b) as starting material and isolated (375 mg, 53%) as a white solid; MS (ESI, m/z): 479.0 (M+H$^+$).

d) 5-Cyclopropyl-4-(2,2,2-trifluoro-ethoxy)-pyridine-2-carboxylic acid [1,3,3-trimethyl-1-(5-methyl-[1,2,4]oxadiazol-3-yl)-butyl]-amide To a solution of 5-Bromo-4-(2,2,2-trifluoro-ethoxy)-pyridine-2-carboxylic acid [1-(N-hydroxycarbamimidoyl)-1,3,3-trimethyl-butyl]-amide (Example 97c, 0.175 g, 365 µmol) in toluene (2 ml) under an argon atmosphere was added potassium cyclopropyltrifluoroborate (108 mg, 730 µmol), palladium (II) acetate (4.1 mg, 18.3 µmol), butyldi-1-adamantylphosphine (13.1 mg, 36.5 µmol) and cesium carbonate (243 µl, 730 µmol). The reaction was stirred at 125° C. for 18 hours. The reaction was filtered through a pad of celite. The filtrate was diluted with ethylacetate and was extracted with an 1.0M aqueous solution of sodium bicarbonate. The organic phase was dried over sodium sulfate and evaporated down to dryness. The crude material was purified by flash chromatography on silica eluting with a heptane/ethylacetate gradient to yield the title compound (154 mg, 96%) as a light yellow oil. MS (ESI, m/z): 441.7 (M+H$^+$).

Example 98

5-Cyclopropyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide (enantiomer A)

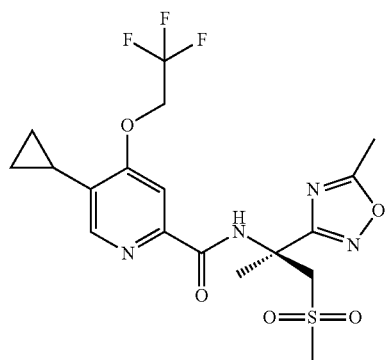 [SMILES: Cc1nc([C@@](C)(CS(C)(=O)=O)NC(=O)c2cc(OCC(F)(F)F)c(C3CC3)cn2)no1]

The racemate (Example 84d) was separated into its enantiomers by preparative chiral HPLC (Lux Cellulose, ethanol/heptane) and the title compound was the first enantiomer collected and isolated as a white solid; MS (ESI, m/z): 463.6 (M+H$^+$).

Example 99

5-Cyclopropyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide (enantiomer B)

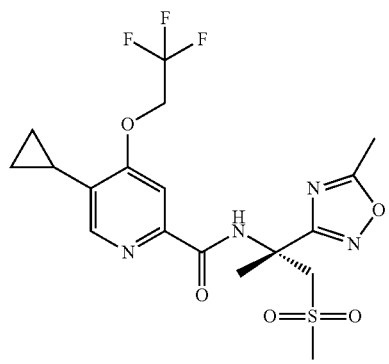 [SMILES: Cc1nc([C@](C)(CS(C)(=O)=O)NC(=O)c2cc(OCC(F)(F)F)c(C3CC3)cn2)no1]

The racemate (Example 84d) was separated into its enantiomers by preparative chiral HPLC (Lux Cellulose, ethanol/heptane) and the title compound was the second enantiomer collected and isolated as a white solid; MS (ESI, m/z): 463.6 (M+H$^+$).

Example 100

5-Cyclopropyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide (epimer A)

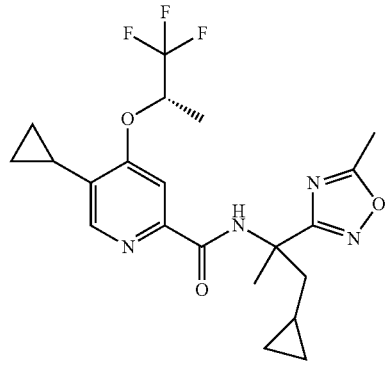 [SMILES: Cc1nc(C(C)(CC2CC2)NC(=O)c2cc(O[C@@H](C)C(F)(F)F)c(C3CC3)cn2)no1]

a) 5-Bromo-4-((S)-2,2,2-trifluoro-1-methyl-ethoxy)-pyridine-2-carboxylic acid (methyl-cyano-cyclopropylmethyl)-amide

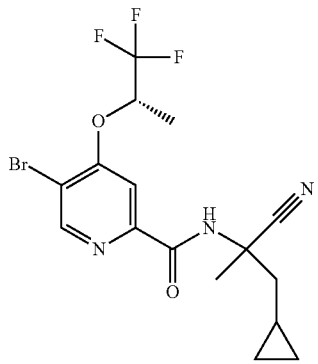 [SMILES: C[C@H](Oc1cc(C(=O)NC(C)(C#N)CC2CC2)ncc1Br)C(F)(F)F]

The title compound was synthesized in analogy to Example 78e, using 5-Bromo-4-((S)-2,2,2-trifluoro-1-methyl-ethoxy)-pyridine-2-carboxylic acid (Example 96d) and 2-amino-2-cyclopropylpropanenitrile (CAN 37024-73-0) as starting materials and isolated (607 mg, 65%) as a yellow oil; MS (ESI, m/z): 420.4 (M+H$^+$).

b) 5-Bromo-4-((S)-2,2,2-trifluoro-1-methyl-ethoxy)-pyridine-2-carboxylic acid [2-cyclopropyl-1-(N-hydroxycarbamimidoyl)-1-methyl-ethyl]-amide

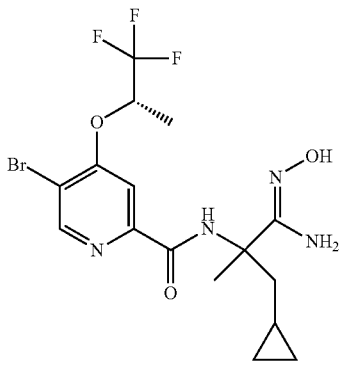 [SMILES: C[C@H](Oc1cc(C(=O)NC(C)(CC2CC2)/C(N)=N/O)ncc1Br)C(F)(F)F]

The title compound was synthesized in analogy to Example 78f, using 5-Bromo-4-((S)-2,2,2-trifluoro-1-methyl-ethoxy)-pyridine-2-carboxylic acid (methyl-cyano-cyclopropylmethyl)-amide (Example 100a) as starting material and isolated (647 mg, 100%) as a yellow gum; MS (ESI, m/z): 453.4 (M+H$^+$).

c) 5-Bromo-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide

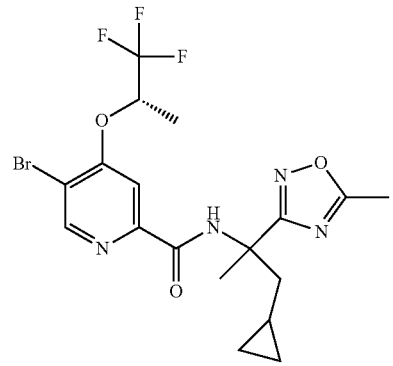 [SMILES: Cc1nc(C(C)(CC2CC2)NC(=O)c2cc(O[C@@H](C)C(F)(F)F)c(Br)cn2)no1]

The title compound was synthesized in analogy to Example 78g, using 5-Bromo-4-((S)-2,2,2-trifluoro-1-methyl-ethoxy)-pyridine-2-carboxylic acid [2-cyclopropyl-1-(N-hydroxycarbamimidoyl)-1-methyl-ethyl]-amide (Example 100c) as starting material and isolated (355 mg, 53%) as a yellow oil; MS (ESI, m/z): 477.4 (M+H$^+$).

d) 5-Cyclopropyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide

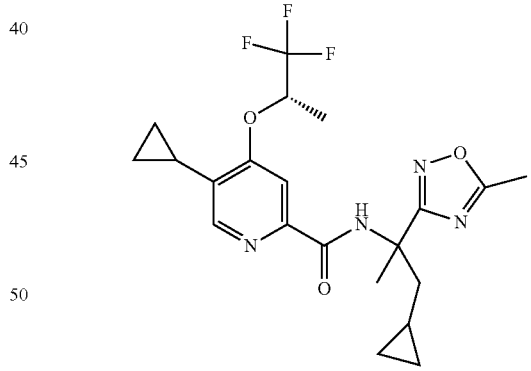

To a solution of 5-Bromo-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide (Example 100c, 160 mg, 0.335 mmol) in toluene (4.8 mL) were added cyclopropylboronic acid (43.2 mg, 0.503 mmol), 1,1'-bis(diphenylphosphino)ferrocene-palladium(II)dichloride dichloromethane complex (12.3 mg, 17 µmol) and 2M aqueous solution sodium carbonate (335 µL, 0.670 mmol). Reaction was stirred at 80° C. for 18 hours. The reaction mixture was diluted with ethylacetate and extracted with water. The organic layer was dried on sodium sulfate and evaporated down to dryness. The crude material was purified by flash chromatography on silica eluting with a heptane/ethyl acetate gradient to yield the mixture of epimers (151 mg, 100%). The mixture of epimers was separated by preparative chiral HPLC (Chiralpak AD, isopropanol/heptane) and the title compound was the first epimer collected and isolated as colorless oil; MS (ESI, m/z): 439.7 (M+H$^+$).

Example 101

5-Cyclopropyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide (epimer B)

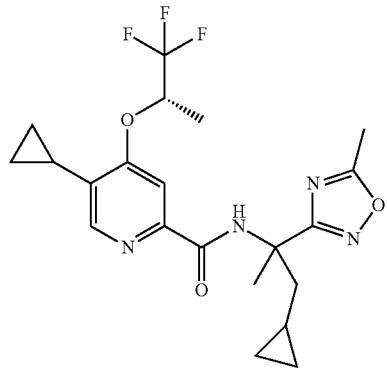 [SMILES: Cc1nc(C(C)(CC2CC2)NC(=O)c2cc(O[C@@H](C)C(F)(F)F)c(C3CC3)cn2)no1]

The mixture of epimers (Example 100d) was separated by preparative chiral HPLC (Chiralpak AD, isopropanol/heptane) and the title compound was the second epimer collected and isolated as colorless oil; MS (ESI, m/z): 439.7 (M+H$^+$).

Example 102

5-(3,3-Difluoro-azetidin-1-yl)-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide (epimer A)

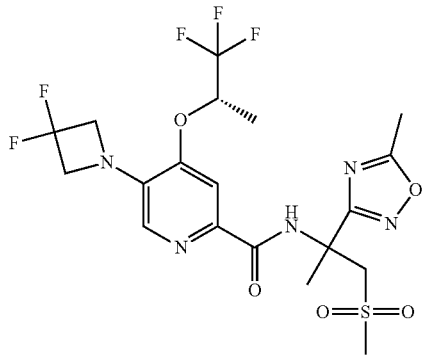 [SMILES: Cc1nc(C(C)(CS(C)(=O)=O)NC(=O)c2cc(O[C@@H](C)C(F)(F)F)c(N3CC(F)(F)C3)cn2)no1]

a) 5-Bromo-4-((S)-2,2,2-trifluoro-1-methyl-ethoxy)-pyridine-2-carboxylic acid (methanesulfonylmethyl-methyl-cyano-methyl)-amide

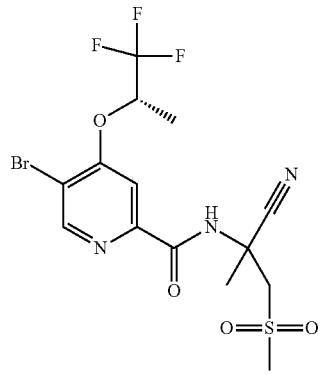 [SMILES: C[C@H](Oc1cc(C(=O)NC(C)(C#N)CS(C)(=O)=O)ncc1Br)C(F)(F)F]

The title compound was synthesized in analogy to Example 78e, using 5-Bromo-4-((S)-2,2,2-trifluoro-1-methyl-ethoxy)-pyridine-2-carboxylic acid (Example 96d) and 2-Amino-3-methanesulfonyl-2-methyl-propionitrile (Example 80a) as starting materials and isolated (690 mg, 50%) as a yellow oil; MS (ESI, m/z): 458.3 (M+H$^+$).

b) 5-Bromo-4-((S)-2,2,2-trifluoro-1-methyl-ethoxy)-pyridine-2-carboxylic acid [1-(N-hydroxycarbamimidoyl)-2-methanesulfonyl-1-methyl-ethyl]-amide

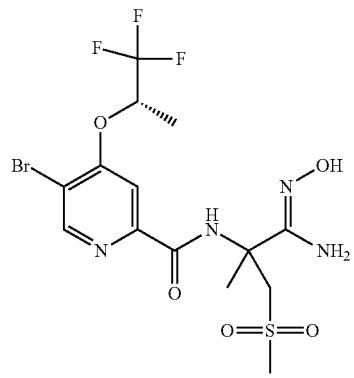 [SMILES: C[C@H](Oc1cc(C(=O)NC(C)(CS(C)(=O)=O)/C(N)=N/O)ncc1Br)C(F)(F)F]

The title compound was synthesized in analogy to Example 78f, using 5-Bromo-4-((S)-2,2,2-trifluoro-1-methyl-ethoxy)-pyridine-2-carboxylic acid (methanesulfonyl-methyl-methyl-cyano-methyl)-amide (Example 102a) as starting material and isolated (512 mg, 70%) as a yellow oil; MS (ESI, m/z): 491.6 (M+H$^+$).

c) 5-Bromo-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide

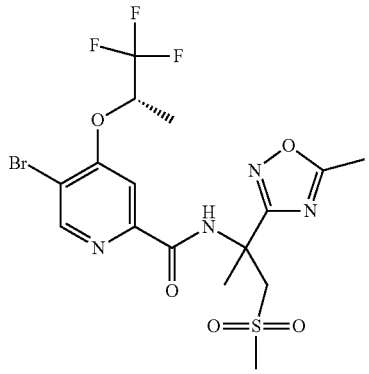 [SMILES: Cc1nc(C(C)(CS(C)(=O)=O)NC(=O)c2cc(O[C@@H](C)C(F)(F)F)c(Br)cn2)no1]

The title compound was synthesized in analogy to Example 78g, using 5-Bromo-4-((S)-2,2,2-trifluoro-1-methyl-ethoxy)-pyridine-2-carboxylic acid [1-(N-hydroxycarbamimidoyl)-2-methanesulfonyl-1-methyl-ethyl]-amide (Example 102b) as starting material and isolated (261 mg, 50%) as a yellow oil; MS (ESI, m/z): 515.5 (M+H$^+$).

d) 5-(3,3-Difluoro-azetidin-1-yl)-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide (epimer A)

The mixture of epimers was synthesized in analogy to Example 78h, using 5-Bromo-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide (Example 102c) as starting material and isolated (101 mg, 76%) as a yellow oil. The mixture of epimers was separated by preparative chiral HPLC (Chiralpak AD, isopropanol/heptane) and the title compound was the first epimer collected and isolated as a white solid; MS (ESI, m/z): 528.6 (M+H$^+$).

Example 103

5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide (epimer A)

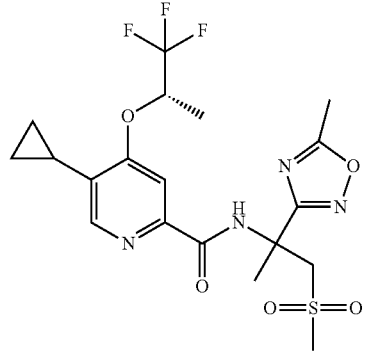 [SMILES: Cc1nc(C(C)(CS(C)(=O)=O)NC(=O)c2cc(O[C@@H](C)C(F)(F)F)c(C3CC3)cn2)no1]

The mixture of epimers was synthesized in analogy to Example 100d, using 5-Bromo-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide (Example 102c) as starting material and isolated (101 mg, 76%) as a yellow oil. The mixture of epimers was separated into its epimers by preparative chiral HPLC (Chiralpak AD, ethanol/heptane) and the title compound was the first epimer collected and isolated as a white solid; MS (ESI, m/z): 477.6 (M+H$^+$).

Example 104

5-Cyclopropyl-4-(2,2,2-trifluoro-ethoxy)-pyridine-2-carboxylic acid [1,3,3-trimethyl-1-(5-methyl-[1,2,4]oxadiazol-3-yl)-butyl]-amide (enantiomer A)

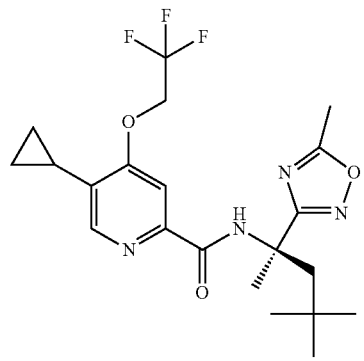 [SMILES: Cc1nc([C@@](C)(CC(C)(C)C)NC(=O)c2cc(OCC(F)(F)F)c(C3CC3)cn2)no1]

The racemate (Example 97d) was separated into its enantiomers by preparative chiral HPLC (Chiralpak AD, ethanol/heptane) and the title compound was the first enantiomer collected and isolated as colorless oil; MS (ESI, m/z): 441.7 (M+H$^+$).

Example 105

5-Cyclopropyl-4-(2,2,2-trifluoro-ethoxy)-pyridine-2-carboxylic acid [1,3,3-trimethyl-1-(5-methyl-[1,2,4]oxadiazol-3-yl)-butyl]-amide (enantiomer B)

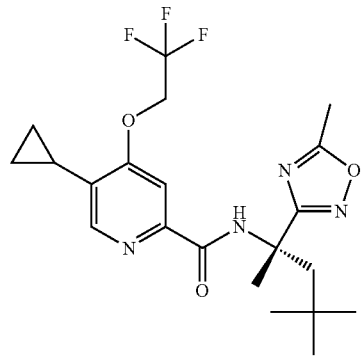 [SMILES: Cc1nc([C@](C)(CC(C)(C)C)NC(=O)c2cc(OCC(F)(F)F)c(C3CC3)cn2)no1]

The racemate (Example 97d) was separated into its enantiomers by preparative chiral HPLC (Chiralpak AD, ethanol/

Example 106

5-Cyclopropyl-4-cyclopropylmethoxy-pyridine-2-carboxylic acid tert-butyl-ethyl-amide

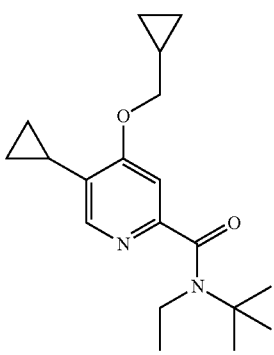 [SMILES: CCN(C(=O)c1cc(OCC2CC2)c(C2CC2)cn1)C(C)(C)C]

The title compound was synthesized in analogy to Example 23b, using 5-Cyclopropyl-4-cyclopropylmethoxy-pyridine-2-carboxylic acid (Example 42c) and N-ethyl-2-methylpropan-2-amine (CAN 4432-77-3) as starting materials and isolated (9 mg, 4.5%) as colorless oil; MS (ESI, m/z): 317.6 (M+H$^+$).

Example 107

5-Cyclopropyl-4-(2,2,2-trifluoro-ethoxy)-pyridine-2-carboxylic acid tert-butyl-ethyl-amide

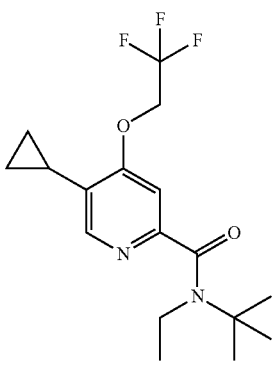 [SMILES: CCN(C(=O)c1cc(OCC(F)(F)F)c(C2CC2)cn1)C(C)(C)C]

The title compound was synthesized in analogy to Example 23b, using 5-Cyclopropyl-4-(2,2,2-trifluoro-ethoxy)-pyridine-2-carboxylic acid (Example 48c) and N-ethyl-2-methylpropan-2-amine (CAN 4432-77-3) as starting materials and isolated (50 mg, 47%) as a light yellow solid; MS (ESI, m/z): 345.7 (M+H$^+$).

Example 108

5-Cyclobutyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide

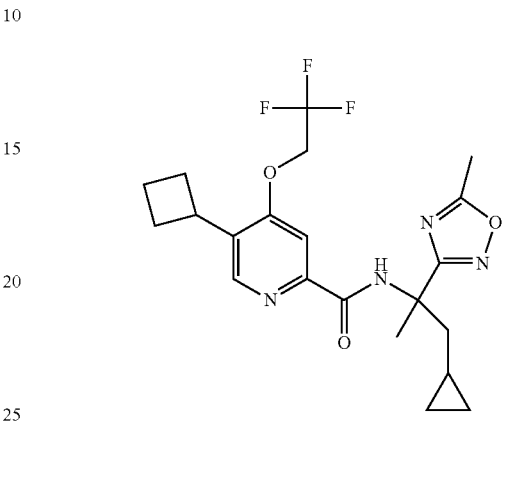

a) 1-(4-Chloro-pyridin-3-yl)-cyclobutanol

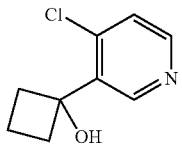 [SMILES: OC1(c2cnccc2Cl)CCC1]

To a solution of 3-bromo-4-chloropyridine (CAN 36953-42-1, 1 g, 5.2 mmol) in dry THF (25.0 ml) cooled down to −15° C. under an argon atmosphere was added isopropyl magnesium chloride, lithium chloride complex 1.3M solution in THF (4.2 ml, 5.46 mmol) and the reaction mixture was stirred at −15° C. for 1 hour. To the reaction mixture at −15° C. was slowly added cyclobutanone (CAN 1191-95-3, 401 mg, 428 μl, 5.72 mmol) and the reaction was stirred at −15° C. for 2 hours. The reaction was then let to warm up to 0° C. and stirred at 0° C. for 2 hours. Reaction was quenched by addition of water and the reaction mixture was concentrated in vacuo. The residue was dissolved in ethylacetate and extraction with an 3.0M aqueous solution of ammonium chloride. The organic phase was dried over sodium sulfate and evaporated down to dryness. The crude material was purified by flash chromatography on silica eluting with a heptane/ethylacetate gradient to yield the title compound (832 mg, 78%) as a yellow oil. MS (ESI, m/z): 184.3 (MH+).

--- heptane) and the title compound was the second enantiomer collected and isolated as colorless oil; MS (ESI, m/z): 441.7 (M+H$^+$).

b) 1-[4-(2,2,2-Trifluoro-ethoxy)-pyridin-3-yl]-cyclobutanol

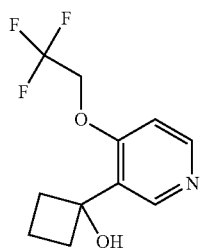 [SMILES: OC1(c2cnccc2OCC(F)(F)F)CCC1]

To a solution of 1-(4-chloropyridin-3-yl)cyclobutanol (Example 108a, 0.83 g, 4.52 mmol) in dry DMF (20 ml) under an argon atmosphere was added 2,2,2-trifluoroethanol (CAN 75-89-8, 904 mg, 653 µl, 9.04 mmol) and potassium tert-butoxide (533 mg, 4.75 mmol). The reaction mixture was stirred at room temperature for 20 minutes and stirred at 90° C. for 18 hours. The reaction mixture was concentrated in vacuo. The residue was dissolved in ethylacetate and extracted with an 1.0M aqueous solution of sodium bicarbonate. The organic phase was collected, dried over sodium sulfate and evaporated down to dryness. The crude material was purified by flash chromatography on silica eluting with a heptane/(solution 3% Et3N in ethylacetate) to yield the title compound (885 mg, 71%) as a yellow oil. MS (ESI, m/z): 248.5 (M+H$^+$).

c) 3-Cyclobutyl-4-(2,2,2-trifluoro-ethoxy)-pyridine

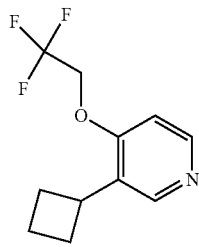 [SMILES: FC(F)(F)COc1ccncc1C1CCC1]

To a solution of 1-[4-(2,2,2-Trifluoro-ethoxy)-pyridin-3-yl]-cyclobutanol (Example 108b, 3.88 g, 15.7 mmol) in ethanol (50 ml) under argon atmosphere was added sulfuric acid 97% (4.62 g, 2.51 ml, 47.1 mmol) and palladium(0) on charcoal 10% (384 mg, 3.61 mmol). The reaction vessel was pressurized with hydrogen to 2.5 bar and stirred at 50° C. for 18 hours. The reaction mixture was cooled down to room temperature, filtered through a pad of Celite and the filter cake was washed twice with ethanol. The filtrate was evaporated down to dryness, the residue was dissolved in ethylacetate and extracted with an 2.0M aqueous solution of sodium carbonate. The organic phase was collected and the aqueous phase was back-extracted with ethylacetate. The organic phases were combined, dried over sodium sulfate and evaporated down to dryness. The crude material was purified by flash chromatography on silica eluting with a dichloromethane/methanol gradient to yield the title compound (3.05 g, 84%) as yellow oil. MS (ESI, m/z): 232.6 (M+H$^+$).

d) 3-Cyclobutyl-4-(2,2,2-trifluoro-ethoxy)-pyridine 1-oxide

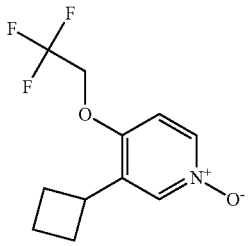 [SMILES: [O-][n+]1ccc(OCC(F)(F)F)c(C2CCC2)c1]

To a solution of 3-cyclobutyl-4-(2,2,2-trifluoroethoxy)pyridine (Example 108c, 3.81 g, 16.5 mmol) in dichloromethane (100 ml) was added 3-chloroperoxybenzoic acid (5.54 g, 24.7 mmol). The reaction mixture was stirred at room temperature for 18 hours. The reaction mixture was transferred into a separatory funnel and extracted with an 2.0M aqueous solution of sodium carbonate. The organic phase was collected and the aqueous phase was back-extracted with dichloromethane. The organic phases were combined, dried over sodium sulfate and evaporated down to dryness. The crude material was purified by flash chromatography on silica eluting with a dichloromethane/methanol gradient to yield the title compound (3.52 gr, 82%) as a white solid. MS (ESI, m/z): 248.5 (M+H$^+$).

e) 5-Cyclobutyl-4-(2,2,2-trifluoro-ethoxy)-pyridine-2-carbonitrile

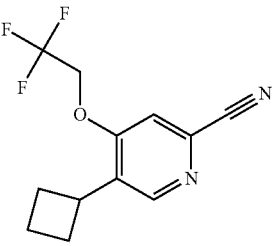 [SMILES: N#Cc1cc(OCC(F)(F)F)c(C2CCC2)cn1]

To a solution of 3-cyclobutyl-4-(2,2,2-trifluoroethoxy)pyridine 1-oxide (Example 108d, 3.5 g, 14.2 mmol) in dichloromethane (55 ml) under argon atmosphere was added trimethylsilylcyanide (1.83 g, 2.47 ml, 18.4 mmol) followed by addition of dimethylcarbamoyl chloride (CAN 79-44-7, 2.28 g, 1.95 ml, 21.2 mmol). The reaction mixture was then stirred at room temperature for 18 hours. The reaction mixture was diluted with dichloromethane and extracted with an 1.0M aqueous solution of sodium bicarbonate. The organic phase was dried over sodium sulfate and evaporated down to dryness. The crude material was purified by flash chromatography on silica eluting with a heptane/ethylacetate gradient to

117 yield the title compound (2.95 g, 77%) as light yellow solid. MS (ESI, m/z): 257.5 (M+H⁺).

f) 5-Cyclobutyl-4-(2,2,2-trifluoro-ethoxy)-pyridine-2-carboxylic acid

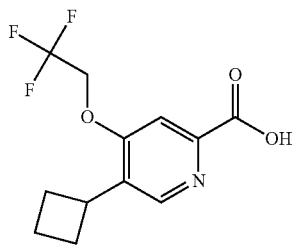 [SMILES: O=C(O)c1cc(OCC(F)(F)F)c(C2CCC2)cn1]

5-cyclobutyl-4-(2,2,2-trifluoroethoxy)picolinonitrile (Example 108e, 2.95 g, 11.5 mmol) was dissolved in 25% aqueous solution hydrochloric acid (66.0 g, 55 mL, 453 mmol). Reaction mixture was stirred at 110° C. for 3 hours. The reaction was cooled down to room temperature and excess of hydrochloric acid was neutralized by addition of sodium hydroxide pellets until pH was basic. Afterwards pH of the solution was adjusted to 1-2 by addition of aqueous solution 2.0M of hydrochloric acid. A precipitate formed which was isolated by filtration to yield the title compound (3.05 g, 96%) as an off-white solid. MS (ESI, m/z): 276.4 (M+H⁺).

g) 5-Cyclobutyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide The title compound was synthesized in analogy to Example 23b, using 5-Cyclobutyl-4-(2,2,2-trifluoro-ethoxy)-pyridine-2-carboxylic acid (Example 108f) and 1-cyclopropyl-2-(5-methyl-1,2,4-oxadiazol-3-yl)propan-2-amine (Example 66d) as starting materials and isolated (57 mg, 45%) as colorless oil; MS (ESI, m/z): 439.6 (M+H⁺).

Example 109

5-Cyclobutyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide

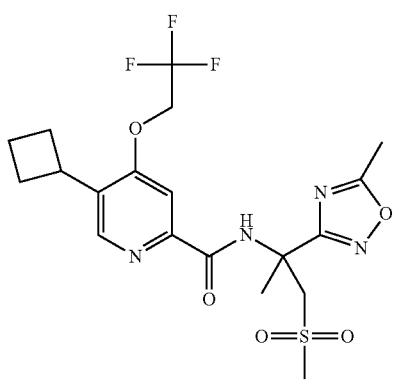 [SMILES: Cc1nc(C(C)(CS(C)(=O)=O)NC(=O)c2cc(OCC(F)(F)F)c(C3CCC3)cn2)no1]

118 a) (1-Cyano-2-methanesulfonyl-1-methyl-ethyl)-carbamic acid benzyl ester

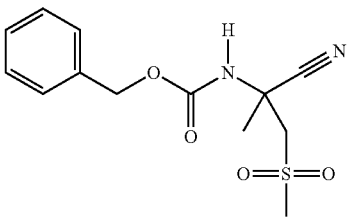 [SMILES: CC(C#N)(CS(C)(=O)=O)NC(=O)OCc1ccccc1]

To a solution of 2-Amino-3-methanesulfonyl-2-methyl-propionitrile (Example 80a, 5.01 g, 30.9 mmol) in dry THF (119 mL) was added DIEA (12.1 mL, 67.9 mmol) and benzyl carbonochloridate (CAN 501-53-1, 5.57 mL, 37.1 mmol). Reaction was stirred at 45° C. for 18 hours. The reaction mixture was concentrated in vacuo. The residue was dissolved in ethylacetate and was extracted with an 1.0M aqueous solution of sodium bicarbonate. The organic layer was dried over sodium sulfate and evaporated down to dryness. The crude was purified by flash chromatography on silica eluting with a heptane/ethyl acetate gradient to yield the title compound (8.12, 89%) as a yellow oil. MS (ESI, m/z): 297.5 (M+H⁺).

b) [1-(N-Hydroxycarbamimidoyl)-2-methanesulfonyl-1-methyl-ethyl]-carbamic acid benzyl ester

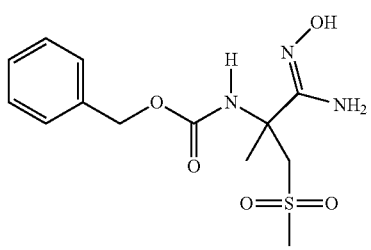 [SMILES: CC(CS(C)(=O)=O)(NC(=O)OCc1ccccc1)/C(N)=N/O]

To a solution of (1-Cyano-2-methanesulfonyl-1-methyl-ethyl)-carbamic acid benzyl ester (Example 109a, 3.07 g, 10.4 mmol) in dry ethanol (58 ml) were added triethylamine (2.17 mL, 15.5 mmol) and hydroxylamine hydrochloride (936 mg, 13.5 mmol). The reaction mixture was then stirred at 60° C. for 18 hours. The reaction mixture was concentrated in vacuo. The residue was dissolved in ethylacetate and extracted with an 1.0M aqueous solution of sodium carbonate. The organic phase was collected and the aqueous phase was back-extracted with ethylacetate. The combined organic phases were dried over sodium sulfate and evaporated down to dryness. The crude material was purified by flash chromatography on silica eluting with a ethyl acetate/heptane gradient to yield the title compound (2.04 gr, 60%) as a white powder. MS (ESI, m/z): 330.6 (M+H⁺).

c) [2-Methanesulfonyl-1-methyl-1-(5-methyl-[1,2,4]oxadiazol-3-yl)-ethyl]-carbamic acid benzyl ester

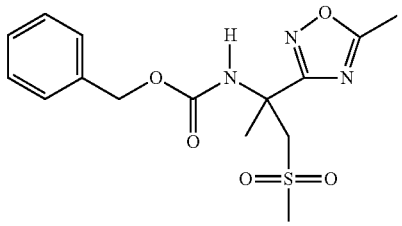 [SMILES: Cc1nc(C(C)(CS(C)(=O)=O)NC(=O)OCc2ccccc2)no1]

To a solution of [1-(N-Hydroxycarbamimidoyl)-2-methanesulfonyl-1-methyl-ethyl]-carbamic acid benzyl ester (Example 109b, 2.04 g, 6.19 mmol) in dry DMF (30 mL) were added triethylamine (1.73 mL, 12.4 mmol) and acetyl chloride (572 μL, 8.05 mmol). the reaction was stirred 30 minutes at room temperature. Reaction was then stirred at 130° C. for 18 hours. The reaction mixture was concentrated in vacuo. The residue was dissolved in ethyl acetate and extracted with an 1.0M aqueous solution of sodium bicarbonate. The organic layer was dried over sodium sulfate and evaporated down to dryness. The crude material was purified by flash chromatography on silica eluting with a heptane/ethyl acetate gradient to yield the title compound (1.21 g, 55%) as yellow oil. MS (ESI, m/z): 354.5 (M+H⁺).

d) 2-Methanesulfonyl-1-methyl-1-(5-methyl-[1,2,4]oxadiazol-3-yl)-ethylamine

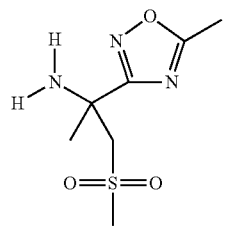

To a solution of [2-Methanesulfonyl-1-methyl-1-(5-methyl-[1,2,4]oxadiazol-3-yl)-ethyl]-carbamic acid benzyl ester (Example 109c, 0.085 g, 241 μmol) in dry CH2Cl2 (1 ml) under argon atmosphere cooled down at 0° C. was slowly added a 1.0M solution of boron tribromide in dichloromethane (265 μl, 265 μmol). The reaction mixture was stirred at 0° C. for 20 minutes and stirred for 1 hour at room temperature The reaction was diluted with dichloromethane and an 2.0M aqueous solution of sodium carbonate was added. The two phases mixture was stirred at room temperature for 30 minutes and was poured into a separatory funnel and the organic phase was collected. The aqueous phase was back-extracted with dichloromethane. The combined organic phases were dried over sodium sulfate and evaporated down to dryness. The crude material was purified by flash chromatography on silica eluting with a dichloromethane/methanol gradient to yield the title compound (21 mg, 40%) as yellow oil. MS (ESI, m/z): 220.3 (M+H⁺).

e) 5-Cyclobutyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide The title compound was synthesized in analogy to Example 23b, using 5-Cyclobutyl-4-(2,2,2-trifluoro-ethoxy)-pyridine-2-carboxylic acid (Example 108f) and 2-Methanesulfonyl-1-methyl-1-(5-methyl-[1,2,4]oxadiazol-3-yl)-ethylamine (Example 109d) as starting materials and isolated (62 mg, 45%) as colorless oil; MS (ESI, m/z): 477.6 (M+H⁺).

Example 110

5-Cyclobutyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide

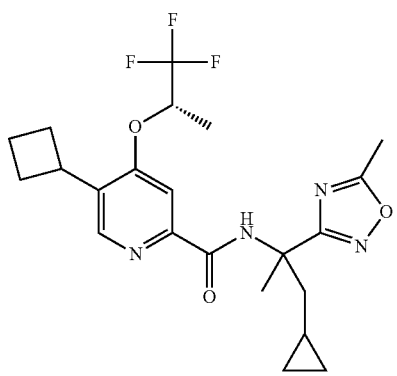 [SMILES: Cc1nc(C(C)(CC2CC2)NC(=O)c2cc(O[C@@H](C)C(F)(F)F)c(C3CCC3)cn2)no1]

a) 1-[4-((S)-2,2,2-Trifluoro-1-methyl-ethoxy)-pyridin-3-yl]-cyclobutanol

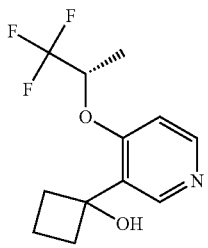 [SMILES: C[C@H](Oc1ccncc1C1(O)CCC1)C(F)(F)F]

The title compound was synthesized in analogy to Example 108b, using 1-(4-Chloro-pyridin-3-yl)-cyclobutanol (Example 108a) and (S)-1,1,1-trifluoropropan-2-ol (CAN 3539-97-7) as starting materials and isolated (3.22 g, 57%) as yellow oil; MS (ESI, m/z): 262.3 (M+H$^+$).

b) 3-Cyclobutyl-4-((S)-2,2,2-trifluoro-1-methyl-ethoxy)-pyridine

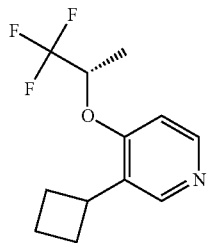 [SMILES: C[C@H](Oc1ccncc1C1CCC1)C(F)(F)F]

The title compound was synthesized in analogy to Example 108c, using 1-[4-((S)-2,2,2-Trifluoro-1-methyl-ethoxy)-pyridin-3-yl]-cyclobutanol (Example 110a) as starting material and isolated (1.39 g, 82%) as yellow oil; MS (ESI, m/z): 246.3 (M+H$^+$).

c) 3-Cyclobutyl-4-((S)-2,2,2-trifluoro-1-methyl-ethoxy)-pyridine 1-oxide

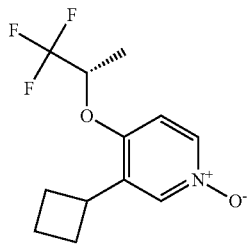 [SMILES: C[C@H](Oc1cc[n+]([O-])cc1C1CCC1)C(F)(F)F]

The title compound was synthesized in analogy to Example 108d, using 3-Cyclobutyl-4-((S)-2,2,2-trifluoro-1-methyl-ethoxy)-pyridine (Example 110b) as starting material and isolated (1.02 g, 64%) as a white solid; MS (ESI, m/z): 262.3 (M+H$^+$).

d) 5-Cyclobutyl-4-((S)-2,2,2-trifluoro-1-methyl-ethoxy)-pyridine-2-carbonitrile

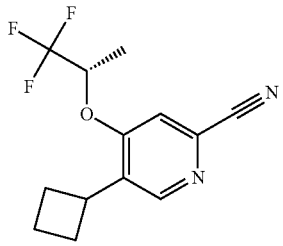 [SMILES: C[C@H](Oc1cc(C#N)ncc1C1CCC1)C(F)(F)F]

The title compound was synthesized in analogy to Example 108e, using 3-Cyclobutyl-4-((S)-2,2,2-trifluoro-1-methyl-ethoxy)-pyridine 1-oxide (Example 110c) as starting material and isolated (641 mg, 62%) as a white solid; MS (ESI, m/z): 271.5 (M+H$^+$).

e) 5-Cyclobutyl-4-((S)-2,2,2-trifluoro-1-methyl-ethoxy)-pyridine-2-carboxylic acid

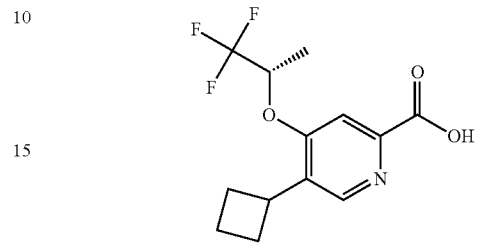

The title compound was synthesized in analogy to Example 108f, using 5-Cyclobutyl-4-((S)-2,2,2-trifluoro-1-methyl-ethoxy)-pyridine-2-carbonitrile (Example 110d) as starting material and isolated (454 mg, 66%) as a white solid; MS (ESI, m/z): 290.5 (M+H$^+$).

f) 5-Cyclobutyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide The title compound was synthesized in analogy to Example 23b, using 5-Cyclobutyl-4-((S)-2,2,2-trifluoro-1-methyl-ethoxy)-pyridine-2-carboxylic acid (Example 110e) and 1-cyclopropyl-2-(5-methyl-1,2,4-oxadiazol-3-yl)propan-2-amine (Example 66d) as starting materials and isolated (85 mg, 68%) as colorless oil; MS (ESI, m/z): 453.6 (M+H$^+$).

Example 111

5-Cyclobutyl-4-((S)-2,2,2-trifluoro-1-methyl-ethoxy)-pyridine-2-carboxylic acid [2-methanesulfo-nyl-1-methyl-1-(5-methyl-[1,2,4]oxadiazol-3-yl)-ethyl]-amide

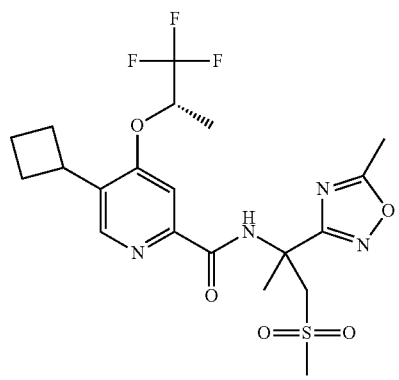 [SMILES: Cc1nc(C(C)(CS(C)(=O)=O)NC(=O)c2cc(O[C@@H](C)C(F)(F)F)c(C3CCC3)cn2)no1]

The title compound was synthesized in analogy to Example 23b, using 5-Cyclobutyl-4-((S)-2,2,2-trifluoro-1-methyl-ethoxy)-pyridine-2-carboxylic acid (Example 110e) and 2-Methanesulfonyl-1-methyl-1-(5-methyl-[1,2,4]oxadiazol-3-yl)-ethylamine (Example 109d) as starting materials and isolated (77 mg, 57%) as a white solid; MS (ESI, m/z): 491.6 (M+H⁺).

Example 112

5-cyclopropyl-N-[2-(5-methyl-1,2,4-oxadiazol-3-yl)-1-phenylmethoxypropan-2-yl]-4-(2,2,2-trifluoroethoxy)pyridine-2-carboxamide

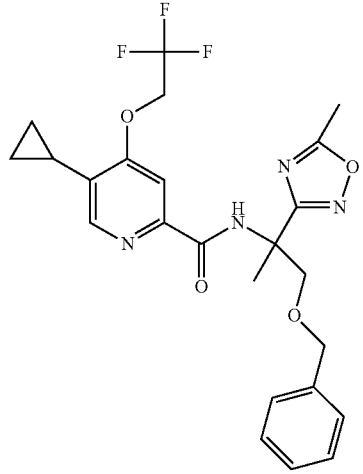 [SMILES: Cc1nc(C(C)(COCc2ccccc2)NC(=O)c2cc(OCC(F)(F)F)c(C3CC3)cn2)no1]

a) N-(2-benzyloxy-1-cyano-1-methyl-ethyl)-2-methyl-propane-2-sulfinamide

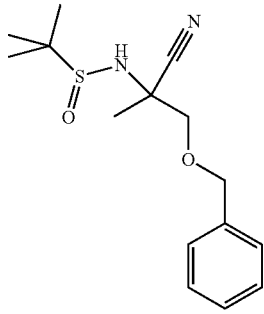 [SMILES: CC(C#N)(COCc1ccccc1)NS(=O)C(C)(C)C]

To a solution of (E)-N-(1-(benzyloxy)propan-2-ylidene)-2-methylpropane-2-sulfinamide (CAN 393536-49-7, 3.1 g, 11.6 mmol) in dry THF (55 ml) under an argon atmosphere was added cesium fluoride (1.94 g, 12.8 mmol) followed by addition of trimethylsilyl cyanide (1.27 g, 1.71 ml, 12.8 mmol). The reaction mixture was stirred at room temperature overnight. The reaction mixture was diluted with ethyl acetate and poured into a separatory funnel. Organic phase was extracted with a 1M aqueous solution of sodium bicarbonate and the organic phase was collected. The aqueous phase was back-extracted with ethyl acetate. The combined organic phases were dried over sodium sulfate and evaporated down to dryness. The crude material was purified by flash chromatography on silica eluting with a heptane/ethyl acetate gradient to yield the title compound (2.53 gr, 74%); MS (ESI, m/z): 295.6 (M+H⁺).

b) 3-benzyloxy-2-(tert-butylsulfinylamino)-N'-hydroxy-2-methyl-propanamidine

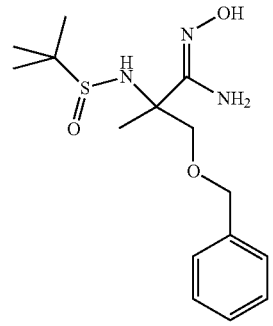 [SMILES: CC(COCc1ccccc1)(NS(=O)C(C)(C)C)/C(N)=N/O]

The title compound was synthesized in analogy to Example 78f, using N-(1-(benzyloxy)-2-cyanopropan-2-yl)-2-methylpropane-2-sulfinamide (Example 112a) as starting materials and was isolated by flash chromatography on silica eluting with a dichloromethane\methanol gradient (3.22 g, 57%); MS (ESI, m/z): 328.6 (M+H⁺).

c) N-[2-benzyloxy-1-methyl-1-(5-methyl-1,2,4-oxadiazol-3-yl)ethyl]-2-methyl-propane-2-sulfinamide

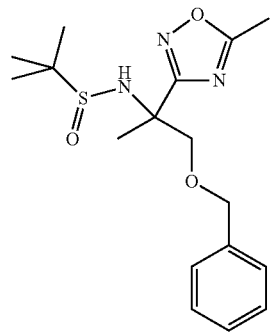 [SMILES: Cc1nc(C(C)(COCc2ccccc2)NS(=O)C(C)(C)C)no1]

To a solution of (Z)-3-(benzyloxy)-2-(1,1-dimethylethylsulfinamido)-N'-hydroxy-2-methylpropanimidamide (Example 112b, 1.25 g, 3.82 mmol) in dry DMF (25 ml) was added potassium carbonate (633 mg, 4.58 mmol) followed by addition of acetic anhydride (390 mg, 360 uL, 3.82 mmol). The reaction mixture was stirred at room temperature for 1 hour and was then stirred at 120° C. for 2 hours. DMF was removed in vacuo and the residue was dissolved in ethyl acetate which was extracted with a 1.0M aqueous solution of sodium bicarbonate. The organic phase was dried over sodium sulfate and evaporated down to dryness. The crude material was purified by flash chromatography on silica eluting with a heptane/ethylacetate gradient to yield the title compound (1.20 g, purity: 80%, 72%) as a light yellow oil. MS (ESI, m/z): 352.6 (M+H⁺).

d) 1-(benzyloxy)-2-(5-methyl-1,2,4-oxadiazol-3-yl)propan-2-amine

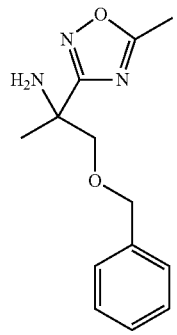 [SMILES: Cc1nc(C(C)(N)COCc2ccccc2)no1]

To a solution of N-(1-(benzyloxy)-2-(5-methyl-1,2,4-oxadiazol-3-yl)propan-2-yl)-2-methylpropane-2-sulfinamide (example 112c, 1.2 g, 2.73 mmol) in methanol (15 ml) was added a 4.0M solution of hydrochloric acid in Dioxane (2.05 ml, 8.19 mmol). The reaction mixture was stirred at room temperature for 2 hours. Volatiles were removed in vacuo and the residue was dissolved in ethyl acetate. The organic phase was extracted with a 1.0M aqueous solution of sodium bicarbonate and the organic phase was collected. The aqueous phase was back-extracted with ethyl acetate. The combined organic phases were dried over sodium sulfate and evaporated down to dryness. The crude material was purified by flash chromatography on silica eluting with a heptane\ethyl acetate gradient to yield the title compound (577 mg, 85%) as a light yellow oil. MS (ESI, m/z): 248.6 (M+H$^+$).

e) 5-cyclopropyl-N-[2-(5-methyl-1,2,4-oxadiazol-3-yl)-1-phenylmethoxypropan-2-yl]-4-(2,2,2-trifluoroethoxy)pyridine-2-carboxamide

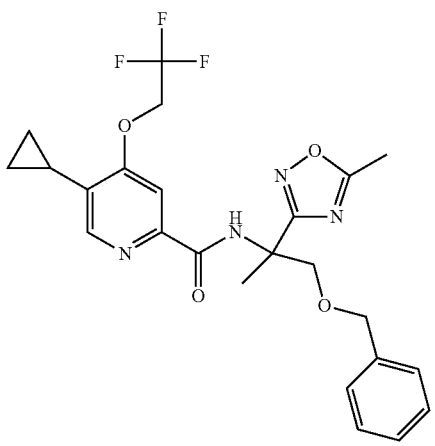 [SMILES: Cc1nc(C(C)(COCc2ccccc2)NC(=O)c2cc(OCC(F)(F)F)c(C3CC3)cn2)no1]

To a solution of 5-Cyclopropyl-4-(2,2,2-trifluoro-ethoxy)-pyridine-2-carboxylic acid (example 48c, 0.58 g, 2.22 mmol) in dry DMF (10 ml) was added triethylamine (270 mg, 371 µl, 2.66 mmol) and TBTU (713 mg, 2.22 mmol). The reaction mixture was stirred at room temperature for 30 minutes followed by addition of 1-(benzyloxy)-2-(5-methyl-1,2,4-oxadiazol-3-yl)propan-2-amine (example 112d, 577 mg, 2.33 mmole) and the reaction was then stirred at room temperature overnight. DMF was removed in vacuo and the residue was dissolved in ethyl acetate. The organic phase was extracted with a 2M aqueous solution of sodium carbonate and the organic phase was collected. The organic phase was dried over sodium sulfate and evaporated down to dryness. The crude material was purified by flash chromatography on silica eluting with a heptane/ethyl acetate gradient to yield the title compound (805 mg, 74%) as a light yellow oil. MS (ESI, m/z): 491.5 (M+H$^+$).

Example 113

5-cyclopropyl-N-[1-hydroxy-2-(5-methyl-1,2,4-oxadiazol-3-yl)propan-2-yl]-4-(2,2,2-trifluoroethoxy)pyridine-2-carboxamide

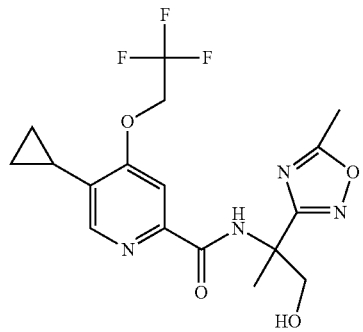 [SMILES: Cc1nc(C(C)(CO)NC(=O)c2cc(OCC(F)(F)F)c(C3CC3)cn2)no1]

To a solution of 5-cyclopropyl-N-[2-(5-methyl-1,2,4-oxadiazol-3-yl)-1-phenylmethoxypropan-2-yl]-4-(2,2,2-trifluoroethoxy)pyridine-2-carboxamide (example 112e, 570 mg, 1.16 mmol) in dry dichloromethane (6 ml) cooled down to 0° C. under an argon atmosphere was added a 1.0M solution of boron tribromide in dichloromethane (1.28 ml, 1.28 mmol). The reaction mixture was stirred at 0° C. for 15 minutes followed by stirring at room temperature for 1 hour. The reaction was diluted with dichloromethane, quenched by addition of a 2M aqueous solution of sodium carbonate and the bi-phasic mixture was stirred for 10 minutes. The bi-phasic mixture was poured into a separatory funnel and extracted. The organic phase was collected and the aqueous phase was back-extracted with dichloromethane. The combined organic phases were dried over sodium sulfate and evaporated down to dryness. The crude material was purified by flash chromatography on silica eluting with a heptane/ethyl acetate gradient to yield the title compound (394 mg, 85%). MS (ESI, m/z): 401.6 (M+H$^+$).

Example 114

(2S)-1-[5-cyclopropyl-4-(cyclopropylmethoxy)pyridine-2-carbonyl]-4,4-difluoropyrrolidine-2-carboxamide

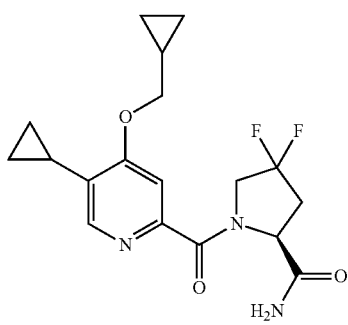 [SMILES: NC(=O)[C@@H]1CC(F)(F)CN1C(=O)c1cc(OCC2CC2)c(C2CC2)cn1]

The title compound was synthesized in analogy to Example 112e, using 5-Cyclopropyl-4-cyclopropylmethoxy-pyridine-2-carboxylic acid (Example 42c) and (R)-4,4-difluoropyrrolidine-2-carboxamide hydrochloride (CAN 719267-96-6) as starting materials and isolated (160 mg, 51%); MS (ESI, m/z): 366.2 (M+H⁺).

Example 115

(2S)-1-[5-cyclopropyl-4-(2,2,2-trifluoroethoxy)pyridine-2-carbonyl]-4,4-difluoropyrrolidine-2-carboxamide

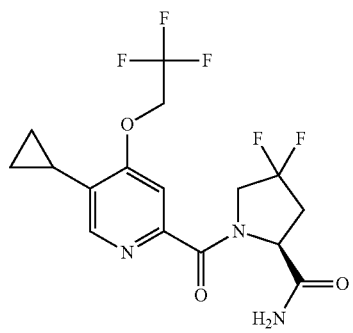 [SMILES: NC(=O)[C@@H]1CC(F)(F)CN1C(=O)c1cc(OCC(F)(F)F)c(C2CC2)cn1]

The title compound was synthesized in analogy to Example 112e, using 5-Cyclopropyl-4-(2,2,2-trifluoroethoxy)-pyridine-2-carboxylic acid (Example 48c) and (R)-4,4-difluoropyrrolidine-2-carboxamide hydrochloride (CAN 719267-96-6) as starting materials and isolated (33 mg, 44%); MS (ESI, m/z): 394.5 (M+H⁺).

Example 116

5-cyclobutyl-N-[1-cyclopropyl-2-(5-methyl-1,2,4-oxadiazol-3-yl)propan-2-yl]-4-(2,2,2-trifluoroethoxy)pyridine-2-carboxamide (enantiomer A)

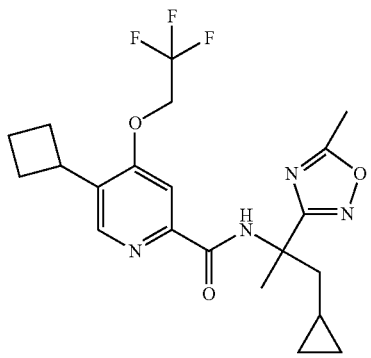 [SMILES: Cc1nc(C(C)(CC2CC2)NC(=O)c2cc(OCC(F)(F)F)c(C3CCC3)cn2)no1]

The racemate (Example 108g) was separated into its enantiomers by preparative chiral HPLC (Chiralpak AD, ethanol/heptane) and the title compound was the first enantiomer collected and isolated as colorless oil; MS (ESI, m/z): 439.6 (M+H⁺).

Example 117

5-cyclobutyl-N-[1-cyclopropyl-2-(5-methyl-1,2,4-oxadiazol-3-yl)propan-2-yl]-4-(2,2,2-trifluoroethoxy)pyridine-2-carboxamide (enantiomer B)

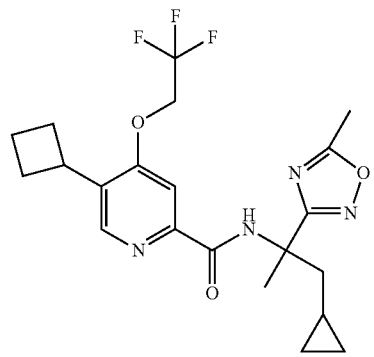

The racemate (Example 108g) was separated into its enantiomers by preparative chiral HPLC (Chiralpak AD, ethanol/heptane) and the title compound was the second enantiomer collected and isolated as colorless oil; MS (ESI, m/z): 439.6 (M+H⁺).

Example 118

5-cyclobutyl-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide (epimer A)

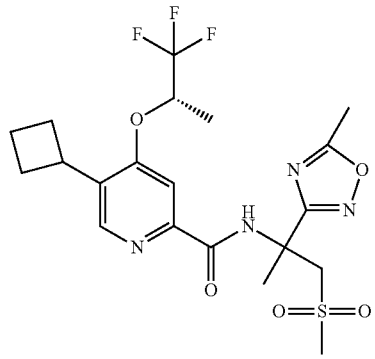 [SMILES: Cc1nc(C(C)(CS(C)(=O)=O)NC(=O)c2cc(O[C@@H](C)C(F)(F)F)c(C3CCC3)cn2)no1]

The mixture of epimers (Example 111) was separated into its individual epimers by preparative chiral HPLC (Chiralpak AD, ethanol/heptane) and the title compound was the first epimer collected and isolated as colorless oil; MS (ESI, m/z): 491.6 (M+H⁺).

Example 119

5-cyclobutyl-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide (epimer B)

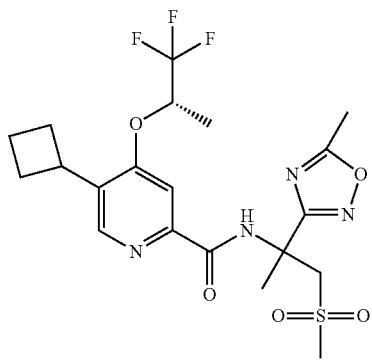 [SMILES: Cc1nc(C(C)(CS(C)(=O)=O)NC(=O)c2cc(O[C@@H](C)C(F)(F)F)c(C3CCC3)cn2)no1]

The mixture of epimers (Example 111) was separated into its individual epimers by preparative chiral HPLC (Chiralpak AD, ethanol/heptane) and the title compound was the second epimer collected and isolated as colorless oil; MS (ESI, m/z): 491.6 (M+H⁺).

Example 120

5-cyclobutyl-N-[1-cyclopropyl-2-(5-methyl-1,2,4-oxadiazol-3-yl)propan-2-yl]-4-[(2S)-1,1,1-trifluoropropan-2-yl]oxypyridine-2-carboxamide (epimer A)

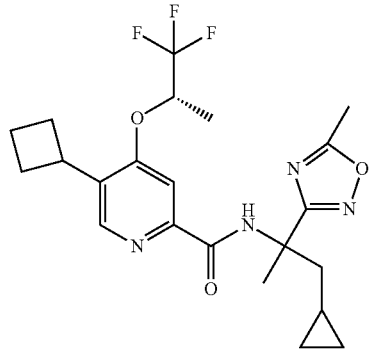 [SMILES: Cc1nc(C(C)(CC2CC2)NC(=O)c2cc(O[C@@H](C)C(F)(F)F)c(C3CCC3)cn2)no1]

The mixture of epimers (Example 110f) was separated into its individual epimers by preparative chiral HPLC (Chiralpak AD, ethanol/heptane) and the title compound was the first epimer collected and isolated as colorless oil; MS (ESI, m/z): 453.6 (M+H⁺).

Example 121

5-cyclobutyl-N-[1-cyclopropyl-2-(5-methyl-1,2,4-oxadiazol-3-yl)propan-2-yl]-4-[(2S)-1,1,1-trifluoropropan-2-yl]oxypyridine-2-carboxamide (epimer B)

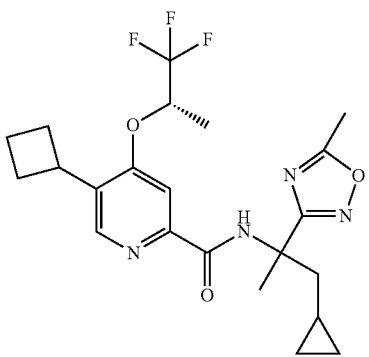

The mixture of epimers (Example 110f) was separated into its individual epimers by preparative chiral HPLC (Chiralpak AD, ethanol/heptane) and the title compound was the second epimer collected and isolated as colorless oil; MS (ESI, m/z): 453.6 (M+H⁺).

Example 122

(2R)-1-[5-cyclopropyl-4-(2,2,2-trifluoroethoxy)pyridine-2-carbonyl]-4,4-difluoropyrrolidine-2-carboxamide

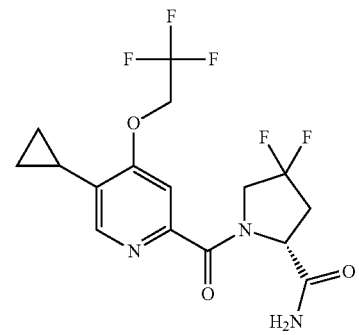 [SMILES: NC(=O)[C@H]1CC(F)(F)CN1C(=O)c1cc(OCC(F)(F)F)c(C2CC2)cn1]

The title compound was synthesized in analogy to Example 112e, using 5-Cyclopropyl-4-(2,2,2-trifluoroethoxy)-pyridine-2-carboxylic acid (Example 48c) and (R)-4,4-difluoropyrrolidine-2-carboxamide hydrochloride (CAN 1315304-75-6) as starting materials and isolated (20 mg, 32%); MS (ESI, m/z): 394.5 (M+H⁺).

Example 123

N-[1-cyclopropyl-2-(5-methyl-1,2,4-oxadiazol-3-yl)propan-2-yl]-5-(3-hydroxyoxetan-3-yl)-4-(2,2,2-trifluoroethoxy)pyridine-2-carboxamide

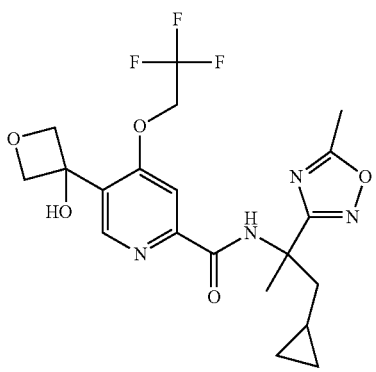 [SMILES: Cc1nc(C(C)(CC2CC2)NC(=O)c2cc(OCC(F)(F)F)c(C3(O)COC3)cn2)no1]

a) 3-(4,6-dichloro-3-pyridyl)oxetan-3-ol

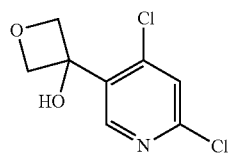

To a solution of 5-bromo-2,4-dichloropyridine (CAN 849937-96-8, 15 g, 66.1 mmol) in dry THF (300 ml) cooled down to −15° C. under an argon atmosphere was added isopropyl magnesium chloride, lithium chloride complex (53.4 ml, 69.4 mmol) and the mixture was stirred at −15° C. for 1 hour. Then oxetan-3-one (5.24 g, 72.7 mmol) was added neat to the reaction mixture cooled at −15° C., reaction mixture was stirred and let to warm up to room temperature overnight. Reaction was quenched by addition of water and stirred for 5 minutes. Reaction was diluted with ethyl acetate and was transferred into a separatory funnel. The organic phase was extracted with a saturated aqueous solution of ammonium chloride and the organic phase was collected. The aqueous phase was back-extracted with ethyl acetate. The combined organic phases were dried over sodium sulfate and evaporated down to dryness. The crude material was purified by flash chromatography on silica eluting with a heptane/ethyl acetate gradient to yield the title compound (10.5 mg, 72%). MS (ESI, m/z): 220.4 (M+H$^+$)

b) 4-chloro-5-(3-hydroxyoxetan-3-yl)pyridine-2-carbonitrile

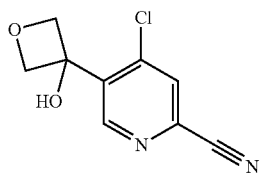 [SMILES: N#Cc1cc(Cl)c(C2(O)COC2)cn1]

To a solution of 3-(4,6-dichloropyridin-3-yl)oxetan-3-ol (example 123a, 5.0 g, 22.7 mmol) in dry DMF (100 ml) under argon atmosphere was added dicyanozinc (1.47 g, 12.5 mmol), DPPF (1.26 g, 2.27 mmol) and Pd2(dba)3 (1.04 g, 1.14 mmol). The reaction mixture was then stirred at 100° C. for two hours. DMF was removed in vacuo and the obtained residue was dissolved in ethyl acetate and poured into a separatory funnel. The organic phase was extracted with a saturated solution of ammonium chloride (colloids formed and were removed by filtration on a pad of celite). The organic phase was collected and the aqueous phase was back-extracted with ethyl acetate. Combined organic phases were dried over sodium sulfate and evaporated down to dryness. The crude material was purified by flash chromatography on silica eluting with a heptane/ethyl acetate gradient to yield the title compound (4.1 gr, 86%); MS (ESI, m/z): 211.1 (M+H$^+$).

c) 5-(3-hydroxyoxetan-3-yl)-4-(2,2,2-trifluoroethoxy)pyridine-2-carbonitrile

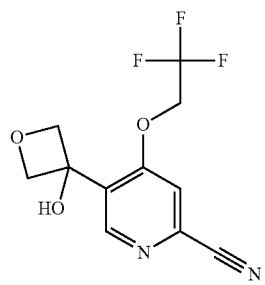 [SMILES: N#Cc1cc(OCC(F)(F)F)c(C2(O)COC2)cn1]

To a solution of 4-chloro-5-(3-hydroxyoxetan-3-yl)pyridine-2-carbonitrile (example 123b, 1 g, 4.75 mmol) in dry DMF (20 ml) under an argon atmosphere cooled down to 0° C. was added 2,2,2-trifluoroethanol (570 mg, 412 µl, 5.7 mmol) followed by addition of potassium tert-butoxide (639 mg, 5.7 mmol). The reaction was stirred at 0° C. for 10 minutes and then stirred at 80° C. for 2 hours. DMF was removed in vacuo and the residue was dissolved in ethylacetate. The organic phase was extracted with a 2M aqueous solution of sodium carbonate. The organic phase was collected and the aqueous phase back-extracted with ethylacetate. The combined organic phases were dried over sodium sulfate and evaporated down to dryness. The crude material was purified by flash chromatography on silica eluting with a heptane/ethyl acetate gradient to yield the title compound (1.2 gr, 92%); MS (ESI, m/z): 275.4 (M+H$^+$).

d) 5-(3-hydroxyoxetan-3-yl)-4-(2,2,2-trifluoroethoxy)pyridine-2-carboxylic acid

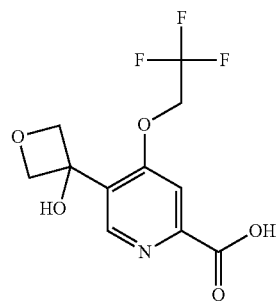 [SMILES: O=C(O)c1cc(OCC(F)(F)F)c(C2(O)COC2)cn1]

133

To a solution of 5-(3-hydroxyoxetan-3-yl)-4-(2,2,2-trifluoroethoxy)pyridine-2-carbonitrile (example 123c, 1.3 g, 4.74 mmol) in ethanol (20 ml) was added a 4M aqueous solution of potassium hydroxide (4.74 ml, 19.0 mmol). The reaction mixture was stirred at 100° C. under microwave radiation for 60 min. Volatiles were removed in vacuo and the residue was dissolved in DMSO for direct purification by preparative HPLC to yield the title compound (360 mg, 26%); MS (ESI, m/z): 294.4 (M+H$^+$).

e) N-[1-cyclopropyl-2-(5-methyl-1,2,4-oxadiazol-3-yl)propan-2-yl]-5-(3-hydroxyoxetan-3-yl)-4-(2,2,2-trifluoroethoxy)pyridine-2-carboxamide

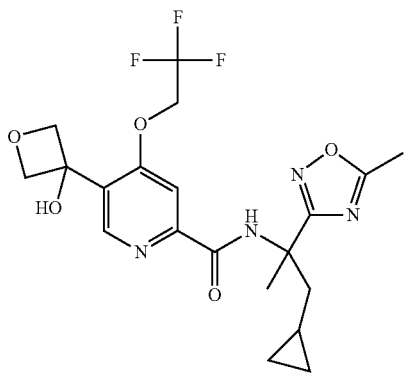 [SMILES: Cc1nc(C(C)(CC2CC2)NC(=O)c2cc(OCC(F)(F)F)c(C3(O)COC3)cn2)no1]

The title compound was synthesized in analogy to Example 112e, using 5-(3-hydroxyoxetan-3-yl)-4-(2,2,2-trifluoroethoxy)pyridine-2-carboxylic acid (Example 112d) and 2-Cyclopropyl-1-methyl-1-(5-methyl-[1,2,4]oxadiazol-3-yl)-ethylamine (example 66e) as starting materials and isolated (37 mg, 47%); MS (ESI, m/z): 457.5 (M+H$^+$).

Example 124

5-cyclobutyl-N-[1-methyl-1-(5-methyl-1,2,4-oxadiazol-3-yl)-2-methylsulfonyl-ethyl]-4-(2,2,2-trifluoroethoxy)pyridine-2-carboxamide (enantiomer A)

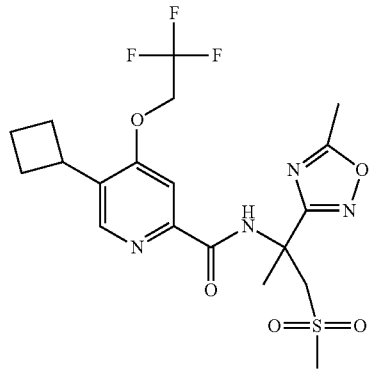 [SMILES: Cc1nc(C(C)(CS(C)(=O)=O)NC(=O)c2cc(OCC(F)(F)F)c(C3CCC3)cn2)no1]

134 a) benzyl N-[1-methyl-1-(5-methyl-1,2,4-oxadiazol-3-yl)-2-methylsulfonyl-ethyl]carbamate (enantiomer A)

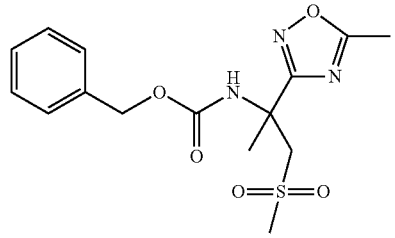 [SMILES: Cc1nc(C(C)(CS(C)(=O)=O)NC(=O)OCc2ccccc2)no1]

The racemate (Example 109c) was separated into its enantiomers by preparative chiral HPLC (Chiralcel OD (OD-H), isopropanol/heptane) and the title compound was the second enantiomer collected and isolated as colorless oil; MS (ESI, m/z): 354.5 (M+H$^+$).

b) 2-(5-methyl-1,2,4-oxadiazol-3-yl)-1-methylsulfonyl-propan-2-amine;hydrobromide (enantiomer A)

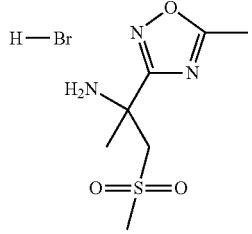

benzyl N-[1-methyl-1-(5-methyl-1,2,4-oxadiazol-3-yl)-2-methylsulfonyl-ethyl]carbamate (enantiomer A) (example 124a, 710 mg, 2.01 mmole) was dissolved in 10 mL hydrobromic acid 33% in acetic acid and stirred for 1 hour at room temperature. Volatiles were removed in vacuo and the residue was dissolved in 1-2 ml of ethanol. To the crude solution was added a mixture of dichloromethane-heptane which gave a precipitate isolated by filtration (precipitate is very hygroscopic) to yield the title compound (590 mg, 98%); MS (ESI, m/z): 220.0 (M+H$^+$).

c) 5-cyclobutyl-N-[1-methyl-1-(5-methyl-1,2,4-oxadiazol-3-yl)-2-methylsulfonyl-ethyl]-4-(2,2,2-trifluoroethoxy)pyridine-2-carboxamide (enantiomer A)

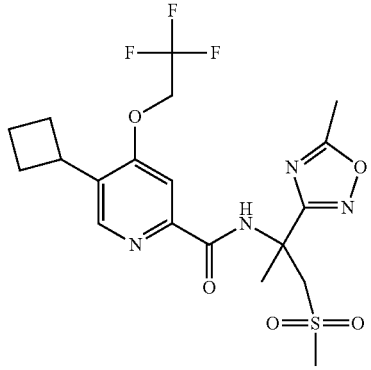

To a solution of 5-Cyclobutyl-4-(2,2,2-trifluoro-ethoxy)-pyridine-2-carboxylic acid (example 108f, 40 mg, 145 µmol) in dry DMF (1.00 ml) was added DIEA (76.2 µl, 436 µmol) and TBTU (49.0 mg, 153 µmol) and the reaction mixture was stirred at room temperature for 20 minutes. Addition of 2-(5-methyl-1,2,4-oxadiazol-3-yl)-1-methylsulfonyl-propan-2-amine;hydrobromide (enantiomer A) (example 124b, 45.8 mg, 153 µmol) to the reaction mixture and the latter was stirred at room temperature for 2 hours. The crude was directly purified by preparative HPLC without any work-up to yield the title compound (15 mg, 22%); MS (ESI, m/z): 477.5 (M+H$^+$).

Example 125

5-cyclobutyl-N-[1-methyl-1-(5-methyl-1,2,4-oxadiazol-3-yl)-2-methylsulfonyl-ethyl]-4-(2,2,2-trifluoro-ethoxy)pyridine-2-carboxamide (enantiomer B)

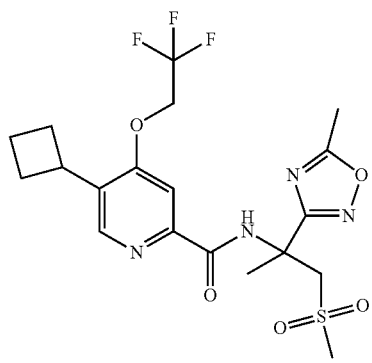 [SMILES: Cc1nc(C(C)(CS(C)(=O)=O)NC(=O)c2cc(OCC(F)(F)F)c(C3CCC3)cn2)no1]

a) benzyl N-[1-methyl-1-(5-methyl-1,2,4-oxadiazol-3-yl)-2-methylsulfonyl-ethyl]carbamate (enantiomer B)

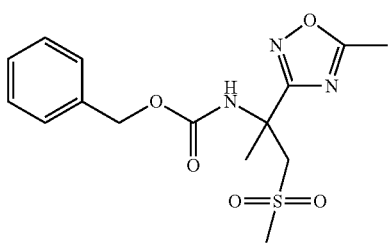 [SMILES: Cc1nc(C(C)(CS(C)(=O)=O)NC(=O)OCc2ccccc2)no1]

The racemate (Example 109c) was separated into its enantiomers by preparative chiral HPLC (Chiralcel OD (OD-H), isopropanol/heptane) and the title compound was the first enantiomer collected and isolated as colorless oil; MS (ESI, m/z): 354.5 (M+H$^+$).

b) 2-(5-methyl-1,2,4-oxadiazol-3-yl)-1-methylsulfonyl-propan-2-amine;hydrobromide (enantiomer B)

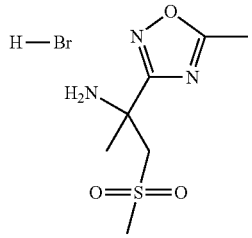

benzyl N-[1-methyl-1-(5-methyl-1,2,4-oxadiazol-3-yl)-2-methylsulfonyl-ethyl]carbamate (enantiomer B) (example 125a, 605 mg, 1.71 mmole) was dissolved in 12 mL hydrobromic acid 33% in acetic acid and stirred for 1 hour at room temperature. Volatiles were removed in vacuo and the residue was dissolved in 1-2 ml of ethanol. To the crude solution was added a mixture of dichloromethane-heptane which gave a precipitate isolated by filtration (precipitate is very hygroscopic) to yield the title compound (466 mg, 91%); MS (ESI, m/z): 220.0 (M+H$^+$).

c) 5-cyclobutyl-N-[1-methyl-1-(5-methyl-1,2,4-oxadiazol-3-yl)-2-methylsulfonyl-ethyl]-4-(2,2,2-trifluoroethoxy)pyridine-2-carboxamide (enantiomer B)

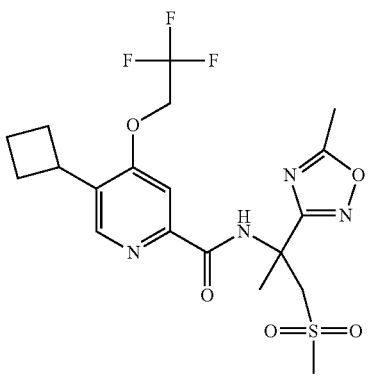

To a solution of 5-Cyclobutyl-4-(2,2,2-trifluoro-ethoxy)-pyridine-2-carboxylic acid (example 108f, 40 mg, 145 µmol) in dry DMF (1.00 ml) was added DIEA (76.2 µl, 436 µmol) and TBTU (49.0 mg, 153 µmol) and the reaction mixture was stirred at room temperature for 20 minutes. Addition of 2-(5-methyl-1,2,4-oxadiazol-3-yl)-1-methylsulfonyl-propan-2-amine;hydrobromide (enantiomer B) (example 125b, 45.8 mg, 153 µmol) to the reaction mixture and the latter was stirred at room temperature for 2 hours. The crude was directly purified by preparative HPLC without any work-up to yield the title compound (20 mg, 29%); MS (ESI, m/z): 477.5 (M+H$^+$).

Example 126

5-(1-hydroxycyclobutyl)-N-[2-(5-methyl-1,2,4-oxa-diazol-3-yl)-1-methylsulfonylpropan-2-yl]-4-[(2S)-1,1,1-trifluoropropan-2-yl]oxypyridine-2-carboxamide

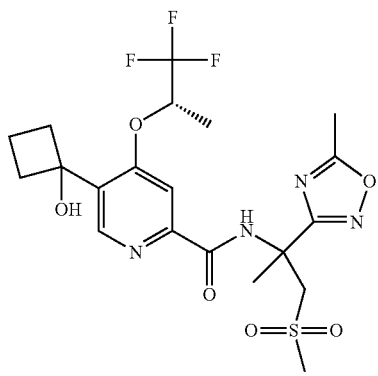 [SMILES: Cc1nc(C(C)(CS(C)(=O)=O)NC(=O)c2cc(O[C@@H](C)C(F)(F)F)c(C3(O)CCC3)cn2)no1]

a) 1-(4,6-dichloro-3-pyridyl)cyclobutanol

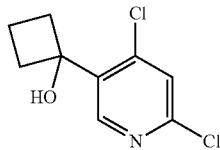 [SMILES: OC1(c2cnc(Cl)cc2Cl)CCC1]

The title compound was synthesized in analogy to Example 123a, using 5-bromo-2,4-dichloropyridine (CAN 849937-96-8) and cyclobutanone (CAN 1191-95-3) as starting materials and isolated (5.1 g, 76%); MS (ESI, m/z): 218.4 (M+H$^+$).

b) 4-chloro-5-(1-hydroxycyclobutyl)pyridine-2-carbonitrile

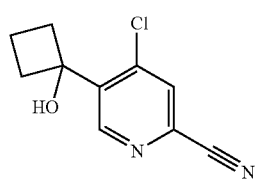

The title compound was synthesized in analogy to Example 123b, using 1-(4,6-dichloro-3-pyridyl)cyclobutanol (example 126a) as starting material and isolated (1.61 g, 33%); MS (ESI, m/z): 209.2 (M+H$^+$).

c) 5-(1-hydroxycyclobutyl)-4-[(1S)-2,2,2-trifluoro-1-methyl-ethoxy]pyridine-2-carbonitrile

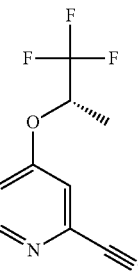

The title compound was synthesized in analogy to Example 123c, using 4-chloro-5-(1-hydroxycyclobutyl)pyridine-2-carbonitrile (example 126b) and (S)-1,1,1-Trifluoropropan-2-ol (CAN 3539-97-7) as starting materials and isolated (1.2 g, 92%); MS (ESI, m/z): 287.5 (M+H$^+$).

d) 5-(1-hydroxycyclobutyl)-4-[(1S)-2,2,2-trifluoro-1-methyl-ethoxy]pyridine-2-carboxylic acid

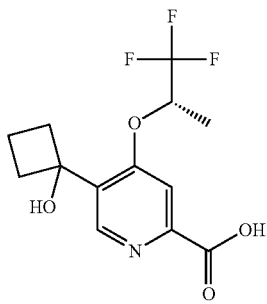 [SMILES: C[C@H](Oc1cc(C(=O)O)ncc1C1(O)CCC1)C(F)(F)F]

A suspension of 5-(1-hydroxycyclobutyl)-4-[(1S)-2,2,2-trifluoro-1-methyl-ethoxy]pyridine-2-carbonitrile (example 126c, 2.7 g, 9.43 mmol) in 25% aqueous solution of hydrochloric acid (55 ml) was stirred at 110° C. for 3 hours. Reaction was cooled down to room temperature and the ph was set to 10-12 by addition of sodium hydroxide pellets. The ph of the solution was adjusted to 1-2 by addition of a 25% aqueous solution of hydrochloric acid and the formed precipitate was isolated by filtration. The solids were again purified by preparative HPLC to yield the title compound (232 mg, 8%); MS (ESI, m/z): 306.1 (M+H$^+$).

e) 5-(1-hydroxycyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide

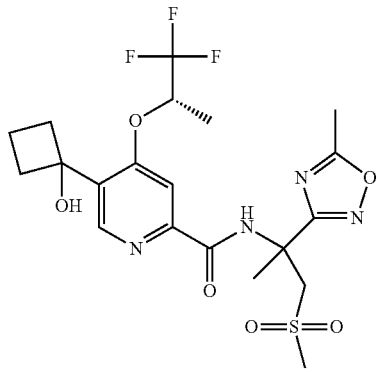 [SMILES: Cc1nc(C(C)(CS(C)(=O)=O)NC(=O)c2cc(O[C@@H](C)C(F)(F)F)c(C3(O)CCC3)cn2)no1]

The title compound was synthesized in analogy to Example 112e, using 5-(1-hydroxycyclobutyl)-4-[(1S)-2,2,2-trifluoro-1-methyl-ethoxy]pyridine-2-carboxylic acid (Example 126d) and 2-Methanesulfonyl-1-methyl-1-(5-methyl-[1,2,4]oxadiazol-3-yl)-ethylamine (example 109d) as starting materials and isolated (28 mg, 42%); MS (ESI, m/z): 507.5 (M+H⁺).

Example 127

5-(cyclobuten-1-yl)-N-[2-(5-methyl-1,2,4-oxadiazol-3-yl)-1-methylsulfonylpropan-2-yl]-4-(2,2,2-trifluoroethoxy)pyridine-2-carboxamide

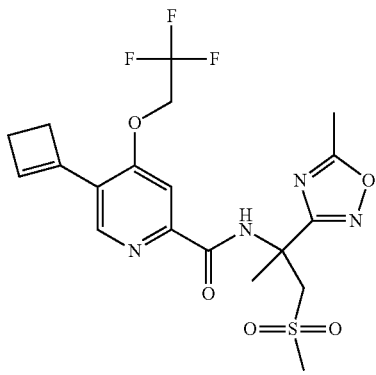 [SMILES: Cc1nc(C(C)(CS(C)(=O)=O)NC(=O)c2cc(OCC(F)(F)F)c(C3=CCC3)cn2)no1]

a) 3-(1-fluorocyclobutyl)-4-(2,2,2-trifluoroethoxy)pyridine

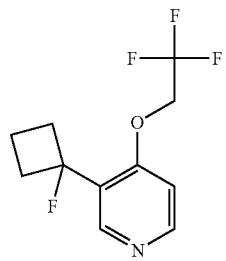 [SMILES: FC(F)(F)COc1ccncc1C1(F)CCC1]

To a solution of 1-[4-(2,2,2-Trifluoro-ethoxy)-pyridin-3-yl]-cyclobutanol (example 108b, 1.7 g, 6.88 mmol) in dry dichloromethane (25.0 ml) under an argon atmosphere cooled down to 0° C. was added DAST (1.36 ml, 10.3 mmol). The reaction mixture was stirred at 0° C. for 30 minutes. The reaction was quenched by addition of a 2M aqueous solution of sodium carbonate and the bi-phasic mixture was stirred for 20 minutes. The bi-phasic mixture was transferred into a separatory funnel and the organic phase was collected. The organic phase was dried over sodium sulfate and evaporated down to dryness to yield the title compound (1.68 g, 98%); MS (ESI, m/z): 250.4 (M+H⁺). The crude material was used without any purification for the next step.

b) 3-(1-fluorocyclobutyl)-1-oxido-4-(2,2,2-trifluoroethoxy)pyridin-1-ium

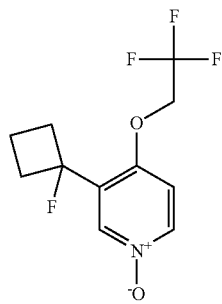

To a solution of 3-(1-fluorocyclobutyl)-4-(2,2,2-trifluoroethoxy)pyridine (example 127a, 1.68 g, 6.74 mmol) in dichloromethane (40 ml) was added m-CPBA (3.49 g, 10.1 mmol). The reaction mixture was stirred at room temperature overnight. The reaction mixture was transferred into a separatory funnel and extracted with a 2M aqueous solution of sodium carbonate. The organic phase was collected and the aqueous phase was back-extracted with dichloromethane. The combined organic phases were dried over sodium sulfate and evaporated down to dryness to yield the crude title compound (1.68 g, 94%) which was used without any purification for the next step; MS (ESI, m/z): 266.5 (M+H⁺).

c) 5-(1-fluorocyclobutyl)-4-(2,2,2-trifluoroethoxy)pyridine-2-carbonitrile

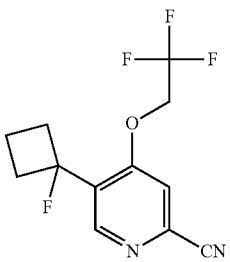 [SMILES: N#Cc1cc(OCC(F)(F)F)c(C2(F)CCC2)cn1]

To a solution of 3-(1-fluorocyclobutyl)-1-oxido-4-(2,2,2-trifluoroethoxy)pyridin-1-ium (example 127b, 1.65 g, 6.22 mmol) in dichloromethane (25 ml) was added trimethylsilanecarbonitrile (945 mg, 1.19 ml, 9.33 mmol) and dimethylcarbamic chloride (833 µl, 8.71 mmol). The reaction mixture was stirred at room temperature overnight. The reaction mixture was poured into a separation funnel and extracted with a 1M aqueous solution of sodium bicarbonate. The organic phase was dried over sodium sulfate and evaporated down to dryness. The crude material was purified by flash chromatography on silica eluting with a heptane/ethyl acetate gradient to yield the title compound (760 mg, 44%); MS (ESI, m/z): 275.5 (M+H⁺).

d) 5-(cyclobuten-1-yl)-4-(2,2,2-trifluoroethoxy)pyridine-2-carboxylic acid

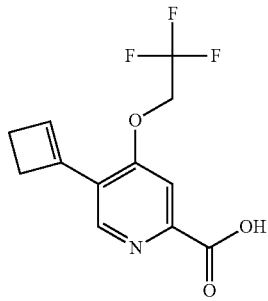 [SMILES: O=C(O)c1cc(OCC(F)(F)F)c(C2=CCC2)cn1]

The title compound was synthesized in analogy to Example 126d, using 5-(1-fluorocyclobutyl)-4-(2,2,2-trifluoroethoxy)pyridine-2-carbonitrile (Example 127c) as starting materials and isolated as a side-product (360 mg, 44%); MS (ESI, m/z): 274.0 (M+H⁺).

e) 5-(cyclobuten-1-yl)-N-[2-(5-methyl-1,2,4-oxadiazol-3-yl)-1-methylsulfonylpropan-2-yl]-4-(2,2,2-trifluoroethoxy)pyridine-2-carboxamide

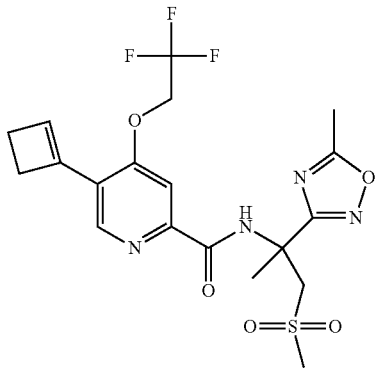 [SMILES: Cc1nc(C(C)(CS(C)(=O)=O)NC(=O)c2cc(OCC(F)(F)F)c(C3=CCC3)cn2)no1]

The title compound was synthesized in analogy to Example 112e, using 5-(cyclobuten-1-yl)-4-(2,2,2-trifluoroethoxy)pyridine-2-carboxylic acid (Example 127d) and 2-Methanesulfonyl-1-methyl-1-(5-methyl-[1,2,4]oxadiazol-3-yl)-ethylamine (example 109d) as starting materials and isolated (25 mg, 14%); MS (ESI, m/z): 475.5 (M+H⁺).

Example 128

5-cyclopropyl-N-[1-(3,3-difluoroazetidin-1-yl)-2-(5-methyl-1,2,4-oxadiazol-3-yl)propan-2-yl]-4-(2,2,2-trifluoroethoxy)pyridine-2-carboxamide

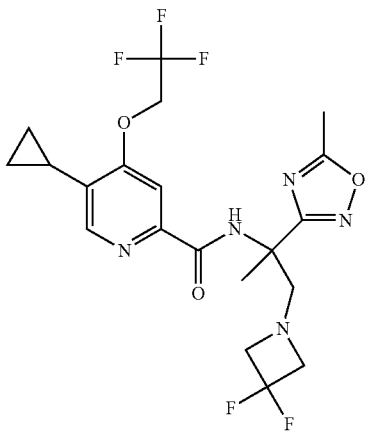 [SMILES: Cc1nc(C(C)(CN2CC(F)(F)C2)NC(=O)c2cc(OCC(F)(F)F)c(C3CC3)cn2)no1]

a) 5-cyclopropyl-N-[1-methyl-1-(5-methyl-1,2,4-oxadiazol-3-yl)-2-oxo-ethyl]-4-(2,2,2-trifluoroethoxy)pyridine-2-carboxamide

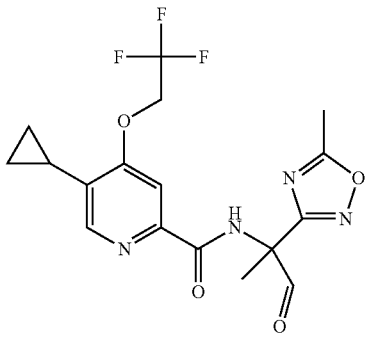 [SMILES: Cc1nc(C(C)(C=O)NC(=O)c2cc(OCC(F)(F)F)c(C3CC3)cn2)no1]

To a solution of 5-cyclopropyl-N-[1-hydroxy-2-(5-methyl-1,2,4-oxadiazol-3-yl)propan-2-yl]-4-(2,2,2-trifluoroethoxy)pyridine-2-carboxamide (example 113, 0.1 g, 250 µmol) in dry dichloromethane (2 ml) was added Dess-Martin periodinane (111 mg, 262 µmol). The reaction mixture was stirred at room temperature for 3 hours. The reaction mixture was diluted with dichloromethane and quenched with a 1.0M aqueous solution of sodium bicarbonate with 5% sodium thiosulfate. The bi-phasic mixture was stirred for 20 minutes and then transferred into a separatory funnel. The organic phase was dried over sodium sulfate and evaporated down to dryness. The crude material was purified by flash chromatography on silica eluting with a heptane/(solution of 3% Et3N in ethyl acetate) gradient to yield the title compound (71 mg, 71%). MS (ESI, m/z): 399.5 (M+H⁺).

b) 5-cyclopropyl-N-[1-(3,3-difluoroazetidin-1-yl)-2-(5-methyl-1,2,4-oxadiazol-3-yl)propan-2-yl]-4-(2,2,2-trifluoroethoxy)pyridine-2-carboxamide

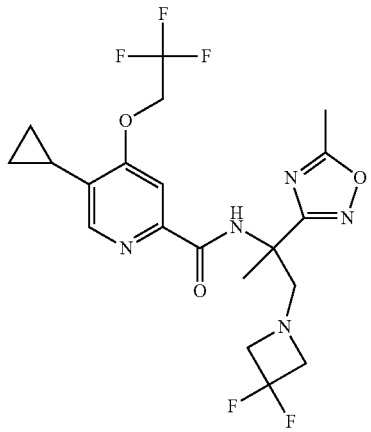 [SMILES: Cc1nc(C(C)(CN2CC(F)(F)C2)NC(=O)c2cc(OCC(F)(F)F)c(C3CC3)cn2)no1]

To a solution of 5-cyclopropyl-N-[1-methyl-1-(5-methyl-1,2,4-oxadiazol-3-yl)-2-oxo-ethyl]-4-(2,2,2-trifluoroethoxy)pyridine-2-carboxamide (example 128a, 0.075 g, 188 µmol) in dichloromethane (1 ml) was added 3,3-difluoroazetidine hydrochloride (26.8 mg, 207 µmol) and triethylamine (21.0 mg, 28.9 µl, 207 µmol). The reaction mixture was sonicated to completely dissolve solids and reaction mixture was then stirred at room temperature for 30 minutes, followed by addition of sodium triacetoxyborohydride (59.9 mg, 282 µmol). The reaction mixture was then stirred at room temperature overnight. The reaction was diluted with dichloromethane and extracted with a 2M aqueous solution of sodium carbonate. The organic phase was dried over sodium sulfate and evaporated down to dryness. The crude material was purified by flash chromatography on silica eluting with a heptane/ethyl acetate gradient to yield the title compound (9.2 mg, 10%). MS (ESI, m/z): 476.5 (M+H$^+$).

Example 129

5-(1-hydroxycyclobutyl)-N-[2-(5-methyl-1,2,4-oxadiazol-3-yl)-1-methylsulfonylpropan-2-yl]-4-(2,2,2-trifluoroethoxy)pyridine-2-carboxamide

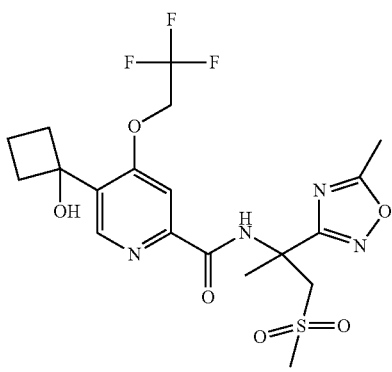 [SMILES: Cc1nc(C(C)(CS(C)(=O)=O)NC(=O)c2cc(OCC(F)(F)F)c(C3(O)CCC3)cn2)no1]

a) 5-(1-hydroxycyclobutyl)-4-(2,2,2-trifluoroethoxy)pyridine-2-carbonitrile

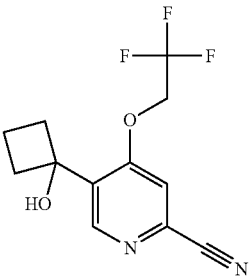 [SMILES: N#Cc1cc(OCC(F)(F)F)c(C2(O)CCC2)cn1]

The title compound was synthesized in analogy to Example 123c, using 4-chloro-5-(1-hydroxycyclobutyl)pyridine-2-carbonitrile (Example 126b) and 2,2,2-Trifluoroethanol (CAN 75-89-8) as starting material and isolated (609 mg, 71%); MS (ESI, m/z): 273.4 (M+H$^+$).

b) 5-(1-hydroxycyclobutyl)-4-(2,2,2-trifluoroethoxy)pyridine-2-carboxylic acid

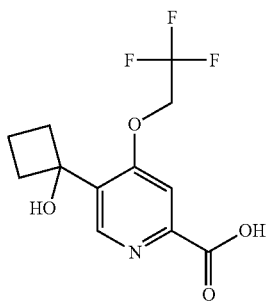 [SMILES: O=C(O)c1cc(OCC(F)(F)F)c(C2(O)CCC2)cn1]

The title compound was synthesized in analogy to Example 126d, using 5-(1-hydroxycyclobutyl)-4-(2,2,2-trifluoroethoxy)pyridine-2-carbonitrile (Example 129a) as starting material and isolated (125 mg, 19%); MS (ESI, m/z): 292.4 (M+H$^+$).

c) 5-(1-hydroxycyclobutyl)-N-[2-(5-methyl-1,2,4-oxadiazol-3-yl)-1-methylsulfonylpropan-2-yl]-4-(2,2,2-trifluoroethoxy)pyridine-2-carboxamide

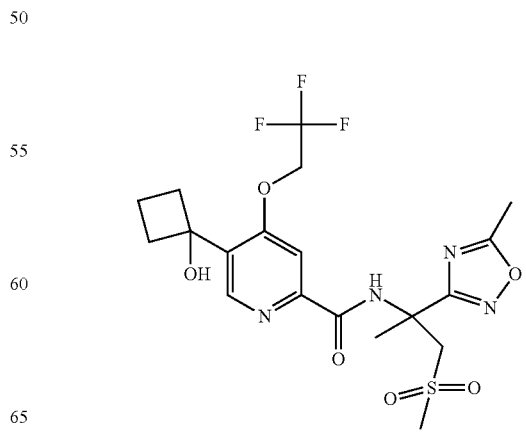

The title compound was synthesized in analogy to Example 112e, using 5-(1-hydroxycyclobutyl)-4-(2,2,2-trifluoroethoxy)pyridine-2-carboxylic acid (Example 129b) and 2-Methanesulfonyl-1-methyl-1-(5-methyl-[1,2,4]oxadiazol-3-yl)-ethylamine (example 109d) as starting materials and isolated (25 mg, 37%); MS (ESI, m/z): 493.3 (M+H⁺).

Example 130

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide

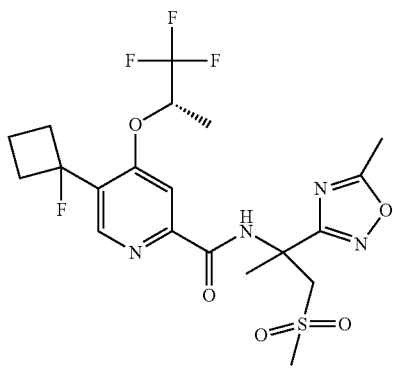 [SMILES: Cc1nc(C(C)(CS(C)(=O)=O)NC(=O)c2cc(O[C@@H](C)C(F)(F)F)c(C3(F)CCC3)cn2)no1]

To a solution of 5-(1-hydroxycyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide (example 126e, 21 mg, 41.5 µmol) in dry dichloromethane (200 µl) under an argon atmosphere cooled down to 0° C. was added DAST (10.0 mg, 8.22 µl, 62.2 µmol). The reaction mixture was stirred at 0° C. for 1 h and quenched by addition of a 2M aqueous solution of sodium carbonate. The bi-phasic mixture was stirred for 15 minutes and the organic phase was collected. The organic phase was evaporated down to dryness and the crude material was purified by preparative HPLC to yield the title compound (9.2 mg, 44%). MS (ESI, m/z): 509.5 (M+H⁺).

Example 131

N-[1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide

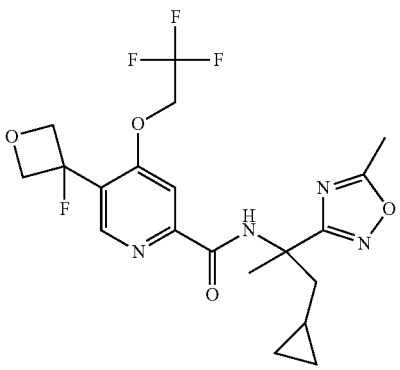 [SMILES: Cc1nc(C(C)(CC2CC2)NC(=O)c2cc(OCC(F)(F)F)c(C3(F)COC3)cn2)no1]

a) 4-chloro-5-(3-fluorooxetan-3-yl)pyridine-2-carbonitrile

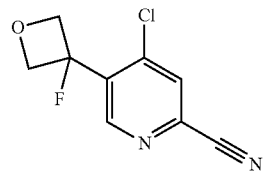 [SMILES: N#Cc1cc(Cl)c(C2(F)COC2)cn1]

To a solution of 4-chloro-5-(3-hydroxyoxetan-3-yl)pyridine-2-carbonitrile (example 123b, 2.0 g, 9.5 mmol) in dry dichloromethane (50 ml) under an argon atmosphere cooled down to −75° C. was added DAST (1.61 g, 1.32 ml, 9.97 mmol). The reaction was stirred at −75° C. for 15 min, then let to warm up to 0° C. and stirred at 0° C. for 1 hour. The reaction was then quenched by addition of a 2M aqueous solution of sodium carbonate. The bi-phasic mixture was stirred at room temperature for 15 minutes, poured into a separatory funnel and extraction was carried out. The organic phase was dried over sodium sulfate and evaporated down to dryness. The crude material was purified by flash chromatography on silica eluting with a heptane/ethyl acetate gradient to yield the title compound (1.81 g, 90%). MS (ESI, m/z): 213.0 (M+H⁺).

b) 5-(3-fluorooxetan-3-yl)-4-(2,2,2-trifluoroethoxy)pyridine-2-carboxylic acid

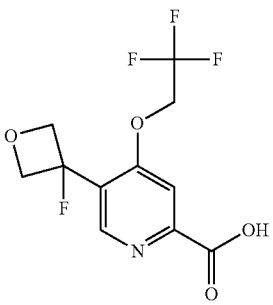 [SMILES: O=C(O)c1cc(OCC(F)(F)F)c(C2(F)COC2)cn1]

To a solution of 4-chloro-5-(3-fluorooxetan-3-yl)pyridine-2-carbonitrile (example 131a, 1.15 g, 5.41 mmol) in 2,2,2-trifluoroethanol (18 mL, 249 mmol) was added a 4M aqueous solution of potassium hydroxide (4.06 mL, 16.2 mmol). The reaction was stirred at 100° C. for 60 minutes under microwave radiation. Volatiles were removed in vacuo and the crude material was directly purified by preparative HPLC to yield the title compound (345 mg, 22%). MS (ESI, m/z): 296.4 (M+H⁺).

c) N-[1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide

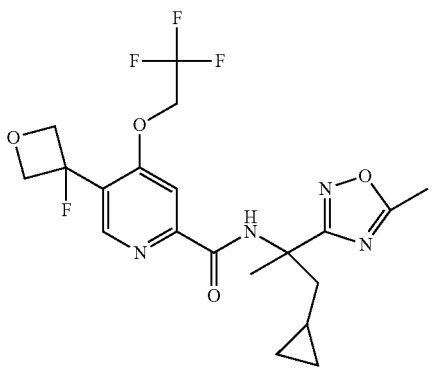 [SMILES: Cc1nc(C(C)(CC2CC2)NC(=O)c2cc(OCC(F)(F)F)c(C3(F)COC3)cn2)no1]

The title compound was synthesized in analogy to Example 112e, using 5-(3-fluorooxetan-3-yl)-4-(2,2,2-trifluoroethoxy)pyridine-2-carboxylic acid (Example 131b) and 2-Cyclopropyl-1-methyl-1-(5-methyl-[1,2,4]oxadiazol-3-yl)-ethylamine (example 66e) as starting materials and isolated (42 mg, 54%); MS (ESI, m/z): 459.6 (M+H$^+$).

Example 132

5-(3-fluorooxetan-3-yl)-N-[2-(5-methyl-1,2,4-oxadiazol-3-yl)-1-methylsulfonylpropan-2-yl]-4-(2,2,2-trifluoroethoxy)pyridine-2-carboxamide (enantiomer A)

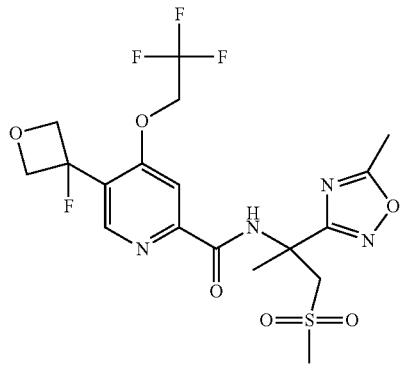 [SMILES: Cc1nc(C(C)(CS(C)(=O)=O)NC(=O)c2cc(OCC(F)(F)F)c(C3(F)COC3)cn2)no1]

The title compound was synthesized in analogy to Example 112e, using 5-(3-fluorooxetan-3-yl)-4-(2,2,2-trifluoroethoxy)pyridine-2-carboxylic acid (Example 131b) and 2-(5-methyl-1,2,4-oxadiazol-3-yl)-1-methylsulfonyl-propan-2-amine;hydrobromide (enantiomer A) (example 124b) as starting materials and isolated (40 mg, 47%); MS (ESI, m/z): 497.5 (M+H$^+$).

Example 133

5-(3-fluorooxetan-3-yl)-N-[2-(5-methyl-1,2,4-oxadiazol-3-yl)-1-methylsulfonylpropan-2-yl]-4-(2,2,2-trifluoroethoxy)pyridine-2-carboxamide (enantiomer B)

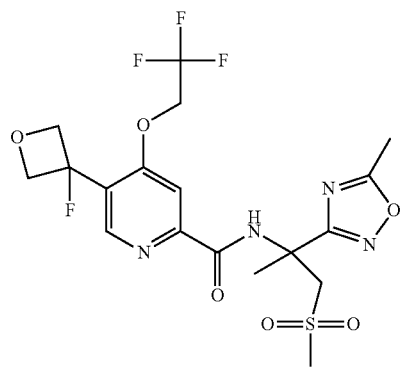 [SMILES: Cc1nc(C(C)(CS(C)(=O)=O)NC(=O)c2cc(OCC(F)(F)F)c(C3(F)COC3)cn2)no1]

The title compound was synthesized in analogy to Example 112e, using 5-(3-fluorooxetan-3-yl)-4-(2,2,2-trifluoroethoxy)pyridine-2-carboxylic acid (Example 131b) and 2-(5-methyl-1,2,4-oxadiazol-3-yl)-1-methylsulfonyl-propan-2-amine;hydrobromide (enantiomer B) (example 125b) as starting materials and isolated (35 mg, 42%); MS (ESI, m/z): 497.6 (M+H$^+$).

Example 134

N-(1-amino-2-methyl-3-methylsulfonyl-1-oxopropan-2-yl)-5-cyclopropyl-4-(2,2,2-trifluoroethoxy)pyridine-2-carboxamide

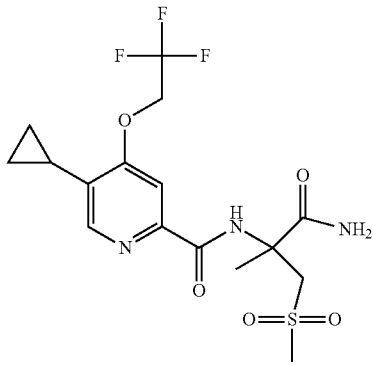 [SMILES: CC(CS(C)(=O)=O)(NC(=O)c1cc(OCC(F)(F)F)c(C2CC2)cn1)C(N)=O]

149 a) N-(1-cyano-1-methyl-2-methylsulfonyl-ethyl)-5-cyclopropyl-4-(2,2,2-trifluoroethoxy)pyridine-2-carboxamide

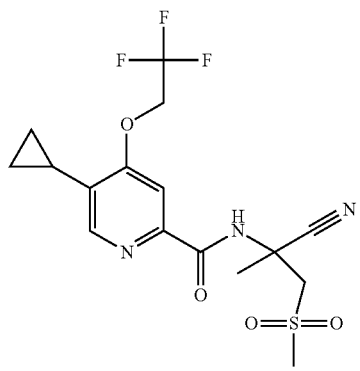 [SMILES: CC(C#N)(CS(C)(=O)=O)NC(=O)c1cc(OCC(F)(F)F)c(C2CC2)cn1]

The title compound was synthesized in analogy to Example 112e, using 5-Cyclopropyl-4-(2,2,2-trifluoroethoxy)-pyridine-2-carboxylic acid (Example 48c) and 2-Amino-3-methanesulfonyl-2-methyl-propionitrile (example 80a) as starting materials and isolated (1.22 g, 98%); MS (ESI, m/z): 406.6 (M+H$^+$).

b) N-(1-amino-2-methyl-3-methylsulfonyl-1-oxopropan-2-yl)-5-cyclopropyl-4-(2,2,2-trifluoroethoxy)pyridine-2-carboxamide

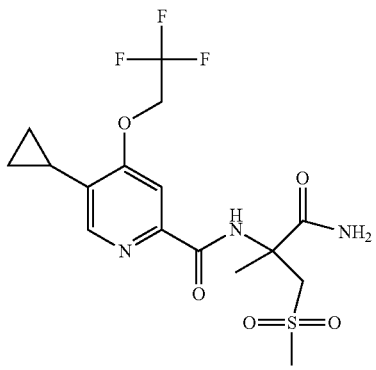 [SMILES: CC(CS(C)(=O)=O)(NC(=O)c1cc(OCC(F)(F)F)c(C2CC2)cn1)C(N)=O]

The title compound was synthesized in analogy to Example 78f, using N-(1-cyano-1-methyl-2-methylsulfonyl-ethyl)-5-cyclopropyl-4-(2,2,2-trifluoroethoxy)pyridine-2-carboxamide (Example 134a) as starting material and isolated as a by-product of a side reaction (226 mg, 17%); MS (ESI, m/z): 424.2 (M+H$^+$).

150

Example 135

N-[1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide (enantiomer A)

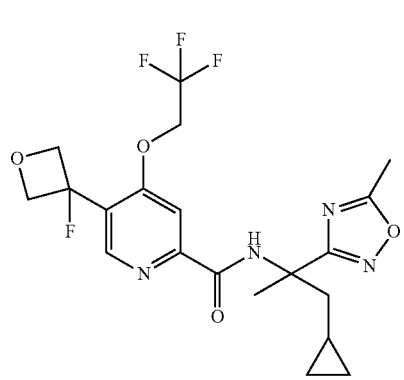 [SMILES: Cc1nc(C(C)(CC2CC2)NC(=O)c2cc(OCC(F)(F)F)c(C3(F)COC3)cn2)no1]

The racemate (Example 131c) was separated into its enantiomers by preparative chiral HPLC (Chiralpak AD, ethanol/heptane) and the title compound was the first enantiomer collected and isolated as colorless oil; MS (ESI, m/z): 459.3 (M+H$^+$).

Example 136

N-[1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide (enantiomer B)

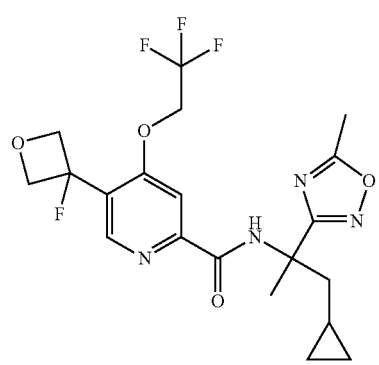 [SMILES: Cc1nc(C(C)(CC2CC2)NC(=O)c2cc(OCC(F)(F)F)c(C3(F)COC3)cn2)no1]

The racemate (Example 131c) was separated into its enantiomers by preparative chiral HPLC (Chiralpak AD, ethanol/heptane) and the title compound was the first enantiomer collected and isolated as colorless oil; MS (ESI, m/z): 459.3 (M+H$^+$).

Example 137

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide (epimer A)

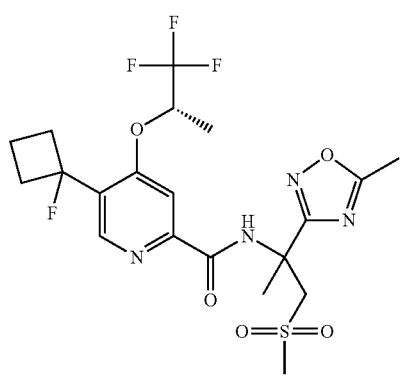 [SMILES: Cc1nc(C(C)(CS(C)(=O)=O)NC(=O)c2cc(O[C@@H](C)C(F)(F)F)c(C3(F)CCC3)cn2)no1]

a) 5-(1-hydroxycyclobutyl)-N-[1-methyl-1-(5-methyl-1,2,4-oxadiazol-3-yl)-2-methylsulfonyl-ethyl]-4-[(1S)-2,2,2-trifluoro-1-methyl-ethoxy]pyridine-2-carboxamide (epimer A)

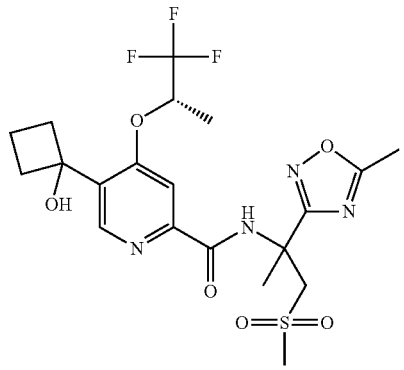 [SMILES: Cc1nc(C(C)(CS(C)(=O)=O)NC(=O)c2cc(O[C@@H](C)C(F)(F)F)c(C3(O)CCC3)cn2)no1]

The title compound was synthesized in analogy to Example 112e, using 5-(1-hydroxycyclobutyl)-4-[(1S)-2,2,2-trifluoro-1-methyl-ethoxy]pyridine-2-carboxylic acid (Example 126c) and 2-(5-methyl-1,2,4-oxadiazol-3-yl)-1-methylsulfonyl-propan-2-amine;hydrobromide (enantiomer A) (example 124b) as starting materials and isolated (24 mg, 63%); MS (ESI, m/z): 507.5 (M+H⁺).

b) 5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide (epimer A)

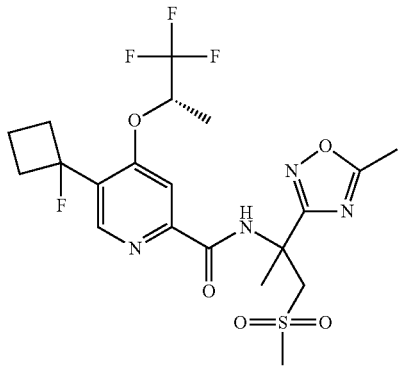 [SMILES: Cc1nc(C(C)(CS(C)(=O)=O)NC(=O)c2cc(O[C@@H](C)C(F)(F)F)c(C3(F)CCC3)cn2)no1]

The title compound was synthesized in analogy to Example 130, using 5-(1-hydroxycyclobutyl)-N-[1-methyl-1-(5-methyl-1,2,4-oxadiazol-3-yl)-2-methylsulfonyl-ethyl]-4-[(1S)-2,2,2-trifluoro-1-methyl-ethoxy]pyridine-2-carboxamide (epimer A) (Example 137a) as starting material and isolated (13 mg, 65%); MS (ESI, m/z): 509.5 (M+H⁺).

Example 138

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide (epimer B)

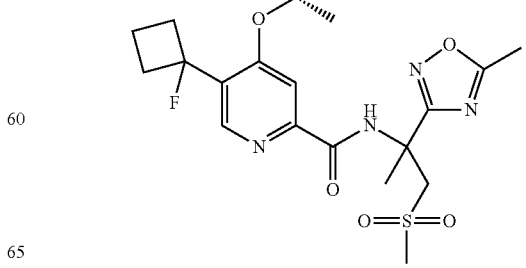

153 a) 5-(1-hydroxycyclobutyl)-N-[1-methyl-1-(5-methyl-1,2,4-oxadiazol-3-yl)-2-methylsulfonyl-ethyl]-4-[(1S)-2,2,2-trifluoro-1-methyl-ethoxy]pyridine-2-carboxamide (epimer B)

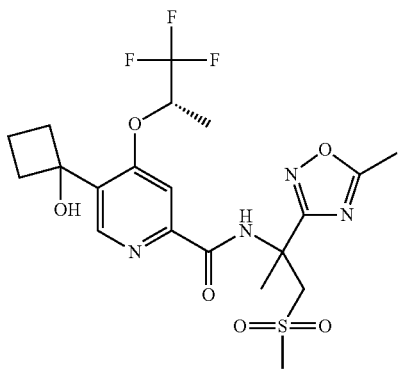 [SMILES: Cc1nc(C(C)(CS(C)(=O)=O)NC(=O)c2cc(O[C@@H](C)C(F)(F)F)c(C3(O)CCC3)cn2)no1]

The title compound was synthesized in analogy to Example 112e, using 5-(1-hydroxycyclobutyl)-4-[(1S)-2,2,2-trifluoro-1-methyl-ethoxy]pyridine-2-carboxylic acid (Example 126c) and 2-(5-methyl-1,2,4-oxadiazol-3-yl)-1-methylsulfonyl-propan-2-amine;hydrobromide (enantiomer B) (example 125b) as starting materials and isolated (13 mg, 40%); MS (ESI, m/z): 507.5 (M+H$^+$).

b) 5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide (epimer B)

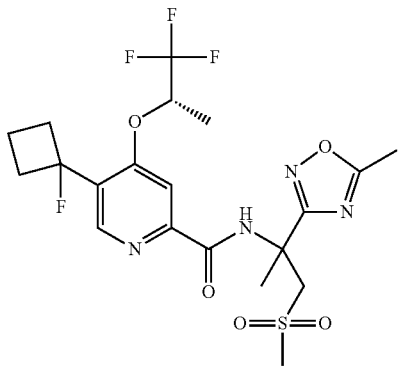 [SMILES: Cc1nc(C(C)(CS(C)(=O)=O)NC(=O)c2cc(O[C@@H](C)C(F)(F)F)c(C3(F)CCC3)cn2)no1]

The title compound was synthesized in analogy to Example 130, using 5-(1-hydroxycyclobutyl)-N-[1-methyl-1-(5-methyl-1,2,4-oxadiazol-3-yl)-2-methylsulfonyl-ethyl]-4-[(1S)-2,2,2-trifluoro-1-methyl-ethoxy]pyridine-2-carboxamide (epimer B) (Example 138a) as starting material and isolated (3.1 mg, 24%); MS (ESI, m/z): 509.5 (M+H$^+$).

154

Example 139

N-[1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide

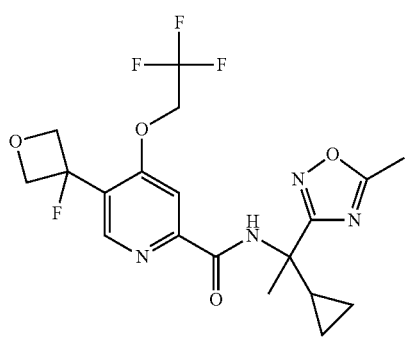 [SMILES: Cc1nc(C(C)(NC(=O)c2cc(OCC(F)(F)F)c(C3(F)COC3)cn2)C2CC2)no1]

The title compound was synthesized in analogy to Example 112e, using 5-(3-fluorooxetan-3-yl)-4-(2,2,2-trifluoroethoxy)pyridine-2-carboxylic acid (Example 131b) and 1-Cyclopropyl-1-(5-methyl-[1,2,4]oxadiazol-3-yl)-ethylamine (CAN 1155536-64-3) as starting materials and isolated (45 mg, 39%); MS (ESI, m/z): 445.5 (M+H$^+$).

Example 140

5-cyclopropyl-N-[1-hydroxy-2-(5-methyl-1,2,4-oxadiazol-3-yl)propan-2-yl]-4-(2,2,2-trifluoroethoxy)pyridine-2-carboxamide (enantiomer A)

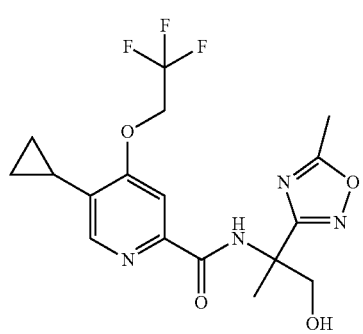 [SMILES: Cc1nc(C(C)(CO)NC(=O)c2cc(OCC(F)(F)F)c(C3CC3)cn2)no1]

The racemate (Example 113) was separated into its enantiomers by preparative chiral HPLC (Reprosil Chiral NR, isopropanol/heptane) and the title compound was the first enantiomer collected and isolated as colorless oil; MS (ESI, m/z): 401.5 (M+H$^+$).

Example 141

5-cyclopropyl-N-[1-hydroxy-2-(5-methyl-1,2,4-oxadiazol-3-yl)propan-2-yl]-4-(2,2,2-trifluoroethoxy)pyridine-2-carboxamide (enantiomer B)

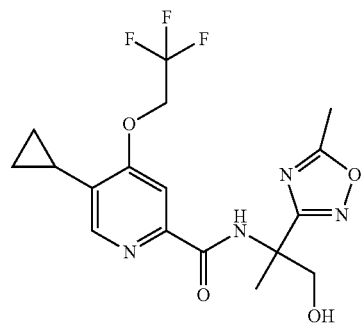 [SMILES: Cc1nc(C(C)(CO)NC(=O)c2cc(OCC(F)(F)F)c(C3CC3)cn2)no1]

The racemate (Example 113) was separated into its enantiomers by preparative chiral HPLC (Reprosil Chiral NR, isopropanol/heptane) and the title compound was the second enantiomer collected and isolated as colorless oil; MS (ESI, m/z): 401.5 (M+H$^+$).

Example 142

N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide

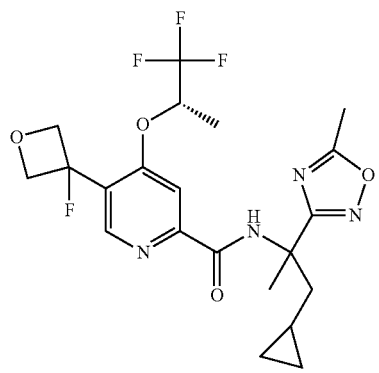 [SMILES: Cc1nc(C(C)(CC2CC2)NC(=O)c2cc(O[C@@H](C)C(F)(F)F)c(C3(F)COC3)cn2)no1]

a) 5-(3-fluorooxetan-3-yl)-4-[(1S)-2,2,2-trifluoro-1-methyl-ethoxy]pyridine-2-carbonitrile

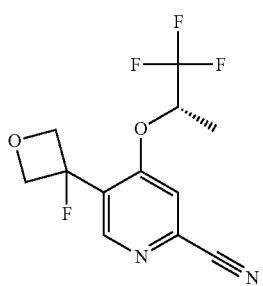 [SMILES: C[C@H](Oc1cc(C#N)ncc1C1(F)COC1)C(F)(F)F]

The title compound was synthesized in analogy to Example 123c, using 4-chloro-5-(3-fluorooxetan-3-yl)pyridine-2-carbonitrile (Example 131a) and (S)-1,1,1-Trifluoropropan-2-ol (CAN 3539-97-7) as starting materials and isolated (1.66 g, 61%); MS (ESI, m/z): 291.4 (M+H$^+$).

b) 5-(3-fluorooxetan-3-yl)-4-[(1S)-2,2,2-trifluoro-1-methyl-ethoxy]pyridine-2-carboxylic acid

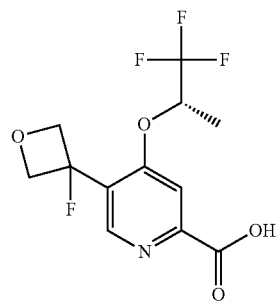 [SMILES: C[C@H](Oc1cc(C(=O)O)ncc1C1(F)COC1)C(F)(F)F]

The title compound was synthesized in analogy to Example 123d, using 5-(3-fluorooxetan-3-yl)-4-[(1S)-2,2,2-trifluoro-1-methyl-ethoxy]pyridine-2-carbonitrile (Example 142a) as starting material and isolated (1.8 g, 70%); MS (ESI, m/z): 310.4 (M+H$^+$).

c) N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide

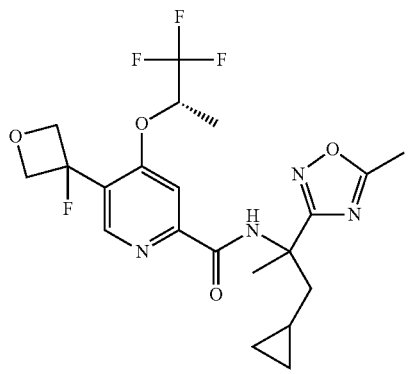 [SMILES: Cc1nc(C(C)(CC2CC2)NC(=O)c2cc(O[C@@H](C)C(F)(F)F)c(C3(F)COC3)cn2)no1]

The title compound was synthesized in analogy to Example 112e, using 5-(3-fluorooxetan-3-yl)-4-[(1S)-2,2,2-trifluoro-1-methyl-ethoxy]pyridine-2-carboxylic acid (Example 142b) and 2-Cyclopropyl-1-methyl-1-(5-methyl-[1,2,4]oxadiazol-3-yl)-ethylamine (example 66e) as starting materials and isolated (31 mg, 26%); MS (ESI, m/z): 473.5 (M+H$^+$).

Example 143

N-(2-cyano-1-cyclopropylpropan-2-yl)-5-(3-fluo-rooxetan-3-yl)-4-[(2S)-1,1,1-trifluoropropan-2-yl]oxypyridine-2-carboxamide

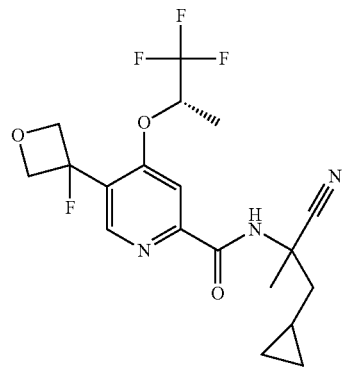 [SMILES: C[C@H](Oc1cc(C(=O)NC(C)(C#N)CC2CC2)ncc1C1(F)COC1)C(F)(F)F]

The title compound was synthesized in analogy to Example 112e, using 5-(3-fluorooxetan-3-yl)-4-[(1S)-2,2,2-trifluoro-1-methyl-ethoxy]pyridine-2-carboxylic acid (Example 142b) and 2-Amino-3-cyclopropyl-2-methyl-propionitrile (example 66a) as starting materials and isolated (27.5 mg, 26%); MS (ESI, m/z): 416.5 (M+H$^+$).

Example 144

N-[1-cyclopropyl-1-(5-methyl-1,2,4-oxadiazol-3-yl)ethyl]-5-(3-fluorooxetan-3-yl)-4-[(2S)-1,1,1-trifluoropropan-2-yl]oxypyridine-2-carboxamide

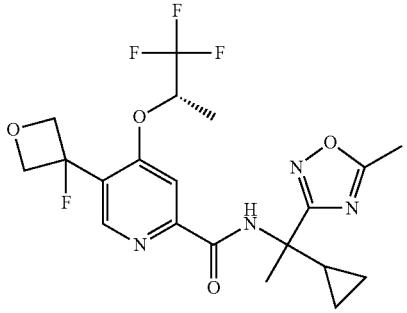 [SMILES: Cc1nc(C(C)(NC(=O)c2cc(O[C@@H](C)C(F)(F)F)c(C3(F)COC3)cn2)C2CC2)no1]

The title compound was synthesized in analogy to Example 112e, using 5-(3-fluorooxetan-3-yl)-4-[(1S)-2,2,2-trifluoro-1-methyl-ethoxy]pyridine-2-carboxylic acid (Example 142b) and 1-Cyclopropyl-1-(5-methyl-[1,2,4]oxadiazol-3-yl)-ethylamine (CAN 1155536-64-3) as starting materials and isolated (32.6 mg, 37%); MS (ESI, m/z): 459.5 (M+H$^+$).

Example 145

5-cyclopropyl-N-[1-cyclopropyl-2-(5-methyl-1,2,4-oxadiazol-3-yl)propan-2-yl]-4-(2,2-difluoroethoxy)pyridine-2-carboxamide

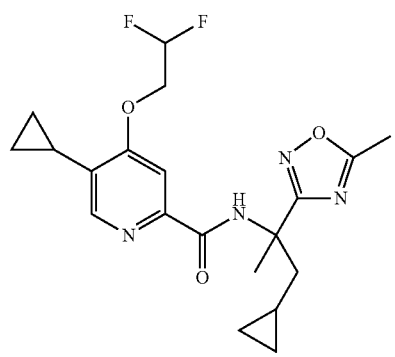 [SMILES: Cc1nc(C(C)(CC2CC2)NC(=O)c2cc(OCC(F)F)c(C3CC3)cn2)no1]

a) 2,4-dichloro-5-cyclopropyl-pyridine

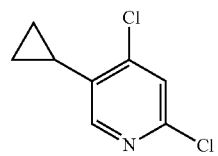 [SMILES: Clc1cc(Cl)c(C2CC2)cn1]

The title compound was synthesized in analogy to Example 48a, using 5-bromo-2,4-dichloropyridine (CAN 849937-96-8) as starting material and isolated (7.4 g, 41%); MS (ESI, m/z): 188.2 (M+H$^+$).

b) 4-chloro-5-cyclopropyl-pyridine-2-carbonitrile

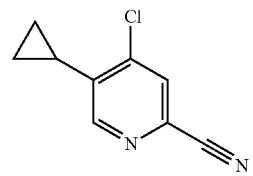 [SMILES: N#Cc1cc(Cl)c(C2CC2)cn1]

To a stirred solution of 2,4-dichloro-5-cyclopropyl-pyridine (example 145a, 2.2 g, 11.76 mmol) in DMF (10 ml) and purged the reaction mixture argon for 10 minutes. To this reaction was added dicyanozinc (926 mg, 7.65 mmol) followed by DPPF (520 mg, 1.02 mmol) and Pd$_2$dba$_3$ (535 mg, 0.58 mmol) at 25° C. and the reaction mixture was again purged with argon for 10 min. The reaction mixture was heated up to 100° C. for 1 hour. The catalyst was filtered off and the solution was diluted with ethyl acetate. The organic phase was poured into a separatory funnel and extracted with brine. The organic phase was dried over sodium sulfate and concentrated under reduced pressure. The crude material was purified by flash chromatography on silica eluting with a heptane/ethyl acetate gradient to yield the title compound (1 g, 50%). MS (ESI, m/z): 179.2 (M+H$^+$).

c) 5-cyclopropyl-4-(2,2-difluoroethoxy)pyridine-2-carbonitrile

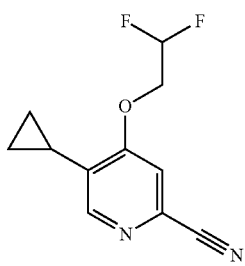 [SMILES: N#Cc1cc(OCC(F)F)c(C2CC2)cn1]

The title compound was synthesized in analogy to Example 123c, using 4-chloro-5-cyclopropyl-pyridine-2-carbonitrile (example 145b), 2,2-Difluoro-ethanol (CAN 359-13-7) as starting materials and sodium hydride as reagent. The title compound was isolated (508 mg, 81%) as a yellow solid; MS (ESI, m/z): 225.2 (M+H$^+$).

d) 5-cyclopropyl-4-(2,2-difluoroethoxy)pyridine-2-carboxylic acid;hydrochloride

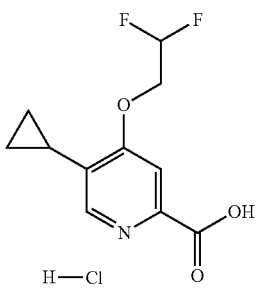

5-cyclopropyl-4-(2,2-difluoroethoxy)picolinonitrile (3.77 g, 16.8 mmol) was dissolved in a 25% aqueous solution of hydrochloric acid (50 ml). Reaction was stirred at 110° C. for 14 hour and then cooled down to room temperature. Excess of hydrochloric acid was neutralized by addition of sodium hydroxide pellets until pH was 12-13. The pH was adjusted back to 1-2 by addition of a 2M aqueous solution of hydrochloric acid and a precipitate formed which was isolated by filtration. The collected precipitate was dried under high vacuum to yield the title compound (4.12 g, 88%); MS (ESI, m/z): 244.3 (M+H$^+$).

e) 5-cyclopropyl-N-[1-cyclopropyl-2-(5-methyl-1,2,4-oxadiazol-3-yl)propan-2-yl]-4-(2,2-difluoroethoxy)pyridine-2-carboxamide

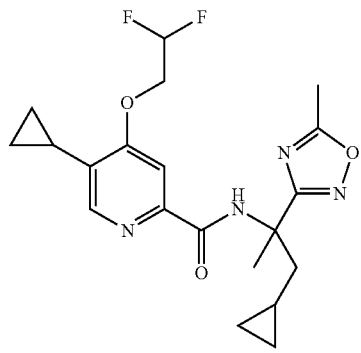 [SMILES: Cc1nc(C(C)(CC2CC2)NC(=O)c2cc(OCC(F)F)c(C3CC3)cn2)no1]

The title compound was synthesized in analogy to Example 112e, using 5-cyclopropyl-4-(2,2-difluoroethoxy)pyridine-2-carboxylic acid (Example 145d) and 2-Cyclopropyl-1-methyl-1-(5-methyl-[1,2,4]oxadiazol-3-yl)-ethylamine (example 66e) as starting materials and isolated (66 mg, 72%); MS (ESI, m/z): 407.6 (M+H$^+$).

Example 146

5-cyclopropyl-N-[1-cyclopropyl-2-(5-methyl-1,2,4-oxadiazol-3-yl)propan-2-yl]-4-(2-fluoroethoxy)pyridine-2-carboxamide

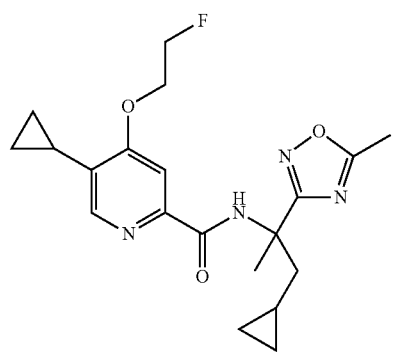 [SMILES: Cc1nc(C(C)(CC2CC2)NC(=O)c2cc(OCCF)c(C3CC3)cn2)no1]

a) 5-cyclopropyl-4-(2-fluoroethoxy)pyridine-2-carbonitrile

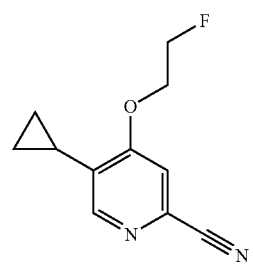 [SMILES: N#Cc1cc(OCCF)c(C2CC2)cn1]

The title compound was synthesized in analogy to Example 123c, using 4-chloro-5-cyclopropyl-pyridine-2-carbonitrile (example 145b), 2-Fluoro-ethanol (CAN 371-62-0) as starting materials and sodium hydride as reagent. The title compound was isolated (267 mg, 68%) as a yellow solid; MS (ESI, m/z): 207.1 (M+H$^+$).

b) 5-cyclopropyl-4-(2-fluoroethoxy)pyridine-2-carboxylic acid;hydrochloride

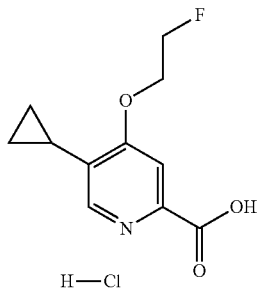

The title compound was synthesized in analogy to Example 145d, using 5-cyclopropyl-4-(2-fluoroethoxy)pyridine-2-carbonitrile (Example 146a) as starting material and isolated (160 mg, 56%); MS (ESI, m/z): 226.1 (M+H$^+$).

c) 5-cyclopropyl-N-[1-cyclopropyl-2-(5-methyl-1,2,4-oxadiazol-3-yl)propan-2-yl]-4-(2-fluoroethoxy)pyridine-2-carboxamide

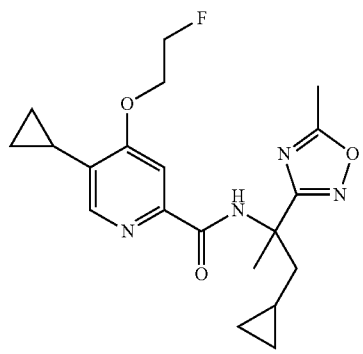 [SMILES: Cc1nc(C(C)(CC2CC2)NC(=O)c2cc(OCCF)c(C3CC3)cn2)no1]

The title compound was synthesized in analogy to Example 112e, using 5-cyclopropyl-4-(2-fluoroethoxy)pyridine-2-carboxylic acid (Example 146b) and 2-Cyclopropyl-1-methyl-1-(5-methyl-[1,2,4]oxadiazol-3-yl)-ethylamine (example 66e) as starting materials and isolated (90 mg, 93%); MS (ESI, m/z): 389.6 (M+H$^+$).

Example 147

5-cyclopropyl-N-[1-(3,3-difluoroazetidin-1-yl)-2-(5-methyl-1,2,4-oxadiazol-3-yl)-1-oxopropan-2-yl]-4-(2,2,2-trifluoroethoxy)pyridine-2-carboxamide

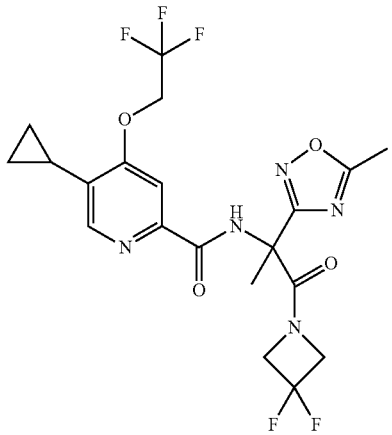 [SMILES: Cc1nc(C(C)(NC(=O)c2cc(OCC(F)(F)F)c(C3CC3)cn2)C(=O)N2CC(F)(F)C2)no1]

a) ethyl 2-amino-2-(5-methyl-1,2,4-oxadiazol-3-yl)propanoate

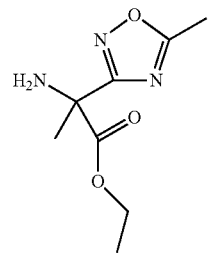

To a solution of 2-(5-Methyl-[1,2,4]oxadiazol-3-yl)-propionic acid ethyl ester (CAN168704-76-5, 0.5 g, 2.71 mmol) in a mixture of dry THF (15 ml)/dry DMF (4 ml) cooled down to 0° C. under an argon atmosphere was slowly added LiHMDS 1.0M solution in THF (2.85 ml, 2.85 mmol). The reaction mixture was stirred at 0° C. for 30 minutes followed by addition of O-(diphenylphosphoryl)hydroxylamine (696 mg, 2.99 mmol). The resulting suspension was let to warm up to room temperature and stirred at room temperature overnight (a white suspension formed). The reaction mixture was filtered through a pad of Celite and the filter cake was washed twice with THF. The filtrate was concentrated in vacuo and the residue was dissolved in ethylacetate. The organic phase was extracted with 5 mL aqueous Na2CO3 2M. The organic phase was collected and the aqueous phase was back-extracted with ethylacetate. The combined organic phases were dried over sodium sulfate and evaporated down to dryness. The crude material was purified by flash chromatography on silica eluting with a gradient of dichloromethane/methanol to yield the title compound (450 mg, 83%). MS (ESI, m/z): 200.2 (M+H$^+$).

b) ethyl 2-[[5-cyclopropyl-4-(2,2,2-trifluoroethoxy)pyridine-2-carbonyl]amino]-2-(5-methyl-1,2,4-oxadiazol-3-yl)propanoate

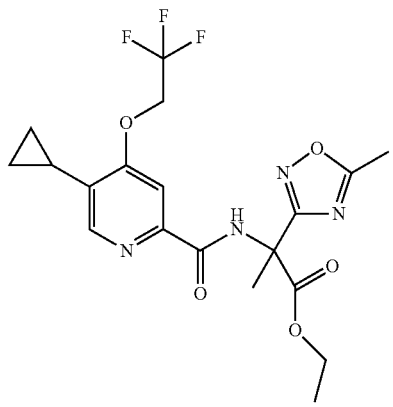 [SMILES: CCOC(=O)C(C)(NC(=O)c1cc(OCC(F)(F)F)c(C2CC2)cn1)c1noc(C)n1]

The title compound was synthesized in analogy to Example 112e, using 5-Cyclopropyl-4-(2,2,2-trifluoroethoxy)-pyridine-2-carboxylic acid (example 48c) and ethyl 2-amino-2-(5-methyl-1,2,4-oxadiazol-3-yl)propanoate (example 147a) as starting materials and isolated (508 mg, 86%); MS (ESI, m/z): 443.5 (M+H$^+$).

c) 2-[[5-cyclopropyl-4-(2,2,2-trifluoroethoxy)pyridine-2-carbonyl]amino]-2-(5-methyl-1,2,4-oxadiazol-3-yl)propanoic acid

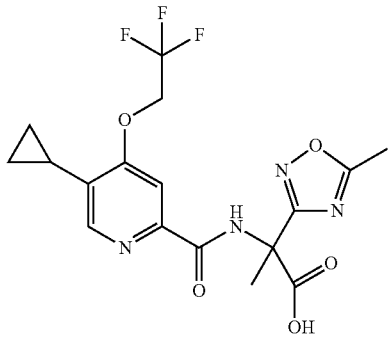 [SMILES: Cc1nc(C(C)(NC(=O)c2cc(OCC(F)(F)F)c(C3CC3)cn2)C(=O)O)no1]

To a solution of ethyl 2-[[5-cyclopropyl-4-(2,2,2-trifluoroethoxy)pyridine-2-carbonyl]amino]-2-(5-methyl-1,2,4-oxadiazol-3-yl)propanoate (example 147b, 0.295 g, 667 µmol) in a mixture of THF (4 ml)/Water (2 ml) was added LiOH monohydrate (83.9 mg, 2.00 mmol). The reaction mixture was sonicated for a few minutes to dissolved solids. The reaction was stirred at room temperature overnight. The reaction was then concentrated in vacuo and the obtained residue was dissolved in ethyl acetate. The organic phase was extracted with a 0.1M aqueous solution hydrochloric acid. The organic phase was collected and the aqueous phase was back-extracted with ethyl acetate. Combined organic phases were dried over sodium sulfate and evaporated down to dryness to yield the title compound (280 mg, 100%) as a crude yellow oil which was used without any purification. MS (ESI, m/z): 415.5 (M+H$^+$).

d) 5-cyclopropyl-N-[1-(3,3-difluoroazetidin-1-yl)-2-(5-methyl-1,2,4-oxadiazol-3-yl)-1-oxopropan-2-yl]-4-(2,2,2-trifluoroethoxy)pyridine-2-carboxamide

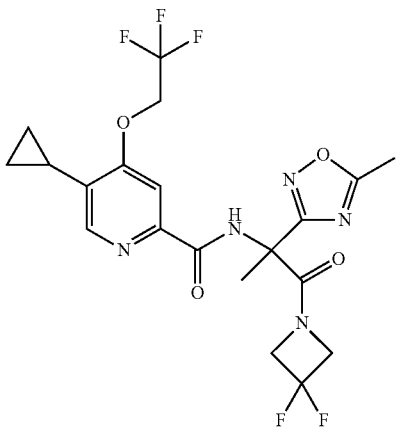 [SMILES: Cc1nc(C(C)(NC(=O)c2cc(OCC(F)(F)F)c(C3CC3)cn2)C(=O)N2CC(F)(F)C2)no1]

The title compound was synthesized in analogy to Example 112e, using 2-[[5-cyclopropyl-4-(2,2,2-trifluoroethoxy)pyridine-2-carbonyl]amino]-2-(5-methyl-1,2,4-oxadiazol-3-yl)propanoic acid (Example 147c) and 3,3-Difluoro-azetidine; hydrochloride (CAN 288315-03-7) as starting materials and isolated (18 mg, 24%); MS (ESI, m/z): 490.5 (M+H$^+$).

Example 148

5-cyclopropyl-N-[2-(5-methyl-1,2,4-oxadiazol-3-yl)-1-(2-oxa-6-azaspiro[3.3]heptan-6-yl)-1-oxopropan-2-yl]-4-(2,2,2-trifluoroethoxy)pyridine-2-carboxamide

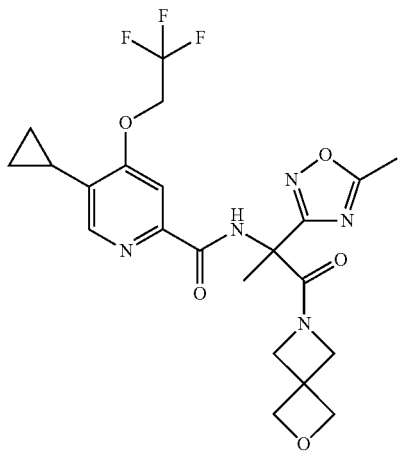 [SMILES: Cc1nc(C(C)(NC(=O)c2cc(OCC(F)(F)F)c(C3CC3)cn2)C(=O)N2CC3(COC3)C2)no1]

The title compound was synthesized in analogy to Example 112e, using 2-[[5-cyclopropyl-4-(2,2,2-trifluoroethoxy)pyridine-2-carbonyl]amino]-2-(5-methyl-1,2,4-oxadiazol-3-yl)propanoic acid (Example 147c) and 2-oxa-6-azaspiro[3.3]heptane oxalate (2:1) (CAN 1045709-32-7) as starting materials and isolated (8 mg, 10%); MS (ESI, m/z): 496.5 (M+H$^+$).

Example 149

5-cyclopropyl-N-[1-(methylamino)-2-(5-methyl-1,2,4-oxadiazol-3-yl)-1-oxopropan-2-yl]-4-(2,2,2-trifluoroethoxy)pyridine-2-carboxamide

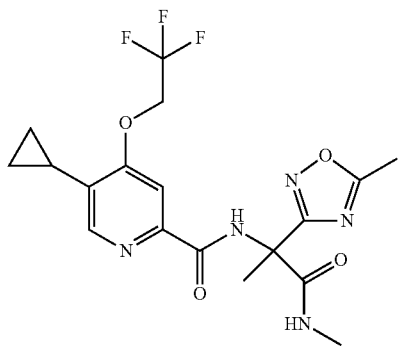 [SMILES: CNC(=O)C(C)(NC(=O)c1cc(OCC(F)(F)F)c(C2CC2)cn1)c1noc(C)n1]

The title compound was synthesized in analogy to Example 112e, using 2-[[5-cyclopropyl-4-(2,2,2-trifluoroethoxy)pyridine-2-carbonyl]amino]-2-(5-methyl-1,2,4-oxadiazol-3-yl)propanoic acid (Example 147c) and methylamine;hydrochloride as starting materials and isolated (5.9 mg, 16%); MS (ESI, m/z): 428.4 (M+H$^+$).

Example 150

5-cyclopropyl-N-[1-cyclopropyl-2-(2-methyltetrazol-5-yl)propan-2-yl]-4-(2,2,2-trifluoroethoxy)pyridine-2-carboxamide

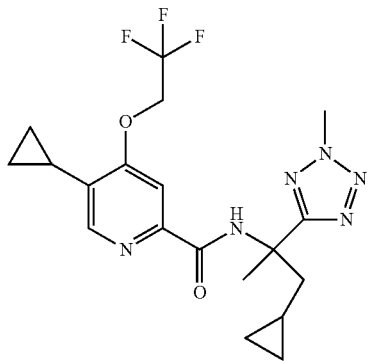 [SMILES: Cn1nnc(C(C)(CC2CC2)NC(=O)c2cc(OCC(F)(F)F)c(C3CC3)cn2)n1]

a) N-(1-cyano-2-cyclopropyl-1-methyl-ethyl)-5-cyclopropyl-4-(2,2,2-trifluoroethoxy)pyridine-2-carboxamide

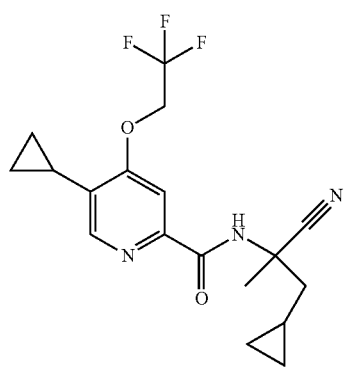 [SMILES: CC(C#N)(CC1CC1)NC(=O)c1cc(OCC(F)(F)F)c(C2CC2)cn1]

The title compound was synthesized in analogy to Example 112e, using 5-Cyclopropyl-4-(2,2,2-trifluoroethoxy)-pyridine-2-carboxylic acid (Example 48c) and 2-Amino-3-cyclopropyl-2-methyl-propionitrile (example 66a) as starting materials and isolated (376 mg, 67%); MS (ESI, m/z): 368.6 (M+H⁺).

b) 5-cyclopropyl-N-[2-cyclopropyl-1-methyl-1-(2H-tetrazol-5-yl)ethyl]-4-(2,2,2-trifluoroethoxy)pyridine-2-carboxamide

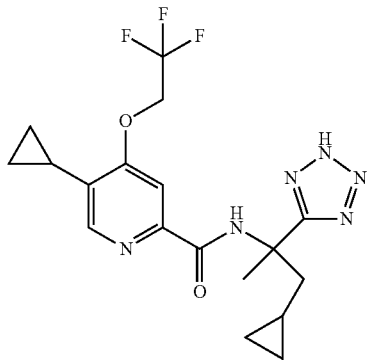 [SMILES: CC(CC1CC1)(NC(=O)c1cc(OCC(F)(F)F)c(C2CC2)cn1)c1nn[nH]n1]

To a solution of N-(1-cyano-2-cyclopropyl-1-methyl-ethyl)-5-cyclopropyl-4-(2,2,2-trifluoroethoxy)pyridine-2-carboxamide (example 150a, 300 mg, 817 µmol) in DMF (4 ml) under an argon atmosphere was added ammonium chloride (218 mg, 4.08 mmol), sodium azide (265 mg, 4.08 mmol). The reaction mixture was stirred at 120° C. under microwave radiation for 45 minutes. After cooling, the reaction mixture was poured into a mixture of ice water (12 mL) and ethyl acetate (4 mL). To the bi-phasic mixture was added sodium nitrite (231 mg, 3.35 mmol) (to decompose the excess of sodium azide), followed by a slow addition of a 4M aqueous solution of hydrochloric acid (until pH=2) under ice cooling. The bi-phasic mixture was then stirred at room temperature for 10 minutes, then diluted with more ethyl acetate and poured into a separatory funnel. After extraction the organic phase was collected and washed with water and brine. The organic phase was dried over sodium sulfate and evaporated down to dryness to yield the title compound (239 mg, 71%) as a crude solid which was used without any purification. MS (ESI, m/z): 411.5 (M+H⁺).

c) 5-cyclopropyl-N-[2-cyclopropyl-1-methyl-1-(2-methyltetrazol-5-yl)ethyl]-4-(2,2,2-trifluoroethoxy)pyridine-2-carboxamide

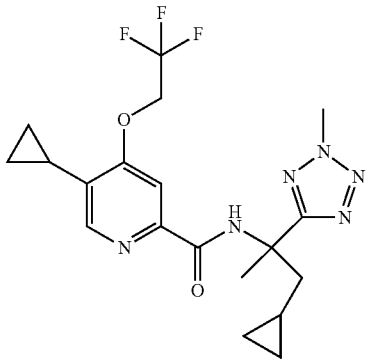 [SMILES: Cn1nnc(C(C)(CC2CC2)NC(=O)c2cc(OCC(F)(F)F)c(C3CC3)cn2)n1]

To a solution of 5-cyclopropyl-N-[2-cyclopropyl-1-methyl-1-(2H-tetrazol-5-yl)ethyl]-4-(2,2,2-trifluoroethoxy)pyridine-2-carboxamide (example 150b, 100 mg, 0.244 mmol) in dry DMF (1.2 ml) was added potassium carbonate (43.8 mg, 0.317 mmol). The reaction mixture was stirred at room temperature for 10 minutes followed by addition of iodomethane (30.5 µl, 0.487 mmol). The reaction mixture was then stirred at room temperature overnight. The reaction mixture was diluted with ethyl acetate and extracted with water and brine. The organic phase was dried over sodium sulfate and evaporated down to dryness. The crude material was purified by preparative HPLC to yield the title compound (40 mg, 39%) and also a second by-product as the regioisomer (11 mg, 10.6%). MS (ESI, m/z): 425.5 (M+H⁺).

Example 151

5-cyclopropyl-N-[1-cyclopropyl-2-(1-methyltetrazol-5-yl)propan-2-yl]-4-(2,2,2-trifluoroethoxy)pyridine-2-carboxamide

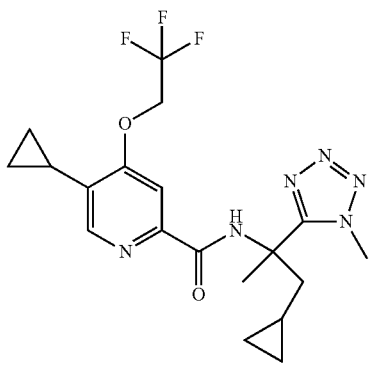 [SMILES: Cn1nnnc1C(C)(CC1CC1)NC(=O)c1cc(OCC(F)(F)F)c(C2CC2)cn1]

To a solution of 5-cyclopropyl-N-[2-cyclopropyl-1-methyl-1-(2H-tetrazol-5-yl)ethyl]-4-(2,2,2-trifluoroethoxy)pyridine-2-carboxamide (example 150b, 100 mg, 0.244 mmol) in dry DMF (1.2 ml) was added potassium carbonate (43.8 mg, 0.317 mmol). The reaction mixture was stirred at room temperature for 10 minutes followed by addition of iodomethane (30.5 µl, 0.487 mmol). The reaction mixture was then stirred at room temperature overnight. The reaction mixture was diluted with ethyl acetate and extracted with water and brine. The organic phase was dried over sodium sulfate and evaporated down to dryness. The crude material was purified by preparative HPLC to yield the title compound (11 mg, 11%) and also a second by-product as the regioisomer (40 mg, 39%). MS (ESI, m/z): 425.5 (M+H⁺).

Example 152

5-cyclopropyl-N-[4-(4-methyl-1,3-thiazol-2-yl)oxan-4-yl]-4-(2,2,2-trifluoroethoxy)pyridine-2-carboxamide

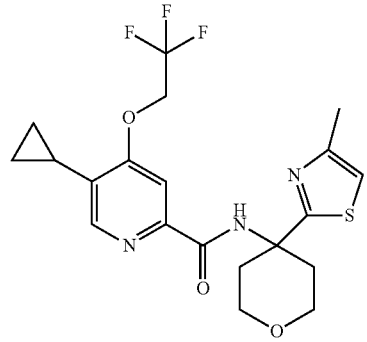 [SMILES: Cc1csc(C2(NC(=O)c3cc(OCC(F)(F)F)c(C4CC4)cn3)CCOCC2)n1]

a) 2-methyl-N-[4-(4-methylthiazol-2-yl)tetrahydropyran-4-yl]propane-2-sulfinamide

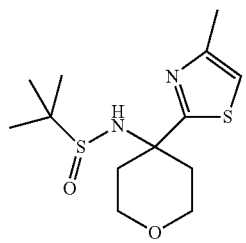 [SMILES: Cc1csc(C2(NS(=O)C(C)(C)C)CCOCC2)n1]

A 2.0M solution of lithium diisopropylamide in THF (492 µl, 984 µmol) was added dropwise to a solution of 4-methylthiazole (97.5 mg, 984 µmol) in dry THF (0.3 ml) cooled to −78° C. and once the addition was complete the reaction was stirred for 30 minutes at −78° C. followed by addition of dry toluene (0.6 ml). To a solution of 2-methyl-N-(2H-pyran-4(3H,5H,6H)-ylidene)propane-2-sulfinamide (CAN 861857-62-7, 100 mg, 492 µmol) in dry toluene (1 mL) was added a 2.0M solution of trimethylaluminum in heptane (271 µl, 541 µmol). The former solution was then added to the reaction mixture cooled at −78° C. The reaction was allowed to warm up to room temperature overnight. The reaction was quenched by the addition of a saturated aqueous solution of ammonium chloride and was then diluted with ethyl acetate. The bi-phasic mixture was poured into a separatory funnel and extracted. The organic phase was collected, dried over sodium sulfate and evaporated down to dryness. The crude material was purified by flash chromatography on silica eluting with a dichloromethane/methanol gradient to yield the title compound (102 mg, 69%). MS (ESI, m/z): 303.5 (M+H⁺).

b) 5-cyclopropyl-N-[4-(4-methyl-1,3-thiazol-2-yl)oxan-4-yl]-4-(2,2,2-trifluoroethoxy)pyridine-2-carboxamide 2-methyl-N-(4-(4-methylthiazol-2-yl)tetrahydro-2H-pyran-4-yl)propane-2-sulfinamide (example 152a, 100 mg, 331 µmol) was dissolved in dioxane (1.5 ml) at room temperature and a 4M solution of hydrochloric acid in dioxane (496 µl, 992 µmol) was added. The reaction mixture was stirred at room temperature for 30 minutes. The reaction mixture was diluted with ethyl acetate and the organic phase was extracted with a 2M aqueous solution of sodium carbonate. The organic phase was dried over sodium sulfate and evaporated down to dryness to yield a crude amine product which was used without any purification for the synthesis of the title compound in analogy to Example 112e, using 5-Cyclopropyl-4-(2,2,2-trifluoro-ethoxy)-pyridine-2-carboxylic acid (Example 48c) as starting material. The title compound was isolated (83 mg, 51%) by preparative HPLC purification; MS (ESI, m/z): 442.4 (M+H⁺).

Example 153

5-cyclopropyl-N-[4-(5-methyl-1,3-thiazol-2-yl)oxan-4-yl]-4-(2,2,2-trifluoroethoxy)pyridine-2-carboxamide

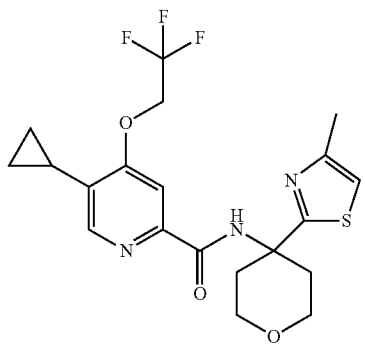 [SMILES: Cc1csc(C2(NC(=O)c3cc(OCC(F)(F)F)c(C4CC4)cn3)CCOCC2)n1]

a) 2-methyl-N-[4-(5-methylthiazol-2-yl)tetrahydropyran-4-yl]propane-2-sulfinamide

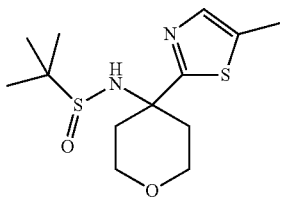 [SMILES: Cc1cnc(C2(NS(=O)C(C)(C)C)CCOCC2)s1]

A 2.0M solution of lithium diisopropylamide in THF (492 µl, 984 µmol) was added dropwise to a solution of 5-methylthiazole (97.5 mg, 984 µmol) in dry THF (0.3 ml) cooled to −78° C. and once the addition was complete the reaction was stirred for 30 minutes at −78° C. followed by addition of dry toluene (0.6 ml). To a solution of 2-methyl-N-(2H-pyran-4 (3H,5H,6H)-ylidene)propane-2-sulfinamide (CAN 861857-62-7, 100 mg, 492 µmol) in dry toluene (1 mL) was added a 2.0M solution of trimethylaluminum in heptane (271 µl, 541 µmol). The former solution was then added to the reaction mixture cooled at −78° C. The reaction was allowed to warm up to room temperature overnight. The reaction was quenched by the addition of a saturated aqueous solution of ammonium chloride and was then diluted with ethyl acetate. The bi-phasic mixture was poured into a separatory funnel and extracted. The organic phase was collected, dried over sodium sulfate and evaporated down to dryness. The crude material was purified by flash chromatography on silica eluting with a dichloromethane-methanol gradient to yield the title compound (102 mg, 69%). MS (ESI, m/z): 303.5 (M+H⁺).

b) 5-cyclopropyl-N-[4-(5-methyl-1,3-thiazol-2-yl) oxan-4-yl]-4-(2,2,2-trifluoroethoxy)pyridine-2-carboxamide

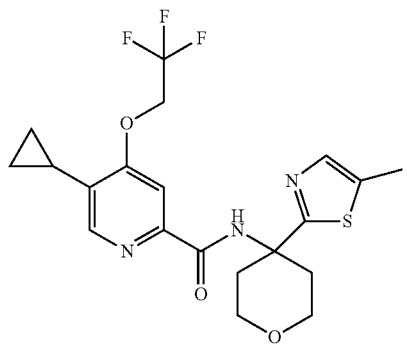 [SMILES: Cc1cnc(C2(NC(=O)c3cc(OCC(F)(F)F)c(C4CC4)cn3)CCOCC2)s1]

2-methyl-N-[4-(5-methylthiazol-2-yl)tetrahydropyran-4-yl]propane-2-sulfinamide (example 153a, 100 mg, 331 µmol) was dissolved in dioxane (1.5 ml) at room temperature and a 4M solution of hydrochloric acid in dioxane (496 µl, 992 µmol) was added. The reaction mixture was stirred at room temperature for 30 minutes. The reaction mixture was diluted with ethyl acetate and the organic phase was extracted with a 2M aqueous solution of sodium carbonate. The organic phase was dried over sodium sulfate and evaporated down to dryness to yield a crude amine product which was used without any purification for the synthesis of the title compound in analogy to Example 112e, using 5-Cyclopropyl-4-(2,2,2-trifluoro-ethoxy)-pyridine-2-carboxylic acid (Example 48c) as starting materials. The title compound was isolated (68 mg, 52%) by preparative HPLC purification; MS (ESI, m/z): 442.4 (M+H⁺).

Example 154

5-cyclopropyl-N-[1-cyclopropyl-2-(5-methyl-1,2,4-oxadiazol-3-yl)propan-2-yl]-4-(2,2-difluoroethoxy) pyridine-2-carboxamide (enantiomer A)

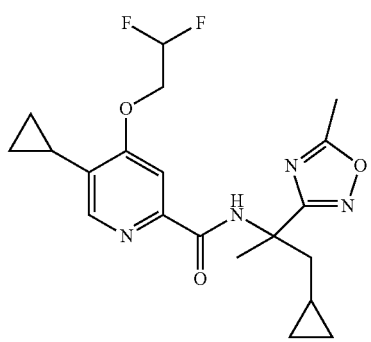 [SMILES: Cc1nc(C(C)(CC2CC2)NC(=O)c2cc(OCC(F)F)c(C3CC3)cn2)no1]

The racemate (Example 145e) was separated into its enantiomers by preparative chiral HPLC (Reprosil Chiral NR, isopropanol/heptane) and the title compound was the first enantiomer collected and isolated as colorless oil; MS (ESI, m/z): 407.6 (M+H+).

Example 155

5-cyclopropyl-N-[1-cyclopropyl-2-(5-methyl-1,2,4-oxadiazol-3-yl)propan-2-yl]-4-(2,2-difluoroethoxy)pyridine-2-carboxamide (enantiomer B)

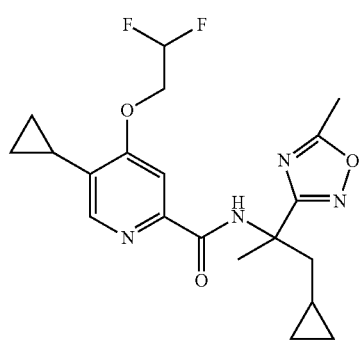 [SMILES: Cc1nc(C(C)(CC2CC2)NC(=O)c2cc(OCC(F)F)c(C3CC3)cn2)no1]

The racemate (Example 145e) was separated into its enantiomers by preparative chiral HPLC (Reprosil Chiral NR, isopropanol/heptane) and the title compound was the second enantiomer collected and isolated as colorless oil; MS (ESI, m/z): 407.6 (M+H+).

Example 156

5-cyclopropyl-N-[1-cyclopropyl-2-(5-methyl-1,2,4-oxadiazol-3-yl)propan-2-yl]-4-(2-fluoroethoxy)pyridine-2-carboxamide (enantiomer A)

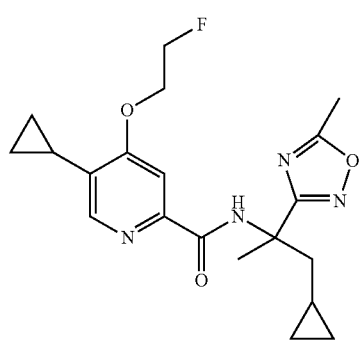 [SMILES: Cc1nc(C(C)(CC2CC2)NC(=O)c2cc(OCCF)c(C3CC3)cn2)no1]

The racemate (Example 146c) was separated into its enantiomers by preparative chiral HPLC (Reprosil Chiral NR, isopropanol/heptane) and the title compound was the first enantiomer collected and isolated as colorless oil; MS (ESI, m/z): 389.6 (M+H+).

Example 157

5-cyclopropyl-N-[1-cyclopropyl-2-(5-methyl-1,2,4-oxadiazol-3-yl)propan-2-yl]-4-(2-fluoroethoxy)pyridine-2-carboxamide (enantiomer B)

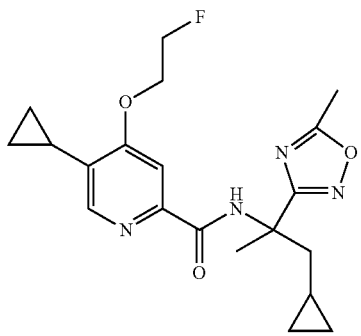 [SMILES: Cc1nc(C(C)(CC2CC2)NC(=O)c2cc(OCCF)c(C3CC3)cn2)no1]

The racemate (Example 146c) was separated into its enantiomers by preparative chiral HPLC (Reprosil Chiral NR, isopropanol/heptane) and the title compound was the second enantiomer collected and isolated as colorless oil; MS (ESI, m/z): 389.6 (M+H+).

Example 158

5-cyclopropyl-N-[1-cyclopropyl-2-(4-methyl-1,3-thiazol-2-yl)propan-2-yl]-4-(2,2,2-trifluoroethoxy)pyridine-2-carboxamide

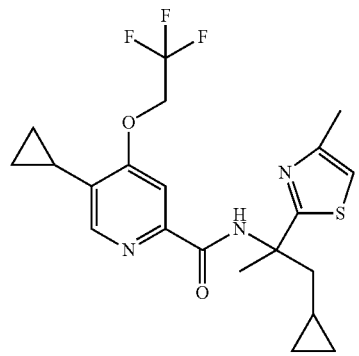 [SMILES: Cc1csc(C(C)(CC2CC2)NC(=O)c2cc(OCC(F)(F)F)c(C3CC3)cn2)n1]

A 2.0M solution of lithium diisopropylamide in THF (745 µl, 1.49 mmol) was added dropwise to a solution of 4-methylthiazole (148 mg, 1.49 mmol) in dry THF (0.5 ml) cooled to −78° C. and once the addition was complete the reaction was stirred for 30 minutes at −78° C. followed by addition of dry toluene (1.5 ml). To a solution of (NE)-N-(2-cyclopropyl-1-methyl-ethylidene)-2-methyl-propane-2-sulfinamide (CAN 1426426-70-1, 150 mg, 745 µmol) in dry toluene (1.5 mL) was added a 2.0M solution of trimethylaluminum in heptane (410 µl, 820 µmol). The solution was then added to the reaction mixture cooled at −78° C. The reaction was allowed to warm up to room temperature overnight. The reaction was quenched by the addition of a saturated aqueous solution of ammonium chloride and was then diluted with ethyl acetate. The bi-phasic mixture was poured into a separatory funnel and extracted. The organic phase was collected, dried over sodium sulfate and evaporated down to dryness to yield the a crude product (198 mg) which was dissolved in dioxane (2 ml) and treated with a 4M solution of hydrochloric acid in dioxane (948 µl, 1.9 mmol). The reaction mixture was then stirred at room temperature for 30 minutes. The reaction mixture was diluted with ethyl acetate and the organic phase was extracted with a 2M aqueous solution of sodium carbonate. The organic phase was dried over sodium sulfate and evaporated down to dryness to yield a crude amine product which was used without any purification for the synthesis of the title compound in analogy to Example 112e, using 5-Cyclopropyl-4-(2,2,2-trifluoro-ethoxy)-pyridine-2-carboxylic acid (Example 48c) as starting materials. The title compound was isolated (74 mg, 24%) by preparative HPLC purification; MS (ESI, m/z): 440.5 (M+H$^+$).

Example 159

5-cyclopropyl-N-[1-cyclopropyl-2-(1H-tetrazol-5-yl)propan-2-yl]-4-(2,2,2-trifluoroethoxy)pyridine-2-carboxamide

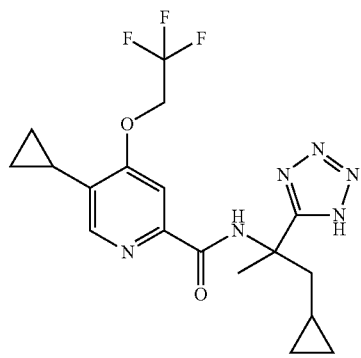 [SMILES: CC(CC1CC1)(NC(=O)c1cc(OCC(F)(F)F)c(C2CC2)cn1)c1nnn[nH]1]

The title compound was synthesized in analogy to Example 150b, using N-(1-cyano-2-cyclopropyl-1-methylethyl)-5-cyclopropyl-4-(2,2,2-trifluoroethoxy)pyridine-2-carboxamide (Example 150a) as starting material and isolated (239 mg, 71%); MS (ESI, m/z): 411.6 (M+H$^+$).

Example 160

N-[3-(2-amino-2-oxoethyl)-1,1-dioxothietan-3-yl]-5-cyclopropyl-4-(2,2,2-trifluoroethoxy)pyridine-2-carboxamide

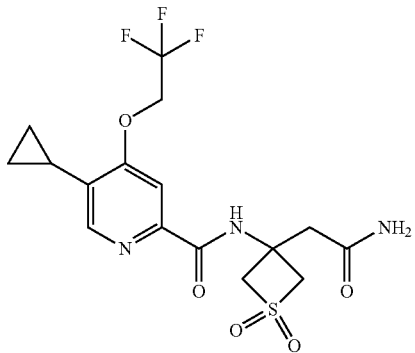 [SMILES: NC(=O)CC1(NC(=O)c2cc(OCC(F)(F)F)c(C3CC3)cn2)CS(=O)(=O)C1]

a) ethyl 2-[3-(benzylamino)thietan-3-yl]acetate

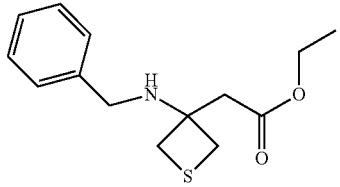 [SMILES: CCOC(=O)CC1(NCc2ccccc2)CSC1]

A mixture of Thietan-3-ylidene-acetic acid ethylester (CAN 1223573-30-5, 1.8 g, 11.4 mmol) and phenylmethanamine (CAN 100-46-9, 1.22 g, 1.24 ml, 11.4 mmol) was stirred for 14 hours at ambient temperature. The crude product was directly purified without any work-up protocol. The crude material was purified by flash chromatography on silica eluting with a heptane-ethyl acetate gradient to yield the title compound (2.4 g, 80%). MS (ESI, m/z): 266.5 (M+H$^+$).

b) ethyl 2-[3-(benzylamino)-1,1-dioxo-thietan-3-yl]acetate

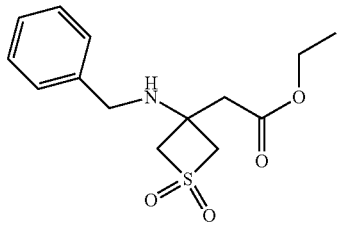 [SMILES: CCOC(=O)CC1(NCc2ccccc2)CS(=O)(=O)C1]

To a solution of ethyl 2-(3-(benzylamino)thietan-3-yl)acetate (example 160a, 3.6 g, 13.6 mmol) in dichloromethane (360 mL) was added titanium(IV) isopropoxide (3.85 g, 3.97 ml, 13.6 mmol) and the solution cooled to 0° C. A 35% aqueous solution of hydrogen peroxide (2.63 g, 2.63 ml, 27.1 mmol) was added, bright yellow solids formed. The mixture was stirred vigorously for 30 min at 0° C., then the mixture was stirred for 2 hours at ambient temperature. The precipitate was filtered and washed with dichloromethane. The filtrate was poured into a separatory funnel and extracted with iced water. The organic phase was collected and the aqueous phase was back-extracted twice with dichloromethane. Combined organic phases were dried over sodium sulfate and evaporated down to dryness. The crude material was purified by flash chromatography on silica eluting with a heptane/ethyl acetate gradient to yield the title compound (102 mg, 69%). MS (ESI, m/z): 298.2 (M+H$^+$).

c) ethyl 2-(3-amino-1,1-dioxo-thietan-3-yl)acetate

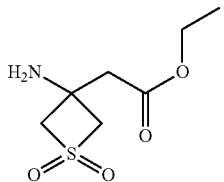

To a solution of ethyl 2-[3-(benzylamino)-1,1-dioxo-thietan-3-yl]acetate (example 160b, 0.5 g, 1.68 mmol) in EtOH (12.5 ml) under an argon atmosphere was added palladium on charcoal 10% (w/w 10%) (50.0 mg, 470 μmol). The reaction flask was put under a pressure of 2.5 bar H2 and the reaction mixture was then stirred at 50° C. for 16 hours. Palladium catalyst was removed by filtration over a pad of Celite and the filter cake was washed with ethanol twice. The filtrate was evaporated down to dryness to yield the title compound (350 mg, 100%) as a crude product which was used without any purification. MS (ESI, m/z): 208.1 (M+H⁺).

d) 2-(3-amino-1,1-dioxo-thietan-3-yl)acetamide

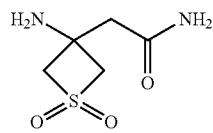

Ethyl 2-(3-amino-1,1-dioxo-thietan-3-yl)acetate (example 160c, 550 mg, 2.65 mmol) was dissolved in ammonia 7.0M in methanol (9 ml, 63.0 mmol) and the reaction flask was sealed (size of the flask was chosen to minimize the volume for gas expansion in order to minimize ammonia evaporation). The reaction was stirred at 45° C. for 2 days. Volatiles were removed in vacuo to yield a crude material (523 mg) containing a 4:1 ratio of amide:methyl ester. The crude material was used without any further purification; MS (ESI, m/z): 179.1 (M+H⁺).

e) N-[3-(2-amino-2-oxoethyl)-1,1-dioxothietan-3-yl]-5-cyclopropyl-4-(2,2,2-trifluoroethoxy)pyridine-2-carboxamide

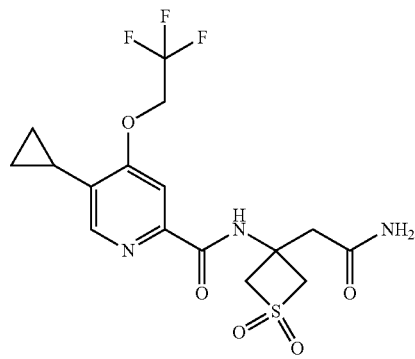 [SMILES: NC(=O)CC1(NC(=O)c2cc(OCC(F)(F)F)c(C3CC3)cn2)CS(=O)(=O)C1]

The title compound was synthesized in analogy to Example 112e, using 5-Cyclopropyl-4-(2,2,2-trifluoroethoxy)-pyridine-2-carboxylic acid (Example 48c) and 2-(3-amino-1,1-dioxo-thietan-3-yl)acetamide (example 160d) as starting materials and isolated (130 mg, 43%); MS (ESI, m/z): 422.2 (M+H⁺).

Example 161

5-cyclopropyl-N-[2,2-dimethyl-1-(5-methyl-1,2,4-oxadiazol-3-yl)propyl]-4-(2,2,2-trifluoroethoxy)pyridine-2-carboxamide

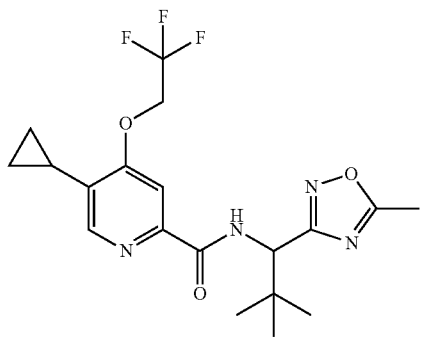 [SMILES: Cc1nc(C(NC(=O)c2cc(OCC(F)(F)F)c(C3CC3)cn2)C(C)(C)C)no1]

a) N-(1-cyano-2,2-dimethyl-propyl)-5-cyclopropyl-4-(2,2,2-trifluoroethoxy)pyridine-2-carboxamide

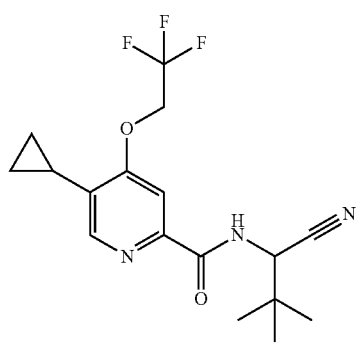 [SMILES: CC(C)(C)C(C#N)NC(=O)c1cc(OCC(F)(F)F)c(C2CC2)cn1]

The title compound was synthesized in analogy to Example 112e, using 5-Cyclopropyl-4-(2,2,2-trifluoroethoxy)-pyridine-2-carboxylic acid (Example 48c) and 2-Amino-3,3-dimethyl-butyronitrile (CAN 77425-86-6) as starting materials and isolated (782 mg, 90%); MS (ESI, m/z): 356.2 (M+H⁺).

b) 5-cyclopropyl-N-[1-[(Z)—N'-hydroxycarbamimidoyl]-2,2-dimethyl-propyl]-4-(2,2,2-trifluoroethoxy)pyridine-2-carboxamide

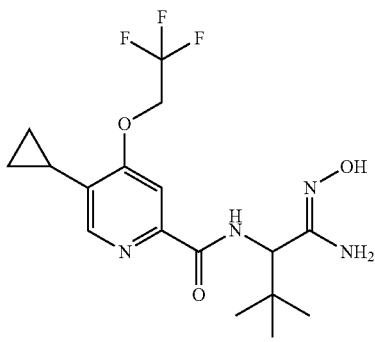 [SMILES: CC(C)(C)C(NC(=O)c1cc(OCC(F)(F)F)c(C2CC2)cn1)/C(N)=N/O]

The title compound was synthesized in analogy to Example 78f, using N-(1-cyano-2,2-dimethyl-propyl)-5-cyclopropyl-4-(2,2,2-trifluoroethoxy)pyridine-2-carboxamide (Example 161a) as starting material and isolated (487 mg, 58%); MS (ESI, m/z): 389.2 (M+H⁺).

c) 5-cyclopropyl-N-[2,2-dimethyl-1-(5-methyl-1,2,4-oxadiazol-3-yl)propyl]-4-(2,2,2-trifluoroethoxy)pyridine-2-carboxamide

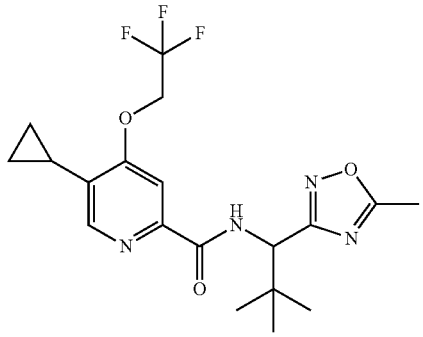 [SMILES: Cc1nc(C(NC(=O)c2cc(OCC(F)(F)F)c(C3CC3)cn2)C(C)(C)C)no1]

The title compound was synthesized in analogy to Example 78g, using 5-cyclopropyl-N-[1-[(Z)—N'-hydroxycarbamimidoyl]-2,2-dimethyl-propyl]-4-(2,2,2-trifluoroethoxy)pyridine-2-carboxamide (Example 161b) as starting material and isolated (53 mg, 50%); MS (ESI, m/z): 413.6 (M+H⁺).

Example 162

5-cyclopropyl-N-[2,2-dimethyl-1-(1H-tetrazol-5-yl)propyl]-4-(2,2,2-trifluoroethoxy)pyridine-2-carboxamide

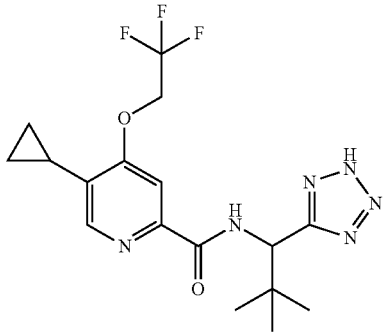 [SMILES: CC(C)(C)C(NC(=O)c1cc(OCC(F)(F)F)c(C2CC2)cn1)c1nn[nH]n1]

The title compound was synthesized in analogy to Example 150b, using N-(1-cyano-2,2-dimethyl-propyl)-5-cyclopropyl-4-(2,2,2-trifluoroethoxy)pyridine-2-carboxamide (Example 161a) as starting material and isolated (143 mg, 71%); MS (ESI, m/z): 399.6 (M+H⁺).

Example 163

5-cyclopropyl-N-[2,2-dimethyl-1-(2-methyltetrazol-5-yl)propyl]-4-(2,2,2-trifluoroethoxy)pyridine-2-carboxamide

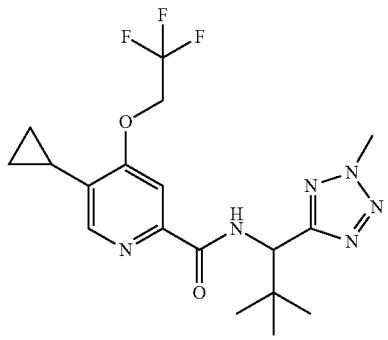 [SMILES: Cn1nnc(C(NC(=O)c2cc(OCC(F)(F)F)c(C3CC3)cn2)C(C)(C)C)n1]

The title compound was synthesized in analogy to Example 150c, using 5-cyclopropyl-N-[2,2-dimethyl-1-(1H-tetrazol-5-yl)propyl]-4-(2,2,2-trifluoroethoxy)pyridine-2-carboxamide (Example 162) as starting material and isolated (58 mg, 43%); MS (ESI, m/z): 413.6 (M+H⁺).

Example 164

5-cyclopropyl-N-[2,2-dimethyl-1-(1-methyltetrazol-5-yl)propyl]-4-(2,2,2-trifluoroethoxy)pyridine-2-carboxamide

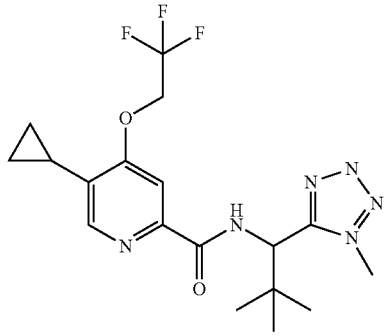

The title compound was synthesized in analogy to Example 150c, using 5-cyclopropyl-N-[2,2-dimethyl-1-(1H-tetrazol-5-yl)propyl]-4-(2,2,2-trifluoroethoxy)pyridine-2-carboxamide (Example 162) as starting material and isolated (30 mg, 22%); MS (ESI, m/z): 413.6 (M+H⁺).

Example 165

N-[2-(5-amino-1,2,4-oxadiazol-3-yl)-1-cyclopropyl-propan-2-yl]-5-cyclopropyl-4-(2,2,2-trifluoroethoxy)pyridine-2-carboxamide

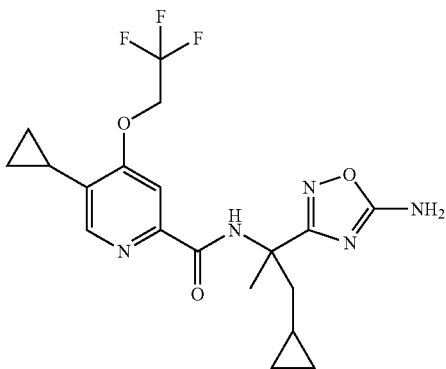 [SMILES: CC(CC1CC1)(NC(=O)c1cc(OCC(F)(F)F)c(C2CC2)cn1)c1noc(N)n1]

a) N-[(2Z)-2-amino-1-(cyclopropylmethyl)-2-hydroxyimino-1-methyl-ethyl]-5-cyclopropyl-4-(2,2,2-trifluoroethoxy)pyridine-2-carboxamide

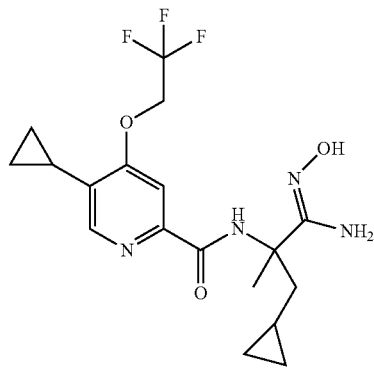 [SMILES: CC(CC1CC1)(NC(=O)c1cc(OCC(F)(F)F)c(C2CC2)cn1)/C(N)=N/O]

The title compound was synthesized in analogy to Example 78f, using N-(1-cyano-2-cyclopropyl-1-methyl-ethyl)-5-cyclopropyl-4-(2,2,2-trifluoroethoxy)pyridine-2-carboxamide (example 150a) as starting material and isolated (132 mg, 61%); MS (ESI, m/z): 401.6 (M+H$^+$).

b) N-[2-(5-amino-1,2,4-oxadiazol-3-yl)-1-cyclopropylpropan-2-yl]-5-cyclopropyl-4-(2,2,2-trifluoroethoxy)pyridine-2-carboxamide

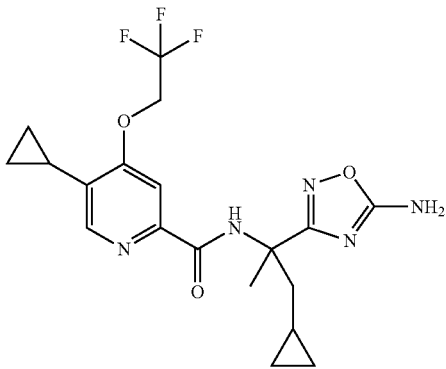 [SMILES: CC(CC1CC1)(NC(=O)c1cc(OCC(F)(F)F)c(C2CC2)cn1)c1noc(N)n1]

A mixture of N-[(2Z)-2-amino-1-(cyclopropylmethyl)-2-hydroxyimino-1-methyl-ethyl]-5-cyclopropyl-4-(2,2,2-trifluoroethoxy)pyridine-2-carboxamide (example 165a, 30 mg, 74.9 μmol) in piperidine-1-carbonitrile (130 mg, 130 μl, 1.18 mmol) was heated at 130° C. in a sealed tube for 2 hours. The reaction mixture was cooled to room temperature and was diluted with ethyl acetate. The organic phase was washed with water. The organic phase was collected and the aqueous phase was back-extracted with ethyl acetate. Combined organic phases were dried over sodium sulfate and evaporated down to dryness. The crude material was purified by flash chromatography on silica eluting with a heptane/ethyl acetate gradient to yield the title compound (21 mg, 67%). MS (ESI, m/z): 426.6 (M+H$^+$).

Example 166

N-[1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide (enantiomer A)

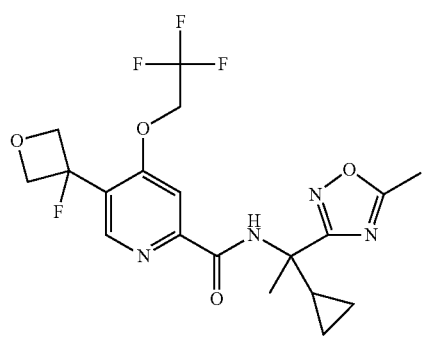 [SMILES: Cc1nc(C(C)(NC(=O)c2cc(OCC(F)(F)F)c(C3(F)COC3)cn2)C2CC2)no1]

The racemate (Example 139) was separated into its enantiomers by preparative chiral HPLC (Chiralpak AD, ethanol/heptane) and the title compound was the first enantiomer collected and isolated as colorless oil; MS (ESI, m/z): 445.5 (M+H$^+$).

Example 167

N-[1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide (enantiomer B)

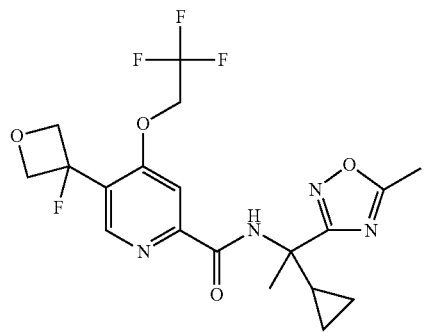 [SMILES: Cc1nc(C(C)(NC(=O)c2cc(OCC(F)(F)F)c(C3(F)COC3)cn2)C2CC2)no1]

The racemate (Example 139) was separated into its enantiomers by preparative chiral HPLC (Chiralpak AD, ethanol/

Example 168

N-[1-cyclopropyl-1-(5-methyl-1,2,4-oxadiazol-3-yl)ethyl]-5-(3-fluorooxetan-3-yl)-4-[(2S)-1,1,1-trifluoropropan-2-yl]oxypyridine-2-carboxamide (epimer A)

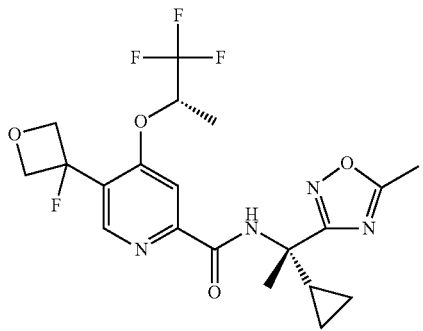 [SMILES: Cc1nc([C@@](C)(NC(=O)c2cc(O[C@@H](C)C(F)(F)F)c(C3(F)COC3)cn2)C2CC2)no1]

The title compound was synthesized in analogy to Example 112e, using 5-(3-fluorooxetan-3-yl)-4-[(1S)-2,2,2-trifluoro-1-methyl-ethoxy]pyridine-2-carboxylic acid (example 142b) and 1-Cyclopropyl-1-(5-methyl-[1,2,4]oxadiazol-3-yl)-ethylamine (CAN1155536-64-3) as starting materials and the mixture of epimers was isolated (72 mg, 40%). The mixture of epimers was separated into its epimers by preparative chiral HPLC (Chiralpak AD, ethanol/heptane) and the title compound was the first epimer collected and isolated as colorless oil; MS (ESI, m/z): 459.5 (M+H⁺).

Example 169

N-[1-cyclopropyl-1-(5-methyl-1,2,4-oxadiazol-3-yl)ethyl]-5-(3-fluorooxetan-3-yl)-4-[(2S)-1,1,1-trifluoropropan-2-yl]oxypyridine-2-carboxamide (epimer B)

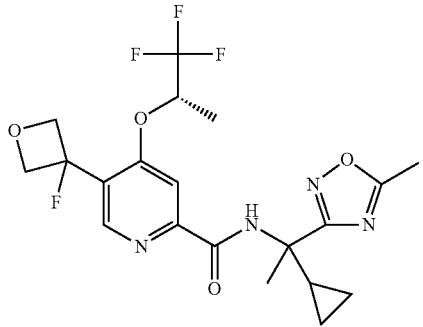 [SMILES: Cc1nc(C(C)(NC(=O)c2cc(O[C@@H](C)C(F)(F)F)c(C3(F)COC3)cn2)C2CC2)no1]

The title compound was synthesized in analogy to Example 112e, using 5-(3-fluorooxetan-3-yl)-4-[(1S)-2,2,2-trifluoro-1-methyl-ethoxy]pyridine-2-carboxylic acid (example 142b) and 1-Cyclopropyl-1-(5-methyl-[1,2,4]oxadiazol-3-yl)-ethylamine (CAN 1155536-64-3) as starting materials and the racemate was isolated (72 mg, 40%). The racemate was separated into its epimers by preparative chiral HPLC (Chiralpak AD, ethanol/heptane) and the title compound was the second epimer collected and isolated as colorless oil; MS (ESI, m/z): 459.5 (M+H⁺).

Example 170

N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide (epimer A)

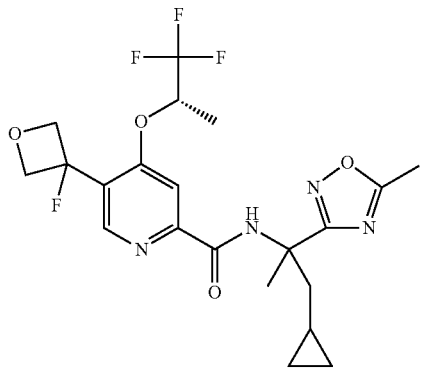 [SMILES: Cc1nc(C(C)(CC2CC2)NC(=O)c2cc(O[C@@H](C)C(F)(F)F)c(C3(F)COC3)cn2)no1]

The mixture of epimers (Example 142c) was separated into its individual epimers by preparative chiral HPLC (Chiralpak AD, ethanol/heptane) and the title compound was the first epimer collected and isolated as colorless oil; MS (ESI, m/z): 473.5 (M+H⁺).

Example 171

N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide (epimer B)

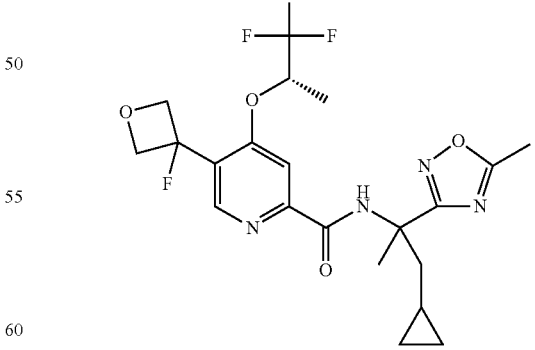

The mixture of epimers (Example 142c) was separated into its individual epimers by preparative chiral HPLC (Chiralpak AD, ethanol/heptane) and the title compound was the second epimer collected and isolated as colorless oil; MS (ESI, m/z): 473.5 (M+H⁺).

Example 172

N-[(2S)-3,3-dimethyl-1-(methylamino)-1-oxobutan-2-yl]-5-(3-fluorooxetan-3-yl)-4-[(2S)-1,1,1-trifluoro-propan-2-yl]oxypyridine-2-carboxamide

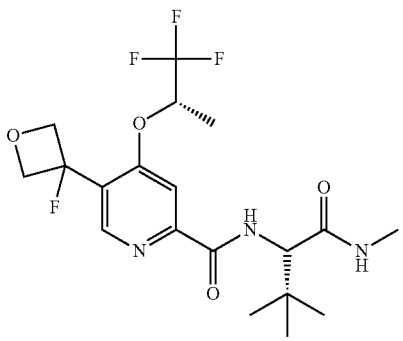

The title compound was synthesized in analogy to Example 112e, using 5-(3-fluorooxetan-3-yl)-4-[(1S)-2,2,2-trifluoro-1-methyl-ethoxy]pyridine-2-carboxylic acid (example 142b) and (S)-2-Amino-3,3,N-trimethyl-butyramide (CAN 89226-12-0) as starting materials and isolated (40 mg, 57%); MS (ESI, m/z): 436.6 (M+H$^+$).

Example 173

5-cyclopropyl-N-[1-cyclopropyl-2-(5-methyl-1,3,4-oxadiazol-2-yl)propan-2-yl]-4-(2,2,2-trifluoroethoxy)pyridine-2-carboxamide

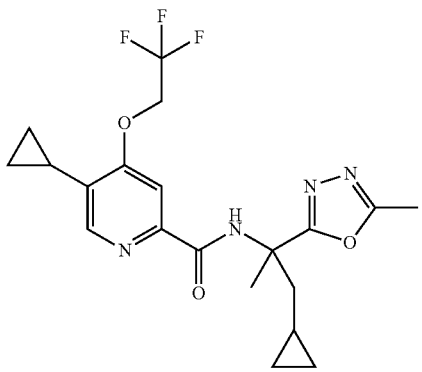 [SMILES: Cc1nnc(C(C)(CC2CC2)NC(=O)c2cc(OCC(F)(F)F)c(C3CC3)cn2)o1]

a) N-[2-cyclopropyl-1-methyl-1-(5-methyl-1,3,4-oxadiazol-2-yl)ethyl]-2-methyl-propane-2-sulfinamide

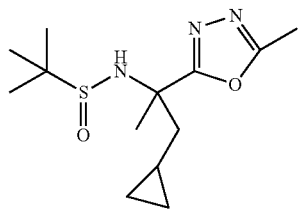 [SMILES: Cc1nnc(C(C)(CC2CC2)NS(=O)C(C)(C)C)o1]

To a solution of 2-bromo-5-methyl-1,3,4-oxadiazole (CAN 864750-58-3, 0.5 g, 3.07 mmol) in dry THF (8 ml) cooled down to −15° C. under an argon atmosphere was added isopropyl magnesium chloride, lithium chloride complex (2.36 ml, 3.07 mmol). (During the addition the temperature was kept below −12° C.). The reaction was then stirred at −15° C. for 30 minutes followed by slow addition of a solution of (Z)—N-(1-cyclopropylpropan-2-ylidene)-2-methyl-propane-2-sulfinamide (CAN 1426426-70-1, 618 mg, 3.07 mmol) and a 2M solution of trimethylaluminum in heptane (1.53 ml, 3.07 mmol) in dry toluene (8 ml). The reaction was allowed to warm up to room temperature overnight. The reaction was cooled down to 0° C. and quenched by addition of water (slow addition because reaction very exothermic). The reaction medium was diluted with ethylacetate and the organic phase was extracted with a saturated aqueous solution of ammonium chloride. The organic phase was collected and the aqueous phase was back-extracted with ethylacetate. The combined organic phases were dried over sodium sulfate and evaporated down to dryness. The crude material was purified by flash chromatography on silica eluting with a dichloromethane/methanol gradient to yield the title compound (521 mg, purity: 90%, 54%). MS (ESI, m/z): 286.5 (M+H$^+$).

b) 1-cyclopropyl-2-(5-methyl-1,3,4-oxadiazol-2-yl)propan-2-amine

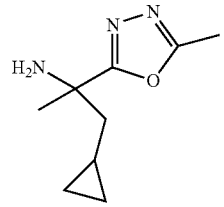

To a solution of N-[2-cyclopropyl-1-methyl-1-(5-methyl-1,3,4-oxadiazol-2-yl)ethyl]-2-methyl-propane-2-sulfinamide (example 173a, 520 mg, 1.46 mmol) in MeOH (8 ml) was added a 4M solution of hydrochloric acid in dioxane (729 µl, 2.92 mmol). The reaction mixture was stirred at room temperature for 1 hour. Reaction was quenched by addition of potassium carbonate and stirred for 15 minutes. The insolubles were removed by filtration and the filtrate was evaporated down to dryness. The crude material was purified by flash chromatography on silica eluting with a dichloromethane-methanol gradient to yield the title compound (130 mg, 50%). MS (ESI, m/z): 182.2 (M+H$^+$).

c) 5-cyclopropyl-N-[1-cyclopropyl-2-(5-methyl-1,3,4-oxadiazol-2-yl)propan-2-yl]-4-(2,2,2-trifluoroethoxy)pyridine-2-carboxamide

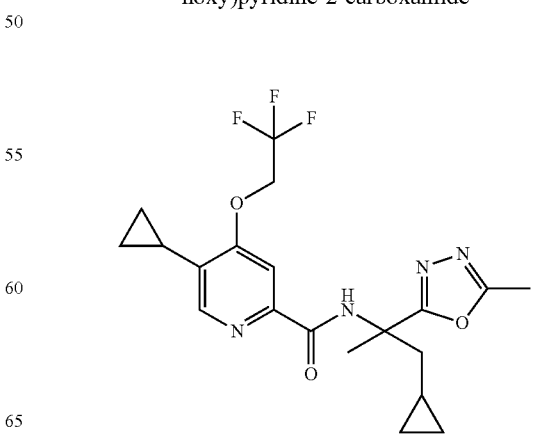

The title compound was synthesized in analogy to Example 112e, using 5-Cyclopropyl-4-(2,2,2-trifluoroethoxy)-pyridine-2-carboxylic acid (Example 48c) and 1-cyclopropyl-2-(5-methyl-1,3,4-oxadiazol-2-yl)propan-2-amine (example 173b) as starting materials and isolated (99 mg, 76%); MS (ESI, m/z): 425.6 (M+H⁺).

Example 174

5-cyclopropyl-N-[2,2-dimethyl-1-(5-methyl-1,3,4-oxadiazol-2-yl)propyl]-4-(2,2,2-trifluoroethoxy)pyridine-2-carboxamide

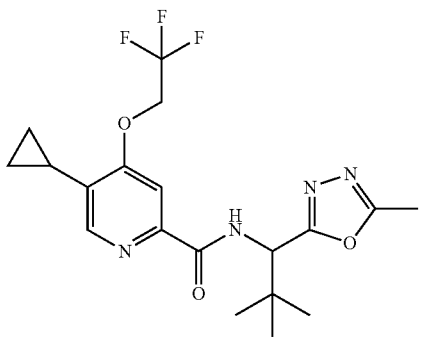 [SMILES: Cc1nnc(C(NC(=O)c2cc(OCC(F)(F)F)c(C3CC3)cn2)C(C)(C)C)o1]

a) N-[2,2-dimethyl-1-(5-methyl-1,3,4-oxadiazol-2-yl)propyl]-2-methyl-propane-2-sulfinamide

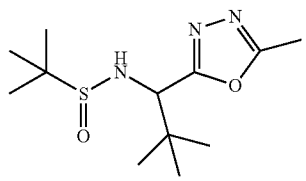 [SMILES: Cc1nnc(C(NS(=O)C(C)(C)C)C(C)(C)C)o1]

To a solution of 2-bromo-5-methyl-1,3,4-oxadiazole (CAN 864750-58-3, 0.473 g, 2.91 mmol) in dry THF (8 ml) cooled down to −15° C. under an argon atmosphere was added isopropyl magnesium chloride, lithium chloride complex (2.23 ml, 2.91 mmol). (During the addition the temperature was kept below −12° C.). The reaction was then stirred at −15° C. for 30 minutes followed by slow addition of a solution of (NE)-N-(2,2-dimethylpropylidene)-2-methyl-propane-2-sulfinamide (CAN 917104-90-6, 500 mg, 2.64 mmol) in dry toluene (8 ml). The reaction was allowed to warm up to room temperature overnight. The reaction was quenched by addition of water. The reaction medium was diluted with ethylacetate and the organic phase was extracted with a saturated aqueous solution of ammonium chloride. The organic phase was collected and the aqueous phase was back-extracted with ethylacetate. The combined organic phases were dried over sodium sulfate and evaporated down to dryness. The crude material was purified by flash chromatography on silica eluting with a dichloromethane/methanol gradient to yield the title compound (462 mg, 64%). MS (ESI, m/z): 274.5 (M+H⁺).

b) 2,2-dimethyl-1-(5-methyl-1,3,4-oxadiazol-2-yl)propan-1-amine

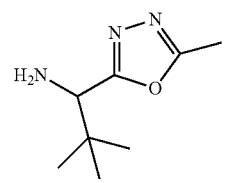

To a solution of N-[2,2-dimethyl-1-(5-methyl-1,3,4-oxadiazol-2-yl)propyl]-2-methyl-propane-2-sulfinamide (example 174a, 462 mg, 1.69 mmol) in methanol (10 ml) was added a 4M solution of hydrochloric acid in dioxane (845 µl, 3.38 mmol). The reaction was stirred for 1 hour at room temperature. The reaction was then concentrated in vacuo and the residue was dissolved in ethylacetate. The organic phase was extracted with a 2M aqueous solution of sodium carbonate. The organic phase was collected and the aqueous phase was back-extracted with ethylacetate. Combined organic phases were dried over sodium sulfate and evaporated down to dryness. The crude material was purified by flash chromatography on silica eluting with a dichloromethane/methanol gradient to yield the title compound (165 mg, 58%). MS (ESI, m/z): 170.5 (M+H⁺).

c) 5-cyclopropyl-N-[2,2-dimethyl-1-(5-methyl-1,3,4-oxadiazol-2-yl)propyl]-4-(2,2,2-trifluoroethoxy)pyridine-2-carboxamide

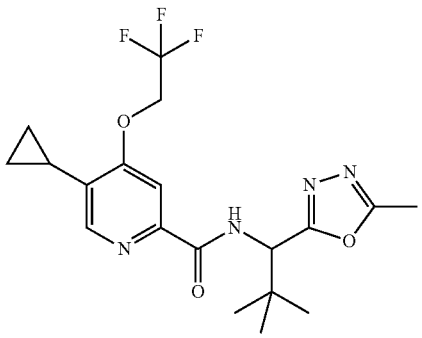 [SMILES: Cc1nnc(C(NC(=O)c2cc(OCC(F)(F)F)c(C3CC3)cn2)C(C)(C)C)o1]

The title compound was synthesized in analogy to Example 112e, using 5-Cyclopropyl-4-(2,2,2-trifluoroethoxy)-pyridine-2-carboxylic acid (Example 48c) and 2,2-dimethyl-1-(5-methyl-1,3,4-oxadiazol-2-yl)propan-1-amine (example 174b) as starting materials and isolated (128 mg, 81%); MS (ESI, m/z): 413.6 (M+H$^+$).

Example 175

N-[2,2-dimethyl-1-(5-methyl-1,3,4-oxadiazol-2-yl)propyl]-5-(3-fluorooxetan-3-yl)-4-[(2S)-1,1,1-trifluoropropan-2-yl]oxypyridine-2-carboxamide

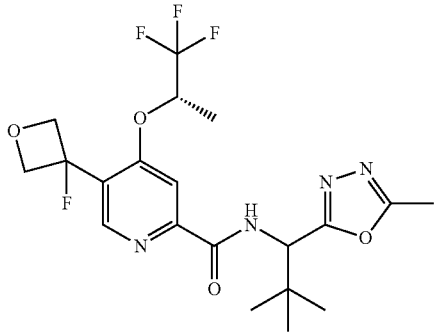 [SMILES: Cc1nnc(C(NC(=O)c2cc(O[C@@H](C)C(F)(F)F)c(C3(F)COC3)cn2)C(C)(C)C)o1]

The title compound was synthesized in analogy to Example 112e, using 5-(3-fluorooxetan-3-yl)-4-[(1S)-2,2,2-trifluoro-1-methyl-ethoxy]pyridine-2-carboxylic acid (example 142b) and 2,2-dimethyl-1-(5-methyl-1,3,4-oxadiazol-2-yl)propan-1-amine (example 174b) as starting materials and isolated (70 mg, 47%); MS (ESI, m/z): 461.5 (M+H$^+$).

Example 176

N-[1-cyclopropyl-2-(5-methyl-1,3,4-oxadiazol-2-yl)propan-2-yl]-5-(3-fluorooxetan-3-yl)-4-[(2S)-1,1,1-trifluoropropan-2-yl]oxypyridine-2-carboxamide

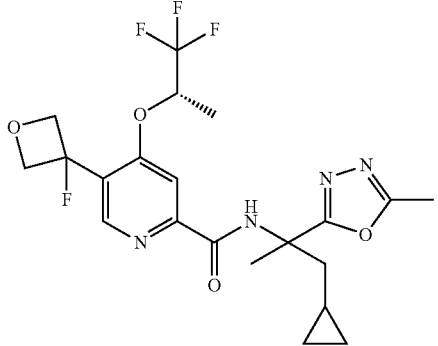 [SMILES: Cc1nnc(C(C)(CC2CC2)NC(=O)c2cc(O[C@@H](C)C(F)(F)F)c(C3(F)COC3)cn2)o1]

The title compound was synthesized in analogy to Example 112e, using 5-(3-fluorooxetan-3-yl)-4-[(1S)-2,2,2-trifluoro-1-methyl-ethoxy]pyridine-2-carboxylic acid (example 142b) and 1-cyclopropyl-2-(5-methyl-1,3,4-oxadiazol-2-yl)propan-2-amine (example 173b) as starting materials and isolated (70 mg, 46%); MS (ESI, m/z): 473.5 (M+H$^+$).

Example 177

5-cyclopropyl-N-[1-cyclopropyl-2-(5-methyl-1,3-thiazol-2-yl)propan-2-yl]-4-(2,2,2-trifluoroethoxy)pyridine-2-carboxamide

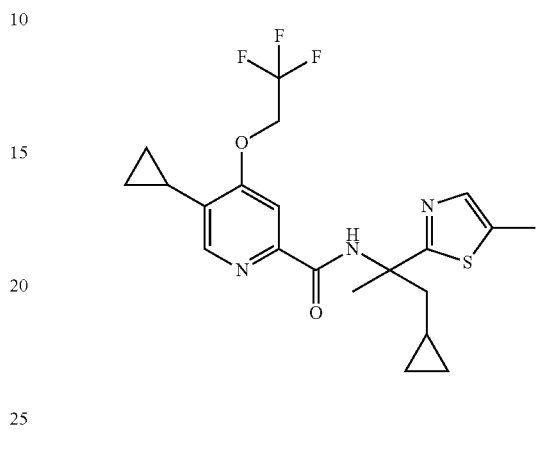

a) N-[2-cyclopropyl-1-methyl-1-(5-methylthiazol-2-yl)ethyl]-2-methyl-propane-2-sulfinamide

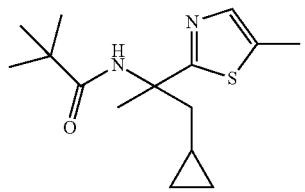 [SMILES: Cc1cnc(C(C)(CC2CC2)NC(=O)C(C)(C)C)s1]

A 2.0M solution of lithium diisopropylamide in THF (745 µl, 1.49 mmol) was added dropwise to a solution of 5-methylthiazole (148 mg, 1.49 mmol) in dry THF (0.5 ml) cooled to −78° C. and once the addition was complete the reaction was stirred for 30 minutes at −78° C. followed by addition of dry toluene (1.5 ml). To a solution of (NE)-N-(2-cyclopropyl-1-methyl-ethylidene)-2-methyl-propane-2-sulfinamide (CAN 1426426-70-1, 150 mg, 745 µmol) in dry toluene (1.5 mL) was added a 2.0M solution of trimethylaluminum in heptane (410 µl, 820 µmol). The previous solution was then added to the reaction mixture cooled at −78° C. The reaction was allowed to warm up to room temperature overnight. The reaction was quenched by the addition of a saturated aqueous solution of ammonium chloride and was then diluted with ethyl acetate. The bi-phasic mixture was poured into a separatory funnel and extracted. The organic phase was collected, dried over sodium sulfate and evaporated down to dryness. The crude material was purified by flash chromatography on silica eluting with a heptane/ethyl acetate gradient to yield the title compound (123 mg, 55%). MS (ESI, m/z): 301.4 (M+H$^+$).

b) 5-cyclopropyl-N-[1-cyclopropyl-2-(5-methyl-1,3-thiazol-2-yl)propan-2-yl]-4-(2,2,2-trifluoroethoxy)pyridine-2-carboxamide

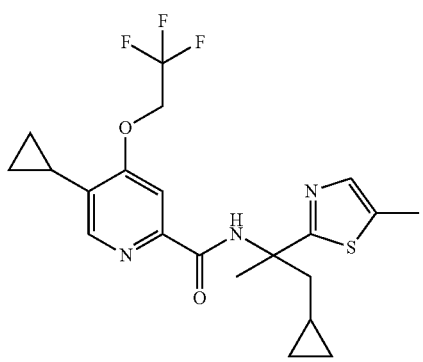 [SMILES: Cc1cnc(C(C)(CC2CC2)NC(=O)c2cc(OCC(F)(F)F)c(C3CC3)cn2)s1]

To a solution of N-[2-cyclopropyl-1-methyl-1-(5-methylthiazol-2-yl)ethyl]-2-methyl-propane-2-sulfinamide (example 177a, 118 mg, 0.393 mmole) in dioxane (2 ml) was added a 4M solution of hydrochloric acid in dioxane (2 ml, 4.0 mmol). The reaction mixture was then stirred at room temperature for 30 minutes. The reaction mixture was diluted with ethyl acetate and the organic phase was extracted with a 2M aqueous solution of sodium carbonate. The organic phase was dried over sodium sulfate and evaporated down to dryness to yield a crude amine product which was used without any purification for the synthesis of the title compound in analogy to Example 112e, using 5-Cyclopropyl-4-(2,2,2-trifluoro-ethoxy)-pyridine-2-carboxylic acid (Example 48c) as starting materials. The title compound was isolated (73 mg, 42%) by preparative HPLC purification; MS (ESI, m/z): 440.5 (M+H$^+$).

Example 178

5-cyclopropyl-N-[2,2-dimethyl-1-(5-methyl-1,3,4-oxadiazol-2-yl)propyl]-4-(2,2,2-trifluoroethoxy)pyridine-2-carboxamide (enantiomer A)

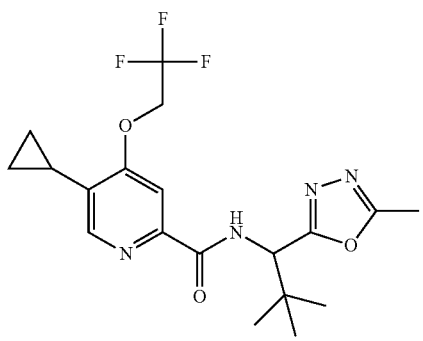 [SMILES: Cc1nnc(C(NC(=O)c2cc(OCC(F)(F)F)c(C3CC3)cn2)C(C)(C)C)o1]

The racemate (Example 174c) was separated into its enantiomers by preparative chiral HPLC (Chiralpak AD, isopropanol/heptane) and the title compound was the first enantiomer collected and isolated as colorless oil; MS (ESI, m/z): 413.6 (M+H$^+$).

Example 179

5-cyclopropyl-N-[2,2-dimethyl-1-(5-methyl-1,3,4-oxadiazol-2-yl)propyl]-4-(2,2,2-trifluoroethoxy)pyridine-2-carboxamide (enantiomer B)

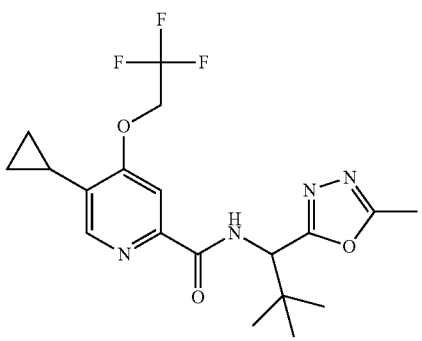 [SMILES: Cc1nnc(C(NC(=O)c2cc(OCC(F)(F)F)c(C3CC3)cn2)C(C)(C)C)o1]

The racemate (Example 174c) was separated into its enantiomers by preparative chiral HPLC (Chiralpak AD, isopropanol/heptane) and the title compound was the second enantiomer collected and isolated as colorless oil; MS (ESI, m/z): 413.6 (M+H$^+$).

Example 180

N-[1-amino-2-(5-methyl-1,2,4-oxadiazol-3-yl)-1-oxopropan-2-yl]-5-cyclopropyl-4-(2,2,2-trifluoroethoxy)pyridine-2-carboxamide

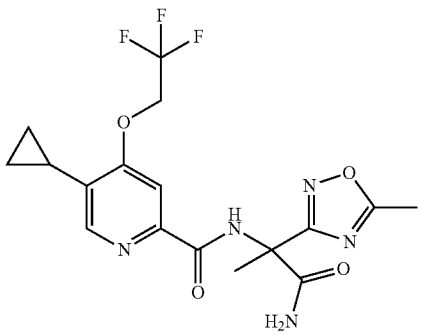 [SMILES: Cc1nc(C(C)(NC(=O)c2cc(OCC(F)(F)F)c(C3CC3)cn2)C(N)=O)no1]

A solution of ethyl 2-[[5-cyclopropyl-4-(2,2,2-trifluoroethoxy)pyridine-2-carbonyl]amino]-2-(5-methyl-1,2,4-oxadiazol-3-yl)propanoate (example 147b, 0.05 g, 113 µmol) in ammonia 7N in MeOH (1.00 ml, 7.01 mmol) was stirred at room temperature overnight. Volatiles were removed in vacuo and the crude material was purified by preparative HPLC without any work-up protocol to yield the title compound (32 mg, 69%). MS (ESI, m/z): 414.5 (M+H⁺).

Example 181

5-cyclopropyl-N-[1-(dimethylamino)-2-(5-methyl-1,2,4-oxadiazol-3-yl)-1-oxopropan-2-yl]-4-(2,2,2-trifluoroethoxy)pyridine-2-carboxamide

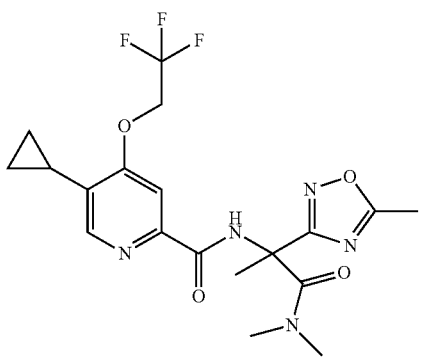 [SMILES: Cc1nc(C(C)(NC(=O)c2cc(OCC(F)(F)F)c(C3CC3)cn2)C(=O)N(C)C)no1]

The title compound was synthesized in analogy to Example 112e, using 2-[[5-cyclopropyl-4-(2,2,2-trifluoroethoxy)pyridine-2-carbonyl]amino]-2-(5-methyl-1,2,4-oxadiazol-3-yl)propanoic acid (example 147c) and dimethylamine hydrochloride as starting materials and isolated (23 mg, 51%); MS (ESI, m/z): 442.5 (M+H⁺).

Example 182

N-[1-(azetidin-1-yl)-2-(5-methyl-1,2,4-oxadiazol-3-yl)-1-oxopropan-2-yl]-5-cyclopropyl-4-(2,2,2-trifluoroethoxy)pyridine-2-carboxamide

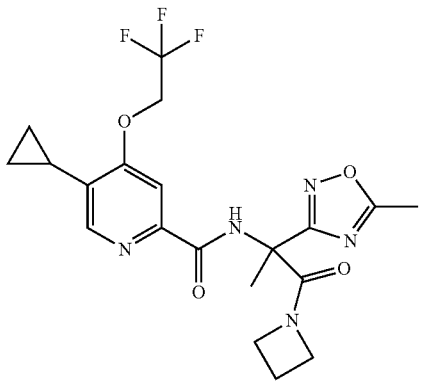 [SMILES: Cc1nc(C(C)(NC(=O)c2cc(OCC(F)(F)F)c(C3CC3)cn2)C(=O)N2CCC2)no1]

The title compound was synthesized in analogy to Example 112e, using 2-[[5-cyclopropyl-4-(2,2,2-trifluoroethoxy)pyridine-2-carbonyl]amino]-2-(5-methyl-1,2,4-oxadiazol-3-yl)propanoic acid (example 147c) and azetidine (CAN 503-29-7) as starting materials and isolated (23 mg, 51%); MS (ESI, m/z): 454.5 (M+H⁺).

Example 183

5-(3-fluorooxetan-3-yl)-N-[1-(methylamino)-2-(5-methyl-1,2,4-oxadiazol-3-yl)-1-oxopropan-2-yl]-4-[(2S)-1,1,1-trifluoropropan-2-yl]oxypyridine-2-carboxamide

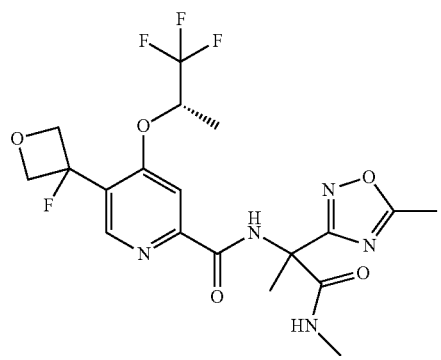 [SMILES: CNC(=O)C(C)(NC(=O)c1cc(O[C@@H](C)C(F)(F)F)c(C2(F)COC2)cn1)c1noc(C)n1]

a) ethyl 2-[[5-(3-fluorooxetan-3-yl)-4-[(1S)-2,2,2-trifluoro-1-methyl-ethoxy]pyridine-2-carbonyl]amino]-2-(5-methyl-1,2,4-oxadiazol-3-yl)propanoate The title compound was synthesized in analogy to Example 112e, using 5-(3-fluorooxetan-3-yl)-4-[(1S)-2,2,2-trifluoro-1-methyl-ethoxy]pyridine-2-carboxylic acid (example 142b) and ethyl 2-amino-2-(5-methyl-1,2,4-oxadiazol-3-yl)propanoate (example 147a) as starting materials and isolated (283 mg, purity: 86%, 57%); MS (ESI, m/z): 491.5 (M+H⁺).

b) 2-[[5-(3-fluorooxetan-3-yl)-4-[(1S)-2,2,2-trifluoro-1-methyl-ethoxy]pyridine-2-carbonyl]amino]-2-(5-methyl-1,2,4-oxadiazol-3-yl)propanoic acid

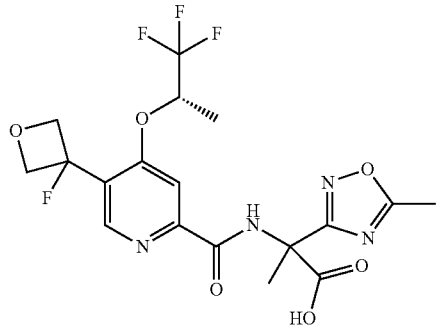 [SMILES: Cc1nc(C(C)(NC(=O)c2cc(O[C@@H](C)C(F)(F)F)c(C3(F)COC3)cn2)C(=O)O)no1]

To a solution of ethyl 2-[[5-(3-fluorooxetan-3-yl)-4-[(1S)-2,2,2-trifluoro-1-methyl-ethoxy]pyridine-2-carbonyl]amino]-2-(5-methyl-1,2,4-oxadiazol-3-yl)propanoate (example 183a, 150 mg, 306 µmol) in a mixture of THF (2 ml)/water (1 ml) was added LiOH monohydrate (25.7 mg, 612 µmol). The reaction mixture was sonicated to dissolve the solids. The reaction was stirred at room temperature overnight. The reaction mixture was diluted with ethyl acetate and extracted with 1 mL of an aqueous solution 2M trifluoroacetic acid. The organic phase was collected and the aqueous phase was back-extracted with ethyl acetate. Combined organic phases were dried over sodium sulfate and evaporated down to dryness. The crude material was dissolved in toluene and evaporated down to dryness to yield to yield the title compound (180 mg, 100%) as a crude solid which was used without any purification. MS (ESI, m/z): 463.5 (M+H⁺).

c) 5-(3-fluorooxetan-3-yl)-N-[1-(methylamino)-2-(5-methyl-1,2,4-oxadiazol-3-yl)-1-oxopropan-2-yl]-4-[(2S)-1,1,1-trifluoropropan-2-yl]oxypyridine-2-carboxamide

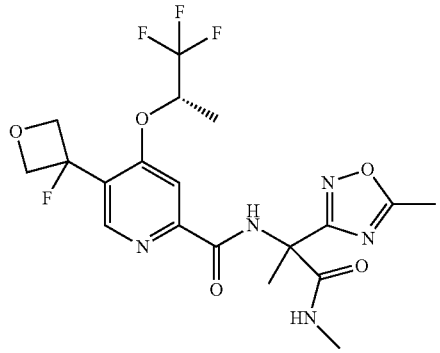 [SMILES: CNC(=O)C(C)(NC(=O)c1cc(O[C@@H](C)C(F)(F)F)c(C2(F)COC2)cn1)c1noc(C)n1]

The title compound was synthesized in analogy to Example 112e, using 2-[[5-(3-fluorooxetan-3-yl)-4-[(1S)-2,2,2-trifluoro-1-methyl-ethoxy]pyridine-2-carbonyl]amino]-2-(5-methyl-1,2,4-oxadiazol-3-yl)propanoic acid (example 183b) and methamine hydrochloride as starting materials and isolated (42 mg, 57%); MS (ESI, m/z): 476.5 (M+H⁺).

Example 184

5-cyclopropyl-N-[1-cyclopropyl-2-(5-methyl-1,3,4-oxadiazol-2-yl)propan-2-yl]-4-(2,2,2-trifluoroethoxy)pyridine-2-carboxamide (enantiomer A)

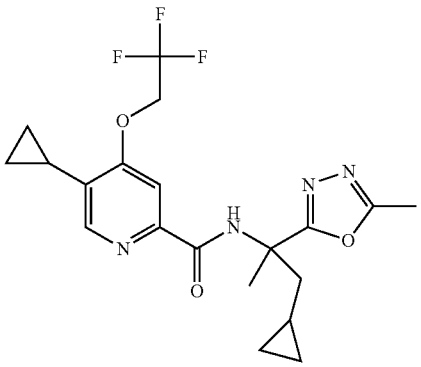 [SMILES: Cc1nnc(C(C)(CC2CC2)NC(=O)c2cc(OCC(F)(F)F)c(C3CC3)cn2)o1]

The racemate (Example 173c) was separated into its enantiomers by preparative chiral HPLC (Chiralpak AD, isopropanol/heptane) and the title compound was the first enantiomer collected and isolated as colorless oil; MS (ESI, m/z): 425.6 (M+H⁺).

Example 185

5-cyclopropyl-N-[1-cyclopropyl-2-(5-methyl-1,3,4-oxadiazol-2-yl)propan-2-yl]-4-(2,2,2-trifluoroethoxy)pyridine-2-carboxamide (enantiomer B)

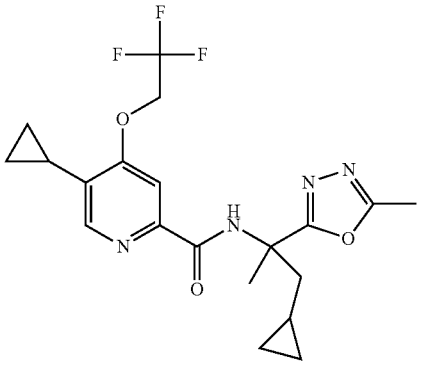 [SMILES: Cc1nnc(C(C)(CC2CC2)NC(=O)c2cc(OCC(F)(F)F)c(C3CC3)cn2)o1]

The racemate (Example 173c) was separated into its enantiomers by preparative chiral HPLC (Chiralpak AD, isopropanol/heptane) and the title compound was the second enantiomer collected and isolated as colorless oil; MS (ESI, m/z): 425.6 (M+H⁺).

Example 186

N-(1-amino-3-cyclopropyl-2-methyl-1-oxopropan-2-yl)-5-cyclopropyl-4-(2,2,2-trifluoroethoxy)pyridine-2-carboxamide

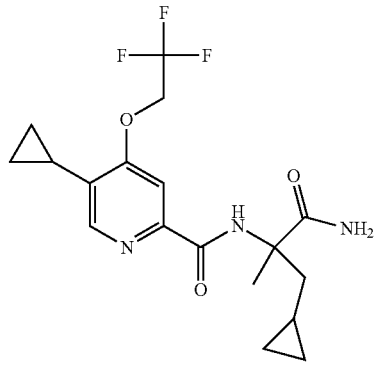 [SMILES: CC(CC1CC1)(NC(=O)c1cc(OCC(F)(F)F)c(C2CC2)cn1)C(N)=O]

a) tert-butyl 2-[(E)-(4-chlorophenyl)methyleneamino]-3-cyclopropyl-2-methyl-propanoate

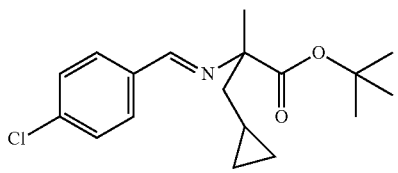 [SMILES: CC(C)(C)OC(=O)C(C)(CC1CC1)/N=C/c1ccc(Cl)cc1]

To a round-bottomed flask (100 ml) under an argon atmosphere was added tert-butyl 2-[(E)-(4-chlorophenyl)methyleneamino]propanoate (CAN 208927-33-7, 1.6 g, 5.97 mmole), 1-bromomethyl cyclopropane (CAN 7051-34-5, 4.5 ml, 51.43 mmole), and tetrabutyl ammonium chloride (0.166 g, 0.6 mmole). A mixture of potassium hydroxide (1.67 g, 29.85 mmole)/potassium carbonate (4.12 g, 29.85 mmole) was finely grained using a mortar and was added to the reaction mixture. The resulting mixture was stirred vigorously at room temperature for 24 h. Dichloromethane was added and the reaction mixture was filtered to remove insolubles. The solids were washed twice with 40 ml dichloromethane and the filtrate was evaporated to dryness on a rotary evaporator. The residue was taken up in ether (80 ml) and the organic solution was washed twice with 80 ml water. The organic phase was dried over sodium sulfate and evaporated in vacuo to yield the title compound (2.08 g) as a crude yellow oil which was used without any purification; MS (ESI, m/z): 322.3 (M+H$^+$).

b) tert-butyl 2-amino-3-cyclopropyl-2-methyl-propanoate

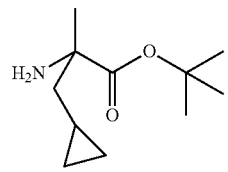

In a 250 mL round-bottomed flask, tert-butyl 2-[(E)-(4-chlorophenyl)methyleneamino]-3-cyclopropyl-2-methyl-propanoate (example 186a, 1.7 g, 5.28 mmol) and citric acid (1.8 g, 9.37 mmol) were combined with THF (30 ml) and water (5 ml) to give a yellow solution. The reaction mixture was stirred at room temperature for 20 h. The reaction mixture was poured into 200 mL ethyl acetate and extracted with an iced 1 M aqueous solution of sodium hydroxide and brine. The aqueous layer was back-extracted with ethyl acetate. The combined organic layers were dried over sodium sulfate and evaporated down to dryness. The crude material was purified by flash chromatography on silica eluting with a heptane/ethyl acetate gradient to yield the title compound (452 mg, 43%). MS (ESI, m/z): 200.1 (M+H$^+$).

c) tert-butyl 3-cyclopropyl-2-[[5-cyclopropyl-4-(2,2,2-trifluoroethoxy)pyridine-2-carbonyl]amino]-2-methyl-propanoate

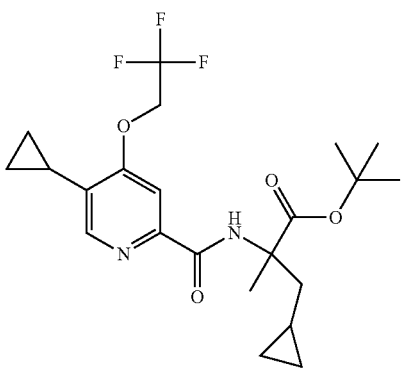 [SMILES: CC(C)(C)OC(=O)C(C)(CC1CC1)NC(=O)c1cc(OCC(F)(F)F)c(C2CC2)cn1]

The title compound was synthesized in analogy to Example 112e, using 5-Cyclopropyl-4-(2,2,2-trifluoroethoxy)-pyridine-2-carboxylic acid (Example 48c) and tert-butyl 2-amino-3-cyclopropyl-2-methyl-propanoate (example 186b) as starting materials and isolated (105 mg, 31%); MS (ESI, m/z): 443.6 (M+H⁺).

d) 3-cyclopropyl-2-[[5-cyclopropyl-4-(2,2,2-trifluoroethoxy)pyridine-2-carbonyl]amino]-2-methyl-propanoic acid

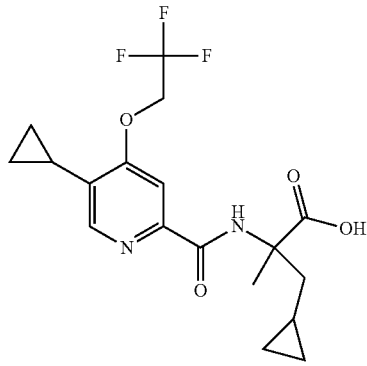 [SMILES: CC(CC1CC1)(NC(=O)c1cc(OCC(F)(F)F)c(C2CC2)cn1)C(=O)O]

To a solution of tert-butyl 3-cyclopropyl-2-[[5-cyclopropyl-4-(2,2,2-trifluoroethoxy)pyridine-2-carbonyl]amino]-2-methyl-propanoate (example 186c, 103 mg, 233 μmol) in dichloromethane (0.5 ml) was added TFA (159 mg, 108 μl, 1.4 mmol). The reaction mixture was stirred at room temperature for 14 hours. Volatiles were removed in vacuo and the residue was dissolved in a mixture of dichlormethane and toluene followed by evaporation to dryness. The procedure was repeated twice until a precipitate formed. The precipitate was dried under high vacuum to yield the title compound (95 mg) as a crude solid which was used without any purification. MS (ESI, m/z): 387.5 (M+H⁺).

e) N-(1-amino-3-cyclopropyl-2-methyl-1-oxopropan-2-yl)-5-cyclopropyl-4-(2,2,2-trifluoroethoxy)pyridine-2-carboxamide

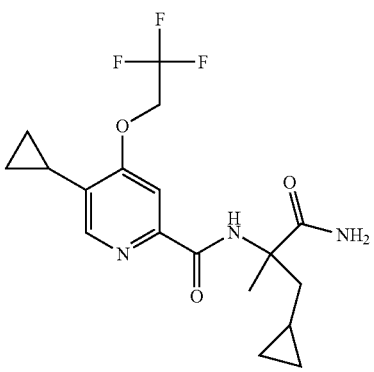 [SMILES: CC(CC1CC1)(NC(=O)c1cc(OCC(F)(F)F)c(C2CC2)cn1)C(N)=O]

The title compound was synthesized in analogy to Example 112e, using 3-cyclopropyl-2-[[5-cyclopropyl-4-(2,2,2-trifluoroethoxy)pyridine-2-carbonyl]amino]-2-methyl-propanoic acid (example 186d) and ammonium chloride as starting materials and isolated (16 mg, 32%); MS (ESI, m/z): 386.6 (M+H⁺).

Example 187

5-cyclopropyl-N-[1-(methylamino)-2-(5-methyl-1,2,4-oxadiazol-3-yl)-1-oxopropan-2-yl]-4-(2,2,2-trifluoroethoxy)pyridine-2-carboxamide (enantiomer A)

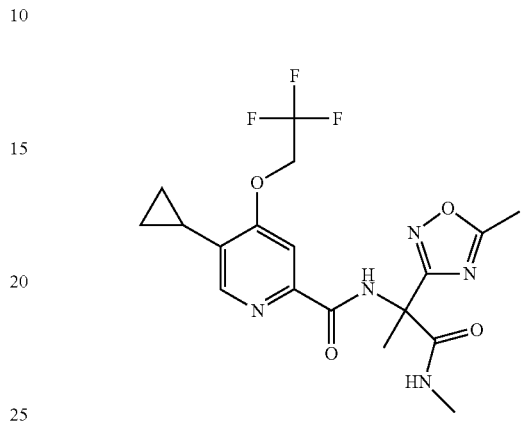

The racemate (Example 149) was separated into its enantiomers by preparative chiral HPLC (Chiralpak AD, ethanol/heptane) and the title compound was the first enantiomer collected and isolated as colorless oil; MS (ESI, m/z): 428.6 (M+H⁺).

Example 188

5-cyclopropyl-N-[1-(methylamino)-2-(5-methyl-1,2,4-oxadiazol-3-yl)-1-oxopropan-2-yl]-4-(2,2,2-trifluoroethoxy)pyridine-2-carboxamide (enantiomer B)

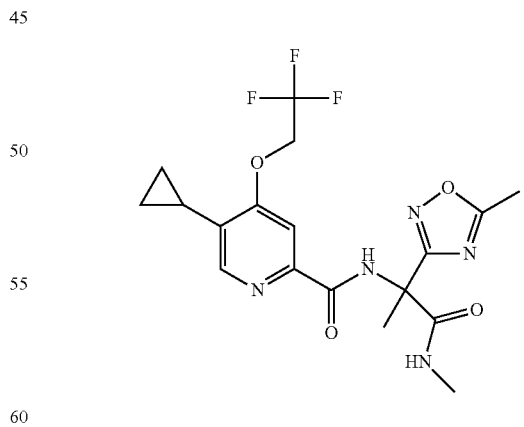

The racemate (Example 149) was separated into its enantiomers by preparative chiral HPLC (Chiralpak AD, ethanol/heptane) and the title compound was the second enantiomer collected and isolated as colorless oil; MS (ESI, m/z): 428.6 (M+H⁺).

Example 189

5-cyclopropyl-N-[3-cyclopropyl-2-methyl-1-(methylamino)-1-oxopropan-2-yl]-4-(2,2,2-trifluoroethoxy)pyridine-2-carboxamide

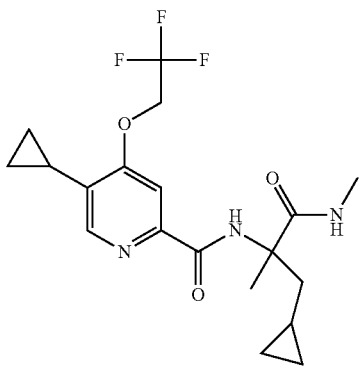 [SMILES: CNC(=O)C(C)(CC1CC1)NC(=O)c1cc(OCC(F)(F)F)c(C2CC2)cn1]

The title compound was synthesized in analogy to Example 112e, using 3-cyclopropyl-2-[[5-cyclopropyl-4-(2,2,2-trifluoroethoxy)pyridine-2-carbonyl]amino]-2-methylpropanoic acid (example 186d) and methamine hydrochloride as starting materials and isolated (18 mg, 35%); MS (ESI, m/z): 400.6 (M+H$^+$).

Example 190

5-cyclopropyl-N-[2-(5-methyl-1,3,4-oxadiazol-2-yl)-1-(oxetan-3-yl)propan-2-yl]-4-[(2S)-1,1,1-trifluoropropan-2-yl]oxypyridine-2-carboxamide

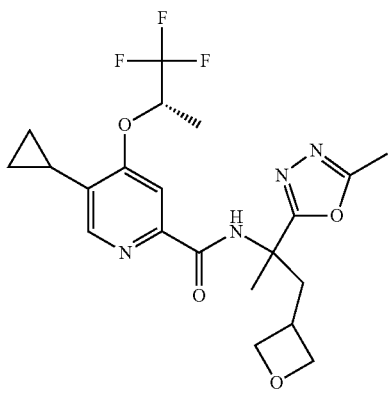 [SMILES: Cc1nnc(C(C)(CC2COC2)NC(=O)c2cc(O[C@@H](C)C(F)(F)F)c(C3CC3)cn2)o1]

a) (NE)-2-methyl-N-[1-methyl-2-(oxetan-3-yl)ethylidene]propane-2-sulfinamide

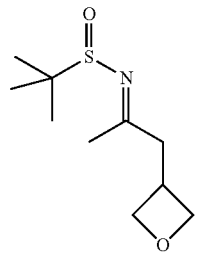

The title compound was synthesized in analogy to Example 112a, using 1-Oxetan-3-yl-propan-2-one (CAN 1207175-39-0) as starting material and isolated (860 mg, 57%); MS (ESI, m/z): 218.5 (M+H$^+$).

b) 2-methyl-N-[1-methyl-1-(5-methyl-1,3,4-oxadiazol-2-yl)-2-(oxetan-3-yl)ethyl]propane-2-sulfinamide

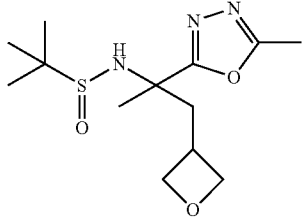 [SMILES: Cc1nnc(C(C)(CC2COC2)NS(=O)C(C)(C)C)o1]

The title compound was synthesized in analogy to Example 173a, using (NE)-2-methyl-N-[1-methyl-2-(oxetan-3-yl)ethylidene]propane-2-sulfinamide (example 190a) as starting material and isolated (246 mg, 36%); MS (ESI, m/z): 302.5 (M+H$^+$).

c) 2-(5-methyl-1,3,4-oxadiazol-2-yl)-1-(oxetan-3-yl)propan-2-amine

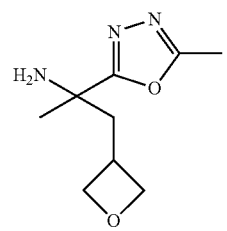

To a solution of 2-methyl-N-[1-methyl-1-(5-methyl-1,3,4-oxadiazol-2-yl)-2-(oxetan-3-yl)ethyl]propane-2-sulfinamide (example 190c, 250 mg, 829 µmol) in methanol (8 ml) was added a 4M solution of hydrochloric acid in dioxane (415 µl, 1.66 mmol). The reaction mixture was stirred at room temperature for 1 hour. The reaction mixture was diluted with ethyl acetate and extracted with a 2M aqueous solution of sodium carbonate. The organic phase was collected and the aqueous phase was back-extracted twice with ethylacetate. Combined organic phases were dried over sodium sulfate and evaporated down to dryness to yield the title compound (168 mg) as a crude oil which was used without any purification. MS (ESI, m/z): 198.3 (M+H$^+$).

d) 5-cyclopropyl-N-[2-(5-methyl-1,3,4-oxadiazol-2-yl)-1-(oxetan-3-yl)propan-2-yl]-4-[(2S)-1,1,1-trifluoropropan-2-yl]oxypyridine-2-carboxamide

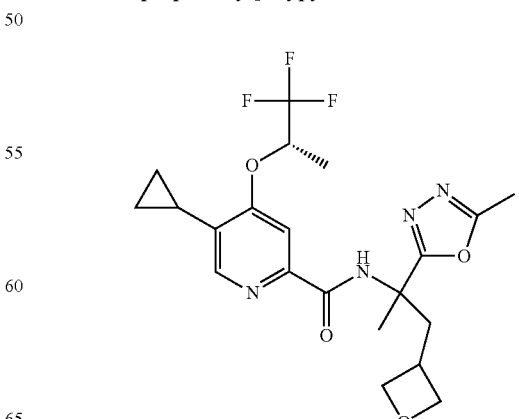

The title compound was synthesized in analogy to Example 112e, using 5-Cyclopropyl-4-((S)-2,2,2-trifluoro-1-methyl-ethoxy)-pyridine-2-carboxylic acid (Example 68a) and 2-(5-methyl-1,3,4-oxadiazol-2-yl)-1-(oxetan-3-yl)propan-2-amine (example 190c) as starting materials and isolated (36 mg, 22%); MS (ESI, m/z): 441.5 (M+H⁺).

Example 191

5-cyclopropyl-N-[2-(5-methyl-1,3,4-oxadiazol-2-yl)-1-(oxetan-3-yl)propan-2-yl]-4-(2,2,2-trifluoroethoxy)pyridine-2-carboxamide

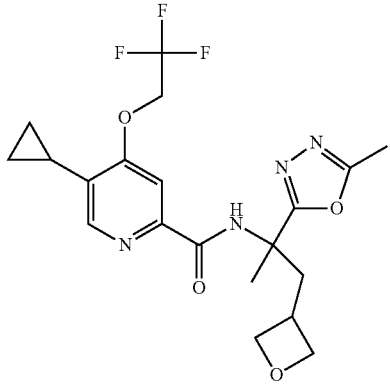 [SMILES: Cc1nnc(C(C)(CC2COC2)NC(=O)c2cc(OCC(F)(F)F)c(C3CC3)cn2)o1]

The title compound was synthesized in analogy to Example 112e, using 5-Cyclopropyl-4-(2,2,2-trifluoroethoxy)-pyridine-2-carboxylic acid (Example 48c) and 2-(5-methyl-1,3,4-oxadiazol-2-yl)-1-(oxetan-3-yl)propan-2-amine (example 190c) as starting materials and isolated (35 mg, 21%); MS (ESI, m/z): 441.5 (M+H⁺).

Example 192

N-[1-(5-amino-1,2,4-oxadiazol-3-yl)-2,2-dimethyl-propyl]-5-cyclopropyl-4-(2,2,2-trifluoroethoxy)pyridine-2-carboxamide

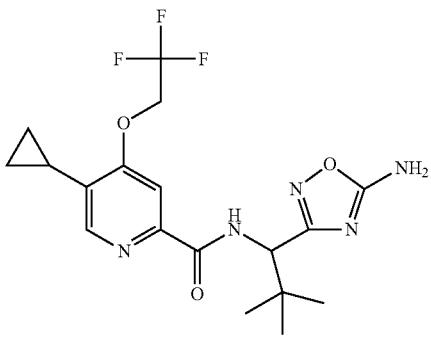 [SMILES: CC(C)(C)C(NC(=O)c1cc(OCC(F)(F)F)c(C2CC2)cn1)c1noc(N)n1]

The title compound was synthesized in analogy to Example 165b, using 5-cyclopropyl-N-[1-[(Z)—N'-hydroxycarbamimidoyl]-2,2-dimethyl-propyl]-4-(2,2,2-trifluoroethoxy)pyridine-2-carboxamide (Example 161b) as starting material and isolated (17 mg, 19%); MS (ESI, m/z): 414.5 (M+H⁺).

Example 193

N-(3-amino-1-cyclopropyl-3-oxopropyl)-5-cyclopropyl-4-(2,2,2-trifluoroethoxy)pyridine-2-carboxamide

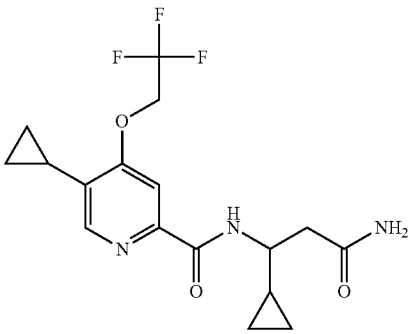 [SMILES: NC(=O)CC(NC(=O)c1cc(OCC(F)(F)F)c(C2CC2)cn1)C1CC1]

The title compound was synthesized in analogy to Example 112e, using 5-Cyclopropyl-4-(2,2,2-trifluoroethoxy)-pyridine-2-carboxylic acid (Example 48c) and 3-amino-3-cyclopropylpropanamide hydrochloride (CAN 1354953-76-6) as starting materials and isolated (50 mg, 35%); MS (ESI, m/z): 372.5 (M+H⁺).

Example 194

N-(1-amino-3,3-dimethyl-1-oxobutan-2-yl)-5-cyclopropyl-4-(2,2,2-trifluoroethoxy)pyridine-2-carboxamide

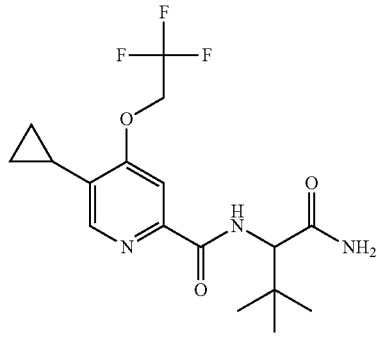 [SMILES: CC(C)(C)C(NC(=O)c1cc(OCC(F)(F)F)c(C2CC2)cn1)C(N)=O]

a) tert-butyl 2-[[5-cyclopropyl-4-(2,2,2-trifluoroethoxy)pyridine-2-carbonyl]amino]-3,3-dimethyl-butanoate

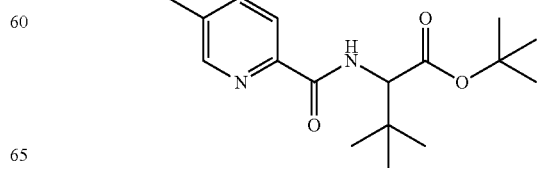

The title compound was synthesized in analogy to Example 112e, using 5-Cyclopropyl-4-(2,2,2-trifluoroethoxy)-pyridine-2-carboxylic acid (Example 48c) and 2-Amino-3,3-dimethyl-butyric acid tert-butyl ester (CAN 99285-38-8) as starting materials and isolated (490 mg, 92%); MS (ESI, m/z): 431.6 (M+H⁺).

b) 2-[[5-cyclopropyl-4-(2,2,2-trifluoroethoxy)pyridine-2-carbonyl]amino]-3,3-dimethyl-butanoic acid

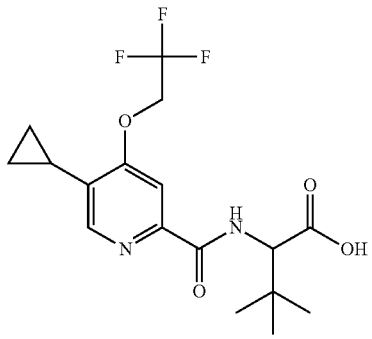 [SMILES: CC(C)(C)C(NC(=O)c1cc(OCC(F)(F)F)c(C2CC2)cn1)C(=O)O]

To a solution of tert-butyl 2-[[5-cyclopropyl-4-(2,2,2-trifluoroethoxy)pyridine-2-carbonyl]amino]-3,3-dimethyl-butanoate (example 194a, 0.47 g, 1.09 mmol) in dichloromethane (3 ml) was added trifluoroacetic acid (3.73 g, 2.52 ml, 32.8 mmol) and the reaction mixture was stirred at room temperature for 14 hours. Volatiles were removed in vacuo and the residue was dissolved in toluene followed by evaporation to dryness. The procedure was repeated twice to yield the title compound (432 mg) as a crude solid which was used without any purification. MS (ESI, m/z): 373.5 (M−H⁺).

c) N-(1-amino-3,3-dimethyl-1-oxobutan-2-yl)-5-cyclopropyl-4-(2,2,2-trifluoroethoxy)pyridine-2-carboxamide

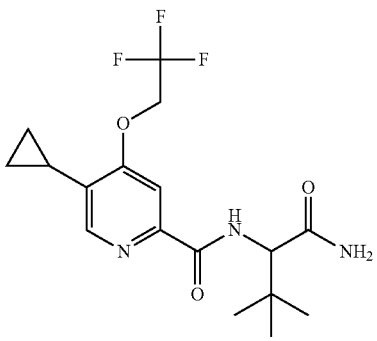 [SMILES: CC(C)(C)C(NC(=O)c1cc(OCC(F)(F)F)c(C2CC2)cn1)C(N)=O]

The title compound was synthesized in analogy to Example 112e, using 2-[[5-cyclopropyl-4-(2,2,2-trifluoroethoxy)pyridine-2-carbonyl]amino]-3,3-dimethyl-butanoic acid (Example 194b) and ammonium chloride as starting materials and isolated (490 mg, 92%); MS (ESI, m/z): 374.5 (M+H⁺).

Example 195

5-cyclopropyl-N-[1-(dimethylamino)-3,3-dimethyl-1-oxobutan-2-yl]-4-(2,2,2-trifluoroethoxy)pyridine-2-carboxamide

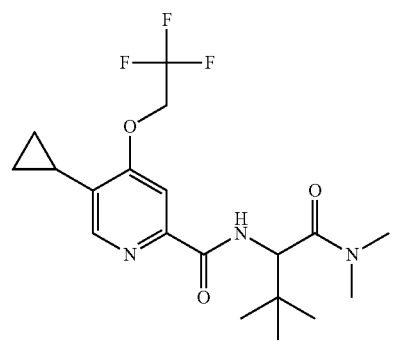 [SMILES: CN(C)C(=O)C(NC(=O)c1cc(OCC(F)(F)F)c(C2CC2)cn1)C(C)(C)C]

The title compound was synthesized in analogy to Example 112e, using 2-[[5-cyclopropyl-4-(2,2,2-trifluoroethoxy)pyridine-2-carbonyl]amino]-3,3-dimethyl-butanoic acid (Example 194b) and dimethylamine hydrochloride as starting materials and isolated (24 mg, 46%); MS (ESI, m/z): 402.6 (M+H⁺).

Example 196

N-[1-(azetidin-1-yl)-3,3-dimethyl-1-oxobutan-2-yl]-5-cyclopropyl-4-(2,2,2-trifluoroethoxy)pyridine-2-carboxamide

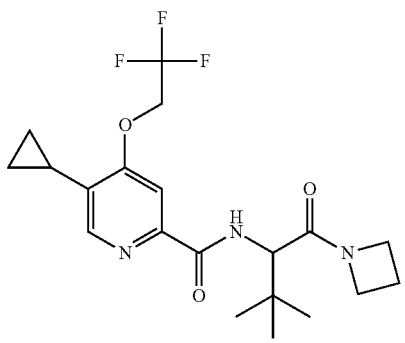 [SMILES: CC(C)(C)C(NC(=O)c1cc(OCC(F)(F)F)c(C2CC2)cn1)C(=O)N1CCC1]

The title compound was synthesized in analogy to Example 112e, using 2-[[5-cyclopropyl-4-(2,2,2-trifluoroethoxy)pyridine-2-carbonyl]amino]-3,3-dimethyl-butanoic acid (Example 194b) and azetidine (CAN 503-29-7) as starting materials and isolated (29 mg, 54%); MS (ESI, m/z): 414.6 (M+H⁺).

Example 197

5-cyclopropyl-N-[1-(3,3-difluoroazetidin-1-yl)-3,3-dimethyl-1-oxobutan-2-yl]-4-(2,2,2-trifluoroethoxy)pyridine-2-carboxamide

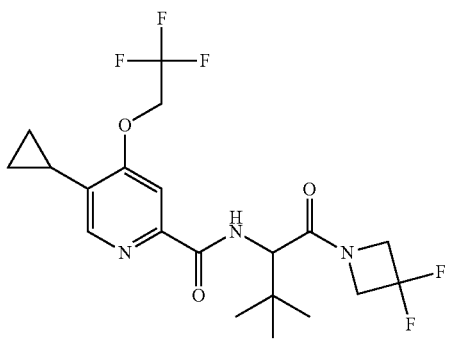 [SMILES: CC(C)(C)C(NC(=O)c1cc(OCC(F)(F)F)c(C2CC2)cn1)C(=O)N1CC(F)(F)C1]

The title compound was synthesized in analogy to Example 112e, using 2-[[5-cyclopropyl-4-(2,2,2-trifluoroethoxy)pyridine-2-carbonyl]amino]-3,3-dimethyl-butanoic acid (Example 194b) and 3,3-Difluoroazetidine hydrochloride (CAN 288315-03-7) as starting materials and isolated (31 mg, 53%); MS (ESI, m/z): 450.5 (M+H$^+$).

Example 198

5-cyclopropyl-N-[3,3-dimethyl-1-(6-oxa-1-azaspiro[3.3]heptan-1-yl)-1-oxobutan-2-yl]-4-(2,2,2-trifluoroethoxy)pyridine-2-carboxamide

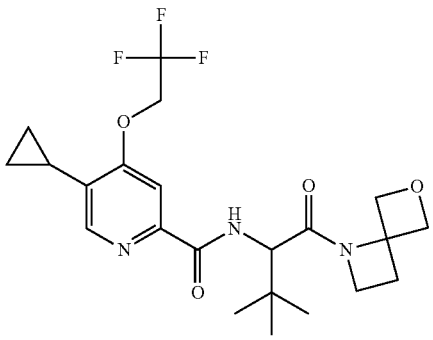 [SMILES: CC(C)(C)C(NC(=O)c1cc(OCC(F)(F)F)c(C2CC2)cn1)C(=O)N1CCC12COC2]

The title compound was synthesized in analogy to Example 112e, using 2-[[5-cyclopropyl-4-(2,2,2-trifluoroethoxy)pyridine-2-carbonyl]amino]-3,3-dimethyl-butanoic acid (Example 194b) and 6-Oxa-1-azaspiro[3.3]heptane, ethanedioate (1:2) (CAN 1380571-72-1) as starting materials and isolated (27 mg, 46%); MS (ESI, m/z): 456.6 (M+H$^+$).

Example 199

N-(1-amino-3,3-dimethyl-1-oxobutan-2-yl)-5-cyclopropyl-4-[(2S)-1,1,1-trifluoropropan-2-yl]oxypyridine-2-carboxamide

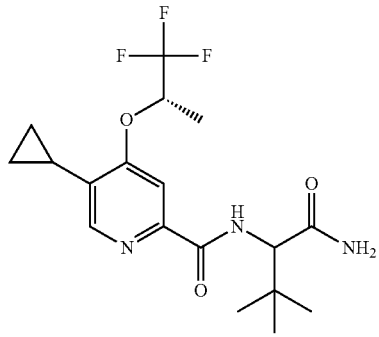 [SMILES: C[C@H](Oc1cc(C(=O)NC(C(N)=O)C(C)(C)C)ncc1C1CC1)C(F)(F)F]

a) tert-butyl 2-[[5-cyclopropyl-4-[(1S)-2,2,2-trifluoro-1-methyl-ethoxy]pyridine-2-carbonyl]amino]-3,3-dimethyl-butanoate

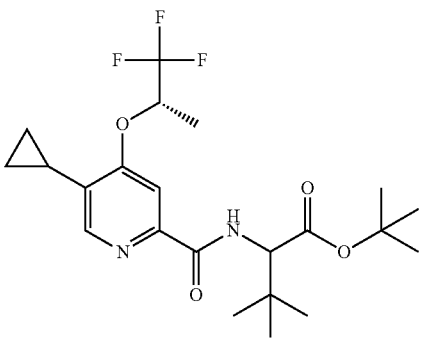 [SMILES: C[C@H](Oc1cc(C(=O)NC(C(=O)OC(C)(C)C)C(C)(C)C)ncc1C1CC1)C(F)(F)F]

The title compound was synthesized in analogy to Example 112e, using 5-Cyclopropyl-4-((S)-2,2,2-trifluoro-1-methyl-ethoxy)-pyridine-2-carboxylic acid (Example 68a) and 2-Amino-3,3-dimethyl-butyric acid tert-butyl ester (CAN 99285-38-8) as starting materials and isolated (526 mg, 87%); MS (ESI, m/z): 445.6 (M+H$^+$).

b) 2-[[5-cyclopropyl-4-[(1S)-2,2,2-trifluoro-1-methyl-ethoxy]pyridine-2-carbonyl]amino]-3,3-dimethyl-butanoic acid

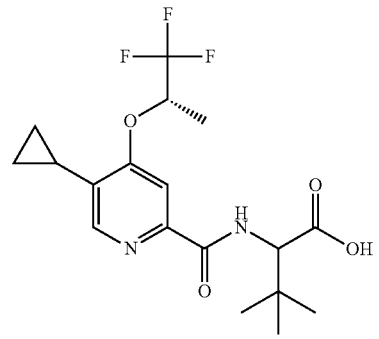

To a solution of tert-butyl 2-[[5-cyclopropyl-4-[(1S)-2,2,2-trifluoro-1-methyl-ethoxy]pyridine-2-carbonyl]amino]-3,3-dimethyl-butanoate (example 199a, 0.485 g, 1.09 mmol) in dichloromethane (3 ml) was added trifluoroacetic acid (3.73 g, 2.52 ml, 32.8 mmol) and the reaction mixture was stirred at room temperature for 14 hours. Volatiles were removed in vacuo and the residue was dissolved in toluene followed by evaporation to dryness. The procedure was repeated twice to yield the title compound (446 mg) as a crude solid which was used without any purification. MS (ESI, m/z): 387.5 (M−H⁺).

c) N-(1-amino-3,3-dimethyl-1-oxobutan-2-yl)-5-cyclopropyl-4-[(2S)-1,1,1-trifluoropropan-2-yl]oxy-pyridine-2-carboxamide

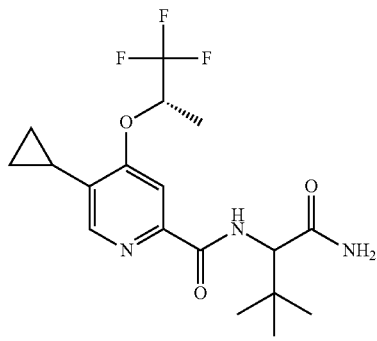 [SMILES: C[C@H](Oc1cc(C(=O)NC(C(N)=O)C(C)(C)C)ncc1C1CC1)C(F)(F)F]

The title compound was synthesized in analogy to Example 112e, using 2-[[5-cyclopropyl-4-[(1S)-2,2,2-trifluoro-1-methyl-ethoxy]pyridine-2-carbonyl]amino]-3,3-dimethyl-butanoic acid (Example 199b) and ammonium chloride as starting materials and isolated (105 mg, 88%); MS (ESI, m/z): 388.6 (M+H⁺).

Example 200

5-cyclopropyl-N-[3,3-dimethyl-1-(methylamino)-1-oxobutan-2-yl]-4-[(2S)-1,1,1-trifluoropropan-2-yl]oxypyridine-2-carboxamide

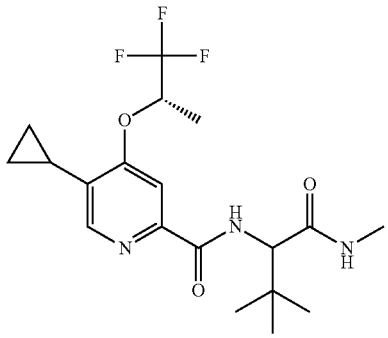 [SMILES: CNC(=O)C(NC(=O)c1cc(O[C@@H](C)C(F)(F)F)c(C2CC2)cn1)C(C)(C)C]

The title compound was synthesized in analogy to Example 112e, using 2-[[5-cyclopropyl-4-[(1S)-2,2,2-trifluoro-1-methyl-ethoxy]pyridine-2-carbonyl]amino]-3,3-dimethyl-butanoic acid (Example 199b) and methanamine hydrochloride as starting materials and isolated (28 mg, 54%); MS (ESI, m/z): 402.6 (M+H⁺).

Example 201

5-cyclopropyl-N-[1-(dimethylamino)-3,3-dimethyl-1-oxobutan-2-yl]-4-[(2S)-1,1,1-trifluoropropan-2-yl]oxypyridine-2-carboxamide

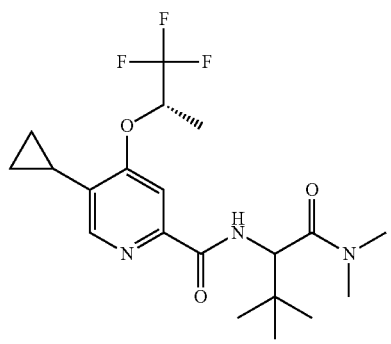 [SMILES: C[C@H](Oc1cc(C(=O)NC(C(=O)N(C)C)C(C)(C)C)ncc1C1CC1)C(F)(F)F]

The title compound was synthesized in analogy to Example 112e, using 2-[[5-cyclopropyl-4-[(1S)-2,2,2-trifluoro-1-methyl-ethoxy]pyridine-2-carbonyl]amino]-3,3-dimethyl-butanoic acid (Example 199b) and dimethylamine hydrochloride as starting materials and isolated (31 mg, 57%); MS (ESI, m/z): 416.6 (M+H⁺).

Example 202

N-[1-(azetidin-1-yl)-3,3-dimethyl-1-oxobutan-2-yl]-5-cyclopropyl-4-[(2S)-1,1,1-trifluoropropan-2-yl]oxypyridine-2-carboxamide

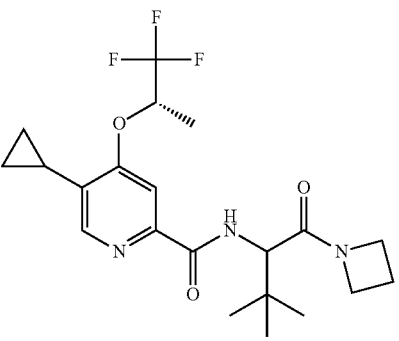 [SMILES: C[C@H](Oc1cc(C(=O)NC(C(=O)N2CCC2)C(C)(C)C)ncc1C1CC1)C(F)(F)F]

The title compound was synthesized in analogy to Example 112e, using 2-[[5-cyclopropyl-4-[(1S)-2,2,2-trifluoro-1-methyl-ethoxy]pyridine-2-carbonyl]amino]-3,3-dimethyl-butanoic acid (Example 199b) and azetidine (CAN 503-29-7) as starting materials and isolated (23 mg, 41%); MS (ESI, m/z): 428.6 (M+H⁺).

Example 203

5-cyclopropyl-N-[1-(3,3-difluoroazetidin-1-yl)-3,3-dimethyl-1-oxobutan-2-yl]-4-[(2S)-1,1,1-trifluoropropan-2-yl]oxypyridine-2-carboxamide

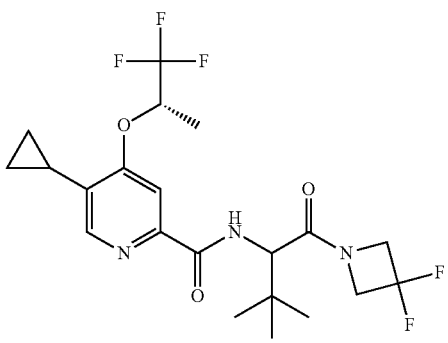 [SMILES: C[C@H](Oc1cc(C(=O)NC(C(=O)N2CC(F)(F)C2)C(C)(C)C)ncc1C1CC1)C(F)(F)F]

The title compound was synthesized in analogy to Example 112e, using 2-[[5-cyclopropyl-4-[(1S)-2,2,2-trifluoro-1-methyl-ethoxy]pyridine-2-carbonyl]amino]-3,3-dimethyl-butanoic acid (Example 199b) and 3,3-Difluoroazetidine hydrochloride (CAN 288315-03-7) as starting materials and isolated (35 mg, 58%); MS (ESI, m/z): 464.6 (M+H⁺).

Example 204

5-cyclopropyl-N-[3,3-dimethyl-1-(6-oxa-1-azaspiro[3.3]heptan-1-yl)-1-oxobutan-2-yl]-4-[(2S)-1,1,1-trifluoropropan-2-yl]oxypyridine-2-carboxamide

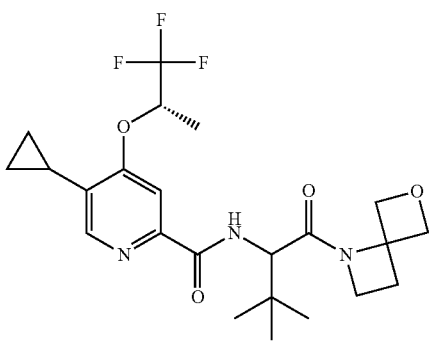 [SMILES: C[C@H](Oc1cc(C(=O)NC(C(=O)N2CCC23COC3)C(C)(C)C)ncc1C1CC1)C(F)(F)F]

The title compound was synthesized in analogy to Example 112e, using 2-[[5-cyclopropyl-4-[(1S)-2,2,2-trifluoro-1-methyl-ethoxy]pyridine-2-carbonyl]amino]-3,3-dimethyl-butanoic acid (Example 199b) and 6-Oxa-1-azaspiro[3.3]heptane, ethanedioate (1:2) (CAN 1380571-72-1) as starting materials and isolated (23 mg, 38%); MS (ESI, m/z): 470.6 (M+H⁺).

Example 205

5-cyclopropyl-N-[2,2-dimethyl-1-(1-methyltetrazol-5-yl)propyl]-4-(2,2,2-trifluoroethoxy)pyridine-2-carboxamide (enantiomer A)

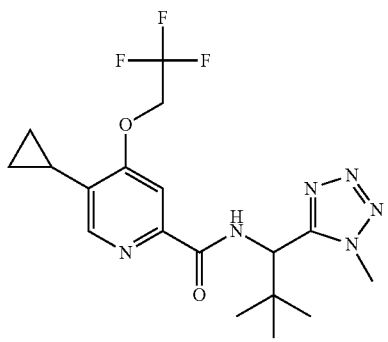 [SMILES: Cn1nnnc1C(NC(=O)c1cc(OCC(F)(F)F)c(C2CC2)cn1)C(C)(C)C]

The racemate (Example 164) was separated into its enantiomers by preparative chiral HPLC (Chiralpak AD, isopropanol/heptane) and the title compound was the first enantiomer collected and isolated as colorless oil; MS (ESI, m/z): 413.6 (M+H⁺).

Example 206

5-cyclopropyl-N-[2,2-dimethyl-1-(1-methyltetrazol-5-yl)propyl]-4-(2,2,2-trifluoroethoxy)pyridine-2-carboxamide (enantiomer B)

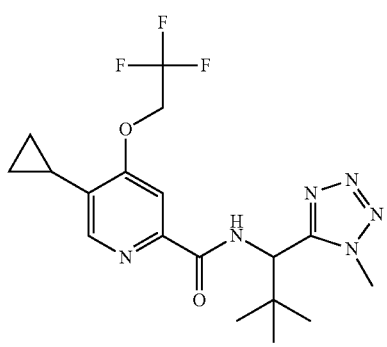 [SMILES: Cn1nnnc1C(NC(=O)c1cc(OCC(F)(F)F)c(C2CC2)cn1)C(C)(C)C]

The racemate (Example 164) was separated into its enantiomers by preparative chiral HPLC (Chiralpak AD, isopropanol/heptane) and the title compound was the second enantiomer collected and isolated as colorless oil; MS (ESI, m/z): 413.6 (M+H⁺).

Example 207

N-[2-(5-amino-1,2,4-oxadiazol-3-yl)-1-cyclopropyl-propan-2-yl]-5-cyclopropyl-4-(2,2,2-trifluoroethoxy)pyridine-2-carboxamide (enantiomer A)

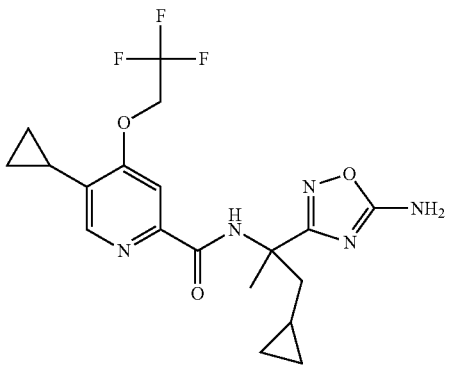 [SMILES: CC(CC1CC1)(NC(=O)c1cc(OCC(F)(F)F)c(C2CC2)cn1)c1noc(N)n1]

The racemate (Example 165b) was separated into its enantiomers by preparative chiral supercritical fluid chromatography (Chiralpak AD-H, 20% methanol+0.2% diethylamine) and the title compound was the first enantiomer collected and isolated as colorless oil; MS (ESI, m/z): 426.5 (M+H⁺).

Example 208

N-[2-(5-amino-1,2,4-oxadiazol-3-yl)-1-cyclopropyl-propan-2-yl]-5-cyclopropyl-4-(2,2,2-trifluoroethoxy)pyridine-2-carboxamide (enantiomer B)

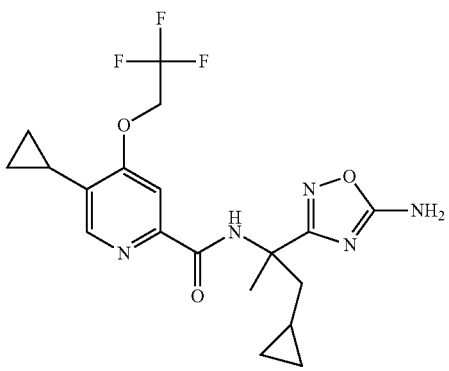 [SMILES: CC(CC1CC1)(NC(=O)c1cc(OCC(F)(F)F)c(C2CC2)cn1)c1noc(N)n1]

The racemate (Example 165b) was separated into its enantiomers by preparative chiral supercritical fluid chromatography (Chiralpak AD-H, 20% methanol+0.2% diethylamine) and the title compound was the second enantiomer collected and isolated as colorless oil; MS (ESI, m/z): 426.5 (M+H⁺).

Example 209

5-cyclopropyl-N-[2,2-dimethyl-1-(2-methyltetrazol-5-yl)propyl]-4-(2,2,2-trifluoroethoxy)pyridine-2-carboxamide (enantiomer A)

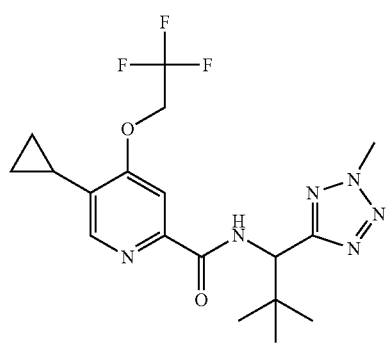 [SMILES: Cn1nnc(C(NC(=O)c2cc(OCC(F)(F)F)c(C3CC3)cn2)C(C)(C)C)n1]

The racemate (Example 163) was separated into its enantiomers by preparative chiral HPLC (Chiralpak AD, isopropanol/heptane) and the title compound was the first enantiomer collected and isolated as colorless oil; MS (ESI, m/z): 413.6 (M+H⁺).

Example 210

5-cyclopropyl-N-[2,2-dimethyl-1-(2-methyltetrazol-5-yl)propyl]-4-(2,2,2-trifluoroethoxy)pyridine-2-carboxamide (enantiomer B)

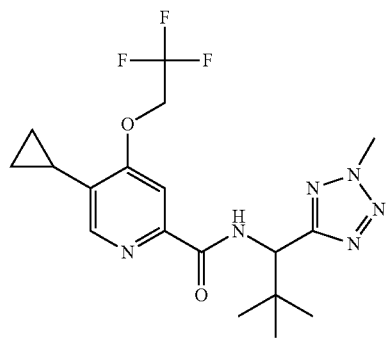 [SMILES: Cn1nnc(C(NC(=O)c2cc(OCC(F)(F)F)c(C3CC3)cn2)C(C)(C)C)n1]

The racemate (Example 163) was separated into its enantiomers by preparative chiral HPLC (Chiralpak AD, isopropanol/heptane) and the title compound was the second enantiomer collected and isolated as colorless oil; MS (ESI, m/z): 413.6 (M+H⁺).

Example 211

5-cyclopropyl-N-[2,2-dimethyl-1-(5-methyl-1,2,4-oxadiazol-3-yl)propyl]-4-(2,2,2-trifluoroethoxy)pyridine-2-carboxamide (enantiomer A)

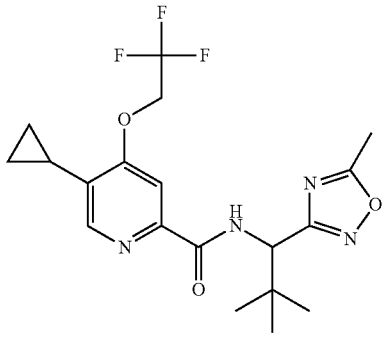 [SMILES: Cc1nc(C(NC(=O)c2cc(OCC(F)(F)F)c(C3CC3)cn2)C(C)(C)C)no1]

The racemate (Example 161c) was separated into its enantiomers by preparative chiral HPLC (Chiralpak AD, isopropanol/heptane) and the title compound was the first enantiomer collected and isolated as colorless oil; MS (ESI, m/z): 413.6 (M+H⁺).

Example 212

5-cyclopropyl-N-[2,2-dimethyl-1-(5-methyl-1,2,4-oxadiazol-3-yl)propyl]-4-(2,2,2-trifluoroethoxy)pyridine-2-carboxamide (enantiomer B)

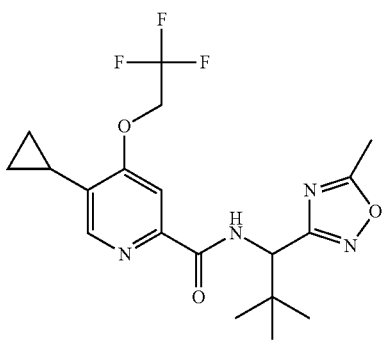 [SMILES: Cc1nc(C(NC(=O)c2cc(OCC(F)(F)F)c(C3CC3)cn2)C(C)(C)C)no1]

The racemate (Example 161c) was separated into its enantiomers by preparative chiral HPLC (Chiralpak AD, isopropanol/heptane) and the title compound was the second enantiomer collected and isolated as colorless oil; MS (ESI, m/z): 413.6 (M+H⁺).

Example 213

N-[1-(5-amino-1,2,4-oxadiazol-3-yl)-2,2-dimethyl-propyl]-5-cyclopropyl-4-[(2S)-1,1,1-trifluoropropan-2-yl]oxypyridine-2-carboxamide

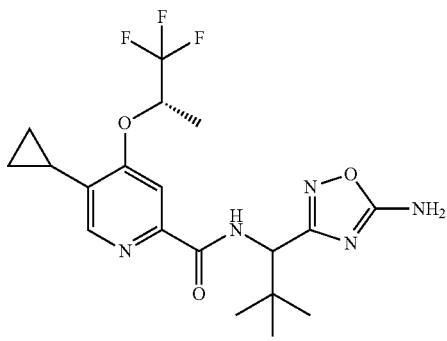 [SMILES: C[C@H](Oc1cc(C(=O)NC(c2noc(N)n2)C(C)(C)C)ncc1C1CC1)C(F)(F)F]

a) N-(1-cyano-2,2-dimethyl-propyl)-5-cyclopropyl-4-[(1S)-2,2,2-trifluoro-1-methyl-ethoxy]pyridine-2-carboxamide

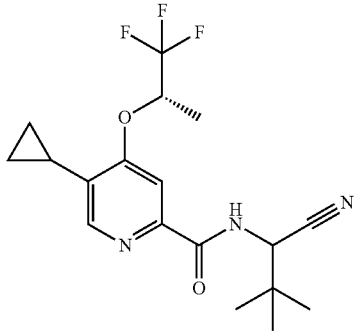 [SMILES: C[C@H](Oc1cc(C(=O)NC(C#N)C(C)(C)C)ncc1C1CC1)C(F)(F)F]

The title compound was synthesized in analogy to Example 112e, using 5-Cyclopropyl-4-((S)-2,2,2-trifluoro-1-methyl-ethoxy)-pyridine-2-carboxylic acid (Example 68a) and 2-Amino-3,3-dimethyl-butyronitrile (CAN 77425-86-6) as starting materials and isolated (2 g, 99%); MS (ESI, m/z): 370.6 (M+H⁺).

b) 5-cyclopropyl-N-[1-[(Z)—N'-hydroxycarbamimidoyl]-2,2-dimethyl-propyl]-4-[(1S)-2,2,2-trifluoro-1-methyl-ethoxy]pyridine-2-carboxamide

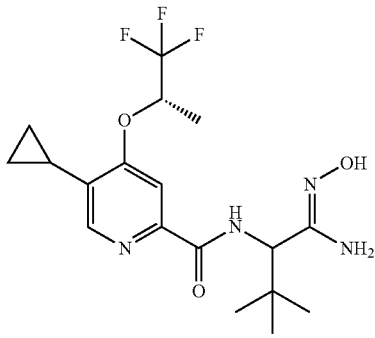 [SMILES: C[C@H](Oc1cc(C(=O)NC(/C(N)=N/O)C(C)(C)C)ncc1C1CC1)C(F)(F)F]

215

The title compound was synthesized in analogy to Example 78f, using N-(1-cyano-2,2-dimethyl-propyl)-5-cyclopropyl-4-[(1S)-2,2,2-trifluoro-1-methyl-ethoxy]pyridine-2-carboxamide (Example 213a) as starting material and isolated (1.16 g, 89%); MS (ESI, m/z): 403.5 (M+H⁺).

c) N-[1-(5-amino-1,2,4-oxadiazol-3-yl)-2,2-dimethylpropyl]-5-cyclopropyl-4-[(2S)-1,1,1-trifluoropropan-2-yl]oxypyridine-2-carboxamide

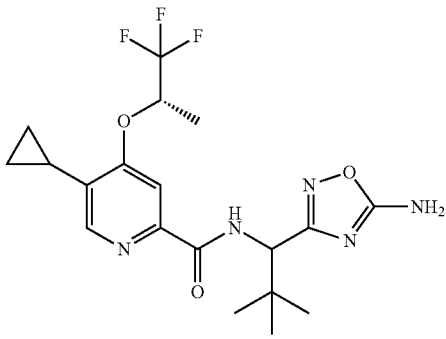 [SMILES: C[C@H](Oc1cc(C(=O)NC(c2noc(N)n2)C(C)(C)C)ncc1C1CC1)C(F)(F)F]

The title compound was synthesized in analogy to Example 165b, using 5-cyclopropyl-N-[1-[(Z)—N'-hydroxycarbamimidoyl]-2,2-dimethyl-propyl]-4-[(1S)-2,2,2-trifluoro-1-methyl-ethoxy]pyridine-2-carboxamide (Example 213b) as starting material and isolated (163 mg, 28%); MS (ESI, m/z): 428.6 (M+H⁺).

Example 214

5-cyclopropyl-N-[2,2-dimethyl-1-(5-methyl-1,2,4-oxadiazol-3-yl)propyl]-4-[(2S)-1,1,1-trifluoropropan-2-yl]oxypyridine-2-carboxamide

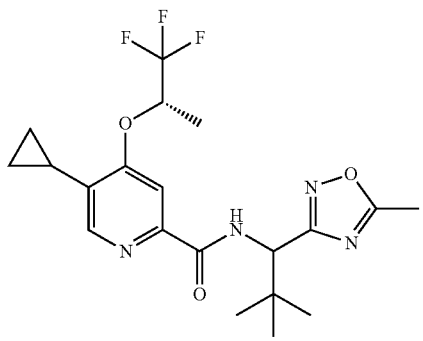 [SMILES: Cc1nc(C(NC(=O)c2cc(O[C@@H](C)C(F)(F)F)c(C3CC3)cn2)C(C)(C)C)no1]

The title compound was synthesized in analogy to Example 78g, using 5-cyclopropyl-N-[1-[(Z)—N'-hydroxycarbamimidoyl]-2,2-dimethyl-propyl]-4-[(1S)-2,2,2-trifluoro-1-methyl-ethoxy]pyridine-2-carboxamide (Example 213b) as starting material and isolated (340 mg, 55%); MS (ESI, m/z): 427.6 (M+H⁺).

Example 215

5-cyclopropyl-4-[(3-methyloxetan-3-yl)methoxy]-N-[2-(5-phenyl-1,3,4-oxadiazol-2-yl)propan-2-yl]pyridine-2-carboxamide

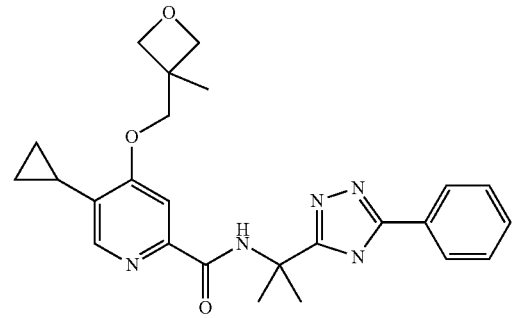 [SMILES: CC1(COc2cc(C(=O)NC(C)(C)c3nnc(-c4ccccc4)[nH]3)ncc2C2CC2)COC1]

a) 2,4-dichloro-5-cyclopropyl-pyridine

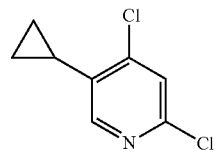

A mixture of 5-bromo-2,4-dichloro-pyridine (CAN 849937-4, 4 g, 17.63 mmol), potassium phosphate tribasic (11.21 g, 52.89 mmol), cyclopropylboronic acid (5.2 g, 35.84 mmol) in toluene (45 ml) and water (5 ml) was degassed with argon for 15 minutes. To this reaction mixture was added palladium (II) acetate (80 mg, 0.35 mmol) and tricyclohexylphosphine (0.487 g, 1.74 mmol) at 25° C. and reaction mixture was again purged with argon for 5 minutes. The reaction mixture was then stirred at 100° C. for 12 hours. The reaction mixture was cooled to 25° C. and the catalyst was filtered off through a pad of celite and the filter pad was washed with ethyl acetate (3×50 ml). The filtrate was washed with brine, dried over sodium sulfate and evaporated to dryness. The crude material was purified by flash chromatography on silica eluting with a gradient of heptane and ethyl acetate to yield the title compound (2 g, 61%) as a light yellow oil. MS (ESI, m/z): 188.2 (M+H⁺).

b) 4-chloro-5-cyclopropyl-pyridine-2-carbonitrile

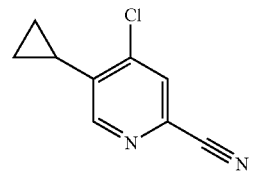 [SMILES: N#Cc1cc(Cl)c(C2CC2)cn1]

A stirred solution of 2,4-dichloro-5-cyclopropylpyridine (example 215a, 2.2 g, 11.76 mmol) in DMF (10 ml) was purged with argon for 10 minutes. To this reaction mixture was added dicyanozinc (926 mg, 7.65 mmol) followed by addition of DPPF (520 mg, 1.02 mmol) and Pd₂dba₃ (535 mg, 0.58 mmol). The reaction mixture was again purged with argon for 10 minutes. The reaction mixture was then stirred at 100° C. for 1 hour. The catalyst was filtered off on a pad of celite and the filtrate was diluted with ethyl acetate. The organic phase was washed with brine, dried over sodium sulfate and evaporated down to dryness. The obtained crude material was purified by flash chromatography on silica eluting with a gradient of heptane and ethyl acetate to yield the title compound (1 g, 50%) as off white crystalline solid. MS (ESI, m/z): 179.2 (M+H⁺).

c) 5-cyclopropyl-4-[(3-methyloxetan-3-yl)methoxy]pyridine-2-carbonitrile

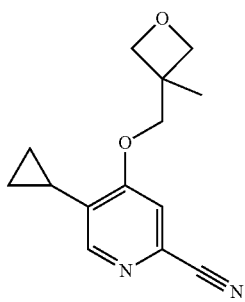 [SMILES: CC1(COc2cc(C#N)ncc2C2CC2)COC1]

The title compound was synthesized in analogy to Example 123c, using 4-chloro-5-cyclopropyl-pyridine-2-carbonitrile (example 215b), (3-methyloxetan-3-yl)methanol (CAN 3143-02-0) as starting materials and isolated (1.73 g, 83%); MS (ESI, m/z): 245.5 (M+H⁺).

d) 5-cyclopropyl-4-[(3-methyloxetan-3-yl)methoxy]pyridine-2-carboxylic acid

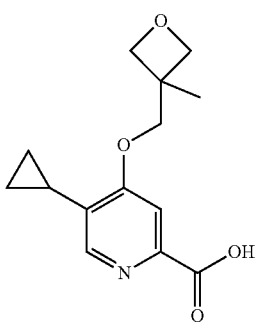 [SMILES: CC1(COc2cc(C(=O)O)ncc2C2CC2)COC1]

To a solution of 5-cyclopropyl-4-((3-methyloxetan-3-yl)methoxy)picolinonitrile (1.73 g, 7.08 mmol) in ethanol (20 ml) in a microwave vial was added a 4.0M aqueous solution of potassium hydroxide (6.2 ml, 24.8 mmol). The vial was sealed and mixture was stirred at 85° C. overnight. The reaction was cooled down to 0° C. followed by addition of formic acid (1.14 g, 951 µl, 24.8 mmol) to acidify the reaction mixture. The crude solution was then evaporated to dryness and the crude material was directly purified by preparative HPLC to yield the title compound (1.34 g, 72%) as white solid. MS (ESI, m/z): 264.5 (M+H⁺).

e) 5-cyclopropyl-4-[(3-methyloxetan-3-yl)methoxy]-N-[2-(5-phenyl-1,3,4-oxadiazol-2-yl)propan-2-yl]pyridine-2-carboxamide

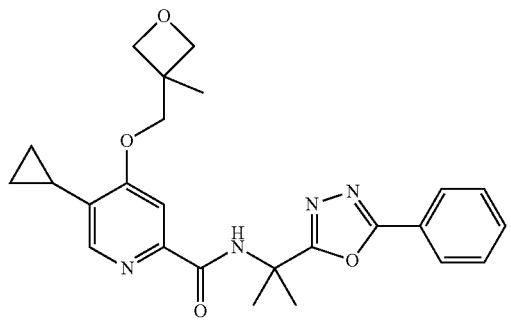 [SMILES: CC1(COc2cc(C(=O)NC(C)(C)c3nnc(-c4ccccc4)o3)ncc2C2CC2)COC1]

To a solution of the acid 5-cyclopropyl-4-((3-methyloxetan-3-yl)methoxy)picolinic acid (20 mg, 76.0 µmol) in dichloromethane (1 ml) was added DIPEA (24.5 mg, 33.2 µl, 190 µmol) and 4-(4,6-dimethoxy-1,3,5-triazin-2-yl)-4-methylmorpholin-4-ium chloride (23.1 mg, 83.6 µmol). The reaction is stirred for 30 minutes at room temperature followed by addition of 2-(5-phenyl-1,3,4-oxadiazol-2-yl)propan-2-amine (CAN 68176-04-5, 15.4 mg, 76.0 µmol) and the reaction mixture was stirred overnight at room temperature. The reaction was diluted with dichloromethane (5 mL) and washed with a 0.2M aqueous solution of hydrochloric acid (3×10 mL) and brine (15 mL). The organic phase is dried over magnesium sulfate and evaporated down to dryness. The crude material was purified by flash chromatography on silica eluting with a gradient of heptane and ethyl acetate to yield the title compound (24.3 mg, 71%). MS (ESI, m/z): 449.7 (M+H⁺).

Example 216

5-cyclopropyl-N-[2,2-dimethyl-1-(2-methyltetrazol-5-yl)propyl]-4-[(2S)-1,1,1-trifluoropropan-2-yl]oxy-pyridine-2-carboxamide

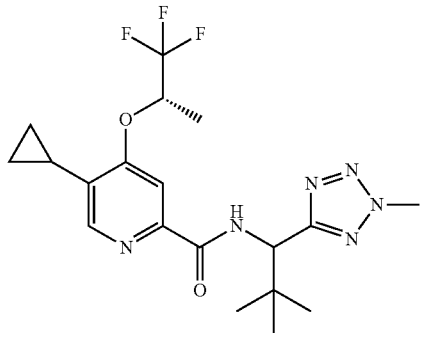 [SMILES: C[C@H](Oc1cc(C(=O)NC(c2nnn(C)n2)C(C)(C)C)ncc1C1CC1)C(F)(F)F]

a) 5-cyclopropyl-N-[2,2-dimethyl-1-(2H-tetrazol-5-yl)propyl]-4-[(1S)-2,2,2-trifluoro-1-methyl-ethoxy]pyridine-2-carboxamide

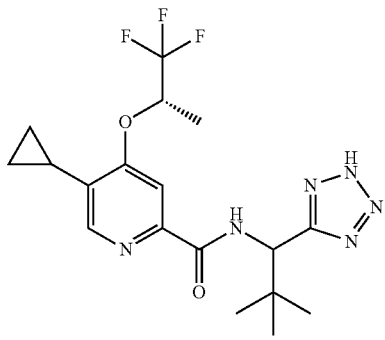 [SMILES: C[C@H](Oc1cc(C(=O)NC(c2nn[nH]n2)C(C)(C)C)ncc1C1CC1)C(F)(F)F]

The title compound was synthesized in analogy to Example 150b, using N-(1-cyano-2,2-dimethyl-propyl)-5-cyclopropyl-4-[(1S)-2,2,2-trifluoro-1-methyl-ethoxy]pyridine-2-carboxamide (Example 213a) as starting material and isolated (835 mg, 93%); MS (ESI, m/z): 413.5 (M+H$^+$).

b) 5-cyclopropyl-N-[2,2-dimethyl-1-(2-methyltetrazol-5-yl)propyl]-4-[(2S)-1,1,1-trifluoropropan-2-yl]oxypyridine-2-carboxamide

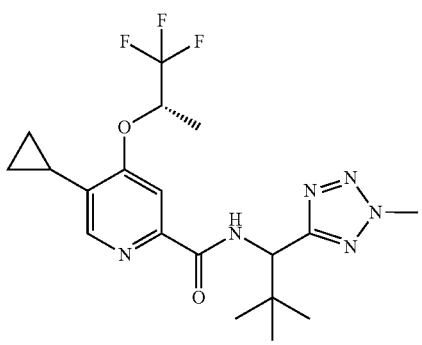 [SMILES: C[C@H](Oc1cc(C(=O)NC(c2nnn(C)n2)C(C)(C)C)ncc1C1CC1)C(F)(F)F]

The title compound was synthesized in analogy to Example 150c, using 5-cyclopropyl-N-[2,2-dimethyl-1-(2H-tetrazol-5-yl)propyl]-4-[(1S)-2,2,2-trifluoro-1-methyl-ethoxy]pyridine-2-carboxamide (Example 216a) as starting material and isolated (351 mg, 46%); MS (ESI, m/z): 427.6 (M+H$^+$).

Example 217

5-cyclopropyl-N-[2,2-dimethyl-1-(1-methyltetrazol-5-yl)propyl]-4-[(2S)-1,1,1-trifluoropropan-2-yl]oxypyridine-2-carboxamide

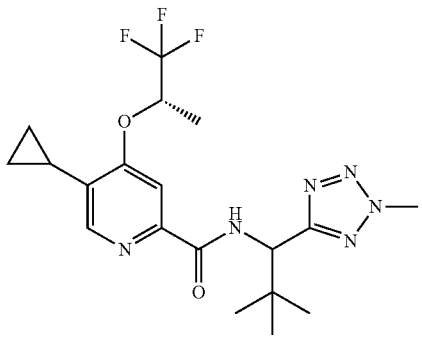 [SMILES: C[C@H](Oc1cc(C(=O)NC(c2nnn(C)n2)C(C)(C)C)ncc1C1CC1)C(F)(F)F]

The title compound was synthesized in analogy to Example 150c, using 5-cyclopropyl-N-[2,2-dimethyl-1-(2H-tetrazol-5-yl)propyl]-4-[(1S)-2,2,2-trifluoro-1-methyl-ethoxy]pyridine-2-carboxamide (Example 216a) as starting material and isolated (143 mg, 19%); MS (ESI, m/z): 427.6 (M+H$^+$).

Example 218

N-[1-(5-amino-1,2,4-oxadiazol-3-yl)-2,2-dimethyl-propyl]-5-cyclopropyl-4-[(2S)-1,1,1-trifluoropropan-2-yl]oxypyridine-2-carboxamide (epimer A)

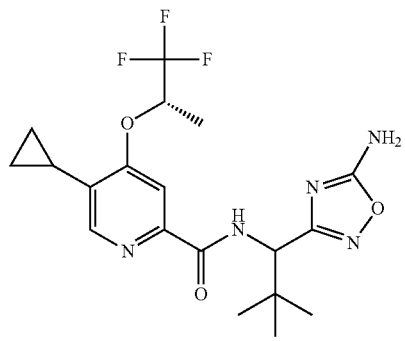 [SMILES: C[C@H](Oc1cc(C(=O)NC(c2noc(N)n2)C(C)(C)C)ncc1C1CC1)C(F)(F)F]

The mixture of epimers (Example 213c) was separated into its individual epimers by preparative chiral HPLC (Reprosil Chiral NR, ethanol/heptane) and the title compound was the first epimer collected and isolated as colorless oil; MS (ESI, m/z): 428.6 (M+H$^+$).

Example 219

N-[1-(5-amino-1,2,4-oxadiazol-3-yl)-2,2-dimethyl-propyl]-5-cyclopropyl-4-[(2S)-1,1,1-trifluoropropan-2-yl]oxypyridine-2-carboxamide (epimer B)

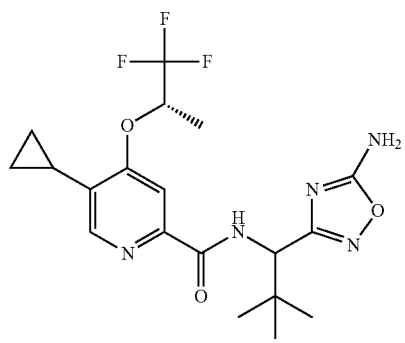 [SMILES: C[C@H](Oc1cc(C(=O)NC(c2noc(N)n2)C(C)(C)C)ncc1C1CC1)C(F)(F)F]

The mixture of epimers (Example 213c) was separated into its individual epimers by preparative chiral HPLC (Reprosil Chiral NR, ethanol/heptane) and the title compound was the second epimer collected and isolated as colorless oil; MS (ESI, m/z): 428.6 (M+H$^+$).

Example 220

5-cyclopropyl-N-[2,2-dimethyl-1-(5-methyl-1,2,4-oxadiazol-3-yl)propyl]-4-[(2S)-1,1,1-trifluoropropan-2-yl]oxypyridine-2-carboxamide (epimer A)

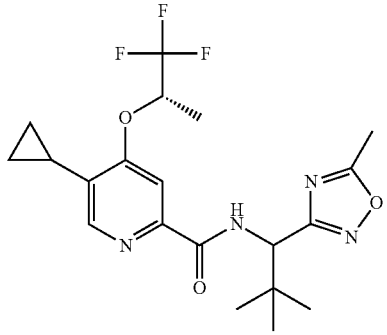 [SMILES: Cc1nc(C(NC(=O)c2cc(O[C@@H](C)C(F)(F)F)c(C3CC3)cn2)C(C)(C)C)no1]

The mixture of epimers (Example 214) was separated into its individual epimers by preparative chiral HPLC (Chiralpak AD, ethanol/heptane) and the title compound was the first epimer collected and isolated as colorless oil; MS (ESI, m/z): 427.6 (M+H$^+$).

Example 221

5-cyclopropyl-N-[2,2-dimethyl-1-(5-methyl-1,2,4-oxadiazol-3-yl)propyl]-4-[(2S)-1,1,1-trifluoropropan-2-yl]oxypyridine-2-carboxamide (epimer B)

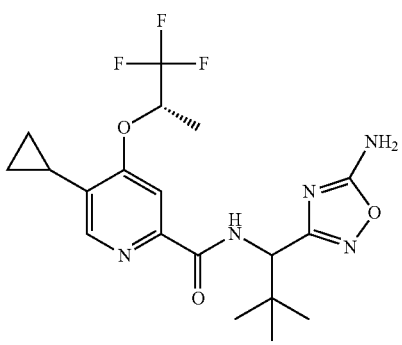 [SMILES: C[C@H](Oc1cc(C(=O)NC(c2noc(N)n2)C(C)(C)C)ncc1C1CC1)C(F)(F)F]

The mixture or epimers (Example 214) was separated into its individual epimers by preparative chiral HPLC (Chiralpak AD, ethanol/heptane) and the title compound was the second epimer collected and isolated as colorless oil; MS (ESI, m/z): 427.6 (M+H$^+$).

Example 222

N-[3-(2-amino-2-oxoethyl)oxetan-3-yl]-4-(cyclopropylmethoxy)-5-(3,3-difluoroazetidin-1-yl)pyridine-2-carboxamide

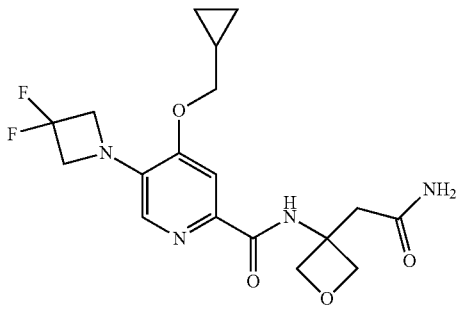 [SMILES: NC(=O)CC1(NC(=O)c2cc(OCC3CC3)c(N3CC(F)(F)C3)cn2)COC1]

The title compound was synthesized in analogy to Example 112e, using 4-Cyclopropylmethoxy-5-(3,3-difluoro-azetidin-1-yl)-pyridine-2-carboxylic acid (Example 53e) and 2-(3-Amino-oxetan-3-yl)-acetamide (CAN 1417638-25-5) as starting material and isolated (31 mg, 36%); MS (ESI, m/z): 397.6 (M+H$^+$).

Example 223

N-[3-(2-amino-2-oxoethyl)oxetan-3-yl]-5-(3,3-difluoroazetidin-1-yl)-4-(2,2,2-trifluoroethoxy)pyridine-2-carboxamide

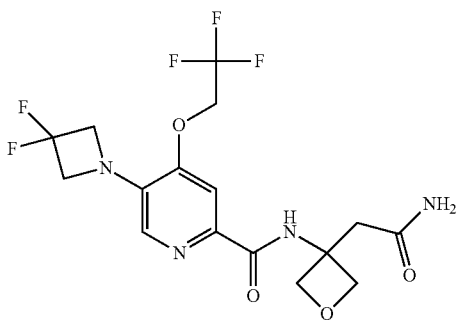

a) 5-(3,3-difluoroazetidin-1-yl)-4-(2,2,2-trifluoroethoxy)pyridine-2-carbonitrile

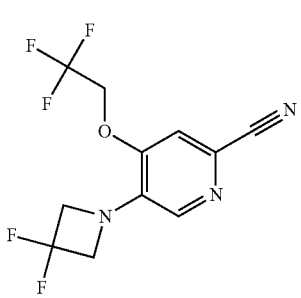 [SMILES: N#Cc1cc(OCC(F)(F)F)c(N2CC(F)(F)C2)cn1]

To a solution of 5-Bromo-4-(2,2,2-trifluoro-ethoxy)-pyridine-2-carbonitrile (example 78c, 587 mg, 2.09 mmol) in dry toluene (10 ml) in a schlenk tube was added 3,3-difluoroazetidine hydrochloride (298 mg, 2.3 mmol), cesium carbonate (1.36 g, 4.18 mmol), palladium diacetate (46.9 mg, 209 µmol) and BINAP (130 mg, 209 µmol). The reaction mixture was stirred at 120° C. for 1 hour. The reaction mixture was filtered over a pad of celite and the filtrate was diluted with ethylacetate. The organic phase was extracted with a 1M aqueous solution of sodium bicarbonate. The organic phase was dried over sodium sulfate and evaporated down to dryness. The crude material was purified by flash chromatography on silica eluting with a heptane/ethyl acetate gradient to yield the title compound (480 mg, 78%). MS (ESI, m/z): 294.2 (M+H$^+$).

b) 5-(3,3-difluoroazetidin-1-yl)-4-(2,2,2-trifluoroethoxy)pyridine-2-carboxylic acid

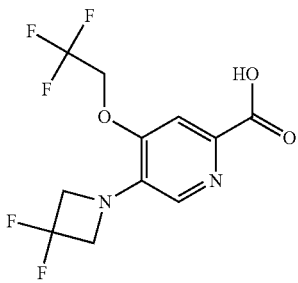 [SMILES: O=C(O)c1cc(OCC(F)(F)F)c(N2CC(F)(F)C2)cn1]

To a solution of 5-(3,3-difluoroazetidin-1-yl)-4-(2,2,2-trifluoroethoxy)pyridine-2-carbonitrile (example 223a, 680 mg, 2.32 mmol) in EtOH (8 ml) in a schlenk tube was added a 4M aqueous solution of potassium hydroxide (651 mg, 11.6 mmol). The reaction mixture was stirred at 105° C. for 2 hours. The reaction mixture was diluted with ethyl acetate and poured in a separatory funnel. The organic phase was extracted with a 1M aqueous solution of hydrochloric acid. The organic phase was collected and the aqueous phase was back-extracted with ethyl acetate. Combined organic phases were dried over sodium sulfate and evaporated down to dryness to yield the title compound (397 mg, 55%) as a crude solid which was used without any purification. MS (ESI, m/z): 311.2 (M−H$^+$).

c) N-[3-(2-amino-2-oxoethyl)oxetan-3-yl]-5-(3,3-difluoroazetidin-1-yl)-4-(2,2,2-trifluoroethoxy)pyridine-2-carboxamide

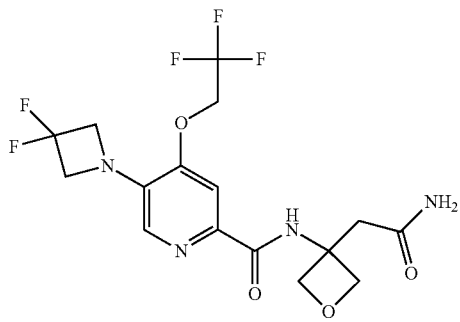 [SMILES: NC(=O)CC1(NC(=O)c2cc(OCC(F)(F)F)c(N3CC(F)(F)C3)cn2)COC1]

The title compound was synthesized in analogy to Example 112e, using 5-(3,3-difluoroazetidin-1-yl)-4-(2,2,2-trifluoroethoxy)pyridine-2-carboxylic acid (Example 223b) and 2-(3-Amino-oxetan-3-yl)-acetamide (CAN 1417638-25-5) as starting material and isolated (42 mg, 31%); MS (ESI, m/z): 425.5 (M+H$^+$).

Example 224

5-cyclopropyl-N-[3,3-dimethyl-1-(methylamino)-1-oxobutan-2-yl]-4-(2,2,2-trifluoroethoxy)pyridine-2-carboxamide (enantiomer A)

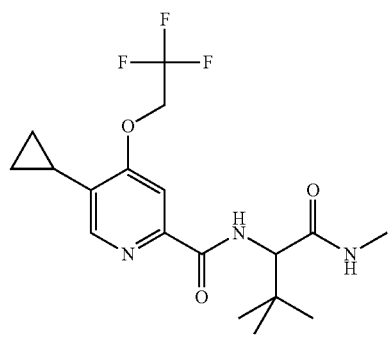 [SMILES: CNC(=O)C(NC(=O)c1cc(OCC(F)(F)F)c(C2CC2)cn1)C(C)(C)C]

a) 5-cyclopropyl-N-[2,2-dimethyl-1-(methylcarbamoyl)propyl]-4-(2,2,2-trifluoroethoxy)pyridine-2-carboxamide

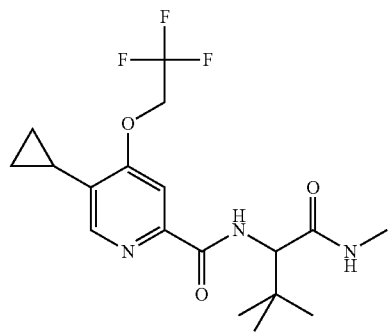 [SMILES: CNC(=O)C(NC(=O)c1cc(OCC(F)(F)F)c(C2CC2)cn1)C(C)(C)C]

The title compound was synthesized in analogy to Example 112e, using 2-[[5-cyclopropyl-4-(2,2,2-trifluoroethoxy)pyridine-2-carbonyl]amino]-3,3-dimethyl-butanoic acid (Example 194b) and methanamine hydrochloride as starting materials and isolated (114 mg, 96%) as a racemate; MS (ESI, m/z): 388.6 (M+H$^+$).

b) 5-cyclopropyl-N-[3,3-dimethyl-1-(methylamino)-1-oxobutan-2-yl]-4-(2,2,2-trifluoroethoxy)pyridine-2-carboxamide (enantiomer A)

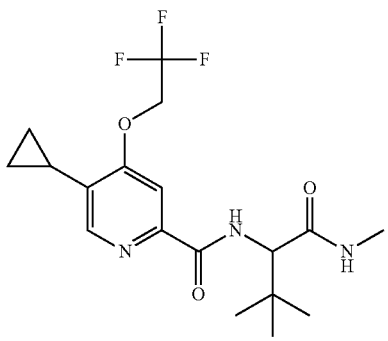 [SMILES: CNC(=O)C(NC(=O)c1cc(OCC(F)(F)F)c(C2CC2)cn1)C(C)(C)C]

The racemate (Example 224a) was separated into its enantiomers by preparative chiral HPLC (Reprosil Chiral NR, ethanol/heptane) and the title compound was the first enantiomer collected and isolated as colorless oil; MS (ESI, m/z): 388.6 (M+H$^+$).

Example 225

5-cyclopropyl-N-[3,3-dimethyl-1-(methylamino)-1-oxobutan-2-yl]-4-(2,2,2-trifluoroethoxy)pyridine-2-carboxamide (enantiomer B)

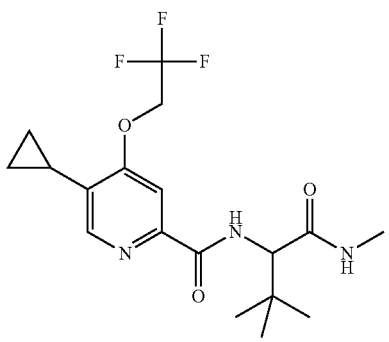 [SMILES: CNC(=O)C(NC(=O)c1cc(OCC(F)(F)F)c(C2CC2)cn1)C(C)(C)C]

The racemate (Example 224a) was separated into its enantiomers by preparative chiral HPLC (Reprosil Chiral NR, ethanol/heptane) and the title compound was the second enantiomer collected and isolated as colorless oil; MS (ESI, m/z): 388.6 (M+H$^+$).

Example 226

N-[1-(5-amino-1,2,4-oxadiazol-3-yl)-2,2-dimethylpropyl]-5-cyclopropyl-4-(2,2,2-trifluoroethoxy)pyridine-2-carboxamide (enantiomer A)

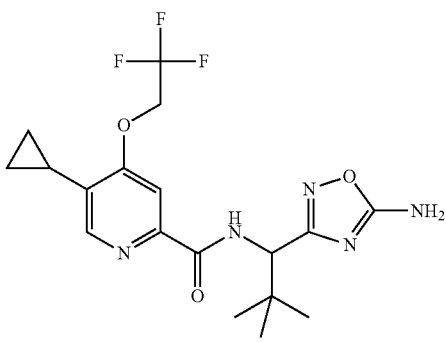 [SMILES: CC(C)(C)C(NC(=O)c1cc(OCC(F)(F)F)c(C2CC2)cn1)c1noc(N)n1]

The racemate (Example 192) was separated into its enantiomers by preparative chiral HPLC (Reprosil Chiral NR, ethanol/heptane) and the title compound was the first enantiomer collected and isolated as colorless oil; MS (ESI, m/z): 414.6 (M+H$^+$).

Example 227

N-[1-(5-amino-1,2,4-oxadiazol-3-yl)-2,2-dimethylpropyl]-5-cyclopropyl-4-(2,2,2-trifluoroethoxy)pyridine-2-carboxamide (enantiomer B)

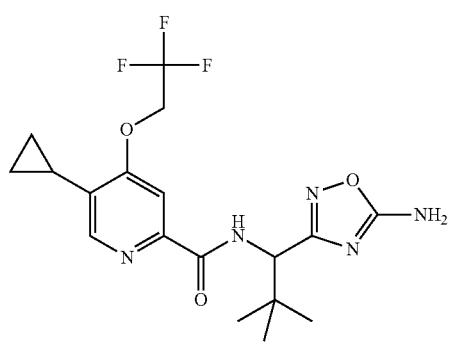 [SMILES: CC(C)(C)C(NC(=O)c1cc(OCC(F)(F)F)c(C2CC2)cn1)c1noc(N)n1]

The racemate (Example 192) was separated into its enantiomers by preparative chiral HPLC (Reprosil Chiral NR, ethanol/heptane) and the title compound was the second enantiomer collected and isolated as colorless oil; MS (ESI, m/z): 414.6 (M+H$^+$).

Example 228

5-cyclopropyl-N-[1-cyclopropyl-2-(1-methyltetrazol-5-yl)propan-2-yl]-4-(2,2,2-trifluoroethoxy)pyridine-2-carboxamide (enantiomer A)

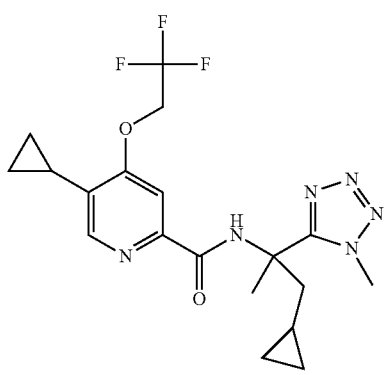 [SMILES: Cn1nnnc1C(C)(CC1CC1)NC(=O)c1cc(OCC(F)(F)F)c(C2CC2)cn1]

The racemate (Example 151) was separated into its enantiomers by preparative chiral HPLC (Chiralpak AD, isopropanol/heptane) and the title compound was the first enantiomer collected and isolated as colorless oil; MS (ESI, m/z): 425.7 (M+H$^+$).

Example 229

5-cyclopropyl-N-[2-cyclopropyl-4-(methylamino)-4-oxobutan-2-yl]-4-(2,2,2-trifluoroethoxy)pyridine-2-carboxamide

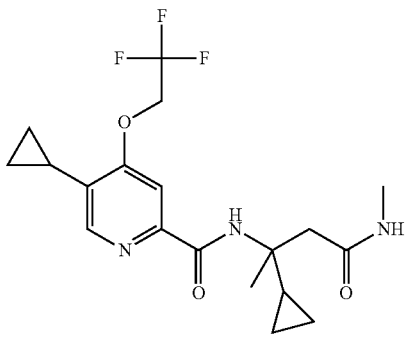 [SMILES: CNC(=O)CC(C)(NC(=O)c1cc(OCC(F)(F)F)c(C2CC2)cn1)C1CC1]

a) tert-butyl 3-(tert-butylsulfinylamino)-3-cyclopropyl-butanoate

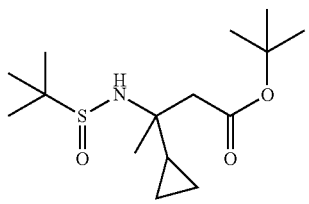 [SMILES: CC(C)(C)OC(=O)CC(C)(NS(=O)C(C)(C)C)C1CC1]

To a solution of tert-butyl acetate (1.29 g, 1.48 ml, 11.1 mmol) in THF (20 ml) cooled to −78° C. was added a 2M solution of lithium diisopropylamine in THF/n-heptane (5.55 ml, 11.1 mmol) over 10 minutes. The reaction mixture was stirred for 40 minutes at −78° C. followed by addition of a solution of (E)-N-(1-cyclopropylethylidene)-2-methylpropane-2-sulfinamide (CAN 1426425-10-6, 1.6 g, 8.54 mmol) in THF (5 ml) to the reaction cooled at −78° C. The reaction was stirred at −78° C. for 90 minutes and then let to warm up to 0° C. After stirring 1 hour at 0° C. the reaction was quenched by addition of water. The reaction mixture was diluted with ethyl acetate and washed with brine. The organic phase was dried over sodium sulfate and evaporated down to dryness. The crude material was purified by flash chromatography on silica eluting with a heptane/ethyl acetate gradient to yield the title compound (1.93 g, 75%). MS (ESI, m/z): 304.5 (M+H$^+$).

b) tert-butyl 3-amino-3-cyclopropyl-butanoate

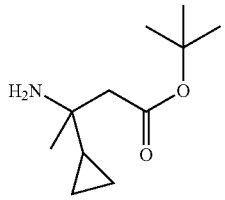

tert-butyl 3-(tert-butylsulfinylamino)-3-cyclopropyl-butanoate (example 229a, 1.93 g, 6.36 mmol) was dissolved in a 4M solution of hydrochloric acid in dioxane (4.77 ml, 19.1 mmol) and the reaction mixture was stirred at room temperature for 30 minutes. The reaction was then diluted with ethyl acetate and poured into a separatory funnel. The organic phase was extracted with a 2M aqueous solution of sodium carbonate. The organic phase was dried over sodium sulfate and evaporated down to dryness to yield the title compound (1.08 g, 85%) as a crude oil which was used without any purification. MS (ESI, m/z): 200.3 (M+H$^+$).

c) tert-butyl 3-cyclopropyl-3-[[5-cyclopropyl-4-(2,2,2-trifluoroethoxy)pyridine-2-carbonyl]amino]butanoate

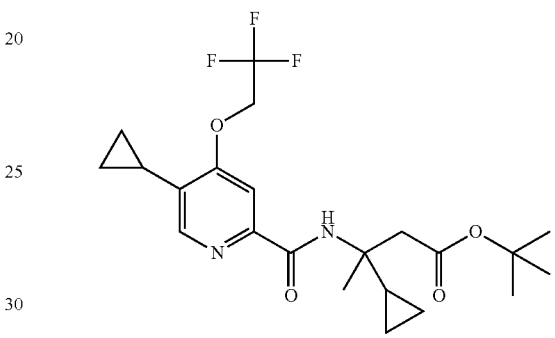

The title compound was synthesized in analogy to Example 112e, using 5-Cyclopropyl-4-(2,2,2-trifluoroethoxy)-pyridine-2-carboxylic acid (Example 48c) and tert-butyl 3-amino-3-cyclopropyl-butanoate (example 229b) as starting materials and isolated (890 mg, 88%); MS (ESI, m/z): 443.6 (M+H$^+$).

d) 3-cyclopropyl-3-[[5-cyclopropyl-4-(2,2,2-trifluoroethoxy)pyridine-2-carbonyl]amino]butanoic acid

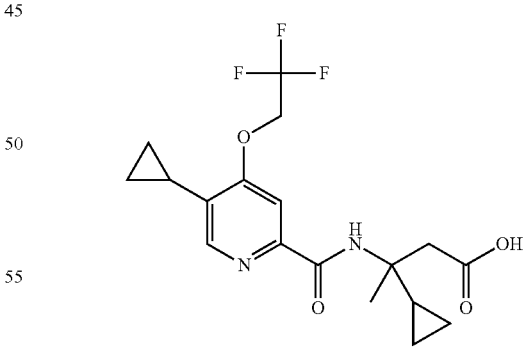

To a solution of tert-butyl 3-cyclopropyl-3-[[5-cyclopropyl-4-(2,2,2-trifluoroethoxy)pyridine-2-carbonyl]amino]butanoate (example 229c, 0.890 g, 2.01 mmol) in dichloromethane (11 ml) was added trifluoroacetic acid (4.59 g, 3.1 ml, 40.2 mmol) and the reaction mixture was stirred at room temperature for 14 hours. Volatiles were removed in vacuo and the residue was dissolved in toluene followed by evaporation to dryness. The procedure was repeated twice to yield e) 5-cyclopropyl-N-[2-cyclopropyl-4-(methylamino)-4-oxobutan-2-yl]-4-(2,2,2-trifluoroethoxy)pyridine-2-carboxamide

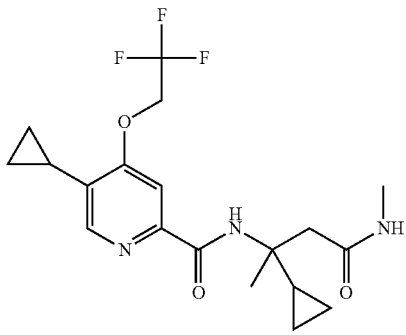 [SMILES: CC(CC(=O)O)(NC(=O)c1cc(OCC(F)(F)F)c(C2CC2)cn1)C1CC1]

The title compound was synthesized in analogy to Example 112e, using 3-cyclopropyl-3-[[5-cyclopropyl-4-(2,2,2-trifluoroethoxy)pyridine-2-carbonyl]amino]butanoic acid (Example 229d) and methanamine hydrochloride as starting materials and isolated (90 mg, 58%); MS (ESI, m/z): 400.5 (M+H$^+$).

Example 230

N-(4-amino-2-cyclopropyl-4-oxobutan-2-yl)-5-cyclopropyl-4-(2,2,2-trifluoroethoxy)pyridine-2-carboxamide

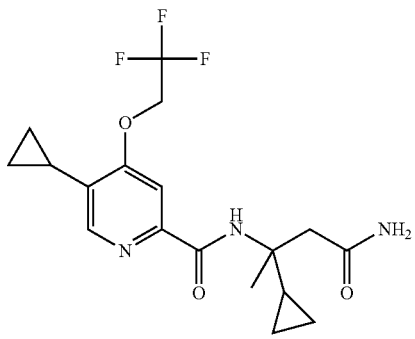 [SMILES: CC(CC(N)=O)(NC(=O)c1cc(OCC(F)(F)F)c(C2CC2)cn1)C1CC1]

The title compound was synthesized in analogy to Example 112e, using 3-cyclopropyl-3-[[5-cyclopropyl-4-(2,2,2-trifluoroethoxy)pyridine-2-carbonyl]amino]butanoic acid (Example 229d) and ammonium chloride as starting materials and isolated (72 mg, 48%); MS (ESI, m/z): 386.6 (M+H$^+$).

Example 231

5-cyclopropyl-N-[3-[2-(methylamino)-2-oxoethyl]oxetan-3-yl]-4-(2,2,2-trifluoroethoxy)pyridine-2-carboxamide

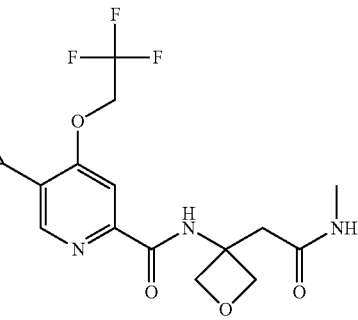

a) 2-(3-aminooxetan-3-yl)-N-methyl-acetamide

A solution of (3-Amino-oxetan-3-yl)-acetic acid ethyl ester (CAN 1207175-54-9, 0.3 g, 1.88 mmol) in methanamine 41% aqueous solution (1.86 g, 2.09 ml, 24.5 mmol) was stirred overnight at 60° C. The reaction was evaporated down to dryness and to yield the title compound (278 mg, 102%) as a crude solid which was used without any purification. MS (ESI, m/z): 145.2 (M+H$^+$).

b) 5-cyclopropyl-N-[3-[2-(methylamino)-2-oxoethyl]oxetan-3-yl]-4-(2,2,2-trifluoroethoxy)pyridine-2-carboxamide

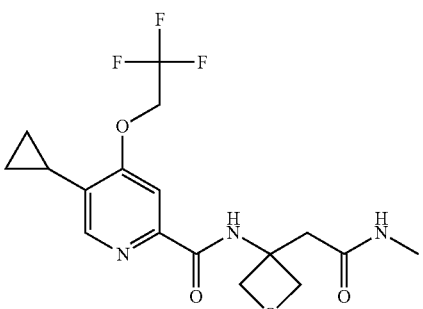

The title compound was synthesized in analogy to Example 112e, using 5-Cyclopropyl-4-(2,2,2-trifluoroethoxy)-pyridine-2-carboxylic acid (Example 48c) and 2-(3- aminooxetan-3-yl)-N-methyl-acetamide (example 231a) as starting materials and isolated (25 mg, 43%); MS (ESI, m/z): 388.6 (M+H+).

Example 232

5-cyclopropyl-N-[3-[2-(methylamino)-2-oxoethyl]oxetan-3-yl]-4-[(2S)-1,1,1-trifluoropropan-2-yl]oxy-pyridine-2-carboxamide

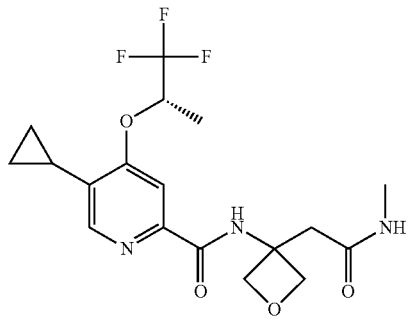 [SMILES: CNC(=O)CC1(NC(=O)c2cc(O[C@@H](C)C(F)(F)F)c(C3CC3)cn2)COC1]

The title compound was synthesized in analogy to Example 112e, using 5-Cyclopropyl-4-((S)-2,2,2-trifluoro-1-methyl-ethoxy)-pyridine-2-carboxylic acid (Example 68a) and 2-(3-aminooxetan-3-yl)-N-methyl-acetamide (example 231a) as starting materials and isolated (25 mg, 43%); MS (ESI, m/z): 402.6 (M+H+).

Example 233

5-(3,3-difluoroazetidin-1-yl)-N-[3-[2-(methylamino)-2-oxoethyl]oxetan-3-yl]-4-(2,2,2-trifluoroethoxy)pyridine-2-carboxamide

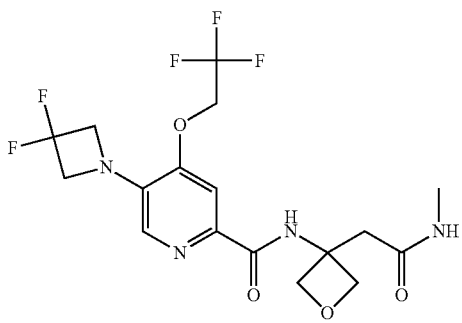 [SMILES: CNC(=O)CC1(NC(=O)c2cc(OCC(F)(F)F)c(N3CC(F)(F)C3)cn2)COC1]

The title compound was synthesized in analogy to Example 112e, using 5-(3,3-difluoroazetidin-1-yl)-4-(2,2,2-trifluoroethoxy)pyridine-2-carboxylic acid (Example 223b) and 2-(3-aminooxetan-3-yl)-N-methyl-acetamide (example 231a) as starting materials and isolated (25 mg, 43%); MS (ESI, m/z): 439.5 (M+H+).

Example 234

5-cyclopropyl-N-[3-(3-fluoropropylcarbamoyl)pentan-3-yl]-4-[(3-methyloxetan-3-yl)methoxy]pyridine-2-carboxamide

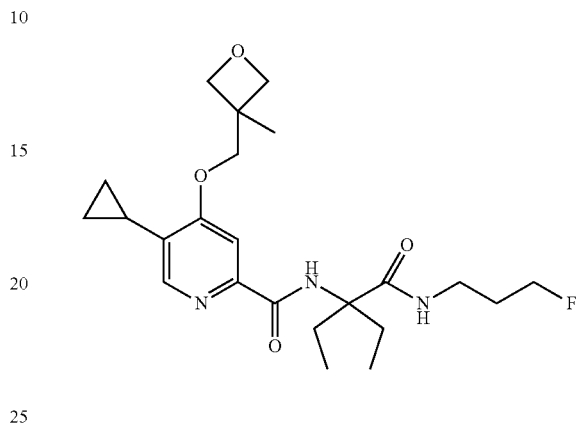

To a solution of the acid 2-(tert-butoxycarbonylamino)-2-ethylbutanoic acid (CAN 139937-99-8, 150 mg, 649 µmol) in dichloromethane (4 ml) was added N-ethyl-N-isopropylpropan-2-amine (210 mg, 283 µl, 1.62 mmol) and 4-(4,6-dimethoxy-1,3,5-triazin-2-yl)-4-methylmorpholin-4-ium chloride (197 mg, 713 µmol). The reaction was stirred for 30 minutes at room temperature followed by addition of 3-fluoropropan-1-amine hydrochloride (73.6 mg, 649 µmol) and the reaction mixture was stirred at 35° C. overnight. The reaction was then diluted with dichloromethane (5 mL) and washed with a 0.2M aqueous solution of hydrochloride (3×10 mL) and brine (15 mL). The organic phase was dried over magnesium sulfate and evaporated down to dryness. The crude material was purified by flash chromatography on silica eluting with a gradient of heptane/ethyl acetate to yield a white powder (128 mg) which was dissolved in dichloromethane (1 mL) followed by addition of a 2.0M solution of hydrochloric acid in diethyl ether (606 uL, 1.21 mmol). The mixture was stirred at room temperature overnight and a white suspension formed. Volatiles were removed in vacuo to give a crude amine (43 mg) as a hydrochloride salt which was used without any purification. To a solution of the acid 5-cyclopropyl-4-((3-methyloxetan-3-yl)methoxy)picolinic acid (example 215d, 20 mg, 76.0 µmol) in dichloromethane (1 ml) was added N-ethyl-N-isopropylpropan-2-amine (24.5 mg, 33.2 µl, 190 µmol) and 4-(4,6-dimethoxy-1,3,5-triazin-2-yl)-4-methylmorpholin-4-ium chloride (23.1 mg, 83.6 µmol). The reaction was stirred for 30 minutes at room temperature followed by addition of previous crude amine (17.2 mg, 76.0 µmol) and the reaction mixture was stirred at room temperature overnight. The reaction was diluted with dichloromethane (5 mL) and washed with a 0.2M aqueous solution of hydrochloric acid (3×10 mL) and brine (15 mL). The organic phase was dried over magnesium sulfate and evaporated down to dryness. The crude material was purified by flash chromatography on silica eluting with a gradient of

Example 235

N-[3-[[3-chloro-2-fluoropropyl]carbamoyl]pentan-3-yl]-5-cyclopropyl-4-[(3-methyloxetan-3-yl)methoxy]pyridine-2-carboxamide

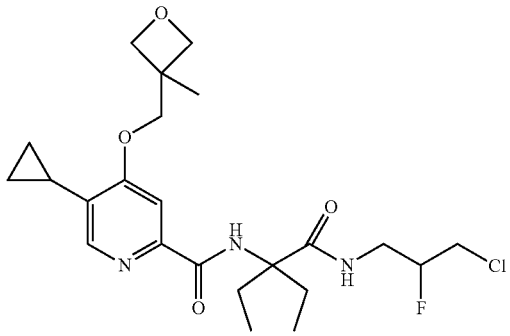 [SMILES: CCC(CC)(NC(=O)c1cc(OCC2(C)COC2)c(C2CC2)cn1)C(=O)NCC(F)CCl]

To a solution of the acid 2-(tert-butoxycarbonylamino)-2-ethylbutanoic acid (CAN 139937-99-8, 150 mg, 649 µmol) in dichloromethane (4 ml) was added N-ethyl-N-isopropylpropan-2-amine (210 mg, 283 µl, 1.62 mmol) and 4-(4,6-dimethoxy-1,3,5-triazin-2-yl)-4-methylmorpholin-4-ium chloride (197 mg, 713 µmol). The reaction was stirred for 30 minutes at room temperature followed by addition of 3-fluoroazetidine hydrochloride (72.3 mg, 649 µmol) and the reaction mixture was stirred at 35° C. overnight. The reaction was then diluted with dichloromethane (5 mL) and washed with a 0.2M aqueous solution of hydrochloride (3×10 mL) and brine (15 mL). The organic phase was dried over magnesium sulfate and evaporated down to dryness. The crude material was purified by flash chromatography on silica eluting with a gradient of heptane/ethyl acetate to yield a white powder (72 mg) which was dissolved in dichloromethane (1 mL) followed by addition of a 2.0M solution of hydrochloric acid in diethyl ether (999 uL, 2.0 mmol). The mixture was stirred at room temperature overnight. Volatiles were removed in vacuo to give a crude amine as a hydrochloride salt (71 mg) which was used without any purification and was contaminated with a side-product where the azetidine ring had been opened by hydrochloric acid. To a solution of the acid 5-cyclopropyl-4-((3-methyloxetan-3-yl)methoxy)picolinic acid (example 215d, 20 mg, 76.0 µmol) in dichloromethane (1 ml) was added N-ethyl-N-isopropylpropan-2-amine (24.5 mg, 33.2 µl, 190 µmol) and 4-(4,6-dimethoxy-1,3,5-triazin-2-yl)-4-methylmorpholin-4-ium chloride (23.1 mg, 83.6 µmol). The reaction was stirred for 30 minutes at room temperature followed by addition of previous crude amine (17.2 mg, 76.0 µmol) and the reaction mixture was stirred at room temperature overnight. The reaction was diluted with dichloromethane (5 mL) and washed with a 0.2M aqueous solution of hydrochloric acid (3×10 mL) and brine (15 mL). The organic phase was dried over magnesium sulfate and evaporated down to dryness. The crude material was purified by flash chromatography on silica eluting with a gradient of heptane/ethyl acetate to yield the title compound (1.8 mg, 5%) as a side-product. MS (ESI, m/z): 470.7 (M+H$^+$).

Example 236

5-cyclopropyl-N-[3-hydroxy-3-methyl-1-(methylamino)-1-oxobutan-2-yl]-4-(2,2,2-trifluoroethoxy)pyridine-2-carboxamide

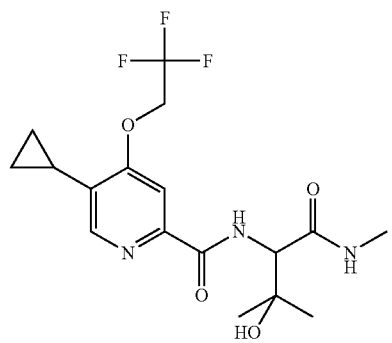 [SMILES: CNC(=O)C(NC(=O)c1cc(OCC(F)(F)F)c(C2CC2)cn1)C(C)(C)O]

a) tert-butyl N-[2-hydroxy-2-methyl-1-(methylcarbamoyl)propyl]carbamate

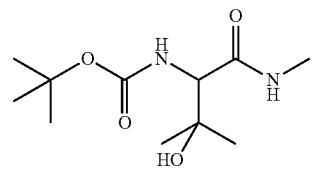 [SMILES: CNC(=O)C(NC(=O)OC(C)(C)C)C(C)(C)O]

The title compound was synthesized in analogy to Example 112e, using 2-tert-Butoxycarbonylamino-3-hydroxy-3-methyl-butyric acid (CAN 105504-72-1) and methanamine hydrochloride as starting materials and isolated (486 mg, 38%); MS (ESI, m/z): 247.2 (M+H$^+$).

b) 5-cyclopropyl-N-[3-hydroxy-3-methyl-1-(methylamino)-1-oxobutan-2-yl]-4-(2,2,2-trifluoroethoxy)pyridine-2-carboxamide

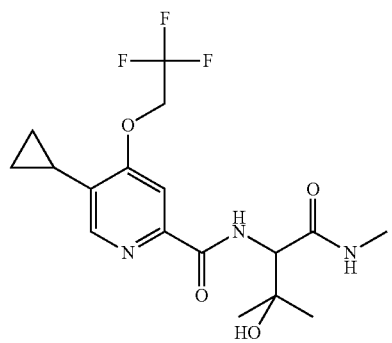 [SMILES: CNC(=O)C(NC(=O)c1cc(OCC(F)(F)F)c(C2CC2)cn1)C(C)(C)O]

To a solution of tert-butyl N-[2-hydroxy-2-methyl-1-(methylcarbamoyl)propyl]carbamate (example 236a, 760 mg, 1.94 mmol) in dichloromethane (3 ml) was added trifluoroacetic acid (3.00 ml). The reaction mixture was stirred at room temperature overnight. The reaction mixture was evaporated down to dryness and the crude residue was dissolved in toluene. Volatiles were removed in vacuo to afford a white solid which was dried in HV overnight to yield the crude amine (680 mg) as a trifluroacetate salt which was used without any purification.

The crude amine salt was used to synthesize the title compound in analogy to Example 112e, using 5-Cyclopropyl-4-(2,2,2-trifluoro-ethoxy)-pyridine-2-carboxylic acid (Example 48c) as starting materials and isolated (25 mg, 25%); MS (ESI, m/z): 390.6 (M+H⁺).

Example 237

5-cyclopropyl-N-[3-fluoro-3-methyl-1-(methylamino)-1-oxobutan-2-yl]-4-(2,2,2-trifluoroethoxy)pyridine-2-carboxamide

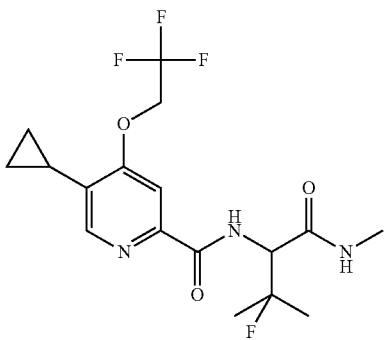 [SMILES: CNC(=O)C(NC(=O)c1cc(OCC(F)(F)F)c(C2CC2)cn1)C(C)(C)F]

To a solution of 5-cyclopropyl-N-[3-hydroxy-3-methyl-1-(methylamino)-1-oxobutan-2-yl]-4-(2,2,2-trifluoroethoxy)pyridine-2-carboxamide (example 236b, 75 mg, 193 µmol) in dry dichloromethane (2 ml) under an argon atmosphere was added DAST (38.8 mg, 31.8 µl, 241 µmol). The reaction mixture was stirred at room temperature overnight. The reaction was diluted with dichloromethane and extracted with a 1M aqueous solution of sodium bicarbonate. The organic phase was dried over sodium sulfate and evaporated down to dryness. The crude material was purified by flash chromatography on silica eluting with a heptane/ethyl acetate gradient to yield the title compound (25 mg, 33%). MS (ESI, m/z): 392.6 (M+H⁺).

Example 238

5-cyclopropyl-N-[3-hydroxy-3-methyl-1-(methylamino)-1-oxobutan-2-yl]-4-[(2S)-1,1,1-trifluoropropan-2-yl]oxypyridine-2-carboxamide

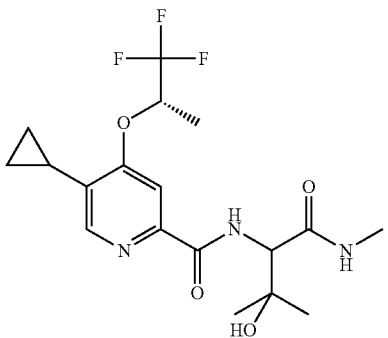 [SMILES: CNC(=O)C(NC(=O)c1cc(O[C@@H](C)C(F)(F)F)c(C2CC2)cn1)C(C)(C)O]

To a solution of tert-butyl N-[2-hydroxy-2-methyl-1-(methylcarbamoyl)propyl]carbamate (example 236a, 760 mg, 1.94 mmol) in dichloromethane (3 ml) was added trifluoroacetic acid (3.00 ml). The reaction mixture was stirred at room temperature overnight. The reaction mixture was evaporated down to dryness and the crude residue was dissolved in toluene. Volatiles were removed in vacuo to afford a white solid which was dried in HV overnight to yield the crude amine (680 mg) as a trifluroacetate salt which was used without any purification. The crude amine salt was used to synthesize the title compound in analogy to Example 112e, using 5-Cyclopropyl-4-((S)-2,2,2-trifluoro-1-methyl-ethoxy)-pyridine-2-carboxylic acid (Example 68a) as starting materials and the title compound was isolated (76 mg, 59%); MS (ESI, m/z): 404.6 (M+H⁺).

Example 239

N-(1-amino-3,3-dimethyl-1-oxobutan-2-yl)-5-cyclopropyl-4-[(2S)-1,1,1-trifluoropropan-2-yl]oxypyridine-2-carboxamide (epimer A)

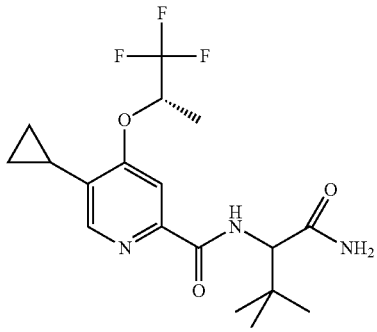 [SMILES: C[C@H](Oc1cc(C(=O)NC(C(N)=O)C(C)(C)C)ncc1C1CC1)C(F)(F)F]

The mixture of epimers (Example 199c) was separated into its individual epimers by preparative chiral HPLC (Chiralpak AD, isopropanol/heptane) and the title compound was the first epimer collected and isolated as colorless oil; MS (ESI, m/z): 388.6 (M+H⁺).

Example 240

N-(1-amino-3,3-dimethyl-1-oxobutan-2-yl)-5-cyclopropyl-4-[(2S)-1,1,1-trifluoropropan-2-yl]oxypyridine-2-carboxamide (epimer B)

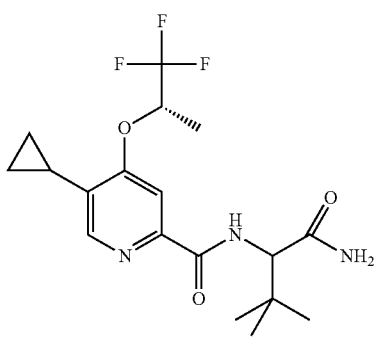 [SMILES: C[C@H](Oc1cc(C(=O)NC(C(N)=O)C(C)(C)C)ncc1C1CC1)C(F)(F)F]

The mixture of epimers (Example 199c) was separated into its individual epimers by preparative chiral HPLC (Chiralpak AD, isopropanol/heptane) and the title compound was the second epimer collected and isolated as colorless oil; MS (ESI, m/z): 388.6 (M+H⁺).

Example 241

5-cyclopropyl-N-[2-cyclopropyl-4-(methylamino)-4-oxobutan-2-yl]-4-(2,2,2-trifluoroethoxy)pyridine-2-carboxamide (enantiomer A)

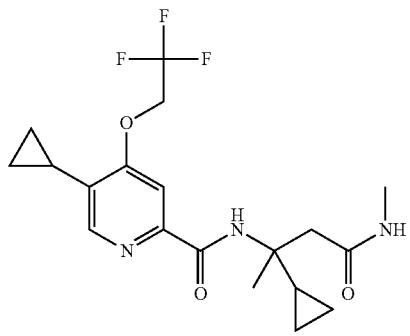

The racemate (Example 229e) was separated into its enantiomers by preparative chiral HPLC (Chiralpak AD, ethanol/heptane) and the title compound was the first enantiomer collected and isolated as colorless oil; MS (ESI, m/z): 400.6 (M+H⁺).

Example 242

5-cyclopropyl-N-[2-cyclopropyl-4-(methylamino)-4-oxobutan-2-yl]-4-(2,2,2-trifluoroethoxy)pyridine-2-carboxamide (enantiomer B)

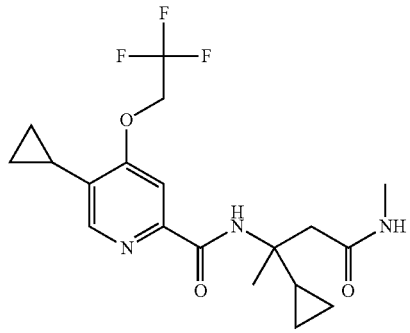

The racemate (Example 229e) was separated into its enantiomers by preparative chiral HPLC (Chiralpak AD, ethanol/heptane) and the title compound was the second enantiomer collected and isolated as colorless oil; MS (ESI, m/z): 400.6 (M+H⁺).

Example 243

N-[4-amino-2-cyclopropyl-4-oxobutan-2-yl]-5-cyclopropyl-4-(2,2,2-trifluoroethoxy)pyridine-2-carboxamide (enantiomer A)

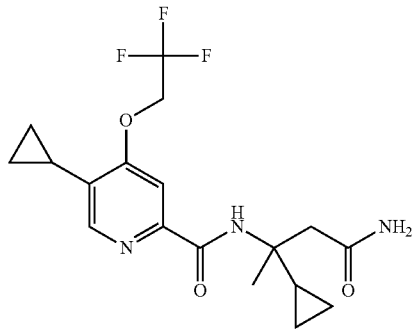 [SMILES: CC(CC(N)=O)(NC(=O)c1cc(OCC(F)(F)F)c(C2CC2)cn1)C1CC1]

The racemate (Example 230) was separated into its enantiomers by preparative chiral HPLC (Chiralpak AD, isopropanol/heptane) and the title compound was the first enantiomer collected and isolated as colorless oil; MS (ESI, m/z): 386.6 (M+H⁺).

Example 244

N-[4-amino-2-cyclopropyl-4-oxobutan-2-yl]-5-cyclopropyl-4-(2,2,2-trifluoroethoxy)pyridine-2-carboxamide (enantiomer B)

The racemate (Example 230) was separated into its enantiomers by preparative chiral HPLC (Chiralpak AD, isopropanol/heptane) and the title compound was the second enantiomer collected and isolated as colorless oil; MS (ESI, m/z): 386.6 (M+H⁺).

Example 245

5-cyclopropyl-N-[(5-methyl-1,3,4-oxadiazol-2-yl)-(3-methyloxetan-3-yl)methyl]-4-(2,2,2-trifluoroethoxy)pyridine-2-carboxamide

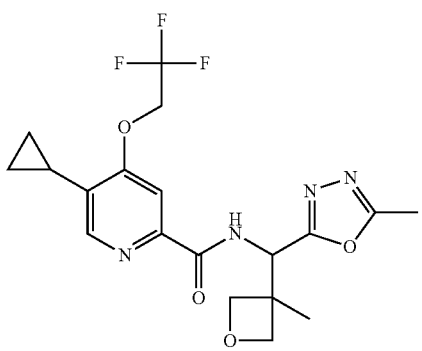 [SMILES: Cc1nnc(C(NC(=O)c2cc(OCC(F)(F)F)c(C3CC3)cn2)C2(C)COC2)o1]

a) 2-methyl-N-[(5-methyl-1,3,4-oxadiazol-2-yl)-(3-methyloxetan-3-yl)methyl]propane-2-sulfinamide

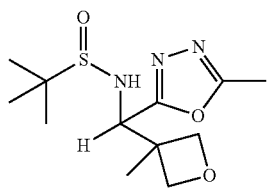 [SMILES: Cc1nnc(C(NS(=O)C(C)(C)C)C2(C)COC2)o1]

The title compound was synthesized in analogy to Example 174a, using (NE)-2-methyl-N-[(3-methyloxetan-3-yl)methylene]propane-2-sulfinamide (CAN 1450658-44-2) as starting material and isolated (1.23 g, 67%); MS (ESI, m/z): 288.5 (M+H$^+$).

b) (5-methyl-1,3,4-oxadiazol-2-yl)-(3-methyloxetan-3-yl)methanamine

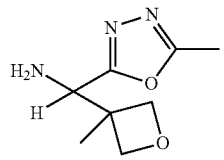

To a solution of 2-methyl-N-[(5-methyl-1,3,4-oxadiazol-2-yl)-(3-methyloxetan-3-yl)methyl]propane-2-sulfinamide (example 245a, 1.23 g, 4.28 mmol) in methanol (20 ml) was added a 4M solution of hydrochloric acid in dioxane (1.61 ml, 6.42 mmol) and the reaction mixture was stirred at room temperature for 2 hours. Reaction mixture was concentrated in vacuo and the residue was dissolved in ethyl acetate. The organic phase was extracted with 5 ml of a 2M aqueous solution of sodium carbonate. The organic phase was collected and the aqueous phase was back-extracted with ethyl acetate. The combined organic phases were dried over sodium sulfate and evaporated down to dryness. The crude material was purified by flash chromatography on silica eluting with a dichloromethane/methanol gradient to yield the title compound (179 mg, 23%). MS (ESI, m/z): 184.5 (M+H$^+$).

c) 5-cyclopropyl-N-[(5-methyl-1,3,4-oxadiazol-2-yl)-(3-methyloxetan-3-yl)methyl]-4-(2,2,2-trifluoroethoxy)pyridine-2-carboxamide

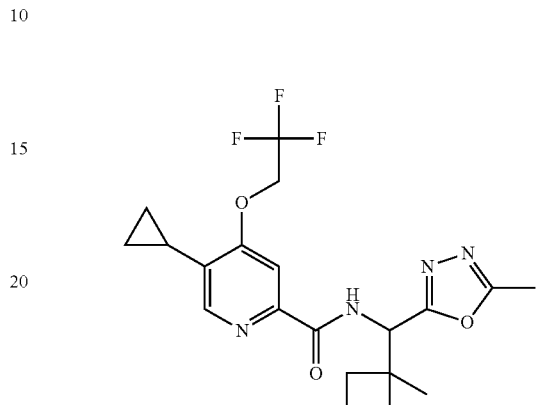

The title compound was synthesized in analogy to Example 112e, using 5-Cyclopropyl-4-(2,2,2-trifluoroethoxy)-pyridine-2-carboxylic acid (example 48c) and (5-methyl-1,3,4-oxadiazol-2-yl)-(3-methyloxetan-3-yl)methanamine (example 245b) as starting materials and isolated (25 mg, 35%); MS (ESI, m/z): 427.7 (M+H$^+$).

Example 246

5-cyclopropyl-N-[(5-methyl-1,3,4-oxadiazol-2-yl)-(3-methyloxetan-3-yl)methyl]-4-[(2S)-1,1,1-trifluoropropan-2-yl]oxypyridine-2-carboxamide

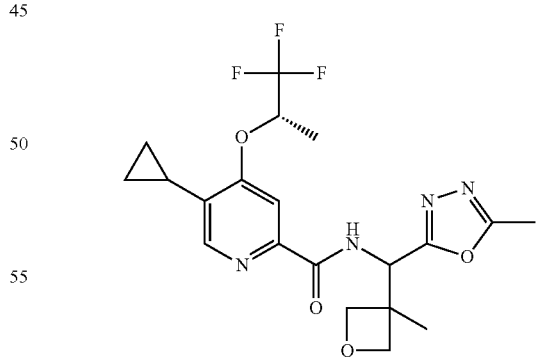

The title compound was synthesized in analogy to Example 112e, using 5-Cyclopropyl-4-((S)-2,2,2-trifluoro-1-methyl-ethoxy)-pyridine-2-carboxylic acid (example 68a) and (5-methyl-1,3,4-oxadiazol-2-yl)-(3-methyloxetan-3-yl)methanamine (example 245b) as starting materials and isolated (31 mg, 44%); MS (ESI, m/z): 441.7 (M+H$^+$).

Example 247

5-cyclopropyl-N-[2-cyclopropyl-4-(methylamino)-4-oxobutan-2-yl]-4-[(2S)-1,1,1-trifluoropropan-2-yl]oxypyridine-2-carboxamide

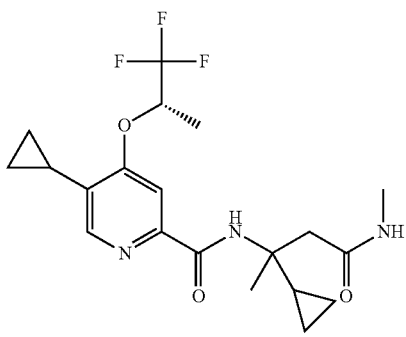

a) tert-butyl 3-cyclopropyl-3-[[5-cyclopropyl-4-[(1S)-2,2,2-trifluoro-1-methyl-ethoxy]pyridine-2-carbonyl]amino]butanoate

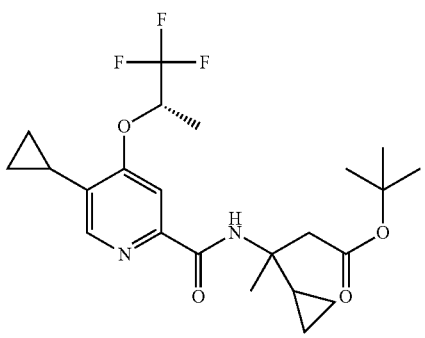 [SMILES: C[C@H](Oc1cc(C(=O)NC(C)(CC(=O)OC(C)(C)C)C2CC2)ncc1C1CC1)C(F)(F)F]

The title compound was synthesized in analogy to Example 112e, using 5-Cyclopropyl-4-((S)-2,2,2-trifluoro-1-methyl-ethoxy)-pyridine-2-carboxylic acid (example 68a) and tert-butyl 3-amino-3-cyclopropyl-butanoate (example 229b) as starting materials and isolated (467 mg, 56%); MS (ESI, m/z): 457.6 (M+H⁺).

b) 3-cyclopropyl-3-[[5-cyclopropyl-4-[(1S)-2,2,2-trifluoro-1-methyl-ethoxy]pyridine-2-carbonyl]amino]butanoic acid

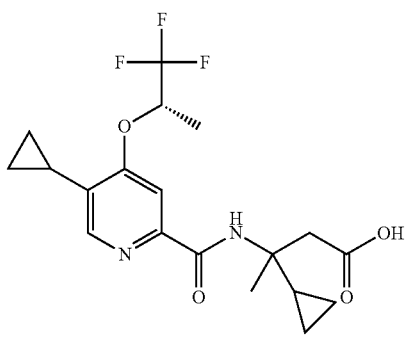 [SMILES: C[C@H](Oc1cc(C(=O)NC(C)(CC(=O)O)C2CC2)ncc1C1CC1)C(F)(F)F]

The title compound was synthesized in analogy to Example 229d, using tert-butyl 3-cyclopropyl-3-[[5-cyclopropyl-4-[(1S)-2,2,2-trifluoro-1-methyl-ethoxy]pyridine-2-carbonyl]amino]butanoate (example 247a) as starting material and isolated (424 mg) as a crude solid; MS (ESI, m/z): 401.2 (M+H⁺).

c) 5-cyclopropyl-N-[2-cyclopropyl-4-(methylamino)-4-oxobutan-2-yl]-4-[(2S)-1,1,1-trifluoropropan-2-yl]oxypyridine-2-carboxamide

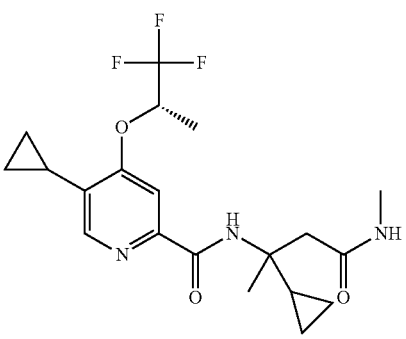 [SMILES: CNC(=O)CC(C)(NC(=O)c1cc(O[C@@H](C)C(F)(F)F)c(C2CC2)cn1)C1CC1]

The title compound was synthesized in analogy to Example 112e, using 3-cyclopropyl-3-[[5-cyclopropyl-4-[(1S)-2,2,2-trifluoro-1-methyl-ethoxy]pyridine-2-carbonyl]amino]butanoic acid (example 247b) and methanamine hydrochloride as starting materials and isolated (180 mg, 83%); MS (ESI, m/z): 414.2 (M+H⁺).

Example 248

N-(4-amino-2-cyclopropyl-4-oxobutan-2-yl)-5-cyclopropyl-4-[(2S)-1,1,1-trifluoropropan-2-yl]oxypyridine-2-carboxamide

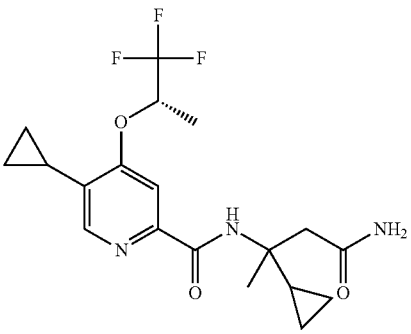 [SMILES: C[C@H](Oc1cc(C(=O)NC(C)(CC(N)=O)C2CC2)ncc1C1CC1)C(F)(F)F]

The title compound was synthesized in analogy to Example 112e, using 3-cyclopropyl-3-[[5-cyclopropyl-4-[(1S)-2,2,2-trifluoro-1-methyl-ethoxy]pyridine-2-carbonyl]amino]butanoic acid (example 247b) and ammonium chloride as starting materials and isolated (150 mg, 72%); MS (ESI, m/z): 400.2 (M+H⁺).

Example 249

5-cyclopropyl-N-[2-cyclopropyl-4-(methylamino)-4-oxobutan-2-yl]-4-[(2S)-1,1,1-trifluoropropan-2-yl]oxypyridine-2-carboxamide (epimer A)

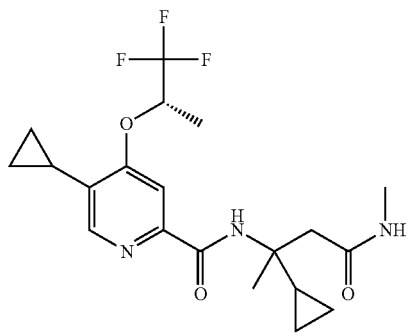 [SMILES: CNC(=O)CC(C)(NC(=O)c1cc(O[C@@H](C)C(F)(F)F)c(C2CC2)cn1)C1CC1]

The mixture of epimers (Example 247c) was separated into its individual epimers by preparative chiral HPLC (Chiralpak AD, ethanol/heptane) and the title compound was the first epimer collected and isolated as colorless oil; MS (ESI, m/z): 414.3 (M+H$^+$).

Example 250

5-cyclopropyl-N-[2-cyclopropyl-4-(methylamino)-4-oxobutan-2-yl]-4-[(2S)-1,1,1-trifluoropropan-2-yl]oxypyridine-2-carboxamide (epimer B)

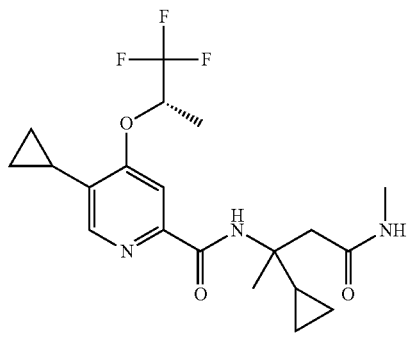 [SMILES: CNC(=O)CC(C)(NC(=O)c1cc(O[C@@H](C)C(F)(F)F)c(C2CC2)cn1)C1CC1]

The mixture of epimers (Example 247c) was separated into its individual epimers by preparative chiral HPLC (Chiralpak AD, ethanol/heptane) and the title compound was the second epimer collected and isolated as colorless oil; MS (ESI, m/z): 414.3 (M+H$^+$).

Example 251

N-[2-amino-1-(3-methyloxetan-3-yl)-2-oxoethyl]-5-cyclopropyl-4-[(2S)-1,1,1-trifluoropropan-2-yl]oxy-pyridine-2-carboxamide (enantiomer B)

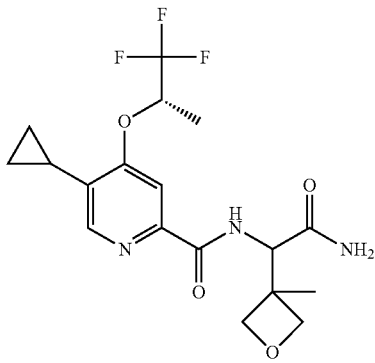 [SMILES: C[C@H](Oc1cc(C(=O)NC(C(N)=O)C2(C)COC2)ncc1C1CC1)C(F)(F)F]

a) N-[cyano-(3-methyloxetan-3-yl)methyl]-2-methyl-propane-2-sulfinamide

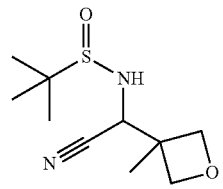

To a solution of (NE)-2-methyl-N-[(3-methyloxetan-3-yl)methylene]propane-2-sulfinamide (CAN 1450658-44-2, 1.3 g, 6.39 mmole) in dry THF (35 ml) under argon atmosphere was added cesium fluoride (1.17 g, 7.67 mmol) followed by trimethylsilyl cyanide (761 mg, 1.03 ml, 7.67 mmol). The reaction mixture was stirred at room temperature for 4 hours. The reaction mixture was concentrated in vacuo followed by dilution with ethylacetate. The organic phase was extracted with water and brine. The organic phase was dried over sodium sulfate and evaporated down to dryness. The crude material was purified by flash chromatography on silica eluting with a heptane/ethyl acetate gradient to yield the title compound (1.21 g, 82%). MS (ESI, m/z): 231.6 (M+H$^+$).

b) 2-amino-2-(3-methyloxetan-3-yl)acetonitrile

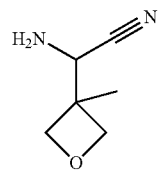

To a solution of N-[cyano-(3-methyloxetan-3-yl)methyl]-2-methyl-propane-2-sulfinamide (example 251a, 1.5 g, 6.51 mmol) in methanol (40 ml) cooled at 0° C. was added a solution of hydrochloric acid in dioxane (2.44 ml, 9.77 mmol)

and the reaction mixture was stirred at 0° C. for 2 hours. Triethylamine (1.32 g, 1.82 ml, 13.0 mmol) was added to the reaction mixture which was then concentrated in vacuo. The residue was directly purified by flash chromatography on silica eluting with a dichloromethane/methanol gradient to yield the title compound (854 mg) as a yellow oil which was not totally pure and was used without any further purification. MS (ESI, m/z): 127.1 (M+H$^+$).

c) N-[cyano-(3-methyloxetan-3-yl)methyl]-5-cyclopropyl-4-[(1S)-2,2,2-trifluoro-1-methyl-ethoxy]pyridine-2-carboxamide

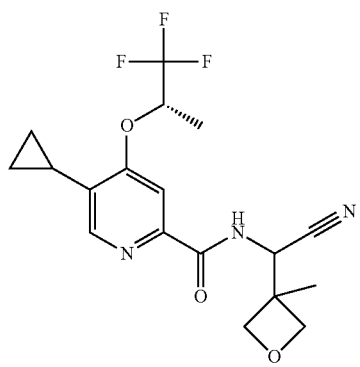 [SMILES: C[C@H](Oc1cc(C(=O)NC(C#N)C2(C)COC2)ncc1C1CC1)C(F)(F)F]

The title compound was synthesized in analogy to Example 112e, using 5-Cyclopropyl-4-((S)-2,2,2-trifluoro-1-methyl-ethoxy)-pyridine-2-carboxylic acid (example 68a) and 2-amino-2-(3-methyloxetan-3-yl)acetonitrile (example 251b) as starting materials and isolated (180 mg, 83%); MS (ESI, m/z): 384.6 (M+H$^+$).

d) N-[2-amino-1-(3-methyloxetan-3-yl)-2-oxoethyl]-5-cyclopropyl-4-[(2S)-1,1,1-trifluoropropan-2-yl]oxypyridine-2-carboxamide (epimer B)

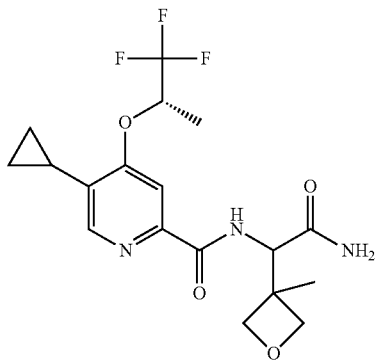 [SMILES: C[C@H](Oc1cc(C(=O)NC(C(N)=O)C2(C)COC2)ncc1C1CC1)C(F)(F)F]

To a solution of N-[cyano-(3-methyloxetan-3-yl)methyl]-5-cyclopropyl-4-[(1S)-2,2,2-trifluoro-1-methyl-ethoxy]pyridine-2-carboxamide (example 251c, 0.17 g, 443 µmol) in ethanol (3 ml) was added a 4M aqueous solution of sodium hydroxide (554 µl, 2.22 mmol) and H2O2 35% aqueous solution (215 mg, 190 µl, 2.22 mmol). The reaction mixture was stirred at room temperature overnight. The reaction was then concentrated in vacuo and diluted with ethyl acetate. The organic phase was extracted with a 1M aqueous solution of sodium bicarbonate. The organic phase was collected and the aqueous phase was back-extracted with ethyl acetate. The combined organic phases were dried over sodium sulfate and evaporated down to dryness. The crude material was purified by flash chromatography on silica eluting with a heptane-ethyl acetate gradient to yield the mixture of epimers which was then separated into its individual epimers by preparative chiral HPLC (Chiralpak AD, ethanol/heptane) and the title compound was the second epimer collected and isolated as colorless oil; MS (ESI, m/z): 402.6 (M+H$^+$).

Example 252

5-cyclopropyl-N-[3-hydroxy-3-methyl-1-(methylamino)-1-oxobutan-2-yl]-4-[(2S)-1,1,1-trifluoropropan-2-yl]oxypyridine-2-carboxamide (epimer A)

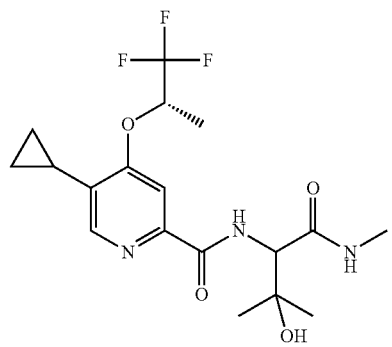 [SMILES: CNC(=O)C(NC(=O)c1cc(O[C@@H](C)C(F)(F)F)c(C2CC2)cn1)C(C)(C)O]

The mixture of epimers (Example 238) was separated into its individual epimers by preparative chiral HPLC (Chiralpak AD, ethanol/heptane) and the title compound was the first epimer collected and isolated as colorless oil; MS (ESI, m/z): 404.3 (M+H$^+$).

Example 253

5-cyclopropyl-N-[3-hydroxy-3-methyl-1-(methylamino)-1-oxobutan-2-yl]-4-[(2S)-1,1,1-trifluoropropan-2-yl]oxypyridine-2-carboxamide (epimer B)

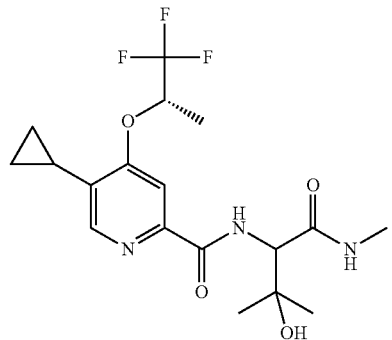 [SMILES: CNC(=O)C(NC(=O)c1cc(O[C@@H](C)C(F)(F)F)c(C2CC2)cn1)C(C)(C)O]

The mixture of epimers (Example 238) was separated into its individual epimers by preparative chiral HPLC (Chiralpak AD, ethanol/heptane) and the title compound was the second epimer collected and isolated as colorless oil; MS (ESI, m/z): 404.3 (M+H$^+$).

Example 254

5-cyclopropyl-N-[(5-methyl-1,2,4-oxadiazol-3-yl)-(3-methyloxetan-3-yl)methyl]-4-[(2S)-1,1,1-trifluoropropan-2-yl]oxypyridine-2-carboxamide (epimer A)

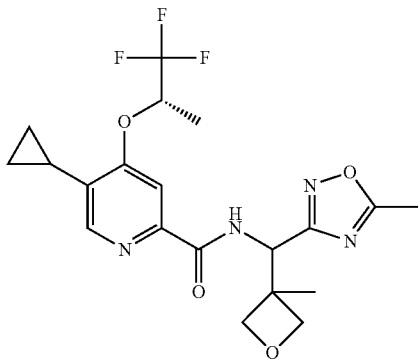 [SMILES: Cc1nc(C(NC(=O)c2cc(O[C@@H](C)C(F)(F)F)c(C3CC3)cn2)C2(C)COC2)no1]

a) 2-(tert-butylsulfinylamino)-N'-hydroxy-2-(3-methyloxetan-3-yl)acetamidine

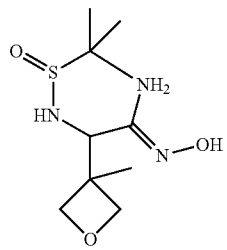 [SMILES: CC1(C2NS(=O)C(C)(C)N/C2=N\O)COC1]

To a solution of N-[cyano-(3-methyloxetan-3-yl)methyl]-2-methyl-propane-2-sulfinamide (example 251a, 680 mg, 2.95 mmol) in Ethanol (15 ml) was added potassium carbonate (408 mg, 2.95 mmol) and hydroxylamine hydrochloride (226 mg, 3.25 mmol). The reaction mixture was stirred at room temperature for 30 minutes followed by stirring at 50° C. overnight. The reaction was diluted with ethanol and sonicated a few minutes followed by removal of insolubles by filtration. The filtrate was concentrated in vacuo to dryness to yield a crude yellow gum of the title compound (892 mg) which was used without any purification. MS (ESI, m/z): 264.3 (M+H$^+$).

b) (5-methyl-1,2,4-oxadiazol-3-yl)-(3-methyloxetan-3-yl)methanamine

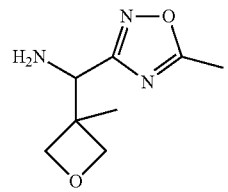

To a solution of 2-(tert-butylsulfinylamino)-N'-hydroxy-2-(3-methyloxetan-3-yl)acetamidine (example 254a, 0.25 g, 949 µmol) in isopropanol (5.00 ml) was added 1,1-dimethoxy-N,N-dimethylethanamine (506 mg, 3.8 mmol) and the reaction mixture was stirred at room temperature overnight. A solution of 4M hydrochloric acid in dioxane (1.19 ml, 4.75 mmol) was added to the reaction mixture cooled down to 0° C. and the reaction was stirred at 0° C. for 2 hours. The reaction mixture was diluted with ethyl acetate and extracted with a 2M aqueous solution of sodium carbonate. The organic phase was collected and the aqueous phase was back-extracted with ethyl acetate. The combined organic phases were dried over sodium sulfate and evaporated down to dryness. The crude material was purified by flash chromatography on silica eluting with a dichloromethane-methanol gradient to yield the title compound (35 mg, 20%) as a yellow oil which was not totally pure and was used without any further purification. MS (ESI, m/z): 184.1 (M+H$^+$).

c) 5-cyclopropyl-N-[(5-methyl-1,2,4-oxadiazol-3-yl)-(3-methyloxetan-3-yl)methyl]-4-[(2S)-1,1,1-trifluoropropan-2-yl]oxypyridine-2-carboxamide

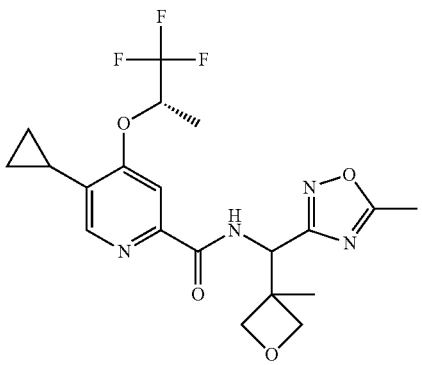 [SMILES: Cc1nc(C(NC(=O)c2cc(O[C@@H](C)C(F)(F)F)c(C3CC3)cn2)C2(C)COC2)no1]

The title compound was synthesized in analogy to Example 112e, using 5-Cyclopropyl-4-((S)-2,2,2-trifluoro-1-methyl-ethoxy)-pyridine-2-carboxylic acid (example 68a) and (5-methyl-1,2,4-oxadiazol-3-yl)-(3-methyloxetan-3-yl)methanamine (example 254b) as starting materials and isolated (47 mg, 55%); MS (ESI, m/z): 441.3 (M+H$^+$).

d) 5-cyclopropyl-N-[(5-methyl-1,2,4-oxadiazol-3-yl)-(3-methyloxetan-3-yl)methyl]-4-[(2S)-1,1,1-trifluoropropan-2-yl]oxypyridine-2-carboxamide (epimer A)

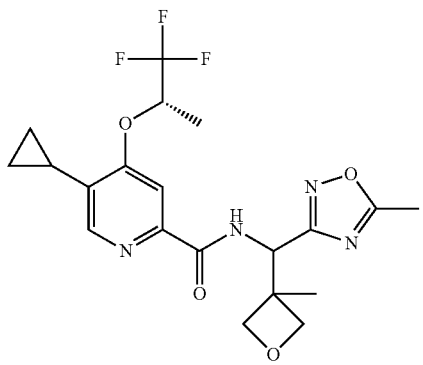 [SMILES: Cc1nc(C(NC(=O)c2cc(O[C@@H](C)C(F)(F)F)c(C3CC3)cn2)C2(C)COC2)no1]

The mixture of epimers (Example 254c) was separated into its individual epimers by preparative chiral HPLC (Chiralpak AD, isopropanol/heptane) and the title compound was the first epimer collected and isolated as colorless oil; MS (ESI, m/z): 441.3 (M+H$^+$).

Example 255

5-cyclopropyl-N-[(5-methyl-1,2,4-oxadiazol-3-yl)-(3-methyloxetan-3-yl)methyl]-4-[(2S)-1,1,1-trifluoropropan-2-yl]oxypyridine-2-carboxamide (epimer B)

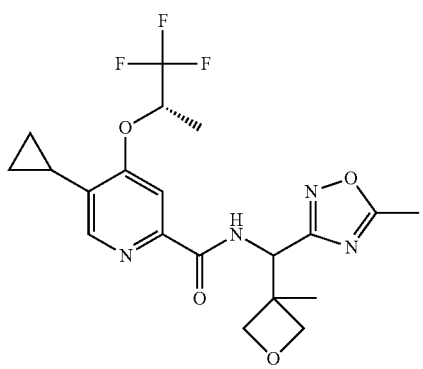 [SMILES: Cc1nc(C(NC(=O)c2cc(O[C@@H](C)C(F)(F)F)c(C3CC3)cn2)C2(C)COC2)no1]

The mixture of epimers (Example 254c) was separated into its individual epimers by preparative chiral HPLC (Chiralpak AD, isopropanol/heptane) and the title compound was the second epimer collected and isolated as colorless oil; MS (ESI, m/z): 441.3 (M+H$^+$).

Example 256

N-(1-amino-3,3-dimethyl-1-oxobutan-2-yl)-5-(3,3-difluoroazetidin-1-yl)-4-(2,2,2-trifluoroethoxy)pyridine-2-carboxamide

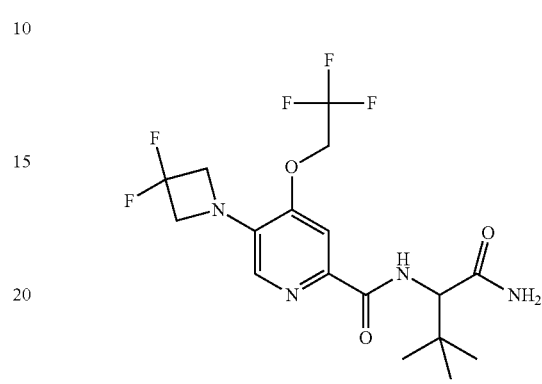

The title compound was synthesized in analogy to Example 112e, using 5-(3,3-difluoroazetidin-1-yl)-4-(2,2,2-trifluoroethoxy)pyridine-2-carboxylic acid (example 223b) and 2-Amino-3,3-dimethyl-butyramide; hydrochloride (CAN 113582-42-6) as starting materials and isolated (32 mg, 47%); MS (ESI, m/z): 425.3 (M+H$^+$).

Example 257

N-(1-amino-3,3-dimethyl-1-oxobutan-2-yl)-4-(cyclopropylmethoxy)-5-(3,3-difluoroazetidin-1-yl)pyridine-2-carboxamide

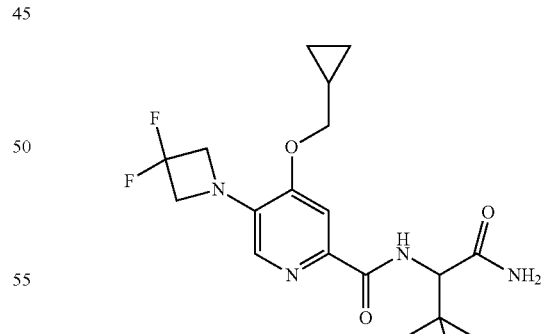

The title compound was synthesized in analogy to Example 112e, using 4-Cyclopropylmethoxy-5-(3,3-difluoro-azetidin-1-yl)-pyridine-2-carboxylic acid (example 53e) and 2-Amino-3,3-dimethyl-butyramide; hydrochloride (CAN 113582-42-6) as starting materials and isolated (58 mg, 83%); MS (ESI, m/z): 397.3 (M+H$^+$).

Example 258

N-(4-amino-2-cyclopropyl-4-oxobutan-2-yl)-5-cyclopropyl-4-[(2S)-1,1,1-trifluoropropan-2-yl]oxypyridine-2-carboxamide (epimer A)

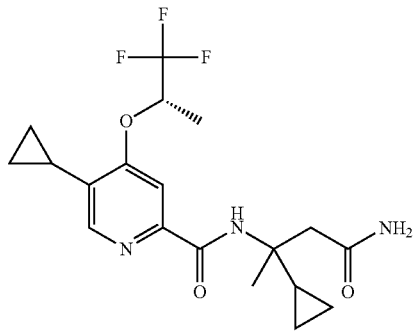 [SMILES: C[C@H](Oc1cc(C(=O)NC(C)(CC(N)=O)C2CC2)ncc1C1CC1)C(F)(F)F]

The mixture of epimers (Example 248) was separated into its individual epimers by preparative chiral HPLC (Lux 5u Amylose-2, isopropanol/heptane) and the title compound was the first epimer collected and isolated as colorless oil; MS (ESI, m/z): 400.2 (M+H⁺).

Example 259

N-(4-amino-2-cyclopropyl-4-oxobutan-2-yl)-5-cyclopropyl-4-[(2S)-1,1,1-trifluoropropan-2-yl]oxypyridine-2-carboxamide (epimer B)

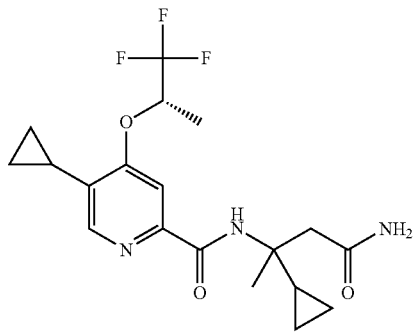 [SMILES: C[C@H](Oc1cc(C(=O)NC(C)(CC(N)=O)C2CC2)ncc1C1CC1)C(F)(F)F]

The mixture of epimers (Example 248) was separated into its individual epimers by preparative chiral HPLC (Lux 5u Amylose-2, isopropanol/heptane) and the title compound was the second epimer collected and isolated as colorless oil; MS (ESI, m/z): 400.2 (M+H⁺).

Example 260

N-[1-amino-3,3-dimethyl-1-oxobutan-2-yl]-4-(cyclopropylmethoxy)-5-(3,3-difluoroazetidin-1-yl)pyridine-2-carboxamide (enantiomer A)

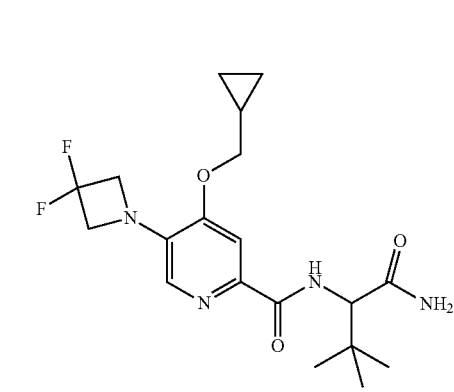 [SMILES: CC(C)(C)C(NC(=O)c1cc(OCC2CC2)c(N2CC(F)(F)C2)cn1)C(N)=O]

The racemate (Example 257) was separated into its enantiomers by preparative chiral HPLC (Reprosil Chiral NR, ethanol/heptane) and the title compound was the first enantiomer collected and isolated as colorless oil; MS (ESI, m/z): 397.3 (M+H⁺).

Example 261

N-[1-amino-3,3-dimethyl-1-oxobutan-2-yl]-4-(cyclopropylmethoxy)-5-(3,3-difluoroazetidin-1-yl)pyridine-2-carboxamide (enantiomer B)

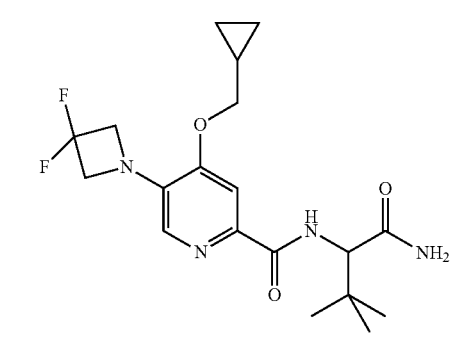 [SMILES: CC(C)(C)C(NC(=O)c1cc(OCC2CC2)c(N2CC(F)(F)C2)cn1)C(N)=O]

The racemate (Example 257) was separated into its enantiomers by preparative chiral HPLC (Reprosil Chiral NR, ethanol/heptane) and the title compound was the second enantiomer collected and isolated as colorless oil; MS (ESI, m/z): 397.3 (M+H⁺).

Example 262

N-[1-amino-3,3-dimethyl-1-oxobutan-2-yl]-5-(3,3-difluoroazetidin-1-yl)-4-(2,2,2-trifluoroethoxy)pyridine-2-carboxamide (enantiomer A)

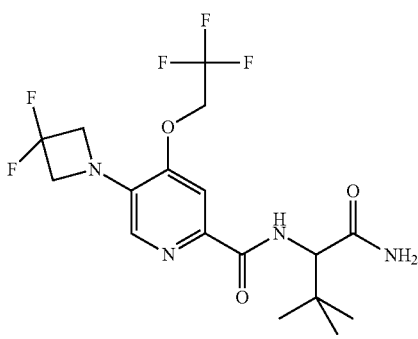 [SMILES: CC(C)(C)C(NC(=O)c1cc(OCC(F)(F)F)c(N2CC(F)(F)C2)cn1)C(N)=O]

The racemate (Example 256) was separated into its enantiomers by preparative chiral HPLC (Reprosil Chiral NR, ethanol/heptane) and the title compound was the first enantiomer collected and isolated as colorless oil; MS (ESI, m/z): 425.3 (M+H$^+$).

Example 263

N-[1-amino-3,3-dimethyl-1-oxobutan-2-yl]-5-(3,3-difluoroazetidin-1-yl)-4-(2,2,2-trifluoroethoxy)pyridine-2-carboxamide (enantiomer B)

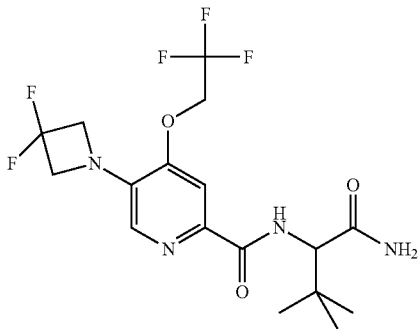 [SMILES: CC(C)(C)C(NC(=O)c1cc(OCC(F)(F)F)c(N2CC(F)(F)C2)cn1)C(N)=O]

The racemate (Example 256) was separated into its enantiomers by preparative chiral HPLC (Reprosil Chiral NR, ethanol/heptane) and the title compound was the second enantiomer collected and isolated as colorless oil; MS (ESI, m/z): 425.3 (M+H$^+$).

Example 264

N-[3-(2-amino-2-oxoethyl)-1,1-dioxothietan-3-yl]-5-(3,3-difluoroazetidin-1-yl)-4-(2,2,2-trifluoroethoxy)pyridine-2-carboxamide

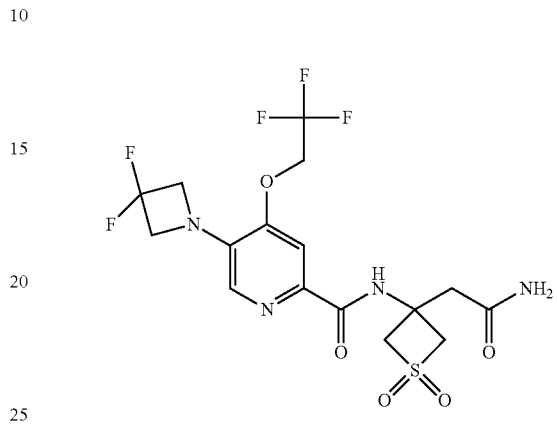

The title compound was synthesized in analogy to Example 112e, using 5-(3,3-difluoroazetidin-1-yl)-4-(2,2,2-trifluoroethoxy)pyridine-2-carboxylic acid (example 223b) and 2-(3-amino-1,1-dioxo-thietan-3-yl)acetamide (example 160d) as starting materials and isolated (20 mg, 27%); MS (ESI, m/z): 473.3 (M+H$^+$).

Example 265

N-[3-(2-amino-2-oxoethyl)-1,1-dioxothietan-3-yl]-5-(3-fluorooxetan-3-yl)-4-[(2S)-1,1,1-trifluoropropan-2-yl]oxypyridine-2-carboxamide

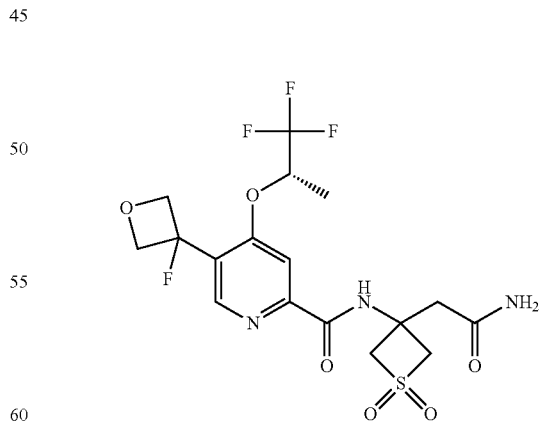

The title compound was synthesized in analogy to Example 112e, using 5-(3-fluorooxetan-3-yl)-4-[(1S)-2,2,2-trifluoro-1-methyl-ethoxy]pyridine-2-carboxylic acid (example 142b) and 2-(3-amino-1,1-dioxo-thietan-3-yl)acetamide (example 160d) as starting materials and isolated (9.3 mg, 12%); MS (ESI, m/z): 470.3 (M+H⁺).

Example 266

N-[3-(2-amino-2-oxoethyl)-1,1-dioxothietan-3-yl]-5-cyclopropyl-4-[(2S)-1,1,1-trifluoropropan-2-yl]oxy-pyridine-2-carboxamide

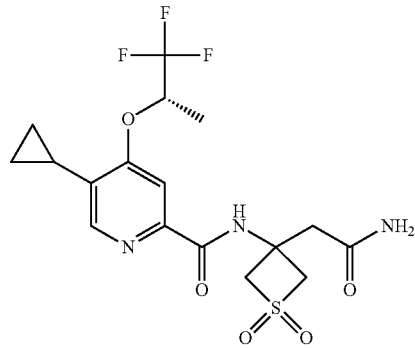 [SMILES: C[C@H](Oc1cc(C(=O)NC2(CC(N)=O)CS(=O)(=O)C2)ncc1C1CC1)C(F)(F)F]

The title compound was synthesized in analogy to Example 112e, using 5-Cyclopropyl-4-((S)-2,2,2-trifluoro-1-methyl-ethoxy)-pyridine-2-carboxylic acid (example 68a) and 2-(3-amino-1,1-dioxo-thietan-3-yl)acetamide (example 160d) as starting materials and isolated (19.3 mg, 28%); MS (ESI, m/z): 436.3 (M+H⁺).

Example 267

N-[3-(2-amino-2-oxoethyl)-1,1-dioxothietan-3-yl]-4-(cyclopropylmethoxy)-5-(3,3-difluoroazetidin-1-yl)pyridine-2-carboxamide

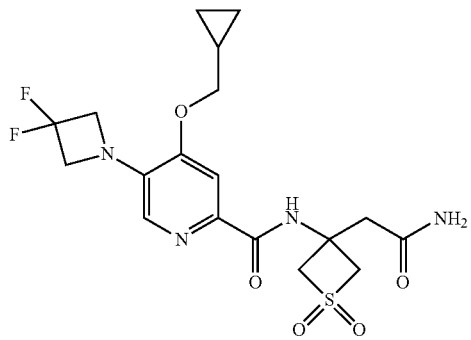 [SMILES: NC(=O)CC1(NC(=O)c2cc(OCC3CC3)c(N3CC(F)(F)C3)cn2)CS(=O)(=O)C1]

The title compound was synthesized in analogy to Example 112e, using 4-Cyclopropylmethoxy-5-(3,3-difluoro-azetidin-1-yl)-pyridine-2-carboxylic acid (example 53e) and 2-(3-amino-1,1-dioxo-thietan-3-yl)acetamide (example 160d) as starting materials and isolated (35 mg, 42%); MS (ESI, m/z): 445.3 (M+H⁺).

Example 268

N-[2-amino-1-(3-methyloxetan-3-yl)-2-oxoethyl]-5-cyclopropyl-4-(2,2,2-trifluoroethoxy)pyridine-2-carboxamide (enantiomer A)

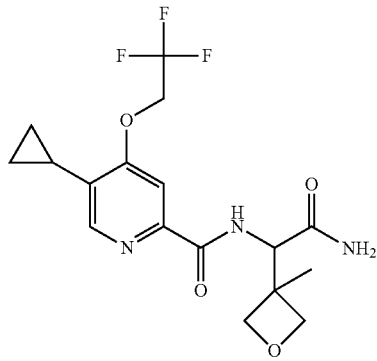 [SMILES: CC1(C(NC(=O)c2cc(OCC(F)(F)F)c(C3CC3)cn2)C(N)=O)COC1]

a) N-[cyano-(3-methyloxetan-3-yl)methyl]-5-cyclopropyl-4-(2,2,2-trifluoroethoxy)pyridine-2-carboxamide

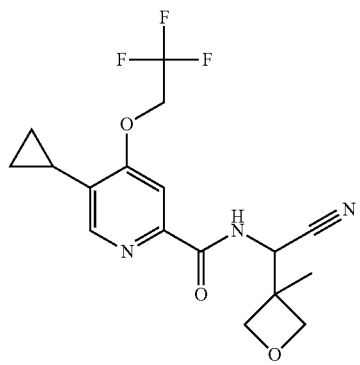 [SMILES: CC1(C(C#N)NC(=O)c2cc(OCC(F)(F)F)c(C3CC3)cn2)COC1]

The title compound was synthesized in analogy to Example 112e, using 5-Cyclopropyl-4-(2,2,2-trifluoroethoxy)-pyridine-2-carboxylic acid (example 48c) and 2-amino-2-(3-methyloxetan-3-yl)acetonitrile (example 251b) as starting materials and isolated (105 mg, 85%); MS (ESI, m/z): 370.3 (M+H⁺).

b) N-[2-amino-1-(3-methyloxetan-3-yl)-2-oxoethyl]-5-cyclopropyl-4-(2,2,2-trifluoroethoxy)pyridine-2-carboxamide

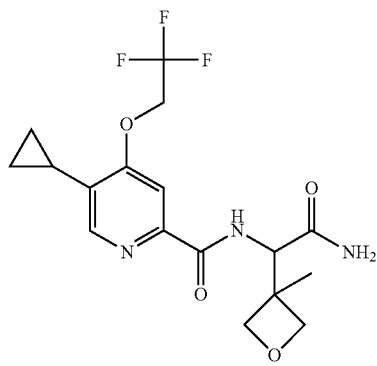 [SMILES: CC1(C(NC(=O)c2cc(OCC(F)(F)F)c(C3CC3)cn2)C(N)=O)COC1]

The title compound was synthesized in analogy to Example 251d, using N-[cyano-(3-methyloxetan-3-yl)methyl]-5-cyclopropyl-4-(2,2,2-trifluoroethoxy)pyridine-2-carboxamide (example 268a) as starting material and isolated (79 mg, 72%); MS (ESI, m/z): 388.3 (M+H⁺).

c) N-[2-amino-1-(3-methyloxetan-3-yl)-2-oxoethyl]-5-cyclopropyl-4-(2,2,2-trifluoroethoxy)pyridine-2-carboxamide (enantiomer A)

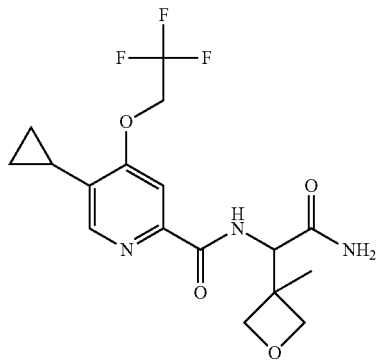 [SMILES: CC1(C(NC(=O)c2cc(OCC(F)(F)F)c(C3CC3)cn2)C(N)=O)COC1]

The racemate (Example 268b) was separated into its enantiomers by preparative chiral HPLC (Reprosil Chiral NR, isopropanol/heptane) and the title compound was the first enantiomer collected and isolated as colorless oil; MS (ESI, m/z): 388.6 (M+H⁺).

Example 269

N-[2-amino-1-(3-methyloxetan-3-yl)-2-oxoethyl]-5-cyclopropyl-4-(2,2,2-trifluoroethoxy)pyridine-2-carboxamide (enantiomer B)

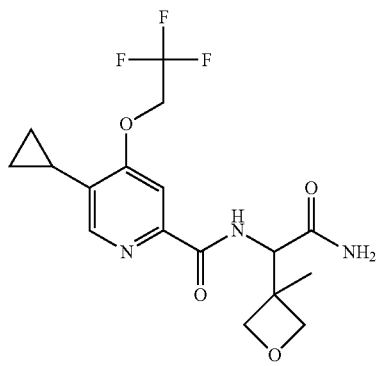 [SMILES: CC1(C(NC(=O)c2cc(OCC(F)(F)F)c(C3CC3)cn2)C(N)=O)COC1]

The racemate (Example 268b) was separated into its enantiomers by preparative chiral HPLC (Reprosil Chiral NR, isopropanol/heptane) and the title compound was the second enantiomer collected and isolated as colorless oil; MS (ESI, m/z): 388.6 (M+H⁺).

Example 270

N-[4-amino-2-cyclopropyl-4-oxobutan-2-yl]-5-cyclopropyl-4-(2-fluoroethoxy)pyridine-2-carboxamide (enantiomer A)

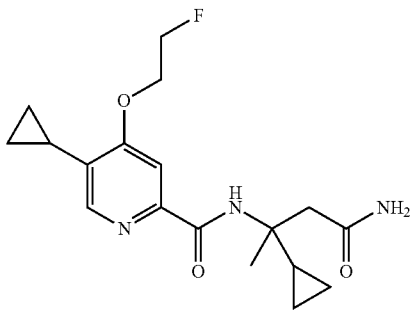 [SMILES: CC(CC(N)=O)(NC(=O)c1cc(OCCF)c(C2CC2)cn1)C1CC1]

a) ethyl 3-(tert-butylsulfinylamino)-3-cyclopropyl-butanoate

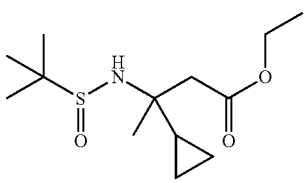 [SMILES: CCOC(=O)CC(C)(NS(=O)C(C)(C)C)C1CC1]

To a flask containing zinc (Note: the zinc powder was activated by stirring 10 gr in 20 mL of 2.0M aqueous solution HCl (caution: strong exotherm occurs)) (3.49 g, 53.4 mmol) and copper (I) chloride (529 mg, 5.34 mmol) under a stream of argon was added dry THF (10.0 ml), the suspension was stirred at reflux for 30 minutes then the heating bath was removed. Slow addition of a solution of ethyl 2-bromoacetate (1.78 g, 10.7 mmol, Eq: 2.0) in dry THF (5.00 ml) (caution: reaction exothermic), when addition completed the suspension was stirred for 30 min at rt then 30 min at 50° C. The reaction was then cooled down to 0° C. and a solution of (E)-N-(1-cyclopropylethylidene)-2-methylpropane-2-sulfinamide (1 g, 5.34 mmol) in dry THF (5.00 ml) was added to the reaction. The reaction was then stirred at 0° C. and let to warm up to room temperature overnight. The reaction mixture was filtered through a pad of Celite and the filter pad was washed twice with ethyl acetate. The filtrate was washed with a 0.25M aqueous solution of citric acid, a 1M aqueous solution of sodium bicarbonate. The organic phase was dried over sodium sulfate and concentrated in vacuo. The crude material was purified by flash chromatography on silica eluting with a gradient of heptane/ethyl acetate to yield the title compound (1.16 g, 79%) as a yellow oil; MS (ESI, m/z): 276.3 (M+H⁺).

b) 3-(tert-butylsulfinylamino)-3-cyclopropyl-butanamide

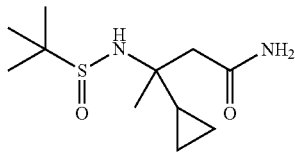 [SMILES: CC(CC(N)=O)(NS(=O)C(C)(C)C)C1CC1]

A solution of ethyl 3-cyclopropyl-3-(1,1-dimethylethylsulfinamido)butanoate (1.16 g, 4.21 mmol) in ammonia 7N in methanol (20 ml, 140 mmol) in a microwave sealed tube was stirred at 45° C. overnight. The volatiles were removed in vacuo and the residue was directly purified by flash chromatography on silica eluting with a gradient of dichloromethane/methanol to yield the title compound (155 mg, 15%); MS (ESI, m/z): 247.2 (M+H$^+$).

c) 3-amino-3-cyclopropyl-butanamide

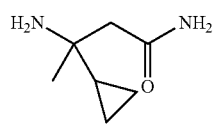

To a solution of 3-cyclopropyl-3-(1,1-dimethylethylsulfinamido)butanamide (442 mg, 1.79 mmol) in methanol (8 ml) was added a 4.0M solution of hydrochloric acid in dioxane (1.35 ml, 5.38 mmol) and the reaction mixture was stirred at room temperature for 1 h. Volatiles were removed in vacuo and the residue was dissolved in ethyl acetate. The organic phase was extracted with a 2M aqueous solution of sodium carbonate. The organic phase was collected and the aqueous phase was back-extracted with ethyl acetate. The combined organic phases were dried over sodium sulfate and evaporated down to dryness. The crude material was purified by flash chromatography on silica eluting with a gradient of dichloromethane/(solution of 3% aq. NH3 in methanol) to yield the title compound (213 mg, 83%); MS (ESI, m/z): 143.1 (M+H$^+$).

d) N-(3-amino-1-cyclopropyl-1-methyl-3-oxo-propyl)-5-cyclopropyl-4-(2-fluoroethoxy)pyridine-2-carboxamide

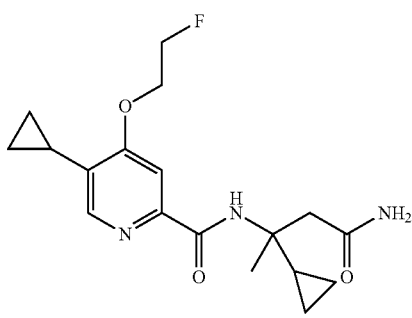 [SMILES: CC(CC(N)=O)(NC(=O)c1cc(OCCF)c(C2CC2)cn1)C1CC1]

The title compound was synthesized in analogy to Example 112e, using 5-cyclopropyl-4-(2-fluoroethoxy)pyridine-2-carboxylic acid (example 146b) and 3-amino-3-cyclopropyl-butanamide (example 270c) as starting materials and isolated (65 mg, 56%) as; MS (ESI, m/z): 350.3 (M+H$^+$).

e) N-[4-amino-2-cyclopropyl-4-oxobutan-2-yl]-5-cyclopropyl-4-(2-fluoroethoxy)pyridine-2-carboxamide (enantiomer A)

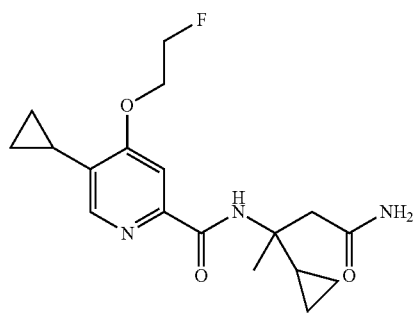 [SMILES: CC(CC(N)=O)(NC(=O)c1cc(OCCF)c(C2CC2)cn1)C1CC1]

The racemate (Example 270d) was separated into its enantiomers by preparative chiral HPLC (chiralpak AD, ethanol/heptane) and the title compound was the first enantiomer collected and isolated as colorless oil; MS (ESI, m/z): 350.3 (M+H$^+$).

Example 271

N-[4-amino-2-cyclopropyl-4-oxobutan-2-yl]-5-cyclopropyl-4-(2-fluoroethoxy)pyridine-2-carboxamide (enantiomer B)

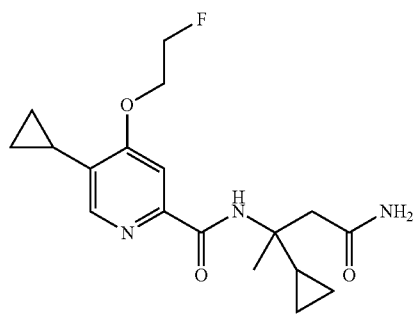 [SMILES: CC(CC(N)=O)(NC(=O)c1cc(OCCF)c(C2CC2)cn1)C1CC1]

The racemate (Example 270d) was separated into its enantiomers by preparative chiral HPLC (chiralpak AD, ethanol/heptane) and the title compound was the second enantiomer collected and isolated as colorless oil; MS (ESI, m/z): 350.3 (M+H$^+$). The collected enantiomer shows levorotation properties according to the observed optical activity measured during preparative chiral HPLC.

Example 272

N-[4-amino-2-cyclopropyl-4-oxobutan-2-yl]-5-cyclopropyl-4-(2,2-difluoroethoxy)pyridine-2-carboxamide (enantiomer A)

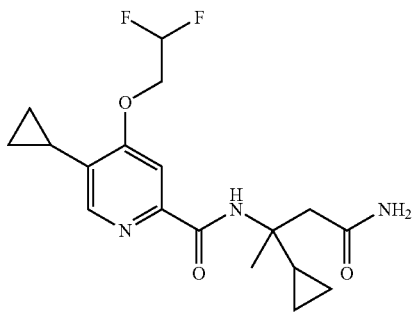 [SMILES: CC(CC(N)=O)(NC(=O)c1cc(OCC(F)F)c(C2CC2)cn1)C1CC1]

a) N-(3-amino-1-cyclopropyl-1-methyl-3-oxo-propyl)-5-cyclopropyl-4-(2,2-difluoroethoxy)pyridine-2-carboxamide

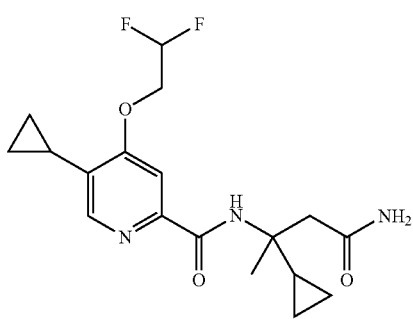 [SMILES: CC(CC(N)=O)(NC(=O)c1cc(OCC(F)F)c(C2CC2)cn1)C1CC1]

The title compound was synthesized in analogy to Example 112e, using 5-cyclopropyl-4-(2,2-difluoroethoxy)pyridine-2-carboxylic acid (example 145d) and 3-amino-3-cyclopropyl-butanamide (example 270c) as starting materials and isolated (55 mg, 52%) as a racemate; MS (ESI, m/z): 368.3 (M+H$^+$).

b) N-[4-amino-2-cyclopropyl-4-oxobutan-2-yl]-5-cyclopropyl-4-(2,2-difluoroethoxy)pyridine-2-carboxamide (enantiomer A)

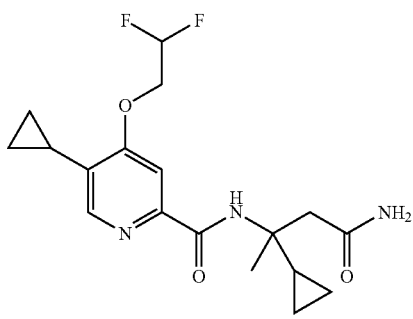 [SMILES: CC(CC(N)=O)(NC(=O)c1cc(OCC(F)F)c(C2CC2)cn1)C1CC1]

The racemate (Example 272a) was separated into its enantiomers by preparative chiral HPLC (chiralpak AD, ethanol/heptane) and the title compound was the first enantiomer collected and isolated as colorless oil; MS (ESI, m/z): 368.3 (M+H$^+$).

Example 273

N-[4-amino-2-cyclopropyl-4-oxobutan-2-yl]-5-cyclopropyl-4-(2,2-difluoroethoxy)pyridine-2-carboxamide (enantiomer B)

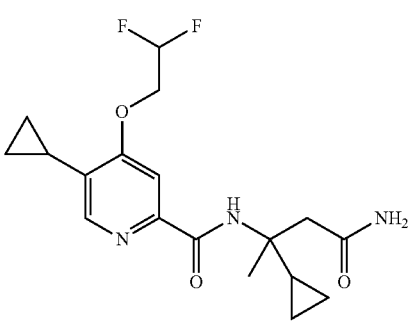 [SMILES: CC(CC(N)=O)(NC(=O)c1cc(OCC(F)F)c(C2CC2)cn1)C1CC1]

The racemate (Example 272b) was separated into its enantiomers by preparative chiral HPLC (chiralpak AD, ethanol/heptane) and the title compound was the second enantiomer collected and isolated as colorless oil; MS (ESI, m/z): 368.3 (M+H$^+$).

Example 274

N-[3-(2-amino-2-oxoethyl)-1,1-dioxothietan-3-yl]-5-cyclopropyl-4-(2,2-difluoroethoxy)pyridine-2-carboxamide

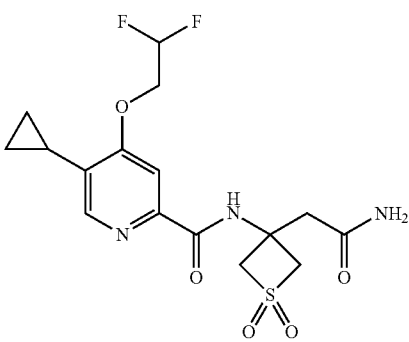 [SMILES: NC(=O)CC1(NC(=O)c2cc(OCC(F)F)c(C3CC3)cn2)CS(=O)(=O)C1]

The title compound was synthesized in analogy to Example 112e, using 5-cyclopropyl-4-(2,2-difluoroethoxy)pyridine-2-carboxylic acid (example 145d) and 2-(3-amino-1,1-dioxo-thietan-3-yl)acetamide (example 160d) as starting materials and isolated (51 mg, 59%); MS (ESI, m/z): 404.3 (M+H$^+$).

Example 275

N-[4-amino-2-cyclopropyl-4-oxobutan-2-yl]-5-(3,3-difluoroazetidin-1-yl)-4-(2,2,2-trifluoroethoxy)pyridine-2-carboxamide (enantiomer A)

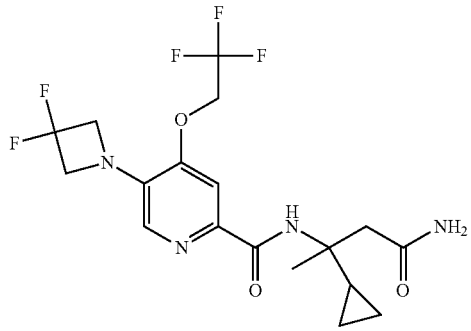 [SMILES: CC(CC(N)=O)(NC(=O)c1cc(OCC(F)(F)F)c(N2CC(F)(F)C2)cn1)C1CC1]

a) N-[4-amino-2-cyclopropyl-4-oxobutan-2-yl]-5-(3,3-difluoroazetidin-1-yl)-4-(2,2,2-trifluoroethoxy)pyridine-2-carboxamide

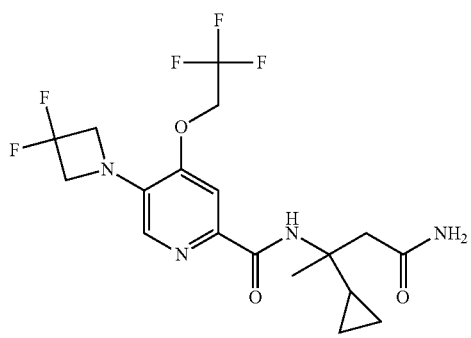 [SMILES: CC(CC(N)=O)(NC(=O)c1cc(OCC(F)(F)F)c(N2CC(F)(F)C2)cn1)C1CC1]

The title compound was synthesized in analogy to Example 112e, using 5-(3,3-difluoroazetidin-1-yl)-4-(2,2,2-trifluoroethoxy)pyridine-2-carboxylic acid (example 223b) and 3-amino-3-cyclopropyl-butanamide (example 270c) as starting materials and isolated (70 mg, 63%) as a racemate; MS (ESI, m/z): 437.3 (M+H$^+$).

b) N-[4-amino-2-cyclopropyl-4-oxobutan-2-yl]-5-(3,3-difluoroazetidin-1-yl)-4-(2,2,2-trifluoroethoxy)pyridine-2-carboxamide (enantiomer A)

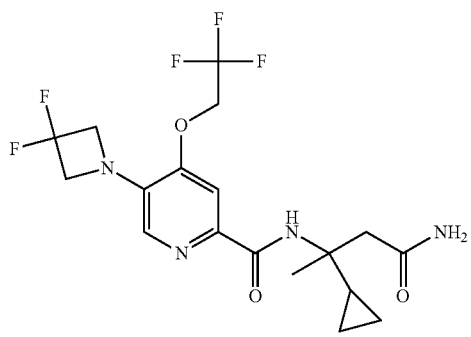 [SMILES: CC(CC(N)=O)(NC(=O)c1cc(OCC(F)(F)F)c(N2CC(F)(F)C2)cn1)C1CC1]

The racemate (Example 277a) was separated into its enantiomers by preparative chiral HPLC (chiralpak AD, isopropanol/heptane) and the title compound was the first enantiomer collected and isolated as colorless oil; MS (ESI, m/z): 437.4 (M+H$^+$).

Example 276

N-[4-amino-2-cyclopropyl-4-oxobutan-2-yl]-5-(3,3-difluoroazetidin-1-yl)-4-(2,2,2-trifluoroethoxy)pyridine-2-carboxamide (enantiomer B)

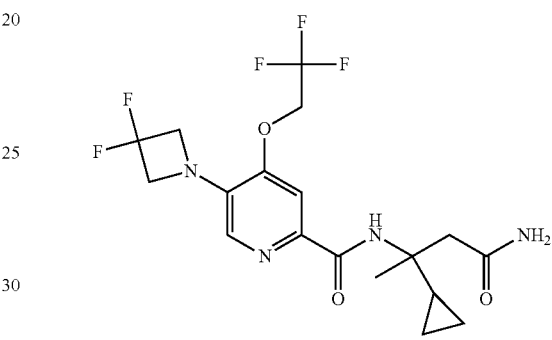

The racemate (Example 277a) was separated into its enantiomers by preparative chiral HPLC (chiralpak AD, isopropanol/heptane) and the title compound was the second enantiomer collected and isolated as colorless oil; MS (ESI, m/z): 437.4 (M+H$^+$).

Example 277

N-(4-amino-2-cyclopropyl-4-oxobutan-2-yl)-5-(3-fluorooxetan-3-yl)-4-[(2S)-1,1,1-trifluoropropan-2-yl]oxypyridine-2-carboxamide (enantiomer A)

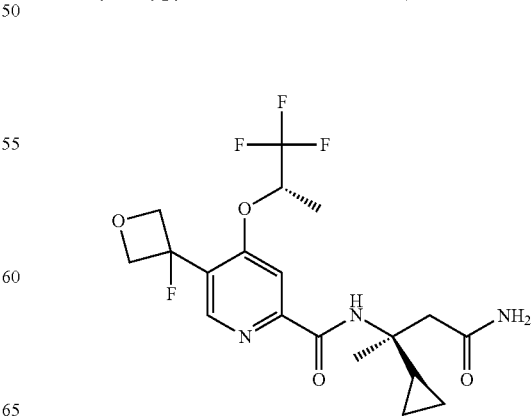

a) N-(4-amino-2-cyclopropyl-4-oxobutan-2-yl)-5-(3-fluorooxetan-3-yl)-4-[(2S)-1,1,1-trifluoropropan-2-yl]oxypyridine-2-carboxamide

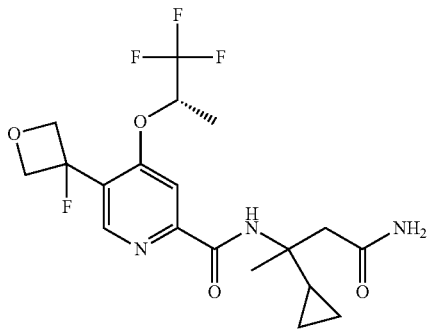 [SMILES: C[C@H](Oc1cc(C(=O)NC(C)(CC(N)=O)C2CC2)ncc1C1(F)COC1)C(F)(F)F]

The title compound was synthesized in analogy to Example 112e, using 5-(3-fluorooxetan-3-yl)-4-[(1S)-2,2,2-trifluoro-1-methyl-ethoxy]pyridine-2-carboxylic acid (example 142b) and 3-amino-3-cyclopropyl-butanamide (example 270c) as starting materials and isolated (55 mg, 39%); MS (ESI, m/z): 434.3 (M+H$^+$).

b) N-(4-amino-2-cyclopropyl-4-oxobutan-2-yl)-5-(3-fluorooxetan-3-yl)-4-[(2S)-1,1,1-trifluoropropan-2-yl]oxypyridine-2-carboxamide (enantiomer A)

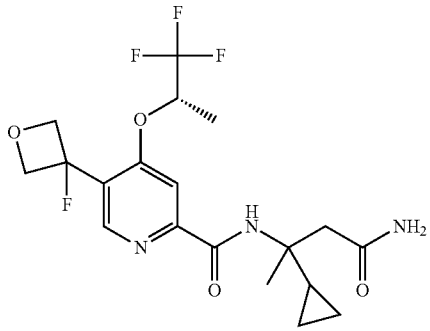 [SMILES: C[C@H](Oc1cc(C(=O)NC(C)(CC(N)=O)C2CC2)ncc1C1(F)COC1)C(F)(F)F]

The mixture of epimers (Example 277a) was separated into its individual epimers by preparative chiral HPLC (chiralpak AD, ethanol/heptane) and the title compound was the first epimer collected and isolated as colorless oil; MS (ESI, m/z): 434.3 (M+H$^+$).

Example 278

N-(4-amino-2-cyclopropyl-4-oxobutan-2-yl)-5-(3-fluorooxetan-3-yl)-4-[(2S)-1,1,1-trifluoropropan-2-yl]oxypyridine-2-carboxamide (enantiomer B)

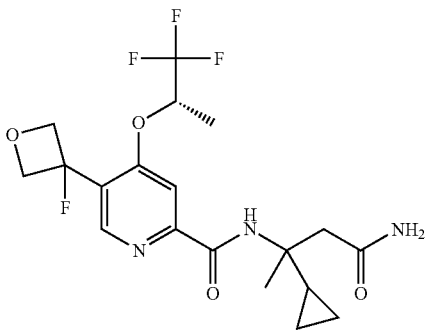 [SMILES: C[C@H](Oc1cc(C(=O)NC(C)(CC(N)=O)C2CC2)ncc1C1(F)COC1)C(F)(F)F]

The mixture of epimers (Example 277a) was separated into its individual epimers by preparative chiral HPLC (chiralpak AD, ethanol/heptane) and the title compound was the second epimer collected and isolated as colorless oil; MS (ESI, m/z): 434.3 (M+H$^+$).

Example 279

5-cyclopropyl-4-(2-fluoroethoxy)-N-[2-(5-methyl-1,2,4-oxadiazol-3-yl)-1-methylsulfonylpropan-2-yl]pyridine-2-carboxamide (enantiomer A)

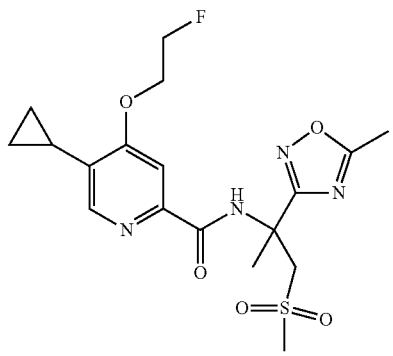 [SMILES: Cc1nc(C(C)(CS(C)(=O)=O)NC(=O)c2cc(OCCF)c(C3CC3)cn2)no1]

The title compound was synthesized in analogy to Example 112e, using 5-cyclopropyl-4-(2-fluoroethoxy)pyridine-2-carboxylic acid (example 146b) and 2-(5-methyl-1,2,4-oxadiazol-3-yl)-1-methylsulfonyl-propan-2-amine;hydrobromide (enantiomer B) (example 125b) as starting materials and isolated (56 mg, 59%); MS (ESI, m/z): 427.2 (M+H⁺).

Example 280

5-cyclopropyl-4-(2-fluoroethoxy)-N-[2-(5-methyl-1,2,4-oxadiazol-3-yl)-1-methylsulfonylpropan-2-yl]pyridine-2-carboxamide (enantiomer B)

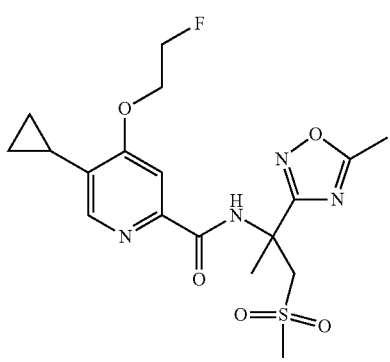 [SMILES: Cc1nc(C(C)(CS(C)(=O)=O)NC(=O)c2cc(OCCF)c(C3CC3)cn2)no1]

The title compound was synthesized in analogy to Example 112e, using 5-cyclopropyl-4-(2-fluoroethoxy)pyridine-2-carboxylic acid (example 146b) and 2-(5-methyl-1,2,4-oxadiazol-3-yl)-1-methylsulfonyl-propan-2-amine;hydrobromide (enantiomer A) (example 124b) as starting materials and isolated (59 mg, 62%); MS (ESI, m/z): 427.2 (M+H⁺).

Example 281

N-[3-(2-amino-2-oxoethyl)-1,1-dioxothietan-3-yl]-5-cyclopropyl-4-(2-fluoroethoxy)pyridine-2-carboxamide

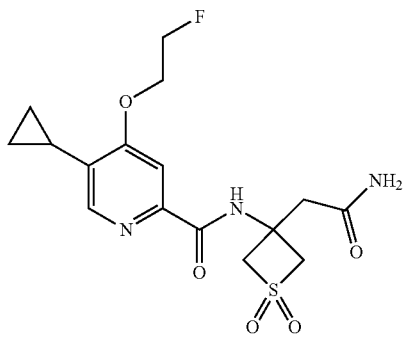 [SMILES: NC(=O)CC1(NC(=O)c2cc(OCCF)c(C3CC3)cn2)CS(=O)(=O)C1]

The title compound was synthesized in analogy to Example 112e, using 5-cyclopropyl-4-(2-fluoroethoxy)-pyridine-2-carboxylic acid (example 146b) and 2-(3-amino-1,1-dioxo-thietan-3-yl)acetamide (example 160d) as starting materials and isolated (30 mg, 34%); MS (ESI, m/z): 386.2 (M+H⁺).

Example 282

5-cyclopropyl-N-[3-[2-(methylamino)-2-oxoethyl]-1,1-dioxothietan-3-yl]-4-(2,2,2-trifluoroethoxy)pyridine-2-carboxamide

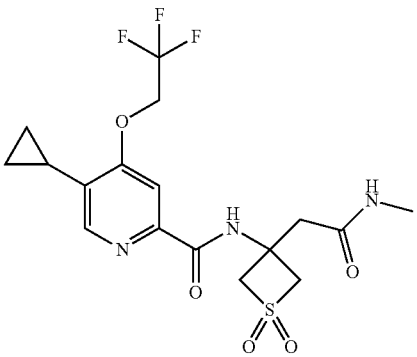 [SMILES: CNC(=O)CC1(NC(=O)c2cc(OCC(F)(F)F)c(C3CC3)cn2)CS(=O)(=O)C1]

a) 2-(3-amino-1,1-dioxo-thietan-3-yl)-N-methyl-acetamide

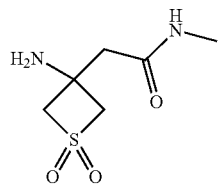

ethyl 2-(3-amino-1,1-dioxo-thietan-3-yl)acetate (example 160c, 548 mg, 2.64 mmole) was dissolved in a solution 2.0M of methylamine in methanol (19.8 mL, 39.7 mmole) and the reaction mixture was stirred at 45° C. overnight. Removal of volatiles in vacuo yielded the title compound (505 mg, 99%) as crude light brown oil which was used without any further purification; MS (ESI, m/z): 193.1 (M+H⁺).

b) 5-cyclopropyl-N-[3-[2-(methylamino)-2-oxoethyl]-1,1-dioxothietan-3-yl]-4-(2,2,2-trifluoroethoxy)pyridine-2-carboxamide

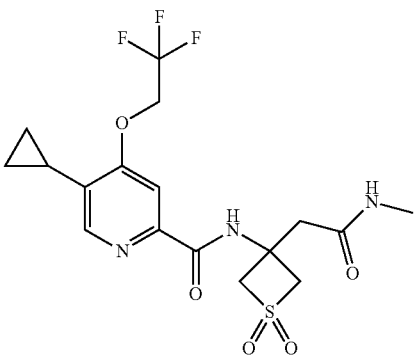 [SMILES: CNC(=O)CC1(NC(=O)c2cc(OCC(F)(F)F)c(C3CC3)cn2)CS(=O)(=O)C1]

The title compound was synthesized in analogy to Example 112e, using 5-Cyclopropyl-4-(2,2,2-trifluoro-

Example 283

5-cyclopropyl-4-(2,2-difluoroethoxy)-N-(2-(5-methyl-1,2,4-oxadiazol-3-yl)-1-(methylsulfonyl)propan-2-yl)picolinamide (enantiomer A)

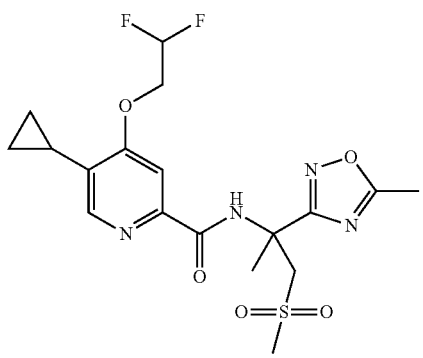 [SMILES: Cc1nc(C(C)(CS(C)(=O)=O)NC(=O)c2cc(OCC(F)F)c(C3CC3)cn2)no1]

The title compound was synthesized in analogy to Example 112e, using 5-cyclopropyl-4-(2,2-difluoroethoxy)pyridine-2-carboxylic acid;hydrochloride (example 145d) and 2-(5-methyl-1,2,4-oxadiazol-3-yl)-1-methylsulfonyl-propan-2-amine;hydrobromide (enantiomer A) (example 124b) as starting materials and isolated (16 mg, 20%); MS (ESI, m/z): 445.3 (M+H$^+$).

Example 284

5-cyclopropyl-4-(2,2-difluoroethoxy)-N-(2-(5-methyl-1,2,4-oxadiazol-3-yl)-1-(methylsulfonyl)propan-2-yl)picolinamide (enantiomer B)

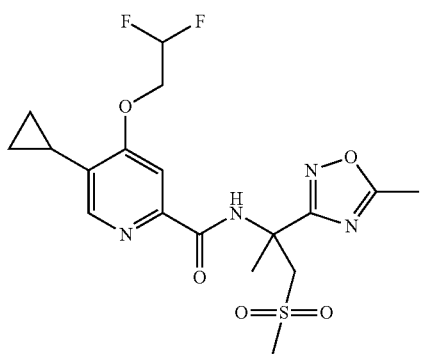 [SMILES: Cc1nc(C(C)(CS(C)(=O)=O)NC(=O)c2cc(OCC(F)F)c(C3CC3)cn2)no1]

The title compound was synthesized in analogy to Example 112e, using 5-cyclopropyl-4-(2,2-difluoroethoxy)pyridine-2-carboxylic acid;hydrochloride (example 145d) and 2-(5-methyl-1,2,4-oxadiazol-3-yl)-1-methylsulfonyl-propan-2-amine;hydrobromide (enantiomer B) (example 125b) as starting materials and isolated (25 mg, 31%); MS (ESI, m/z): 445.3 (M+H$^+$).

Example 285

5-(1-fluorocyclobutyl)-N-[3-[2-(methylamino)-2-oxoethyl]-1,1-dioxothietan-3-yl]-4-(2,2,2-trifluoroethoxy)pyridine-2-carboxamide

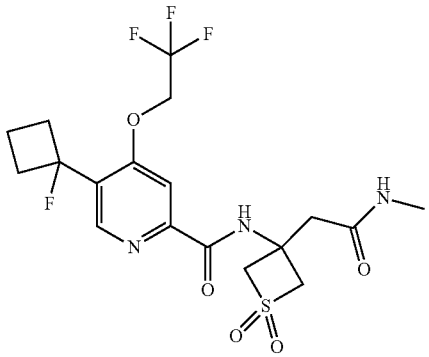 [SMILES: CNC(=O)CC1(NC(=O)c2cc(OCC(F)(F)F)c(C3(F)CCC3)cn2)CS(=O)(=O)C1]

a) 5-(1-fluorocyclobutyl)-4-(2,2,2-trifluoroethoxy)pyridine-2-carboxylic acid

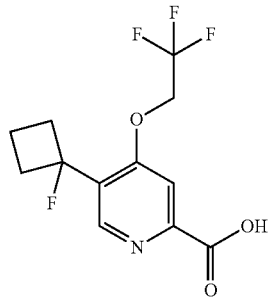 [SMILES: O=C(O)c1cc(OCC(F)(F)F)c(C2(F)CCC2)cn1]

The title compound was synthesized in analogy to Example 123d, using 5-(1-fluorocyclobutyl)-4-(2,2,2-trifluoroethoxy)pyridine-2-carbonitrile (example 127c) as starting material and isolated (661 mg, 53%); MS (ESI, m/z): 294.2 (M+H$^+$).

b) 5-(1-fluorocyclobutyl)-N-[3-[2-(methylamino)-2-oxoethyl]-1,1-dioxothietan-3-yl]-4-(2,2,2-trifluoroethoxy)pyridine-2-carboxamide

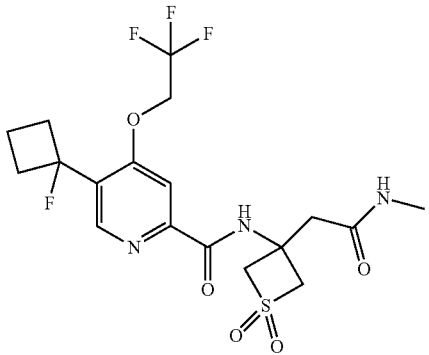 [SMILES: CNC(=O)CC1(NC(=O)c2cc(OCC(F)(F)F)c(C3(F)CCC3)cn2)CS(=O)(=O)C1]

The title compound was synthesized in analogy to Example 112e, using 5-(1-fluorocyclobutyl)-4-(2,2,2-trifluoroethoxy)pyridine-2-carboxylic acid (example 285a) and 2-(3-amino-1,1-dioxo-thietan-3-yl)-N-methyl-acetamide (example 282a) as starting materials and isolated (15 mg, 19%); MS (ESI, m/z): 468.3 (M+H⁺).

Example 286

N-[3-(2-amino-2-oxoethyl)-1,1-dioxothietan-3-yl]-5-(1-fluorocyclobutyl)-4-(2,2,2-trifluoroethoxy)pyridine-2-carboxamide

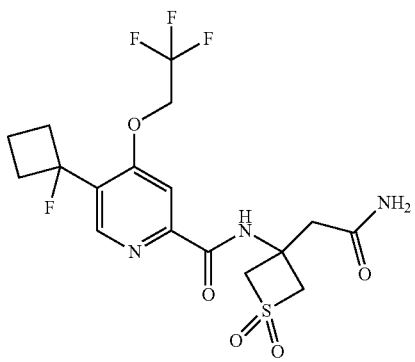 [SMILES: NC(=O)CC1(NC(=O)c2cc(OCC(F)(F)F)c(C3(F)CCC3)cn2)CS(=O)(=O)C1]

The title compound was synthesized in analogy to Example 112e, using 5-(1-fluorocyclobutyl)-4-(2,2,2-trifluoroethoxy)pyridine-2-carboxylic acid (example 285a) and 2-(3-amino-1,1-dioxo-thietan-3-yl)acetamide (example 160d) as starting materials and isolated (16 mg, 21%); MS (ESI, m/z): 454.3 (M+H⁺).

Example 287

5-cyclopropyl-N-(1-cyclopropyl-2-(5-methyl-1,2,4-oxadiazol-3-yl)propan-2-yl)-4-(1-fluoropropan-2-yloxy)picolinamide (stereoisomer A)

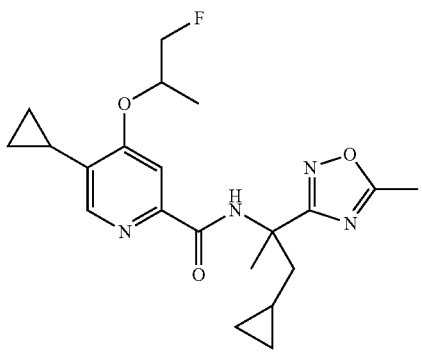 [SMILES: Cc1nc(C(C)(CC2CC2)NC(=O)c2cc(OC(C)CF)c(C3CC3)cn2)no1]

a) 3-bromo-4-(2-fluoro-1-methyl-ethoxy)pyridine

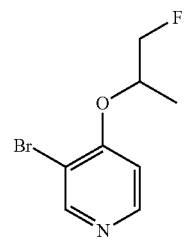

The title compound was synthesized in analogy to Example 108b, using 3-bromo-4-chloropyridine (CAN 36953-42-1), 1-fluoropropan-2-ol (CAN 430-50-2) as starting materials and sodium hydride as reagent. The title compound was isolated (7.55 g, 62%) as a yellow oil; MS (ESI, m/z): 235.9 (M+H⁺).

b) 3-cyclopropyl-4-(2-fluoro-1-methyl-ethoxy)pyridine

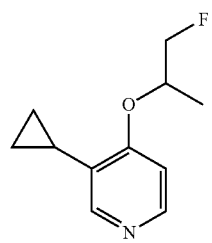

The title compound was synthesized in analogy to Example 48a, using 3-bromo-4-(2-fluoro-1-methyl-ethoxy)-pyridine (example 287a) as starting material. The title compound was isolated as a crude and used without any purification (6.2 g, 98%) as a yellow oil; MS (ESI, m/z): 196.1 (M+H⁺).

c) 5-cyclopropyl-4-(2-fluoro-1-methyl-ethoxy)pyridine-2-carbonitrile

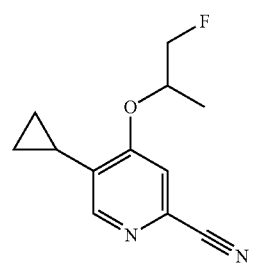

To a solution of 3-cyclopropyl-4-(2-fluoro-1-methyl-ethoxy)pyridine (example 287b, 6.26 g, 32.1 mmole) in dichloromethane (100 mL) was added m-cpba 77% (10.8 g, 48.1 mmole) and the reaction was stirred at room temperature for 16 hours. Reaction mixture was diluted with dichloromethane and extracted with a 1M aqueous solution of sodium bicarbonate. Organic phase was collected and the aqueous phase was back-extracted with dichloromethane.

Combined organic phases were dried over magnesium sulfate and evaporated down to dryness. The crude pyridine-oxide intermediate (6.97 g) was used without any purification. To a solution of the crude pyridine-oxide (6.97 g, 33.0 mmole) in dichloromethane (110 mL) was added dimethylcarbamoyl-chloride (CAN 79-44-7, 5.32 g, 4.55 mL, 49.5 mmole) and trimethylsilylcyanide (8.18 g, 10.3 mL, 82.5 mmole). The reaction mixture was stirred at room temperature for 16 hours and the reaction was quenched by addition of a 1M aqueous solution of sodium bicarbonate. The bi-phasic mixture was vigorously stirred for 10 minutes and then poured into a separatory funnel. The organic phase was extracted and collected. The aqueous phase was back-extracted with dichloromethane. Combined organic phases were dried over magnesium sulfate and evaporated down to dryness. The crude material was purified by flash chromatography on silica eluting with a gradient of heptane and ethyl acetate to yield the title compound (1.5 g, 21%). MS (ESI, m/z): 221.6 (M+H$^+$).

d) 5-cyclopropyl-4-(2-fluoro-1-methyl-ethoxy)pyridine-2-carbonitrile (enantiomer A)

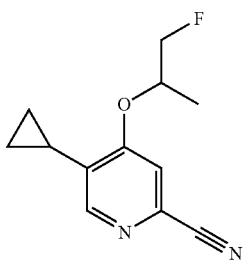 [SMILES: CC(CF)Oc1cc(C#N)ncc1C1CC1]

The racemate (Example 287c) was separated into its enantiomers by preparative chiral HPLC (Reprosil Chiral NR, isopropanol/heptane) and the title compound was the first enantiomer collected and isolated as colorless oil; MS (ESI, m/z): 221.1 (M+H$^+$).

e) 5-cyclopropyl-4-[2-fluoro-1-methyl-ethoxy]pyridine-2-carboxylic acid (enantiomer A)

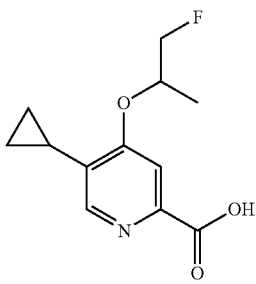 [SMILES: CC(CF)Oc1cc(C(=O)O)ncc1C1CC1]

The title compound was synthesized in analogy to Example 126d, using 5-cyclopropyl-4-(2-fluoro-1-methyl-ethoxy)pyridine-2-carbonitrile (enantiomer A) (example 287d) as starting material and isolated (450 mg, 71%) as a white solid; MS (ESI, m/z): 240.2 (M+H$^+$).

f) 5-cyclopropyl-N-(1-cyclopropyl-2-(5-methyl-1,2,4-oxadiazol-3-yl)propan-2-yl)-4-(1-fluoropropan-2-yloxy)picolinamide (stereoisomer A)

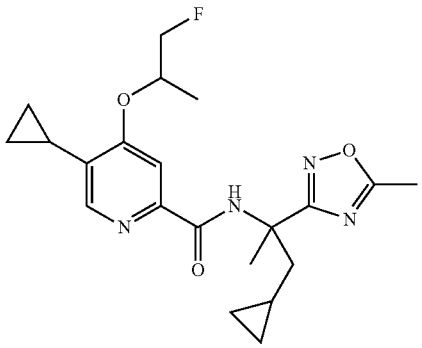 [SMILES: Cc1nc(C(C)(CC2CC2)NC(=O)c2cc(OC(C)CF)c(C3CC3)cn2)no1]

To a solution of 5-cyclopropyl-4-(1-fluoropropan-2-yloxy)picolinic acid (enantiomer A) (example 287e, 0.08 g, 334 μmol) in dry DMF (2 ml) was added TBTU (113 mg, 351 μmol) and triethylamine (102 mg, 140 μl, 1.00 mmol). The reaction was stirred at room temperature for 30 minutes followed by addition of 1-cyclopropyl-2-(5-methyl-1,2,4-oxadiazol-3-yl)propan-2-amine hydrochloride (example 66e, 72.8 mg, 334 μmol). The reaction was then stirred at room temperature overnight. The reaction was diluted with ethyl acetate and extracted with a 1M aqueous solution of sodium bicarbonate. The organic phase was collected and the aqueous phase was back-extracted with ethyl acetate. Combined organic phases were dried over sodium sulfate and evaporated down to dryness. The crude material was purified by flash chromatography on silica eluting with a gradient of heptane and ethyl acetate to give a mixture of epimers. The epimers was then separated by preparative chiral HPLC (Chiralpak AD, isopropanol/heptane) and the title compound was the first epimer collected (26 mg, 19%); MS (ESI, m/z): 403.4 (M+H$^+$).

Example 288

5-cyclopropyl-N-(1-cyclopropyl-2-(5-methyl-1,2,4-oxadiazol-3-yl)propan-2-yl)-4-(1-fluoropropan-2-yloxy)picolinamide (stereoisomer B)

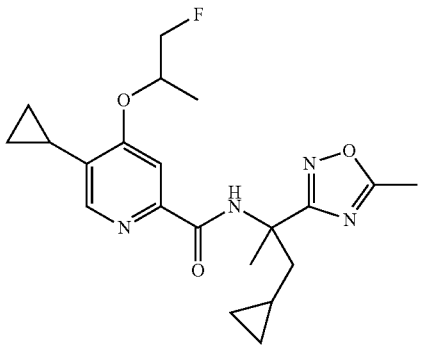 [SMILES: Cc1nc(C(C)(CC2CC2)NC(=O)c2cc(OC(C)CF)c(C3CC3)cn2)no1]

To a solution of 5-cyclopropyl-4-(1-fluoropropan-2-yloxy)picolinic acid (enantiomer A) (example 287e, 0.08 g, 334 µmol) in dry DMF (2 ml) was added TBTU (113 mg, 351 µmol) and triethylamine (102 mg, 140 µl, 1.00 mmol). The reaction was stirred at room temperature for 30 minutes followed by addition of 1-cyclopropyl-2-(5-methyl-1,2,4-oxadiazol-3-yl)propan-2-amine hydrochloride (example 66e, 72.8 mg, 334 µmol). The reaction was then stirred at room temperature overnight. The reaction was diluted with ethyl acetate and extracted with a 1M aqueous solution of sodium bicarbonate. The organic phase was collected and the aqueous phase was back-extracted with ethyl acetate. Combined organic phases were dried over sodium sulfate and evaporated down to dryness. The crude material was purified by flash chromatography on silica eluting with a gradient of heptane and ethyl acetate to give the a mixture of epimers. The epimers were then separated by preparative chiral HPLC (Chiralpak AD, isopropanol/heptane) and the title compound was the second epimer collected (23 mg, 17%); MS (ESI, m/z): 403.4 (M+H$^+$).

Example 289

5-cyclopropyl-N-(1-cyclopropyl-2-(5-methyl-1,2,4-oxadiazol-3-yl)propan-2-yl)-4-(1-fluoropropan-2-yloxy)picolinamide (stereoisomer C)

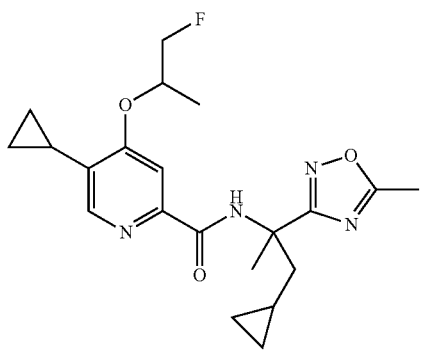 [SMILES: Cc1nc(C(C)(CC2CC2)NC(=O)c2cc(OC(C)CF)c(C3CC3)cn2)no1]

a) 5-cyclopropyl-4-(2-fluoro-1-methyl-ethoxy)pyridine-2-carbonitrile (enantiomer B)

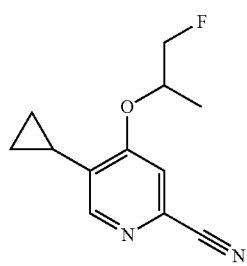 [SMILES: CC(CF)Oc1cc(C#N)ncc1C1CC1]

The racemate (Example 287c) was separated into its enantiomers by preparative chiral HPLC (Reprosil Chiral NR, isopropanol/heptane) and the title compound was the second enantiomer collected and isolated as colorless oil; MS (ESI, m/z): 221.1 (M+H$^+$).

b) 5-cyclopropyl-4-[2-fluoro-1-methyl-ethoxy]pyridine-2-carboxylic acid (enantiomer B)

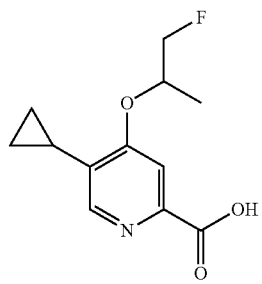 [SMILES: CC(CF)Oc1cc(C(=O)O)ncc1C1CC1]

The title compound was synthesized in analogy to Example 126d, using 5-cyclopropyl-4-(2-fluoro-1-methylethoxy)-pyridine-2-carbonitrile (enantiomer B) (example 289a) as starting material and isolated (385 mg, 54%) as a white solid; MS (ESI, m/z): 240.1 (M+H$^+$).

c) 5-cyclopropyl-N-(1-cyclopropyl-2-(5-methyl-1,2,4-oxadiazol-3-yl)propan-2-yl)-4-(1-fluoropropan-2-yloxy)picolinamide (stereoisomer C)

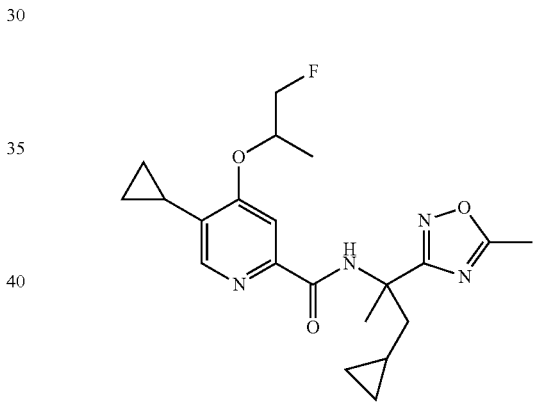

To a solution of 5-cyclopropyl-4-(1-fluoropropan-2-yloxy)picolinic acid (enantiomer B) (example 289b, 0.08 g, 334 µmol) in dry DMF (2 ml) was added TBTU (113 mg, 351 µmol) and triethylamine (102 mg, 140 µl, 1.00 mmol). The reaction was stirred at room temperature for 30 minutes followed by addition of 1-cyclopropyl-2-(5-methyl-1,2,4-oxadiazol-3-yl)propan-2-amine hydrochloride (example 66e, 72.8 mg, 334 µmol). The reaction was then stirred at room temperature overnight. The reaction was diluted with ethyl acetate and extracted with a 1M aqueous solution of sodium bicarbonate. The organic phase was collected and the aqueous phase was back-extracted with ethyl acetate. Combined organic phases were dried over sodium sulfate and evaporated down to dryness. The crude material was purified by flash chromatography on silica eluting with a gradient of heptane and ethyl acetate to give a mixture of epimers. The epimers were then separated by preparative chiral HPLC (Chiralpak AD, isopropanol/heptane) and the title compound was the first epimer collected (12.5 mg, 9%); MS (ESI, m/z): 403.4 (M+H$^+$).

Example 290

5-cyclopropyl-N-(1-cyclopropyl-2-(5-methyl-1,2,4-oxadiazol-3-yl)propan-2-yl)-4-(1-fluoropropan-2-yloxy)picolinamide (stereoisomer D)

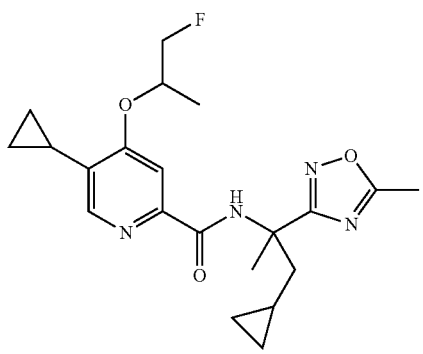 [SMILES: Cc1nc(C(C)(CC2CC2)NC(=O)c2cc(OC(C)CF)c(C3CC3)cn2)no1]

To a solution of 5-cyclopropyl-4-(1-fluoropropan-2-yloxy)picolinic acid (enantiomer B) (example 289b, 0.08 g, 334 µmol) in dry DMF (2 ml) was added TBTU (113 mg, 351 µmol) and triethylamine (102 mg, 140 µl, 1.00 mmol). The reaction was stirred at room temperature for 30 minutes followed by addition of 1-cyclopropyl-2-(5-methyl-1,2,4-oxadiazol-3-yl)propan-2-amine hydrochloride (example 66e, 72.8 mg, 334 µmol). The reaction was then stirred at room temperature overnight. The reaction was diluted with ethyl acetate and extracted with a 1M aqueous solution of sodium bicarbonate. The organic phase was collected and the aqueous phase was back-extracted with ethyl acetate. Combined organic phases were dried over sodium sulfate and evaporated down to dryness. The crude material was purified by flash chromatography on silica eluting with a gradient of heptane and ethyl acetate to give a mixture of epimers. The epimers were then separated by preparative chiral HPLC (Chiralpak AD, isopropanol/heptane) and the title compound was the second epimer collected (12.4 mg, 9%); MS (ESI, m/z): 403.4 (M+H⁺).

Example 291

N-[3-(2-amino-2-oxoethyl)-1,1-dioxothietan-3-yl]-5-cyclopropyl-4-[1-fluoropropan-2-yl]oxypyridine-2-carboxamide (enantiomer A)

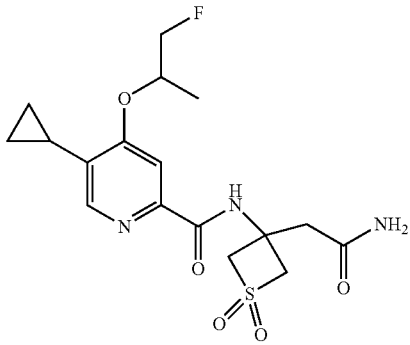 [SMILES: CC(CF)Oc1cc(C(=O)NC2(CC(N)=O)CS(=O)(=O)C2)ncc1C1CC1]

The title compound was synthesized in analogy to Example 112e, using 5-cyclopropyl-4-(1-fluoropropan-2-yloxy)picolinic acid (enantiomer A) (example 287e) and 2-(3-amino-1,1-dioxo-thietan-3-yl)acetamide (example 160d) as starting materials and isolated (37.5 mg, 56%); MS (ESI, m/z): 400.3 (M+H⁺).

Example 292

N-[3-(2-amino-2-oxoethyl)-1,1-dioxothietan-3-yl]-5-cyclopropyl-4-[1-fluoropropan-2-yl]oxypyridine-2-carboxamide (enantiomer B)

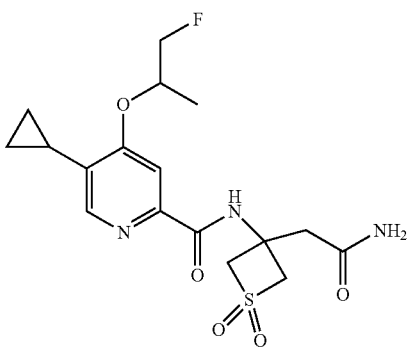 [SMILES: CC(CF)Oc1cc(C(=O)NC2(CC(N)=O)CS(=O)(=O)C2)ncc1C1CC1]

The title compound was synthesized in analogy to Example 112e, using 5-cyclopropyl-4-(1-fluoropropan-2-yloxy)picolinic acid (enantiomer B) (example 289b) and 2-(3-amino-1,1-dioxo-thietan-3-yl)acetamide (example 160d) as starting materials and isolated (33.8 mg, 51%); MS (ESI, m/z): 400.3 (M+H⁺).

Example 293

N-(4-amino-2-cyclopropyl-4-oxobutan-2-yl)-5-cyclopropyl-4-(1-fluoropropan-2-yloxy)picolinamide (Mixture of epimers A)

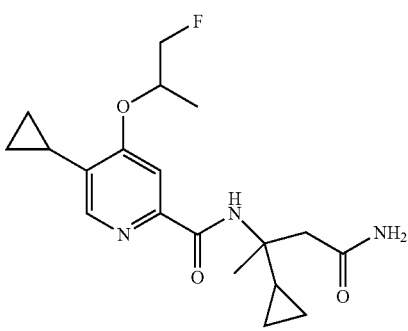 [SMILES: CC(CF)Oc1cc(C(=O)NC(C)(CC(N)=O)C2CC2)ncc1C1CC1]

The title compound was synthesized in analogy to Example 112e, using 5-cyclopropyl-4-(1-fluoropropan-2-yloxy)picolinic acid (enantiomer A) (example 287e) and 3-amino-3-cyclopropyl-butanamide (example 270c) as starting materials and isolated (80 mg, 75%); MS (ESI, m/z): 364.4 (M+H⁺).

Example 294

N-(4-amino-2-cyclopropyl-4-oxobutan-2-yl)-5-cyclopropyl-4-(1-fluoropropan-2-yloxy)picolinamide (Mixture of epimers B)

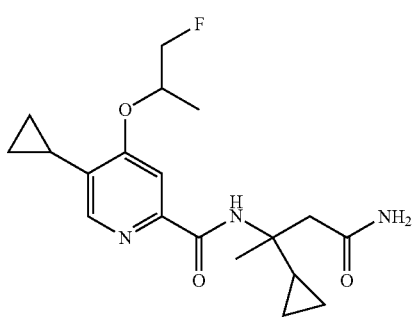 [SMILES: CC(CF)Oc1cc(C(=O)NC(C)(CC(N)=O)C2CC2)ncc1C1CC1]

The title compound was synthesized in analogy to Example 112e, using 5-cyclopropyl-4-(1-fluoropropan-2-yloxy)picolinic acid (enantiomer B) (example 289b) and 3-amino-3-cyclopropyl-butanamide (example 270c) as starting materials and isolated (85.4 mg, 80%); MS (ESI, m/z): 364.4 (M+H⁺).

Example 295

5-cyclopropyl-4-(1-fluoropropan-2-yloxy)-N-(2-(5-methyl-1,2,4-oxadiazol-3-yl)-1-(methylsulfonyl)propan-2-yl)picolinamide (stereoisomer A)

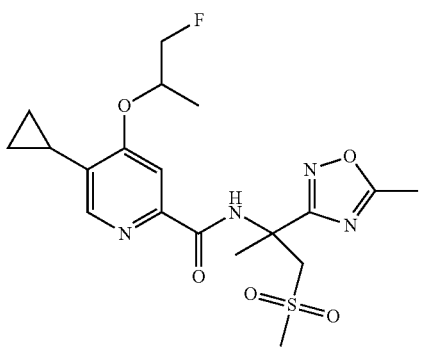 [SMILES: Cc1nc(C(C)(CS(C)(=O)=O)NC(=O)c2cc(OC(C)CF)c(C3CC3)cn2)no1]

The title compound was synthesized in analogy to Example 112e, using 5-cyclopropyl-4-(1-fluoropropan-2-yloxy)picolinic acid (enantiomer A) (example 287e) and 2-(5-methyl-1,2,4-oxadiazol-3-yl)-1-methylsulfonyl-propan-2-amine;hydrobromide (enantiomer A) (example 124b) as starting materials and isolated (37.5 mg, 51%); MS (ESI, m/z): 441.4 (M+H⁺).

Example 296

5-cyclopropyl-4-(1-fluoropropan-2-yloxy)-N-(2-(5-methyl-1,2,4-oxadiazol-3-yl)-1-(methylsulfonyl)propan-2-yl)picolinamide (stereoisomer B)

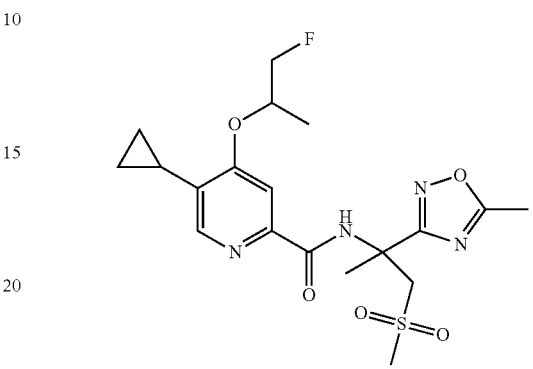

The title compound was synthesized in analogy to Example 112e, using 5-cyclopropyl-4-(1-fluoropropan-2-yloxy)picolinic acid (enantiomer A) (example 287e) and 2-(5-methyl-1,2,4-oxadiazol-3-yl)-1-methylsulfonyl-propan-2-amine;hydrobromide (enantiomer B) (example 125b) as starting materials and isolated (52.6 mg, 71%); MS (ESI, m/z): 441.4 (M+H⁺).

Example 297

5-cyclopropyl-4-(1-fluoropropan-2-yloxy)-N-(2-(5-methyl-1,2,4-oxadiazol-3-yl)-1-(methylsulfonyl)propan-2-yl)picolinamide (stereoisomer C)

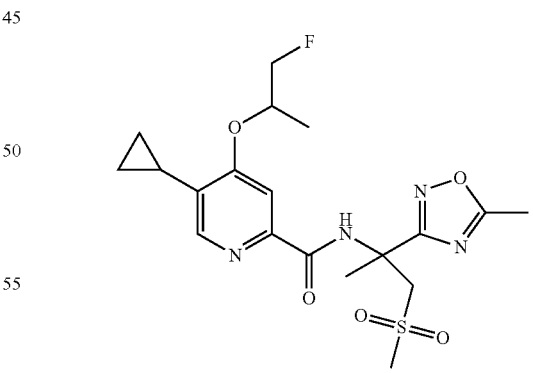

The title compound was synthesized in analogy to Example 112e, using 5-cyclopropyl-4-(1-fluoropropan-2-yloxy)picolinic acid (enantiomer B) (example 289b) and 2-(5-methyl-1,2,4-oxadiazol-3-yl)-1-methylsulfonyl-propan-2-amine;hydrobromide (enantiomer A) (example 124b) as starting materials and isolated (52.5 mg, 71%); MS (ESI, m/z): 441.4 (M+H⁺).

Example 298

5-cyclopropyl-4-(1-fluoropropan-2-yloxy)-N-(2-(5-methyl-1,2,4-oxadiazol-3-yl)-1-(methylsulfonyl)propan-2-yl)picolinamide (stereoisomer D)

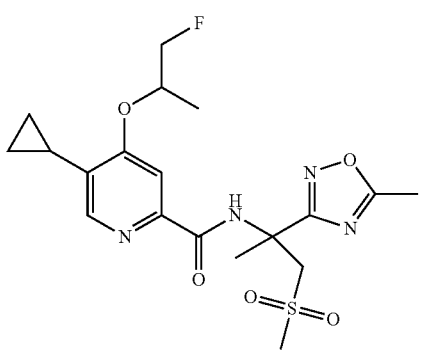 [SMILES: Cc1nc(C(C)(CS(C)(=O)=O)NC(=O)c2cc(OC(C)CF)c(C3CC3)cn2)no1]

The title compound was synthesized in analogy to Example 112e, using 5-cyclopropyl-4-(1-fluoropropan-2-yloxy)picolinic acid (enantiomer B) (example 289b) and 2-(5-methyl-1,2,4-oxadiazol-3-yl)-1-methylsulfonyl-propan-2-amine;hydrobromide (enantiomer B) (example 125b) as starting materials and isolated (51.2 mg, 70%); MS (ESI, m/z): 441.4 (M+H$^+$).

Example 299

N-[3-(2-amino-2-oxoethyl)-1,1-dioxothietan-3-yl]-5-cyclobutyl-4-(2,2,2-trifluoroethoxy)pyridine-2-carboxamide

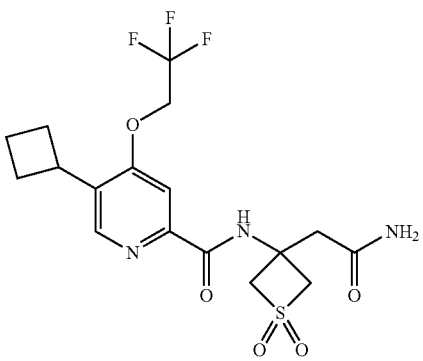 [SMILES: NC(=O)CC1(NC(=O)c2cc(OCC(F)(F)F)c(C3CCC3)cn2)CS(=O)(=O)C1]

The title compound was synthesized in analogy to Example 112e, using 5-Cyclobutyl-4-(2,2,2-trifluoroethoxy)-pyridine-2-carboxylic acid (example 108f) and 2-(3-amino-1,1-dioxo-thietan-3-yl)acetamide (example 160d) as starting materials and isolated (16.5 mg, 21%); MS (ESI, m/z): 436.3 (M+H$^+$).

Example 300

N-(4-amino-2-cyclopropyl-4-oxobutan-2-yl)-5-(1-fluorocyclobutyl)-4-(2,2,2-trifluoroethoxy)picolinamide

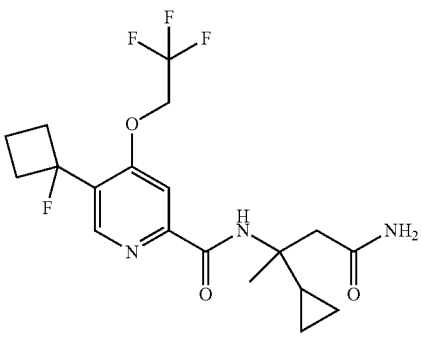 [SMILES: CC(CC(N)=O)(NC(=O)c1cc(OCC(F)(F)F)c(C2(F)CCC2)cn1)C1CC1]

The title compound was synthesized in analogy to Example 112e, using 5-(1-fluorocyclobutyl)-4-(2,2,2-trifluoroethoxy)pyridine-2-carboxylic acid (example 285a) and 3-amino-3-cyclopropyl-butanamide (example 270c) as starting materials and isolated (55 mg, 49%); MS (ESI, m/z): 418.4 (M+H$^+$).

Example 301

N-(4-amino-2-cyclopropyl-4-oxobutan-2-yl)-5-cyclopropyl-4-(1-fluoropropan-2-yloxy)picolinamide (Stereoisomer A)

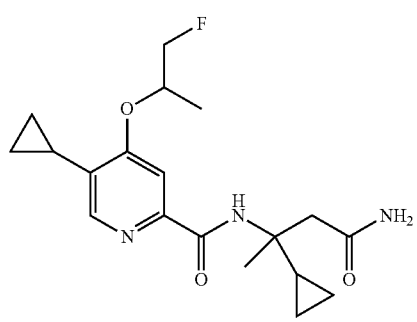 [SMILES: CC(CF)Oc1cc(C(=O)NC(C)(CC(N)=O)C2CC2)ncc1C1CC1]

The mixture of epimers (Example 293) was separated into its individual epimers by preparative chiral HPLC (Lux Amylose, ethanol/heptane) and the title compound was the first epimer collected and isolated as colorless oil; MS (ESI, m/z): 364.3 (M+H$^+$).

Example 302

N-(4-amino-2-cyclopropyl-4-oxobutan-2-yl)-5-cyclopropyl-4-(1-fluoropropan-2-yloxy)picolinamide (Stereoisomer B)

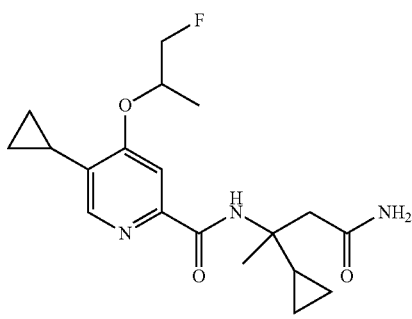 [SMILES: CC(CF)Oc1cc(C(=O)NC(C)(CC(N)=O)C2CC2)ncc1C1CC1]

The mixture of epimers (Example 293) was separated into its individual epimers by preparative chiral HPLC (Lux Amylose, ethanol/heptane) and the title compound was the second epimer collected and isolated as colorless oil; MS (ESI, m/z): 364.3 (M+H$^+$).

Example 303

N-(4-amino-2-cyclopropyl-4-oxobutan-2-yl)-5-cyclopropyl-4-(1-fluoropropan-2-yloxy)picolinamide (Stereoisomer C)

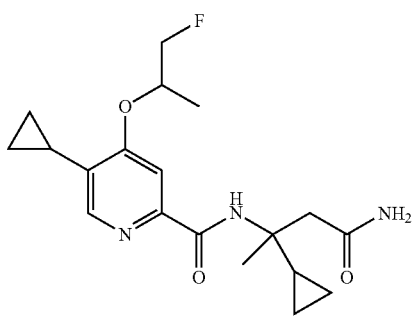 [SMILES: CC(CF)Oc1cc(C(=O)NC(C)(CC(N)=O)C2CC2)ncc1C1CC1]

The mixture of epimers (Example 294) was separated into its individual epimers by preparative chiral HPLC (Lux Amylose, ethanol/heptane) and the title compound was the first epimer collected and isolated as colorless oil; MS (ESI, m/z): 364.3 (M+H$^+$).

Example 304

N-(4-amino-2-cyclopropyl-4-oxobutan-2-yl)-5-cyclopropyl-4-(1-fluoropropan-2-yloxy)picolinamide (Stereoisomer D)

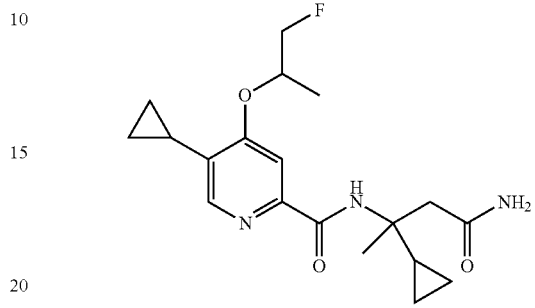

The mixture of epimers (Example 294) was separated into its individual epimers by preparative chiral HPLC (Lux Amylose, ethanol/heptane) and the title compound was the second epimer collected and isolated as colorless oil; MS (ESI, m/z): 364.3 (M+H$^+$).

Example 305

N-[3-(2-amino-2-oxoethyl)-1,1-dioxothietan-3-yl]-5-(1-fluorocyclobutyl)-4-[(2S)-1,1,1-trifluoropropan-2-yl]oxypyridine-2-carboxamide

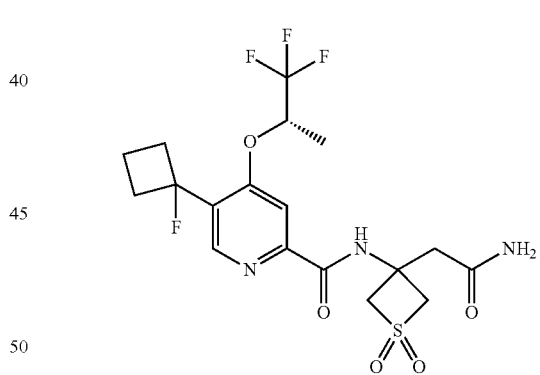

a) 4-chloro-3-(1-fluorocyclobutyl)pyridine

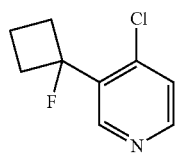 [SMILES: FC1(c2cnccc2Cl)CCC1]

The title compound was synthesized in analogy to Example 127a, using 1-(4-chloro-3-pyridyl)-cyclobutanol (example 108a) as starting material and isolated (7 g, 65%) as a yellow oil; MS (ESI, m/z): 186.1 (M+H⁺).

b) 4-chloro-3-(1-fluorocyclobutyl)-1-oxido-pyridin-1-ium

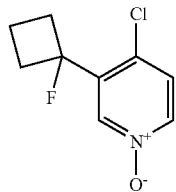 [SMILES: [O-][n+]1ccc(Cl)c(C2(F)CCC2)c1]

The title compound was synthesized in analogy to Example 108d, using 4-chloro-3-(1-fluorocyclobutyl)pyridine (example 305a) as starting materials and isolated (7 g, 77%) as a solid; MS (ESI, m/z): 202.3 (M+H⁺).

c) 4-chloro-5-(1-fluorocyclobutyl)pyridine-2-carbonitrile

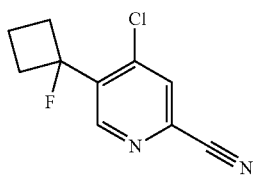 [SMILES: N#Cc1cc(Cl)c(C2(F)CCC2)cn1]

The title compound was synthesized in analogy to Example 108e, using 4-chloro-3-(1-fluorocyclobutyl)-1-oxido-pyridin-1-ium (example 305b) as starting material and isolated (5 g, 42%); MS (ESI, m/z): 211.2 (M+H⁺).

d) 5-(1-fluorocyclobutyl)-4-[(1S)-2,2,2-trifluoro-1-methyl-ethoxy]pyridine-2-carbonitrile

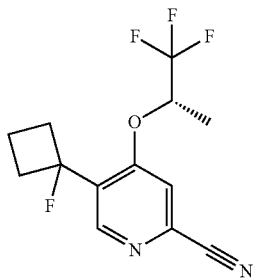 [SMILES: C[C@H](Oc1cc(C#N)ncc1C1(F)CCC1)C(F)(F)F]

The title compound was synthesized in analogy to Example 123c, using 4-chloro-5-(1-fluorocyclobutyl)-pyridine-2-carbonitrile (example 305c) and (S)-1,1,1-Trifluoropropan-2-ol (CAN 3539-97-7) as starting materials and sodium hydride as reagent. The title was isolated (1.23 g, 90%) as a yellow oil; MS (ESI, m/z): 289.2 (M+H⁺).

e) 5-(1-fluorocyclobutyl)-4-[(1S)-2,2,2-trifluoro-1-methyl-ethoxy]pyridine-2-carboxylic acid

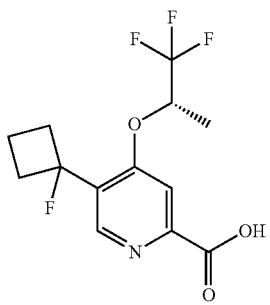 [SMILES: C[C@H](Oc1cc(C(=O)O)ncc1C1(F)CCC1)C(F)(F)F]

The title compound was synthesized in analogy to Example 123d, using 5-(1-fluorocyclobutyl)-4-[(1S)-2,2,2-trifluoro-1-methyl-ethoxy]pyridine-2-carbonitrile (example 305d) as starting material and isolated (782 mg, 60%); MS (ESI, m/z): 308.2 (M+H⁺).

f) N-[3-(2-amino-2-oxoethyl)-1,1-dioxothietan-3-yl]-5-(1-fluorocyclobutyl)-4-[(2S)-1,1,1-trifluoropropan-2-yl]oxypyridine-2-carboxamide

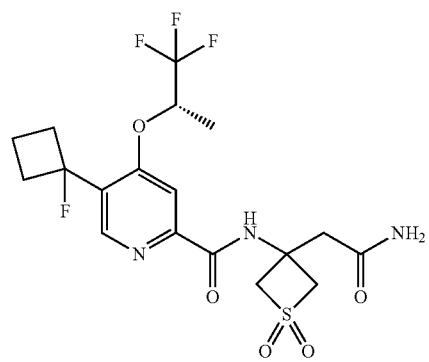 [SMILES: C[C@H](Oc1cc(C(=O)NC2(CC(N)=O)CS(=O)(=O)C2)ncc1C1(F)CCC1)C(F)(F)F]

The title compound was synthesized in analogy to Example 112e, using 5-(1-fluorocyclobutyl)-4-[(1S)-2,2,2-trifluoro-1-methyl-ethoxy]pyridine-2-carboxylic acid (example 305e) and 2-(3-amino-1,1-dioxo-thietan-3-yl)acetamide (example 160d) as starting materials and isolated (19 mg, 49%); MS (ESI, m/z): 468.3 (M+H⁺).

Example 306

N-(1-cyclopropyl-1-(5-methyl-1,2,4-oxadiazol-3-yl)ethyl)-5-(1-fluorocyclobutyl)-4-(2,2,2-trifluoroethoxy)picolinamide (enantiomer A)

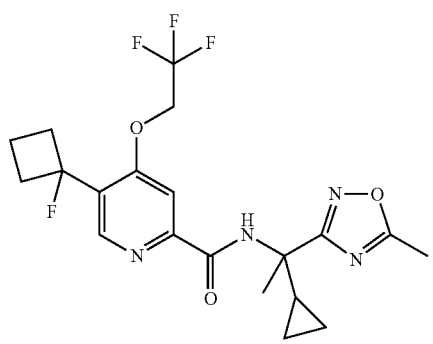 [SMILES: Cc1nc(C(C)(NC(=O)c2cc(OCC(F)(F)F)c(C3(F)CCC3)cn2)C2CC2)no1]

287

The title compound was synthesized in analogy to Example 112e, using 5-(1-fluorocyclobutyl)-4-(2,2,2-trifluoroethoxy)pyridine-2-carboxylic acid (example 285a) and 1-Cyclopropyl-1-(5-methyl-[1,2,4]oxadiazol-3-yl)-ethylamine (CAN 1155536-64-3) as starting materials and the racemate was separated into its enantiomers by preparative chiral HPLC (Chiralpak AD, ethanol/heptane). The title compound was the first enantiomer collected; MS (ESI, m/z): 443.3 (M+H⁺).

Example 307

N-(1-cyclopropyl-1-(5-methyl-1,2,4-oxadiazol-3-yl)ethyl)-5-(1-fluorocyclobutyl)-4-(2,2,2-trifluoroethoxy)picolinamide (enantiomer B)

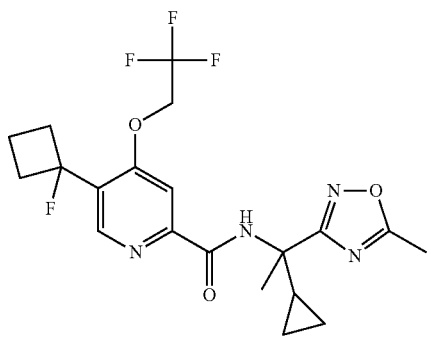 [SMILES: Cc1nc(C(C)(NC(=O)c2cc(OCC(F)(F)F)c(C3(F)CCC3)cn2)C2CC2)no1]

The title compound was synthesized in analogy to Example 112e, using 5-(1-fluorocyclobutyl)-4-(2,2,2-trifluoroethoxy)pyridine-2-carboxylic acid (example 285a) and 1-Cyclopropyl-1-(5-methyl-[1,2,4]oxadiazol-3-yl)-ethylamine (CAN 1155536-64-3) as starting materials and the racemate was separated into its enantiomers by preparative chiral HPLC (Chiralpak AD, ethanol/heptane). The title compound was the second enantiomer collected; MS (ESI, m/z): 443.3 (M+H⁺).

Example 308

N-(1-cyclopropyl-1-(5-methyl-1,2,4-oxadiazol-3-yl)ethyl)-5-(1-fluorocyclobutyl)-4-(2,2,2-trifluoroethoxy)picolinamide

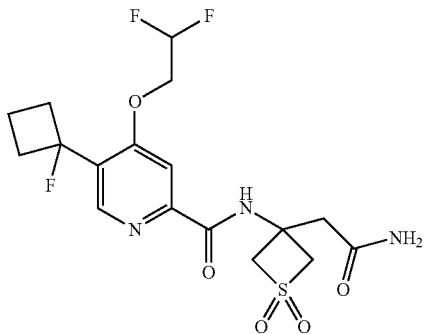 [SMILES: NC(=O)CC1(NC(=O)c2cc(OCC(F)F)c(C3(F)CCC3)cn2)CS(=O)(=O)C1]

288 a) 4-(2,2-difluoroethoxy)-5-(1-fluorocyclobutyl)pyridine-2-carbonitrile

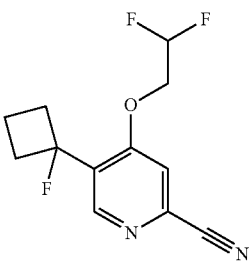 [SMILES: N#Cc1cc(OCC(F)F)c(C2(F)CCC2)cn1]

The title compound was synthesized in analogy to Example 123c, using 4-chloro-5-(1-fluorocyclobutyl)-pyridine-2-carbonitrile (example 305c) and 2,2-Difluoro-ethanol (CAN 359-13-7) as starting materials and sodium hydride as reagent. The title was isolated (1 g, 83%) as a yellow oil; MS (ESI, m/z): 257.1 (M+H⁺).

b) 4-(2,2-difluoroethoxy)-5-(1-fluorocyclobutyl)pyridine-2-carboxylic acid

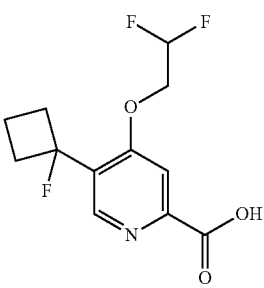 [SMILES: O=C(O)c1cc(OCC(F)F)c(C2(F)CCC2)cn1]

The title compound was synthesized in analogy to Example 123d, using 4-(2,2-difluoroethoxy)-5-(1-fluorocyclobutyl)pyridine-2-carbonitrile (example 308a) as starting material and isolated (600 mg, 55%); MS (ESI, m/z): 276.1 (M+H⁺).

c) N-[3-(2-amino-2-oxoethyl)-1,1-dioxothietan-3-yl]-4-(2,2-difluoroethoxy)-5-(1-fluorocyclobutyl)pyridine-2-carboxamide

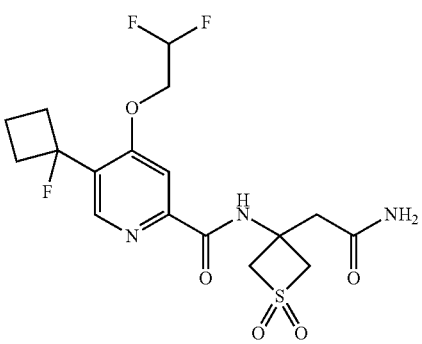 [SMILES: NC(=O)CC1(NC(=O)c2cc(OCC(F)F)c(C3(F)CCC3)cn2)CS(=O)(=O)C1]

The title compound was synthesized in analogy to Example 112e, using 4-(2,2-difluoroethoxy)-5-(1-fluorocyclobutyl)pyridine-2-carboxylic acid (example 308b) and 2-(3-amino-1,1-dioxo-thietan-3-yl)acetamide (example 160d) as starting materials and isolated (11.5 mg, 14%); MS (ESI, m/z): 436.3 (M+H$^+$).

Example 309

N-[4-amino-2-cyclopropyl-4-oxobutan-2-yl]-5-(1-fluorocyclobutyl)-4-(2,2,2-trifluoroethoxy)pyridine-2-carboxamide (enantiomer A)

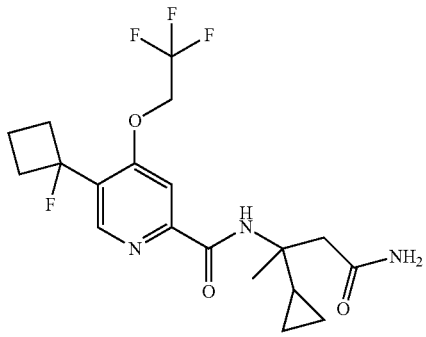 [SMILES: CC(CC(N)=O)(NC(=O)c1cc(OCC(F)(F)F)c(C2(F)CCC2)cn1)C1CC1]

The racemate (Example 300) was separated into its enantiomers by preparative chiral HPLC (Chiralpak AD, isopropanol/heptane) and the title compound was the first enantiomer collected and isolated as colorless oil; MS (ESI, m/z): 418.3 (M+H$^+$).

Example 310

N-[4-amino-2-cyclopropyl-4-oxobutan-2-yl]-5-(1-fluorocyclobutyl)-4-(2,2,2-trifluoroethoxy)pyridine-2-carboxamide (enantiomer B)

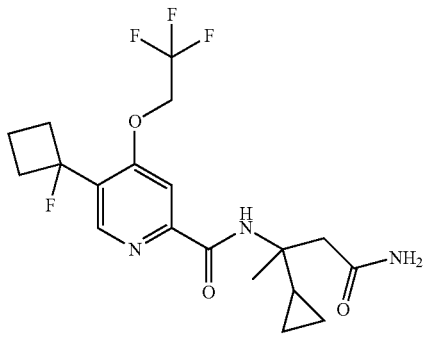 [SMILES: CC(CC(N)=O)(NC(=O)c1cc(OCC(F)(F)F)c(C2(F)CCC2)cn1)C1CC1]

The racemate (Example 300) was separated into its enantiomers by preparative chiral HPLC (Chiralpak AD, isopropanol/heptane) and the title compound was the second enantiomer collected and isolated as colorless oil; MS (ESI, m/z): 418.3 (M+H$^+$).

Example 311

Pharmacological Tests

The following tests were carried out in order to determine the activity of the compounds of formula (I):

Radioligand Binding Assay

The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl2, 2.5 mM EDTA, and 0.5% (wt/vol) fatty acid free BSA, pH 7.4 for CB1 receptor and 50 mM Tris, 5 mM MgCl$_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 μM, more particularly of 1 nM to 3 μM and most particularly of 1 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% CO$_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 μl and incubated for 30 min at 30° C. Using the cAMP-Nano-TRF detection kit the assay (Roche Diagnostics) was stopped by the addition of 50 μl lysis reagent (Tris, NaCl, 1.5% Triton X100, 2.5% NP40, 10% NaN$_3$) and 50 μl detection solutions (20 μM mAb Alexa700-cAMP 1:1, and 48 μM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 μM to 0.13 nM cAMP.

EC$_{50}$ values were determined using Activity Base analysis (ID Business Solution, Limited). The EC$_{50}$ values for a wide range of cannabinoid agonists generated from this assay were in agreement with the values published in the scientific literature.

The compounds of the invention are CB2 receptor agonists with EC$_{50}$ below 1 μM and selectivity versus CB1 in the corresponding assay of at least 10 fold. Particular compound of the invention are CB2 receptor agonists with EC$_{50}$ below 0.05 μM and selectivity versus CB1 in the corresponding assay of at least 500 fold.

For example, the following compounds showed the following human EC$_{50}$ values in the functional cAMP assay described above:

| Example | Human CB2 EC$_{50}$ (uM) | Human CB1 EC$_{50}$ (uM) |
| --- | --- | --- |
| 1 | 0.0356 | >10 |
| 2 | 0.0963 | >10 |
| 3 | 0.4663 | >10 |
| 4 | 0.1147 | >10 |
| 5 | 0.1069 | >10 |
| 6 | 0.0524 | >10 |
| 7 | 0.0523 | >10 |
| 8 | 0.1588 | >10 |
| 9 | 0.0329 | >10 |
| 10 | 0.0119 | >10 |
| 11 | 0.0554 | >10 |
| 12 | 0.0092 | >10 |
| 13 | 0.1458 | >10 |
| 14 | 0.0128 | 6.98 |
| 15 | 0.0058 | >10 |
| 16 | 0.0031 | 0.8146 |
| 17 | 0.0473 | >10 |
| 18 | 0.1491 | >10 |
| 19 | 0.0615 | >10 |
| 20 | 0.0232 | >10 |
| 21 | 0.0404 | >10 |
| 22 | 0.0057 | >10 |
| 23 | 0.2045 | >10 |
| 24 | 0.0098 | >10 |
| 25 | 0.0119 | >10 |
| 26 | 0.0476 | >10 |
| 27 | 0.0224 | >10 |
| 28 | 0.0263 | >10 |
| 29 | 0.0646 | >10 |
| 30 | 0.0192 | >10 |
| 31 | 0.0095 | >10 |
| 32 | 0.0746 | >10 |
| 33 | 0.0244 | >10 |
| 34 | 0.2678 | >10 |
| 35 | 0.1432 | >10 |
| 36 | 0.0517 | >10 |
| 37 | 0.0167 | >10 |
| 38 | 0.0408 | >10 |
| 39 | 0.1282 | >10 |
| 40 | 0.005 | 0.0901 |
| 41 | 0.0033 | 0.1446 |
| 42 | 0.0116 | >10 |
| 43 | 0.0032 | >10 |
| 44 | 0.0007 | >10 |
| 45 | 0.017 | >10 |
| 46 | 0.0067 | >10 |
| 47 | 0.0118 | >10 |
| 48 | 0.001575 | 0.6607 |
| 49 | 0.0017 | >10 |
| 50 | 0.0058 | >10 |
| 51 | 0.0122 | >10 |
| 52 | 0.0778 | >10 |
| 53 | 0.0726 | >10 |
| 54 | 0.0185 | >10 |
| 55 | 0.0157 | >10 |
| 56 | 0.0181 | >10 |
| 57 | 0.013 | >10 |
| 58 | 0.0637 | >10 |
| 59 | 0.0816 | >10 |
| 60 | 0.481 | >10 |
| 61 | 0.0276 | >10 |
| 62 | 0.0089 | >10 |
| 63 | 0.2826 | >10 |
| 64 | 0.515 | >10 |
| 65 | 0.027 | >10 |
| 66 | 0.00595 | >10 |
| 67 | 0.0037 | 5.285 |
| 68 | 0.00395 | >10 |
| 69 | 0.00025 | 0.015 |
| 70 | 0.0104 | >10 |
| 71 | 0.5857 | >10 |
| 72 | 0.0027 | 0.19 |
| 73 | 0.00025 | 0.017 |
| 74 | 0.0133 | >10 |
| 75 | 0.1098 | >10 |
| 76 | 0.1672 | >10 |
| 77 | 0.1368 | >10 |
| 78 | 0.0061 | >10 |
| 79 | 0.0065 | 0.19 |
| 80 | 0.9691 | >10 |
| 81 | 0.0053 | 0.19 |
| 82 | 0.0805 | >10 |
| 83 | 0.025 | >10 |
| 84 | 0.0488 | >10 |
| 85 | 0.3618 | >10 |
| 86 | 0.1447 | >10 |
| 87 | 0.0568 | >10 |
| 88 | 0.0105 | 1.79 |
| 89 | 0.0483 | >10 |
| 90 | 0.0177 | >10 |
| 91 | 0.0303 | >10 |
| 92 | 0.0214 | >10 |
| 93 | 0.0651 | >10 |
| 94 | 0.0747 | >10 |
| 95 | 0.0554 | >10 |
| 96 | 0.0014 | 0.11 |
| 97 | 0.0059 | >10 |
| 98 | 0.07055 | >10 |
| 99 | 0.10375 | >10 |
| 100 | 0.0006 | >10 |
| 101 | 0.0007 | 0.21 |
| 102 | 0.1158 | >10 |
| 103 | 0.0034 | 0.48 |
| 104 | 0.0298 | >10 |
| 105 | 0.0023 | 0.33 |
| 106 | 0.0095 | >10 |
| 107 | 0.0822 | >10 |
| 108 | 0.0027 | 0.79 |
| 109 | 0.0157 | >10 |
| 110 | 0.0008 | 0.31 |
| 111 | 0.003 | 0.43 |
| 112 | 0.0436 | >10 |
| 113 | 0.263 | >10 |
| 114 | 1.0013 | >10 |
| 115 | 1.2634 | >10 |
| 116 | 0.0041 | >10 |
| 117 | 0.0024 | >10 |
| 118 | 0.0017 | >10 |
| 119 | 0.0091 | >10 |
| 120 | 0.0008 | >10 |
| 121 | 0.0006 | >10 |
| 122 | 0.3992 | >10 |
| 123 | 0.9976 | >10 |
| 124 | 0.0159 | >10 |
| 125 | 0.011 | >10 |
| 126 | 0.2191 | >10 |
| 127 | 0.0196 | >10 |
| 128 | 0.0653 | >10 |
| 129 | 1.0949 | >10 |
| 130 | 0.0234 | >10 |
| 131 | 0.0263 | >10 |
| 132 | 0.3334 | >10 |
| 133 | 0.5677 | >10 |
| 134 | 0.8879 | >10 |
| 135 | 0.1444 | >10 |
| 136 | 0.1246 | >10 |
| 137 | 0.0105 | >10 |
| 138 | 0.0217 | >10 |
| 139 | 0.0006 | >10 |
| 140 | 0.5107 | >10 |
| 141 | 0.0968 | >10 |
| 142 | 0.0041 | >10 |
| 143 | 0.2462 | >10 |
| 144 | 0.0141 | >10 |
| 145 | 0.0034 | >10 |
| 146 | 0.0018 | >10 |
| 147 | 0.0454 | >10 |
| 148 | 0.2045 | >10 |
| 149 | 0.0127 | >10 |
| 150 | 0.109 | >10 |
| 151 | 0.0198 | >10 |
| 152 | 0.1854 | >10 |

| Example | Human CB2 EC$_{50}$ (uM) | Human CB1 EC$_{50}$ (uM) |
| --- | --- | --- |
| 153 | 0.0407 | >10 |
| 154 | 0.0037 | >10 |
| 155 | 0.0058 | >10 |
| 156 | 0.0047 | >10 |
| 157 | 0.0036 | >10 |
| 158 | 0.0958 | >10 |
| 159 | 0.9346 | >10 |
| 160 | 0.0118 | >10 |
| 161 | 0.0088 | >10 |
| 162 | 0.0717 | >10 |
| 163 | 0.0045 | >10 |
| 164 | 0.0168 | >10 |
| 165 | 0.022 | >10 |
| 166 | 0.3104 | >10 |
| 167 | 0.0281 | >10 |
| 168 | 0.2806 | >10 |
| 169 | 0.0055 | >10 |
| 170 | 0.0254 | >10 |
| 171 | 0.0149 | >10 |
| 172 | 0.0329 | >10 |
| 173 | 0.0544 | >10 |
| 174 | 0.0218 | >10 |
| 175 | 0.0955 | >10 |
| 176 | 0.4425 | >10 |
| 177 | 0.0124 | >10 |
| 178 | 0.0105 | >10 |
| 179 | 0.0351 | >10 |
| 180 | 0.1493 | >10 |
| 181 | 0.002 | >10 |
| 182 | 0.0054 | >10 |
| 183 | 0.9174 | >10 |
| 184 | 0.0856 | >10 |
| 185 | 0.0302 | >10 |
| 186 | 0.3434 | >10 |
| 187 | 0.4163 | >10 |
| 188 | 0.0206 | >10 |
| 189 | 0.2925 | >10 |
| 190 | 0.5588 | >10 |
| 191 | 0.7072 | >10 |
| 192 | 0.0044 | >10 |
| 193 | 0.1135 | >10 |
| 194 | 0.0151 | >10 |
| 195 | 0.0034 | >10 |
| 196 | 0.0012 | >10 |
| 197 | 0.0076 | >10 |
| 198 | 0.0364 | >10 |
| 199 | 0.0078 | >10 |
| 200 | 0.0026 | >10 |
| 201 | 0.0024 | >10 |
| 202 | 0.0022 | >10 |
| 203 | 0.0051 | >10 |
| 204 | 0.0646 | >10 |
| 205 | 0.108 | >10 |
| 206 | 0.0393 | >10 |
| 207 | 0.0083 | >10 |
| 208 | 0.0092 | >10 |
| 209 | 0.0048 | >10 |
| 210 | 0.0042 | >10 |
| 211 | 0.0048 | >10 |
| 212 | 0.005 | >10 |
| 213 | 0.0111 | >10 |
| 214 | 0.008 | >10 |
| 215 | 0.0309 | >10 |
| 216 | 0.0047 | >10 |
| 217 | 0.0029 | >10 |
| 218 | 0.0068 | >10 |
| 219 | 0.001 | >10 |
| 220 | 0.0027 | >10 |
| 221 | 0.0084 | >10 |
| 222 | 0.0467 | >10 |
| 223 | 0.1655 | >10 |
| 224 | 0.0573 | >10 |
| 225 | 0.0004 | >10 |
| 226 | 0.0065 | >10 |
| 227 | 0.015 | >10 |
| 228 | 0.0346 | >10 |
| 229 | 0.0114 | >10 |
| 230 | 0.0009 | >10 |
| 231 | 0.5473 | >10 |
| 232 | 0.1164 | >10 |
| 233 | 0.915 | >10 |
| 234 | 0.4547 | >10 |
| 235 | 0.2932 | >10 |
| 236 | 0.0512 | >10 |
| 237 | 0.017 | >10 |
| 238 | 0.0274 | >10 |
| 239 | 0.0015 | >10 |
| 240 | 0.0552 | >10 |
| 241 | 0.0119 | >10 |
| 242 | 0.2369 | >10 |
| 243 | 0.0005 | >10 |
| 244 | 0.0284 | >10 |
| 245 | 0.9974 | >10 |
| 246 | 0.1861 | >10 |
| 247 | 0.0193 | >10 |
| 248 | 0.0009 | >10 |
| 249 | 0.001 | >10 |
| 250 | 0.0332 | >10 |
| 251 | 0.0089 | >10 |
| 252 | 0.3435 | >10 |
| 253 | 0.0019 | >10 |
| 254 | 0.0065 | >10 |
| 255 | 0.0067 | >10 |
| 256 | 0.0132 | >10 |
| 257 | 0.003 | >10 |
| 258 | 0.013 | >10 |
| 259 | 0.0005 | >10 |
| 260 | 0.0209 | >10 |
| 261 | 0.0211 | >10 |
| 262 | 0.2613 | >10 |
| 263 | 0.0338 | >10 |
| 264 | 0.1784 | >10 |
| 265 | 0.1016 | >10 |
| 266 | 0.0016 | >10 |
| 267 | 0.0105 | >10 |
| 268 | 0.2246 | >10 |
| 269 | 0.7711 | >10 |
| 270 | 0.0689 | >10 |
| 271 | 0.0015 | >10 |
| 272 | 0.0495 | >10 |
| 273 | 0.0017 | >10 |
| 274 | 0.0101 | >10 |
| 275 | 0.0227 | >10 |
| 276 | 0.1369 | >10 |
| 277 | 0.0431 | >10 |
| 278 | 0.0929 | >10 |
| 279 | 0.1727 | >10 |
| 280 | 0.0786 | >10 |
| 281 | 0.0231 | >10 |
| 282 | 0.6592 | >10 |
| 283 | 0.0533 | >10 |
| 284 | 0.0453 | >10 |
| 285 | 1.441 | >10 |
| 286 | 0.0459 | >10 |
| 287 | 0.0014 | >10 |
| 288 | 0.0008 | >10 |
| 289 | 0.001 | >10 |
| 290 | 0.0006 | >10 |
| 291 | 0.0003 | >10 |
| 292 | 0.0019 | >10 |
| 293 | 0.0013 | >10 |
| 294 | 0.0006 | >10 |
| 295 | 0.0024 | >10 |
| 296 | 0.0422 | >10 |
| 297 | 0.0032 | >10 |
| 298 | 0.0579 | >10 |
| 299 | 0.002 | >10 |

| Example | Human CB2 EC$_{50}$ (uM) | Human CB1 EC$_{50}$ (uM) |
| --- | --- | --- |
| 300 | 0.0067 | >10 |
| 301 | 0.0304 | >10 |
| 302 | 0.001 | 0.869 |
| 303 | 0.0485 | >10 |
| 304 | 0.0021 | 0.82 |
| 305 | 0.0051 | >10 |
| 306 | 0.0118 | >10 |
| 307 | 0.0034 | 0.032 |
| 308 | 0.073 | >10 |
| 309 | 0.002 | 0.475 |
| 310 | 0.0154 | 2.437 |

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
| --- | --- |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound of formula (I)

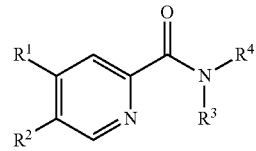

wherein
$R^1$ is halogen, halophenyl, cycloalkylalkoxy, halophenylalkyl, oxetanyloxy, haloalkoxy, halophenylalkoxy or alkyloxetanylalkoxy;
$R^2$ is halogen, cycloalkyl, haloazetidinyl, halopyrrolidinyl, cycloalkenyl, halocycloalkyl or halooxetanyl;
one of $R^3$ and $R^4$ is hydrogen or alkyl and the other one is —(CR$^5$R$^6$)—(CR$^7$R$^8$)$_n$—R$^9$;
or $R^3$ and $R^4$ together with the nitrogen atom to which they are attached form 2-oxo-5-aza-spiro[3.4]octyl, haloazetidinyl or halopyrrolidinyl;
$R^5$ and $R^6$ are independently selected from hydrogen, alkyl, cycloalkylalkyl, haloalkyl, cycloalkyl, alkylsulfonylalkyl, phenylalkoxyalkyl, hydroxyalkyl, haloazetidinylalkyl, haloazetidinylcarbonyl, 2-oxa-6-azaspiro[3.3]heptanylcarbonyl, alkylaminocarbonyl, di alkylaminocarbonyl, aminocarbonyl, azetidinylcarbonyl, oxetanyl alkyl and alkyl oxetanyl;
or $R^5$ and $R^6$ together with the carbon atom to which they are attached form cycloalkyl, oxetanyl, oxanyl or dioxothietanyl;
$R^7$ and $R^8$ are independently selected from hydrogen, alkyl and cycloalkyl;
or $R^7$ and $R^8$ together with the carbon atom to which they are attached form cycloalkyl;
$R^9$ is alkyl, alkoxycarbonyl, hydroxyl, hydroxyalkyl, aminocarbonyl, cyano, pyridinyl, alkylaminocarbonyl, thiazol-2-yl, oxazol-2-yl, 5-alkyl-[1,2,4]oxadiazol-3-yl, alkyltetrazolyl, alkylthiazol-2-yl, 1H-tetrazolyl, 5-amino-[1,2,4]-oxadiazol-3-yl, 5-alkyl-[1,3,4]-oxadiazol-2-yl, azetidinylcarbonyl, haloazetidinylcarbonyl, 6-oxa-1-azaspiro[3.3]heptanyl, 5-phenyl-[1,3,4]-oxadiazol-2-yl or haloalkylaminocarbonyl; and
n is 0 or 1;
provided that when $R^3$ and $R^4$ are both alkyl at the same time, then $R^1$ and $R^2$ are not both halogen at the same time;
or a pharmaceutically acceptable salt or ester thereof.

2. A compound according to claim 1, wherein $R^1$ is haloalkoxy.

3. A compound according to claim 1, wherein $R^1$ is trifluoroethoxy, trifluoropropyloxy, difluoroethyloxy, fluoroethyloxy or fluoropropyloxy.

4. A compound according to claim 1, wherein $R^2$ is cycloalkyl or haloazetidinyl.

5. A compound according to claim 1, wherein $R^2$ is cyclopropyl, cyclobutyl or difluoroazetidinyl.

6. A compound according to claim 1, wherein one of $R^3$ and $R^4$ is hydrogen and the other one is —$(CR^5R^6)$—$(CR^7R^8)_n$—$R^9$.

7. A compound according to claim 1, wherein $R^5$ and $R^6$ are independently selected from alkyl, cycloalkylalkyl, alkylsulfonylalkyl and cycloalkyl, or $R^5$ and $R^6$ together with the carbon atom to which they are attached form dioxothietanyl.

8. A compound according to claim 1, wherein $R^5$ and $R^6$ are independently selected from methyl, cyclopropylmethyl, methylsulfonylmethyl and cyclopropyl, or $R^5$ and $R^6$ together with the carbon atom to which they are attached form dioxothietanyl.

9. A compound according to claim 1, wherein $R^9$ is 5-alkyl-[1,2,4]oxadiazol-3-yl or aminocarbonyl.

10. A compound according to claim 1, wherein $R^9$ is 5-methyl-[1,2,4]oxadiazol-3-yl or aminocarbonyl.

11. A compound according to claim 1, $R^7$ and $R^8$ are independently selected from hydrogen, methyl and ethyl, or $R^7$ and $R^8$ together with the carbon atom to which they are attached form cyclopentyl or cyclohexyl.

12. A compound according to claim 1, wherein $R^7$ and $R^8$ are both hydrogen at the same time.

13. A compound according to claim 1, wherein n is 0.

14. A compound according to claim 1 selected from

2-[(5-Chloro-4-iodo-pyridine-2-carbonyl)-amino]-2-methyl-propionic acid methyl ester;

5-Chloro-4-(3-chloro-phenyl)-pyridine-2-carboxylic acid (2-hydroxy-1,1-dimethyl-ethyl)-amide;

5-Chloro-4-(3-chloro-phenyl)-pyridine-2-carboxylic acid ((S)-1-carbamoyl-3-methyl-butyl)-amide;

5-Chloro-4-cyclopropylmethoxy-pyridine-2-carboxylic acid ((S)-1-carbamoyl-2-cyclopropyl-ethyl)-amide;

5-Chloro-4-cyclopropylmethoxy-pyridine-2-carboxylic acid (1-hydroxy-cyclohexylmethyl)-amide;

5-Chloro-4-cyclopropylmethoxy-pyridine-2-carboxylic acid (1-hydroxymethyl-cyclopentyl)-amide;

5-Chloro-4-cyclopropylmethoxy-pyridine-2-carboxylic acid ((S)-1-hydroxymethyl-3-methyl-butyl)-amide;

5-Chloro-4-cyclopropylmethoxy-pyridine-2-carboxylic acid (cyano-dimethyl-methyl)-amide;

5-Bromo-4-cyclopropylmethoxy-pyridine-2-carboxylic acid ((R)-1-carbamoyl-3-methyl-butyl)-amide;

5-Chloro-4-cyclopropylmethoxy-pyridine-2-carboxylic acid ((S)-1-hydroxymethyl-1,2-dimethyl-propyl)-amide;

5-Chloro-4-cyclopropylmethoxy-pyridine-2-carboxylic acid ((R)-1-hydroxymethyl-2-methyl-propyl)-amide;

5-Chloro-4-cyclobutylmethoxy-pyridine-2-carboxylic acid ((R)-1-hydroxymethyl-1,2-dimethyl-propyl)-amide;

5-Chloro-4-cyclopropylmethoxy-pyridine-2-carboxylic acid ((R)-1-hydroxymethyl-butyl)-amide;

5-Chloro-4-cyclopropylmethoxy-pyridine-2-carboxylic acid ((R)-1-hydroxymethyl-1,2-dimethyl-propyl)-amide;

5-Chloro-4-(4-fluoro-benzyl)-pyridine-2-carboxylic acid ((R)-1-hydroxymethyl-1,2-dimethyl-propyl)-amide;

5-Chloro-4-cyclopropylmethoxy-pyridine-2-carboxylic acid ((R)-2,2,2-trifluoro-1-pyridin-2-yl-ethyl)-amide;

5-Chloro-4-cyclopropylmethoxy-pyridine-2-carboxylic acid (3-hydroxy-2,2-dimethyl-propyl)-amide;

5-Chloro-4-cyclopropylmethoxy-pyridine-2-carboxylic acid [1-(2-hydroxy-ethyl)-2-methyl-propyl]-amide;

5-Chloro-4-cyclopropylmethoxy-pyridine-2-carboxylic acid (1-cyclopropyl-3-hydroxy-propyl)-amide;

5-Chloro-4-cyclopropylmethoxy-pyridine-2-carboxylic acid (1-hydroxymethyl-cyclopentylmethyl)-amide;

5-Chloro-4-cyclopropylmethoxy-pyridine-2-carboxylic acid (1-ethyl-1-hydroxymethyl-propyl)-amide;

5-Chloro-4-cyclopropylmethoxy-pyridine-2-carboxylic acid ((S)-2,2,2-trifluoro-1-pyridin-3-yl-ethyl)-amide;

5-Chloro-4-(oxetan-3-yloxy)-pyridine-2-carboxylic acid ((S)-2,2-dimethyl-1-methylcarbamoyl-propyl)-amide;

5-Chloro-4-(2,2,2-trifluoro-ethoxy)-pyridine-2-carboxylic acid ((S)-2,2-dimethyl-1-methylcarbamoyl-propyl)-amide;

5-Chloro-4-cyclopropylmethoxy-pyridine-2-carboxylic acid (1-hydroxymethyl-1,3-dimethyl-butyl)-amide;

5-Chloro-4-cyclopropylmethoxy-pyridine-2-carboxylic acid (1-hydroxymethyl-1-methyl-propyl)-amide;

5-Chloro-4-cyclopropylmethoxy-pyridine-2-carboxylic acid ((S)-1-hydroxymethyl-1,3-dimethyl-butyl)-amide;

5-Chloro-4-cyclopropylmethoxy-pyridine-2-carboxylic acid ((R)-1-hydroxymethyl-1,3-dimethyl-butyl)-amide;

5-Chloro-4-cyclopropylmethoxy-pyridine-2-carboxylic acid ((R)-1-hydroxymethyl-2,2-dimethyl-propyl)-amide;

5-Chloro-4-cyclopropylmethoxy-pyridine-2-carboxylic acid ((R)-1-hydroxymethyl-1-methyl-propyl)-amide;

Methyl 3-({[5-chloro-4-(cyclopropylmethoxy)pyridin-2-yl]carbonyl}amino)-2,3-dimethylbutanoate 5-Chloro-4-cyclopropylmethoxy-pyridine-2-carboxylic acid (3-thiazol-2-yl-oxetan-3-yl)-amide;

5-Chloro-4-cyclopropylmethoxy-pyridine-2-carboxylic acid (1-hydroxymethyl-1-methyl-butyl)-amide;

5-Chloro-4-cyclopropylmethoxy-pyridine-2-carboxylic acid ((S)-1,1-dimethyl-2-methylcarbamoyl-propyl)-amide;

5-Chloro-4-cyclopropylmethoxy-pyridine-2-carboxylic acid ((R)-1,1-dimethyl-2-methylcarbamoyl-propyl)-amide;

5-Chloro-4-cyclopropylmethoxy-pyridine-2-carboxylic acid (3-oxazol-2-yl-oxetan-3-yl)-amide;

5-Chloro-4-cyclopropylmethoxy-pyridine-2-carboxylic acid ((S)-1-hydroxymethyl-1-methyl-butyl)-amide;

5-Chloro-4-(2,2,2-trifluoro-ethoxy)-pyridine-2-carboxylic acid (2,2-dimethyl-1-thiazol-2-yl-propyl)-amide;

5-Chloro-4-(oxetan-3-yloxy)-pyridine-2-carboxylic acid (2,2-dimethyl-1-thiazol-2-yl-propyl)-amide;

5-Chloro-4-(4-fluoro-benzyloxy)-pyridine-2-carboxylic acid ((S)-2,2,2-trifluoro-1-pyridin-3-yl-ethyl)-amide;

5-Chloro-4-(4-fluoro-benzyl)-pyridine-2-carboxylic acid ((S)-2,2,2-trifluoro-1-pyridin-3-yl-ethyl)-amide;

5-Cyclopropyl-4-cyclopropylmethoxy-pyridine-2-carboxylic acid (3-thiazol-2-yl-oxetan-3-yl)-amide;

5-Cyclopropyl-4-cyclopropylmethoxy-pyridine-2-carboxylic acid (2,2-dimethyl-1-thiazol-2-yl-propyl)-amide;

5-Cyclopropyl-4-cyclopropylmethoxy-pyridine-2-carboxylic acid [1-cyclopropyl-1-(5-methyl-[1,2,4]oxadiazol-3-yl)-ethyl]-amide;

5-Cyclopropyl-4-cyclopropylmethoxy-pyridine-2-carboxylic acid (1-ethyl-1-methylcarbamoyl-propyl)-amide;

5-Cyclopropyl-4-cyclopropylmethoxy-pyridine-2-carboxylic acid (2,2,2-trifluoro-1-pyridin-2-yl-ethyl)-amide;
5-Cyclopropyl-4-cyclopropylmethoxy-pyridine-2-carboxylic acid ((S)-1-carbamoyl-3-methyl-butyl)-amide;
5-Cyclopropyl-4-(2,2,2-trifluoro-ethoxy)-pyridine-2-carboxylic acid ((S)-2,2-dimethyl-1-methylcarbamoyl-propyl)-amide;
5-Cyclopropyl-4-(2,2,2-trifluoro-ethoxy)-pyridine-2-carboxylic acid [1-cyclopropyl-1-(5-methyl-[1,2,4]oxadiazol-3-yl)-ethyl]-amide;
5-Cyclopropyl-4-(2,2,2-trifluoro-ethoxy)-pyridine-2-carboxylic acid (2,2-dimethyl-1-thiazol-2-yl-propyl)-amide;
5-Cyclopropyl-4-(2,2,2-trifluoro-ethoxy)-pyridine-2-carboxylic acid (2,2,2-trifluoro-1-pyridin-2-yl-ethyl)-amide;
5-Cyclopropyl-4-(2,2,2-trifluoro-ethoxy)-pyridine-2-carboxylic acid ((S)-1-carbamoyl-3-methyl-butyl)-amide;
4-Cyclopropylmethoxy-5-(3,3-difluoro-azetidin-1-yl)-pyridine-2-carboxylic acid (1-hydroxymethyl-cyclopropyl)-amide;
5-Cyclopropyl-4-(2,2,2-trifluoro-ethoxy)-pyridine-2-carboxylic acid (1-ethyl-1-hydroxymethyl-propyl)-amide;
5-Cyclopropyl-4-(2,2,2-trifluoro-ethoxy)-pyridine-2-carboxylic acid (1-hydroxymethyl-cyclohexyl)-amide;
5-Cyclopropyl-4-cyclopropylmethoxy-pyridine-2-carboxylic acid (1-hydroxy-cyclopentylmethyl)-amide;
5-Cyclopropyl-4-cyclopropylmethoxy-pyridine-2-carboxylic acid (1-hydroxy-cyclohexylmethyl)-amide;
5-Cyclopropyl-4-cyclopropylmethoxy-pyridine-2-carboxylic acid (2-hydroxy-butyl)-amide;
5-Cyclopropyl-4-cyclopropylmethoxy-pyridine-2-carboxylic acid (2-hydroxy-2-methyl-propyl)-amide;
5-Cyclopropyl-4-(2,2,2-trifluoro-ethoxy)-pyridine-2-carboxylic acid (2-hydroxy-2-methyl-propyl)-amide;
5-Cyclopropyl-4-(2,2,2-trifluoro-ethoxy)-pyridine-2-carboxylic acid [(S)-1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [1-cyclopropyl-1-(5-methyl-[1,2,4]oxadiazol-3-yl)-ethyl]-amide;
5-Cyclopropyl-4-((R)-2,2,2-trifluoro-1-methyl-ethoxy)-pyridine-2-carboxylic acid (3-carbamoylmethyl-oxetan-3-yl)-amide;
5-Cyclopropyl-4-((S)-2,2,2-trifluoro-1-methyl-ethoxy)-pyridine-2-carboxylic acid (3-carbamoylmethyl-oxetan-3-yl)-amide;
5-Cyclopropyl-4-(2,2,2-trifluoro-ethoxy)-pyridine-2-carboxylic acid ((R)-1-carbamoylmethyl-3-methyl-butyl)-amide;
5-Cyclopropyl-4-(2,2,2-trifluoro-ethoxy)-pyridine-2-carboxylic acid [(R)-2-cyclopropyl-1-methyl-1-(5-methyl-[1,2,4]oxadiazol-3-yl)-ethyl]-amide;
5-Cyclopropyl-4-(2,2,2-trifluoro-ethoxy)-pyridine-2-carboxylic acid [(S)-2-cyclopropyl-1-methyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Cyclopropyl-4-(2,2,2-trifluoro-ethoxy)-pyridine-2-carboxylic acid tert-butylamide;
[5-Cyclopropyl-4-(2,2,2-trifluoro-ethoxy)-pyridin-2-yl]-(2-oxa-5-aza-spiro[3.4]oct-5-yl)-methanone;
5-Cyclopropyl-4-((R)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Cyclopropyl-4-((R)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [(R)-1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [(S)-1-cyclopropyl-1-(5-methyl-[1,2,4]oxadiazol-3-yl)-ethyl]-amide;
[5-Cyclopropyl-4-(2,2,2-trifluoro-ethoxy)-pyridin-2-yl]-(3,3-difluoro-azetidin-1-yl)-methanone;
5-Cyclopropyl-4-(2,2,2-trifluoro-ethoxy)-pyridine-2-carboxylic acid (1-carbamoyl-1-methyl-propyl)-amide;
5-(3,3-Difluoro-azetidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide;
5-(3,3-Difluoro-pyrrolidin-1-yl)-4-(2,2,2-trifluoro-ethoxy)-pyridine-2-carboxylic acid [1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;
5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;
5-Cyclopropyl-4-(2,2,2-trifluoro-ethoxy)-pyridine-2-carboxylic acid (1-carbamoyl-1,3-dimethyl-butyl)-amide;
5-Chloro-4-(2,2,2-trifluoro-ethoxy)-pyridine-2-carboxylic acid [1,3,3-trimethyl-1-(5-methyl-[1,2,4]oxadiazol-3-yl)-butyl]-amide;
5-Cyclopropyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;
5-Chloro-4-(2,2,2-trifluoro-ethoxy)-pyridine-2-carboxylic acid (3-dimethylcarbamoylmethyl-oxetan-3-yl)-amide;
5-(3,3-Difluoro-azetidin-1-yl)-4-(2,2,2-trifluoro-ethoxy)-pyridine-2-carboxylic acid [(R)-1-cyclopropyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [(S)-1-cyclopropyl-1-(5-methyl-[1,2,4]oxadiazol-3-yl)-ethyl]-amide;
5-Chloro-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [(R)-2-cyclopropyl-1-methyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [(S)-2-cyclopropyl-1-methyl-1-(5-methyl-[1,2,4]oxadiazol-3-yl)-ethyl]-amide;
5-Chloro-4-(2,2,2-trifluoro-ethoxy)-pyridine-2-carboxylic acid [(R)-2-cyclopropyl-1-methyl-1-(5-methyl-[1,2,4]oxadiazol-3-yl)-ethyl]-amide;
5-Chloro-4-(2,2,2-trifluoro-ethoxy)-pyridine-2-carboxylic acid [(S)-2-cyclopropyl-1-methyl-1-(5-methyl-[1,2,4]oxadiazol-3-yl)-ethyl]-amide;
5-(3,3-Difluoro-azetidin-1-yl)-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;

5-(3,3-Difluoro-azetidin-1-yl)-4-((S)-2,2,2-trifluoro-1-methyl-ethoxy)-pyridine-2-carboxylic acid [1-cyclopropyl-1-(5-methyl-[1,2,4]oxadiazol-3-yl)-ethyl]-amide;

5-Cyclopropyl-4-(2,2,2-trifluoro-ethoxy)-pyridine-2-carboxylic acid [1,3,3-trimethyl-1-(5-methyl-[1,2,4]oxadiazol-3-yl)-butyl]-amide;

5-Cyclopropyl-4-(2,2,2-trifluoro-ethoxy)-pyridine-2-carboxylic acid [(S)-2-methanesulfonyl-1-methyl-1-(5-methyl-[1,2,4]oxadiazol-3-yl)-ethyl]-amide;

5-Cyclopropyl-4-(2,2,2-trifluoro-ethoxy)-pyridine-2-carboxylic acid [(R)-2-methanesulfonyl-1-methyl-1-(5-methyl-[1,2,4]oxadiazol-3-yl)-ethyl]-amide;

5-Cyclopropyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide;

5-Cyclopropyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide;

5-(3,3-Difluoro-azetidin-1-yl)-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;

5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;

5-Cyclopropyl-4-(2,2,2-trifluoro-ethoxy)-pyridine-2-carboxylic acid [(R)-1,3,3-trimethyl-1-(5-methyl-[1,2,4]oxadiazol-3-yl)-butyl]-amide;

5-Cyclopropyl-4-(2,2,2-trifluoro-ethoxy)-pyridine-2-carboxylic acid [(S)-1,3,3-trimethyl-1-(5-methyl-[1,2,4]oxadiazol-3-yl)-butyl]-amide;

5-Cyclopropyl-4-cyclopropylmethoxy-pyridine-2-carboxylic acid tert-butyl-ethyl-amide;

5-Cyclopropyl-4-(2,2,2-trifluoro-ethoxy)-pyridine-2-carboxylic acid tert-butyl-ethyl-amide;

5-Cyclobutyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide;

5-Cyclobutyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;

5-Cyclobutyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide;

5-Cyclobutyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;

5-cyclopropyl-N-[2-(5-methyl-1,2,4-oxadiazol-3-yl)-1-phenylmethoxypropan-2-yl]-4-(2,2,2-trifluoroethoxy)pyridine-2-carboxamide;

5-cyclopropyl-N-[1-hydroxy-2-(5-methyl-1,2,4-oxadiazol-3-yl)propan-2-yl]-4-(2,2,2-trifluoroethoxy)pyridine-2-carboxamide;

(2S)-1-[5-cyclopropyl-4-(cyclopropylmethoxy)pyridine-2-carbonyl]-4,4-difluoropyrrolidine-2-carboxamide;

(2S)-1-[5-cyclopropyl-4-(2,2,2-trifluoroethoxy)pyridine-2-carbonyl]-4,4-difluoropyrrolidine-2-carboxamide;

5-cyclobutyl-N-[(2R)-1-cyclopropyl-2-(5-methyl-1,2,4-oxadiazol-3-yl)propan-2-yl]-4-(2,2,2-trifluoroethoxy)pyridine-2-carboxamide;

5-cyclobutyl-N-[(2S)-1-cyclopropyl-2-(5-methyl-1,2,4-oxadiazol-3-yl)propan-2-yl]-4-(2,2,2-trifluoroethoxy)pyridine-2-carboxamide;

5-cyclobutyl-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

5-cyclobutyl-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

5-cyclobutyl-N-[1-cyclopropyl-2-(5-methyl-1,2,4-oxadiazol-3-yl)propan-2-yl]-4-[(2S)-1,1,1-trifluoropropan-2-yl]oxypyridine-2-carboxamide;

5-cyclobutyl-N-[1-cyclopropyl-2-(5-methyl-1,2,4-oxadiazol-3-yl)propan-2-yl]-4-[(2S)-1,1,1-trifluoropropan-2-yl]oxypyridine-2-carboxamide;

(2R)-1-[5-cyclopropyl-4-(2,2,2-trifluoroethoxy)pyridine-2-carbonyl]-4,4-difluoropyrrolidine-2-carboxamide;

N-[1-cyclopropyl-2-(5-methyl-1,2,4-oxadiazol-3-yl)propan-2-yl]-5-(3-hydroxyoxetan-3-yl)-4-(2,2,2-trifluoroethoxy)pyridine-2-carboxamide;

5-cyclobutyl-N-[(2S)-2-(5-methyl-1,2,4-oxadiazol-3-yl)-1-methylsulfonylpropan-2-yl]-4-(2,2,2-trifluoroethoxy)pyridine-2-carboxamide;

5-cyclobutyl-N-[(2R)-2-(5-methyl-1,2,4-oxadiazol-3-yl)-1-methylsulfonylpropan-2-yl]-4-(2,2,2-trifluoroethoxy)pyridine-2-carboxamide;

5-(1-hydroxycyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

5-(cyclobuten-1-yl)-N-[2-(5-methyl-1,2,4-oxadiazol-3-yl)-1-methylsulfonylpropan-2-yl]-4-(2,2,2-trifluoroethoxy)pyridine-2-carboxamide;

5-cyclopropyl-N-[1-(3,3-difluoroazetidin-1-yl)-2-(5-methyl-1,2,4-oxadiazol-3-yl)propan-2-yl]-4-(2,2,2-trifluoroethoxy)pyridine-2-carboxamide;

5-(1-hydroxycyclobutyl)-N-[2-(5-methyl-1,2,4-oxadiazol-3-yl)-1-methylsulfonylpropan-2-yl]-4-(2,2,2-trifluoroethoxy)pyridine-2-carboxamide;

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

N-[1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide;

5-(3-fluorooxetan-3-yl)-N-[(2S)-2-(5-methyl-1,2,4-oxadiazol-3-yl)-1-methylsulfonylpropan-2-yl]-4-(2,2,2-trifluoroethoxy)pyridine-2-carboxamide;

5-(3-fluorooxetan-3-yl)-N-[(2R)-2-(5-methyl-1,2,4-oxadiazol-3-yl)-1-methylsulfonylpropan-2-yl]-4-(2,2,2-trifluoroethoxy)pyridine-2-carboxamide;

N-(1-amino-2-methyl-3-methylsulfonyl-1-oxopropan-2-yl)-5-cyclopropyl-4-(2,2,2-trifluoroethoxy)pyridine-2-carboxamide;

N-[(2R)-1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide;

N-[(2S)-1-cyclopropyl-2-(5-methyl-1,2,4-oxadiazol-3-yl)propan-2-yl]-5-(3-fluorooxetan-3-yl)-4-(2,2,2-trifluoroethoxy)pyridine-2-carboxamide;

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

5-(1-fluorocyclobutyl)-N-[2-(5-methyl-1,2,4-oxadiazol-3-yl)-1-methylsulfonylpropan-2-yl]-4-[(2S)-1,1,1-trifluoropropan-2-yl]oxypyridine-2-carboxamide;

N-[1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide;

5-cyclopropyl-N-[(2S)-1-hydroxy-2-(5-methyl-1,2,4-oxadiazol-3-yl)propan-2-yl]-4-(2,2,2-trifluoroethoxy)pyridine-2-carboxamide;

5-cyclopropyl-N-[(2R)-1-hydroxy-2-(5-methyl-1,2,4-oxadiazol-3-yl)propan-2-yl]-4-(2,2,2-trifluoroethoxy)pyridine-2-carboxamide;

N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide;

N-(2-cyano-1-cyclopropylpropan-2-yl)-5-(3-fluorooxetan-3-yl)-4-[(2S)-1,1,1-trifluoropropan-2-yl]oxypyridine-2-carboxamide;

N-[1-cyclopropyl-1-(5-methyl-1,2,4-oxadiazol-3-yl)ethyl]-5-(3-fluorooxetan-3-yl)-4-[(2S)-1, 1, 1-trifluoropropan-2-yl]oxypyridine-2-carboxamide;

5-cyclopropyl-N-[i-cyclopropyl-2-(5-methyl-1,2,4-oxadiazol-3-yl)propan-2-yl]-4-(2,2-difluoroethoxy)pyridine-2-carboxamide;

5-cyclopropyl-N-[i-cyclopropyl-2-(5-methyl-1,2,4-oxadiazol-3-yl)propan-2-yl]-4-(2-fluoroethoxy)pyridine-2-carboxamide;

5-cyclopropyl-N-[1-(3,3-difluoroazetidin-1-yl)-2-(5-methyl-1,2,4-oxadiazol-3-yl)-1-oxopropan-2-yl]-4-(2,2,2-trifluoroethoxy)pyridine-2-carboxamide;

5-cyclopropyl-N-[2-(5-methyl-1,2,4-oxadiazol-3-yl)-1-(2-oxa-6-azaspiro[3.3]heptan-6-yl)-1-oxopropan-2-yl]-4-(2,2,2-trifluoroethoxy)pyridine-2-carboxamide;

5-cyclopropyl-N-[1-(methylamino)-2-(5-methyl-1,2,4-oxadiazol-3-yl)-1-oxopropan-2-yl]-4-(2,2,2-trifluoroethoxy)pyridine-2-carboxamide;

5-cyclopropyl-N-[1-cyclopropyl-2-(2-methyltetrazol-5-yl)propan-2-yl]-4-(2,2,2-trifluoroethoxy)pyridine-2-carboxamide;

5-cyclopropyl-N-[1-cyclopropyl-2-(1-methyltetrazol-5-yl)propan-2-yl]-4-(2,2,2-trifluoroethoxy)pyridine-2-carboxamide;

5-cyclopropyl-N-[4-(4-methyl-1,3-thiazol-2-yl)oxan-4-yl]-4-(2,2,2-trifluoroethoxy)pyridine-2-carboxamide;

5-cyclopropyl-N-[4-(5-methyl-1,3-thiazol-2-yl)oxan-4-yl]-4-(2,2,2-trifluoroethoxy)pyridine-2-carboxamide;

5-cyclopropyl-N-[(2R)-1-cyclopropyl-2-(5-methyl-1,2,4-oxadiazol-3-yl)propan-2-yl]-4-(2,2-difluoroethoxy)pyridine-2-carboxamide;

5-cyclopropyl-N-[(2S)-1-cyclopropyl-2-(5-methyl-1,2,4-oxadiazol-3-yl)propan-2-yl]-4-(2,2-difluoroethoxy)pyridine-2-carboxamide;

5-cyclopropyl-N-[(2R)-1-cyclopropyl-2-(5-methyl-1,2,4-oxadiazol-3-yl)propan-2-yl]-4-(2-fluoroethoxy)pyridine-2-carboxamide;

5-cyclopropyl-N-[(2S)-1-cyclopropyl-2-(5-methyl-1,2,4-oxadiazol-3-yl)propan-2-yl]-4-(2-fluoroethoxy)pyridine-2-carboxamide;

5-cyclopropyl-N-[1-cyclopropyl-2-(4-methyl-1,3-thiazol-2-yl)propan-2-yl]-4-(2,2,2-trifluoroethoxy)pyridine-2-carboxamide;

5-cyclopropyl-N-[1-cyclopropyl-2-(1H-tetrazol-5-yl)propan-2-yl]-4-(2,2,2-trifluoroethoxy)pyridine-2-carboxamide;

N-[3-(2-amino-2-oxoethyl)-1,1-dioxothietan-3-yl]-5-cyclopropyl-4-(2,2,2-trifluoroethoxy)pyridine-2-carboxamide;

5-cyclopropyl-N-[2,2-dimethyl-1-(5-methyl-1,2,4-oxadiazol-3-yl)propyl]-4-(2,2,2-trifluoroethoxy)pyridine-2-carboxamide;

5-cyclopropyl-N-[2,2-dimethyl-1-(1H-tetrazol-5-yl)propyl]-4-(2,2,2-trifluoroethoxy)pyridine-2-carboxamide;

5-cyclopropyl-N-[2,2-dimethyl-1-(2-methyltetrazol-5-yl)propyl]-4-(2,2,2-trifluoroethoxy)pyridine-2-carboxamide;

5-cyclopropyl-N-[2,2-dimethyl-1-(1-methyltetrazol-5-yl)propyl]-4-(2,2,2-trifluoroethoxy)pyridine-2-carboxamide;

N-[2-(5-amino-1,2,4-oxadiazol-3-yl)-1-cyclopropylpropan-2-yl]-5-cyclopropyl-4-(2,2,2-trifluoroethoxy)pyridine-2-carboxamide;

N-[(1R)-1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide;

N-[(1S)-1-cyclopropyl-1-(5-methyl-1,2,4-oxadiazol-3-yl)ethyl]-5-(3-fluorooxetan-3-yl)-4-(2,2,2-trifluoroethoxy)pyridine-2-carboxamide;

N-[1-cyclopropyl-1-(5-methyl-1,2,4-oxadiazol-3-yl)ethyl]-5-(3-fluorooxetan-3-yl)-4-[(2S)-1,1-trifluoropropan-2-yl]oxypyridine-2-carboxamide;

N-[1-cyclopropyl-1-(5-methyl-1,2,4-oxadiazol-3-yl)ethyl]-5-(3-fluorooxetan-3-yl)-4-[(2S)-1,1-trifluoropropan-2-yl]oxypyridine-2-carboxamide;

N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide;

N-[1-cyclopropyl-2-(5-methyl-1,2,4-oxadiazol-3-yl)propan-2-yl]-5-(3-fluorooxetan-3-yl)-4-[(2S)-1,1,1-trifluoropropan-2-yl]oxypyridine-2-carboxamide;

N-[(2S)-3,3-dimethyl-1-(methylamino)-1-oxobutan-2-yl]-5-(3-fluorooxetan-3-yl)-4-[(2S)-1, 1,1-trifluoropropan-2-yl]oxypyridine-2-carboxamide;

5-cyclopropyl-N-[1-cyclopropyl-2-(5-methyl-1,3,4-oxadiazol-2-yl)propan-2-yl]-4-(2,2,2-trifluoroethoxy)pyridine-2-carboxamide;

5-cyclopropyl-N-[2,2-dimethyl-1-(5-methyl-1,3,4-oxadiazol-2-yl)propyl]-4-(2,2,2-trifluoroethoxy)pyridine-2-carboxamide;

N-[2,2-dimethyl-1-(5-methyl-1,3,4-oxadiazol-2-yl)propyl]-5-(3-fluorooxetan-3-yl)-4-[(2S)-1,1,1-trifluoropropan-2-yl]oxypyridine-2-carboxamide;

N-[1-cyclopropyl-2-(5-methyl-1,3,4-oxadiazol-2-yl)propan-2-yl]-5-(3-fluorooxetan-3-yl)-4-[(2S)-1,1,1-trifluoropropan-2-yl]oxypyridine-2-carboxamide;

5-cyclopropyl-N-[1-cyclopropyl-2-(5-methyl-1,3-thiazol-2-yl)propan-2-yl]-4-(2,2,2-trifluoroethoxy)pyridine-2-carboxamide;

5-cyclopropyl-N-[(1R)-2,2-dimethyl-1-(5-methyl-1,3,4-oxadiazol-2-yl)propyl]-4-(2,2,2-trifluoroethoxy)pyridine-2-carboxamide;

5-cyclopropyl-N-[(1S)-2,2-dimethyl-1-(5-methyl-1,3,4-oxadiazol-2-yl)propyl]-4-(2,2,2-trifluoroethoxy)pyridine-2-carboxamide;

N-[1-amino-2-(5-methyl-1,2,4-oxadiazol-3-yl)-1-oxopropan-2-yl]-5-cyclopropyl-4-(2,2,2-trifluoroethoxy)pyridine-2-carboxamide;

5-cyclopropyl-N-[1-(dimethylamino)-2-(5-methyl-1,2,4-oxadiazol-3-yl)-1-oxopropan-2-yl]-4-(2,2,2-trifluoroethoxy)pyridine-2-carboxamide;

N-[1-(azetidin-1-yl)-2-(5-methyl-1,2,4-oxadiazol-3-yl)-1-oxopropan-2-yl]-5-cyclopropyl-4-(2,2,2-trifluoroethoxy)pyridine-2-carboxamide;

5-(3-fluorooxetan-3-yl)-N-[1-(methylamino)-2-(5-methyl-1,2,4-oxadiazol-3-yl)-1-oxopropan-2-yl]-4-[(2S)-1,1,1-trifluoropropan-2-yl]oxypyridine-2-carboxamide;

5-cyclopropyl-N-[(2R)-1-cyclopropyl-2-(5-methyl-1,3,4-oxadiazol-2-yl)propan-2-yl]-4-(2,2,2-trifluoroethoxy)pyridine-2-carboxamide;

5-cyclopropyl-N-[(2S)-1-cyclopropyl-2-(5-methyl-1,3,4-oxadiazol-2-yl)propan-2-yl]-4-(2,2,2-trifluoroethoxy)pyridine-2-carboxamide;

N-(1-amino-3-cyclopropyl-2-methyl-1-oxopropan-2-yl)-5-cyclopropyl-4-(2,2,2-trifluoroethoxy)pyridine-2-carboxamide;

5-cyclopropyl-N-[(2 S)-1-(methylamino)-2-(5-methyl-1,2,4-oxadiazol-3-yl)-1-oxopropan-2-yl]-4-(2,2,2-trifluoroethoxy)pyridine-2-carboxamide;

5-cyclopropyl-N-[(2R)-1-(methylamino)-2-(5-methyl-1,2,4-oxadiazol-3-yl)-1-oxopropan-2-yl]-4-(2,2,2-trifluoroethoxy)pyridine-2-carboxamide;

5-cyclopropyl-N-[3-cyclopropyl-2-methyl-1-(methylamino)-1-oxopropan-2-yl]-4-(2,2,2-trifluoroethoxy)pyridine-2-carboxamide;

5-cyclopropyl-N-[2-(5-methyl-1,3,4-oxadiazol-2-yl)-1-(oxetan-3-yl)propan-2-yl]-4-[(2S)-1,1,1-trifluoropropan-2-yl]oxypyridine-2-carboxamide;

5-cyclopropyl-N-[2-(5-methyl-1,3,4-oxadiazol-2-yl)-1-(oxetan-3-yl)propan-2-yl]-4-(2,2,2-trifluoroethoxy)pyridine-2-carboxamide;

N-[1-(5-amino-1,2,4-oxadiazol-3-yl)-2,2-dimethylpropyl]-5-cyclopropyl-4-(2,2,2-trifluoroethoxy)pyridine-2-carboxamide;

N-(3-amino-1-cyclopropyl-3-oxopropyl)-5-cyclopropyl-4-(2,2,2-trifluoroethoxy)pyridine-2-carboxamide;

N-(1-amino-3,3-dimethyl-1-oxobutan-2-yl)-5-cyclopropyl-4-(2,2,2-trifluoroethoxy)pyridine-2-carboxamide;

5-cyclopropyl-N-[1-(dimethylamino)-3,3-dimethyl-1-oxobutan-2-yl]-4-(2,2,2-trifluoroethoxy)pyridine-2-carboxamide;

N-[1-(azetidin-1-yl)-3,3-dimethyl-1-oxobutan-2-yl]-5-cyclopropyl-4-(2,2,2-trifluoroethoxy)pyridine-2-carboxamide;

5-cyclopropyl-N-[1-(3,3-difluoroazetidin-1-yl)-3,3-dimethyl-1-oxobutan-2-yl]-4-(2,2,2-trifluoroethoxy)pyridine-2-carboxamide;

5-cyclopropyl-N-[3,3-dimethyl-1-(6-oxa-1-azaspiro[3.3]heptan-1-yl)-1-oxobutan-2-yl]-4-(2,2,2-trifluoroethoxy)pyridine-2-carboxamide;

N-(1-amino-3,3-dimethyl-1-oxobutan-2-yl)-5-cyclopropyl-4-[(2S)-1,1,1-trifluoropropan-2-yl]oxypyridine-2-carboxamide;

5-cyclopropyl-N-[3,3-dimethyl-1-(methylamino)-1-oxobutan-2-yl]-4-[(2S)-1,1,1-trifluoropropan-2-yl]oxypyridine-2-carboxamide;

5-cyclopropyl-N-[1-(dimethylamino)-3,3-dimethyl-1-oxobutan-2-yl]-4-[(2S)-1,1,1-trifluoropropan-2-yl]oxypyridine-2-carboxamide;

N-[1-(azetidin-1-yl)-3,3-dimethyl-1-oxobutan-2-yl]-5-cyclopropyl-4-[(2S)-1,1,1-trifluoropropan-2-yl]oxypyridine-2-carboxamide;

5-cyclopropyl-N-[1-(3,3-difluoroazetidin-1-yl)-3,3-dimethyl-1-oxobutan-2-yl]-4-[(2S)-1,1,1-trifluoropropan-2-yl]oxypyridine-2-carboxamide;

5-cyclopropyl-N-[3,3-dimethyl-1-(6-oxa-1-azaspiro[3.3]heptan-1-yl)-1-oxobutan-2-yl]-4-[(2S)-1,1,1-trifluoropropan-2-yl]oxypyridine-2-carboxamide;

5-cyclopropyl-N-[(1R)-2,2-dimethyl-1-(1-methyltetrazol-5-yl)propyl]-4-(2,2,2-trifluoroethoxy)pyridine-2-carboxamide;

5-cyclopropyl-N-[(1S)-2,2-dimethyl-1-(1-methyltetrazol-5-yl)propyl]-4-(2,2,2-trifluoroethoxy)pyridine-2-carboxamide;

N-[(2R)-2-(5-amino-1,2,4-oxadiazol-3-yl)-1-cyclopropylpropan-2-yl]-5-cyclopropyl-4-(2,2,2-trifluoroethoxy)pyridine-2-carboxamide;

N-[(2S)-2-(5-amino-1,2,4-oxadiazol-3-yl)-1-cyclopropylpropan-2-yl]-5-cyclopropyl-4-(2,2,2-trifluoroethoxy)pyridine-2-carboxamide;

5-cyclopropyl-N-[(1R)-2,2-dimethyl-1-(2-methyltetrazol-5-yl)propyl]-4-(2,2,2-trifluoroethoxy)pyridine-2-carboxamide;

5-cyclopropyl-N-[(1S)-2,2-dimethyl-1-(2-methyltetrazol-5-yl)propyl]-4-(2,2,2-trifluoroethoxy)pyridine-2-carboxamide;

5-cyclopropyl-N-[(1R)-2,2-dimethyl-1-(5-methyl-1,2,4-oxadiazol-3-yl)propyl]-4-(2,2,2-trifluoroethoxy)pyridine-2-carboxamide;

5-cyclopropyl-N-[(1S)-2,2-dimethyl-1-(5-methyl-1,2,4-oxadiazol-3-yl)propyl]-4-(2,2,2-trifluoroethoxy)pyridine-2-carboxamide;

N-[1-(5-amino-1,2,4-oxadiazol-3-yl)-2,2-dimethylpropyl]-5-cyclopropyl-4-[(2S)-1,1,1-trifluoropropan-2-yl]oxypyridine-2-carboxamide;

5-cyclopropyl-N-[2,2-dimethyl-1-(5-methyl-1,2,4-oxadiazol-3-yl)propyl]-4-[(2S)-1,1,1-trifluoropropan-2-yl]oxypyridine-2-carboxamide;

5-cyclopropyl-4-[(3-methyloxetan-3-yl)methoxy]-N-[2-(5-phenyl-1,3,4-oxadiazol-2-yl)propan-2-yl]pyridine-2-carboxamide;

5-cyclopropyl-N-[2,2-dimethyl-1-(2-methyltetrazol-5-yl)propyl]-4-[(2S)-1,1,1-trifluoropropan-2-yl]oxypyridine-2-carboxamide;

5-cyclopropyl-N-[2,2-dimethyl-1-(1-methyltetrazol-5-yl)propyl]-4-[(2S)-1,1,1-trifluoropropan-2-yl]oxypyridine-2-carboxamide;

N-[1-(5-amino-1,2,4-oxadiazol-3-yl)-2,2-dimethylpropyl]-5-cyclopropyl-4-[(2S)-1,1,1-trifluoropropan-2-yl]oxypyridine-2-carboxamide;

N-[1-(5-amino-1,2,4-oxadiazol-3-yl)-2,2-dimethylpropyl]-5-cyclopropyl-4-[(2S)-1,1,1-trifluoropropan-2-yl]oxypyridine-2-carboxamide;

5-cyclopropyl-N-[2,2-dimethyl-1-(5-methyl-1,2,4-oxadiazol-3-yl)propyl]-4-[(2S)-1,1,1-trifluoropropan-2-yl]oxypyridine-2-carboxamide;

5-cyclopropyl-N-[2,2-dimethyl-1-(5-methyl-1,2,4-oxadiazol-3-yl)propyl]-4-[(2S)-1,1,1-trifluoropropan-2-yl]oxypyridine-2-carboxamide;

N-[3-(2-amino-2-oxoethyl)oxetan-3-yl]-4-(cyclopropylmethoxy)-5-(3,3-difluoroazetidin-1-yl)pyridine-2-carboxamide;

N-[3-(2-amino-2-oxoethyl)oxetan-3-yl]-5-(3,3-difluoroazetidin-1-yl)-4-(2,2,2-trifluoroethoxy)pyridine-2-carboxamide;

5-cyclopropyl-N-[(2S)-3,3-dimethyl-1-(methylamino)-1-oxobutan-2-yl]-4-(2,2,2-trifluoroethoxy)pyridine-2-carboxamide;

5-cyclopropyl-N-[(2R)-3,3-dimethyl-1-(methylamino)-1-oxobutan-2-yl]-4-(2,2,2-trifluoroethoxy)pyridine-2-carboxamide;

N-[(1R)-1-(5-amino-1,2,4-oxadiazol-3-yl)-2,2-dimethylpropyl]-5-cyclopropyl-4-(2,2,2-trifluoroethoxy)pyridine-2-carboxamide;

N-[(1S)-1-(5-amino-1,2,4-oxadiazol-3-yl)-2,2-dimethylpropyl]-5-cyclopropyl-4-(2,2,2-trifluoroethoxy)pyridine-2-carboxamide;

5-cyclopropyl-N-[(2R)-1-cyclopropyl-2-(1-methyltetrazol-5-yl)propan-2-yl]-4-(2,2,2-trifluoroethoxy)pyridine-2-carboxamide;

5-cyclopropyl-N-[2-cyclopropyl-4-(methylamino)-4-oxobutan-2-yl]-4-(2,2,2-trifluoroethoxy)pyridine-2-carboxamide;

N-(4-amino-2-cyclopropyl-4-oxobutan-2-yl)-5-cyclopropyl-4-(2,2,2-trifluoroethoxy)pyridine-2-carboxamide;

5-cyclopropyl-N-[3-[2-(methylamino)-2-oxoethyl]ox-etan-3-yl]-4-(2,2,2-trifluoroethoxy)pyridine-2-carboxamide;
5-cyclopropyl-N-[3-[2-(methylamino)-2-oxoethyl]ox-etan-3-yl]-4-[(2S)-1,1,1-trifluoropropan-2-yl]oxypyridine-2-carboxamide;
5-(3,3-difluoroazetidin-1-yl)-N-[3-[2-(methylamino)-2-oxoethyl]oxetan-3-yl]-4-(2,2,2-trifluoroethoxy)pyridine-2-carboxamide;
5-cyclopropyl-N-[3-(3-fluoropropylcarbamoyl)pentan-3-yl]-4-[(3-methyloxetan-3-yl)methoxy]pyridine-2-carboxamide;
N-[3-[[3-chloro-2-fluoropropyl]carbamoyl]pentan-3-yl]-5-cyclopropyl-4-[(3-methyloxetan-3-yl)methoxy]pyridine-2-carboxamide;
5-cyclopropyl-N-[3-hydroxy-3-methyl-1-(methylamino)-1-oxobutan-2-yl]-4-(2,2,2-trifluoroethoxy)pyridine-2-carboxamide;
5-cyclopropyl-N-[3-fluoro-3-methyl-1-(methyl amino)-1-oxobutan-2-yl]-4-(2,2,2-trifluoroethoxy)pyridine-2-carboxamide;
5-cyclopropyl-N-[3-hydroxy-3-methyl-1-(methyl amino)-1-oxobutan-2-yl]-4-[(2S)-1,1,1-trifluoropropan-2-yl]oxypyridine-2-carboxamide;
N-(1-amino-3,3-dimethyl-1-oxobutan-2-yl)-5-cyclopropyl-4-[(2S)-1,1,1-trifluoropropan-2-yl]oxypyridine-2-carboxamide;
N-(1-amino-3,3-dimethyl-1-oxobutan-2-yl)-5-cyclopropyl-4-[(2S)-1,1,1-trifluoropropan-2-yl]oxypyridine-2-carboxamide;
5-cyclopropyl-N-[(2S)-2-cyclopropyl-4-(methylamino)-4-oxobutan-2-yl]-4-(2,2,2-trifluoroethoxy)pyridine-2-carboxamide;
5-cyclopropyl-N-[(2R)-2-cyclopropyl-4-(methylamino)-4-oxobutan-2-yl]-4-(2,2,2-trifluoroethoxy)pyridine-2-carboxamide;
N-[(2S)-4-amino-2-cyclopropyl-4-oxobutan-2-yl]-5-cyclopropyl-4-(2,2,2-trifluoroethoxy)pyridine-2-carboxamide;
N-[(2R)-4-amino-2-cyclopropyl-4-oxobutan-2-yl]-5-cyclopropyl-4-(2,2,2-trifluoroethoxy)pyridine-2-carboxamide;
5-cyclopropyl-N-[(5-methyl-1,3,4-oxadiazol-2-yl)-(3-methyloxetan-3-yl)methyl]-4-(2,2,2-trifluoroethoxy)pyridine-2-carboxamide;
5-cyclopropyl-N-[(5-methyl-1,3,4-oxadiazol-2-yl)-(3-methyloxetan-3-yl)methyl]-4-[(2S)-1,1,1-trifluoropropan-2-yl]oxypyridine-2-carboxamide;
5-cyclopropyl-N-[2-cyclopropyl-4-(methylamino)-4-oxobutan-2-yl]-4-[(2S)-1,1,1-trifluoropropan-2-yl]oxypyridine-2-carboxamide;
N-(4-amino-2-cyclopropyl-4-oxobutan-2-yl)-5-cyclopropyl-4-[(2S)-1,1,1-trifluoropropan-2-yl]oxypyridine-2-carboxamide;
5-cyclopropyl-N-[2-cyclopropyl-4-(methylamino)-4-oxobutan-2-yl]-4-[(2S)-1,1,1-trifluoropropan-2-yl]oxypyridine-2-carboxamide;
5-cyclopropyl-N-[2-cyclopropyl-4-(methylamino)-4-oxobutan-2-yl]-4-[(2S)-1,1,1-trifluoropropan-2-yl]oxypyridine-2-carboxamide;
N-[2-amino-1-(3-methyloxetan-3-yl)-2-oxoethyl]-5-cyclopropyl-4-[(2S)-1,1,1-trifluoropropan-2-yl]oxypyridine-2-carboxamide;
5-cyclopropyl-N-[3-hydroxy-3-methyl-1-(methyl amino)-1-oxobutan-2-yl]-4-[(2S)-1,1,1-trifluoropropan-2-yl]oxypyridine-2-carboxamide;
5-cyclopropyl-N-[3-hydroxy-3-methyl-1-(methyl amino)-1-oxobutan-2-yl]-4-[(2S)-1,1,1-trifluoropropan-2-yl]oxypyridine-2-carboxamide;
5-cyclopropyl-N-[(5-methyl-1,2,4-oxadiazol-3-yl)-(3-methyloxetan-3-yl)methyl]-4-[(2S)-1,1,1-trifluoropropan-2-yl]oxypyridine-2-carboxamide;
5-cyclopropyl-N-[(5-methyl-1,2,4-oxadiazol-3-yl)-(3-methyloxetan-3-yl)methyl]-4-[(2S)-1,1,1-trifluoropropan-2-yl]oxypyridine-2-carboxamide;
N-(1-amino-3,3-dimethyl-1-oxobutan-2-yl)-5-(3,3-difluoroazetidin-1-yl)-4-(2,2,2-trifluoroethoxy)pyridine-2-carboxamide;
N-(1-amino-3,3-dimethyl-1-oxobutan-2-yl)-4-(cyclopropylmethoxy)-5-(3,3-difluoroazetidin-1-yl)pyridine-2-carboxamide;
N-(4-amino-2-cyclopropyl-4-oxobutan-2-yl)-5-cyclopropyl-4-[(2S)-1,1,1-trifluoropropan-2-yl]oxypyridine-2-carboxamide;
N-(4-amino-2-cyclopropyl-4-oxobutan-2-yl)-5-cyclopropyl-4-[(2S)-1,1,1-trifluoropropan-2-yl]oxypyridine-2-carboxamide;
N-[(2R)-1-amino-3,3-dimethyl-1-oxobutan-2-yl]-4-(cyclopropylmethoxy)-5-(3,3-difluoroazetidin-1-yl)pyridine-2-carboxamide;
N-[(2S)-1-amino-3,3-dimethyl-1-oxobutan-2-yl]-4-(cyclopropylmethoxy)-5-(3,3-difluoroazetidin-1-yl)pyridine-2-carboxamide;
N-[(2R)-1-amino-3,3-dimethyl-1-oxobutan-2-yl]-5-(3,3-difluoroazetidin-1-yl)-4-(2,2,2-trifluoroethoxy)pyridine-2-carboxamide;
N-[(2S)-1-amino-3,3-dimethyl-1-oxobutan-2-yl]-5-(3,3-difluoroazetidin-1-yl)-4-(2,2,2-trifluoroethoxy)pyridine-2-carboxamide;
N-[3-(2-amino-2-oxoethyl)-1,1-dioxothietan-3-yl]-5-(3,3-difluoroazetidin-1-yl)-4-(2,2,2-trifluoroethoxy)pyridine-2-carboxamide;
N-[3-(2-amino-2-oxoethyl)-1,1-dioxothietan-3-yl]-5-(3-fluorooxetan-3-yl)-4-[(2S)-1,1,1-trifluoropropan-2-yl]oxypyridine-2-carboxamide;
N-[3-(2-amino-2-oxoethyl)-1,1-dioxothietan-3-yl]-5-cyclopropyl-4-[(2S)-1,1,1-trifluoropropan-2-yl]oxypyridine-2-carboxamide;
N-[3-(2-amino-2-oxoethyl)-1,1-dioxothietan-3-yl]-4-(cyclopropylmethoxy)-5-(3,3-difluoroazetidin-1-yl)pyridine-2-carboxamide;
N-[(1R)-2-amino-1-(3-methyloxetan-3-yl)-2-oxoethyl]-5-cyclopropyl-4-(2,2,2-trifluoroethoxy)pyridine-2-carboxamide;
N-[(1S)-2-amino-1-(3-methyloxetan-3-yl)-2-oxoethyl]-5-cyclopropyl-4-(2,2,2-trifluoroethoxy)pyridine-2-carboxamide;
N-[(2S)-4-amino-2-cyclopropyl-4-oxobutan-2-yl]-5-cyclopropyl-4-(2-fluoroethoxy)pyridine-2-carboxamide;
N-[(2R)-4-amino-2-cyclopropyl-4-oxobutan-2-yl]-5-cyclopropyl-4-(2-fluoroethoxy)pyridine-2-carboxamide;
N-[(2S)-4-amino-2-cyclopropyl-4-oxobutan-2-yl]-5-cyclopropyl-4-(2,2-difluoroethoxy)pyridine-2-carboxamide;
N-[(2R)-4-amino-2-cyclopropyl-4-oxobutan-2-yl]-5-cyclopropyl-4-(2,2-difluoroethoxy)pyridine-2-carboxamide;
N-[3-(2-amino-2-oxoethyl)-1,1-dioxothietan-3-yl]-5-cyclopropyl-4-(2,2-difluoroethoxy)pyridine-2-carboxamide;
N-[(2S)-4-amino-2-cyclopropyl-4-oxobutan-2-yl]-5-(3,3-difluoroazetidin-1-yl)-4-(2,2,2-trifluoroethoxy)pyridine-2-carboxamide;

N-[(2R)-4-amino-2-cyclopropyl-4-oxobutan-2-yl]-5-(3,3-difluoroazetidin-1-yl)-4-(2,2,2-trifluoroethoxy)pyridine-2-carboxamide;

N-(4-amino-2-cyclopropyl-4-oxobutan-2-yl)-5-(3-fluorooxetan-3-yl)-4-[(2S)-1,1,1-trifluoropropan-2-yl]oxypyridine-2-carboxamide;

N-(4-amino-2-cyclopropyl-4-oxobutan-2-yl)-5-(3-fluorooxetan-3-yl)-4-[(2S)-1,1,1-trifluoropropan-2-yl]oxypyridine-2-carboxamide;

5-cyclopropyl-4-(2-fluoroethoxy)-N-[(2R)-2-(5-methyl-1,2,4-oxadiazol-3-yl)-1-methylsulfonylpropan-2-yl]pyridine-2-carboxamide;

5-cyclopropyl-4-(2-fluoroethoxy)-N-[(2S)-2-(5-methyl-1,2,4-oxadiazol-3-yl)-1-methylsulfonylpropan-2-yl]pyridine-2-carboxamide;

N-[3-(2-amino-2-oxoethyl)-1,1-dioxothietan-3-yl]-5-cyclopropyl-4-(2-fluoroethoxy)pyridine-2-carboxamide;

5-cyclopropyl-N-[3-[2-(methylamino)-2-oxoethyl]-1,1-dioxothietan-3-yl]-4-(2,2,2-trifluoroethoxy)pyridine-2-carboxamide;

(S)-5-cyclopropyl-4-(2,2-difluoroethoxy)-N-(2-(5-methyl-1,2,4-oxadiazol-3-yl)-1-(methylsulfonyl)propan-2-yl)picolinamide;

(R)-5-cyclopropyl-4-(2,2-difluoroethoxy)-N-(2-(5-methyl-1,2,4-oxadiazol-3-yl)-1-(methylsulfonyl)propan-2-yl)picolinamide;

5-(1-fluorocyclobutyl)-N-[3-[2-(methylamino)-2-oxoethyl]-1,1-dioxothietan-3-yl]-4-(2,2,2-trifluoroethoxy)pyridine-2-carboxamide;

N-[3-(2-amino-2-oxoethyl)-1,1-dioxothietan-3-yl]-5-(1-fluorocyclobutyl)-4-(2,2,2-trifluoroethoxy)pyridine-2-carboxamide;

5-cyclopropyl-N—((R)-1-cyclopropyl-2-(5-methyl-1,2,4-oxadiazol-3-yl)propan-2-yl)-4-((S)-1-fluoropropan-2-yloxy)picolinamide;

5-cyclopropyl-N—((S)-1-cyclopropyl-2-(5-methyl-1,2,4-oxadiazol-3-yl)propan-2-yl)-4-((S)-1-fluoropropan-2-yloxy)picolinamide;

5-cyclopropyl-N—((R)-1-cyclopropyl-2-(5-methyl-1,2,4-oxadiazol-3-yl)propan-2-yl)-4-((R)-1-fluoropropan-2-yloxy)picolinamide;

5-cyclopropyl-N—((S)-1-cyclopropyl-2-(5-methyl-1,2,4-oxadiazol-3-yl)propan-2-yl)-4-((R)-1-fluoropropan-2-yloxy)picolinamide;

N-[3-(2-amino-2-oxoethyl)-1,1-dioxothietan-3-yl]-5-cyclopropyl-4-[(2S)-1-fluoropropan-2-yl]oxypyridine-2-carboxamide;

N-[3-(2-amino-2-oxoethyl)-1,1-dioxothietan-3-yl]-5-cyclopropyl-4-[(2R)-1-fluoropropan-2-yl]oxypyridine-2-carboxamide;

N-(4-amino-2-cyclopropyl-4-oxobutan-2-yl)-5-cyclopropyl-4-((S)-1-fluoropropan-2-yloxy)picolinamide;

N-(4-amino-2-cyclopropyl-4-oxobutan-2-yl)-5-cyclopropyl-4-((R)-1-fluoropropan-2-yloxy)picolinamide;

5-cyclopropyl-4-((S)-1-fluoropropan-2-yloxy)-N—((S)-2-(5-methyl-1,2,4-oxadiazol-3-yl)-1-(methylsulfonyl)propan-2-yl)picolinamide;

5-cyclopropyl-4-((S)-1-fluoropropan-2-yloxy)-N—((R)-2-(5-methyl-1,2,4-oxadiazol-3-yl)-1-(methylsulfonyl)propan-2-yl)picolinamide;

5-cyclopropyl-4-((R)-1-fluoropropan-2-yloxy)-N—((S)-2-(5-methyl-1,2,4-oxadiazol-3-yl)-1-(methylsulfonyl)propan-2-yl)picolinamide;

5-cyclopropyl-4-((R)-1-fluoropropan-2-yloxy)-N—((R)-2-(5-methyl-1,2,4-oxadiazol-3-yl)-1-(methylsulfonyl)propan-2-yl)picolinamide;

N-[3-(2-amino-2-oxoethyl)-1,1-dioxothietan-3-yl]-5-cyclobutyl-4-(2,2,2-trifluoroethoxy)pyridine-2-carboxamide;

N-(4-amino-2-cyclopropyl-4-oxobutan-2-yl)-5-(1-fluorocyclobutyl)-4-(2,2,2-trifluoroethoxy)picolinamide;

N-[3-(2-amino-2-oxoethyl)-1,1-dioxothietan-3-yl]-5-(1-fluorocyclobutyl)-4-[(2S)-1,1,1-trifluoropropan-2-yl]oxypyridine-2-carboxamide;

N-[3-(2-amino-2-oxoethyl)-1,1-dioxothietan-3-yl]-4-(2,2-difluoroethoxy)-5-(1-fluorocyclobutyl)pyridine-2-carboxamide;

(S)—N-(1-cyclopropyl-1-(5-methyl-1,2,4-oxadiazol-3-yl)ethyl)-5-(1-fluorocyclobutyl)-4-(2,2,2-trifluoroethoxy)picolinamide;

(R)—N-(1-cyclopropyl-1-(5-methyl-1,2,4-oxadiazol-3-yl)ethyl)-5-(1-fluorocyclobutyl)-4-(2,2,2-trifluoroethoxy)picolinamide;

N—((S)-4-amino-2-cyclopropyl-4-oxobutan-2-yl)-5-cyclopropyl-4-((S)-1-fluoropropan-2-yloxy)picolinamide;

N—((R)-4-amino-2-cyclopropyl-4-oxobutan-2-yl)-5-cyclopropyl-4-((S)-1-fluoropropan-2-yloxy)picolinamide;

N—((S)-4-amino-2-cyclopropyl-4-oxobutan-2-yl)-5-cyclopropyl-4-((R)-1-fluoropropan-2-yloxy)picolinamide;

N—((R)-4-amino-2-cyclopropyl-4-oxobutan-2-yl)-5-cyclopropyl-4-((R)-1-fluoropropan-2-yloxy)picolinamide;

N-[(2S)-4-amino-2-cyclopropyl-4-oxobutan-2-yl]-5-(1-fluorocyclobutyl)-4-(2,2,2-trifluoroethoxy)pyridine-2-carboxamide; and N-[(2R)-4-amino-2-cyclopropyl-4-oxobutan-2-yl]-5-(1-fluorocyclobutyl)-4-(2,2,2-trifluoroethoxy)pyridine-2-carboxamide.

15. A compound according to claim 1 selected from

5-Cyclopropyl-4-(2,2,2-trifluoro-ethoxy)-pyridine-2-carboxylic acid [(R)-2-cyclopropyl-1-methyl-1-(5-methyl-[1,2,4]oxadiazol-3-yl)-ethyl]-amide;

5-Cyclopropyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;

5-(3,3-Difluoro-azetidin-1-yl)-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;

5-Cyclobutyl-4-(2,2,2-trifluoro-ethoxy)-pyridine-2-carboxylic acid [2-cyclopropyl-1-methyl-1-(5-methyl-[1,2,4]oxadiazol-3-yl)-ethyl]-amide;

5-Cyclobutyl-4-(2,2,2-trifluoro-ethoxy)-pyridine-2-carboxylic acid [2-methanesulfonyl-1-methyl-1-(5-methyl-[1,2,4]oxadiazol-3-yl)-ethyl]-amide;

5-Cyclobutyl-4-((S)-2,2,2-trifluoro-1-methyl-ethoxy)-pyridine-2-carboxylic acid [2-cyclopropyl-1-methyl-1-(5-methyl-[1,2,4]oxadiazol-3-yl)-ethyl]-amide;

5-Cyclobutyl-4-((S)-2,2,2-trifluoro-1-methyl-ethoxy)-pyridine-2-carboxylic acid [2-methanesulfonyl-1-methyl-1-(5-methyl-[1,2,4]oxadiazol-3-yl)-ethyl]-amide;

5-cyclopropyl-N-[1-cyclopropyl-2-(5-methyl-1,2,4-oxadiazol-3-yl)propan-2-yl]-4-(2,2-difluoroethoxy)pyridine-2-carboxamide;

5-cyclopropyl-N-[1-cyclopropyl-2-(5-methyl-1,2,4-oxadiazol-3-yl)propan-2-yl]-4-(2-fluoroethoxy)pyridine-2-carboxamide;

5-cyclopropyl-N-[(2S)-1-cyclopropyl-2-(5-methyl-1,2,4-oxadiazol-3-yl)propan-2-yl]-4-(2,2-difluoroethoxy)pyridine-2-carboxamide;

5-cyclopropyl-N-[(2S)-1-cyclopropyl-2-(5-methyl-1,2,4-oxadiazol-3-yl)propan-2-yl]-4-(2-fluoroethoxy)pyridine-2-carboxamide;

N-[3-(2-amino-2-oxoethyl)-1,1-dioxothietan-3-yl]-5-cyclopropyl-4-(2,2,2-trifluoroethoxy)pyridine-2-carboxamide;

5-cyclopropyl-N-[1-cyclopropyl-2-(5-methyl-1,3,4-oxadiazol-2-yl)propan-2-yl]-4-(2,2,2-trifluoroethoxy)pyridine-2-carboxamide;

5-cyclopropyl-N-[(2S)-1-cyclopropyl-2-(5-methyl-1,3,4-oxadiazol-2-yl)propan-2-yl]-4-(2,2,2-trifluoroethoxy)pyridine-2-carboxamide;

N-(4-amino-2-cyclopropyl-4-oxobutan-2-yl)-5-cyclopropyl-4-(2,2,2-trifluoroethoxy)pyridine-2-carboxamide;

N-(4-amino-2-cyclopropyl-4-oxobutan-2-yl)-5-cyclopropyl-4-[(2S)-1,1,1-trifluoropropan-2-yl]oxypyridine-2-carboxamide;

N-(4-amino-2-cyclopropyl-4-oxobutan-2-yl)-5-cyclopropyl-4-[(2S)-1,1,1-trifluoropropan-2-yl]oxypyridine-2-carboxamide;

N-[3-(2-amino-2-oxoethyl)-1,1-dioxothietan-3-yl]-5-cyclopropyl-4-[(2S)-1,1,1-trifluoropropan-2-yl]oxypyridine-2-carboxamide;

N-[(2R)-4-amino-2-cyclopropyl-4-oxobutan-2-yl]-5-cyclopropyl-4-(2-fluoroethoxy)pyridine-2-carboxamide;

N-[(2R)-4-amino-2-cyclopropyl-4-oxobutan-2-yl]-5-cyclopropyl-4-(2,2-difluoroethoxy)pyridine-2-carboxamide; and 5-cyclopropyl-4-((S)-1-fluoropropan-2-yloxy)-N—((S)-2-(5-methyl-1,2,4-oxadiazol-3-yl)-1-(methylsulfonyl)propan-2-yl)picolinamide.

16. A process for the preparation of a compound according to claim 1 comprising the reaction of a compound of formula (B)

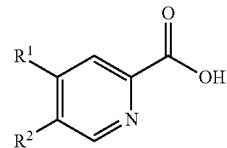

(B)

in the presence of $NHR^3R^4$, an amide coupling agent and a base, wherein $R^1$ to $R^4$ are as defined in claim 1.

17. A compound manufactured according to a process of claim 16.

18. A pharmaceutical composition comprising a compound in accordance with claim 1 and a therapeutically inert carrier.

19. A method for the treatment of pain, atherosclerosis, age-related macular degeneration, diabetic retinopathy, glaucoma, retinal vein occlusion, retinopathy of prematurity, ocular ischemic syndrome, geographic atrophy, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, amyotrophic lateral sclerosis, stroke, transient ischemic attack or uveitis, which method comprises administering an effective amount of a compound as defined in claim 1 to a patient in need thereof.

* * * * *